US011932637B2

(12) United States Patent
Chen et al.

(10) Patent No.: US 11,932,637 B2
(45) Date of Patent: Mar. 19, 2024

(54) CHROMANE AMIDINE MONOBACTAM COMPOUNDS FOR THE TREATMENT OF BACTERIAL INFECTIONS

(71) Applicant: Merck Sharp & Dohme LLC, Rahway, NJ (US)

(72) Inventors: Helen Y. Chen, Florham Park, NJ (US); Shuzhi Dong, Plainsboro, NJ (US); Zhiyong Hu, Livingston, NJ (US); Jing Su, Scotch Plains, NJ (US); Tao Yu, Edison, NJ (US); Yong Zhang, West Windsor, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 18/055,874

(22) Filed: Nov. 16, 2022

(65) Prior Publication Data

US 2023/0159517 A1 May 25, 2023

Related U.S. Application Data

(60) Provisional application No. 63/327,385, filed on Apr. 5, 2022, provisional application No. 63/280,728, filed on Nov. 18, 2021.

(51) Int. Cl.

| | |
|---|---|
| ***C07D 417/14*** | (2006.01) |
| ***A61K 31/424*** | (2006.01) |
| ***A61K 31/427*** | (2006.01) |
| ***A61K 31/431*** | (2006.01) |
| ***A61K 31/55*** | (2006.01) |
| ***A61K 31/551*** | (2006.01) |
| ***A61K 31/69*** | (2006.01) |
| ***A61P 31/04*** | (2006.01) |

(52) U.S. Cl.

CPC .......... *C07D 417/14* (2013.01); *A61K 31/424* (2013.01); *A61K 31/427* (2013.01); *A61K 31/431* (2013.01); *A61K 31/55* (2013.01); *A61K 31/551* (2013.01); *A61K 31/69* (2013.01); *A61P 31/04* (2018.01)

(58) Field of Classification Search

CPC ............................... C07D 417/14; A61P 31/04

See application file for complete search history.

(56) References Cited

U.S. PATENT DOCUMENTS

| | | | | |
|---|---|---|---|---|
| 5,250,691 A * | 10/1993 | Straub | C07D 215/233 546/156 |
| 5,290,929 A * | 3/1994 | Koster | C07C 271/66 560/160 |
| 11,230,543 B2 * | 1/2022 | Tang | A61K 31/427 |
| 11,433,055 B2 * | 9/2022 | Biftu | C07D 417/14 |
| 2014/0275007 A1 | 9/2014 | Glinka et al. | |
| 2015/0045340 A1 | 2/2015 | Klenke et al. | |
| 2015/0266867 A1 | 9/2015 | Aulakh et al. | |
| 2020/0093814 A1 * | 3/2020 | Wiegand | A61K 31/424 |
| 2020/0297702 A1 * | 9/2020 | Biftu | A61K 31/517 |
| 2023/0150996 A1 * | 5/2023 | Yang | A61K 45/06 514/210.18 |
| 2023/0295149 A1 * | 9/2023 | Yang | C07D 417/12 514/210.15 |

FOREIGN PATENT DOCUMENTS

| | | |
|---|---|---|
| WO | 2007065288 A2 | 6/2007 |
| WO | 2012073138 A1 | 6/2012 |
| WO | 2013110643 A1 | 8/2013 |

(Continued)

OTHER PUBLICATIONS

Fung-Tomc; Antimicrob Agents Chemother. 1997, 41, 1010-1016. https://doi.org/10.1128/aac.41.5.1010 (Year: 1997).*

(Continued)

*Primary Examiner* — Daniel R Carcanague

(74) *Attorney, Agent, or Firm* — Baerbel R. Brown; Catherine D. Fitch

(57) ABSTRACT

The present invention relates to monobactam compounds of Formula I:

(I)

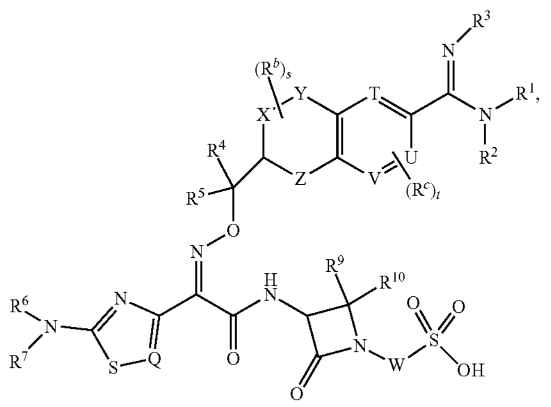

and pharmaceutically acceptable salts thereof. The present invention also relates to compositions which comprise a monobactam compound of structural formula I or a pharmaceutically acceptable salt thereof, and a pharmaceutically acceptable carrier. The invention further relates to methods for treating a bacterial infection comprising administering to the patient a therapeutically effective amount of a compound of structural formula I, either alone or in combination with a therapeutically effective amount of a second beta-lactam antibiotic.

49 Claims, No Drawings

(56) References Cited

FOREIGN PATENT DOCUMENTS

| | | | | | |
|---|---|---|---|---|---|
| WO | 2015103583 | A1 | | 7/2015 | |
| WO | 2017106064 | A1 | | 6/2017 | |
| WO | 2019020810 | A1 | | 1/2019 | |
| WO | 2019070492 | A1 | | 4/2019 | |
| WO | WO-2019144969 | A1 | * | 8/2019 | .............. A61P 11/00 |
| WO | WO-2021121387 | A1 | * | 6/2021 | ........... A61K 31/427 |

OTHER PUBLICATIONS

Reck; Bioorganic & Medicinal Chemistry Letters 2018, 28, 748-755. https://doi.org/10.1016/j.bmcl.2018.01.006 (Year: 2018).*
International Application PCT/US2022/050027, Written Opinion of the International Searching Authority, dated May 25, 2023. (Year: 2023).*
Brown, Matthew, F. et al., Pyridone-Conjugated Monobactam Antibiotics with Gram-Negative Activity, Journal of Medicinal Chemistry, 2013, p. 5541-5552, vol. 56.
Director, Dr. Tom Frieden, MD, MPH, Antibiotic Resistance Threats in the United States, 2013, U.S. Centers for Disease Control and Prevention, 2013, 1-17, N/A.
Drawz, Sarah, M. et al., Three Decades of B-Lactamase Inhibitors, Clinical Microbiology Reviews, 2010, p. 160-201, vol. 23, No. 1.
Hanaki et al., TOC-39, a Novel Parenteral Broad-Spectrum Cephalosporin with Excellent Activity against Methicillin-Resistant *Staphylococcus aureus*, Antimicrobial Agents and Chemotherapy, 1995, 1120-1126, 30.
Mitton-Fry, Mark, J. et al., Novel monobactams utilizing a siderophore uptake mechanism for the treatment of gram-negative infections, Bioorganic & Medicinal Chemistry Letters, 2012, p. 5989-5994, vol. 22.
Payne et al., Comparative Activities of Clavulanic Acid, Sulbactam, and Tazobactam against Clinically Important beta-Lactamases, Antimicrobial Agents and Chemotherapy, 1994, 767-772, 38.
Troy, David (Editor), Solutions, Emulsions, Suspensions, and Extracts, Remington, The Science and Practice of Pharmacy, 2006, 21st Edition, 745-928, Chapters 39, 40, 41, 42, 43, 44 + 45.
Waley, S. G., B-Lactasmase: mechanism of action, The Chemistry of B-Lactams, M. I. Page (ed.), 1992, p. 198-228.

* cited by examiner

CHROMANE AMIDINE MONOBACTAM COMPOUNDS FOR THE TREATMENT OF BACTERIAL INFECTIONS

CROSS-REFERENCE TO RELATED APPLICATIONS

This application is a U.S. Non Provisional application which claims priority from and the benefit of both U.S. Provisional Application Ser. No. 63/327,385, filed Apr. 5, 2022 and U.S. Provisional Application Ser. No. 63/280,728, filed Nov. 18, 2021.

FIELD OF THE INVENTION

This invention relates to novel monobactam compounds, processes for their preparation and their use as therapeutic agents. In particular, the invention relates to monobactam compounds useful as antibiotic agents for the treatment of bacterial infections.

BACKGROUND OF THE INVENTION

The introduction of antibiotics for treatment of bacterial infections is one of the great medical achievements of the 20$^{th}$ century. Over the past few decades, however, bacteria resistant to multiple antibiotics have begun to emerge throughout the world, threatening the effectiveness of antibiotic therapy. In the United States alone, at least 23,000 people each year die as a direct result of infections caused by antibiotic-resistant bacteria, and numerous others die from pre-existing conditions exacerbated by similar infections. *Antibiotic Resistance Threats in the United States,* 2013, Centers for Disease Control, Atlanta, Georgia New antibiotics are needed to combat the current and future threat of multidrug resistant bacteria.

β-lactams are the most widely used antibiotics for treatment of serious bacterial infections. These include carbapenems, cephalosporins, penicillins, and monobactams. As has been observed for other antibiotic classes, resistance to β-lactams has emerged. For most Gram-negative bacteria, this resistance is primarily driven by the expression of β-lactamases, enzymes that hydrolyze β-lactam compounds. There are 4 different classes of β-lactamases (A, B, C, and D) capable of hydrolyzing overlapping but distinct subsets of β-lactams (Drawz and Bonomo, *Clin. Micro. Rev.,* 2010, 23:160-201). While the class B β-lactamases, also known as metallo β-lactamases (MBLs), are not the most prevalent β-lactamases found in the clinic, the frequency and distribution of their expression is on the rise and represent a significant medical threat because (i) MBLs have the ability to hydrolze all β-lactams except monobactams, and (ii) unlike the class A and C β-lactamases, there are no inhibitors available for the MBLs.

Aztreonam, a monobactam, was first approved in the U.S in 1986 for the treatment of aerobic Gram-negative bacterial infections and remains the only monobactam in use in the U.S. today. However, aztreonam has poor activity against *Pseudomonas* and *Acinetobacter* strains. Because monobactams are inherently resistant to hydrolysis by MBLs, several companies have begun developing novel monobactam compounds for the treatment of infections caused by Gram-negative bacteria. Monobactam compounds comprising a siderophore moiety are disclosed in WO 2007/065288, WO2012/073138, *J. Medicinal Chemistry* 56: 5541-5552 (2013), and *Bioorganic and Medicinal Chemstry Letters* 22:5989 (2012).

WO 2019/070492 discloseschromane monobactam compounds for treating bacterial infections. WO2017/106064 discloses biaryl monobactam compounds and their use to treat bacterial infections. WO 2013/110643 discloses novel amidine substituted monobactam derivatives and their use as antimicrobial reagents. WO 2015/103583 discloses monobactam derivatives useful for treating infectious disease which is bacterial infection. U.S. Patent Application Publication No US 2015/0045340 and No. US 2014/0275007 disclose oxamazin monobactams and their use as antibacterial agents. U.S. Patent Application Publication No. US 2015/0266867 discloses novel monobactam compounds for the use as antibacterial agents.

The need for new antibiotics to overcome multidrug resistance continues. Compounds disclosed in this invention are designed to fill this medical need, through administration either on their own or in combination with a suitable β-lactamase inhibitor.

SUMMARY OF THE INVENTION

The invention relates to the design and synthesis of monobactam analogs, a novel class of highly potent antibiotics effective against a broad range of Gram-negative bacteria. These compounds and their pharmaceutically acceptable salts may be useful as therapeutic agents for clinical treatment of various infections caused by Gram-negative bacteria, including strains that are multidrug resistant. The compounds can be used alone or in combination with a suitable p-lactamase inhibitor. The present invention includes the compounds of Formula I:

(I)

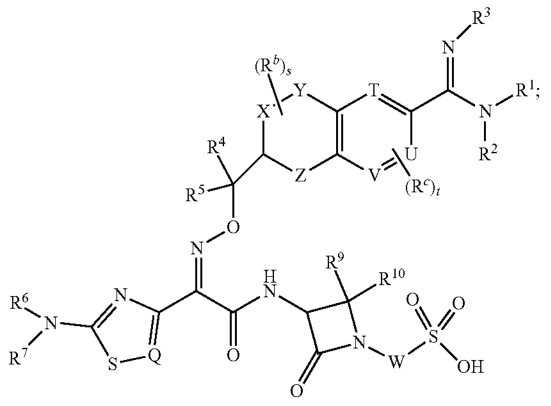

and pharmaceutically acceptable salts thereof.

The present invention also relates to a pharmaceutical composition for treating a bacterial infection in a subject, including infection with multidrug resistant Gram-negative bacterial strains, comprising a monobactam compound of structural formula I or a pharmaceutically acceptable salt thereof, and a pharmaceutically acceptable carrier, diluent or excipient.

The Compounds of Formula (I), also referred to herein as the "monobactam compounds", and pharmaceutically acceptable salts thereof can be useful, for example, for inhibiting the growth of Gram-negative bacterial strains, including but not limited to, *Pseudomonas, Klebsiella* and *Acinetobacter* strains, including *Pseudomonas aeruginosa, Klebsiella pneumoniae* and *Acinetobacter baumannii*, and/or for treating or preventing the clinical maifestations thereof in a patient.

The present invention is also directed to methods of treating Gram-negative bacterial infections in a subject in need of treatment thereof, comprising administering to the subject an effective amount of a monobactam compound of the invention. In specific embodiments of the invention, the method includes administration of a beta lactamase inhibitor compound. Embodiments, sub-embodiments and features of the present invention are either further described in or will be apparent from the ensuing description, examples and appended claims.

DETAILED DESCRIPTION OF THE INVENTION

The present invention is concerned with novel compounds of structural Formula I:

(I)

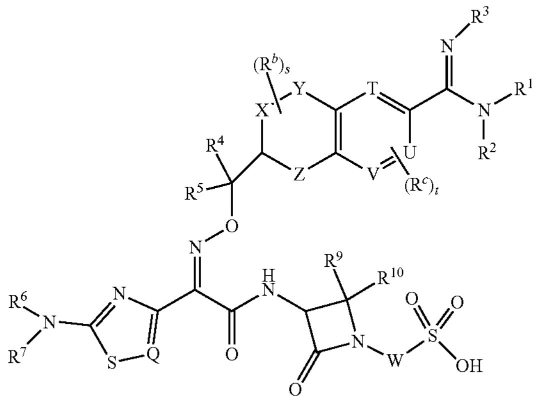

or a pharmaceutically acceptable salt thereof, wherein:

T is CH, or N, provided that no more than two of T, U and V are N;

U is CH, or N;

V is CH or N;

X is selected from the group consisting of

1) O, and

2) $CH_2$;

Y is selected from the group consisting of:

1) O,

2) $NR^8$,

3) S, and

4) $CH_2$, provided that when Y is O, $NR^8$ or S then X is not O;

Z is

1) O,

2) S,

3) $CH_2$, or

4 NH, provided that when Z is O, S or NH, then X is not O;

W is selected from the group consisting of:

1) bond, and

2) O;

Q is selected from the group consisting of:

1) N, and

2) $CR^8$;

$R^1$ is selected from the group consisting of:

1) —$C_{3-12}$cycloalkyl,

2) —$C_{3-12}$cycloalkenyl,

3) $C_{2-11}$cycloheteroalkyl,

4) $C_{2-11}$cycloheteroalkenyl, 5) aryl, and 6) heteroaryl, wherein alkyl, cycloalkyl, cycloalkenyl, cycloheteroalkyl, cycloheteroalkenyl, aryl and heteroaryl are unsubstituted or substituted with one to five substituents selected from $R^a$; $R^2$ is selected from the group consisting of:

1) hydrogen,

2) $C_{1-6}$alkyl,

3) $C_{1-6}$alkyl-$OR^4$, and

4) $C_{1-6}$alkyl-$NHR^4$, wherein alkyl is unsubstituted or substituted with one to three halogens;

$R^3$ is selected from the group consisting of:

1) hydrogen, and

2) OH;

$R^4$ is selected from the group consisting of:

1) hydrogen,

2) $C_{1-3}$alkyl, and

3) $C_3$cycloalkyl, wherein alkyl and cycloalkyl are unsubstituted or substituted with one to three halogens or $OC_{1-3}$alkyl;

$R^5$ is selected from the group consisting of:

1) —$CO_2H$, and 2) tetrazole;

$R^6$ and $R^7$ are selected from the group consisting of:

1) hydrogen, and

2) $C_{1-6}$alkyl, wherein alkyl is unsubstituted or substituted with one to three halogens, provided that at least one of $R^6$ and $R^7$ is hydrogen;

$R^8$ is independently selected from the group consisting of:

1) hydrogen,

2) $C_{1-4}$alkyl, 3) halogen, and

4) $C_{3-7}$cycloalkyl, wherein alkyl and cycloalkyl are unsubstituted or substituted with one to three substituents selected from: —OH, halogen, $NH_2$, and —$OC_{1-3}$alkyl;

$R^9$ and $R^{10}$ are selected from the group consisting of:

1) hydrogen, and

2) $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl, provided that one or both of $R^9$ and $R^{10}$ are $C_{1-6}$alkyl, or alternatively $R^9$ and $R^{10}$ together with the carbon to which they are attached form a monocyclic $C_{3-5}$cycloalkyl or a monocyclic $C_{2-5}$cycloheteroalkyl, wherein cycloalkyl and cycloheteroalkyl are unsubstituted or substituted with one to three substituents independently selected from halogen, —OH and —$OC_{1-3}$alkyl;

each $R^a$ is independently selected from the group consisting of:

1) halogen,

2) —$C_{1-6}$alkyl,

3) —$C_{0-6}$alkyl-O—$C_{1-6}$alkyl,

4) —$C_{0-6}$alkyl-OH,

5) —$C_{0-6}$alkyl $S(O)_jR^i$,

6) —$C_{0-6}$alkyl $S(O)_jNR^kR^l$,

7) —$C_{0-6}$alkyl $C(O)R^i$,

8) —$C_{0-6}$alkyl $OC(O)R^i$,

9) —$C_{0-6}$alkyl $C(O)OR^i$,

10) —$C_{0-6}$alkyl CN,

11) —$C_{0-6}$alkyl $C(O)NR^kR^l$,

12) —$C_{0-6}$alkyl $C(NH)NR^kR^l$,

13) —$C_{0-6}$alkyl$NR^kR^l$,

14) $-C_{0-6}$alkyl $N(R^k)(C(O)R^i)$,

15) $-C_{0-6}$alkyl $N(R^k)(C(O)OR^h)$,

16) $-C_{0-6}$alkyl $N(R^k)(C(O)NR^fR^g)$, and

17) $-C_{0-6}$alkyl $N(R^k)(S(O)_vR^j)$, wherein alkyl is unsubstituted or substituted with one to three substituents selected from: halogen, OH, $-OC_{1-3}$alkyl, $-C_{1-3}$alkyl, $-CO_2C_{1-3}$alkyl, $-C(O)NH_2$, $-C_{0-6}$alkylNH$_2$, and $-C_{0-6}$alkylNH($C_{1-3}$alkyl);

each $R^b$ is independently selected from the group consisting of:

1) hydrogen,

2) $C_{1-6}$alkyl,

3) $C_{0-6}$alkyl-O—$C_{1-6}$alkyl,

4) $C_{0-6}$alkyl-OH,

5) $C_{0-6}$alkyl-$S(O)_uR^d$,

6) $C_{1-6}$alkyl-C(O—$N(R^e)_2$,

7) $C_{1-6}$alkyl$N(R^e)C(O)R^e$,

8) $C_{0-6}$alkyl-$N(R^e)_2$, and 9) halogen, wherein alkyl is unsubstituted or substituted with one to three halogens, or wherein two $R^b$ substituents together with the atoms they are attached to can cyclize to form a 3 to 6 membered ring;

each $R^e$ is independently selected from the group consisting of:

1) hydrogen,

2) $C_{1-6}$alkyl,

3) $C_{0-6}$alkyl-O—$C_{1-6}$alkyl,

4) $C_{0-6}$alkyl-OH,

5) $C_{0-6}$alkyl-$S(O)_vR^f$,

6) $C_{0-6}$alkyl-$S(O)_vN(R^g)_2$,

7) $C_{1-6}$alkyl C(O)—$N(R^g)_2$,

8) $C_{1-6}$alkyl$N(R^g)C(O)R^g$,

9) $C_{0-6}$alkyl-$N(R^g)_2$, and 10) halogen, wherein alkyl is unsubstituted or substituted with one to three halogens;

each $R^d$ is independently selected from the group consisting of:

1) hydrogen, and

2) $-C_{1-6}$alkyl, wherein each alkyl is unsubstituted or substituted with one to three halogens;

each $R^f$ is independently selected from the group consisting of:

1) hydrogen, and

2) $-C_{1-6}$alkyl, wherein each alkyl is unsubstituted or substituted with one to three halogens;

each $R^g$ is independently selected from the group consisting of:

1) hydrogen, and

2) $-C_{1-6}$alkyl, wherein each alkyl is unsubstituted or substituted with one to three halogens;

each $R^g$ is independently selected from the group consisting of:

1) hydrogen, and

2) $-C_{1-6}$ alkyl, wherein each alkyl is unsubstituted or substituted with one to three halogens;

each $R^h$ is independently selected from the group consisting of:

1) hydrogen, and

2) $-C_{1-6}$ alkyl, wherein each alkyl is unsubstituted or substituted with one to three halogens;

each $R^i$ is $-C_{1-6}$ alkyl, wherein each alkyl is unsubstituted or substituted with one to three halogens;

each $R^j$ is independently selected from the group consisting of:

1) hydrogen,

2) OH, and

3) $-C_{1-6}$ alkyl, wherein each alkyl is unsubstituted or substituted with one to three halogens;

each $R^k$ is independently selected from the group consisting of:

1) hydrogen,

2) —C1-6 alkyl, wherein each alkyl is unsubstituted or substituted with one to three halogens;

each $R^l$ is independently selected from the group consisting of:

1) hydrogen,

2) —C1-6 alkyl, wherein each alkyl is unsubstituted or substituted with one to three halogens;

each r is independently 0, 1 or 2;

each s is independently 0, 1, 2, 3, 4 or 5;

each t is independently 0, 1, 2 or 3;

each u is independently selected from 0, 1 or 2; and each v is independently selected from 0, 1 or 2.

The invention relates to novel monobactam analogs, a class of highly potent antibiotics effective against a broad range of Gram-negative bacteria. These compounds have utility as therapeutic agents for clinical treatment of various infections caused by Gram-negative bacteria, including strains that are multidrug resistant, and for the treatment or prevention of the clinical pathologies associated therewith.

In each of the various embodiments of the compounds of the invention described herein, each variable including those of Formula (I), and the various embodiments thereof, is selected independently of the others unless otherwise indicated.

The present invention includes the compounds of Formula (I), and the individual diastereoisomers, enantiomers, and epimers of the compounds of Formula (I), and mixtures of diastereoisomers and/or enantiomers thereof including racemic mixtures. The present invention also encompasses any solvates, hydrates, stereoisomers, and tautomers of the compounds of Formula (I), and of any pharmaceutically acceptable salts thereof.

In one embodiment of the present invention, T is CH or N, provided that no more than two of T, U and V are N; U is CH or N; and V═CH or N.

In another embodiment of the present invention, T is CH or N, provided that no more than two of T, U and V are N. In a class of this embodiment, T is CH or N. In another class of this embodiment, T is CH. In another class of this embodiment, T is N.

In another embodiment of the present invention, U is CH or N. In a class of this embodiment, U is CH. In another class of this embodiment, U is N.

In another embodiment of the present invention, V═CH or N. In a class of this embodiment, V is CH. In another class of this embodiment, V is N.

In another embodiment of the present invention, T, U and V are CH.

In another embodiment of the present invention, W is a bond or O. In a class of this embodiment, W is a bond. In another class of this embodiment, W is O.

In another embodiment of the present invention, Q is N or $CR^8$. In a class of this embodiment, Q is N. In another class of this embodiment, Q is $CR^8$.

In another embodiment of the present invention, X is O or $CH_2$. In a class of this embodiment, X is O. In another class of this embodiment, X is $CH_2$.

In another embodiment, Y is O, $NR^8$, S or $CH_2$, provided that when Y is O, $NR^8$ or S, then X is not O. In another embodiment, Y is O, $NR^8$, S or $CH_2$, provided that when Y is Y is O, $NR^8$ or S, then X is $CH_2$.

In another embodiment, Y is O, $NR^8$, S or $CH_2$. In a class of this embodiment, Y is O or $CH_2$. In another class of this embodiment, Y is $NR^8$ or S. In another class of this embodiment, Y is O. In another class of this embodiment, Y is $NR^8$. In another class of this embodiment, Y is S.

In another class of this embodiment, Y is $CH_2$.

In another embodiment, Z is O, S, $CH_2$ or NH, provided that when Z is O, S or NH, then X is not O. In a class of this embodiment, Z is O, S, $CH_2$, or NH. In another class of this embodiment, Z is O or $CH_2$. In another class of this embodiment, Z is S or NH. In another class of this embodiment, Z is S. In another class of this embodiment, Z is $CH_2$. In another class of this embodiment, Z is NH. In another class of this embodiment, Z is O.

In another embodiment of the present invention, $R^1$ is selected from $R^1$ is selected from the group consisting of: —$C_{3-9}$cycloalkyl, —$C_{2-8}$cycloheteroalkyl, $C_{2-8}$cycloheteroalkenyl, aryl, and heteroaryl, wherein cycloalkyl, cycloalkenyl, cycloheteroalkyl, cycloheteroalkenyl, aryl and heteroaryl are unsubstituted or substituted with one to five substituents selected from $R^a$.

In another embodiment of the present invention, $R^1$ is selected from the group consisting of: —$C_{3-9}$cycloalkyl, $C_{2-7}$cycloheteroalkyl, aryl, and heteroaryl, wherein cycloalkyl, cycloheteroalkyl, aryl and heteroaryl are unsubstituted or substituted with one to five substituents selected from $R^a$.

In another embodiment of the present invention, $R^1$ is selected from the group consisting of: —$C_{3-9}$cycloalkyl, $C_{2-8}$cycloheteroalkyl, and aryl, wherein cycloalkyl, cycloheteroalkyl, and aryl and are unsubstituted or substituted with one to five substituents selected from $R^a$. In a class of this embodiment, $R^1$ is selected from the group consisting of: cyclopropane, cyclobutane, cyclopentane, cyclohexane, cycloheptane, bicyclo[1.1.1]pentane, bicyclo[3.1.1]heptane, bicyclo[4.1.0]heptane, bicyclo[2.2.2]octane, spiro[3.3]heptane, spiro[3.5]nonane, spiro[2.3]hexane, azetidine, pyrrolidine, piperidine, azepane, 2-oxabicyclo[2.1.1]hexane, 3-azabicyclo[3.1.0]hexane, 3-azabicyclo[3.2.1]octane, 8-azabicyclo[3.2.1]octane, 2-azaspiro[3.5]nonane, 2-azaspiro[3.3]heptane, 3-azabicyclo[3.2.0]heptane, 1-azaspiro[3.3]heptane, 6-azaspiro[3.5]nonane, 7-azaspiro[3.5]nonane, 6-azaspiro[3.4]octane, and phenyl, wherein $R^1$ is unsubstituted or substituted with one to five substituents selected from $R^a$. In another embodiment of the present invention, $R^1$ is aryl, wherein aryl is unsubstituted or substituted with one to five substituents selected from $R^a$. In a class of this embodiment, $R^1$ is phenyl, wherein phenyl is unsubstituted or substituted with one to five substituents selected from $R^a$.

In another embodiment of the present invention, $R^1$ is selected from the group consisting of: —$C_{3-9}$cycloalkyl, and $C_{2-8}$cycloheteroalkyl, wherein cycloalkyl, and cycloheteroalkyl are unsubstituted or substituted with one to five substituents selected from $R^a$. In a class of this embodiment, $R^1$ is selected from the group consisting of: cyclopropane, cyclobutane, cyclopentane, cyclohexane, cycloheptane, bicyclo[1.1.1]pentane, bicyclo[3.1.1]heptane, bicyclo[4.1.0]heptane, bicyclo[2.2.2]octane, spiro[3.3]heptane, spiro[3.5]nonane, spiro[2.3]hexane, azetidine, pyrrolidine, piperidine, azepane, 2-oxabicyclo[2.1.1]hexane, 3-azabicyclo[3.1.0]hexane, 3-azabicyclo[3.2.1]octane, 8-azabicyclo[3.2.1]octane, 2-azaspiro[3.5]nonane, 2-azaspiro[3.3]heptane, 3-azabicyclo[3.2.0]heptane, 1-azaspiro[3.3]heptane, 6-azaspiro[3.5]nonane, 7-azaspiro[3.5]nonane, and 6-azaspiro[3.4]octane, wherein $R^1$ is unsubstituted or substituted with one to five substituents selected from $R^a$. In another class of this embodiment, In a class of this embodiment, $R^1$ is selected from the group consisting of: cyclobutane, cyclohexane, cycloheptane, bicyclo[4.1.0]heptane, piperidine, and azepane, wherein $R^1$ is unsubstituted or substituted with one to five substituents selected from $R^a$.

In another embodiment of the present invention, $R^1$ is selected from the group consisting of: —$C_{3-9}$cycloalkyl, wherein cycloalkyl is unsubstituted or substituted with one to five substituents selected from $R^a$. In a class of this embodiment, $R^1$ is selected from the group consisting of: cyclopropane, cyclobutane, cyclopentane, cyclohexane, cycloheptane, bicyclo[1.1.1]pentane, bicyclo[3.1.1]heptane, bicyclo[4.1.0]heptane, bicyclo[2.2.2]octane, spiro[3.3]heptane, spiro[3.5]nonane, and spiro[2.3]hexane, wherein $R^1$ is unsubstituted or substituted with one to five substituents selected from $R^a$. In another 4 class of this embodiment, $R^1$ is selected from the group consisting of: cyclobutane, cyclohexane, cycloheptane, and bicyclo[4.1.0]heptane, wherein $R^1$ is unsubstituted or substituted with one to five substituents selected from $R^a$. In another class of this embodiment, $R^1$ is cyclobutane, wherein $R^1$ is unsubstituted or substituted with one to five substituents selected from $R^a$. In another class of this embodiment, $R^1$ is cyclohexane, wherein $R^1$ is unsubstituted or substituted with one to five substituents selected from $R^a$. In another class of this embodiment, $R^1$ is bicyclo[4.1.0]heptane, wherein $R^1$ is unsubstituted or substituted with one to five substituents selected from $R^a$. In another class of this embodiment, $R^1$ is cycloheptane, wherein $R^1$ is unsubstituted or substituted with one to five substituents selected from $R^a$.

In another embodiment of the present invention, $R^1$ is $C_{2-7}$cycloheteroalkyl, wherein cycloheteroalkyl is unsubstituted or substituted with one to five substituents selected from $R^a$. In a class of this embodiment, $R^1$ is selected from the group consisting of: azetidine, pyrrolidine, piperidine, azepane, 2-oxabicyclo[2.1.1]hexane, 3-azabicyclo[3.1.0]-hexane, 3-azabicyclo[3.2.1]octane, 8-azabicyclo[3.2.1]octane, 2-azaspiro[3.5]nonane, 2-azaspiro[3.3]heptane, 3-azabicyclo[3.2.0]heptane, 1-azaspiro[3.3]heptane, 6-azaspiro-[3.5]nonane, 7-azaspiro[3.5]nonane, and 6-azaspiro[3.4]octane, wherein $R^1$ is unsubstituted or substituted with one to five substituents selected from $R^a$. In another class of this embodiment, $R^1$ is selected from the group consisting of: piperidine and azepane, wherein $R^1$ is unsubstituted or substituted with one to five substituents selected from $R^a$. In another class of this embodiment, $R^1$ is piperidine, wherein $R^1$ is unsubstituted or substituted with one to five substituents selected from $R^a$. In another class of this embodiment, $R^1$ is azepane, wherein $R^1$ is unsubstituted or substituted with one to five substituents selected from $R^a$.

In another embodiment of the present invention, $R^2$ is selected from the group consisting of: hydrogen, —$C_{1-6}$alkyl, —$C_{1-6}$alkyl-$OR^4$, and —$C_{1-6}$alkyl-$NHR^4$, wherein alkyl is unsubstituted or substituted with one to three halogens. In a class of this embodiment, $R^2$ is selected from the group consisting of: hydrogen and $C_{1-6}$alkyl, wherein alkyl is unsubstituted or substituted with one to three halogens. In another class of this embodiment, $R^2$ is $C_{1-3}$alkyl, wherein alkyl is unsubstituted or substituted with one to three halogens. In another class of this embodiment, $R^2$ is $C_{1-3}$alkyl. In another class of this embodiment, $R^2$ is hydrogen.

In another embodiment of the present invention, $R^3$ is selected from the group consisting of: hydrogen, and OH. In a class of this embodiment, $R^3$ is OH. In another class of this embodiment, $R^3$ is hydrogen.

In another embodiment of the present invention, $R^4$ is selected from the group consisting of: hydrogen, —$C_{1-3}$alkyl, and $C_3$cycloalkyl, wherein alkyl and cycloalkyl are unsubstituted or substituted with one to three halogens or $OC_{1-3}$alkyl. In a class of this embodiment, $R^4$ is selected from the group consisting of: hydrogen, $CH_3$, and cyclopropane, wherein methyl and cyclopropane are unsubstituted or substituted with one to three halogens or $OC_{1-3}$alkyl. In another class of this embodiment, $R^4$ is selected from the group consisting of: hydrogen, $CH_3$, and cyclopropane.

In another embodiment of the present invention, $R^4$ is selected from the group consisting of: hydrogen, and $C_{1-3}$alkyl, wherein alkyl is unsubstituted or substituted with one to three halogens or $OC_{1-3}$alkyl. In a class of this embodiment, $R^4$ is selected from the group consisting of: hydrogen, and $C_{1-3}$alkyl. In another class of this embodiment, $R^4$ is hydrogen. In another class of this embodiment, $R^4$ is $C_{1-3}$alkyl, wherein alkyl is unsubstituted or substituted with one to three halogens or $OC_{1-3}$alkyl. In another class of this embodiment, $R^4$ is $C_{1-3}$alkyl. In a subclass of this class, $R^4$ is —$CH_3$.

In another class of the present invention, $R^4$ is selected from the group consisting of: $C_{1-3}$alkyl, and $C_3$cycloalkyl, wherein alkyl and cycloalkyl are unsubstituted or substituted with one to three halogens or $OC_{1-3}$alkyl. In a class of this embodiment, $R^4$ is selected from the group consisting of: $C_{1-3}$alkyl, and $C_3$cycloalkyl.

In another class of the present invention, $R^4$ is cyclopropyl, wherein cyclopropyl is unsubstituted or substituted with one to three halogens or $OC_{1-3}$alkyl.

In another class of the present invention, $R^4$ is $C_{1-3}$alkyl, wherein alkyl is unsubstituted or substituted with one to three halogens or $OC_{1-3}$alkyl. In a class of this embodiment, $R^4$ is $C_{1-3}$alkyl.

In another embodiment of the present invention, $R^5$ is selected from the group consisting of: —$CO_2H$, and tetrazole. In a class of this embodiment, $R^5$ is tetrazole. In another class of this embodiment, $R^5$ is —$CO_2H$.

In another embodiment of the present invention, $R^6$ and $R^7$ are selected from the group consisting of: hydrogen, and $C_{1-6}$alkyl, wherein alkyl is unsubstituted or substituted with one to three halogens, provided that at least one of $R^6$ and $R^7$ is hydrogen.

In another embodiment, $R^6$ is independently selected from the group consisting of: hydrogen, and $C_{1-6}$alkyl, wherein alkyl is unsubstituted or substituted with one to three halogens, provided that at least one of $R^6$ and $R^7$ is hydrogen.

In another embodiment, $R^6$ is independently selected from the group consisting of: hydrogen, and $C_{1-6}$alkyl, wherein alkyl is unsubstituted or substituted with one to three halogens. In a class of this embodiment, $R^6$ is $C_{1-6}$alkyl, wherein alkyl is unsubstituted or substituted with one to three halogens. In another class of this embodiment, $R^6$ is $C_{1-6}$alkyl. In another class of this embodiment, $R^6$ is hydrogen.

In another embodiment, $R^7$ is independently selected from the group consisting of: hydrogen, and $C_{1-6}$alkyl, wherein alkyl is unsubstituted or substituted with one to three halogens, provided that at least one of $R^6$ and $R^7$ is hydrogen.

In another embodiment, $R^7$ is independently selected from the group consisting of: hydrogen, and $C_{1-6}$alkyl, wherein alkyl is unsubstituted or substituted with one to three halogens. In a class of this embodiment, $R^7$ is $C_{1-6}$alkyl, wherein alkyl is unsubstituted or substituted with one to three halogens. In another class of this embodiment, $R^7$ is $C_{1-6}$alkyl. In another class of this embodiment, $R^7$ is hydrogen.

In another embodiment of the present invention, $R^8$ is independently selected from the group consisting of: hydrogen, $C_{1-4}$alkyl, halogen, and $C_3$-$C_7$cycloalkyl, wherein alkyl and cycloalkyl are unsubstituted or substituted with one to three substituents selected from: —OH, halogen, $NH_2$, and —$OC_{1-3}$alkyl. In a class of this embodiment, $R^8$ is independently selected from the group consisting of: hydrogen, $C_{1-4}$alkyl, and halogen, wherein $C_1$-$C_4$ alkyl is unsubstituted or substituted with one to three substituents selected from: —OH, halogen, $NH_2$, and —$OC_{1-3}$alkyl. In another class of this embodiment, $R^8$ is independently selected from the group consisting of: hydrogen, and $C_{1-4}$alkyl, wherein $C_1$-$C_4$ alkyl is unsubstituted or substituted with one to three substituents selected from: —OH, halogen, $NH_2$, and —$OC_{1-3}$alkyl. In another class of this embodiment, $R^8$ is $C_{1-4}$alkyl, wherein $C_1$-$C_4$ alkyl is unsubstituted or substituted with one to three substituents selected from: —OH, halogen, $NH_2$, and —$OC_{1-3}$alkyl. In another class of this embodiment, $R^8$ is independently selected from the group consisting of: hydrogen, and $C_{1-4}$alkyl, In another class of this embodiment, $R^8$ is hydrogen.

In another embodiment of the present invention, $R^9$ and $R^{10}$ are selected from the group consisting of: hydrogen, and $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl, provided that one or both of $R^9$ and $R^{10}$ are $C_{1-6}$alkyl, or alternatively $R^9$ and $R^{10}$ together with the carbon to which they are attached form a monocyclic $C_{3-5}$cycloalkyl or a monocyclic $C_{2-5}$cycloheteroalkyl, wherein cycloalkyl and cycloheteroalkyl are unsubstituted or substituted with one to three substituents independently selected from halogen, —OH and —$OC_{1-3}$alkyl. In a class of this embodiment, $R^9$ and $R^{10}$ are selected from the group consisting of: hydrogen, and $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl, provided that one or both of $R^9$ and $R^{10}$ are $C_{1-6}$alkyl. In another class of this embodiment, $R^9$ and $R^{10}$ are selected from the group consisting of: hydrogen, —$CH_3$, and —$CH_2CH_3$. In another class of this embodiment, $R^9$ and $R^{10}$ are selected from $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, or $SC_{1-3}$alkyl, provided that one or both of $R^9$ and $R^{10}$ are $C_{1-6}$alkyl. In another class of this embodiment, $R^9$ and $R^{10}$ are selected from $C_{1-6}$alkyl. In another class of this embodiment, $R^9$ and $R^{10}$ are selected from: —$CH_3$ and —$CH_2CH_3$. In another class of this embodiment, $R^9$ and $R^{10}$ are each —$CH_2CH_3$. In another class of this embodiment, $R^9$ and $R^{10}$ are each —$CH_3$.

In another embodiment of the present invention, $R^9$ is independently $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl, or alternatively $R^9$ and $R^{10}$ together with the carbon to which they are attached form a monocyclic $C_{3-5}$cycloalkyl or a monocyclic $C_{2-5}$cycloheteroalkyl, wherein cycloalkyl and cycloheteroalkyl are unsubstituted or substituted with one to three substituents independently selected from halogen, —OH and —$OC_{1-3}$alkyl. In another class of this embodiment, $R^9$ is independently selected from the group consisting of: $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl.

In another class of this embodiment, $R^9$ is independently selected from the group consisting of: $C_{1-6}$alkyl. In another class of this embodiment, $R^9$ is independently selected from the group consisting of: —$CH_3$, and —$CH_2CH_3$. In another class of this embodiment, $R^9$ is —$CH_2CH_3$. In another class of this embodiment, $R^9$ is —$CH_3$.

In another embodiment of the present invention, $R^{10}$ is independently $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl, or alternatively $R^9$ and $R^{10}$ together with the carbon to which they are attached form a monocyclic $C_{3-5}$cycloalkyl or a monocyclic $C_{2-5}$cycloheteroalkyl, wherein cycloalkyl and cycloheteroalkyl are unsubstituted or substituted with one to three substituents independently selected from halogen, —OH and —$OC_{1-3}$alkyl. In another class of this embodiment, $R^{10}$ is independently selected from the group consisting of: $C_{1-6}$alkyl, wherein alkyl is unsubstituted or substituted with one to three substituents selected from: halogen, OH, —$OC_{1-3}$alkyl, —$NHC(O)C_{1-3}$alkyl, —$C(O)NHC_{1-3}$alkyl, $NHC_{1-3}$alkyl, and $SC_{1-3}$alkyl.

In another class of this embodiment, $R^{10}$ is independently selected from the group consisting of: $C_{1-6}$alkyl. In another class of this embodiment, $R^{10}$ is independently selected from the group consisting of: —$CH_3$, and —$CH_2CH_3$. In another class of this embodiment, $R^{10}$ is —$CH_2CH_3$. In another class of this embodiment, $R^{10}$ is —$CH_3$.

In another embodiment of the present invention, each $R^a$ is independently selected from the group consisting of: halogen, —$C_{1-6}$alkyl, —$C_{0-6}$alkyl-O—$C_{1-6}$alkyl, —$C_{0-6}$alkyl-OH, —$C_{0-6}$alkyl $S(O)_rR^j$, —$C_{0-6}$alkyl $S(O)_rNR^kR^l$, —$C_{0-6}$alkyl $C(O)R^i$, —$C_{0-6}$alkyl $OC(O)R^i$, —$C_6$alkyl $C(O)OR^i$, —$C_{0-6}$alkyl CN, —$C_{0-6}$alkyl $C(O)NR^kR^l$, —$C_{0-6}$alkyl $C(NH)NR^kR^l$, —$C_{0-6}$alkylNR$^k$R$^l$, —$C_{0-6}$alkyl $N(R^k)(C(O)R^i)$, —$C_{0-6}$alkyl $N(R^k)(C(O)OR^h)$, —$C_{0-6}$alkyl $N(R^k)(C(O)NR^fR^g)$, and —$C_{0-6}$alkyl $N(R^k)(S(O)_vR^j)$, wherein alkyl is unsubstituted or substituted with one to three substituents selected from: halogen, OH, —$OC_{1-3}$alkyl, —$C_{1-3}^{alkyl}$, —$CO_2C_{1-3}$alkyl, —$C(O)NH_2$, —$C_{0-6}$alkyl$NH_2$, and —$C_{0-6}$alkylNH($C_{1-3}$alkyl).

In another embodiment of the present invention, each $R^a$ is independently selected from the group consisting of: halogen, —$C_{1-6}$alkyl, —$C_{0-6}$alkyl-O—$C_{1-6}$alkyl, —$C_{0-6}$alkyl-OH, and —$C_{0-6}$alkylNR$^k$R$^l$, wherein alkyl is unsubstituted or substituted with one to three substituents selected from: halogen, OH, —$OC_{1-3}$alkyl, —$C_{1-3}$alkyl, —$CO_2C_{1-3}$alkyl, —$C(O)NH_2$, —$C_{0-6}$alkylNH$_2$, and —$C_{0-6}$alkylNH($C_{1-3}$alkyl). In a class of this embodiment, each $R^a$ is independently selected from the group consisting of: halogen, —$C_{1-6}$alkyl, —$C_{0-6}$alkyl-O—$C_{1-6}$alkyl, —$C_{0-6}$alkyl-OH, and —$C_{0-6}$alkylNR$^k$R$^l$, wherein alkyl is unsubstituted or substituted with one to three substituents selected from: halogen, OH, —$OC_{1-3}$alkyl, and —$C_{1-3}$alkyl. In another class of this embodiment, each $R^a$ is independently selected from the group consisting of: F, —$CH_3$, —$OCH_3$, —$CH_2OCH_3$, —$(CH_2)_2OCH_3$, —OH, —$CH_2OH$, —$(CH_2)_2OH$, —$(CH_2)_3OH$, —$CH(OH)CH_2OH$, —$CH_2CH(OH)CH_2OH$, —$NH_2$, —$CH_2NH_2$, —$(CH_2)_2NH_2$, —$C(CH_3)_2NH_2$, —$(CH_2)_3NH_2$, —$NH(CH_3)$, —$CH_2NH(CH_3)$, and —$CH_2CH(OH)CH_2NH_2$.

In another embodiment of the present invention, each $R^a$ is halogen. In a class of this embodiment, each $R^a$ is F.

In another embodiment of the present invention, each $R^a$ is independently selected from the group consisting of: —$C_{0-6}$alkyl-O—$C_{1-6}$alkyl, wherein alkyl is unsubstituted or substituted with one to three substituents selected from: halogen, OH, and —$C_{1-3}$alkyl. In a class of this embodiment, each $R^a$ is independently selected from the group consisting of: —$OCH_3$, —$CH_2OCH_3$, and —$(CH_2)_2OCH_3$.

In another embodiment of the present invention, each $R^a$ is independently selected from the group consisting of: —$C_{1-6}$alkyl, —$C_{0-6}$alkyl-OH, and —$C_{0-6}$alkylNR$^k$R$^l$, wherein alkyl is unsubstituted or substituted with one to three substituents selected from: halogen, OH, —$OC_{1-3}$alkyl, —$C_{1-3}$alkyl, —$CO_2C_{1-3}$alkyl, —$C(O)NH_2$, —$C_{0-6}$alkylNH$_2$, and —$C_{0-6}$alkylNH($C_{1-3}$alkyl). In a class of this embodiment, each $R^a$ is independently selected from the group consisting of: —$C_{1-6}$alkyl, —$C_{0-6}$alkyl-OH, and —$C_{0-6}$alkylNR$^k$R$^l$, wherein alkyl is unsubstituted or substituted with one to three substituents selected from: halogen, OH, and —$C_{1-3}$alkyl. In another class of this embodiment, each $R^a$ is independently selected from the group consisting of: —$CH_3$, —OH, —$CH_2OH$, —$(CH_2)_2OH$, —$(CH_2)_3OH$, —$CH(OH)CH_2OH$, —$CH_2CH(OH)CH_2OH$, —$NH_2$, —$CH_2NH_2$, —$(CH_2)_2NH_2$, —$C(CH_3)_2NH_2$, —$(CH_2)_3NH_2$, —$NH(CH_3)$, —$CH_2NH(CH_3)$, and —$CH_2CH(OH)$ $CH_2NH_2$. In another class of this embodiment, each $R^a$ is independently selected from the group consisting of: —$CH_3$, —OH, —$NH_2$, —$CH_2NH_2$, and —$CH_2CH(OH)CH_2NH_2$.

In another embodiment of the present invention, each $R^a$ is independently selected from the group consisting of: —$C_{1-6}$alkyl, wherein alkyl is unsubstituted or substituted with one to three substituents selected from: halogen, OH, —$OC_{1-3}$alkyl, and —$C_{1-3}$alkyl. In a class of this embodiment, each $R^a$ is —$CH_3$.

In another embodiment of the present invention, each $R^a$ is —$C_{0-6}$alkyl-OH, wherein alkyl is unsubstituted or substituted with one to three substituents selected from: halogen, OH, —$OC_{1-3}$alkyl, and —$C_{1-3}$alkyl. In a class of this embodiment, each $R^a$ is independently selected from the group consisting of: —OH, —$CH_2OH$, —$(CH_2)_2OH$, —$(CH_2)_3OH$, —$CH(OH)CH_2OH$, and —$CH_2CH(OH)$ $CH_2OH$.

In another embodiment of the present invention, each $R^a$ is —$C_{0-6}$alkylNR$^k$R$^l$, wherein alkyl is unsubstituted or substituted with one to three substituents selected from: halogen, OH, —$OC_{1-3}$alkyl, and —$C_{1-3}$alkyl. In a class of this embodiment, each $R^a$ is independently selected from the group consisting of: —$NH_2$, —$CH_2NH_2$, —$(CH_2)_2NH_2$, —$C(CH_3)_2NH_2$, —$(CH_2)_3NH_2$, —$NH(CH_3)$, —$CH_2NH(CH_3)$, and —$CH_2CH(OH)CH_2NH_2$.

In another embodiment of the present invention, each $R^b$ is independently selected from the group consisting of: hydrogen, —$C_{1-6}$alkyl, —$C_{0-6}$alkyl-O—$C_{1-6}$alkyl, —$C_{0-6}$alkyl-OH, —$C_{0-6}$alkyl-S(O)$_uR^d$, —$C_{1-6}$alkyl-C(O—N(R$^e$)$_2$, —$C_{1-6}$alkylN(R$^e$)C(O)R$^e$, —$C_{0-6}$alkyl-N(R$^e$)$_2$, and halogen, wherein alkyl is unsubstituted or substituted with one to three halogens, and wherein two $R^b$ substituents together with the atoms they are attached to can cyclize to form a monocyclic $C_{3-6}$cycloalkyl or a monocyclic $C_{2-6}$cycloheteroalkyl ring.

In another embodiment of the present invention, each $R^b$ is independently selected from the group consisting of: hydrogen, —$C_{1-6}$alkyl, —$C_{0-6}$alkyl-O—$C_{1-6}$alkyl, —$C_{0-6}$alkyl-OH, and halogen, wherein alkyl is unsubstituted or substituted with one to three halogens, and wherein two $R^b$ substituents together with the atoms they are attached to can cyclize to form a monocyclic $C_{3-6}$cycloalkyl or a monocyclic $C_{2-6}$cycloheteroalkyl ring.

In another embodiment of the present invention, each $R^b$ is independently selected from the group consisting of: hydrogen, —$C_{1-6}$alkyl, —$C_{0-6}$alkyl-O—$C_{1-6}$alkyl, —$C_{0-6}$alkyl-OH, and halogen, wherein alkyl is unsubstituted or substituted with one to three halogens, and wherein two $R^b$ substituents together with the atoms they are attached to can cyclize to form a monocyclic $C_{3-6}$cycloalkyl or a monocyclic $C_{2-6}$cycloheteroalkyl ring.

In another embodiment of the present invention, each $R^b$ is independently selected from the group consisting of: hydrogen, $C_{1-6}$alkyl, and halogen, wherein alkyl is unsubstituted or substituted with one to three halogens, and wherein two $R^b$ substituents together with the atoms they are attached to can cyclize to form a 3 to 6 membered ring. In a class of this embodiment, each $R^b$ is independently selected from the group consisting of: hydrogen, and —$C_{1-6}$alkyl, wherein alkyl is unsubstituted or substituted with one to three halogens, and wherein two $R^b$ substituents together with the atoms they are attached to can cyclize to form a 3 to 6 membered ring. In another class of embodiment, each $R^b$ is $C_{1-6}$alkyl, wherein alkyl is unsubstituted or substituted with one to three halogens, and wherein two $R^b$ substituents together with the atoms they are attached to can cyclize to form a 3 to 6 membered ring. In another class of this embodiment, each $R^b$ is $C_{1-6}$alkyl, wherein alkyl is unsubstituted or substituted with one to three halogens. In another class of this embodiment, each $R^b$ is hydrogen.

In another embodiment of the present invention, each $R^e$ is independently selected from the group consisting of: hydrogen, —$C_{1-6}$alkyl, —$C_{0-6}$alkyl-O—$C_{1-6}$alkyl, —$C_{0-6}$alkyl-OH, —$C_{0-6}$alkyl-$S(O)_vR^f$, —$C_{0-6}$alkyl-$S(O)_vN(R^g)_2$, —$C_{1-6}$alkyl C(O)—$N(R^g)_2$, —$C_{1-6}$alkyl$N(R^g)C(O)R^g$, —$C_{0-6}$alkyl-$N(R^g)_2$, and halogen, wherein alkyl is unsubstituted or substituted with one to three halogens.

In another embodiment of the present invention, each $R^e$ is independently selected from the group consisting of: hydrogen, —$C_{1-6}$alkyl, —$C_{0-6}$alkyl-O—$C_{1-6}$alkyl, —$C_{0-6}$alkyl-OH, and halogen, wherein alkyl is unsubstituted or substituted with one to three halogens.

In another embodiment of the present invention, each $R^e$ is independently selected from the group consisting of: hydrogen, —$C_{1-6}$alkyl, —$C_{0-6}$alkyl-O—$C_{1-6}$alkyl, and halogen, wherein alkyl is unsubstituted or substituted with one to three halogens. In a class of this embodiment, each $R^e$ is independently selected from the group consisting of: hydrogen, —$C_{1-6}$alkyl, —O—$C_{1-6}$alkyl, and halogen, wherein alkyl is unsubstituted or substituted with one to three halogens.

In another embodiment of the present invention, each $R^e$ is independently selected from the group consisting of: hydrogen, —$C_{1-6}$alkyl, and —$C_{0-6}$alkyl-O—$C_{1-6}$alkyl, wherein alkyl is unsubstituted or substituted with one to three halogens. In a class of this embodiment, each $R^e$ is independently selected from the group consisting of: hydrogen, —$C_{1-6}$alkyl, and —O—$C_{1-6}$alkyl, wherein alkyl is unsubstituted or substituted with one to three halogens. In another class of this embodiment, each $R^e$ is independently selected from the group consisting of: hydrogen, —$CH_3$, and —$OCH_3$.

In another embodiment of the present invention, each $R^e$ is independently selected from the group consisting of: $C_{1-6}$alkyl, and $C_{0-6}$alkyl-O—$C_{1-6}$alkyl, wherein alkyl is unsubstituted or substituted with one to three halogens. In a class of this embodiment, each $R^e$ is independently selected from the group consisting of: $C_{1-6}$alkyl, and —O—$C_{1-6}$alkyl, wherein alkyl is unsubstituted or substituted with one to three halogens. In another class of this embodiment, each $R^e$ is independently selected from the group consisting of: —$CH_3$, and —$OCH_3$.

In another embodiment of the present invention, each $R^e$ is $C_{1-6}$alkyl, wherein alkyl is unsubstituted or substituted with one to three halogens. In a class of this embodiment, each $R^e$ is —$CH_3$.

In another embodiment of the present invention, $R^d$ is independently selected from the group consisting of: hydrogen, and —$C_{1-6}$ alkyl, wherein each alkyl is unsubstituted or substituted with one to three halogens. In a class of this embodiment, $R^d$ is —$C_{1-6}$alkyl, wherein each alkyl is unsubstituted or substituted with one to three halogens. In another class of this embodiment, $R^d$ is hydrogen.

In another embodiment of the present invention, $R^e$ is independently selected from the group consisting of: hydrogen, and —$C_{1-6}$ alkyl, wherein each alkyl is unsubstituted or substituted with one to three halogens. In a class of this embodiment, $R^e$ is —$C_{1-6}$alkyl, wherein each alkyl is unsubstituted or substituted with one to three halogens. In another class of this embodiment, $R^e$ is hydrogen.

In another embodiment of the present invention, $R^f$ is independently selected from the group consisting of: hydrogen, and —$C_{1-6}$alkyl, wherein each alkyl is unsubstituted or substituted with one to three halogens. In a class of this embodiment, $R^f$ is —$C_{1-6}$alkyl, wherein each alkyl is unsubstituted or substituted with one to three halogens. In another class of this embodiment, $R^f$ is hydrogen.

In another embodiment of the present invention, $R^g$ is independently selected from the group consisting of: hydrogen, and —$C_{1-6}$ alkyl, wherein each alkyl is unsubstituted or substituted with one to three halogens. In a class of this embodiment, $R^g$ is —$C_{1-6}$alkyl, wherein each alkyl is unsubstituted or substituted with one to three halogens. In another class of this embodiment, $R^g$ is hydrogen.

In another embodiment of the present invention, $R^h$ is independently selected from the group consisting of: hydrogen, and —$C_{1-6}$alkyl, wherein each alkyl is unsubstituted or substituted with one to three halogens. In a class of this embodiment, $R^h$ is —$C_{1-6}$alkyl, wherein each alkyl is unsubstituted or substituted with one to three halogens. In another class of this embodiment, $R^h$ is hydrogen.

In another embodiment of the present invention, each $R^i$ is —$C_{1-6}$alkyl, wherein each alkyl is unsubstituted or substituted with one to three halogens. In a class of this embodiment, each $R^i$ is —$C_{1-6}$alkyl. In another class of this embodiment, each $R^i$ is —$CH_3$.

In another embodiment of the present invention, $R^j$ is independently selected from the group consisting of: hydrogen, OH and —$C_{1-6}$alkyl, wherein each alkyl is unsubstituted or substituted with one to three halogens. In a class of this embodiment, $R^j$ is independently selected from the group consisting of: hydrogen, and —$C_{1-6}$ alkyl, wherein each alkyl is unsubstituted or substituted with one to three halogens. In another class of this embodiment, $R^j$ is hydrogen or OH. In another class of this embodiment, $R^j$ is OH. In another class of this embodiment, $R^j$ is hydrogen. In another class of this embodiment, $R^j$ is $—C_{1-6}$alkyl, wherein each alkyl is unsubstituted or substituted with one to three halogens.

In another embodiment of the present invention, $R^k$ is independently selected from the group consisting of: hydrogen, and $—C_{1-6}$alkyl, wherein each alkyl is unsubstituted or substituted with one to three halogens. In a class of this embodiment, $R^k$ is $—C_{1-6}$alkyl, wherein each alkyl is unsubstituted or substituted with one to three halogens. In another class of this embodiment, $R^k$ is hydrogen.

In another embodiment of the present invention, $R^l$ is independently selected from the group consisting of: hydrogen, and $—C_{1-6}$alkyl, wherein each alkyl is unsubstituted or substituted with one to three halogens. In a class of this embodiment, $R^l$ is $—C_{1-6}$alkyl, wherein each alkyl is unsubstituted or substituted with one to three halogens. In another class of this embodiment, $R^l$ is hydrogen.

In another embodiment of the present invention, each r is independently 0, 1, or 2. In a class of this embodiment, r is O or 1. In another class of this embodiment, r is 1 or 2. In another class of this embodiment, r is O or 2. In another class of this embodiment, r is 0. In another class of this embodiment, r is 1. In another class of this embodiment, r is 2.

In another embodiment of the present invention, each s is independently 0, 1, 2, 3, 4 or 5. In a class of this embodiment, each s is independently 0, 1, 2, 3 or 4. In another class of this embodiment, each s is independently 0, 1, 2, or 3. In another class of this embodiment, each s is independently 1, 2, or 3. In another class of this embodiment, each s is independently 1 or 3. In another class of this embodiment, s is O or 1. In another class of this embodiment, s is 1 or 2. In another class of this embodiment, s is O or 2. In another class of this embodiment, s is 0. In another class of this embodiment, s is 1. In another class of this embodiment, s is 2. In another class of this embodiment, s is 3. In another class of this embodiment, s is 4. In another class of this embodiment, s is 5.

In another embodiment of the present invention, each t is independently 0, 1, 2, or 3. In a class of this embodiment, t is 0, 1, or 2. In another class of this embodiment, t is O or 1. In another class of this embodiment, t is 1 or 2. In another class of this embodiment, t is O or 2. In another class of this embodiment, t is 0. In another class of this embodiment, t is 1. In another class of this embodiment, t is 2. In another class of this embodiment, t is 3.

In another embodiment of the present invention, each u is independently 0, 1, or 2. In a class of this embodiment, u is O or 1. In another class of this embodiment, u is 1 or 2. In another class of this embodiment, u is O or 2. In another class of this embodiment, u is 0. In another class of this embodiment, u is 1. In another class of this embodiment, u is 2.

In another embodiment of the present invention, each v is independently 0, 1, or 2. In a class of this embodiment, v is O or 1. In another class of this embodiment, v is 1 or 2. In another class of this embodiment, v is O or 2. In another class of this embodiment, v is 0. In another class of this embodiment, v is 1. In another class of this embodiment, v is 2.

In another embodiment of the present invention, the invention relates to compounds of structural formula Ia:

Ia

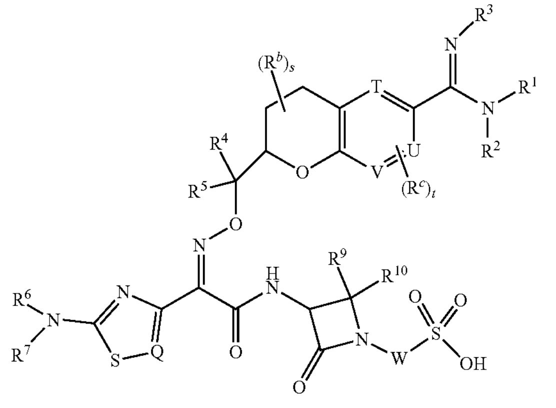

or a pharmaceutically acceptable salt thereof.

In another embodiment of the present invention, the invention relates to compounds of structural formula Ib:

Ib

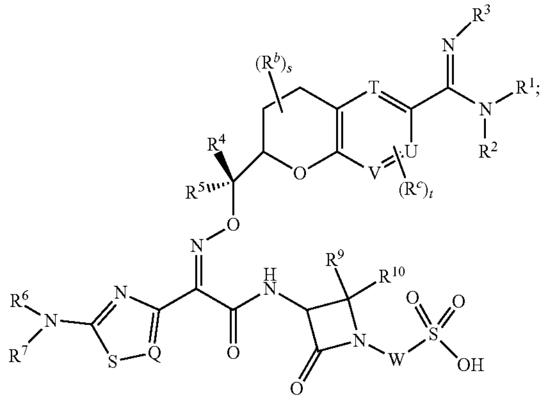

or a pharmaceutically acceptable salt thereof.

In another embodiment of the present invention, the invention relates to compounds of structural formula Ic:

Ic

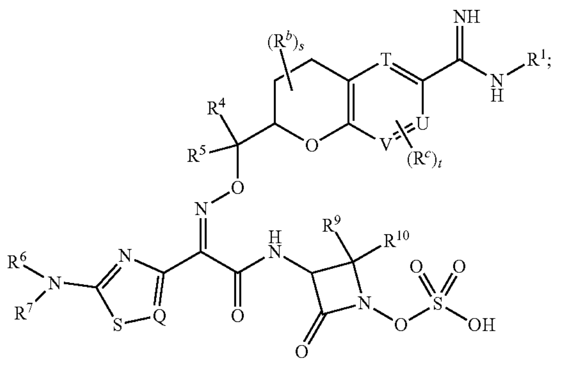

or a pharmaceutically acceptable salt thereof.

In another embodiment of the present invention, the invention relates to compounds of structural formula Id:

Id

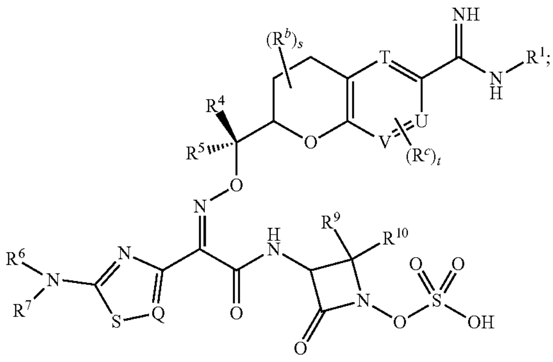

or a pharmaceutically acceptable salt thereof.

In another embodiment of the present invention, the invention relates to compounds of structural formula Ie:

Ie

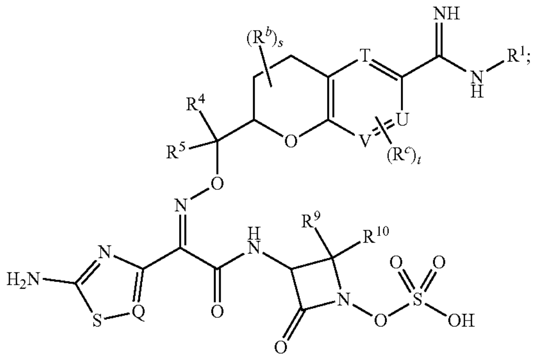

or a pharmaceutically acceptable salt thereof.

In another embodiment of the present invention, the invention relates to compounds of structural formula If:

If

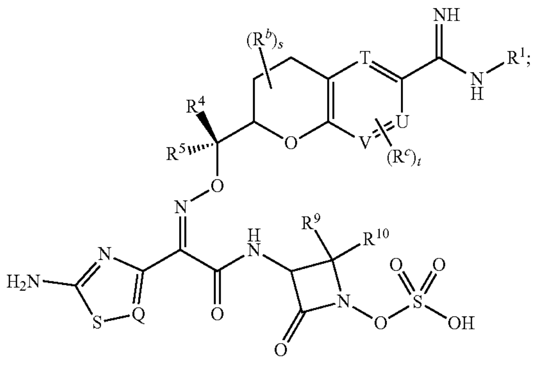

or a pharmaceutically acceptable salt thereof.

In another embodiment of the present invention, the invention relates to compounds of structural formula Ig:

Ig

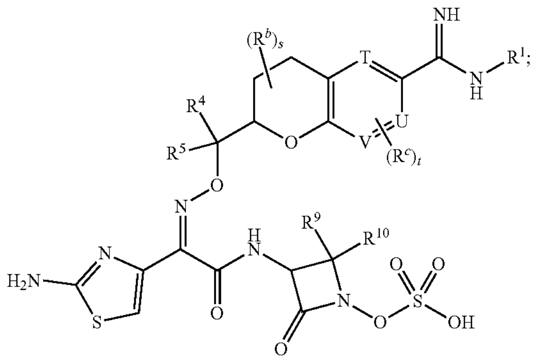

or a pharmaceutically acceptable salt thereof.

In another embodiment of the present invention, the invention relates to compounds of structural formula Ih:

Ih

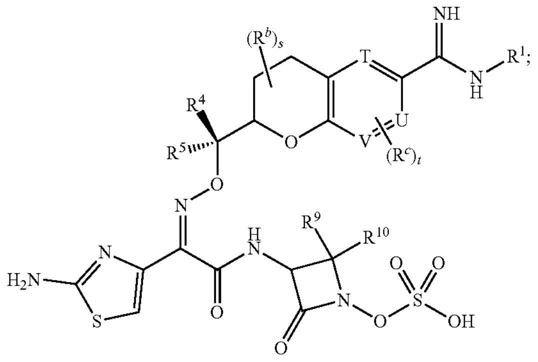

or a pharmaceutically acceptable salt thereof.

In another embodiment of the present invention, the invention relates to compounds of structural formula Ii:

Ii

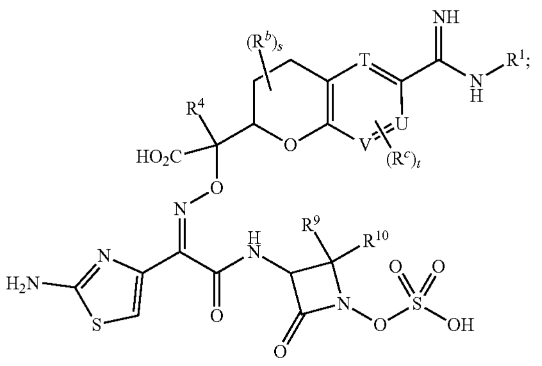

or a pharmaceutically acceptable salt thereof.

In another embodiment of the present invention, the invention relates to compounds of structural formula Ij:

Ij

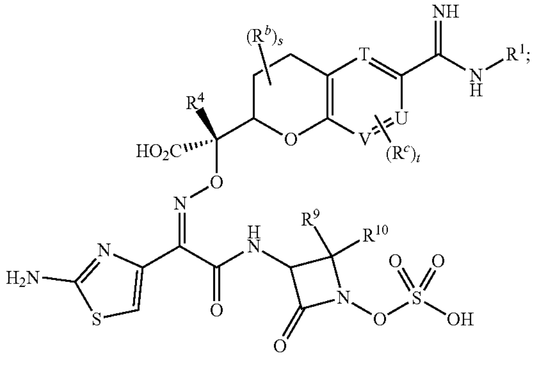

or a pharmaceutically acceptable salt thereof.

In another embodiment of the present invention, the invention relates to compounds of structural formula Ik:

Ik

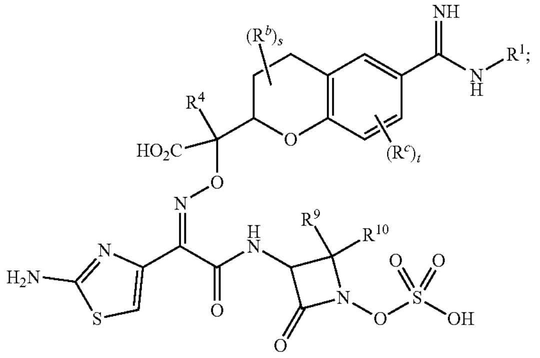

or a pharmaceutically acceptable salt thereof.

In another embodiment of the present invention, the invention relates to compounds of structural formula Il:

Il

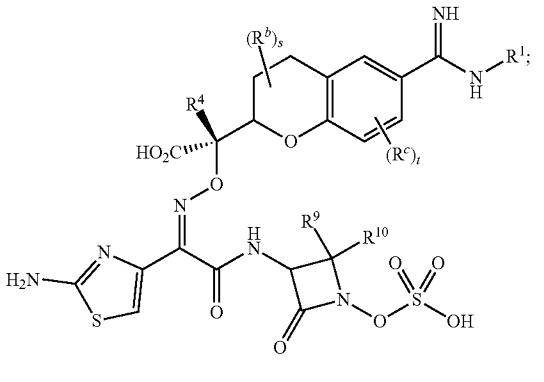

or a pharmaceutically acceptable salt thereof.

In another embodiment of the present invention, the invention relates to compounds of structural formula Im:

Im

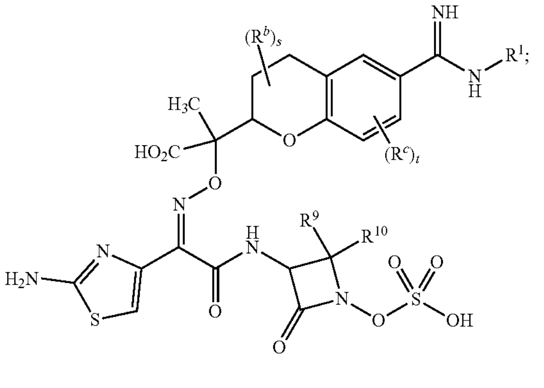

or a pharmaceutically acceptable salt thereof.

In another embodiment of the present invention, the invention relates to compounds of structural formula In:

In

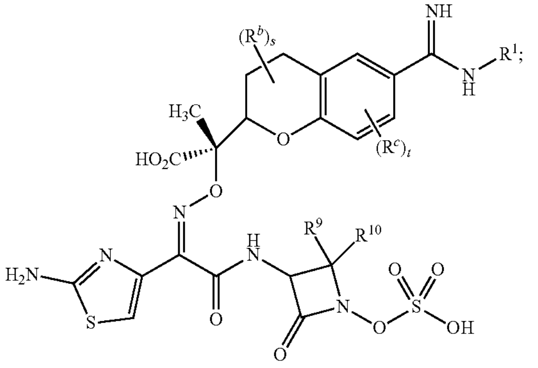

or a pharmaceutically acceptable salt thereof.

The compound of structural formula I includes the compounds of structural formulas Ia, Ib, Ic, Id, Ie, If, Ig, Ih, Ii, Ij, Ik, Il, Im and In, and pharmaceutically acceptable salts, hydrates and solvates thereof.

Another embodiment of the present invention relates to compounds of structural formula I wherein:

T is CH;
U is CH;
V is CH;
X is $CH_2$;
Y is O or $CH_2$;
Z is O or $CH_2$;
W is bond or O;
Q is $CR^8$;
$R^1$ is selected from the group consisting of:
1) $-C_{3-9}$cycloalkyl,
2) $-C_{2-8}$cycloheteroalkyl,
3) aryl, and
4) heteroaryl, wherein cycloalkyl, cycloheteroalkyl, aryl and heteroaryl are unsubstituted or substituted with one to five substituents selected from $R^a$;

$R^2$ is hydrogen;
$R^3$ is hydrogen;

$R^4$ is selected from the group consisting of:
1) $C_{1-3}$alkyl, and
2) $C_3$cycloalkyl,
wherein alkyl and cycloalkyl are unsubstituted or substituted with one to three substituents selected from: halogen and $OC_{1-3}$alkyl;
$R^5$ is —$CO_2H$ or tetrazole;
$R^6$ is hydrogen;
$R^7$ is hydrogen;
$R^8$ is hydrogen;
$R^9$ is $C_{1-6}$alkyl;
$R^{10}$ is $C_{1-6}$alkyl; and
$R^a$, $R^b$, $R^c$, $R^d$, $R^e$, $R^f$, $R^g$, $R^h$, $R^i$, $R^j$, $R^k$, $R^l$, r, s, t, u, and v are as defined above; or a pharmaceutically acceptable salt thereof.

Another embodiment of the present invention relates to compounds of structural formula I wherein:
T is CH;
U is CH;
V is CH;
X is $CH_2$;
Y is $CH_2$;
Z is O;
W is O;
Q is $CR^8$;
$R^1$ is selected from the group consisting of:
1) —$C_{3-9}$cycloalkyl,
2) —$C_{2-8}$cycloheteroalkyl, and
3) aryl,
wherein cycloalkyl, cycloheteroalkyl, and aryl are unsubstituted or substituted with one to five substituents selected from $R^a$;
$R^2$ is hydrogen;
$R^3$ is hydrogen;
$R^4$ is $C_{1-3}$alkyl;
$R^5$ is —$CO_2H$;
$R^6$ is hydrogen;
$R^7$ is hydrogen;
$R^8$ is hydrogen;
$R^9$ is $C_{1-6}$alkyl;
$R^{10}$ is $C_{1-6}$alkyl; and
$R^a$, $R^b$, $R^c$, $R^d$, $R^e$, $R^f$, $R^g$, $R^h$, $R^i$, $R^j$, $R^k$, $R^l$, r, s, t, u, and v are as defined above;
or a pharmaceutically acceptable salt thereof.

Another embodiment of the present invention relates to compounds of structural formula I wherein:
T is CH;
U is CH;
V is CH;
X is $CH_2$;
Y is $CH_2$;
Z is O;
W is O;
Q is $CR^8$;
$R^1$ is selected from the group consisting of:
1) —$C_{3-9}$cycloalkyl, and
2) —$C_{2-8}$cycloheteroalkyl,
wherein cycloalkyl, and cycloheteroalkyl are unsubstituted or substituted with one to five substituents selected from $R^a$;
$R^2$ is hydrogen;
$R^3$ is hydrogen;
R is $C_{1-3}$alkyl;
$R^5$ is —$CO_2H$;
$R^6$ is hydrogen;
$R^7$ is hydrogen;
$R^8$ is hydrogen;
$R^9$ is $C_{1-6}$alkyl;
$R^{10}$ is $C_{1-6}$alkyl; and
$R^a$, $R^b$, $R^c$, $R^d$, $R^e$, $R^f$, $R^g$, $R^h$, $R^i$, $R^j$, $R^k$, $R^l$, r, s, t, u, and v are as defined above; or a pharmaceutically acceptable salt thereof.

Illustrative, but non-limiting, examples of the compounds of the present invention are the following compounds:
1) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-pyrrolidin-3-yl)carbamimidoyl)-chroman-2-yl)propanoic acid;
2) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-pyrrolidin-3-yl)-carbamimidoyl)-chroman-2-yl)propanoic acid;
3) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3S,5R)-5-(hydroxymethyl)-pyrrolidin-3-yl)carbamimidoyl)chroman-2-yl) propanoic acid;
4) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3R,5R)-5-(hydroxymethyl)pyrrolidin-3-yl)carbamimidoyl)chroman-2-yl) propanoic acid;
5) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-azepan-4-yl)carbamimidoyl)chroman-2-yl)propanoic acid;
6) (S)-2-((R)-6-(N-((1s,4S)-4-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxo-ethylidene)amino)oxy)propanoic acid;
7) (S)-2-((R)-6-(N-((1s,3S)-3-aminocyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;
8) (S)-2-((R)-6-(N-((1r,3R)-3-aminocyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;
9) (S)-2-((R)-6-(N-(3-(aminomethyl)bicyclo[1.1.1]pentan-1-yl)carbamimidoyl)-chroman-2-yl)-2-((((Z)-1-(2-aminothiazol-4-yl)-2-(((S)-2,2-dimethyl-4-oxo-1-(sulfooxy) azetidin-3-yl)amino)-2-oxoethylidene)amino)oxy) propanoic acid;
10) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-azepan-3-yl)carbamimidoyl)-chroman-2-yl)propanoic acid;
11) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-azepan-3-yl)carbamimidoyl)-chroman-2-yl)propanoic acid;
12) (S)-2-((R)-6-(N-(1-(aminomethyl)-2-oxabicyclo[2.1.1]hexan-4-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy) propanoic acid;
13) (S)-2-((R)-6-(N-(2-azaspiro[3.5]nonan-7-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;
14) (S)-2-((R)-6-(N-(2-azaspiro[3.3]heptan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

15) (S)-2-((R)-6-(N-(5-aminobicyclo[3.1.1]heptan-1-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

16) (2S)-2-((2R)-6-(N-((1S,5R)-3-azabicyclo[3.2.0]heptan-6-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

17) (S)-2-((R)-6-(N-((4R,6s)-1-azaspiro[3.3]heptan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

18) (S)-2-((R)-6-(N-((4S,6r)-1-azaspiro[3.3]heptan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

19) (S)-2-((R)-6-(N-((2s,4R)-6-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

20) (S)-2-((R)-6-(N-((2r,4S)-6-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

21) (S)-2-((R)-6-(N-(7-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

22) (S)-2-((R)-6-(N-((2r,4S)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

23) (S)-2-((R)-6-(N-((2s,4R)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

24) (S)-2-((R)-6-(N-((1S,2R,5R,6R)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

25) (S)-2-((R)-6-(N-((1R,2R,5S,6S)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

26) (S)-2-((R)-6-(N-((1S,2S,5R,6R)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

27) (S)-2-((R)-6-(N-((1R,2S,5S,6S)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

28) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(piperidin-4-yl)carbamimidoyl)chroman-2-yl)propanoic acid;

29) (S)-2-((R)-6-(N-(1-((R)-3-amino-2-hydroxypropyl)piperidin-4-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

30) (S)-2-((R)-6-(N-(1-((S)-3-amino-2-hydroxypropyl)piperidin-4-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

31) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-azepan-4-yl)carbamimidoyl)chroman-2-yl)propanoic acid;

32) (S)-2-((R)-6-(N-((1r,4R)-4-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

33) (S)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)-2-((R)-6-(N-((3R,5S)-5-(hydroxymethyl)pyrrolidin-3-yl)carbamimidoyl)chroman-2-yl)propanoic acid;

34) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1r,4R)-4-(methylamino)cyclohexyl)-carbamimidoyl)chroman-2-yl)propanoic acid;

35) (S)-2-((R)-6-(N-(4-aminobicyclo[2.2.2]octan-1-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

36) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(azetidin-3-yl)carbamimidoyl)chroman-2-yl)propanoic acid;

37) (S)-2-((R)-6-(N-((1R,5S,6s)-3-azabicyclo[3.1.0]hexan-6-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

38) (S)-2-((R)-6-(N-(4-(aminomethyl)phenyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

39) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-piperidin-3-yl)carbamimidoyl)-chroman-2-yl)propanoic acid;

40) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-piperidin-3-yl)carbamimidoyl)-chroman-2-yl)propanoic acid;

41) (S)-2-((R)-6-(N-((1s,4S)-4-(aminomethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

42) (S)-2-((R)-6-(N-((1r,4R)-4-(aminomethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

43) (S)-2-((R)-6-(N-((2s,4R)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

44) (S)-2-((R)-6-(N-((2r,4S)-6-azaspiro[3.4]octan-2-yl)carbamimidoyl)chroman-2-yl)-2-((((Z)-1-(2-aminothiazol- 4-yl)-2-(((S)-2,2-dimethyl-4-oxo-1-(sulfooxy)azetidin-3-yl)amino)-2-oxoethylidene)amino)oxy)propanoic acid;

45) (S)-2-((R)-6-(N-((1R,3S)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

46) (S)-2-((R)-6-(N-((1S,3R)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

47) (S)-2-((R)-6-(N-((1S,3S)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

48) (S)-2-((R)-6-(N-((1R,3R)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid);

49) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-3,3-dimethylpiperidin-4-yl)carbamimidoyl)chroman-2-yl)propanoic acid;

50) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-3,3-dimethylpiperidin-4-yl)carbamimidoyl)chroman-2-yl)propanoic acid;

51) (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((3R,4S)-3-(hydroxymethyl)-piperidin-4-yl)carbamimidoyl)chroman-2-yl)propanoic acid;

52) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3S,4R)-3-(hydroxymethyl)-piperidin-4-yl)carbamimidoyl)chroman-2-yl)propanoic acid;

53) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2S,4S)-2-(hydroxymethyl)-piperidin-4-yl)carbamimidoyl)chroman-2-yl)propanoic acid;

54) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2R,4R)-2-(hydroxymethyl)-piperidin-4-yl)carbamimidoyl)chroman-2-yl)propanoic acid;

55) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2R,4R)-2-methylpiperidin-4-yl)carbamimidoyl)chroman-2-yl)propanoic acid;

56) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2S,4S)-2-methylpiperidin-4-yl)carbamimidoyl)chroman-2-yl)propanoic acid;

57) (S)-2-((R)-6-(N-((1r,4R)-4-amino-4-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

58) (S)-2-((R)-6-(N-((1s,4S)-4-amino-4-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

59) (S)-2-((R)-6-(N-((1s,4S)-4-(aminomethyl)-4-hydroxycyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

60) (S)-2-((R)-6-(N-((1r,4R)-4-(aminomethyl)-4-hydroxycyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

61) (S)-2-((R)-6-(N-((2R,4r,6R)-6-aminospiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

62) (S)-2-((R)-6-(N-((2S,4s,6S)-6-aminospiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

63) (S)-2-((R)-6-(N-((1s,4S)-4-amino-4-(2-methoxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

64) (S)-2-((R)-6-(N-((1r,4R)-4-amino-4-(2-methoxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

65) (S)-2-((R)-6-(N-((1s,4S)-4-amino-4-(2-hydroxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

66) (S)-2-((R)-6-(N-((1r,4R)-4-amino-4-(2-hydroxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

67) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(trans-3-(methylamino)cyclobutyl)-carbamimidoyl)chroman-2-yl)propanoic acid;

68) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(cis-3-(methylamino)cyclobutyl)-carbamimidoyl)chroman-2-yl)propanoic acid;

69) (S)-2-((R)-6-(N-((1r,4R)-4-amino-4-(hydroxymethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

70) (S)-2-((R)-6-(N-((1s,4S)-4-amino-4-(hydroxymethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

71) (S)-2-((R)-6-(N-((1r,4R)-4-amino-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

72) (S)-2-((R)-6-(N-((1s,4S)-4-amino-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

73) (S)-2-((R)-6-(N-((1s,4S)-4-(aminomethyl)-4-methoxy-cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

74) (S)-2-((R)-6-(N-((1r,3R)-3-amino-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

75) (S)-2-((R)-6-(N-((1s,3S)-3-amino-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

76) (S)-2-((R)-6-(N-((1R,5S,8s)-3-azabicyclo[3.2.1]octan-8-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

77) (S)-2-((R)-6-(N-((1R,5S,8r)-3-azabicyclo[3.2.1]octan-8-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

78) (S)-2-((R)-6-(N-((1r,3R)-3-(aminomethyl)-3-(hydroxymethyl)cyclobutyl)-carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)-oxy)propanoic acid;

79) (S)-2-((R)-6-(N-((1s,3S)-3-(aminomethyl)-3-(hydroxymethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

80) (S)-2-((R)-6-(N-((1s,3S)-3-(aminomethyl)-3-hydroxy-cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

81) (S)-2-((R)-6-(N-((1r,3R)-3-(aminomethyl)-3-hydroxy-cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

82) (S)-2-((R)-6-(N-((1r,3R)-3-(aminomethyl)-3-methoxy-cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

83) (S)-2-((R)-6-(N-((1s,3S)-3-(aminomethyl)-3-methoxy-cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

84) (S)-2-((R)-6-(N-((1r,3R)-3-amino-1-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

85) (S)-2-((R)-6-(N-((1s,3S)-3-amino-1-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

86) (S)-2-((R)-6-(N-((1s,3S)-3-amino-3-(2-hydroxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

87) (S)-2-((R)-6-(N-((1r,3R)-3-amino-3-(2-hydroxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

88) (S)-2-((R)-6-(N-((1r,3R)-3-amino-3-(hydroxymethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

89) (S)-2-((R)-6-(N-((1s,3S)-3-amino-3-(hydroxymethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

90) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1r,3R)-3-(hydroxymethyl)-3-(methylamino)cyclobutyl)carbamimidoyl)chroman-2-yl)propanoic acid;

91) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1s,3S)-3-(hydroxymethyl)-3-(methylamino)cyclobutyl)carbamimidoyl)chroman-2-yl)propanoic acid;

92) (S)-2-((R)-6-(N-((1r,3R)-3-amino-3-(2-methoxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

93) (S)-2-((R)-6-(N-((1s,3S)-3-amino-3-(2-methoxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

94) (S)-2-((R)-6-(N-((1S,3R)-3-amino-3-((S)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

95) (S)-2-((R)-6-(N-((1R,3R)-3-amino-3-((R)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

96) (S)-2-((R)-6-(N-((1R,3S)-3-amino-3-((S)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

97) (S)-2-((R)-6-(N-((1S,3S)-3-amino-3-((R)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

98) (S)-2-((R)-6-(N-((1S,3R)-3-amino-3-((S)-1,2-dihydroxyethyl)cyclobutyl)-carbamimidoyl)chroman-2-yl)-2-

((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

99) (S)-2-((R)-6-(N-((1R,3R)-3-amino-3-((R)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

100) (S)-2-((R)-6-(N-((1S,3S)-3-amino-3-((R)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

101) (S)-2-((R)-6-(N-((1R,3S)-3-amino-3-((S)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

102) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1s,4S)-4-((methylamino)methyl)-cyclohexyl)carbamimidoyl)chroman-2-yl)propanoic acid;

103) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1r,4R)-4-((methylamino)methyl)cyclohexyl)carbamimidoyl)chroman-2-yl)propanoic acid;

104) (S)-2-((R)-6-(N-((1R,4S)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

105) (S)-2-((R)-6-(N-((1R,4R)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

106) (S)-2-((R)-6-(N-((1S,4S)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

107) (S)-2-((R)-6-(N-((1S,4R)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

108) (S)-2-((R)-6-(N-((1R,3R)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

109) (S)-2-((R)-6-(N-((1S,3S)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

110) (S)-2-((R)-6-(N-((1R,3S)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

111) (S)-2-((R)-6-(N-((1S,3R)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

112) (S)-2-((R)-6-(N-((1s,3S)-3-(aminomethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

113) (S)-2-((R)-6-(N-((1r,3R)-3-(aminomethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

114) (S)-2-((R)-6-(N-((1S,3S)-3-amino-2,2-dimethylcyclobutyl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

115) (S)-2-((R)-6-(N-((2S,4s,7S)-2-aminospiro[3.5]nonan-7-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

116) (S)-2-((R)-6-(N-((2R,4r,7R)-2-aminospiro[3.5]nonan-7-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

117) (S)-2-((R)-6-(N-((1s,3S)-3-(aminomethyl)-3-methylcyclobutyl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

118) (S)-2-((R)-6-(N-((1r,3R)-3-(aminomethyl)-3-methylcyclobutyl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

119) (S)-2-((R)-6-(N-(6-(aminomethyl)-6-fluorospiro[3.3]heptan-2-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

120) (S)-2-((R)-6-(N-((1R,3S)-3-(aminomethyl)-2,2-dimethylcyclobutyl)-carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

121) (2S)-2-((2R)-6-(N-(6-(aminomethyl)spiro[3.3]heptan-2-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

122) (2S)-2-((2R)-6-(N-((1S)-1-aminospiro[2.3]hexan-5-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

123) (2S)-2-((2R)-6-(N-((1R)-1-aminospiro[2.3]hexan-5-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

124) (S)-2-((R)-6-(N-((1s,3S)-3-aminocyclobutyl)carbamimidoyl)-5-(methoxymethyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

125) (S)-2-((R)-6-(N-((1s,3S)-3-aminocyclobutyl)carbamimidoyl)-7-(methoxymethyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

126) (S)-2-((R)-6-(N-((1s,4S)-4-amino-1-(methoxymethyl)cyclohexyl)-carbamimidoyl)-chroman-2-yl)-2-((((Z)-1-

(2-aminothiazol-4-yl)-2-(((S)-2,2-dimethyl-4-oxo-1-(sulfooxy)-azetidin-3-yl)amino)-2-oxoethylidene)amino)oxy)propanoic acid;

127) (S)-2-((R)-6-(N-((1r,4R)-4-amino-1-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

128) (S)-2-((R)-6-(N-((1s,4S)-4-amino-4-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

129) (S)-2-((R)-6-(N-((1r,4R)-4-amino-4-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

130) (S)-2-((R)-6-(N-((1s,4S)-4-(aminomethyl)-1-methylcyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

131) (S)-2-((R)-6-(N-((1r,4R)-4-(aminomethyl)-1-methylcyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

132) (S)-2-((R)-6-(N-((1s,4S)-4-(2-aminopropan-2-yl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

133) (S)-2-((R)-6-(N-((1r,4R)-4-(2-aminopropan-2-yl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

134) (S)-2-((R)-6-(N-((1s,3S)-3-aminocyclobutyl)carbamimidoyl)-7-methylchroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

135) (S)-2-((R)-6-(N-((1r,4R)-4-amino-4-(hydroxymethyl)-1-methylcyclohexyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

136) (S)-2-((R)-6-(N-((1R,3r,5S)-8-azabicyclo[3.2.1]octan-3-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

137) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3S,5S)-5-(hydroxymethyl)pyrrolidin-3-yl)carbamimidoyl)chroman-2-yl)propanoic acid;

138) (S)-2-((R)-6-(N-(1-(2-aminoethyl)cyclopropyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

139) (S)-2-((R)-6-(N-(1-(3-aminopropyl)cyclopropyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid; and 140) (S)-2-((R)-6-(N-(1-(2-aminoethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

and pharmaceutically acceptable salts thereof.

Illustrative, but non-limiting, examples of the compounds of the present invention are the following compounds:

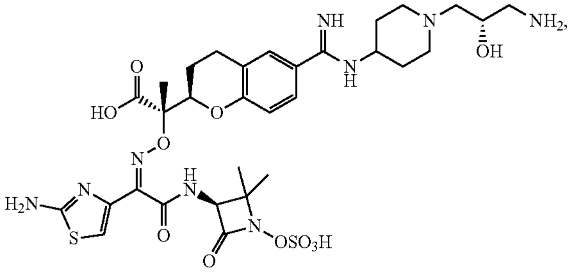

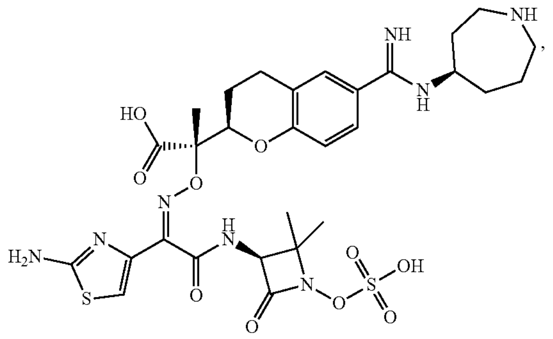

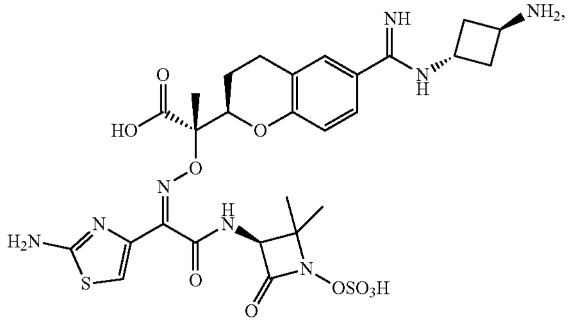

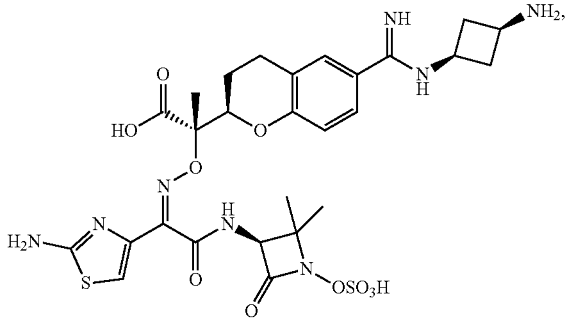

-continued

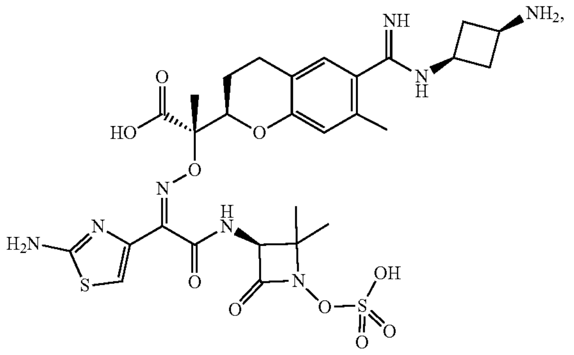

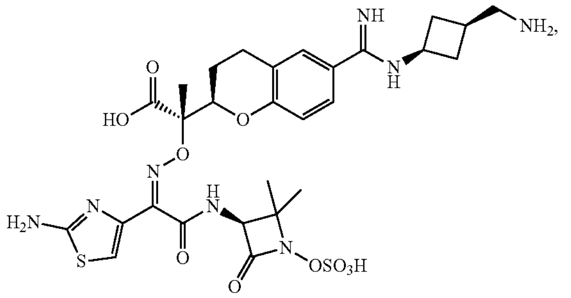

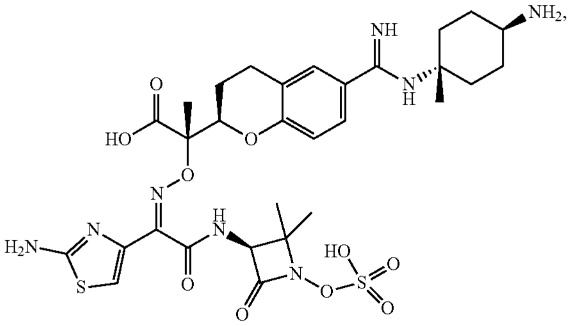

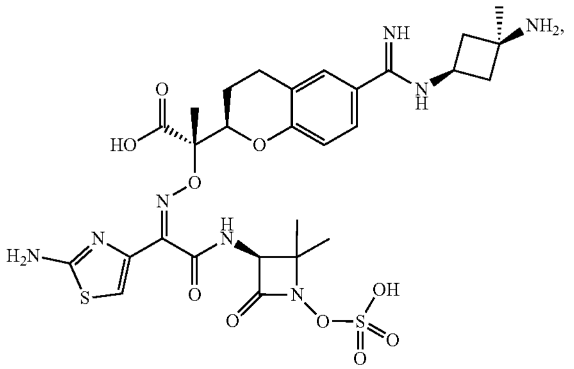

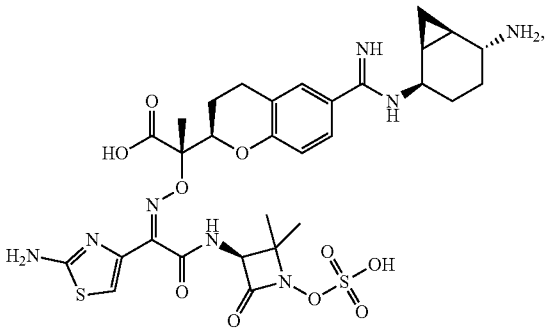

-continued

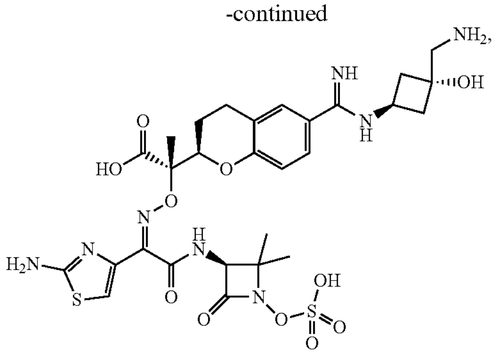

and

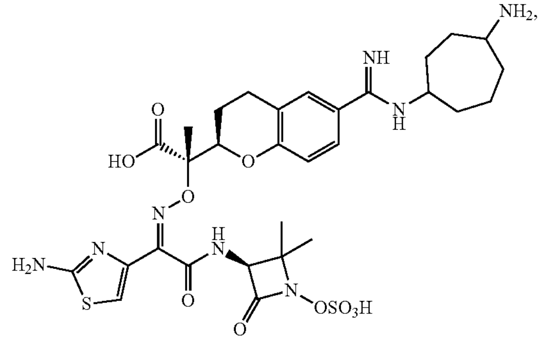

or a diastereomer thereof, and pharmaceutically acceptable salts thereof.

Other embodiments of the present invention include the following:

(a) A pharmaceutical composition comprising an effective amount of a compound of Formula (I) as defined herein, or a pharmaceutically acceptable salt thereof, and a pharmaceutically acceptable carrier.

(b) The pharmaceutical composition of (a), further comprising a second compound, wherein the second compound is a beta-lactamase inhibitor.

(c) The pharmaceutical composition of (b), wherein the second compound is selected from the group consisting of: relebactam, tazobactam, clavulanic acid, sulbactam, avibactam, taniborbactam, nacubactam, vaborbactam, zidebactam, durlobactam, enmetazobactam and QPX7728 (xeruborbactam), or a pharmaceutically acceptable salt thereof.

(d) A pharmaceutical composition comprising (i) a compound of Formula (I), or a pharmaceutically acceptable salt thereof, and (ii) a second compound, wherein the second compound is an beta-lactamase inhibitor compound, wherein the compound of Formula (I), and the second compound are each employed in an amount that renders the combination effective for treating or preventing bacterial infection.

(e) The combination of (d), wherein the second compound is selected from the group consisting of: relebactam, tazobactam, clavulanic acid, sulbactam, avibactam, taniborbactam, nacubactam, vaborbactam, zidebactam, durlobactam, enmetazobactam and QPX7728 (xeruborbactam), or a pharmaceutically acceptable salt thereof.

(f) A method for treating a bacterial infection in a subject which comprises administering to a subject in need of such treatment an effective amount of a compound of Formula (I), or a pharmaceutically acceptable salt thereof.

(g) A method for preventing and/or treating a bacterial infection which comprises administering to a subject in need of such treatment a pharmaceutical composition comprising an effective amount of a compound of Formula (I), or a pharmaceutically acceptable salt thereof, and a pharmaceutically acceptable carrier.

(h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to Gram negative bacteria.

(j) The method of treating a bacterial infection as set forth in (f), (g), (h), or (i), wherein the bacterial infection is due to *Pseudomonas aeruginosa* or *Acinetobacter baumannii.*

The present invention also includes a compound of Formula (I), or a pharmaceutically acceptable salt thereof, (i) for use in, (ii) for use as a medicament for, or (iii) for use in the preparation (or manufacture) of a medicament for, medicine or treating bacterial infection, including infection with a multidrug resistant bacterial strain. In these uses, the compounds of the present invention can optionally be employed in combination with one or more second therapeutic agents including relebactam, tazobactam, clavulanic acid, sulbactam, avibactam, taniborbactam, nacubactam, vaborbactam, zidebactam, durlobactam, enmetazobactam and QPX7728 (xeruborbactam), or a pharmaceutically acceptable salt thereof.

Additional embodiments of the invention include the pharmaceutical compositions, combinations and methods set forth in (a)-(j) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (j) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula (I) or its salt and a pharmaceutically acceptable carrier and optionally one or more excipients, it is understood that the term "substantially pure" is in reference to a compound of Formula (I) or its salt per se; i.e., the purity of this active ingredient in the composition.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "β-lactamase inhibitor" refers to a compound which is capable of inhibiting enzyme activity from β-lactamases. As used herein, inhibiting β-lactamase activity means inhibiting the activity of a class A, C, and/or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include metallo-β-lactamases of *Escherichia coli* (such as New Delhi Metallo-β-lactamase, NDM), *Serratia marcescens* (such as IMP), and *Klebsiella* spp. (such as Verona integron-encoded metallo-β-lactamase, VIM).). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics include penicillins, cephalosporins and carbapenems.

The term "β-lactam antibiotic" refers to a compound with antibiotic properties that contains a β-lactam functionality. Non-limiting examples of β-lactam antibiotics include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of 1%, 2%, 3%, 4%, 5%, 10%, or 20%.

Another embodiment of the present invention is a compound of Formula (I), or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula (I) or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula (I). Unless a specific stereochemistry is indicated, the present invention is meant to comprehend all such isomeric forms of these compounds. Centers of asymmetry that are present in the compounds of Formula (I) can all independently of one another have (R) configuration or (S) configuration.

When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula (I) or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Aryl" means a monocyclic, bicyclic or fused carbocyclic aromatic ring or ring system containing carbon atoms, wherein at least one of the rings is aromatic. The term aryl also encompasses an aryl group, as defined above, which is fused to an aryl, cycloalkyl, cycloalkenyl, cycloheteroalkyl, cycloheteroalkenyl or heteroaryl ring. Examples of aryl include phenyl and naphthyl. In one embodiment of the present invention, aryl is phenyl.

"Cycloalkyl," as used herein, refers to a saturated monocyclic ring or bicyclic, tricyclic, fused, spirocyclic or bridged ring system comprising 3 to 14 carbon atoms. The cycloalkyl ring system contains more than one ring, the rings can be joined via a ring carbon. Examples of cycloalkyl include cyclopropyl, cyclobutyl, cyclopentyl, cyclohexyl, cycloheptyl, indanyl, and the like. In one embodiment of the present invention, cycloalkyl is selected from: cyclopropane, cyclobutane, cyclopentane, and cyclohexane. In another embodiment, cycloalkyl is selected from cyclobutane, and cyclohexane. In another embodiment, cycloalkyl is cyclobutane. In another embodiment, cycloalkyl is cyclohexane. In another embodiment cycloalkyl is selected from: cyclopropane, cyclobutane, cyclopentane, cyclohexane, cycloheptane, bicyclo[1.1.1]pentane, bicyclo[3.1.1]heptane, bicyclo[4.1.0]heptane, bicyclo[2.2.2]octane, spiro[3.3]heptane, spiro[3.5]nonane, spiro[2.3]hexane. In another embodiment of the present invention, $-C_{3-9}$cycloalkyl is selected from: cyclopropane, cyclobutane, cyclopentane, cyclohexane, cycloheptane, bicyclo[1.1.1]pentane, bicyclo[3.1.1]heptane, bicyclo[4.1.0]heptane, bicyclo[2.2.2]octane, spiro[3.3]heptane, spiro[3.5]nonane, and spiro[2.3]hexane. In another embodiment of the present invention, —$C_{3-9}$cycloalkyl is selected from: cyclobutane, cyclohexane, cycloheptane, and bicyclo[4.1.0]heptane. In another embodiment of the present invention, —$C_{3-9}$cycloalkyl is bicyclo[4.1.0]heptane. In another embodiment of the present invention, —$C_{3-9}$cycloalkyl is cycloheptane. In another embodiment of the present invention, —$C_{3-9}$cycloalkyl is cyclohexane. In another embodiment of the present invention, —$C_{3-9}$cycloalkyl is cyclobutane.

"Cycloalkenyl" means a monocyclic ring or bicyclic, spirocyclic, fused or bridged carbocyclic ring system having a specified number of carbon atoms containing at least one double bond. Examples of cycloalkenyl include cyclopropenyl, cyclobutenyl, cyclopentenyl, cycloheptenyl, and the like.

"Cycloheteroalkyl," as used herein, refers to a saturated monocyclic ring or bicyclic, tricyclic, spirocyclic, fused or bridged ring system comprising 3 to 14 ring atoms, wherein from 1 to 4 of the ring atoms are independently N, NH, S (including SO and $SO_2$) and O, and the remainder of the ring atoms are carbon atoms. When a heterocycloalkyl contains two or more rings, the rings may be fused, bridged or spirocyclic. The cycloheteroalkyl group can be joined via a ring carbon or ring nitrogen atom (if present). Where the ring or ring system contains one or more N atoms, the N can be in the form of quaternary amine. The nitrogen or sulfur atom of the heterocycloalkyl (if present) can be optionally oxidized to the corresponding N-oxide, S-oxide or S,S-dioxide. The cycloheteroalkyl ring may be substituted on the ring carbons and/or the ring nitrogen or sulfur. Examples of cycloheteroalkyl include, oxetanyl, piperidyl, pyrrolidinyl, piperazinyl, morpholinyl, thiomorpholinyl, thiazolidinyl, 1,4-dioxanyl, tetrahydrofuranyl, delta-lactam, delta-lactone, silacyclopentane, silapyrrolidine, pyrrolidinyl, azetidinyl, piperidine, piperazine, azepane, azocane, morpholine, thiomorpholine, and the like. In one embodiment of the present invention, cycloheteroalkyl is selected from azetidine, pyrrolidine, piperidine, azepane, 2-oxabicyclo[2.1.1]hexane, 3-azabicyclo[3.1.0]hexane, 3-azabicyclo[3.2.1]octane, 8-azabicyclo[3.2.1]octane, 2-azaspiro[3.5]nonane, 2-azaspiro[3.3]heptane, 3-azabicyclo[3.2.0]heptane, 1-azaspiro[3.3]heptane, 6-azaspiro[3.5]nonane, 7-azaspiro[3.5]nonane, and 6-azaspiro[3.4]octane. In another embodiment, cycloheteroalkyl is selected from piperidine, and azepane. In another embodiment, $C_{2-8}$cycloheteroalkyl is selected from the group consisting of: azetidine, pyrrolidine, piperidine, azepane, 2-oxabicyclo[2.1.1]hexane, 3-azabicyclo[3.1.0]hexane, 3-azabicyclo[3.2.1]octane, 8-azabicyclo[3.2.1]octane, 2-azaspiro[3.5]nonane, 2-azaspiro[3.3]heptane, 3-azabicyclo[3.2.0]heptane, 1-azaspiro[3.3]heptane, 6-azaspiro[3.5]nonane, 7-azaspiro[3.5]nonane, 6-azaspiro[3.4]octane. In another embodiment, $C_{2-8}$cycloheteroalkyl is piperidine. In another embodiment, $C_{2-8}$cycloheteroalkyl is azepane.

"Cycloheteroalkenyl" means a monocyclic ring or bicyclic, fused, spirocyclic or bridged ring system comprising 3 to 14 ring atoms and containing at least one double bond and at least one heteroatom. Examples of cycloheteroalkenyl include dihydropyran and dihydrofuran, and the like.

"Heteroaryl" means a monocyclic ring or bicyclic or fused ring system containing 5-14 ring atoms containing at least one ring heteroatom selected from N, NH, S (including SO and $SO_2$) and O, wherein at least one of the heteroatom containing rings is aromatic. The term heteroaryl encompasses a heteroaryl group, as defined above, which is fused to an aryl, cycloalkyl, cycloalkenyl, cycloheteroalkyl, cycloheteroalkenyl or heteroaryl ring. In the case of a heteroaryl ring system where one or more of the rings are saturated or partially saturated and contain one or more N atoms, the N can be in the form of quaternary amine. Any nitrogen atom of a heteroaryl can be optionally oxidized to the corresponding N-oxide. The heteroaryl group can be optionally substituted by one or more ring system substituents which may be the same or different. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. In one embodiment of the present invention, heteroaryl is selected from: pyridine.

"Halogen" includes fluorine, chlorine, bromine and iodine. In one embodiment, halogen is fluorine, chorine, bromine or iodine. In another embodiment, halogen is fluorine or chlorine. In another embodiment, halogen is chlorine, fluorine or iodine. In another embodiment, halogen is fluorine. In another embodiment, halogen is chlorine. In another embodiment, halogen is bromine. In another embodiment, halogen is iodine.

"Me" represents methyl.

"Oxo" means an oxygen atom connected to another atom by a double bond and represents "═O".

"Quaternary salt" means a cation formed by four covalent bonds to nitrogen.

When any variable (e.g., $R^1$, $R^a$, etc.) occurs more than one time in any constituent or in Formula (I), its definition on each occurrence is independent of its definition at every other occurrence. Also, combinations of substituents and/or variables are permissible only if such combinations result in stable compounds. A squiggly line across a bond in a substituent variable represents the point of attachment.

"Saturated" means containing only single bonds.

"Unsaturated" means containing at least one double or triple bond. In one embodiment, unsaturated means containing at least one double bond. In another embodiment, unsaturated means containing at least one triple bond.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

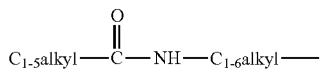

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration or sufficient heavy atoms to make an absolute assignment.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula (I).

In choosing compounds of the present invention, one of ordinary skill in the art will recognize that the various substituents, i.e., $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. When a group, e.g., $C_1$-$C_8$ alkyl, is indicated as being substituted, such substitutions can also occur where such group is part of a larger substituent, e.g., —$C_1$-$C_6$alkyl-$C_3$-$C_7$cycloalkyl and —$C_1$-$C_8$alkyl-aryl.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

It should also be noted that any carbon as well as heteroatom with unsatisfied valences in the text, schemes, examples and tables herein is assumed to have the sufficient number of hydrogen atom(s) to satisfy the valences.

The compounds of the present invention have at least one asymmetric center and can have one or more additional centers as a result of the presence of certain substituents and/or substituent patterns. Accordingly, compounds of the invention can occur as mixtures of stereoisomers, or as individual diastereomers, or enantiomers. All isomeric forms of these compounds, whether individually or in mixtures, are within the scope of the present invention.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The term "Drug resistant" means, in connection with a Gram-negative bacterial strain, a strain which is no longer susceptible to at least one previously effective drug; which has developed the ability to withstand antibiotic attack by at least one previously effective drug. "Multi-drug resistant" means a strain that is no longer susceptible to two or more previously effective drugs; which has developed the ability to withstand antibiotic attack by two or more previously effective drugs. A drug resistant strain may relay that ability to withstand to its progeny. This resistance may be due to random genetic mutations in the bacterial cell that alters its sensitivity to a single drug or to different drugs.

The term "pharmaceutically acceptable salt" refers to a salt which possesses the effectiveness of the parent compound and which is not biologically or otherwise undesirable (e.g., is neither toxic nor otherwise deleterious to the recipient thereof). The term "pharmaceutically acceptable salt" refers to salts prepared from pharmaceutically acceptable non-toxic bases or acids including inorganic or organic bases and inorganic or organic acids.

Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

As set forth above, the present invention includes pharmaceutical compositions comprising a compound of Formula I of the present invention, optionally one other active components (e.g., a β-lactamase inhibitor), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula (I), or a pharmaceutically acceptable salt thereof, optionally in combination with a β-lactamase inhibitor. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula (I) mean providing the compound, or a pharmaceutically acceptable salt thereof, to the individual in need of treatment. When a compound or a salt thereof is provided in combination with one or more other active agents (e.g., a β-lactamase inhibitor), "administration" and its variants are each understood to include provision of the compound or its salt and the other agents at the same time or at different times. When the agents of a combination are administered at the same time, they can be administered together in a single composition or they can be administered separately.

It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein means the amount of active compound sufficient to inhibit bacterial growth and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance). In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, $21^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 microgram/mL, and in additional embodiment at least about 10 micrograms/mL, and at least about 25 micrograms/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula (I). Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula (I) to an experimental cell culture in vitro to prevent the growth of β-lactam resistant bacteria. The method can alternatively involve administration of a compound of Formula I to an animal, including a human, to prevent the growth of β-lactam resistant bacteria in vivo. In these cases the compound of Formula (I) is typically co-administered with a β-lactamase inhibitor.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Compounds of the invention can be employed for the treatment, prophylaxis or inhibition of bacterial growth or infections due to bacteria that are resistant to β-lactam antibiotics. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

The compounds wherein $R^4$ is $C_{1-3}$alkyl, such as $CH_3$, or cyclopropyl and $R^5$ is $CO_2H$ or tetrazole have the unexpected benefit of stability compared to compounds wherein $R^4$ is hydrogen and $R^5$ is $CO_2H$ or tetrazole.

Compounds of the invention can be used in combination with a β-lactamase inhibitor for the treatment of infections caused by β-lactamase producing strains, in addition to those infections which are subsumed within the antibacterial spectrum of the antibiotic agent.

Examples of β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes, Enterobacter asburiae, Citrobacter freundii, Proteus*

*mirabilis, Morganella morganii, Providencia rettgeri, Stenotrophomonas maltophilia* and *Acinetobacter baumannii.*

It is generally advantageous to use a compound of Formula (I) in admixture or conjunction with a β-lactamase inhibitor, or a prodrug thereof. It is advantageous to use a compound of Formula I in combination with a class A and C β-lactamase inhibitor because of the class B β-lactamase resistant properties of the compounds. It is also advantageous to use a compound of Formula I in combination with one or more Class A, C, or D β-lactamase inhibitors to further limit β-lactam susceptability. As already noted, the compound of Formula I and the p-lactamase inhibitor can be administered separately (at the same time or as different times) or in the form of a single composition containing both active ingredients.

Relebactam, tazobactam, clavulanic acid, sulbactam, avibactam, taniborbactam, nacubactam, vaborbactam, zidebactam, durlobactam, enmetazobactam, QPX7728 (xeruborbactam), and other β-lactamase and metallo-β-lactamase inhibitors suitable for use in the present invention include those known to show inhibitory activity to β-lactamases.

Abbreviations

Ac is acetyl; Ambient is room temperature; aq. is aqueous; ACN is acetonitrile; AcOH is acetic acid; Bn is benzyl; BOC (or Boc) is t-butyloxycarbonyl; $BOC_2O$ is di-tert-butyl dicarbonate; BuBr is butyl bromide; CBZ (or Cbz) is carbobenzoxy (alternatively, benzyloxycarbonyl); CBZ—Cl is benzyloxycarbonyl chloride; $CDCl_3$ is deuterated chloroform; CV or cv is column volume(s); $D_2O$ is deuterium oxide; DBU is 1,8-diazabicyclo[5.4.0]undec-7-ene; DCC is dicyclohexyl carbodiimide; DCE is dichloroethane; DCM is dichloromethane; DEAD is diethyl azodicarboxylate; $(DHQD)_2AQN$ is 1,4-bis[(5-ethyl-1-azabicyclo[2.2.2]octan-2-yl)-(6-methoxyquinolin-4-yl)methoxy]anthracene-9,10-dione; DIAD is diisopropyl azodicarboxylate; DIEA or DIPEA is diisopropylethylamine; DMA is dimethylacetamide; DMAP is 4-dimethylaminopyridine or N,N-dimethylamino-pyridine; DME is dimethoxyethane; DMF is N,N-dimethylformamide; DMSO is dimethyl sulfoxide; DPPA is diphenylphosphoryl azide; EDC is 1-ethyl-3-(3-dimethylaminopropyl) carbodiimide; eq. or equiv. is equivalent(s); Et is ethyl; $Et_3N$ is triethyl amine; $Et_2O$ is diethyl ether; EA or EtOAc is ethyl acetate; EtOH is ethanol; g is gram(s); FA is formic acid; h or hr or hrs is hour(s); HATU is 1-[Bis(dimethylamino)methylene]-1H-1,2,3-triazolo[4,5-b]pyridinium 3-oxid hexafluorophosphate; hex is hexane; HMDS is hexamethyl-disilazide; HPLC is high-performance liquid chromatography; Int is intermediate; IPA is isopropyl alcohol; L or 1 is liter(s); LAH is lithium aluminum hydride; LC/MS or LC-MS is liquid chromatography/mass spectrometry; LDA is lithium diisopropylamide; LiHMDS is lithium hexamethyl-disilazide M is molar; min is minute(s); mg is milligram(s); ml, mL or ML is milliliter(s); Me is methyl; MeCN is acetonitrile; MeO is methoxy; MeOH is methanol; Mel is methyl iodide; MPLC is medium pressure liquid chromatography; MTBE is methyl tert-butyl ether; N is normal; $NaBH(OAc)_3$ is sodium triacetoxyborohydride; NBS is N-bromo-succinimide; NCS is N-chlorosuccinimide; $NEt_3$ is trietheyl amine; NMR is nuclear magnetic resonance; MS is mass spectrometry; MW is molecular weight; Pd/C is palladium on carbon; $PdCl_2(dppf)_2$ is [1,1' bis(diphenyl-phosphino)-ferrocene] dichloropalladium(II); di-t-BuDPPF—$PdCl_2$ is 1,1'-bis(di-tert-butylphosphino)-ferrocene palladium dichloride; $Pd(AcO)_2$ is palladium (II) acetate; PE is petroleum ether; PG is protective group; Ph is phenyl; $Ph_3P$ is triphenyl phosphine; RP is reverse phase; RP-HPLCis reverse-phase high-performance liquid chromatography; rt, r.t., R.T. or RT is room temperature; sat'd is saturated; SFC is super critical fluid chromatography; tBu is tert-butyl; tBuOH is tert-butyl alcohol; TBAF is tetrabutylammonium fluoride; TB is tert-butyldimethylsilyl; TBS-Cl is tert-butyldimethylsilyl chloride; TBDPS-Cl is t-butyl (chloro)diphenylsilane; t-BuOH is tert-butyl alcohol; TEA is triethylamine; TFA is trifluoroacetic acid; THF is tetrahydrofuran; TLC is thin layer chromatography; TMS is trimethylsilyl; TMS-Cl is trimethylsilyl chloride; and wt % is weight percentage.

Methods for Making the Compounds of Formula (I):

The compounds disclosed herein can be prepared and tested according to the following reaction schemes and Examples, or modifications thereof, using readily available starting materials, reagents and conventional synthesis procedures. In these reactions, it is also possible to make use of variations which are themselves known to those of ordinary skill in this art, but are not mentioned here in greater detail. Furthermore, other methods for preparing compounds disclosed herein will be readily apparent to the person of ordinary skill in the art in light of the following reaction scheme and Examples. Unless otherwise indicated, all variables are as defined above. The following examples illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Reactions sensitive to moisture or air were performed under nitrogen using anhydrous solvents and reagents. The progress of reactions can be determined by either analytical thin layer chromatography (TLC) performed with E. Merck precoated TLC plates or AnHui Liangchen Guiyuan Co., Ltd., silica gel 60F-254 or GF254, layer thickness 0.25 mm or liquid chromatography-mass spectrum (LC-MS). For HPLC/MS data of intermediates, unless otherwise specified, two main HPLC conditions used were as follows: 1) LC1 (SHIMADZU C18 Xtimate 3 um 2.1×30 mm column with gradient 10:90-80:20 v/v $CH_3CN/H_2O$+v 0.0375% TFA over 0.9 min then hold at 80:20 v/v $CH_3CN/H_2O$+v 0.0375% TFA for 0.6 min; flow rate 1.2 mL/min, UV wavelength 220 & 254 nm); and 2) LC2 (Agilent C18 Xtimate 3 um 2.1×30 mm column with gradient 10:90-80:20 v/v $CH_3CN/H_2O$+v 0.0375% TFA over 3.0 min then hold at 80:20 v/v $CH_3CN/H_2O$+v 0.0375% TFA for 0.5 min; flow rate 0.8 mL/min, UV wavelength 220 & 254 nm). For HPLC/MS data of final products, two main HPLC conditions used were as follows: 1) LC1: Agilent Poroshell 120 EC-C18 1.9 um 3.0×30 mm column with gradient 5:95-80:20 v/v $CH_3CN$ (v 0.0375% TFA)/$H_2O$ (v 0.0188% TFA) over 1.2 min then 80:20-95:5 v/v $CH_3CN$ (v 0.0375% TFA)/$H_2O$ (v 0.0188% TFA) for 1.3 min; flow rate 1.5 mL/min, UV wavelength 220 & 254 nm); and 2) LC2: Agilent Poroshell 120 EC-C18 1.9 um 3.0×30 mm column with gradient 0:100-30:70 v/v $CH_3CN$ (v 0.0375% TFA)/$H_2O$ (v 0.0188% TFA) over 1.2 min then 30:70-95:5 v/v $CH_3CN$ (v 0.0375% TFA)/$H_2O$ (v 0.0188% TFA) for 1.3 min; flow rate 1.5 mL/min, UV wavelength 220 & 254 nm); Mass analysis was performed with electrospray ionization in positive ion detection mode. $^1$H NMR spectra were recorded on Varian or Bruker instruments at 400-500 MHz. Concentration of solutions was carried out on a rotary evaporator under reduced pressure or bubbled with nitrogen stream (a pipette head connecting to the end of nitrogen tube inserted in the mixture) until volatiles were removed completely or by lyophilization. Silica gel chromatography was performed on pre-packed silica gel columns using a commercial MPLC system. The names of compounds in the Examples were generated in Chemdraw™.

GENERAL SCHEME

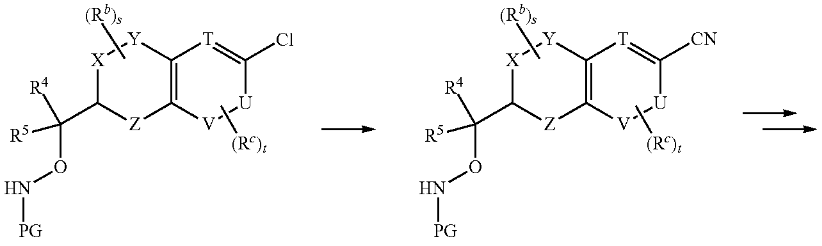

A
PG = protection group

B

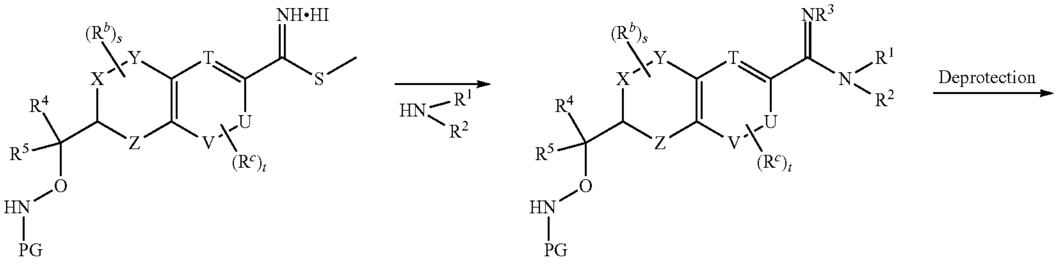

C

D

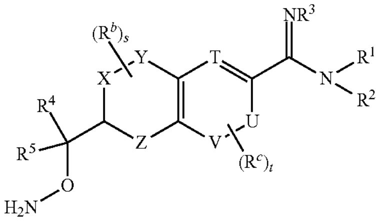

E

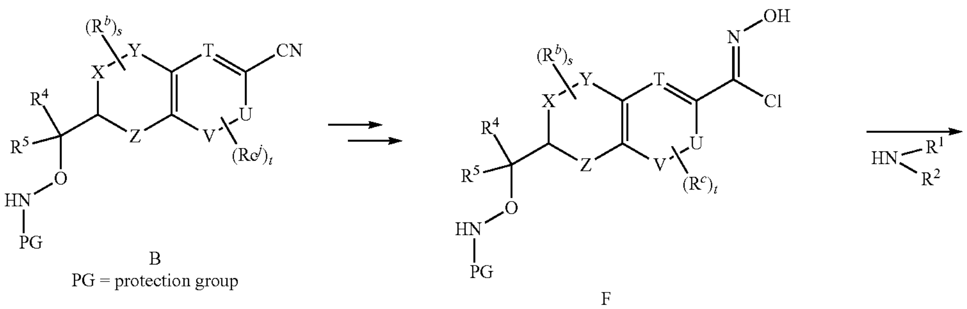

B
PG = protection group

F

-continued

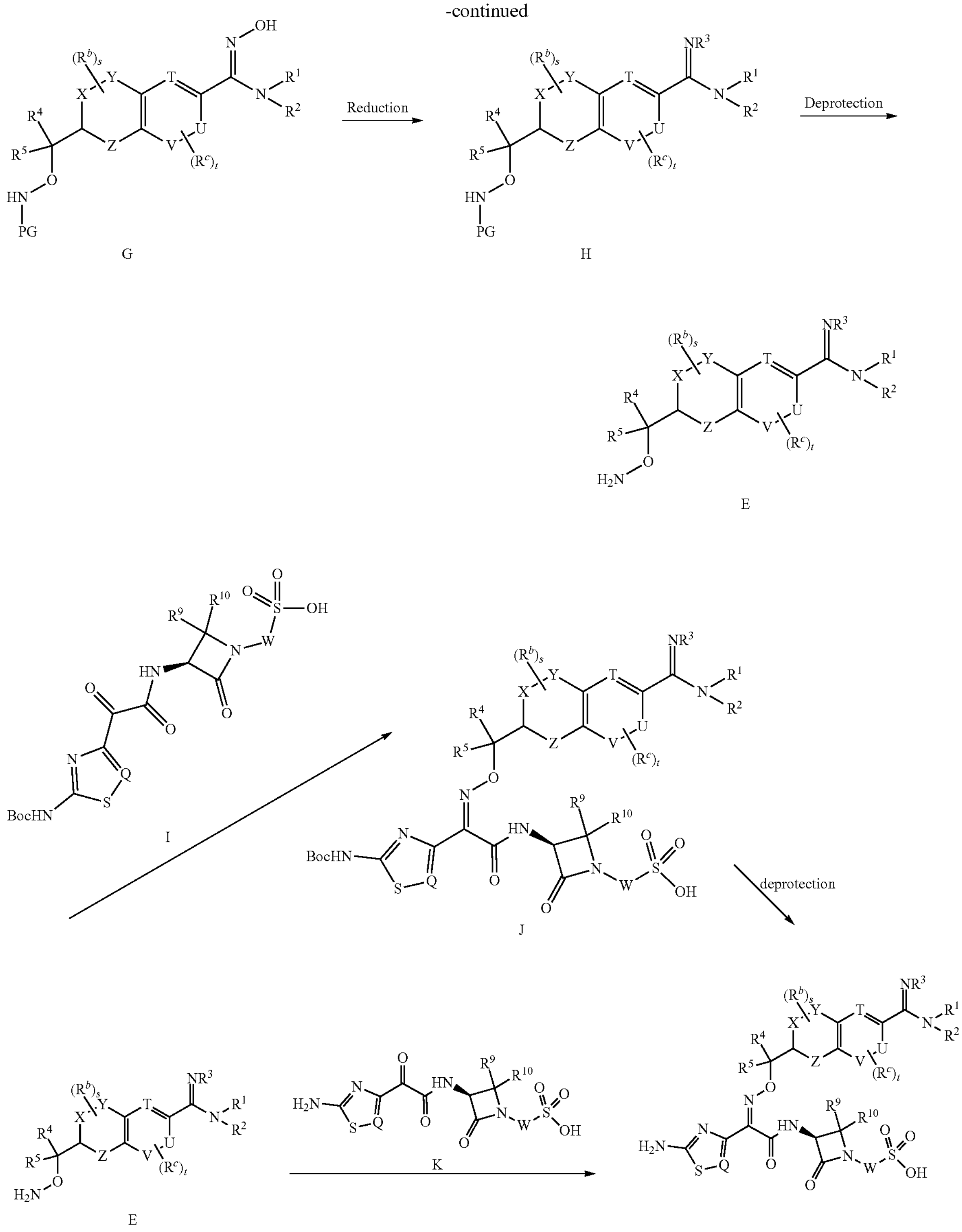

G H E I J K E

The chroman chloride A was converted via a cyanation reaction to intermediate B, which underwent functional group manipulations to provide intermediate C. Amination of intermediate C afforded intermediate D, which was then deprotected to give compound E. Alternatively, intermediate B was converted to intermediate F through functional group manipulation. Amination of intermediate F followed by reduction of hydroxyamidine G and removal of protecting group (PG) in intermediate H to give compound E. The condensation reaction of compound E with intermediate I afforded intermediate J, followed by protecting group removal to give the final product. Alternatively, compound E was coupled with intermediate K to afford the final product directly.

Example 1: Preparation of Intermediate 1c

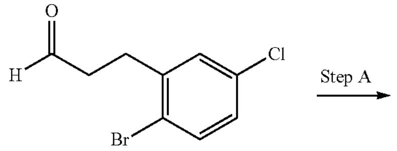

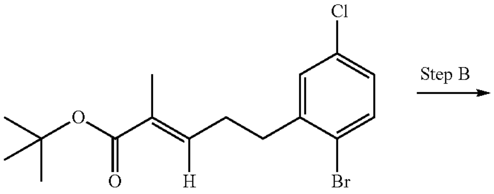

Intermediate 1a

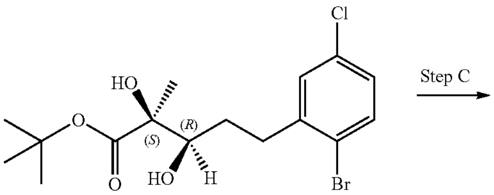

Intermediate 1b

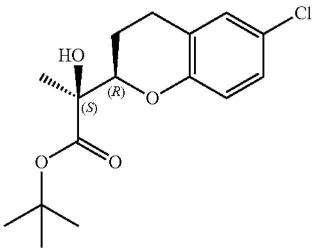

Intermediate 1c

Step A—Synthesis of Intermediate-1a To a solution of tert-butyl 2-(diethoxyphosphoryl)-propanoate (2150.0 g, 8.06 mol, 0.95 eq) in THF (8400 mL) stirred at ambient temperature, was added NaH (339.3 g, 8.48 mol, 60% purity, 1.0 eq) in several portions. The mixture was stirred at 30-40° C. for 3 h. Then a solution of 3-(2-bromo-5-chlorophenyl) propanal (2100.0 g, 8.48 mol, 1.0 eq) in THF (4200 mL) was added dropwise to the above mixture at 30-50° C. After the addition, the mixture was stirred at 20-40° C. for 1 h, then poured into ice water (10 L), and diluted with EtOAc (10 L). The organic layer was separated, and the aqueous phase was extracted with EtOAc (3 L). The combined organic layers were washed with brine (10 L), and concentrated under reduced pressure. The resulting residue was purified by column chromatography on silica gel eluting with petroleum ether:ethyl acetate (1:0~10:1) to give intermediate 1a. $^1$H-NMR (400 MHz, $CDCl_3$): δ 7.47 (d, J=8.5 Hz, 1H), 7.22 (d, J=2.6 Hz, 1H), 7.07 (dd, J=8.5, 2.6 Hz, 1H), 6.71 (td, J=7.5, 1.5 Hz, 1H), 2.93-2.71 (m, 2H), 2.63-2.37 (m, 2H), 1.78 (d, J=1.3 Hz, 3H), 1.52 (s, 9H).

Step B—Synthesis of Intermediate 1b Into a 50 L 4-necked round-bottom flask, purged and maintained with an inert atmosphere of nitrogen, were added $K_2CO_3$ (2188 g, 15.84 mol), potassium ferricyanide (5218 g, 15.84 mol), tetraoxodipotassium osmium (38.1 g, 0.105 mol), $(DHQD)_2AQN$ (90.1 g, 0.105 mol) and a solution of intermediate 1a (1900 g, 5.28 mol) in tert-butanol/water (19 L/19 L). The resulting mixture was stirred at room temperature for 2 days. Then the reaction mixture was extracted with ethyl acetate and the organic layers were combined and dried over anhydrous sodium sulfate. The resulting solids were filtered out. The filtrate was concentrated under vacuum, and the resulting residue was purified by a silica gel column eluting with ethyl acetate/petroleum ether (1/100-1/10) to give intermediate Ib. LC-MS: m/z 417.0 $[M+Na]^+$.

Step C—Synthesis of Intermediate 1c Into a 20-L 4-necked round-bottom flask, purged and maintained with an inert atmosphere of nitrogen, were placed $Cs_2CO_3$ (2317.2 g, 7112.01 mmol) and $Pd(AcO)_2$ (39.9 g, 177.80 mmol) in toluene (14 L). Then 2-(di-tert-butylphosphino) biphenyl (106.1 g, 355.60 mmol) was slowly added over 30 min. To this mixture was added intermediate 1b (1400 g, 3556.01 mmol). The reaction mixture was stirred for 20 h at 90° C., then cooled to room temperature with a water/ice bath. The resulting solids were filtered off, and the filtrate was concentrated under reduced pressure. The resulting residue was purified on a silica gel column eluting with ethyl acetate/petroleum ether (1/100-1/5) to give intermediate Ic. $^1$H-NMR (400 MHz, $CDCl_3$): δ 7.07-7.00 (m, 2H), 6.67 (d, J=8.3 Hz, 1H), 4.14 (dd, J=11.0, 2.4 Hz, 1H), 3.03-2.60 (m, 2H), 2.23-1.86 (m, 2H), 1.53 (s, 9H), 1.41 (s, 3H).

Example 2: Preparation of Intermediate 2b

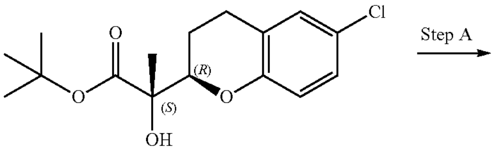

Intermediate 1c

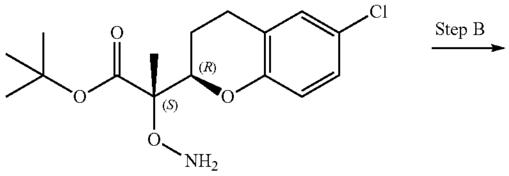

Intermediate 2a

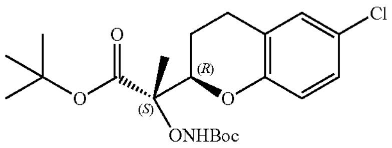

Intermediate 2b

Step A—Synthesis of Intermediate 2a Into a 2-L 4-necked round-bottom flask was placed a solution of intermediate 1c (460 g, 1.47 mol) in toluene (4800 mL), followed by the addition of sodium hydride (60 wt. %, 70.8 g, 1.77 mol) in several batches at 27° C. The mixture was stirred at 27° C. for 1 h. Then a solution of amino 2,4,6-trimethylbenzene-1-sulfonate (380.4 g, 1.77 mol) in DCM (1200 mL) was added dropwise with stirring at 27° C. The reaction mixture was stirred at 27° C. for 2 h. The reaction was then quenched by the addition of water (2000 mL) and extracted with MTBE (2x2 L). The organic layers were combined, dried over anhydrous $Na_2SO_4$ and filtered. The filtrate was concentrated under vacuum. The resulting residue was purified on a silica gel column eluting with EtOAc/PE (1:10) to give intermediate 2a. $^1$H-NMR (400 MHz, $CDCl_3$): δ 7.08-6.96 (m, 2H), 6.96 (overlap, 1H), 6.77 (d, J=9.4 Hz, 1H), 4.20 (dd, J=11.4, 1.9 Hz, 1H), 2.99-2.62 (m, 2H), 2.06 (ddt, J=13.6, 5.9, 2.1 Hz, 1H), 1.87 (dtd, J=13.6, 12.0, 5.8 Hz, 1H), 1.54 (s, 9H), 1.53 (s, 3H).

Step B—Synthesis of Intermediate 2b Into a 5 L 4-necked round-bottom flask was placed intermediate 2a (500 g, 1525.27 mmol) and di-tert-butyl dicarbonate (399.00 g, 1828.18 mmol) in ethyl alcohol (5 L). The reaction was stirred for 5 h at 50° C., then concentrated under vacuum. The resulting crude product was purified by slurrying with hexanes. The solids were collected by filtration to afford intermediate 2b. $^1$H NMR (400 MHz, $CDCl_3$): δ 7.53 (s, 1H), 6.99 (t, 2H), 6.68 (t, 1H), 4.21 (q, 1H), 2.82 (t, 2H), 2.17-2.12 (m, 2H), 1.55-1.45 (m, 21H).

Example 3: Preparation of Intermediates 3a and 3c

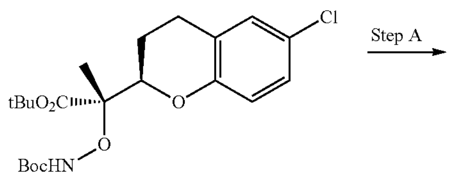

Int-2b

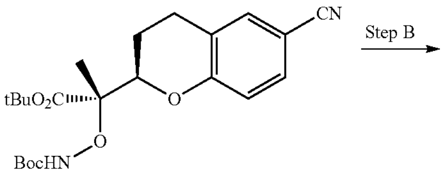

Int-3a

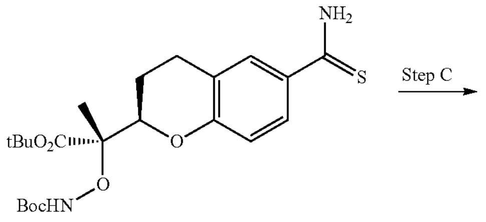

Int-3b

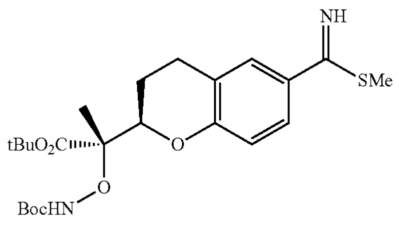

Int-3c

Step A—Synthesis of Intermediate 3a To a mixture of intermediate 2b (8.0 g, 18.69 mmol), potassium hexacyanoferrate(II) trihydrate (3.95 g, 9.35 mmol), sodium carbonate (0.248 g, 2.337 mmol), and chloro(2-dicyclohexylphosphino-2',4',6'-tri-i-propyl-1,1'-biphenyl)(2'-amino-1,1'-biphenyl-2-yl) palladium(II) (1.471 g, 1.869 mmol) were added ACN (64 mL) and water (60 mL), both of which had been sparged with nitrogen for 1 h. The reaction vessel was evacuated and filled with nitrogen before sealing. Then the reaction was heated at 80° C. and stirred for 2 h. The reaction was then partitioned between ethyl acetate and water. The aqueous layer was back-extracted with ethyl acetate and the combined organic layers were washed with brine, dried over anhydrous sodium sulfate, and filtered through a Celite™ pad. The resulting filtrate was concentrated in vacuo to give a crude residue, which was purified via silica gel chromatography (ISCO 220 g; 0-70% EtOAc/hexanes to give the desired compound. LC-MS: m/z 419.2 $[M+H]^+$.

Step B—Synthesis of Intermediate 3b To a mixture of intermediate 3a (4.81 g, 11.49 mmol), $MgCl_2$ (1.641 g, 17.24 mmol), and NaSH (1.933 g, 34.5 mmol) was added nitrogen-sparged anhydrous DMF (20.5 mL) under an atmosphere of nitrogen. The reaction mixture was evacuated and filled with nitrogen before capping and stirring at ambient temperature for 21 h. Then the reaction was cooled to 0° C. and quenched with saturated aqueous $NH_4C_1$ and water. The resulting mixture was extracted with ethyl acetate. The aqueous layer was back-extracted with ethyl acetate and the combined organic layers were washed with brine, dried over anhydrous sodium sulfate, and filtered. The filtrate was concentrated in vacuo to give a crude residue, which was purified via silica gel chromatography (ISCO, 220 g; 0-100% EtOAc/hexanes) to give the desired compound. LC-MS: m/z 453.2 $[M+H]^+$.

Step C—Synthesis of Intermediate 3c To a solution of intermediate 3b (4.85 g, 10.72 mmol) in anhydrous ether (35 mL) was added iodomethane (0.804 mL, 12.86 mmol) at ambient temperature. The reaction was sealed and stirred for 24 h. Then the ether supernatant was decanted off. The insoluble sticky oil was triturated with ether (15 mL). The resulting oil was dried under high vacuum to give intermediate 3c. The decanted ether layers were also combined and concentrated in vacuo. To the resulting residue was added 1:1 hexanes/ether (30 mL), and the resulting solid material was collected by filtration, washed with 1:1 hexanes/$Et_2O$ (20 mL) and dried under vacuum to give an additional amount of intermediate 3c. The combined crude product was used in subsequent reactions without further purification. LC-MS: m/z 468.2 $[M+H]^+$.

Example 4: Preparation of Intermediate 4

Intermediate 4

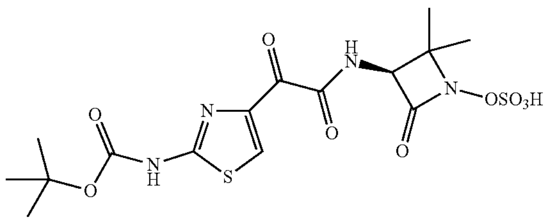

Intermediate 4 was prepared using the method described in Patent Publication No: WO 2017/106064.

Example 5: Preparation of Intermediate 5

Intermediate 5

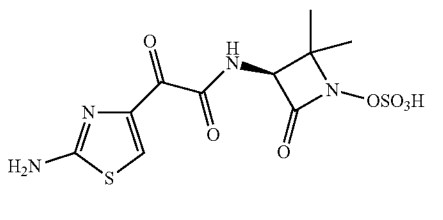

A flask (250 mL) was charged with Intermediate 4 (10 g, 21.5 mmol) and $CH_2Cl_2$ (43 mL), and the solution was cooled to 0° C. Then TFA (86 mL, 1116 mmol) was added via syringe. The reaction mixture was stirred at 0° C. for 5 h, then concentrated under vacuum without heating to give a residue (~20 mL of total volume). DCM (100 mL) was added to the residue and the mixture was concentrated under vacuum without heating to −20 mL total volume. This process was repeated four times to drive out most of the TFA. Finally, the solvent was removed completely under vacuum. To the resulting residue was added water (100 mL). After stirred for 30 min, the mixture was filtered, and the filter cake was rinsed with water (1 volume of cake) and then collected. The filter cake was dissolved in 1:1 acetonitrile/water (50 mL) and the mixture was lyophilized overnight to provide intermediate 5. LC-MS: m/z 365.3 $[M+H]^+$. $^1H$ NMR (500 MHz, DMSO-$d_6$) δ: 9.67 (d, J=7.7 Hz, 1H), 7.88 (s, 1H), 7.57 (s, 2H), 4.59 (d, J=7.9 Hz, 1H), 1.44 (s, 3H), 1.25 (s, 3H).

Example 6: Preparation of Intermediate 6c

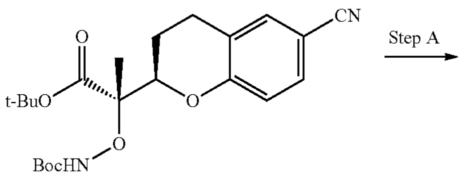

Intermediate 3a

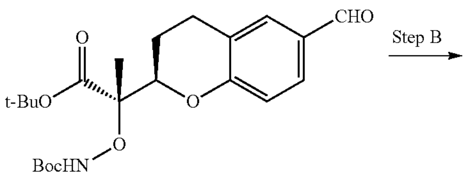

Intermediate 6a

-continued

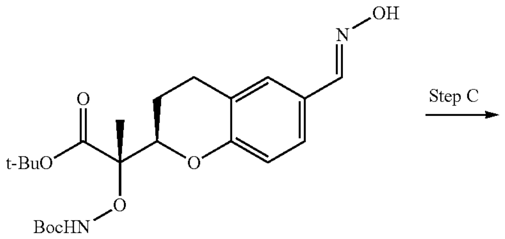

Intermediate 6b

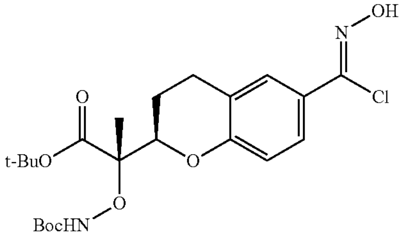

Intermediate 6c

Step A—Synthesis of Intermediate 6a To a solution of intermediate 3a (0.98 g, 2.342 mmol) in a pre-mixed solution of AcOH (3 mL)/pyridine (6 mL)/water (3 mL), were added sodium hypophosphite monohydrate (1.986 g, 18.73 mmol) and Raney nickel (1.45 g). The resulting mixture was stirred at 70° C. for 12 h. Then the mixture was diluted with 100 mL of 50% EtOAc/hexanes and filtered. The filtrate was washed with 100 mL of water (3×), then dried over anhydrous $MgSO_4$, and concentrated under vacuum. The resulting residue was purified by silica gel chromatography (ISCO, 80 g column, gradient elution with 0~100% EtOAc/hexanes) to afford intermediate 6a. MS (ESI) m/z: 422.3 $[M+H]^+$.

Step B—Synthesis of Intermediate 6b To a mixture of intermediate 6a (300 mg, 0.712 mmol) in EtOH (3 mL) and water (3 mL) was added TEA (0.149 mL, 1.068 mmol), followed by hydroxylamine hydrochloride (74.2 mg, 1.068 mmol). The reaction mixture was stirred at 25° C. for 3 h, then diluted with water (40 mL) and extracted with ethyl acetate (80 mL×3). The combined organic layers were washed with brine (40 mL), dried over anhydrous $Na_2SO_4$, filtered, and the filtrate was concentrated in vacuo. The resulting residue was purified by preparative TLC plate ($SiO_2$, 30% ethyl acetate in petroleum ether) to give intermediate 6b. MS (ESI) m/z: 459.0 $[M+Na]^+$.

Step C—Synthesis of Intermediate 6c To a solution of intermediate 6b (500 mg, 1.145 mmol) in DMF (3.4 mL), was added 1-chloropyrrolidine-2,5-dione (199 mg, 1.489 mmol). The reaction was stirred at ambient temperature for 45 min. Then the reaction mixture was diluted with 15 mL of $Et_2O$/hexanes (2:1), and washed with 20 mL of water (2×). The organic layer dried over anhydrous $Na_2SO_4$, then filtered and the filtrate was concentrated under vacuum to give crude intermediate 6c, which was used in subsequent reactions without further purification. MS (ESI) m/z: 471.3 $[M+H]^+$.

Example 7: Preparation of Compound 1

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N—((S)-pyrrolidin-3-yl)carbamimidoyl)chroman-2-yl)propanoic acid

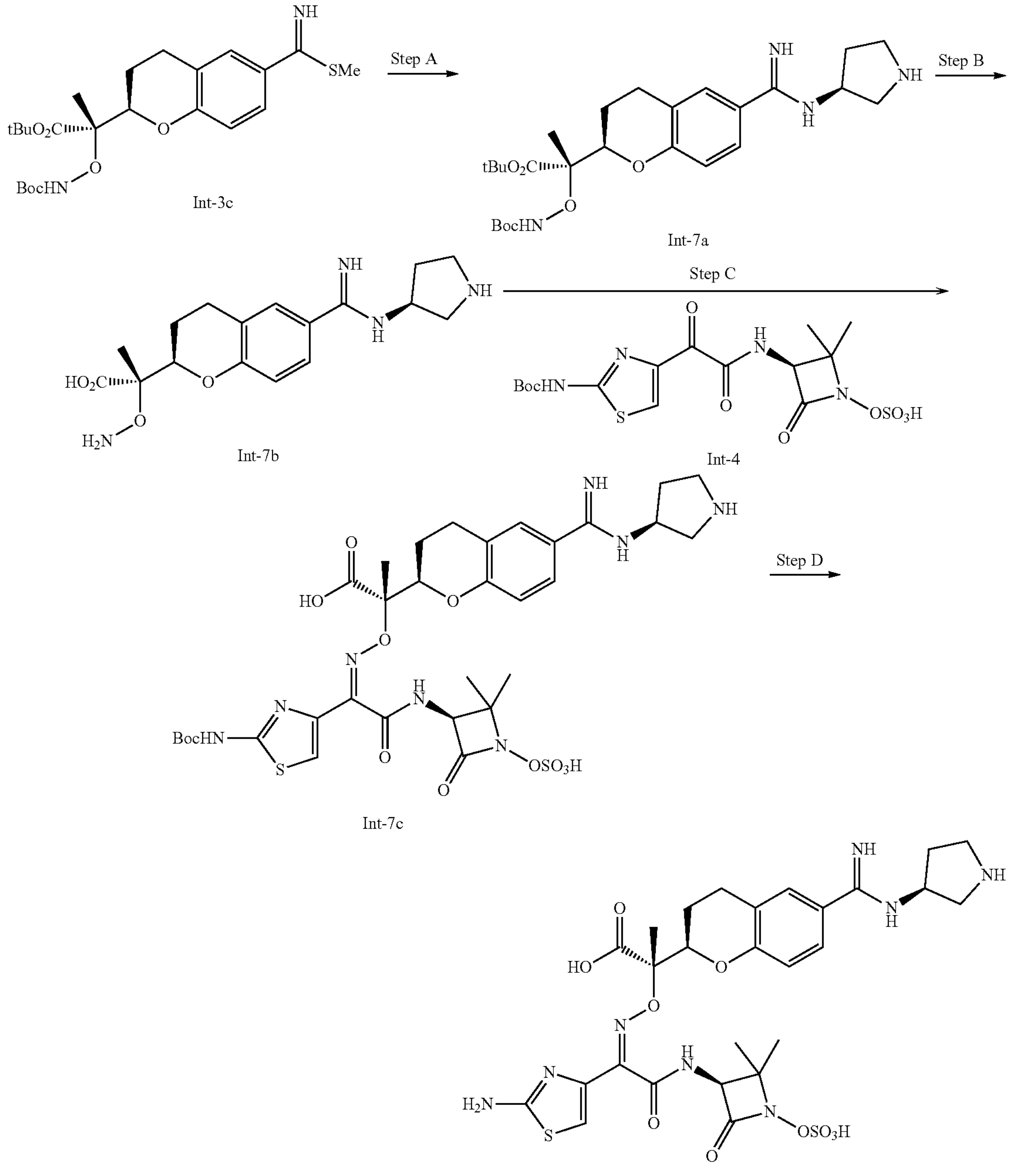

Int-3c

Int-7a

Int-7b

Int-4

Int-7c

Compound 1

Step A—Synthesis of Intermediate 7a To a vial containing a mixture of intermediate 3c (0.2470 g, 0.529 mmol) and (S)-(−)-1-Boc-3-aminopyrrolidine (0.184 mL, 1.059 mmol), was added a pre-made solution of potassium acetate (0.104 g, 1.059 mmol) and acetic acid (0.182 mL, 3.18 mmol) in anhydrous MeOH (5.3 mL). The reaction was heated at 70° C. for 35 min. Then the reaction mixture was directly purified on a reverse phase HPLC (ISCO C18Aq 50 g; 0-100% ACN+0.05% TFA/water+0.05% TFA). The desired fractions were collected and concentrated in vacuo. The resulting aqueous residue was lyophilized to give the desired compound. LC-MS: m/z 605.5 $[M+H]^+$.

Step B—Synthesis of Intermediate 7b To a vial containing intermediate 7a (0.2529 g, 0.418 mmol) was added a mixture of 2:1 trifluoroacetic acid/anhydrous dichloromethane (4.2 mL) at ambient temperature. The reaction mixture was stirred for 16.5 h. Then a solution of 4:1 MeOH/toluene (10 mL) was added to the reaction and the solution was concentrated in vacuo. The resulting residue was azeotroped with 4:1 MeOH/toluene (10 mL) and the resulting residue was dried in vacuo to give the desired compound. LC-MS: m/z 349.2 $[M+H]^+$.

Step C—Synthesis of Intermediate 7c To a flask charged with intermediate 7b (0.043 g, 0.123 mmol) and intermediate 4 (0.057 g, 0.123 mmol) was added anhydrous methanol (1.2 mL) at ambient temperature. The mixture was stirred for 2 h, and then concentrated in vacuo. The crude residue was used in the subsequent reaction without further purification. LC-MS: m/z 795.5 $[M+H]^+$.

Step D—Synthesis of Compound 1 A solution of intermediate 7c (0.123 mmol) in 2:1 anhydrous DCM/TFA (1.2 mL) was at ambient temperature for 1 h. Then the reaction was cooled to 0° C. and MTBE (3 mL) was added with stirring resulting in precipitation of a solid. The mixture was sonicated and then centrifuged (4000 rpm) to collect the insoluble solids. The supernatant was decanted off. Then MTBE was added to the reaction again with stirring, resulting in precipitation of additional solids, which were isolated by centrifugation. The resulting solid was dried in vacuo, and was purified by RP HPLC (XSelect CSH Prep C18; 5 uM OBD; 30×150 mm; 0%-20% (ACN+0.1% FA)/(water+0.1% FA) over 15 min). The product-containing fractions were collected and lyophilized to give the title compound as the formic acid salt. LC-MS: m/z 695.3 $[M+H]^+$. $^1$HNMR (500 MHz, 4:1 $D_2O$/d-DMSO) δ: 7.51 (d, J=2.2 Hz, 1H), 7.47 (dd, J=8.6, 2.4 Hz, 1H), 6.98-6.88 (m, 2H), 4.69 (s, 1H), 4.62-4.56 (m, 1H), 4.45 (dd, J=11.3, 2.1 Hz, 1H), 3.72 (dd, J=13.0, 6.8 Hz, 1H), 3.58-3.44 (m, 3H), 2.95-2.78 (m, 2H), 2.56-2.43 (m, 1H), 2.35-2.22 (m, 1H), 2.14 (d, J=13.7 Hz, 1H), 1.78 (dd, J=13.5, 6.0 Hz, 1H), 1.58 (s, 3H), 1.49 (s, 3H), 1.30 (s, 3H).

Example 8: Preparation of Compounds 2 to 6

Starting from the appropriate commercially available mono-Boc protected diamines or di-Boc protected tri-amines, the following compounds were prepared according to the procedure of Example 7.

| Compound | Structure | $^1$H NMR | LC-MS $[M + H]^+$ |
|---|---|---|---|
| 2 | 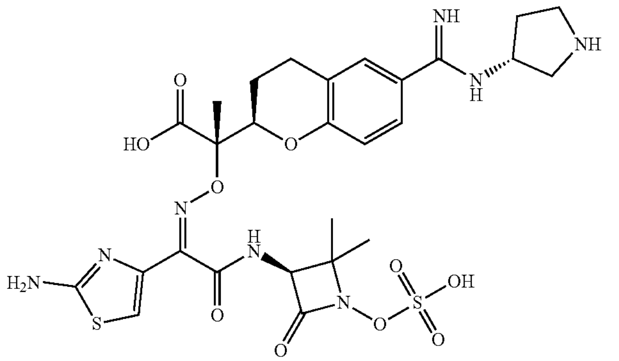 [SMILES: CC1(C)[C@H](NC(=O)/C(=N\O[C@](C)(C(=O)O)[C@H]2CCc3cc(C(=N)N[C@@H]4CCNC4)ccc3O2)c2csc(N)n2)C(=O)N1OS(=O)(=O)O]<br>(S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((R)-pyrrolidin-3-yl)carbamimidoyl)-chroman-2-yl)propanoic acid | $^1$H NMR (500 MHz, 4:1 $D_2O$/d-DMSO) δ: 7.52-7.43 (m, 2H), 6.96-6.91 (m, 2H), 4.69 (s, 1H), 54.59 (dq, J = 6.9, 4.2, 3.5 Hz, 1H), 4.44 (dd, J = 11.3, 1.8 Hz, 1H), 3.71 (d, J = 6.8 Hz, 1H), 3.59-3.45 (m, 3H), 2.92-2.80 (m, 2H), 2.50 (dq, J = 14.9, 8.1 Hz, 1H), 2.28 (dq, J = 13.5, 6.5 Hz, 1H), 2.14 (d, J = 13.7 Hz, 1H), 1.77 (ddt, J = 17.6, 11.8, 6.4 Hz, 1H), 1.58 (s, 3H), 1.49 (s, 3H), 1.30 (s, 3H). | 695.5 |
| 3 | 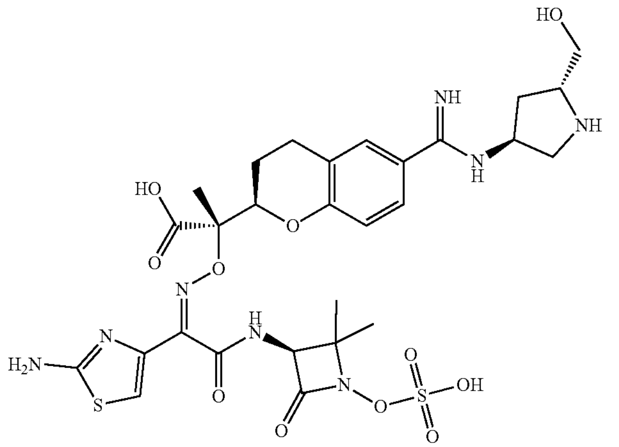 [SMILES: CC1(C)[C@H](NC(=O)/C(=N\O[C@](C)(C(=O)O)[C@H]2CCc3cc(C(=N)N[C@@H]4CN[C@@H](CO)C4)ccc3O2)c2csc(N)n2)C(=O)N1OS(=O)(=O)O]<br>(S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((3S,5R)-5-(hydroxymethyl)-pyrrolidin-3-yl)carbamimidoyl)-chroman-2-yl)propanoic acid | $^1$H NMR (400 MHz, 4:1 $D_2O$/d-DMSO) δ: 7.39 (s, 1H), 7.34 (d, J = 8.9 Hz, 1H), 6.86-6.77 (m, 2H), 4.59 (s, 1H), 4.54-4.47 (m, 1H), 4.31 (d, J = 11.3 Hz, 1H), 3.97-3.89 (m, 1H), 3.80 (dd, J = 12.3, 3.6 Hz, 1H), 3.70-3.59 (m, 2H), 3.49 (d, J = 9.9 Hz, 1H), 2.78-2.69 (m, 2H), 2.22 (dd, J = 18.0, 8.0 Hz, 2H), 2.00 (d, J = 11.8 Hz, 1H), 1.68-1.57 (m, 1H), 1.45 (s, 3H), 1.37 (s, 3H), 1.19 (s, 3H). | 725.6 |

-continued

| Compound | Structure | $^1H$ NMR | LC-MS $[M + H]^+$ |
|---|---|---|---|
| 4 | 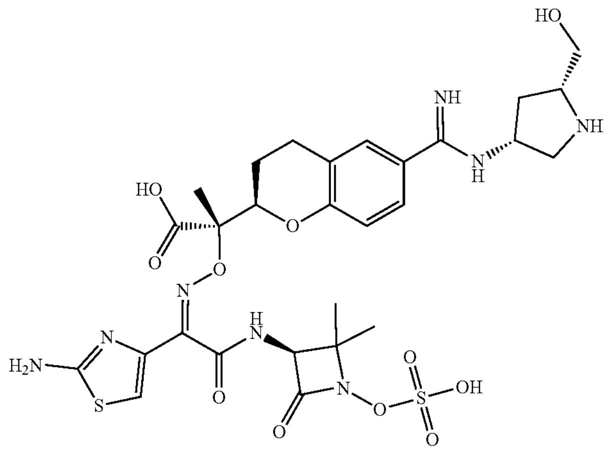 [SMILES: CC1(C)[C@H](NC(=O)/C(=N\O[C@](C)(C(=O)O)[C@H]2CCc3cc(C(=N)N[C@H]4CN[C@@H](CO)C4)ccc3O2)c2csc(N)n2)C(=O)N1OS(=O)(=O)O] (S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((3R,5R)-5-(hydroxymethyl)-pyrrolidin-3-yl)carbamimidoyl)-chroman-2-yl)propanoic acid | $^1H$ NMR (400 MHz, 4:1 $D_2O$/d-DMSO) δ: 7.41-7.31 (m, 2H), 6.85-6.77 (m, 2H), 4.57 (s, 1H), 4.55-4.42 (m, 1H), 4.30 (d, J = 11.1 Hz, 1H), 3.82 (d, J = 12.1 Hz, 2H), 3.70-3.56 (m, 2H), 3.43 (dd, J = 12.7, 4.3 Hz, 1H), 2.79-2.69 (m, 2H), 2.69-2.57 (m, 1H), 1.96 (dd, J = 15.2, 6.9 Hz, 2H), 1.67-1.58 (m, 1H), 1.44 (s, 3H), 1.37 (s, 3H), 1.19 (s, 3H). | 725.4 |
| 5 | 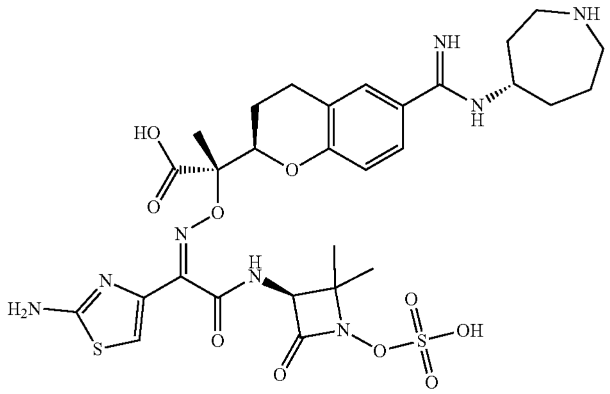 [SMILES: CC1(C)[C@H](NC(=O)/C(=N\O[C@](C)(C(=O)O)[C@H]2CCc3cc(C(=N)N[C@H]4CCCNCC4)ccc3O2)c2csc(N)n2)C(=O)N1OS(=O)(=O)O] (S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((S)-azepan-4-yl)carbamimidoyl)-chroman-2-yl)propanoic acid | $^1HNMR$ (500 MHz, 4:1 $D_2O$/d-DMSO) δ: 7.47 (s, 1H), 7.44 (dd, J = 8.6, 2.3 Hz, 1H), 6.97 (d, J = 8.6 Hz, 1H), 6.91 (s, 1H), 4.69 (s, 1H), 4.46 (dd, J = 11.1, 2.0 Hz, 1H), 3.95 (dq, J = 9.0, 4.5 Hz, 1H), 3.48-3.40 (m, 1H), 3.37-3.30 (m, 1H), 3.27-3.18 (m, 2H), 2.93-2.79 (m, 2H), 2.39-2.23 (m, 2H), 2.16-1.99 (m, 3H), 1.93-1.70 (m, 3H), 1.55 (s, 3H), 1.49 (s, 3H), 1.32 (s, 3H). | 723.5 |
| 6 | 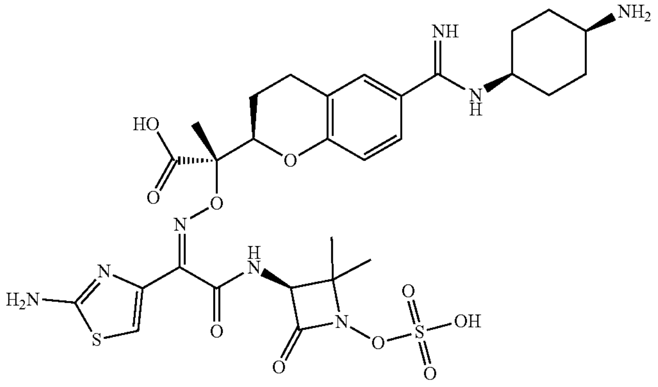 [SMILES: CC1(C)[C@H](NC(=O)/C(=N\O[C@](C)(C(=O)O)[C@H]2CCc3cc(C(=N)N[C@H]4CC[C@@H](N)CC4)ccc3O2)c2csc(N)n2)C(=O)N1OS(=O)(=O)O] (S)-2-((R)-6-(N-((1s,4S)-4-aminocyclo-hexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)-amino)oxy)propanoic acid | $^1H$ NMR (400 MHz, 4:1 $D_2O$/d-DMSO) δ: 7.39-7.31 (m, 2H), 6.89-6.78 (m, 2H), 4.60 (s, 1H), 4.34 (d, J = 10.7 Hz, 1H), 3.80-3.74 (m, 1H), 3.33-3.22 (m, 1H), 2.83-2.69 (s, 2H), 2.02 (d, J = 12.2 Hz, 1H), 1.89-1.60 (m, 9H), 1.46 (s, 3H), 1.38 (s, 3H), 1.20 (s, 3H). | 723.6 |

Example 9: Preparation of Compound 7

(S)-2-((R)-6-(N-((1 s,3S)-3-aminocyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

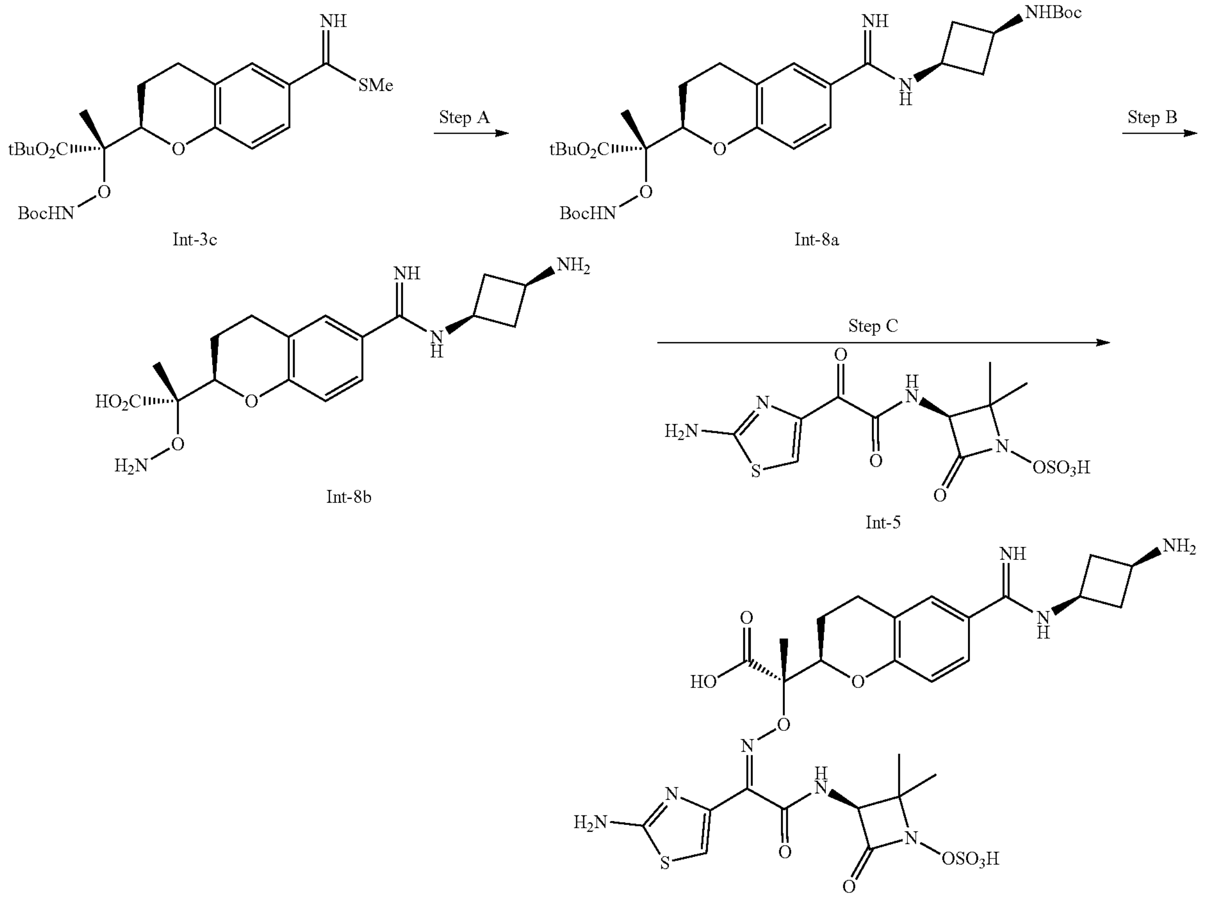

Int-3c

Int-8a

Int-8b

Int-5

Compound 7

Step A—Synthesis of Intermediate 8a To a vial containing a mixture of cis-tert-butyl N-(3-aminocyclobutyl)carbamate (0.065 mL, 0.385 mmol) in anhydrous acetonitrile (1 mL) were added a solution of intermediate 3c (0.11 g, 0.238 mmol) and acetic acid (0.044 mL, 0.771 mmol) in anhydrous acetonitrile (1 mL). The reaction mixture was heated at 65° C. for 2 h, then cooled to ambient temperature and purified via reverse phase HPLC (ISCO $C_{18}$Aq 50 g; product elutes at 65% ACN+0.05% TFA/water+0.05% TFA) with gradient elution 0-100% ACN+0.05% TFA/water+0.05% TFA. The desired fractions were collected and concentrated in vacuo. The resulting aqueous residue was partitioned between brine and ethyl acetate. The brine was back extracted with ethyl acetate. The combined organic layers were dried over anhydrous sodium sulfate, and concentrated in vacuo to give the intermediate 8a. LC-MS: m/z 605.4 $[M+H]^+$.

Step B—Synthesis of Intermediate 8b To a vial containing intermediate 8a (0.1108 g, 0.183 mmol) was added 2:1 trifluoroacetic acid/anhydrous dichloromethane (2 mL) at ambient temperature. The reaction mixture was stirred for 16.5 h, then a solution of 4:1 MeOH/toluene (10 mL) was added to the reaction and the mixture was concentrated in vacuo. The resulting residue was azeotroped with 4:1 MeOH/toluene (10 mL) and dried under high vacuum to give the intermediate 8b. LC-MS: m/z 349.16 $[M+H]^+$.

Step C—Synthesis of Compound 7 To a vial charged with intermediate 8b (0.183 mmol), intermediate 5 (79 wt %, 0.129 g, 0.199 mmol), and powdered molecular sieves 4 Å (325 mesh particle; 0.100 g, dried under high vacuum with heat) was added anhydrous dimethylacetamide (1.2 mL) at ambient temperature. The reaction mixture was stirred for 18 h, then filtered through a Celite™ pad. The Celite™ pad was washed well with MeOH. The filtrate was concentrated in vacuo, and the remaining residue was cooled to 0° C., followed by the addition of DCM (6 mL) with stirring. The resulting precipitate was collected by centrifugation (4000 rpm). The supernatant was decanted and the insoluble solid was triturated with DCM (3 mL). The centrifugation and supernatant decanting steps were repeated to give a crude solid, which was purified by RP HPLC (XSelect CSH Prep C18; 5 uM OBD; 50×250 mm; 0%-13% ACN/(water+0.16% TFA) over 11 min.; isocratic at 13% ACN/(water+0.16% TFA) for 14 min). The product fractions were collected, concentrated in vacuo to remove acetonitrile, and the aqueous layer was directly loaded onto an Amberchrom CG161M column (26 g), washed with 9 CV of (water+0.1% FA), and eluted off with 3 CV of 100% (ACN+0.1% FA) followed by 3 CV of 50% (ACN+0.1% FA)/(water+0.1%

FA). The desired fractions were collected, concentrated in vacuo, and the resulting aqueous residue was lyophilized to give the title compound as the formic acid salt. LC-MS: m/z 695.2 $[M+H]^+$. $^1$HNMR (400 MHz, 4:1 $D_2O$/d-DMSO) δ: 7.36 (s, 1H), 7.35-7.29 (m, 1H), 6.82 (d, J=8.6 Hz, 1H), 6.81 (s, 1H), 4.57 (s, 1H), 4.32 (d, J=11.6 Hz, 1H), 3.96 (t, J=8.0 Hz, 1H), 3.62-3.51 (m, 1H), 2.85 (dt, J=7.5, 2.6 Hz, 2H), 2.72 (i, 2H), 2.27 (q, J=8.9 Hz, 2H), 2.01 (d, J=12.2 Hz, 1H), 1.65 (m 1H), 1.45 (s, 3H), 1.36 (s, 3H), 1.18 (s, 3H).

Example 10: Preparation of Compounds 8 to 20

Starting from the appropriate commercially available mono-Boc protected diamines, the following compounds were prepared according to the procedure of Example 9:

| Compound | Structure | $^1$H NMR | LC-MS $[M + H]^+$ |
|---|---|---|---|
| 8 | 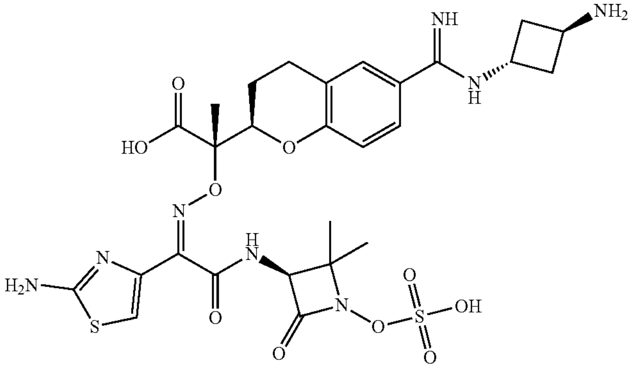 [SMILES: CC1(C)[C@H](NC(=O)/C(=N\O[C@](C)(C(=O)O)[C@H]2CCc3cc(C(=N)N[C@H]4C[C@H](N)C4)ccc3O2)c2csc(N)n2)C(=O)N1OS(=O)(=O)O] (S)-2-((R)-6-(N-((1r,3R)-3-aminocyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)-amino)oxy) propanoic acid | $^1$HNMR (400 MHz, 4:1 $D_2O$/d-DMSO) δ: 7.39-7.29 (m, 2H), 6.87-6.79 (m, 2H), 4.57 (s, 1H), 4.35 (dd, J = 11.2, 2.0 Hz, 1H), 4.26 (td, J = 8.1, 4.1 Hz, 1H), 3.94 (p, J = 7.2, 6.8 Hz, 1H), 2.61 (dt, J = 19.3, 9.3 Hz, 4H), 2.03 (d, J = 13.3 Hz, 1H), 1.74-1.62 (m, 1H), 1.46 (s, 3H), 1.36 (s, 3H), 1.18 (s, 3H). | 695.1 |
| 9 | 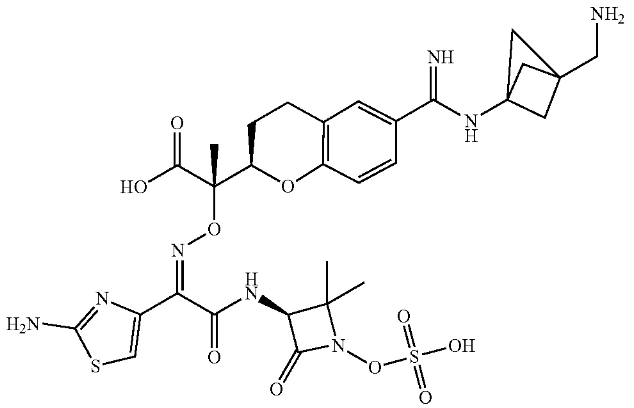 [SMILES: CC1(C)[C@H](NC(=O)/C(=N\O[C@](C)(C(=O)O)[C@H]2CCc3cc(C(=N)NC45CC(CN)(C4)C5)ccc3O2)c2csc(N)n2)C(=O)N1OS(=O)(=O)O] (S)-2-((R)-6-(N-(3-(amino-methyl)bicyclo[1.1.1]pentan-1-yl)carbamimidoyl)chroman-2-yl)-2-((((Z)-1-(2-amino-thiazol-4-yl)-2-(((S)-2,2-dimethyl-4-oxo-1-(sulfooxy)-azetidin-3-yl)amino)-2-oxoethylidene)amino)oxy) propanoic acid | $^1$H NMR (400 MHz, 4:1 $D_2O$/d-DMSO) 7.35-7.25 (m, 2H), 6.86-6.77 (m, 2H), 4.55 (s, 1H), 4.42-4.28 (m, 1H), 3.14 (s, 2H), 2.80-2.65 (m, 2H), 2.22 (s, 6H), 2.02 (d, J = 13.1 Hz, 1H), 1.73-1.55 (m, 1H), 1.45 (s, 3H), 1.35 (s, 3H), 1.18 (s, 3H). | 721.3 |

-continued

| Compound | Structure | $^1$H NMR | LC-MS $[M + H]^+$ |
|---|---|---|---|
| 10 | 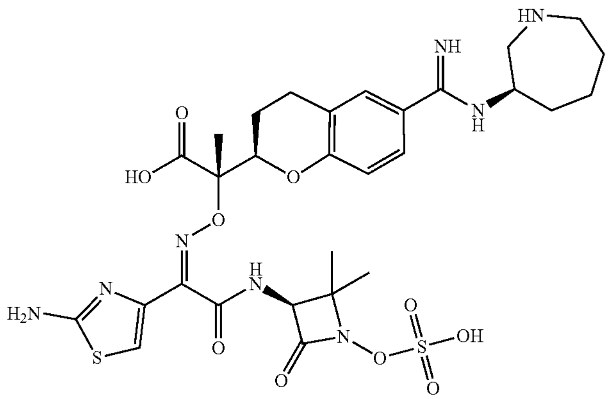 [SMILES: CC1(C)[C@H](NC(=O)/C(=N\O[C@](C)(C(=O)O)[C@H]2CCc3cc(C(=N)N[C@@H]4CCCCNC4)ccc3O2)c2csc(N)n2)C(=O)N1OS(=O)(=O)O] (S)-2-((((Z)-1-(2-amino-thiazol-4-yl)-2-(((S)-2,2-dimethyl-4-oxo-1-(sulfooxy)-azetidin-3-yl)amino)-2-oxoethylidene)-amino)oxy)-2-((R)-6-(N-((R)-azepan-3-yl)-carbamimidoyl)-chroman-2-yl)propanoic acid | $^1$H NMR (400 MHz, 4:1 $D_2O$/d-DMSO) δ: 7.34 (s, 1H), 7.28 (dd, J = 8.5, 2.0 Hz, 1H), 6.84-6.77 (m, 2H), 4.55 (s, 1H), 4.31 (d, J = 11.2 Hz, 1H), 4.07 (dd, J = 8.7, 4.3 Hz, 1H), 3.49-3.41 (m, 1H), 3.30-3.09 (m, 3H), 2.78-2.67 (m, 2H), 2.17-2.08 (m, 1H), 2.00 (d, J = 12.7 Hz, 1H), 1.92-1.60 (m, 5H), 1.58-1.48 (m, 1H), 1.45 (s, 3H), 1.36 (s, 3H), 1.18 (s, 3H). | 723.4 |
| 11 | 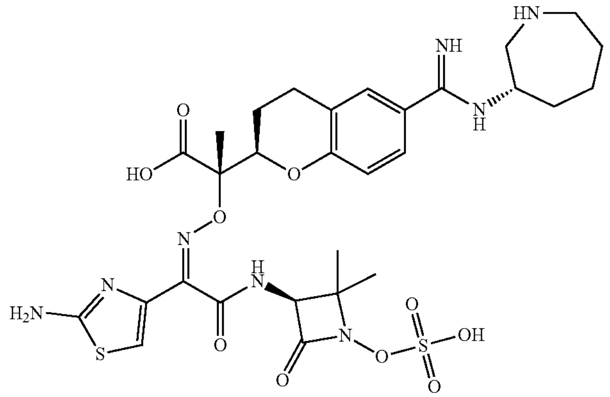 [SMILES: CC1(C)[C@H](NC(=O)/C(=N\O[C@](C)(C(=O)O)[C@H]2CCc3cc(C(=N)N[C@H]4CCCCNC4)ccc3O2)c2csc(N)n2)C(=O)N1OS(=O)(=O)O] (S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((S)-azepan-3-yl)-carbamimidoyl)-chroman-2-yl)-propanoic acid | $^1$H NMR (400 MHz, 4:1 $D_2O$/d-DMSO) δ: 7.37-7.27 (m, 2H), 6.84-6.79 (m, 2H), 4.57 (s, 1H), 4.32 (d, J = 11.5 Hz, 1H), 4.08 (dt, J = 9.1, 4.4 Hz, 1H), 3.47 (dd, J = 14.0, 3.9 Hz, 1H), 3.32-3.19 (m, 2H), 3.18-3.08 (m, 1H), 2.79-2.68 (m, 2H), 2.15 (d, J = 14.1 Hz, 1H), 2.01 (d, J = 13.2 Hz, 1H), 1.92-1.59 (m, 5H), 1.57-1.49 (m, 1H), 1.45 (s, 3H), 1.36 (s, 3H), 1.18 (s, 3H). | 723.4 |
| 12 | 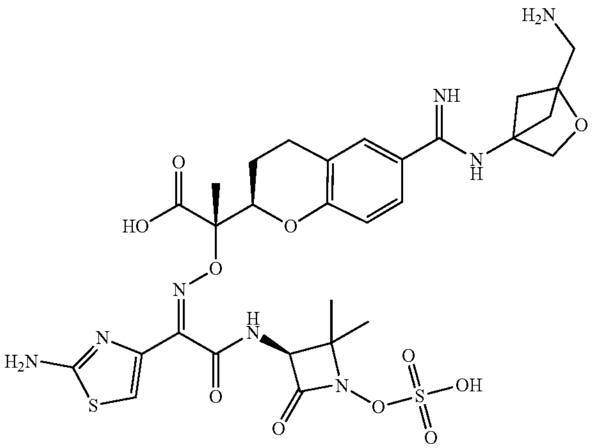 [SMILES: CC1(C)[C@H](NC(=O)/C(=N\O[C@](C)(C(=O)O)[C@H]2CCc3cc(C(=N)NC45COC(CN)(C4)C5)ccc3O2)c2csc(N)n2)C(=O)N1OS(=O)(=O)O] (S)-2-((R)-6-(N-(1-(amino-methyl)-2-oxabicyclo[2.1.1]-hexan-4-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxo-ethylidene)amino)oxy) propanoic acid | $^1$H NMR (400 MHz, 4:1 $D_2O$/d-DMSO) δ: 7.41-7.32 (m, 2H), 6.89-6.78 (m, 2H), 4.56 (s, 1H), 4.39-4.32 (m, 1H), 3.86 (s, 2H), 3.33 (s, 2H), 2.82-2.67 (m, 2H), 2.26 (d, J = 4.5 Hz, 2H), 2.16 (d, J = 4.9 Hz, 2H), 2.02 (d, J = 13.2 Hz, 1H), 1.67 (dd, J = 13.2, 6.0 Hz, 1H), 1.45 (s, 3H), 1.36 (s, 3H), 1.19 (s, 3H). | 737.4 |

-continued

| Compound | Structure | $^1$H NMR | LC-MS $[M + H]^+$ |
|---|---|---|---|
| 13 | 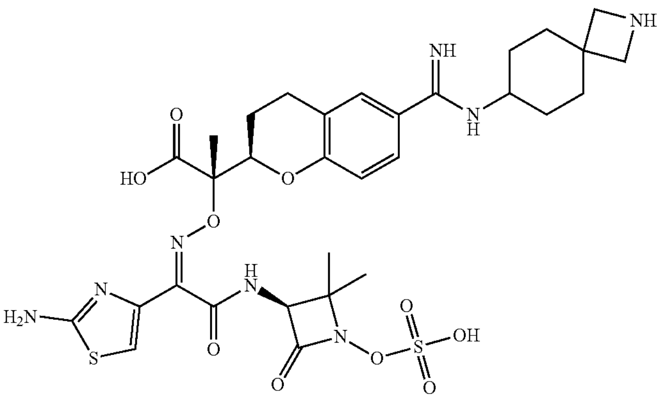 [SMILES: CC1(C)[C@H](NC(=O)/C(=N\O[C@](C)(C(=O)O)[C@H]2CCc3cc(C(=N)NC4CCC5(CC4)CNC5)ccc3O2)c2csc(N)n2)C(=O)N1OS(=O)(=O)O] (S)-2-((R)-6-(N-(2-azaspiro[3.5]-nonan-7-yl)-carbamimidoyl)-chroman-2-yl)-2-((((Z)-1-(2-amino-thiazol-4-yl)-2-(((S)-2,2-dimethyl-4-oxo-1-(sulfooxy)-azetidin-3-yl)amino)-2-oxo-ethylidene)amino)oxy) propanoic acid | $^1$H NMR (400 MHz, 4:1 $D_2O$/d-DMSO) δ: 7.35-7.26 (m, 2H), 6.85-6.79 (m, 2H), 4.56 (s, 1H), 4.34 (d, J = 11.2 Hz, 1H), 3.79 (bs, 2H), 3.70 (bs, 2H), 3.48 (t, J = 10.7 Hz, 1H), 2.80-2.68 (m, 2H), 1.99 (d, J = 12.3 Hz, 3H), 1.90 (d, J = 13.5 Hz, 2H), 1.72-1.61 (m, 1H), 1.55 (t, J = 12.5 Hz, 2H), 1.46 (s, 3H), 1.36 (s, 3H), 1.36-1.24 (m, 2H), 1.31 (s, 1H), 1.17 (s, 3H). | 749.3 |
| 14 | 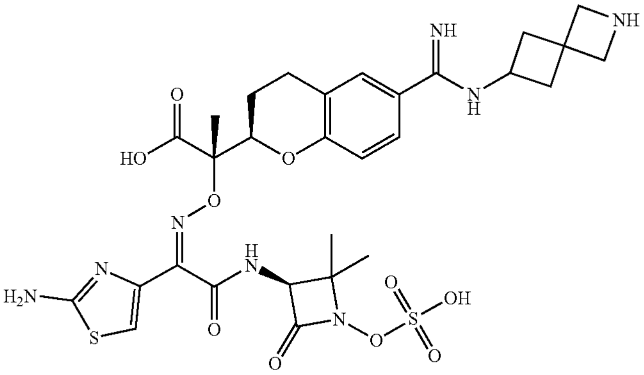 [SMILES: CC1(C)[C@H](NC(=O)/C(=N\O[C@](C)(C(=O)O)[C@H]2CCc3cc(C(=N)NC4CC5(CNC5)C4)ccc3O2)c2csc(N)n2)C(=O)N1OS(=O)(=O)O] (S)-2-((R)-6-(N-(2-azaspiro[3.3]-heptan-6-yl)carbamimidoyl)-chroman-2-yl)-2-((((Z)-1-(2-amino-thiazol-4-yl)-2-(((S)-2,2-dimethyl-4-oxo-1-(sulfooxy)-azetidin-3-yl)amino)-2-oxo-ethylidene)amino)oxy) propanoic acid | $^1$H NMR (400 MHz, 4:1 $D_2O$/d-DMSO) δ: 7.40-7.28 (m, 2H), 6.87-6.82 (m, 2H), 4.57 (s, 1H), 4.37 (dd, J = 11.1, 2.1 Hz, 1H), 4.09 (s, 2H), 4.07-3.95 (m, 3H), 2.76 (ddd, J = 10.2, 7.5, 2.5 Hz, 4H), 2.43-2.32 (m, 2H), 2.03 (d, J = 13.1 Hz, 1H), 1.74-1.60 (m, 1H), 1.47 (s, 3H), 1.36 (s, 3H), 1.17 (s, 3H). | 721.8 |
| 15 | 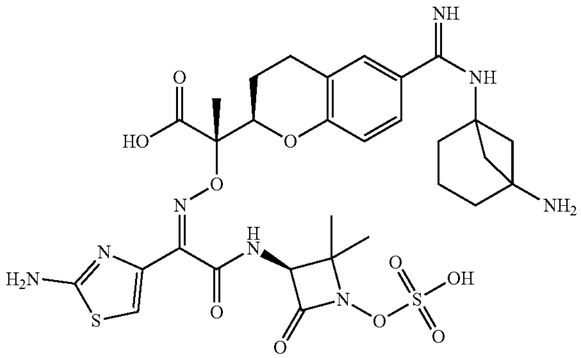 [SMILES: CC1(C)[C@H](NC(=O)/C(=N\O[C@](C)(C(=O)O)[C@H]2CCc3cc(C(=N)NC45CCCC(N)(C4)C5)ccc3O2)c2csc(N)n2)C(=O)N1OS(=O)(=O)O] (S)-2-((R)-6-(N-(5-amino-bicyclo[3.1.1]heptan-1-yl)-carbamimidoyl)chroman-2-yl)-2-((((Z)-1-(2-amino-thiazol-4-yl)-2-(((S)-2,2-dimethyl-4-oxo-1-(sulfooxy)azetidin-3-yl)amino)-2-oxoethylidene)-amino)oxy)propanoic acid | $^1$H NMR (400 MHz, 4:1 $D_2O$/d-DMSO) δ: 7.40-7.27 (m, 2H), 6.90-6.77 (m, 2H), 4.56 (s, 1H), 4.36 (dd, J = 11.2, 2.0 Hz, 1H), 2.81-2.68 (m, 2H), 2.41 (dd, J = 6.9, 2.1 Hz, 2H), 2.31 (d, J = 7.2 Hz, 2H), 2.07-1.83 (m, 7H), 1.75-1.56 (m, 1H), 1.46 (s, 3H), 1.37 (s, 3H), 1.19 (s, 3H). | 735.6 |

-continued

| Compound | Structure | $^1$H NMR | LC-MS $[M + H]^+$ |
|---|---|---|---|
| 16 | 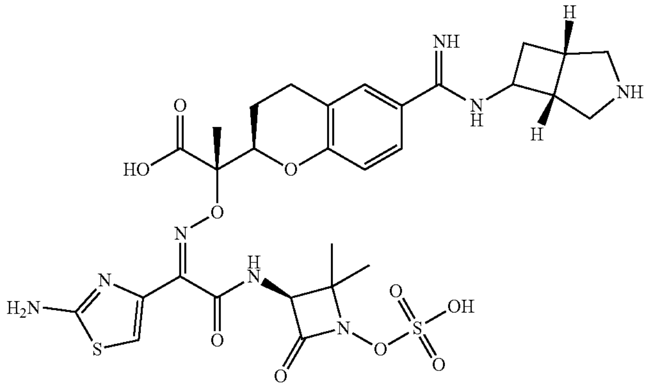 [SMILES: CC1(C)[C@H](NC(=O)/C(=N\O[C@](C)(C(=O)O)[C@H]2CCc3cc(C(=N)NC4C[C@@H]5CNC[C@H]45)ccc3O2)c2csc(N)n2)C(=O)N1OS(=O)(=O)O]<br>(2S)-2-((2R)-6-(N-((1S,5R)-3-azabicyclo[3.2.0]heptan-6-yl)-carbamimidoyl)chroman-2-yl)-2-((((Z)-1-(2-amino-thiazol-4-yl)-2-(((S)-2,2-dimethyl-4-oxo-1-(sulfooxy)-azetidin-3-yl)amino)-2-oxoethylidene)-amino)oxy)-propanoic acid | $^1$H NMR (400 MHz, 4:1 $D_2O$/d-DMSO) δ: 7.48-7.27 (m, 2H), 6.87-6.74 (m, 2H), 4.64 (s, 1H), 4.59 (d, J = 2.2 Hz, 1H), 4.41-4.19 (m, 2H), 3.55-3.46 (m, 1H), 3.41-2.99 (m, 5H), 2.80-2.66 (m, 3H), 2.04-1.89 (m, 2H), 1.69-1.57 (m, 1H), 1.45 (s, 4H), 1.37 (s, 3H), 1.19 (m, 3H). | 721.4 |
| 17 | 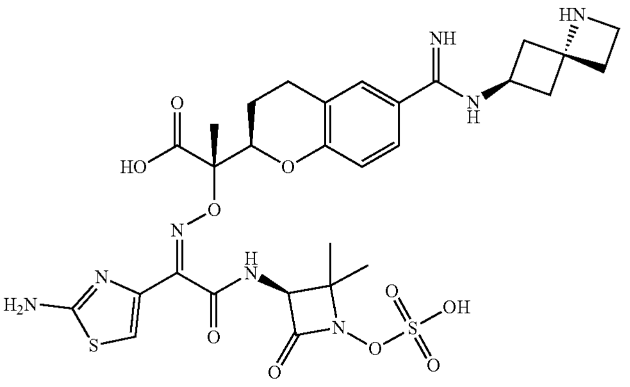 [SMILES: CC1(C)[C@H](NC(=O)/C(=N\O[C@](C)(C(=O)O)[C@H]2CCc3cc(C(=N)N[C@H]4C[C@@]5(CCN5)C4)ccc3O2)c2csc(N)n2)C(=O)N1OS(=O)(=O)O]<br>(S)-2-((R)-6-(N-((4R,6s)-1-azas-piro[3.3]heptan-6-yl)-carbam-imidoyl)chroman-2-yl)-2-((((Z)-1-(2-amino-thiazol-4-yl)-2-(((S)-2,2-dimethyl-4-oxo-1-(sulfooxy)-azetidin-3-yl)amino)-2-oxo-ethylidene)amino)oxy) propanoic acid | $^1$H NMR (400 MHz, $D_2O$/d-DMSO) δ: 7.39-7.26 (m, 2H), 6.89-6.80 (m, 2H), 4.57 (s, 1H), 4.37 (d, J = 10.7 Hz, 1H), 4.25-4.13 (m, 1H), 3.81 (t, J = 8.3 Hz, 2H), 3.09 (dd, J = 14.7, 8.2 Hz, 2H), 2.82-2.69 (m, 2H), 2.59 (q, J = 7.6, 6.8 Hz, 4H), 2.04 (d, J = 11.7 Hz, 1H), 1.74-1.63 (m, 1H), 1.48 (s, 3H), 1.37 (s, 3H), 1.18 (s, 3H). | 721.7 |
| 18 | 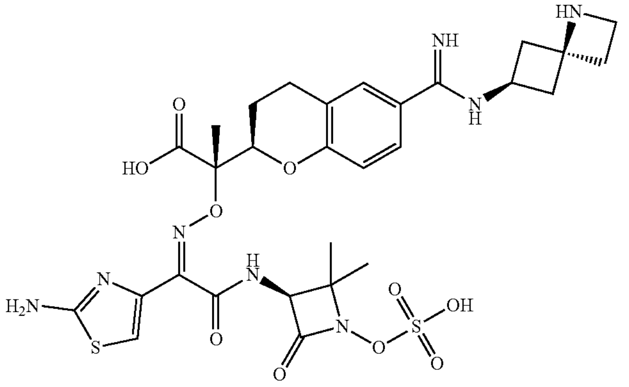 [SMILES: CC1(C)[C@H](NC(=O)/C(=N\O[C@](C)(C(=O)O)[C@H]2CCc3cc(C(=N)N[C@H]4C[C@]5(CCN5)C4)ccc3O2)c2csc(N)n2)C(=O)N1OS(=O)(=O)O]<br>(S)-2-((R)-6-(N-((4S,6r)-1-azaspiro[3.3]heptan-6-yl)-carbamimidoyl)chroman-2-yl)-2-((((Z)-1-(2-amino-thiazol-4-yl)-2-(((S)-2,2-dimethyl-4-oxo-1-(sulfooxy)-azetidin-3-yl)amino)-2-oxoethylidene)-amino)oxy)propanoic acid | $^1$H NMR (400 MHz, 4:1 $D_2O$/d-DMSO) δ: 7.42-7.24 (m, 2H), 6.87-6.80 (m, 2H), 4.57 (s, 1H), 4.35 (d, J = 11.2 Hz, 1H), 4.02 (q, J = 7.8 Hz, 1H), 3.82 (t, J = 8.4 Hz, 2H), 2.94 (dd, J = 10.3, 7.4 Hz, 2H), 2.80-2.58 (m, 6H), 2.03 (d, J = 12.5 Hz, 1H), 1.74-1.60 (m, 1H), 1.47 (s, 3H), 1.36 (s, 3H), 1.17 (s, 3H). | 721.5 |

-continued

| Compound | Structure | $^1H$ NMR | LC-MS $[M + H]^+$ |
|---|---|---|---|
| 19 | 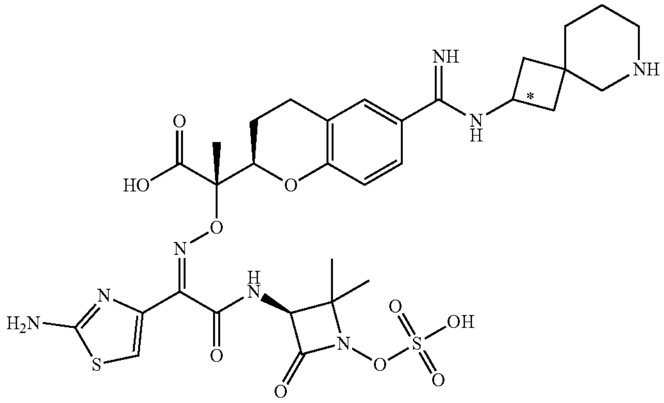 [SMILES: CC1(C)[C@H](NC(=O)/C(=N\O[C@](C)(C(=O)O)[C@H]2CCc3cc(C(=N)NC4CC5(CCCNC5)C4)ccc3O2)c2csc(N)n2)C(=O)N1OS(=O)(=O)O] (S)-2-((R)-6-(N-((2s,4R)-6-azaspiro[3.5]nonan-2-yl)-carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)-amino)oxy)propanoic acid (Single diastereomer, stereochemistry at * marked carbon centers are unassigned) | $^1H$ NMR (400 MHz, 4:1 $D_2O$/d-DMSO) δ: 7.38-7.30 (m, 2H), 6.88-6.79 (m, 2H), 4.57 (s, 1H), 4.36 (d, J = 10.6 Hz, 1H), 4.12 (t, J = 7.9 Hz, 1H), 3.10 (s, 2H), 2.96 (bs, 2H), 2.79-2.69 (m, 2H), 2.50-2.41 (m, 2H), 2.04-1.95 (m, 3H), 1.74-1.58 (m, 5H), 1.47 (s, 3H), 1.37 (s, 3H), 1.19 (s, 3H). | 749.7 |
| 20 | 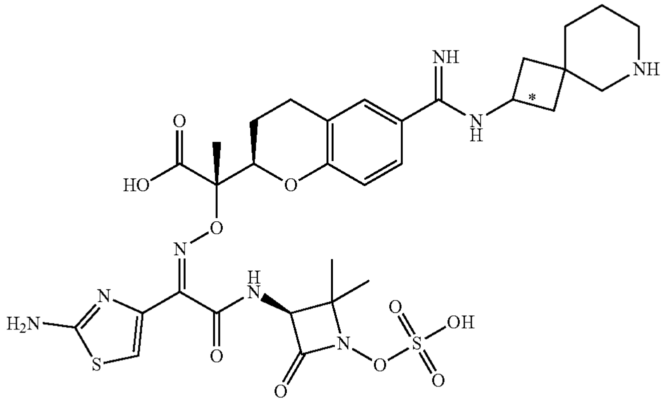 [SMILES: CC1(C)[C@H](NC(=O)/C(=N\O[C@](C)(C(=O)O)[C@H]2CCc3cc(C(=N)NC4CC5(CCCNC5)C4)ccc3O2)c2csc(N)n2)C(=O)N1OS(=O)(=O)O] (S)-2-((R)-6-(N-((2r,4S)-6-azaspiro[3.5]nonan-2-yl)-carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (Single diastereomer, stereochemistry at * marked carbon centers are unassigned) | $^1H$ NMR (400 MHz, 4:1 $D_2O$/d-DMSO) δ: 7.39-7.30 (m, 2H), 6.88-6.80 (m, 2H), 4.56 (s, 1H), 4.35 (d, J = 10.6 Hz, 1H), 4.18 (t, J = 8.0 Hz, 1H), 3.02 (s, 2H), 2.96 (bs, 2H), 2.83-2.69 (m, 2H), 2.43-2.34 (m, 2H), 2.09-1.94 (m, 3H), 1.69 (bs, 5H), 1.47 (s, 3H), 1.37 (s, 3H), 1.18 (s, 3H). | 749.5 |

Example 11: Preparation of Compound 21

(S)-2-((R)-6-(N-(7-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

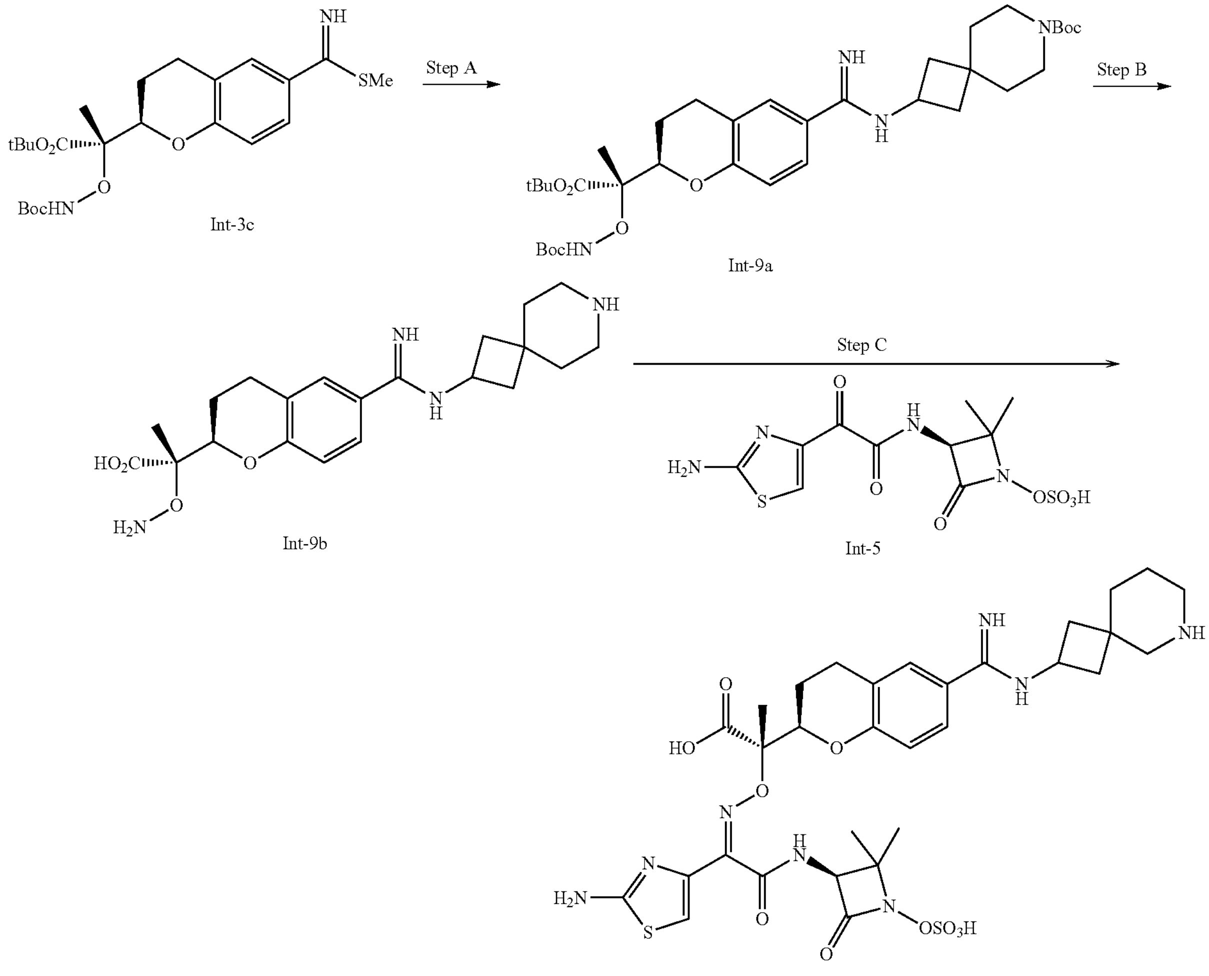

Int-3c

Int-9a

Int-9b

Int-5

Compound 21

Step A—Synthesis of Intermediate 9a To a mixture of 2-amino-7-azaspiro[3.5]nonane-7-carboxylic acid tert-butyl ester (92.6 mg, 0.386 mmol) in anhydrous acetonitrile (1 mL) was added a solution of intermediate 3c (0.11 g, 0.238 mmol) and acetic acid (0.044 mL, 0.771 mmol) in anhydrous acetonitrile (1 mL). The reaction mixture was heated at 65° C. for 2 h, then cooled to ambient temperature and purified on a reverse phase HPLC (ISCO C18Aq 50 g; product elutes at 65% ACN+0.05% TFA/water+0.05% TFA) with gradient elution 0-100% ACN+0.05% TFA/water+0.05% TFA. The desired fractions were collected and concentrated in vacuo. The resulting aqueous residue was partitioned between brine and ethyl acetate, and further back-extracted with ethyl acetate. The combined organic layers were dried over anhydrous sodium sulfate, and then concentrated in vacuo to give intermediate 9a. LC-MS: m/z 659.5 $[M+H]^+$.

Step B—Synthesis of Intermediate 9b To a vial containing intermediate 9a (0.1145 g, 0.174 mmol) was added 2:1 trifluoroacetic acid/anhydrous dichloromethane (2 mL) at ambient temperature. The reaction was stirred for 16.5 h, then a solution of 4:1 MeOH/toluene (10 mL) was added to the reaction and the mixture was concentrated in vacuo. The resulting residue was azeotroped with 4:1 MeOH/toluene (10 mL) and the resulting residue was dried under high vacuum to give intermediate 9b. LC-MS: m/z 403.37 $[M+H]^+$.

Step C—Synthesis of Compound 21 To a vial charged with intermediate 9b (0.174 mmol), intermediate 5 (79% wt, 0.12 g, 0.260 mmol), and powdered molecular sieves 4 Å (325 mesh particle; 0.100 g, dried under high vacuum with heat) was added anhydrous dimethylacetamide (1.2 mL) at ambient temperature. The reaction mixture was stirred for 19 h, then filtered through a Celite™ pad. The Celite™ pad was washed with MeOH, and the filtrate was concentrated in vacuo. The remaining residue was cooled to 0° C., then DCM (6 mL) was added, and the mixture was stirred slowly. The resulting solids were collected by centrifugation (4000 rpm). The supernatant was decanted and the insoluble solid was triturated with DCM (3 mL). The centrifugation and decanting of supernatant was repeated to give the crude product, which was purified by RP HPLC (XSelect CSH Prep C18; 5 uM OBD; 50×250 mm; 0%-13% ACN/(water+0.16% TFA) over 11 min.; isocratic at 13% ACN/(water+

0.16% TFA) for 14 min. The product fractions were collected, and concentrated in vacuo. The resulting aqueous layer was directly loaded onto an Amberchrom CG161M column (26 g), washed with 9 CV of (water+0.1% FA), and eluted off with 3 CV of 100% (ACN+0.1% FA) followed by 3 CV of 50% (ACN+0.1% FA)/(water+0.1% FA). The product fractions were collected, concentrated in vacuo, and the resulting aqueous residue was lyophilized to give compound 21 as the formic acid salt. LC-MS: m/z 749.6 $[M+H]^+$. $^1$HNMR (400 MHz, 4:1 $D_2O/CD_3CN$) δ: 7.51-7.37 (m, 2H), 7.01-6.86 (m, 2H), 4.67 (s, 1H), 4.48 (d, J=10.5 Hz, 1H), 4.23 (t, J=7.8 Hz, 1H), 3.13 (dt, J=25.1, 5.6 Hz, 4H), 2.85 (m, 2H), 2.52 (dd, J=11.8, 9.5 Hz, 2H), 2.19-2.01 (m, 3H), 1.90-1.73 (m, 5H), 1.58 (s, 3H), 1.49 (s, 3H), 1.30 (s, 3H).

Example 12: Preparation of Compounds 22 and 23

(S)-2-((R)-6-(N-((2r,4S)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((2s,4R)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

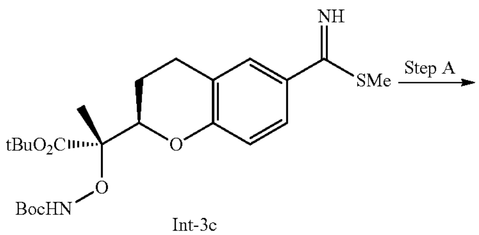

Int-3c

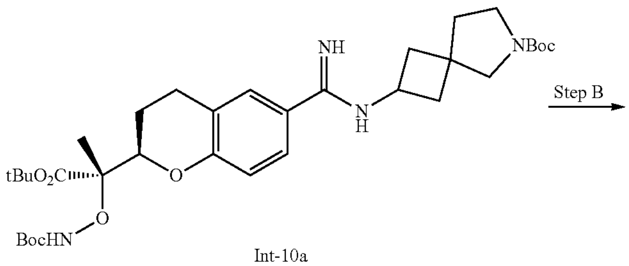

Int-10a

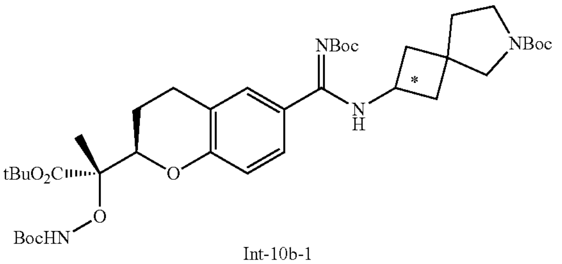

Int-10b-1

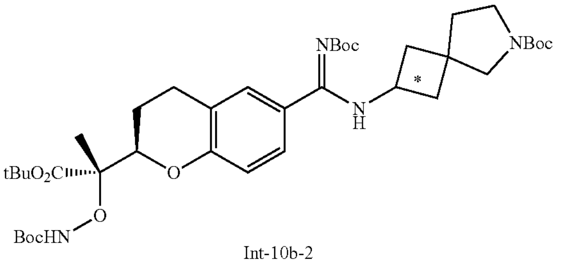

Int-10b-2

-continued

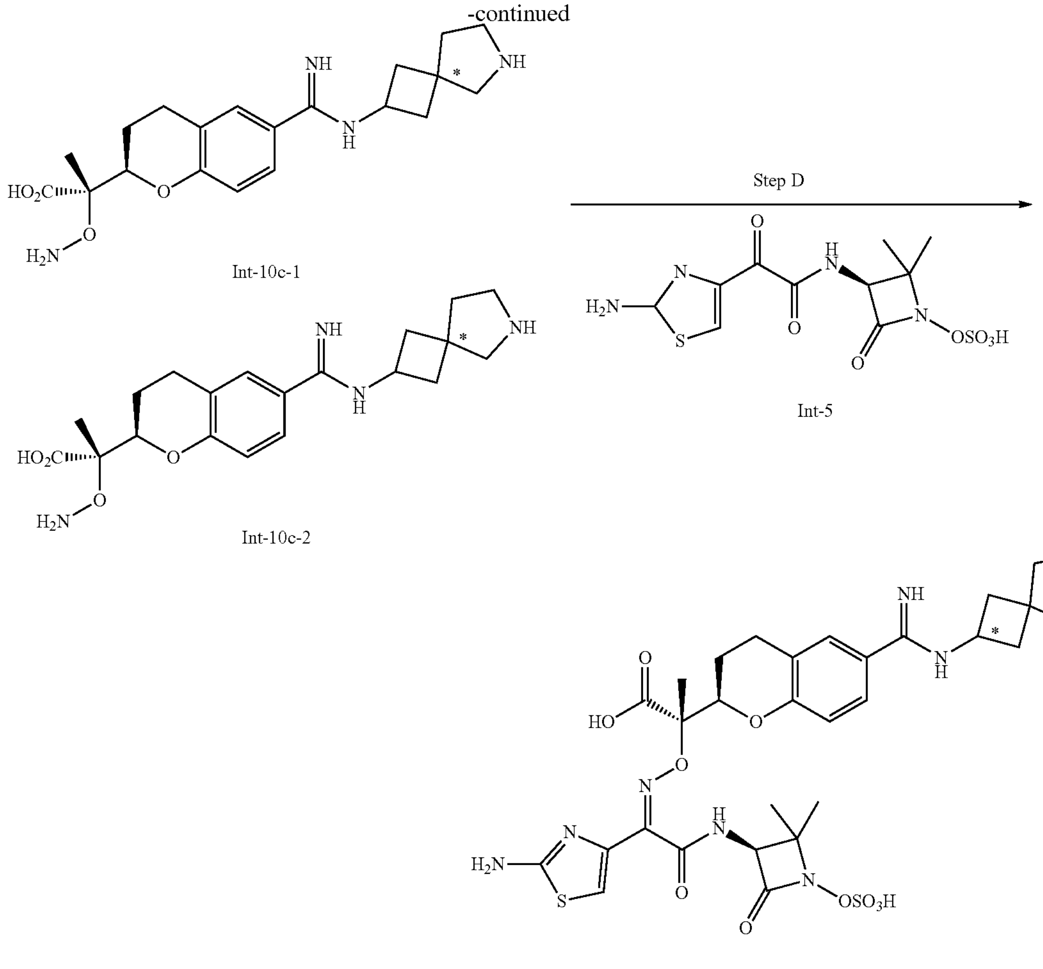

Int-10c-1

Int-10c-2

Int-5

Compound 22
Compound 23

Step A—Synthesis of Intermediate 10a To a vial containing a mixture of 2-amino-6-aza-spiro[3.4]octane-6-carboxylic acid tert-butyl ester (73.0 mg, 0.321 mmol) and intermediate 3c (0.1496 g, 0.321 mmol) was added a pre-made solution of acetic acid (0.055 mL, 0.962 mmol) in anhydrous acetonitrile (2 mL). The reaction mixture was heated at 70° C. for 2.5 h, then cooled to ambient temperature and purified on a reverse phase HPLC (ISCO C18Aq 50 g; product elutes at 65% ACN+0.05% TFA/water+0.05% TFA) with gradient elution 0-100% ACN+0.05% TFA/water+0.05% TFA. The desired fractions were collected and concentrated in vacuo. The resulting aqueous residue was partitioned between brine and ethyl acetate, and further back-extracted with ethyl acetate. The combined organic layers were dried over anhydrous sodium sulfate and concentrated in vacuo to give the desired compound. LC-MS: m/z 645.6 $[M+H]^+$.

Step B—Synthesis of Intermediate 10b To a solution of intermediate 10a (0.1832 g, 0.284 mmol) in anhydrous DCM (1.5 mL) was added triethylamine (0.119 mL, 0.852 mmol), followed by the addition of a solution of $(Boc)_2O$ (0.099 mL, 0.426 mmol) in DCM (1.5 mL). The reaction mixture was stirred at ambient temperature for 6 h. The reaction was then partitioned between EtOAc and saturated aqueous $NH_4Cl$. The organic layer was separated, dried over anhydrous sodium sulfate, and concentrated in vacuo. The resulting residue was purified by silica gel chromatography (Isco 24 g column; 0-100% (3:1 EtOAc/EtOH)/hexanes) to give the desired compound as diastereomers. LC-MS: m/z 745.5 $[M+H]^+$. The diastereomers were separated by chiral chromatography (IA, 2×15 cm column; IPA+0.25% IBA/$CO_2$) to give the two diastereomers: Intermediate 10b-1 (Peak 1); LC-MS: m/z 745.7 $[M+H]^+$, and Intermediate 10b-2 (Peak 2); LC-MS: m/z 745.7 $[M+H]^+$.

Step C—Synthesis of Intermediate 10C-2 To a vial containing intermediate 10b-2 (95 mg, 0.128 mmol) was added 2:1 trifluoroacetic acid/anhydrous dichloromethane (1.3 mL) at ambient temperature. The reaction was stirred for 16 h. Then a solution of 4:1 MeOH/toluene (5 mL) was added, and the mixture was concentrated in vacuo. The resulting residue was azeotroped with MeOH (5 mL) and then dried under high vacuum to give the desired compound. LC-MS: m/z 389.3 $[M+H]^+$.

Intermediate 10c-1 was prepared according to Step C using intermediate 10b-1 (37 mg, 0.050 mmol); LC-MS: m/z 389.3 $[M+H]^+$.

Step D—Synthesis of Compound 22 To a vial charged with intermediate 10c-2 (0.128 mmol), intermediate 5 (80 wt %, 0.0525 g, 0.115 mmol), and powdered molecular sieves 4 Å (325 mesh particle; 0.100 g, dried under high vacuum with heat) was added anhydrous dimethylacetamide (0.5 mL) at ambient temperature. The reaction mixture was stirred for 16.5 h, then filtered to remove the molecular sieves, and the solids were washed with MeOH. The filtrate was concentrated in vacuo, and the resulting residue was cooled to 0° C., followed by the addition of DCM (5 mL) and slowly stirring. The resulting solids were collected by centrifugation (4000 rpm). The supernatant was decanted and the insoluble solid was triturated with DCM (5 mL). The centrifugation and decanting of supernatant was repeated to give a crude solid. The solid was purified by a reverse phase HPLC (XSelect CSH Prep C18; 5 uM OBD; 50×250 mm; 0%-30% ACN/(water+0.16% TFA) over 12 min.; isocratic at 17-18% ACN/(water+0.16% TFA) for 5 min. The product fractions were collected, concentrated in vacuo, and the resulting aqueous layer was directly loaded onto an Amberchrom CG161M column (26 g), washed with 9 CV of (water+0.1% FA), and eluted off with 3 CV of 100% (ACN+0.1% FA) followed by 3 CV of 50% (ACN+0.1% FA)/(water+0.1% FA). The product fractions were collected, concentrated in vacuo, and the resulting aqueous residue was lyophilized to the title compound as the formic acid salt. $^1$HNMR (500 MHz, 4:1 $D_2O$/d-DMSO) δ: 7.50-7.42 (m, 2H), 6.99-6.91 (m, 2H), 4.68 (s, 1H), 4.48 (d, J=9.5 Hz, 1H), 4.36 (ddd, J=14.4, 8.3, 6.1 Hz, 1H), 3.33 (t, J=7.6 Hz, 2H), 3.07-2.99 (m, 2H), 2.88 (m, 2H), 2.63-2.55 (m, 2H), 2.17 (t, J=7.3 Hz, 3H), 2.07-1.97 (m, 2H), 1.88-1.71 (m, 1H), 1.59 (s, 3H), 1.49 (s, 3H), 1.30 (s, 3H). LC-MS: m/z 735.8 $[M+H]^+$.

Compound 23 was prepared according to Step D of Example 12 using intermediate 10c-1 (0.050 mmol). $^1$HNMR (500 MHz, 4:1 $D_2O$/d-DMSO) δ: 7.52-7.44 (m, 2H), 6.98 (d, J=8.6 Hz, 1H), 6.92 (s, 1H), 4.68 (s, 1H), 4.46 (d, J=10.6 Hz, 1H), 4.25-4.18 (m, 1H), 3.29 (t, J=7.3 Hz, 2H), 2.88-2.77 (m, 4H), 2.74-2.67 (m, 2H), 2.11-2.18 (m, 3H), 2.05 (p, J=8.2, 7.6 Hz, 2H), 1.84-1.73 (m, 1H), 1.58 (s, 3H), 1.49 (s, 3H), 1.31 (s, 3H). LC-MS: m/z 735.5 $[M+H]^+$.
*Each compound is a single diastereomer, stereochemistry at * marked carbon unassigned.

Example 13: Preparation of Intermediate 11f

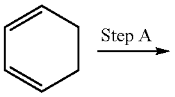

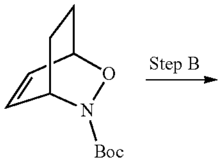

Int-11a

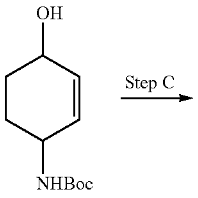

Int-11b

-continued

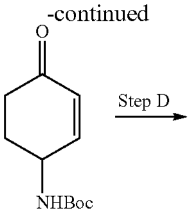

Int-11c

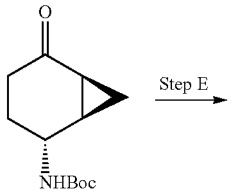

Int-11d

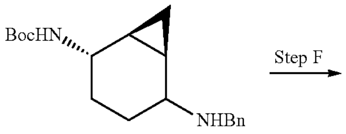

Int-11e

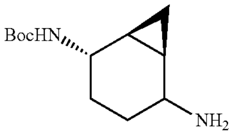

Int-11f

Step A—Synthesis of Intermediate 11a To a stirred solution of N-Boc-hydroxylamine (31.15 g, 0.233 mol) in dry methanol (1 L) cooled to 0° C. was added dropwise 1,3-cyclohexadiene (25 g, 0.311 mol), followed by the dropwise addition of a solution of sodium metaperiodate (52.6 g, 0.246 mol) in water (750 mL) over 30 minutes. The reaction mixture was stirred at room temperature for 16 h, and then filtered. The resulting solid was washed with EtOAc (2×200 mL), and the filtrate was concentrated under reduced pressure at 38° C. The resulting residue was dissolved in EtOAc and washed with brine. The organic layer was dried over $Na_2SO_4$ and concentrated under reduced pressure. The resulting residue was purified by silica gel chromatography eluting with 3-10% EtOAc/DCM in gradient to give intermediate 11a. $^1$H NMR (400 MHz, $CDCl_3$): δ 6.56-6.50 (m, 2H), 4.75-4.70 (m, 2H), 2.2-2.0 (m, 2H), 1.46 (s, 9H), 1.39-1.34 (m, 2H).

Step B—Synthesis of Intermediate 11b To a stirred solution of intermediate 11a (50 g, 0.2367 mol) in acetonitrile (2 L)/water (100 mL) heated to 55° C. was added molybdenum hexacarbonyl (31.27 g, 0.11848 mol) in one portion. The reaction mixture was refluxed at 100° C. for 3 h, followed by stirring at room temperature for 16 h. The reaction mixture was then filtered through Celite™, and the filtrate was concentrated at 40° C. under reduced pressure. The resulting residue was purified by silica gel chromatography eluting with 40% EtOAc/petroleum ether to give intermediate 11b. $^1$H NMR (300 MHz, $CDCl_3$) δ: 5.86-5.80 (m, 1H), 5.78-5.75 (m, 1H), 4.55 (brs, 1H), 4.17-4.1 (m, 2H), 1.9-1.75 (m, 2H), 1.74-1.6 (m, 2H), 1.46 (s, 9H).

Step C—Synthesis of Intermediate 11c A stirred solution of intermediate 11b (30 g, 0.14 mol) in dry dichloromethane (600 mL) was purged with argon for 15 min. and then cooled to 0° C., followed by the addition of Dess-Martin periodinane (89.5 g, 0.211 mol). The reaction mixture was stirred at room temperature for 1 h, then diluted with dichloromethane (500 mL) and washed with aqueous 10% sodium thiosulfate solution (2×500 mL), 10% sodium bicarbonate (2×500 mL), water (500 mL) and brine (500 mL). The organic layer was separated, dried over anhydrous $Na_2SO_4$, and filtered. The filtrate was concentrated under reduced pressure to give intermediate 11c, which was used in the next step without further purification. $^1$H NMR (300 MHz, $CDCl_3$) δ: 6.87-6.80 (m, 1H), 6.1-5.9 (m, 1H), 4.7 (brs, 1H), 4.5 (brs, 1H), 2.56-2.44 (m, 2H), 2.4-2.3 (m, 1H), 1.92-1.85 (m, 1H), 1.47 (s, 9H).

Step D—Synthesis of Intermediate 11d To a suspension of NaH (7.4 g, 0.184 mol) in anhydrous DMSO (900 mL) was added trimethyl sulfoxonium iodide (40.6 g, 0.184 mol). The mixture was cooled to 15° C., then a solution of intermediate 11c (30 g, 0.142 mol) in DMSO (300 mL) was added dropwise. The reaction mixture was then stirred at room temperature for 5 h, followed by the addition of ice. The mixture was extracted with 50% EtOAc in petroleum ether (3×500 mL). The combined organic layers were dried over $Na_2SO_4$ and filtered. The filtrate was concentrated under reduced pressure. The resulting residue was purified by silica gel chromatography (silica gel 60-120 mesh, 25% EtOAc in Petroleum ether) to give intermediate 11d. $^1$H NMR (400 MHz, $CDCl_3$): δ 4.94 (brs, 1H), 4.20 (brs, 1H), 2.25-2.17 (m, 2H), 1.8-1.7 (m, 4H), 1.41 (s, 9H), 1.9-1.65 (m, 2H).

Step E—Synthesis of Intermediate 11e To a solution of intermediate 11d (0.3482 g, 1.546 mmol) in anhydrous $CH_2Cl_2$ (7 mL) was added benzylamine (219 μL, 2.009 mmol) at ambient temperature. The reaction was stirred for 10 minutes, then $NaBH(OAc)_3$ (0.655 g, 3.09 mmol) and AcOH (1 μL, 0.017 mmol) were added. The reaction mixture was stirred for 2 h, then quenched at 0° C. by the slow addition of NaOH (1 N, 5 mL). The resulting mixture was extracted with EtOAc. The organic layer was washed with brine, dried over $Na_2SO_4$, filtered, and the filtrate was concentrated in vacuo. The resulting residue was purified by silica gel chromatography ((Isco Gold 12 g column; 0-100% EtOAc/hexanes) to give the desired compound. LC-MS: m/z 317.6 $[M+H]^+$.

Step F—Synthesis of Intermediate 11f A mixture of intermediate 11e (1.9206 g, 6.07 mmol) and Pd/C (10 wt %, 0.3942 g, 3.70 mmol) in absolute ethanol (20.23 mL) was hydrogenated under atmospheric $H_2$ at ambient temperature for 48 h. The reaction mixture was filtered through a Celite™ pad under a $N_2$ atmosphere. The pad was washed with MeOH, and the filtrate was concentrated in vacuo to give the desired compound. LC-MS: m/z 227.2 $[M+H]^+$.

Example 14: Preparation of Compounds 24 to 27

The following compounds were prepared from intermediate 11f according to the procedure of Step A to Step D of Example 12, where diastereomers were separated in Step B by chiral chromatography (ChiralTek Enantiocel C9-5, 3×25 cm column; $MeOH/CO_2$ followed by AD-H, 3×25 cm, $iPrOH/CO_2$) to give 4 individual diastereomers (absolute stereochemistry at marked carbon center is unassigned; drawings shown represent relative stereochemistry).

| Compound | Structure | $^1$H NMR | LC-MS $[M + H]^+$ |
|---|---|---|---|
| 24 (From Peak 4) | 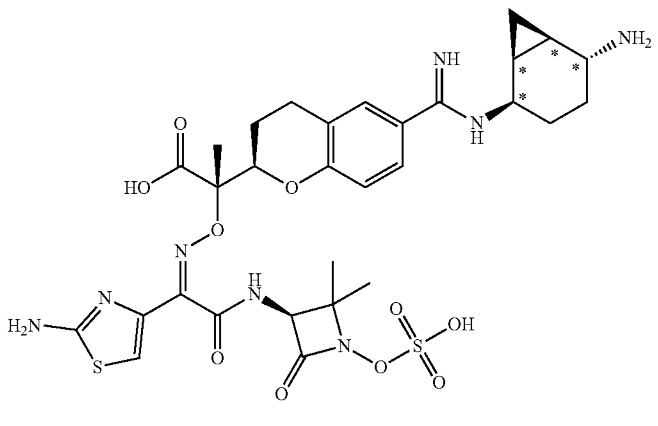 [SMILES: CC1(C)[C@H](NC(=O)/C(=N\O[C@](C)(C(=O)O)[C@H]2CCc3cc(C(=N)N[C@@H]4CC[C@@H](N)[C@@H]5C[C@@H]54)ccc3O2)c2csc(N)n2)C(=O)N1OS(=O)(=O)O] (S)-2-((R)-6-(N-((1S,2R,5R,6R)-5-amino-bicyclo[4.1.0]heptan-2-yl)carbamimidoyl)chroman-2-yl)-2-((((Z)-1-(2-amino-thiazol-4-yl)-2-(((S)-2,2-dimethyl-4-oxo-1-(sulfooxy)azetidin-3-yl)amino)-2-oxoethylidene)-amino)oxy)propanoic acid | $^1$HNMR (400 MHz, 4:1$D_2O$/d-DMSO) δ: 7.41-7.28 (m, 2H), 6.87-6.81 (m, 2H), 4.59 (s, 1H), 4.37 (d, J = 9.8 Hz, 1H), 4.23-4.10 (m, 1H), 3.33 (dd, J = 9.9, 5.4 Hz, 1H), 2.77 (m, 2H), 2.53 (s, 1H), 2.04 (d, J = 12.8 Hz, 1H), 1.89-1.76 (m, 2H), 1.75-1.64 (m, 1H), 1.48 (s + m, 4H), 1.37 (s, 3H), 1.33-1.21 (m, 1H), 1.18 (s, 3H), 1.17-1.08 (m, 1H), 0.85-0.72 (m, 1H), 0.51 (q, J = 5.7 Hz, 1H). | 735.4 |

-continued

| Compound | Structure | $^1$H NMR | LC-MS [M + H]$^+$ |
|---|---|---|---|
| 25 (From Peak 1) | 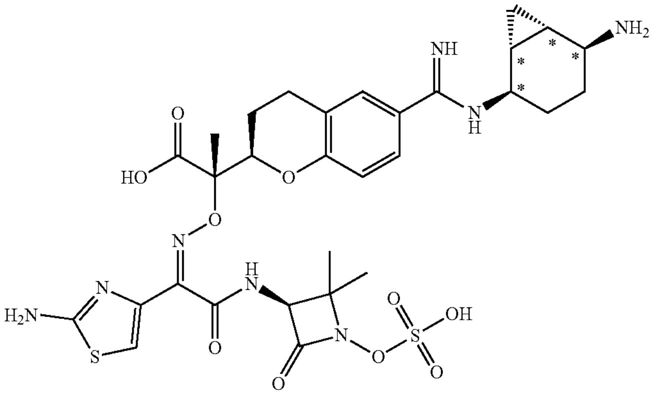 [SMILES: CC1(C)[C@H](NC(=O)/C(=N\O[C@](C)(C(=O)O)[C@H]2CCc3cc(C(=N)N[C@@H]4CC[C@H](N)[C@H]5C[C@H]54)ccc3O2)c2csc(N)n2)C(=O)N1OS(=O)(=O)O] (S)-2-((R)-6-(N-((1R,2R,5S,6S)-5-amino-bicyclo[4.1.0]heptan-2-yl)-carbamimidoyl)-chroman-2-yl)-2-((((Z)-1-(2-amino-thiazol-4-yl)-2-(((S)-2,2-dimethyl-4-oxo-1-(sulfooxy)azetidin-3-yl)amino)-2-oxoethylidene)-amino)oxy)propanoic acid | $^1$H NMR (400 MHz, 4:1$D_2O$/d-DMSO) δ: 7.42-7.33 (m, 2H), 6.89-6.78 (m, 2H), 4.59 (s, 1H), 4.33 (d, J = 11.0 Hz, 1H), 4.02 (s, 1H), 3.51-3.44 (m, 1H), 2.81-2.69 (m, 2H), 2.02 (d, J = 13.4 Hz, 1H), 1.74-1.57 (m, 3H), 1.46 (s, 3H), 1.54-1.39 (m, 2H), 1.37 (s, 3H), 1.27-1.17 (m, 1H), 1.20 (s, 3H), 1.09-0.96 (m, 1H), 0.91 (dd, J = 9.4, 6.0 Hz, 1H), 0.35-0.28 (m, 1H). | 735.4 |
| 26 (From Peak 3) | 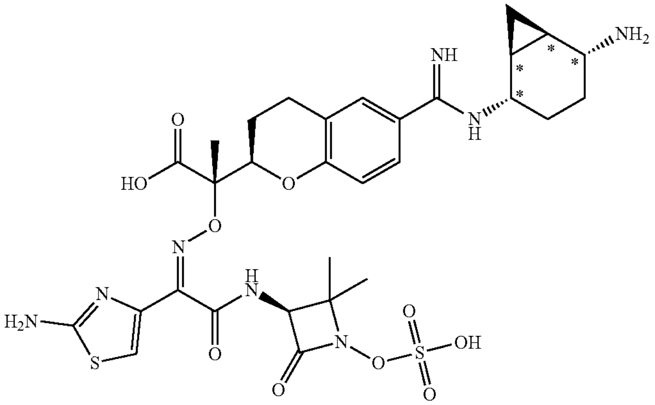 [SMILES: CC1(C)[C@H](NC(=O)/C(=N\O[C@](C)(C(=O)O)[C@H]2CCc3cc(C(=N)N[C@H]4CC[C@@H](N)[C@@H]5C[C@@H]54)ccc3O2)c2csc(N)n2)C(=O)N1OS(=O)(=O)O] (S)-2-((R)-6-(N-((1S,2S,5R,6R)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)propanoic acid | $^1$H NMR (400 MHz, 4:1$D_2O$/d-DMSO) δ: 7.43-7.34 (m, 2H), 6.89-6.80 (m, 2H), 4.60 (s, 1H), 4.35 (d, J = 11.4 Hz, 1H), 4.05-3.99 (m, 1H), 3.50-3.42 (m, 1H), 2.82-2.68 (m, 2H), 2.03 (d, J = 13.4 Hz, 1H), 1.77-1.55 (m, 3H), 1.54-1.40 (m, 2H), 1.47 (s, 3H), 1.37 (s, 3H), 1.26-1.18 (m, 1H), 1.19 (s, 3H), 1.07-1.00 (m, 1H), 0.95-0.86 (m, 1H), 0.35-0.28 (m, 1H). | 735.4 |
| 27 (From Peak 2) | 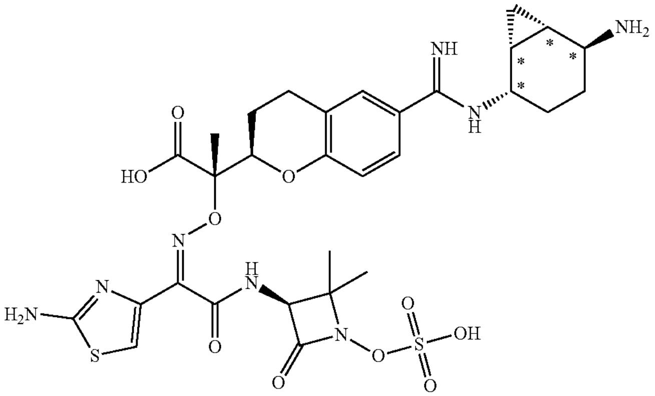 [SMILES: CC1(C)[C@H](NC(=O)/C(=N\O[C@](C)(C(=O)O)[C@H]2CCc3cc(C(=N)N[C@H]4CC[C@H](N)[C@H]5C[C@H]54)ccc3O2)c2csc(N)n2)C(=O)N1OS(=O)(=O)O] (S)-2-((R)-6-(N-((1R,2S,5S,6S)-5-aminobicyclo[4.1.0]heptan-2-yl)carbamimidoylchroman-2-yl)-2-((((Z)-1-(2-amino-thiazol-4-yl)-2-(((S)-2,2-dimethyl-4-oxo-1-(sulfooxy)azetidin-3-yl)amino)-2-oxoethylidene)-amino)oxy)propanoic acid | $^1$H NMR (400 MHz, 4:1$D_2O$/d-DMSO) δ: 7.450-7.43 (m, 2H), 7.00-6.92 (m, 2H), 4.62 (s, 1H), 4.48 (d, J = 10.9 Hz, 1H), 4.32-4.24 (m, 1H), 3.44-3.37 (m, 1H), 2.94-2.84 (m, 2H), 2.16 (d, J = 13.4 Hz, 1H), 2.00-1.87 (m, 2H), 1.85-1.74 (m, 1H), 1.66-1.57 (m, 1H), 1.60 (s, 3H), 1.47 (s, 3H), 1.40-1.34 (m, 1H), 1.28 (s, 3H), 1.32-1.18 (m, 2H), 0.94-0.86 (m, 1H), 0.66-0.59 (m, 1H). | 735.5 |

Example 15: Preparation of Compound 28
(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-(piperidin-4-yl)carbamimidoyl)chroman-2-yl)propanoic acid
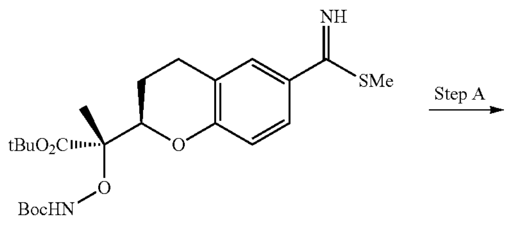
Int-3c
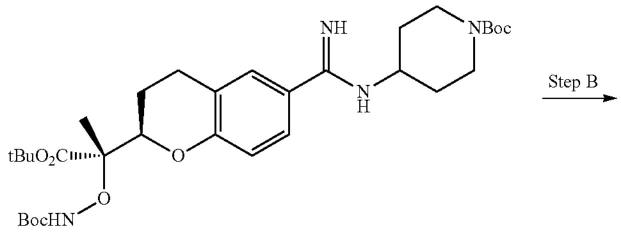
Int-12a
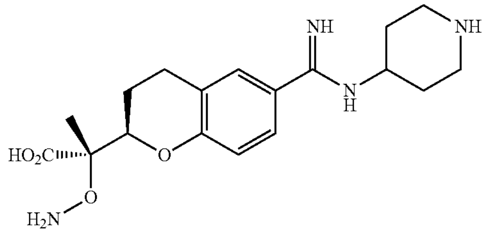
Int-12b
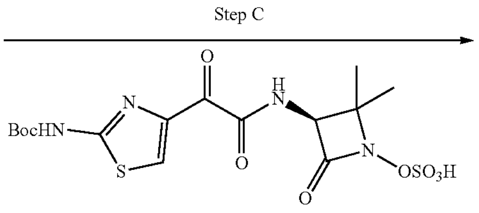
Int-4
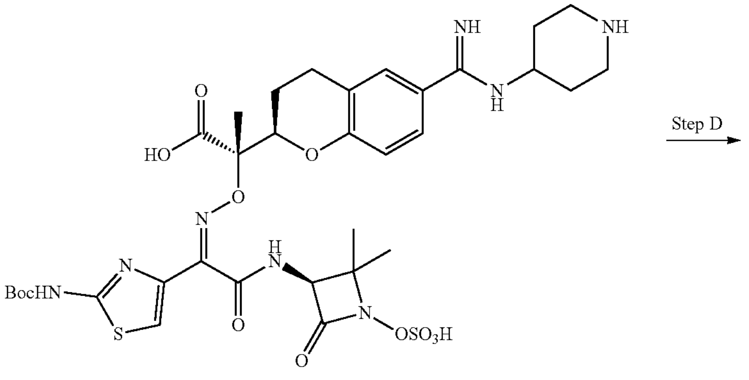
Int-12c -continued

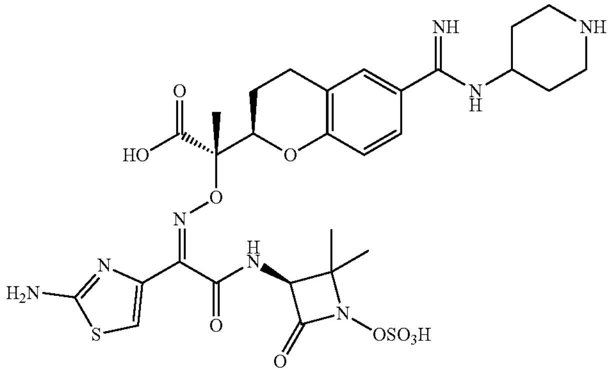

Compound 28

Step A—Synthesis of Intermediate 12a To a vial containing a mixture of intermediate 3c (1.264 g, 2.71 mmol) and 4-amino-1-Boc-piperidine (1.086 g, 5.42 mmol) was added a pre-made solution of potassium acetate (0.532 g, 5.42 mmol) and acetic acid (0.930 mL, 16.26 mmol) in anhydrous MeOH (27 mL). The reaction was heated at 70° C. for 30 minutes, then partitioned between EtOAc and cold saturated aqueous $NaHCO_3$/brine. The organic layer was separated, dried over $Na_2SO_4$, filtered, and the filtrate was concentrated in vacuo to give a foam. The foam was purified by reverse-phase chromatography (ISCO C18 130 g; 0-100% ACN+0.05% TFA/water+0.05% TFA). The product fractions were concentrated in vacuo, and the resulting aqueous residue was extracted with EtOAc (2×). The combined organic layers were dried over $Na_2SO_4$, filtered, and the filtrate was concentrated in vacuo to give the desired compound. LC-MS: m/z 619.6 $[M+H]^+$.

Step B—Synthesis of Intermediate 12b To a vial containing intermediate 12a (0.9292 g, 1.502 mmol) was added 2:1 trifluoroacetic acid/anhydrous dichloromethane (15 mL) at ambient temperature. The reaction was stirred for 16.5 h, then a solution of 4:1 MeOH/toluene (25 mL) was added to the reaction, and the mixture was concentrated in vacuo. The resulting residue was azeotroped with 4:1 MeOH/toluene (25 mL) and dried in vacuo to give the desired compound. LC-MS: m/z 363.32 $[M+H]^+$.

Step C—Synthesis of Intermediate 12c To a flask charged with intermediate 12b (0.544 g, 1.502 mmol) and intermediate 4 (0.6722 g, 1.447 mmol) was added 30% toluene in anhydrous methanol (15 mL) at ambient temperature. The reaction was stirred for 3 h, and then concentrated in vacuo. The resulting residue was purified by reverse-phase chromatography (Isco C18Aq 415 g column; 0-40% ACN+0.05% TFA/water+0.05% TFA over 30 min.) and the aqueous product fractions were concentrated in vacuo. Then the aqueous residue was loaded onto an Amberchrom CG161M column (26 g), washed with 9 CV of (water+0.05% TFA), and eluted off with 3 CV of 100% (ACN+0.05% TFA) followed by 3 CV of 50% (ACN+0.05% TFA)/(water+0.05% TFA). The product fractions were collected, concentrated in vacuo, and the resulting aqueous residue was lyophilized to give the desired compound. LC-MS: m/z 809.6 $[M+H]^+$.

Step D—Synthesis of Compound 28 To intermediate 12c (0.3580 g, 0.443 mmol) was added 2:1 anhydrous DCM/TFA (4.4 mL) at ambient temperature. The reaction mixture was stirred for 1 h, then cooled to 0° C. MTBE (10 mL) was added to the reaction with stirring resulting in precipitation of solid. The reaction mixture was sonicated and then centrifuged (4000 rpm) to collect the insoluble solids. The supernatant was decanted off and the MTBE (5 mL) wash and isolation by centrifugation was repeated a second time. The resulting solid was dried in vacuo, and then purified by a reverse phase HPLC (XSelect CSH Prep C18; 5 uM OBD; 30×150 mm; 0%-15% (ACN+0.1% FA)/(water+0.1% FA) over 15 min). The product fractions were collected and lyophilized to give the title compound as the formic acid salt. LC-MS: m/z 709.6 $[M+H]^+$. $^1$HNMR (400 MHz, 4:1 $D_2O$/d-DMSO) δ: 7.41-7.28 (m, 2H), 6.85 (d, J=8.7 Hz, 1H), 6.80 (s, 1H), 4.58 (s, 1H), 4.34 (d, J=10.7 Hz, 1H), 3.89-3.80 (m, 1H), 3.41 (d, J=13.4 Hz, 2H), 3.01 (t, J=11.9 Hz, 2H), 2.82-2.68 (m, 2H), 2.19 (d, J=13.5 Hz, 2H), 2.02 (d, J=13.6 Hz, 1H), 1.87-1.72 (m, 2H), 1.70-1.60 (m, 1H), 1.45 (s, 3H), 1.37 (s, 3H), 1.19 (s, 3H).

Example 16: Preparation of Compounds 29 and 30

(S)-2-((R)-6-(N-(1-((R)-3-amino-2-hydroxypropyl)piperidin-4-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-(1-((S)-3-amino-2-hydroxypropyl)piperidin-4-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

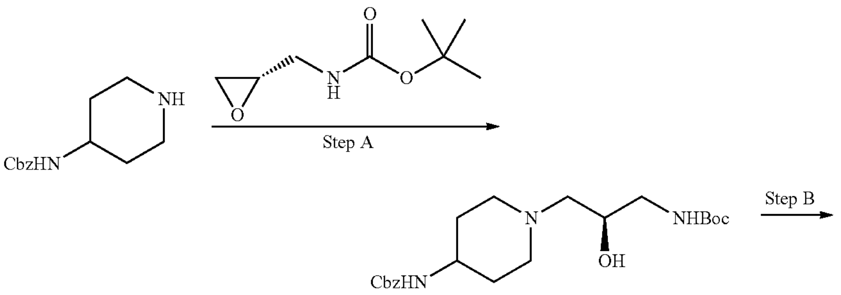

Int-13a

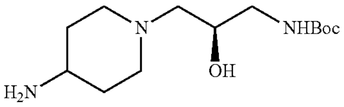

Int-13b

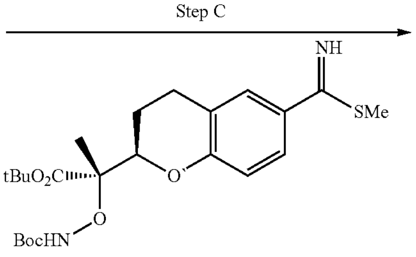

Int-3c

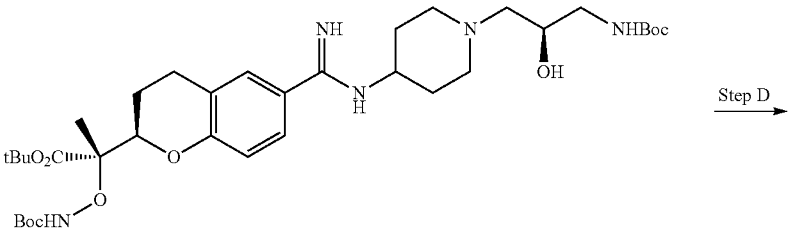

Int-13c

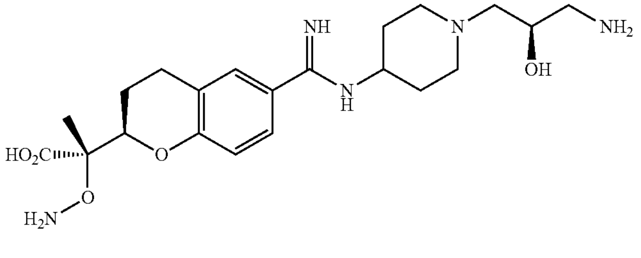

Int-13d

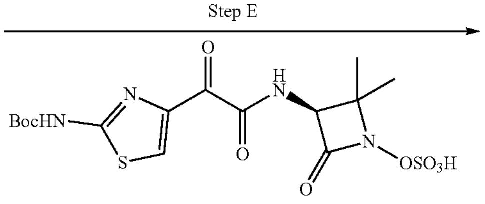

Int-4

-continued

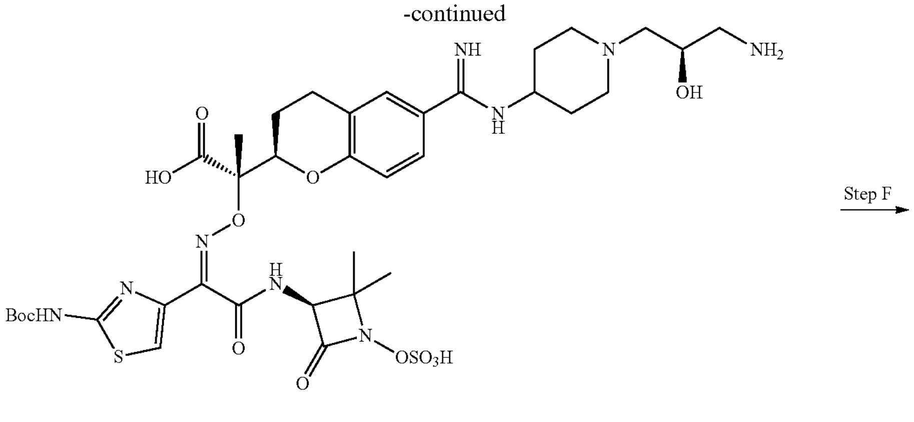

Int-13e

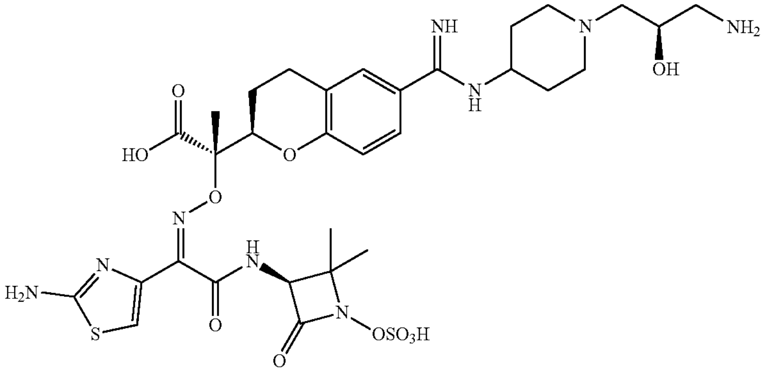

Compound 29

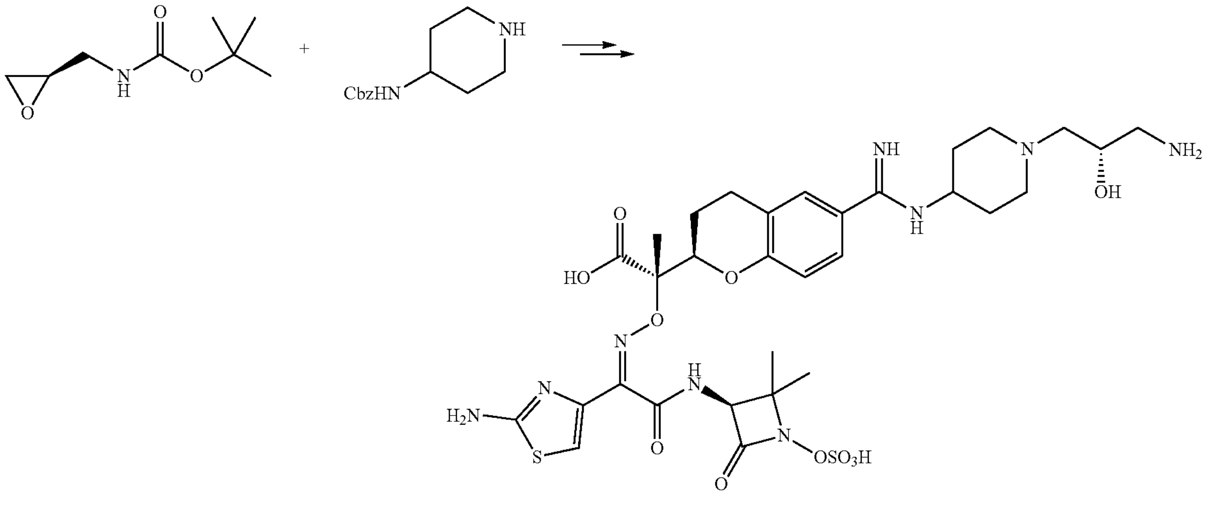

Compound 30

Step A—Synthesis of Intermediate 13a To a vial containing (S)-1-(tert-butoxycarbonyl)-2,3-oxiranylmethylamine (0.095 g, 0.546 mmol) and 4-CBZ-aminopiperidine (0.1066 g, 0.455 mmol) was added anhydrous methanol (4.6 mL) at ambient temperature. The reaction mixture was heated to 60° C. for 4 h, then concentrated in vacuo. The resulting residue was purified by silica gel chromatography (Isco Gold 12 g column; 0-100% (3:1 EtOAc/EtOH)/hexanes) to give the desired compound. LC-MS: m/z 409.3 $[M+H]^+$.

Step B—Synthesis of Intermediate 13b A vial containing intermediate 13a (0.185 g, 0.455 mmol) and Pd/C (10 wt %, 0.0527 g, 0.050 mmol) was evacuated and filled with $N_2$ (3×). Then anhydrous MeOH (4.6 mL) was added under $N_2$, and the reaction vessel was evacuated and filled with $N_2$ (3×) before subjecting to 1 atmosphere of $H_2$ (balloon). The reaction mixture was stirred for 4 h, then filtered through a Celite™ pad. The Celite™ pad was washed with MeOH and the resulting filtrate was concentrated in vacuo to give the desired compound. LC-MS: m/z 274.2 $[M+H]^+$.

Step C—Synthesis of Intermediate 13c To a mixture of intermediate 3c (95.9 mg, 0.161 mmol) and intermediate 13b (81.4 mg, 0.298 mmol) was added a pre-made solution of potassium acetate (31.7 mg, 0.323 mmol) and acetic acid (0.055 mL, 0.968 mmol) in anhydrous MeOH (1.6 mL). The reaction mixture was stirred at room temperature for 1.5 h, snf then concentrated in vacuo. The resulting residue was purified on a reverse phase HPLC (ISCO C18 13 g; 0-100% ACN+0.05% TFA/water+0.05% TFA). The product fractions were collected and lyophilized to give the desired compound. LC-MS: m/z 692.6 $[M+H]^+$.

Step D—Synthesis of Intermediate 13d To a vial containing intermediate 13c (75.8 mg, 0.110 mmol) was added 2:1 trifluoroacetic acid/anhydrous dichloromethane (1.1 mL) at ambient temperature. The reaction mixture was stirred for 16.5 h, then a solution of 4:1 MeOH/toluene (5 mL) was added to the reaction, and the resulting mixture was concentrated in vacuo. The resulting residue was azeotroped with 4:1 MeOH/toluene (5 mL) again and then dried in vacuo to give the desired compound. LC-MS: m/z 436.2 $[M+H]^+$.

Step E—Synthesis of Intermediate 13e To a flask charged with intermediate 13d (0.048 g, 0.110 mmol) and intermediate 4 (0.051 g, 0.110 mmol) was added anhydrous methanol (1.1 mL) at ambient temperature. The reaction was stirred for 2 h, and then concentrated in vacuo. The resulting residue was purified by reverse-phase chromatography (Isco C18Aq 415 g column; 0-40% ACN+0.05% TFA/water+0.05% TFA over 30 min.), and the aqueous product fractions were concentrated in vacuo. The resulting aqueous residue was loaded onto an Amberchrom CG161M column (26 g), washed with 9 CV of (water+0.05% TFA), and eluted off with 3 CV of 100% (ACN+0.05% TFA) followed by 3 CV of 50% (ACN+0.05% TFA)/(water+0.05% TFA). The product fractions were collected, concentrated in vacuo, and the resulting aqueous residue was lyophilized to give the desired compound. LC-MS: m/z 882.7 $[M+H]^+$.

Step F—Synthesis of Compound 29 and 30 To intermediate 13e (97 mg, 0.110 mmol) was added 2:1 anhydrous DCM/TFA (1.1 mL) at ambient temperature. The reaction mixture was stirred for 1 h, then cooled to 0° C., followed by the addition of MTBE (3 mL) and stirring. The resulting mixture was sonicated and then centrifuged (4000 rpm) to collect the insoluble solids. The supernatant was decanted off, and the MTBE wash and isolation by centrifugation steps were repeated. The resulting solid was dried in vacuo, and was purified by RP HPLC (XSelect CSH Prep C18; 5 uM OBD; 30×150 mm; 0%-20% (ACN+0.1% FA)/(water+0.1% FA) over 15 min). The product fractions were collected and lyophilized to give the title compound as the formic acid salt. LC-MS: m/z 782.6 $[M+H]^+$. $^1$HNMR (500 MHz, 4:1 $D_2O$/d-DMSO) δ: 7.50-7.38 (m, 2H), 6.96 (d, J=8.6 Hz, 1H), 6.90 (s, 1H), 4.67 (s, 1H), 4.48 (d, J=11.3 Hz, 1H), 4.39-4.32 (m, 1H), 4.02-3.93 (m, 1H), 3.74-3.60 (m, 2H), 3.34-3.11 (m, 5H), 2.97 (dd, J=13.3, 9.0 Hz, 1H), 2.86 (t, J=17.6 Hz, 2H), 2.39-2.27 (m, 2H), 2.20-1.94 (m, 3H), 1.84-1.72 (m, 1H), 1.58 (s, 3H), 1.48 (s, 3H), 1.30 (s, 3H).

Compound 30 was prepared starting from (R)-1-(tert-butoxycarbonyl)-2,3-oxiranyl-methylamine according to the procedure of Step A to Step F of Example 16. Compound 30: LC-MS: m/z 782.3 $[M+H]^+$. $^1$HNMR (500 MHz, 4:1 $D_2O$/d-DMSO) δ: 7.49-7.40 (m, 2H), 6.96 (d, J=8.6 Hz, 1H), 6.90 (s, 1H), 4.67 (s, 1H), 4.46 (dd, J=11.3, 2.0 Hz, 1H), 4.39-4.31 (m, 1H), 4.02-3.93 (m, 1H), 3.74-3.58 (m, 2H), 3.32-3.20 (m, 3H), 3.17 (dd, J=13.3, 3.2 Hz, 2H), 2.97 (dd, J=13.3, 8.9 Hz, 1H), 2.87 (d, J=16.3 Hz, 2H), 2.33 (bs, 2H), 2.20-1.96 (m, 3H), 1.81-1.75 (m, 1H), 1.57 (s, 3H), 1.48 (s, 3H), 1.30 (s, 3H).

Example 17: Preparation of Compound 31

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N—((R)-azepan-4-yl)carbamimidoyl)chroman-2-yl)propanoic acid

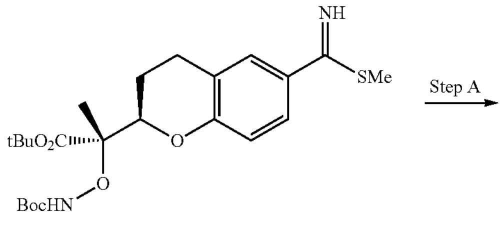

Int-3c

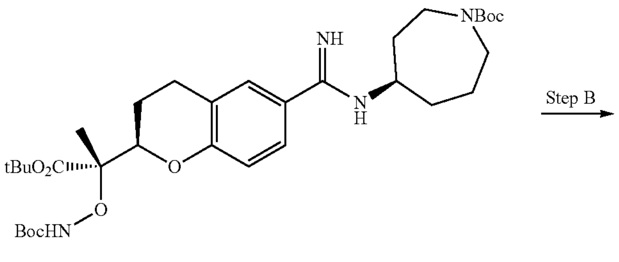

Int-14a

-continued

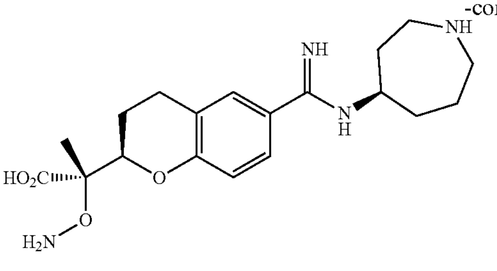

Int-14b

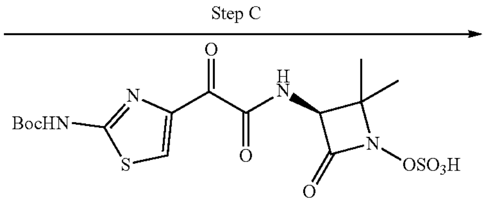

Int-4

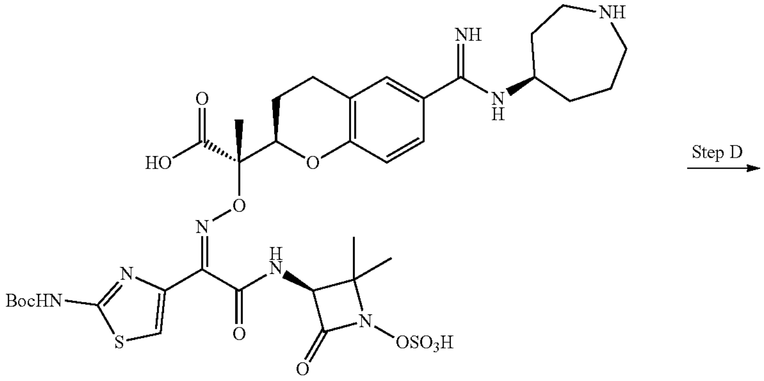

Int-14c

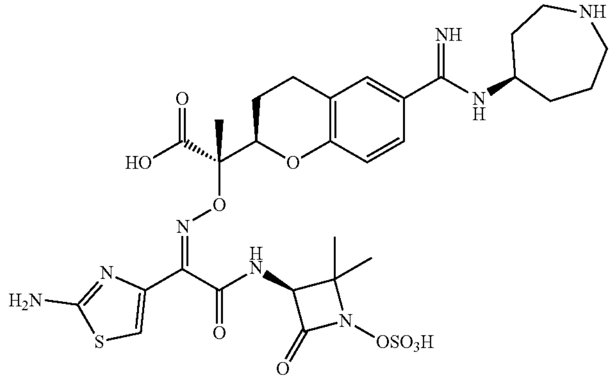

Compound 31

Step A—Synthesis of Intermediate 14a To a vial containing a mixture of 2-methyl-2-propanyl (4S)-4-amino-1-azepanecarboxylate (91.9 mg, 0.429 mmol) and intermediate 3c (0.100 g, 0.214 mmol) was added a solution of potassium acetate (0.631 mg, 0.643 mmol) and acetic acid (0.07 mL, 1.286 mmol) in anhydrous MeOH (2 mL). The reaction was heated at 70° C. for 20 minutes, then cooled, diluted with EtOAc (2 mL), and washed with saturated aqueous $NaHCO_3$ (1 mL). The organic layer was separated, dried over $Na_2SO_4$, and filtered. The filtrate was concentrated in vacuo to give a residue, which was purified via reverse phase HPLC (XSelect CSH Prep C18; 5 uM OBD; 30×150 mm; 35%-70% (ACN+0.05% TFA)/(water+0.05% TFA) over 8 min). The product fractions were collected and lyophilized to give the desired compound. LC-MS: m/z 633.5 $[M+H]^+$.

Step B—Synthesis of Intermediate 14b To a vial containing intermediate 14a (0.0652 g, 0.166 mmol) was added 2:1 trifluoroacetic acid/anhydrous dichloromethane (1.4 mL) at ambient temperature. The reaction was stirred for 16.5 h, then a solution of 4:1 MeOH/toluene (2 mL) was added to the reaction, and the mixture was concentrated in vacuo. The resulting residue was azeotroped with 4:1 MeOH/toluene (2 mL) and dried in vacuo to give the desired compound. LC-MS: m/z 377.3 $[M+H]^+$.

Step C—Synthesis of Intermediate 14c To a flask charged with intermediate 14b (0.166 mmol) and intermediate 4 (0.076 g, 0.164 mmol) was added anhydrous methanol (1.7 mL) at ambient temperature. The reaction was stirred for 3 h, and then concentrated in vacuo. The resulting residue was purified by a reverse phase HPLC (XSelect CSH Prep C18; 5 uM OBD; 30×150 mm; 12%-42% (ACN+0.05% TFA)/(water+0.05% TFA) over 15 min) to give the desired compound. LC-MS: m/z 823.9 $[M+H]^+$.

Step D—Synthesis of Compound 31 To intermediate 14c (47.1 mg, 0.057 mmol) was added 2:1 anhydrous DCM/TFA (572 μL) at ambient temperature. The reaction mixture was stirred for 1 h, then cooled to 0° C., followed by the addition of MTBE (3 mL) with stirring to give a precipitate. The mixture was sonicated and then centrifuged (4000 rpm) to collect the insoluble solids. The supernatant was decanted off, and the MTBE wash and isolation by centrifugation steps were repeated. The resulting solid was dried in vacuo, and purified by RP HPLC (XSelect CSH Prep C18; 5 uM OBD; 19×150 mm; 0%-40% (ACN+0.05% FA)/(water+0.05% FA) over 24 min.; flow rate=17.0 mL/min.; Monitor and collect 254 nM and 215 nM; the product eluted at 17% (ACN+0.05% FA)/(water+0.05% FA)). The product fractions were collected and lyophilized to give the title compound as the formic acid salt. LC-MS: m/z 723.4 $[M+H]^+$. $^1$HNMR (500 MHz, 4:1 $D_2O$/d-DMSO) δ: 7.47 (s, 1H), 7.44 (dd, J=8.6, 2.3 Hz, 1H), 6.97 (d, J=8.6 Hz, 1H), 6.91 (s, 1H), 4.69 (s, 1H), 4.46 (dd, J=11.1, 2.0 Hz, 1H), 3.95 (dq, J=9.0, 4.5 Hz, 1H), 3.45 (dd, J=13.5, 6.5 Hz, 1H), 3.40-3.30 (m, 1H), 3.30-3.17 (m, 2H), 2.92-2.82 (m, 2H), 2.43-2.22 (m, 2H), 2.20-1.99 (m, 3H), 1.91-1.73 (m, 3H), 1.57 (s, 3H), 1.49 (s, 3H), 1.31 (s, 3H).

Example 18: Preparation of Compound 32

(S)-2-((R)-6-(N-((1r,4R)-4-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

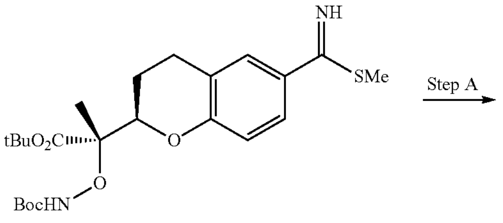

Int-3c

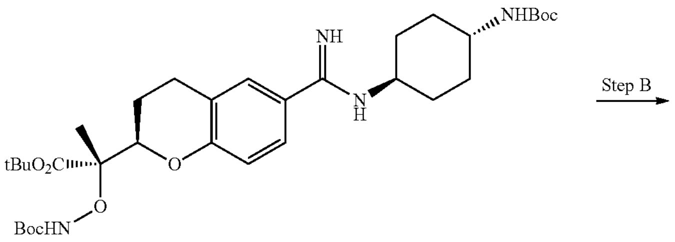

Int-15a

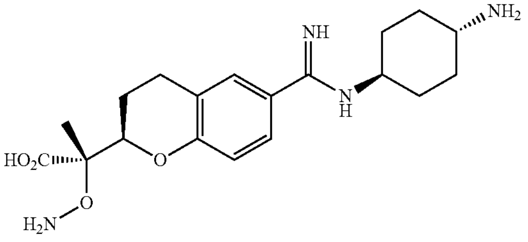

Int-15b

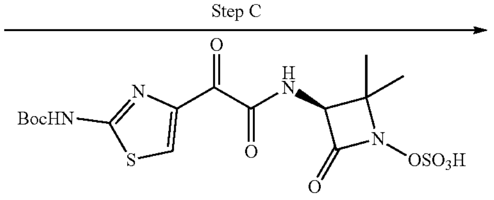

Int-4

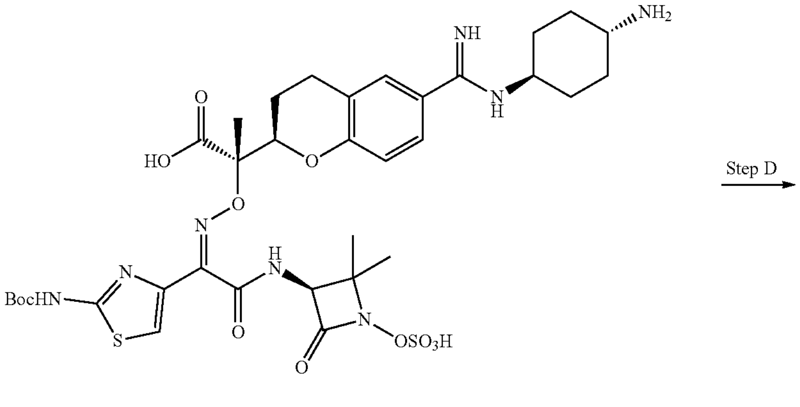

Int-15c

-continued

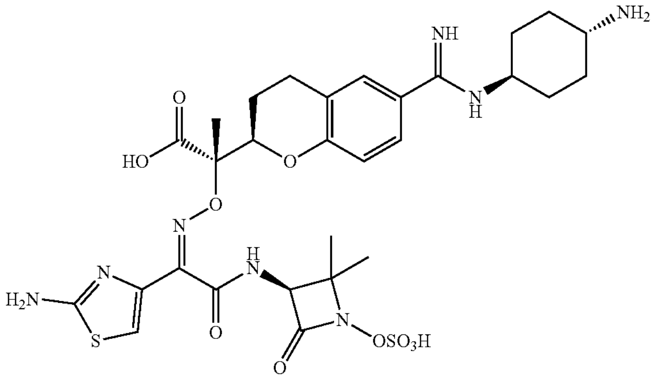

Compound 32

Step A—Synthesis of Intermediate 15a To a vial containing a mixture of trans-N-Boc-1,4-cyclohexanediamine (91.9 mg, 0.429 mmol) and intermediate 3c (0.100 g, 0.214 mmol) was added a solution of potassium acetate (0.631 mg, 0.643 mmol) and acetic acid (0.07 mL, 1.286 mmol) in anhydrous MeOH (2 mL). The reaction was heated at 70° C. for 20 minutes, then cooled, diluted with EtOAc (2 mL), and washed with saturated $NaHCO_3$ (1 mL). The organic layer was separated, dried over $Na_2SO_4$, filtered, and the filtrate was concentrated in vacuo to give a foam. The foam was directly purified on a reverse phase HPLC (XSelect CSH Prep C18; 5 uM OBD; 30×150 mm; 35%-70% (ACN+0.05% TFA)/(water+0.05% TFA) over 8 min). The product fractions were collected and dried in a Genevac™ to give the desired compound. LC-MS: m/z 633.5 $[M+H]^+$.

Step B—Synthesis of Intermediate 15b To a vial containing intermediate 15a (0.0567 g, 0.151 mmol) was added 2:1 trifluoroacetic acid/anhydrous dichloromethane (1.4 mL) at ambient temperature. The reaction was stirred for 16.5 h, then a solution of 4:1 MeOH/toluene (2 mL) was added to the reaction, and the mixture was concentrated in vacuo. The resulting residue was azeotroped with 4:1 MeOH/toluene (2 mL) and dried in vacuo to give the desired compound. LC-MS: m/z 377.3 $[M+H]^+$.

Step C—Synthesis of Intermediate 15c To a flask charged with intermediate 15b (0.151 mmol) and intermediate 4 (0.067 g, 0.144 mmol) was added anhydrous methanol (1.5 mL) at ambient temperature. The reaction was stirred for 3 h, and then concentrated in vacuo. The resulting residue was purified by a reverse phase HPLC (XSelect CSH Prep C18; 5 uM OBD; 30×150 mm; 12%-42% (ACN+0.05% TFA)/(water+0.05% TFA) over 15 min) to give the desired compound. LC-MS: m/z 823.6 $[M+H]^+$.

Step D—Synthesis of Compound 32 To intermediate 15c (62.9 mg, 0.076 mmol) was added 2:1 anhydrous DCM/TFA (764 μL) at ambient temperature. The reaction mixture was stirred for 1 h, then cooled to 0° C. MTBE (10 mL) was added to the reaction with stirring resulting in precipitation of a solid. The mixture was sonicated and then centrifuged (4000 rpm) to collect the insoluble solids. The supernatant was decanted off, and the MTBE wash (5 mL) and isolation by centrifugation was repeated a second time. The resulting solid was dried in vacuo, and then purified by reverse-phase chromatography (Isco C18 Aq 30 g Gold column; 0%-40% (ACN+0.1% FA)/(water+0.1% FA) over 12 min). The product fractions were collected and lyophilized to give the title compound as the formic acid salt. LC-MS: m/z 723.2 $[M+H]^+$. $^1$HNMR (400 MHz, 4:1 $D_2O$/d-DMSO) δ: 7.40-7.25 (m, 2H), 6.84 (d, J=8.6 Hz, 1H), 6.80 (s, 1H), 4.58 (s, 1H), 4.34 (d, J=10.7 Hz, 1H), 3.56-3.42 (m, 1H), 3.16-3.03 (m, 1H), 2.80-2.68 (m, 2H), 2.08-1.98 (m, 5H), 1.73-1.59 (m, 1H), 1.53-1.40 (m, 4H), 1.45 (s, 3H), 1.37 (s, 3H), 1.19 (s, 3H).

Example 19: Preparation of Compound 33

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((3R,5S)-5-(hydroxymethyl)pyrrolidin-3-yl)carbamimidoyl)chroman-2-yl)propanoic acid

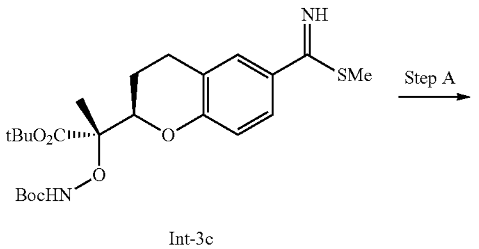

Int-3c

-continued

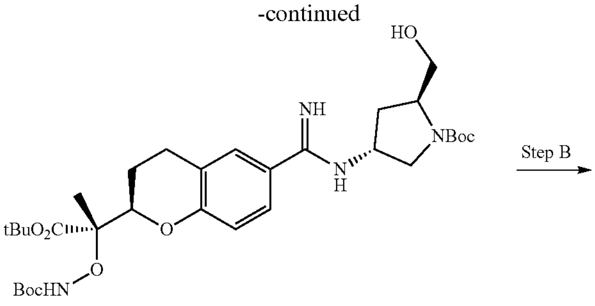

Int-16a

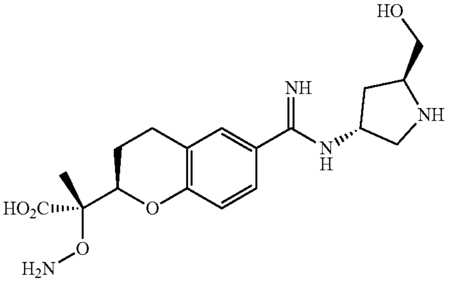

Int-16b

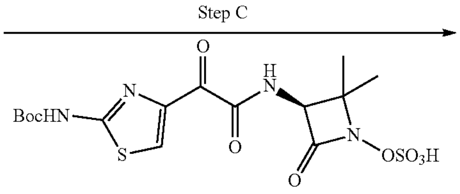

Int-4

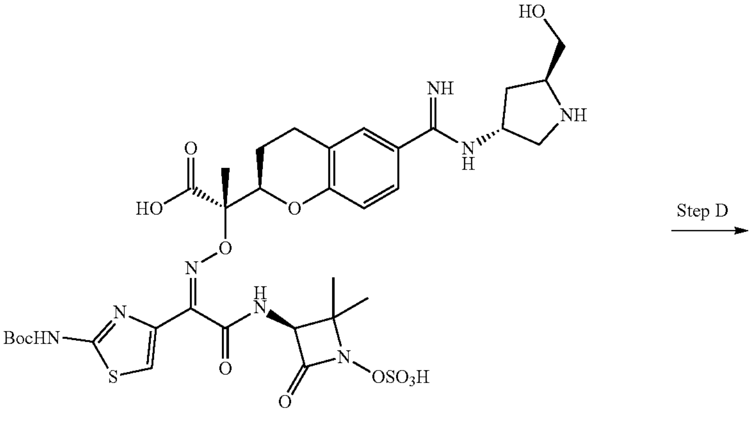

Int-16c

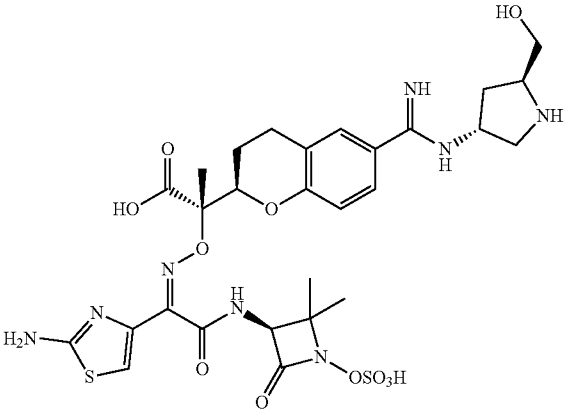

Compound 33

Step A—Synthesis of Intermediate 16a To a vial containing a mixture of (2S,4R)-1-Boc-2-hydroxymethyl-4-amino-pyrrolidine hydrochloride (108.3 mg, 0.429 mmol) and intermediate 3c (0.100 g, 0.214 mmol) was added a solution of potassium acetate (0.631 mg, 0.643 mmol) and acetic acid (0.07 mL, 1.286 mmol) in anhydrous MeOH (2 mL). The reaction was heated at 70° C. for 20 minutes, then cooled, diluted with EtOAc (2 mL), and washed with saturated $NaHCO_3$ (1 mL). The organic layer was separated, dried over $Na_2SO_4$, filtered, and the filtrate was concentrated in vacuo to give a foam. The foam was purified on a reverse phase HPLC (XSelect CSH Prep C18; 5 uM OBD; 30×150 mm; 35%-70% (ACN+0.05% TFA)/(water+0.05% TFA) over 8 min). The product fractions were collected and dried in a Genevac™ to give the desired compound. LC-MS: m/z 635.5 $[M+H]^+$.

Step B—Synthesis of Intermediate 16b To a vial containing intermediate 16a (0.0817 g, 0.19 mmol) was added 2:1 trifluoroacetic acid/anhydrous dichloromethane (1.4 mL) at ambient temperature. The reaction was stirred for 16.5 h. Then a solution of 4:1 MeOH/toluene (2 mL) was added to the reaction and the mixture was concentrated in vacuo. The resulting residue was azeotroped with 4:1 MeOH/toluene (2 mL) again and then dried in vacuo to give the desired compound. LC-MS: m/z 379.3 $[M+H]^+$.

Step C—Synthesis of Intermediate 16c To a flask charged with intermediate 16b (0.19 mmol) and intermediate 4 (0.099 g, 0.213 mmol) was added anhydrous methanol (1.5 mL) at ambient temperature. The reaction was stirred for 3 h, and then concentrated in vacuo. The resulting residue was purified by a reverse phase HPLC (XSelect CSH Prep C18; 5 uM OBD; 30×150 mm; 12%-42% (ACN+0.05% TFA)/(water+0.05% TFA) over 15 min) to give the desired compound. LC-MS: m/z 826.0 $[M+H]^+$.

Step D—Synthesis of Compound 33 To intermediate 16c (87.7 mg, 0.106 mmol) was added 2:1 anhydrous DCM/TFA (1.1 mL) at ambient temperature. The resulting solution was stirred for 1 h, then cooled to 0° C. MTBE (3 mL) was added to the reaction with stirring resulting in precipitation of a solid. The mixture was sonicated and then centrifuged (4000 rpm) to collect the insoluble solids. The supernatant was decanted off and the MTBE wash and isolation by centrifugation were repeated a second time. The resulting solid was dried in vacuo, and then purified by a reverse phase HPLC (XSelect CSH Prep C18; 5 uM OBD; 19λ150 mm; 0%-40% (ACN+0.1% FA)/(water+0.1% FA) over 24 min.; flow rate=17.0 mL/min.; Monitor and collect 254 nM and 215 nM). The product fractions were collected and lyophilized to give the title compound as the formic acid salt. LC-MS: m/z 725.5 $[M+H]^+$. $^1$HNMR (500 MHz, 4:1 $D_2O$/d-DMSO) δ: 7.51 (d, J=2.2 Hz, 1H), 7.47 (dd, J=8.6, 2.4 Hz, 1H), 6.96 (d, J=8.6 Hz, 1H), 6.91 (s, 1H), 4.69 (s, 1H), 4.64 (dt, J=6.5, 3.3 Hz, 1H), 4.44 (dd, J=11.3, 2.0 Hz, 1H), 4.10-4.03 (m, 1H), 3.92 (dd, J=12.5, 3.7 Hz, 1H), 3.83-3.71 (m, 2H), 3.59 (dd, J=13.0, 3.4 Hz, 1H), 2.94-2.79 (m, 2H), 2.43-2.27 (m, 2H), 2.14 (d, J=13.7 Hz, 1H), 1.83-1.73 (m, 1H), 1.57 (s, 3H), 1.49 (s, 3H), 1.31 (s, 3H).

Example 20: Preparation of Compound 34

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((1r,4R)-4-(methylamino)cyclohexyl)carbamimidoyl)chroman-2-yl)propanoic acid

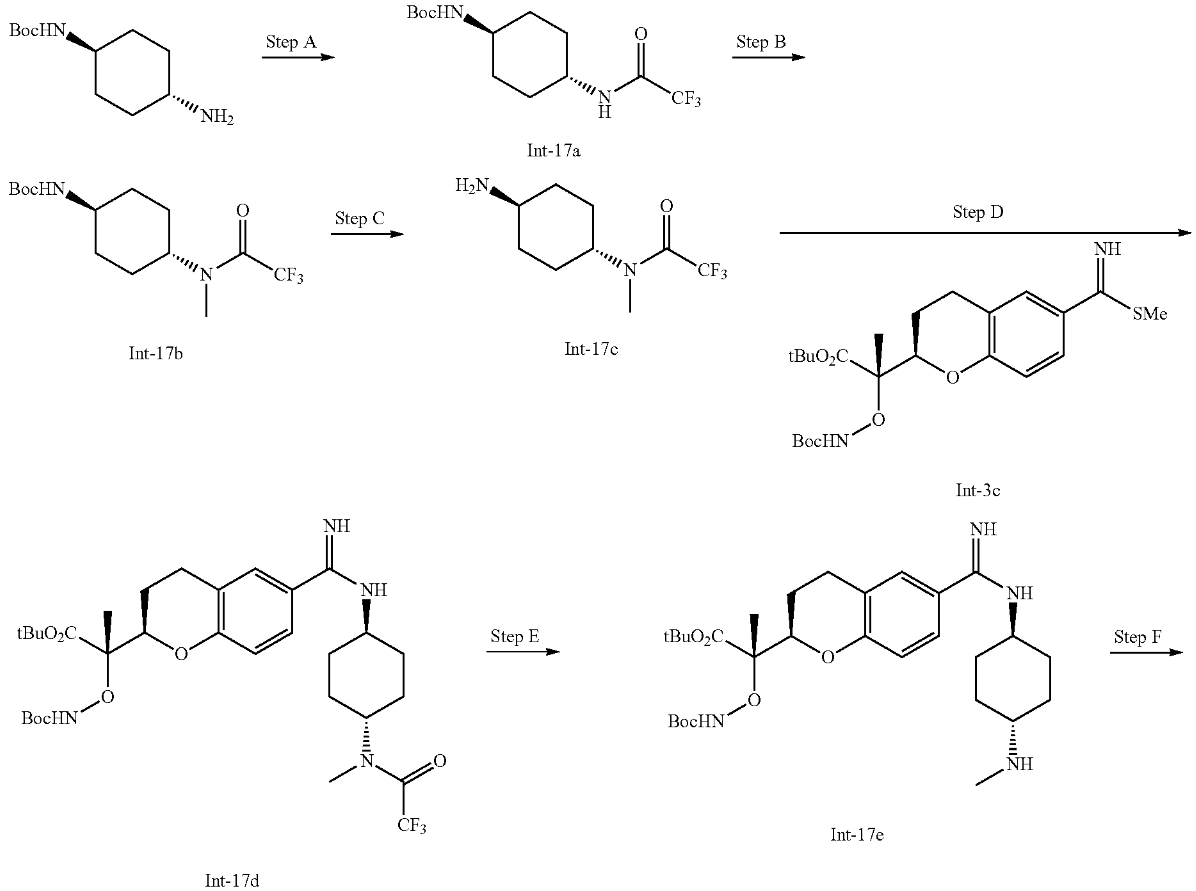

Int-17a

Int-17b

Int-17c

Int-3c

Int-17d

Int-17e

-continued

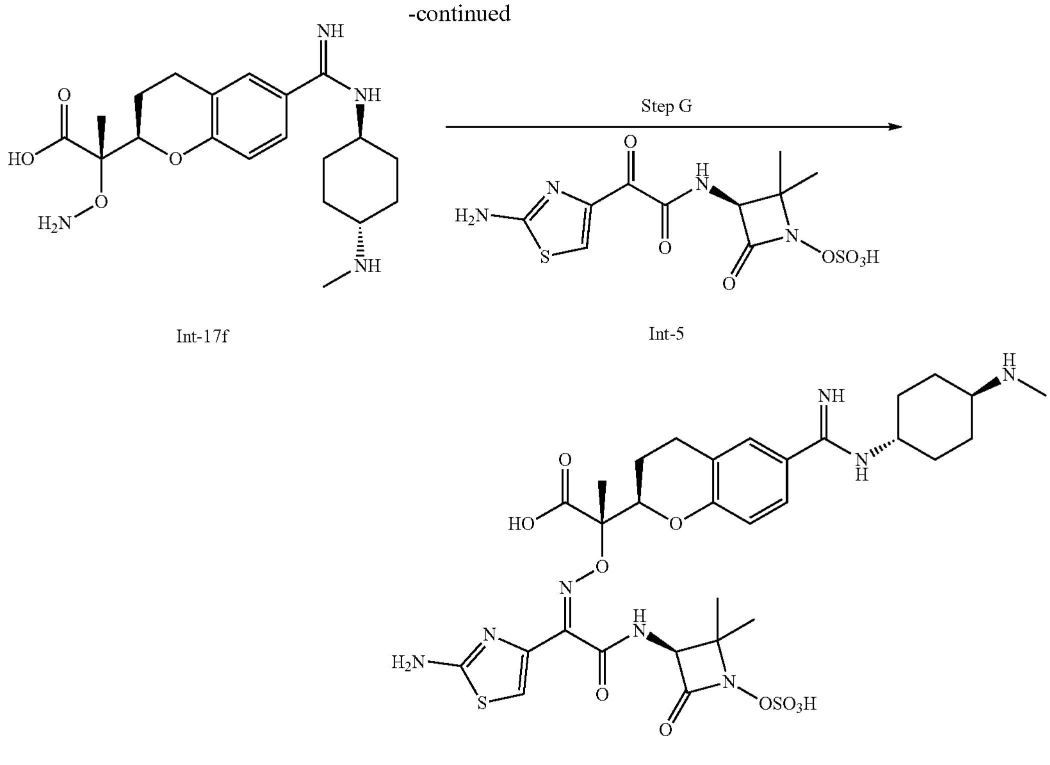

Int-17f

Int-5

Compound 34

Step A— Synthesis of Intermediate 17a To a solution of trans-N-Boc-1,4-cyclohexane-diamine (0.1761 g, 0.822 mmol) in anhydrous MeOH (4.1 mL) was added methyl trifluoroacetate (0.085 mL, 0.838 mmol) at 0° C. After the addition, the ice bath was removed, and the reaction was stirred at ambient temperature for 3 h. Then Hunig's base (0.17 mL, 0.986 mmol) was added and the reaction was stirred for an additional 16 h. The resulting mixture was cooled to 0° C., and the insoluble solids were collected by filtration, washed with cold ether (2x2 mL), and dried in vacuo to give the desired compound. LC-MS: m/z 333.1 $[M+Na]^+$.

Step B— Synthesis of Intermediate 17b To a solution of intermediate 17a (0.0472 g, 0.152 mmol) in anhydrous DMF (1 mL) was added NaH (6.08 mg, 0.152 mmol) at ambient temperature. After 1 h, the reaction was cooled to 0° C., and MeI (8.56 μL, 0.137 mmol) was added dropwise. The reaction was then warmed to ambient temperature, stirred for 15 h, then cooled to 0° C. and quenched with water (5 mL). The resulting mixture was partitioned between EtOAc and brine. The organic layer was separated, dried over $Na_2SO_4$, and concentrated in vacuo. The resulting residue was purified by reverse phase chromatography (Isco C18 26 g column; 0-100% ACN+0.05% TFA/water+0.05% TFA). The product fractions were collected, concentrated in vacuo, and the resulting aqueous residue was extracted with EtOAc (2x). The combined organic layers were dried over $Na_2SO_4$, filtered, and the filtrate concentrated in vacuo to give the desired compound. LC-MS: m/z 347.2 $[M+Na]^+$.

Step C— Synthesis of Intermediate 17c To a solution of intermediate 17b (60 mg, 0.185 mmol) in anhydrous DCM (1850 μL) was added TFA (356 μL, 4.62 mmol) at 0° C. After 1.5 h, the reaction was concentrated in vacuo, and the resulting residue was azeotroped with MeOH (2x5 mL). The residue was then dried under high vacuum to give the desired compound. LC-MS: m/z 225.1 $[M+H]^+$.

Step D—Synthesis of Intermediate 17d To a vial containing a mixture of intermediate 3c (0.0944 g, 0.202 mmol) and intermediate 17c (0.041 g, 0.185 mmol) in acetonitrile (1.3 mL) was added acetic acid (0.069 mL, 1.214 mmol), followed by Hunig's base (0.106 mL, 0.607 mmol). The reaction was heated to 70° C. for 1 h. Then the reaction mixture was cooled to ambient temperature and purified by reverse phase chromatography (Isco C18 Aq 50 g column; 0-100% ACN+0.05% TFA/water+0.05% TFA). The product fractions were collected, concentrated in vacuo, and the resulting aqueous residue was extracted with EtOAc (2x). The combined organic layers were dried over $Na_2SO_4$, filtered, and the filtrate was concentrated in vacuo to give the desired compound. LC-MS: m/z 643.5 $[M+H]^+$.

Step E—Synthesis of Intermediate 17e To a solution of intermediate 17d (79.0 mg, 0.123 mmol) in THF (800 μL)/MeOH (400 μL) was added aqueous LiOH (3 M, 82 μL, 0.246 mmol) at ambient temperature. The reaction was stirred at ambient temperature for 1.5 h, and then stirred at 3-4° C. for 16 h. Then the reaction mixture was concentrated in vacuo, and the resulting residue was purified by reverse phase chromatography (Isco C18 13 g column; 0-100% ACN+0.05% TFA/water+0.05% TFA) to give the desired compound. LC-MS: m/z 547.5 $[M+H]^+$.

Step F—Synthesis of Intermediate 17f To a vial containing intermediate 17e (0.046 g, 0.084 mmol) was added 2:1 TFA/DCM (0.841 mL) at ambient temperature. The reaction was stirred for 20.5 h before adding 30% toluene/MeOH (5 mL) and concentrating in vacuo. The resulting residue was further azeotroped with MeOH (2x5 mL) and dried under high vacuum to give the desired compound. LC-MS: m/z 391.4 $[M+H]^+$.

Step G—Synthesis of Compound 34 To a vial charged with intermediate 17f (32.8 mg, 0.084 mmol), intermediate 5 (80 wt %, 34.4 mg, 0.076 mmol), and powdered molecular sieves 4 Å (325 mesh particle; 0.100 g, dried under high vacuum with heat) was added anhydrous dimethylacetamide (0.34 mL) at ambient temperature. The reaction mixture was stirred for 19 h.

Then reaction was filtered through a Celite™ pad to remove the molecular sieves, and the Celite™ pad was washed with MeOH. The filtrate was concentrated in vacuo. The resulting residue was cooled to 0° C. and DCM (5 mL) was added slowly with stirring resulting in precipitation of a solid. The solids were collected by centrifugation (4000 rpm). The supernatant was decanted, and the insoluble solid was triturated with DCM (3 mL). Centrifugation and decanting of supernatant was repeated to give crude product as a solid, which was purified by a reverse phase HPLC (XSelect CSH Prep C18; 5 uM OBD; 50×250 mm; 0%-17% ACN/(water+0.16% TFA) over 11 min.; isocratic at 17% ACN/(water+0.16% TFA) for 14 min. The product fractions were collected, concentrated in vacuo, and the aqueous layer was directly loaded onto an Amberchrom CG161M column (26 g), washed with 9 CV of (water+0.1% FA), and eluted off with 3 CV of 100% (ACN+0.1% FA) followed by 3 CV of 50% (ACN+0.1% FA)/(water+0.1% FA). The product fractions were collected, concentrated in vacuo, and the resulting aqueous residue was lyophilized to give compound 34 as the formic acid salt. LC-MS: m/z 737.7 $[M+H]^+$. $^1$HNMR (500 MHz, 4:1 $D_2O$/d-DMSO) δ: 7.48-7.41 (m, 2H), 6.99-6.90 (m, 2H), 4.69 (s, 1H), 4.49-4.43 (m, 1H), 3.67-3.60 (m, 1H), 3.11 (t, J=11.3 Hz, 1H), 2.91-2.80 (m, 2H), 2.95-2.77 (m, 2H), 2.68 (s, 3H), 2.24-2.18 (m, 4H), 2.14 (d, J=13.6 Hz, 1H), 1.80 (td, J=12.9, 12.2, 5.7 Hz, 1H), 1.58 (s, 3H), 1.57-1.50 (m, 4H), 1.49 (s, 3H), 1.31 (s, 3H).

Example 21: Preparation of Compound 35

(S)-2-((R)-6-(N-(4-aminobicyclo[2.2.2]octan-1-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

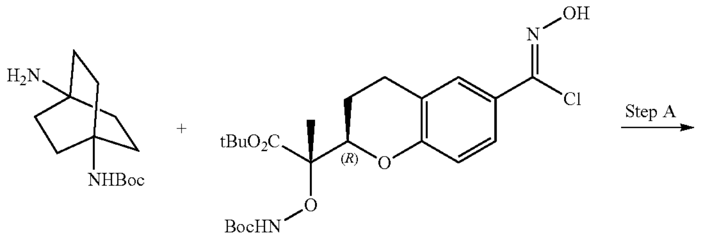

Int-6c

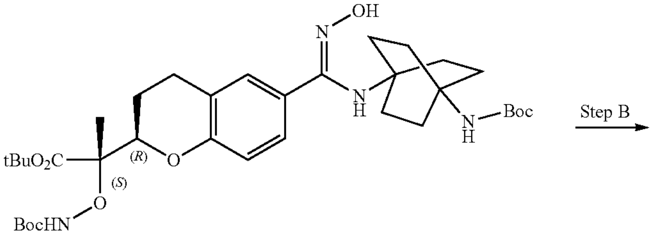

Int-18a

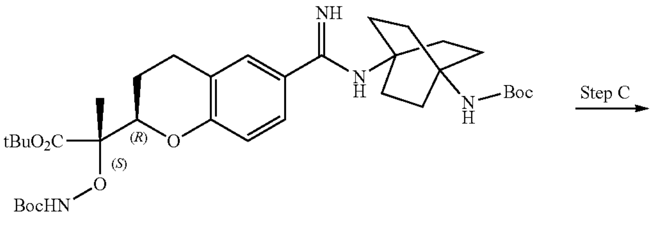

Int-18b

-continued

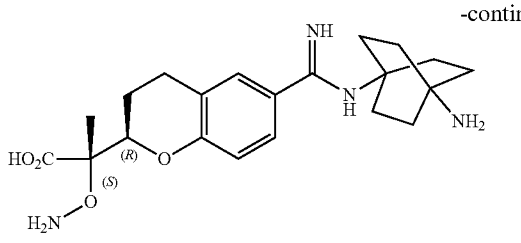

Int-18c

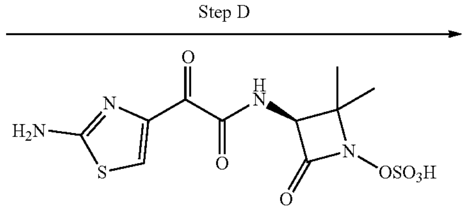

Int-5

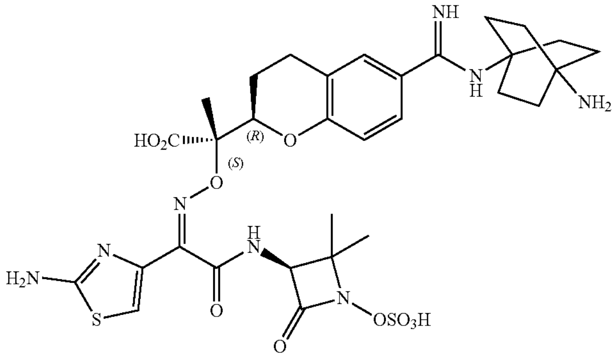

Compound 35

Step A—Synthesis of Intermediate 18a To a solution of tert-butyl (4-aminobicyclo[2.2.2]-octan-1-yl)carbamate (72.0 mg, 0.300 mmol) and intermediate 6c (99 mg, 0.200 mmol) in anhydrous DMF (1.5 mL) was added $NEt_3$ (0.056 mL, 0.399 mmol) at ambient temperature. The reaction was stirred for 30 minutes before partitioning between EtOAc and saturated aqueous $NH_4Cl$/ice-cold HCl (1 N). The organic layer was separated, washed with brine, dried over $Na_2SO_4$, filtered, and the filtrate was concentrated in vacuo. The resulting residue was purified by reverse phase chromatography (Isco C18Aq 30 g column; 0-100% ACN+0.05% TFA/water+0.05% TFA). The product fractions were collected, concentrated in vacuo, and the resulting aqueous residue was extracted with EtOAc (2×). The organic layer was washed with brine, dried over $Na_2SO_4$, filtered, and the filtrate concentrated in vacuo to give the desired compound. LC-MS: m/z 675.4 $[M+H]^+$.

Step B—Synthesis of Intermediate 18b To a mixture of $K_2CO_3$ (121 mg, 0.875 mmol) in MeOH (1.5 mL) was added formic acid (0.067 mL, 1.750 mmol). The mixture was stirred for 10 minutes at ambient temperature before adding it to a solution of intermediate 18a (118.1 mg, 0.175 mmol) in AcOH (0.90 mL). Then Pd/C (10 wt. %, 74.5 mg, 0.070 mmol) was added, and the resulting mixture was stirred at ambient temperature for 21 h. Then the reaction was filtered through a Celite™ pad under an $N_2$ atmosphere and the Celite™ pad was washed with MeOH. The filtrate was then concentrated in vacuo, and the resulting residue was purified by reverse phase chromatography (Isco C18Aq 30 g column; 0-100% ACN+0.05% TFA/water+0.05% TFA). The product fractions were collected, and concentrated in vacuo. The resulting aqueous residue was diluted with brine, and extracted with EtOAc (2×). The organic layers were combined, dried over anhydrous $Na_2SO_4$, filtered, and the filtrate was concentrated in vacuo to give the desired compound. LC-MS: m/z 659.5 $[M+H]^+$.

Step C—Synthesis of Intermediate 18c To a vial containing intermediate 18b (0.1155 g, 0.175 mmol) was added 1:2 DCM/TFA (1.8 mL) at ambient temperature, and the reaction was stirred for 23 h. To the reaction was added 30% toluene/MeOH (5 mL) and the resulting mixture was concentrated in vacuo. The residue was azeotroped with MeOH (2×5 mL) and then dried under high vacuum to give the desired compound. LC-MS: m/z 403.3 $[M+H]^+$.

Step D—Synthesis of Compound 35 To a vial charged with intermediate 18c (0.175 mmol), intermediate 5 (0.159 mmol), and powdered molecular sieves 4 Å (325 mesh particle; 50 mg, dried under high vacuum with heat) was added anhydrous dimethylacetamide (0.6 mL) at ambient temperature. The reaction mixture was stirred for 19 h, then filtered through a Celite™ pad to remove the molecular sieves, and the Celite™ pad was washed with MeOH. The filtrate was concentrated in vacuo, and the resulting residue was cooled to 0° C. Then DCM (10 mL) was added slowly with stirring resulting in precipitation of a solid. The solids were collected by centrifugation (4000 rpm). The supernatant was decanted and the insoluble solids were dried in vacuo. The dried solids were purified by a reverse phase HPLC (XSelect CSH Prep C18; 5 uM OBD; 50×250 mm; 0%-16% ACN/(water+0.16% TFA) over 11 min.; isocratic at 13% ACN/(water+0.16% TFA) for 14 min. The product fractions were collected, concentrated in vacuo, and the aqueous layer was directly loaded onto an Amberchrom CG161M column (26 g), washed with 10 CV of (water+0.1% FA), and eluted off with 3 CV of 100% (ACN+0.1% FA) followed by 3 CV of 50% (ACN+0.1% FA)/(water+0.1% FA). The product fractions were collected, concentrated in vacuo, and resulting aqueous residue was lyophilized to give the title compound as the formic acid salt. LC-MS: m/z 749.5 $[M+H]^+$. $^1H$ NMR (500 MHz, 4:1$D_2O$/d-DMSO) δ: 7.37 (s, 1H), 7.36-7.29 (m, 1H), 6.94-6.83 (m, 2H), 4.66 (s, 1H), 4.41 (d, J=11.1 Hz, 1H), 2.88-2.75 (s, 2H), 2.20-2.04 (m, 7H), 1.96-1.88 (m, 6H), 1.80-1.68 (m, 1H), 1.53 (s, 3H), 1.43 (s, 3H), 1.25 (s, 3H).

Example 22: Preparation of Compound 36
(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-(azetidin-3-yl)carbamimidoyl)chroman-2-yl)propanoic acid
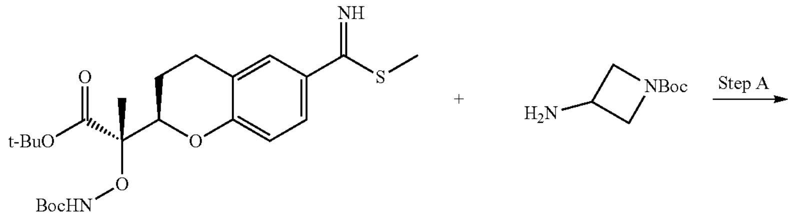
Int-3c
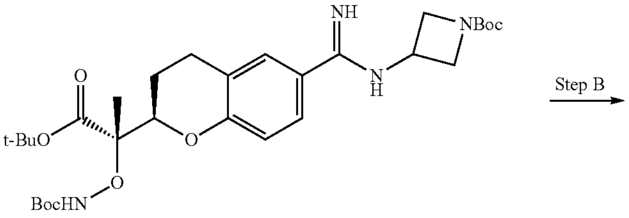
Int-19a
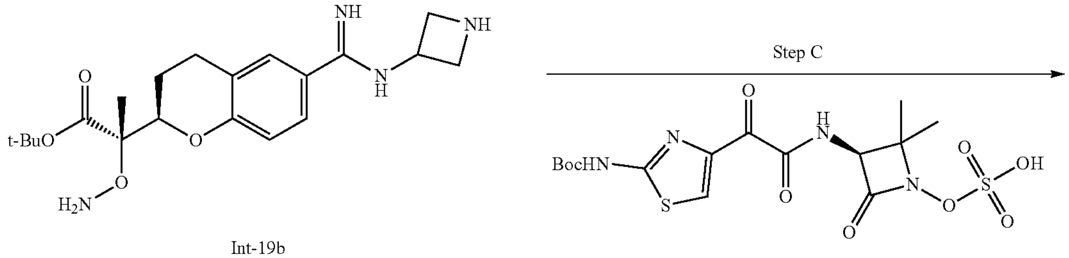
Int-19b
Int-4
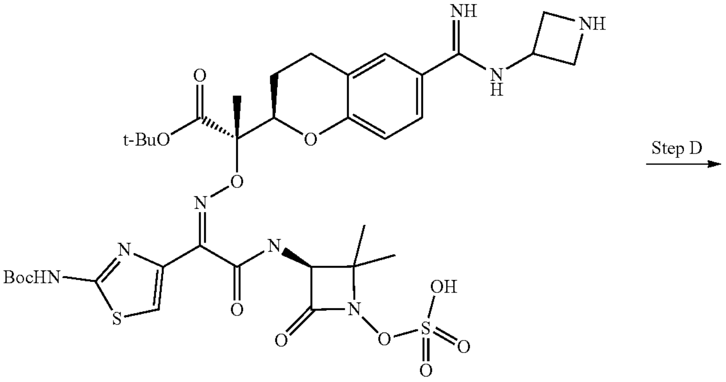
Int-19c -continued

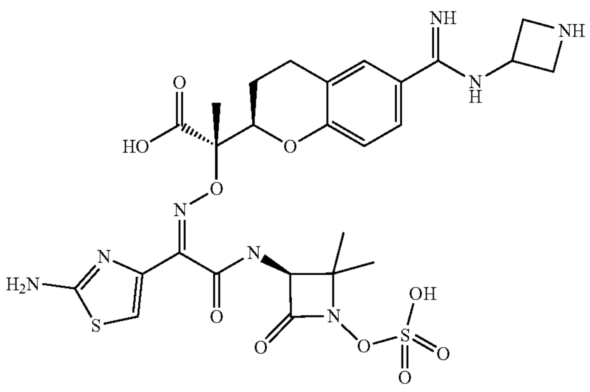

Compound 36

Step A—Synthesis of Intermediate 19a To a solution of tert-butyl 3-aminoazetidine-1-carboxylate (90 mg, 0.523 mmol) and intermediate 3c (300 mg, 0.505 mmol) in MeOH (5 mL) was added acetic acid (0.116 mL, 2.018 mmol), followed by potassium acetate (99 mg, 1.009 mmol) at 23° C. The reaction mixture was stirred at 83° C. for 20 minutes, then cooled to room temperature. The reaction mixture was directly purified by silica gel chromatography (Biotage; 12 g Agela Silica Flash Column, Eluent of 10% MeOH/DCM gradient @ 40 mL/min) to give crude product. The crude product was further purified by a reverse phase HPLC (Boston Uni C18 40*150*5 um. Condition: water (0.1% TFA)-ACN; Begin B 30, End B 60; Gradient Time (min) 11; 100% B Hold Time (min) 2; FlowRate (mL/min) 60; Injections 1) to give intermediate 19a. LC-MS (ESI): m/z 591.3 $[M+H]^+$.

Step B—Synthesis of Intermediate 19b A solution of intermediate 19a (204 mg, 0.345 mmol) in a 2:1 mixture of DCM:TFA (3 mL) was stirred at 25° C. for 0.5 h. Then the reaction mixture was dried with nitrogen gas flow to give intermediate 19b, which was used in the next reaction without further purification. LC-MS (ESI): m/z 391.3 $[M+H]^+$.

Step C—Synthesis of Intermediate 19c A solution of intermediate 19b (135 mg, 0.346 mmol) and intermediate 4 (161 mg, 0.346 mmol) in 3 mL of MeOH was stirred at 25° C. for 1.5 h. Then the reaction mixture was concentrated under vacuum to give intermediate 19c, which was used in the next reaction without further purification. LC-MS (ESI): m/z 837.7 $[M+H]^+$.

Step D—Synthesis of Compound 36 A mixture of intermediate 19c (269 mg, 0.321 mmol) in a 3:1 mixture of TFA:DCM (3 mL) was stirred at 25° C. for 30 minutes. Then the reaction mixture was dried with nitrogen gas flow, and the resulting residue was purified by Prep-HPLC (Column Boston Uni C18 40*150*5 um. Condition: water (0.1% TFA)-ACN; Begin B 1, End B 31; Gradient Time (min) 11; 100% B Hold Time (min) 2; FlowRate (mL/min) 60; Injections 1) to give the crude product. The crude product was further purified by Prep-HPLC (Column YMC-Actus Triart C18 150*30 mm*5 um. Condition: water (0.225% FA)-ACN; Begin B 0, End B 20; Gradient Time (min) 19; 100% B Hold Time (min) 2; FlowRate (mL/min) 25; Injections 3) to give compound 36 as the formic acid salt form. LC-MS (ESI): m/z 681.2 $[M+H]^+$. $^1H$ NMR (400 MHz, DMSO-$d_6$): 7.52 (s, 1H), 7.38 (br d, J=8.6 Hz, 1H), 6.73 (s, 1H), 6.70 (br d, J=8.6 Hz, 1H), 4.62-4.51 (m, 1H), 4.44-4.26 (m, 5H), 4.06-3.95 (m, 1H), 2.86-2.61 (m, 2H), 2.06-1.93 (m, 1H), 1.50 (s, 3H), 1.43-1.38 (m, 1H), 1.36 (s, 3H), 1.21 (s, 3H).

Example 23: Preparation of Compounds 37 to 44

Starting from intermediate 3c, Compounds 37-44 were prepared using the procedure described in Step A through Step D of Example 22 wherein tert-butyl (1-(2-aminoethyl) piperidin-4-yl)carbamate is replaced with the appropriate commercially available mono-Boc protected diamines in Step A.

| Compound | Structure | LC-MS [M + H]+ | 1H NMR |
|---|---|---|---|
| 37 | 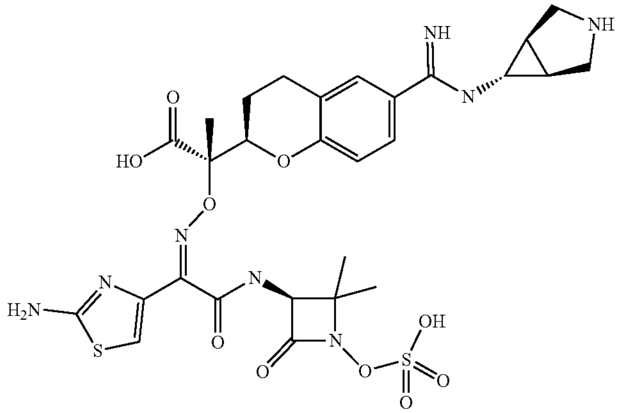 (S)-2-((R)-6-(N-((1R,5S,6s)-3-aza-bicyclo[3.1.0]hexan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy) propanoic acid | 707.2 | $^1$H NMR (400 MHz, $D_2O$ + $CD_3CN$) δ: 7.33 (s, 1H), 7.27 (br d, J = 8.6 Hz, 1H), 6.87-6.80 (m, 2H), 4.62-4.60 (m, 1H), 4.39 (br d, J = 10.6 Hz, 1H), 3.68-3.57 (m, 2H), 3.56-3.46 (m, 2H), 2.85-2.66 (m, 3H), 2.33-2.23 (m, 2H), 2.12-2.01 (m, 1H), 1.78-1.63 (m, 1H), 1.50 (s, 3H), 1.40 (s, 3H), 1.21 (s, 3H). |
| 38 | 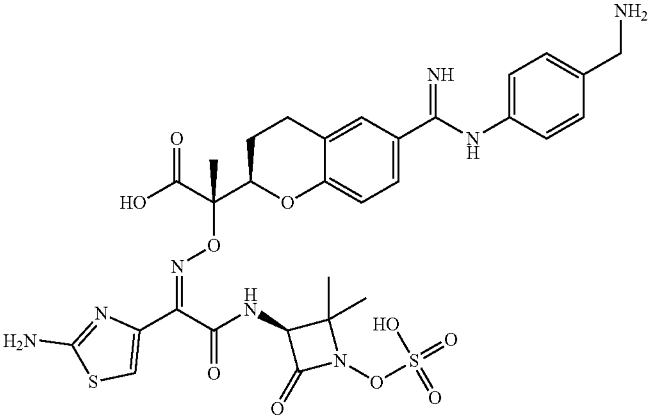 [SMILES: CC1(C)[C@H](NC(=O)/C(=N\O[C@](C)(C(=O)O)[C@H]2CCc3cc(C(=N)Nc4ccc(CN)cc4)ccc3O2)c2csc(N)n2)C(=O)N1OS(=O)(=O)O] (S)-2-((R)-6-(N-(4-(aminomethyl)phenyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-propanoic acid | 731.2 | $^1$H NMR (DMSO-$d_6$, 400 MHz) δ: 7.65-7.46 (m, 4H), 7.35-7.24 (m, 2H), 6.99-6.91 (m, 1H), 6.76 (s, 1H), 4.63 (s, 1H), 4.39 (br d, J = 9.8 Hz, 1H), 4.10-3.96 (m, 2H), 2.82-2.66 (m, 2H), 1.97-1.82 (m, 1H), 1.63-1.51 (m, 1H), 1.50 (s, 3H), 1.40 (s, 3H), 1.25 (s, 3H). |
| 39 | 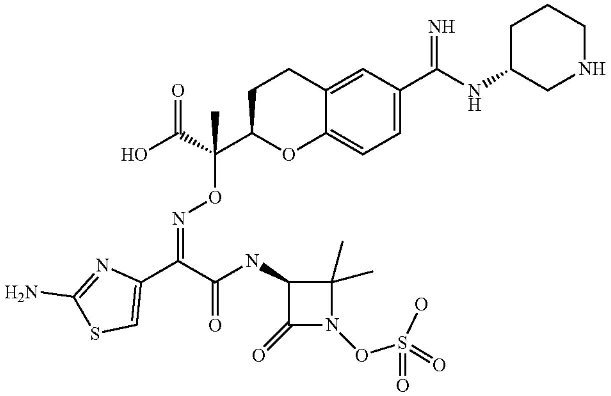 (S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-((R)-6-(N-((R)-piperidin-3-yl)carbamimidoyl)-chroman-2-yl)propanoic acid | 709.2 | $^1$H NMR (400 MHz, DMSO-$d_6$) δ: 7.50 (s, 1H), 7.38 (d, J = 8.6 Hz, 1H), 6.84 (d, J = 8.6 Hz, 1H), 6.73 (s, 1H), 4.56 (s, 1H), 4.31 (br d, J = 11.7 Hz, 1H), 3.98 (br s, 1H), 3.37 (br d, J = 11.7 Hz, 1H), 3.18-3.05 (m, 1H), 3.03-2.86 (m, 2H), 2.85-2.67 (m, 2H), 2.10-1.85 (m, 3H), 1.76-1.47 (m, 3H), 1.45 (br s, 3H), 1.38 (s, 3H), 1.23 (s, 3H). |

-continued

| Compound | Structure | LC-MS $[M + H]^+$ | $^1H$ NMR |
|---|---|---|---|
| 40 | 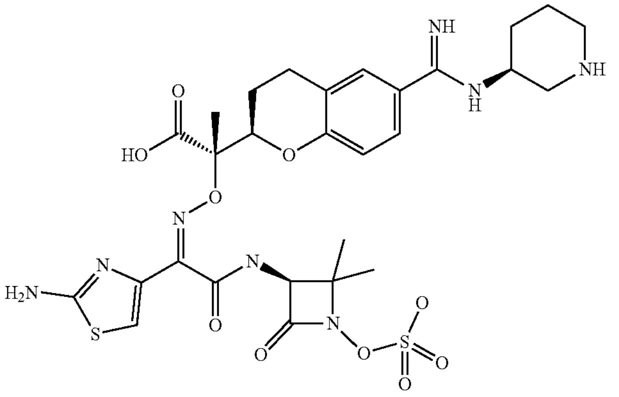 (S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-((R)-6-(N-((S)-piperidin-3-yl)carbamimidoyl)-chroman-2-yl)propanoic acid | 709.3 | $^1H$ NMR (400 MHz, $CD_3CN$) δ: 7.40-7.32 (m, 2H), 6.90 (d, J = 8.6 Hz, 1H), 6.79 (s, 1H), 4.61 (s, 1H), 4.41 (br d, J = 11.0 Hz, 1H), 4.01-3.91 (m, 2H), 3.55-3.48 (m, 1H), 3.34-3.25 (m, 1H), 3.09-3.01 (m, 1H), 2.99-2.88 (m, 1H), 2.87-2.70 (m, 2H), 2.14-2.03 (m, 3H), 1.82-1.66 (m, 2H), 1.54 (s, 3H), 1.44 (s, 3H), 1.26 (s, 3H). |
| 41 | 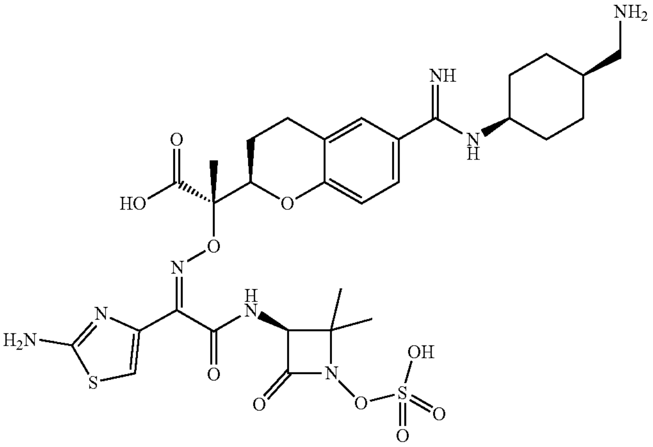 [SMILES: CC1(C)[C@H](NC(=O)/C(=N\O[C@](C)(C(=O)O)[C@H]2CCc3cc(C(=N)N[C@H]4CC[C@@H](CN)CC4)ccc3O2)c2csc(N)n2)C(=O)N1OS(=O)(=O)O] (S)-2-((R)-6-(N-((1s,4S)-4-(amino-methyl)-cyclohexyl)carbamimidoyl)chroman-2-yl)-2-((((Z)-1-(2-amino-thiazol-4-yl)-2-(((S)-2,2-dimethyl-4-oxo-1-(sulfooxy)azetidin-3-yl)amino)-2-oxo-ethylidene)amino)oxy)-propanoic acid | 737.3 | $^1H$ NMR (400 MHz, $CD_3CN$) δ: 7.46-7.34 (m, 2H), 6.90 (d, J = 8.2 Hz, 1H), 6.79 (s, 1H), 4.63 (s, 1H), 4.39 (br d, J = 9.8 Hz, 1H), 3.82-3.73 (m, 1H), 2.91-2.86 (m, 2H), 2.86-2.75 (m, 2H), 2.13-2.04 (m, 1H), 1.78-1.55 (m, 8H), 1.51 (s, 3H), 1.48-1.37 (m, 2H), 1.44 (s, 3H), 1.26 (s, 3H). |
| 42 | 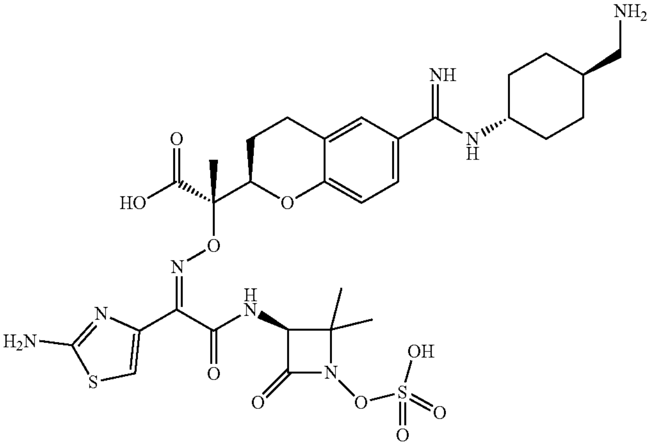 [SMILES: CC1(C)[C@H](NC(=O)/C(=N\O[C@](C)(C(=O)O)[C@H]2CCc3cc(C(=N)N[C@H]4CC[C@H](CN)CC4)ccc3O2)c2csc(N)n2)C(=O)N1OS(=O)(=O)O] (S)-2-((R)-6-(N-((1r,4R)-4-(aminomethyl)-cyclohexyl)carbamimidoyl)chroman-2-yl)-2-((((Z)-1-(2-aminothiazol-4-yl)-2-(((S)-2,2- | 737.2 | $^1H$ NMR (400 MHz, $CD_3CN$) δ: 7.40-7.33 (m, 2H), 6.87 (d, J = 8.2 Hz, 1H), 6.81 (s, 1H), 4.61 (s, 1H), 4.38 (br d, J = 10.6 Hz, 1H), 3.56-3.45 (m, 1H), 2.87-2.71 (m, 4H), 2.11-1.98 (m, 3H), 1.86-1.76 (m, 2H), 1.76-1.53 (m, 2H), 1.49 (s, 3H), 1.46-1.34 (m, 5H), 1.24 (s, 3H), 1.17-1.00 (m, 2H). |

-continued

| Compound | Structure | LC-MS [M + H]+ | $^1$H NMR |
|---|---|---|---|
| | dimethyl-4-oxo-1-(sulfooxy)azetidin-3-yl)amino)-2-oxo-ethylidene)amino)oxy)-propanoic acid | | |
| 43 | 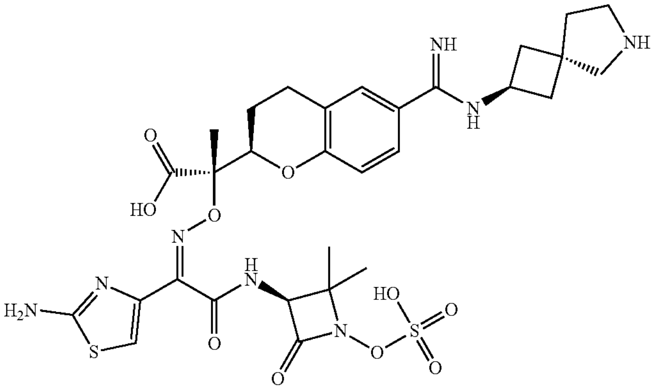 [SMILES: CC1(C)[C@H](NC(=O)/C(=N\O[C@](C)(C(=O)O)[C@H]2CCc3cc(C(=N)N[C@H]4C[C@@]5(CCNC5)C4)ccc3O2)c2csc(N)n2)C(=O)N1OS(=O)(=O)O] (S)-2-((R)-6-(N-((2s,4R)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-propanoic acid | 735.5 | $^1$H NMR (400 MHz, $D_2O$ + $CD_3CN$) δ: 7.46-7.32 (m, 2H), 6.89 (d, J = 8.6 Hz, 1H), 6.79 (s, 1H), 4.60 (s, 1H), 4.39 (br d, J = 10.6 Hz, 1H), 4.17-4.04 (m, 1H), 3.26 (s, 2H), 3.20 (t, J = 7.4 Hz, 2H), 2.88-2.71 (m, 2H), 2.64-2.52 (m, 2H), 2.31-2.22 (m, 2H), 2.13-1.98 (m, 3H), 1.79-1.62 (m, 1H), 1.50 (s, 3H), 1.42 (s, 3H), 1.25 (s, 3H). |
| 44 | 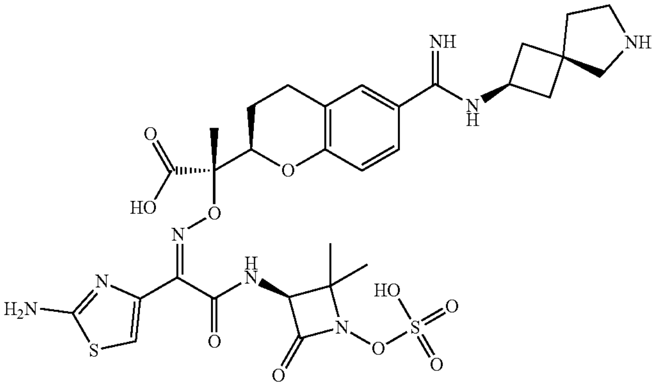 [SMILES: CC1(C)[C@H](NC(=O)/C(=N\O[C@](C)(C(=O)O)[C@H]2CCc3cc(C(=N)N[C@H]4C[C@]5(CCNC5)C4)ccc3O2)c2csc(N)n2)C(=O)N1OS(=O)(=O)O] (S)-2-((R)-6-(N-((2r,4S)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-propanoic acid | 735.1 | $^1$H NMR (400 MHz, $D_2O$ + $CD_3CN$): 7.44-7.35 (m, 2H), 6.88 (d, J = 8.6 Hz, 1H), 6.79 (s, 1H), 4.59 (s, 1H), 4.38 (br d, J = 11.3 Hz, 1H), 4.22-4.10 (m, 1H), 3.24 (t, 7 = 7.2 Hz, 2H), 3.19 (s, 2H), 2.88-2.70 (m, 2H), 2.55-2.44 (m, 2H), 2.33-2.22 (m, 2H), 2.12-1.99 (m, 3H), 1.77-1.62 (m, 1H), 1.49 (s, 3H), 1.42 (s, 3H), 1.24 (s, 3H). |

Example 24: Preparation of Compounds 45 and 46

(S)-2-((R)-6-(N-((1R,3S)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1S,3R)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

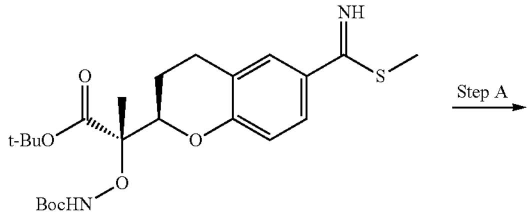

Int-3c

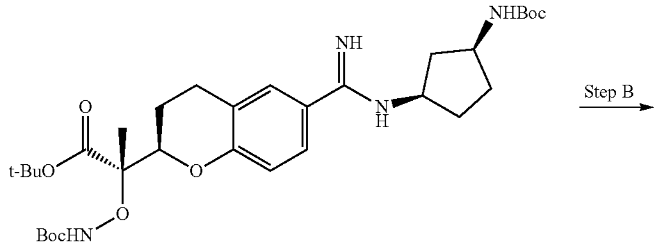

Int-20a

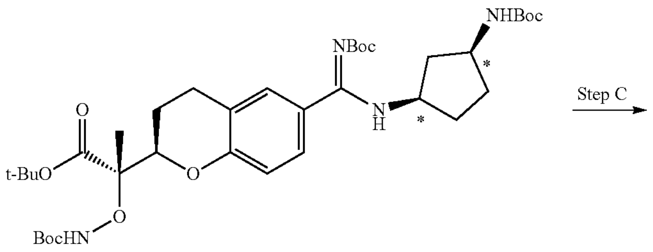

Int-20b-1
Int-20b-2

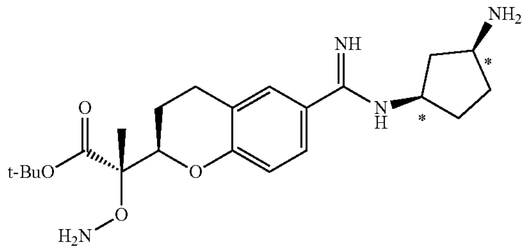

Int-20c-1
Int-20c-2

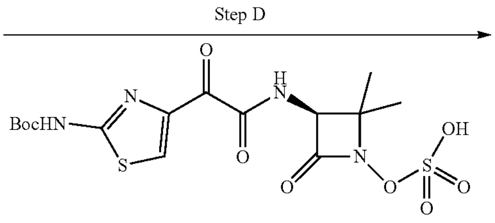

Int-4

-continued

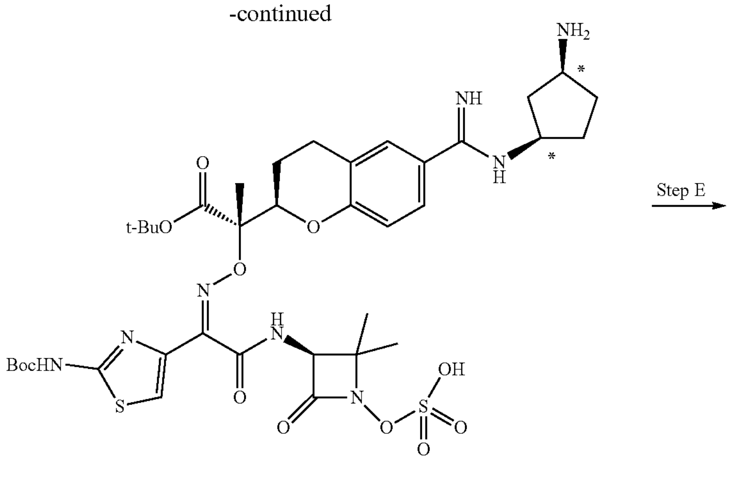

Int-20d-1
Int-20d-2

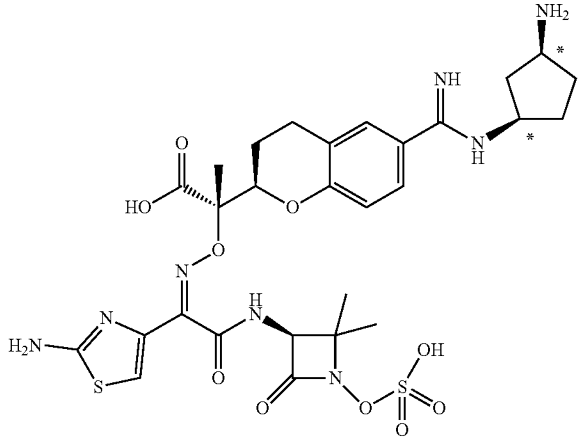

Compound 45
Compound 46

Step A—Synthesis of Intermediate 20a Acetic acid (0.294 mL, 5.14 mmol) and potassium acetate (379 mg, 3.86 mmol) was added to a stirred mixture of racemic cis-3-((tert-butoxycarbonyl)-amino)cyclopentanaminium carboxyformate (448 mg, 1.543 mmol) and intermediate 3c (600 mg, 1.286 mmol) in MeOH (6.0 mL). The reaction mixture was stirred at 80° C. for 10 minutes, then diluted with $H_2O$ (50 mL), extracted with EtOAc (50 mL×3), washed with brine (150 mL), and dried over anhydrous $Na_2SO_4$. After filtration, the filtrate was concentrated under vacuum, the resulting residue was purified by a flash silica gel chromatography (Biotage; 4 g Agela Silica Flash Column, Eluent of 0~10% MeOH/DCM gradient @ 35 mL/min) to give intermediate 20a as a mixture of stereoisomers. LC-MS (ESI): m/z 619.4 $[M+H]^+$.

Step B—Synthesis of Intermediates 20b-1 and 20b-2 To a solution of intermediate 20a (460 mg, 0.743 mmol) in DCM (10 mL) stirred at 0° C., was added $Et_3N$ (0.518 mL, 3.72 mmol) and $(Boc)_2O$ (0.345 mL, 1.487 mmol). The reaction mixture was stirred at 26° C. for 2.5 h, then diluted with saturated aqueous $NH_4Cl$ (30 mL), and the mixture was extracted with DCM (30 mL×3). The combined organic layers were dried over anhydrous $Na_2SO_4$, filtered and concentrated under vacuum. The resulting residue was purified by a flash silica gel chromatography (Biotage; 4 g Agela Silica Flash Column, Eluent of Petroleum ether/EtOAc=0~60% gradient @ 30 mL/min) to give intermediate 20b as a mixture of stereoisomers. LC-MS (ESI): m/z 719.3 $[M+H]^+$. The mixture was further separated by SFC to give intermediate 20b-1 (the first eluting isomer) and intermediate 20b-2 (the second eluting isomer). LC-MS (ESI): m/z 719.4 $[M+H]^+$.

Step C—Synthesis of Intermediate 20c-1 Intermediate 20b-1 (140 mg, 0.195 mmol) was added to a stirred solution of 2:1 DCM/TFA (2.4 mL) at 0° C. The reaction mixture was stirred at 26° C. for 40 minutes, then the solvent was removed under a $N_2$ gas flow to give intermediate 20c-1, which was used in the next reaction without further purification. LC-MS (ESI): m/z 419.3 $[M+H]^+$.

Step D—Synthesis of Intermediate 20d-1 To a solution of intermediate 20c-1 (82 mg, 0.197 mmol) in MeOH (3.0 mL) was added intermediate 4 (91 mg, 0.197 mmol). The reaction mixture was stirred at 26° C. for 2.5 h. Then the reaction mixture was concentrated under $N_2$ gas flow to give intermediate 20d-1, which was used in the next reaction without further purification. LC-MS (ESI): m/z 865.2 $[M+H]^+$.

Step E—Synthesis of Compounds 45 and 46 A solution of intermediate 20d-1 (170 mg, 0.197 mmol) in 1:2 DCM:TFA (2.5 mL) was stirred at 26° C. for 55 min. Then the solvent was removed under a $N_2$ gas flow, and the resulting residue was purified by a reverse phase HPLC (Column: Boston Uni C18 250*50*5 um; Condition: water (0.1% TFA)-ACN; Begin B 1, End B 31; Gradient Time (min) 11; 100% B Hold Time (min) 2; FlowRate (mL/min) 60). The product fractions were combined and lyophilized to give compound 45 as its TFA salt. The TFA salt was converted into the formic acid salt by passing through a reverse phase HPLC (Column: Welch Xtimate C18 150*25 mm*5 um; Condition: water (0.225% FA)-ACN; Begin B 0, End B 18; Gradient Time (min) 15; 100% B Hold Time (min) 2; FlowRate (mL/min) 25) to give compound 45 as the formic acid salt form. LC-MS (ESI): m/z 708.9 $[M+H]^+$. $^1H$ NMR (400 MHz, $CD_3CN+D_2O$) δ: 7.41-7.34 (m, 2H), 6.86 (d, J=8.6 Hz, 1H), 6.79 (s, 1H), 4.61 (s, 1H), 4.34 (br d, J=10.2 Hz, 1H), 4.10-4.01 (m, 1H), 3.67-3.57 (m, 1H), 2.85-2.69 (m, 2H), 2.67-2.57 (m, 1H), 2.15-1.99 (m, 3H), 1.92-1.57 (m, 4H), 1.48 (s, 3H), 1.42 (s, 3H), 1.24 (s, 3H).

Starting from intermediate 20b-2, compound 46 was prepared using the procedure of step C to step E of Example 24.

Compound 46: LC-MS (ESI): m/z 709.1 $[M+H]^+$. $^1H$ NMR (400 MHz, $CD_3CN+D_2O$) δ: 7.42-7.34 (m, 2H), 6.85 (d, J=8.6 Hz, 1H), 6.79 (s, 1H), 4.61 (s, 1H), 4.34 (br d, J=9.8 Hz, 1H), 4.10-4.01 (m, 1H), 3.63 (quin, J=7.5 Hz, 1H), 2.84-2.68 (m, 2H), 2.68-2.58 (m, 1H), 2.14-2.00 (m, 3H), 1.90-1.63 (m, 4H), 1.49 (s, 3H), 1.42 (s, 3H), 1.24 (s, 3H).

*Each compound is a single diastereomer; stereochemistry at * marked carbon centers is unassigned.

Example 25: Preparation of Compounds 47 and 48

(S)-2-((R)-6-(N-((1S,3S)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1R,3R)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

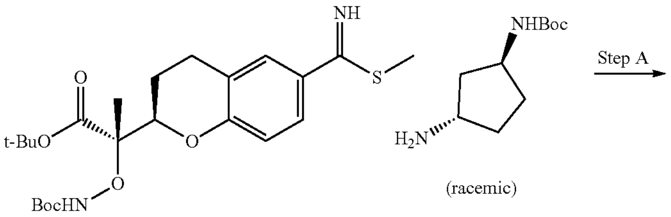

(racemic)

Int-3c

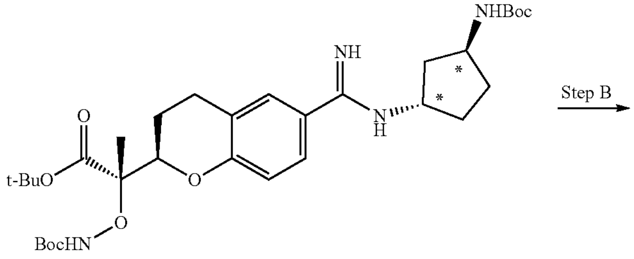

Int-21a-1
Int-21a-2

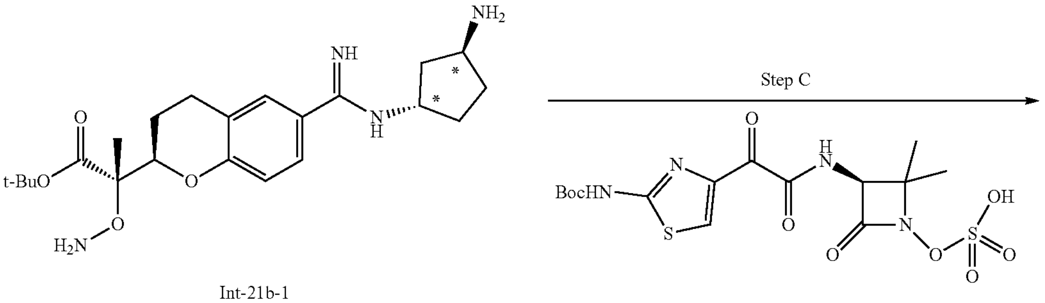

Int-21b-1
Int-21b-2

Int-4

-continued

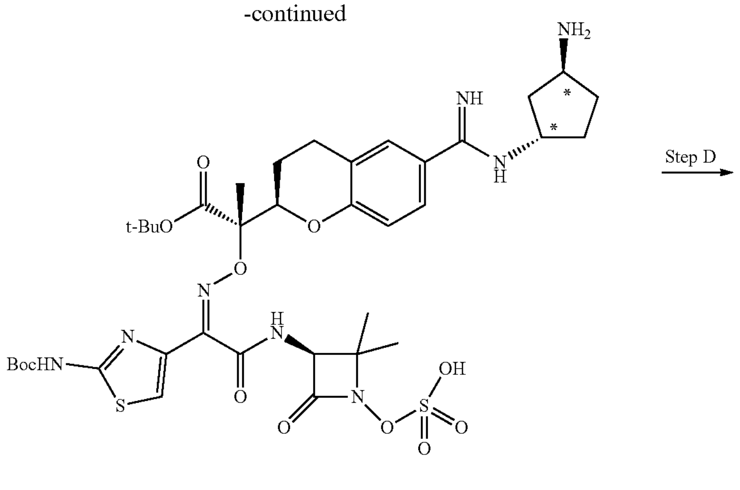

Int-21c-1
Int-21c-2

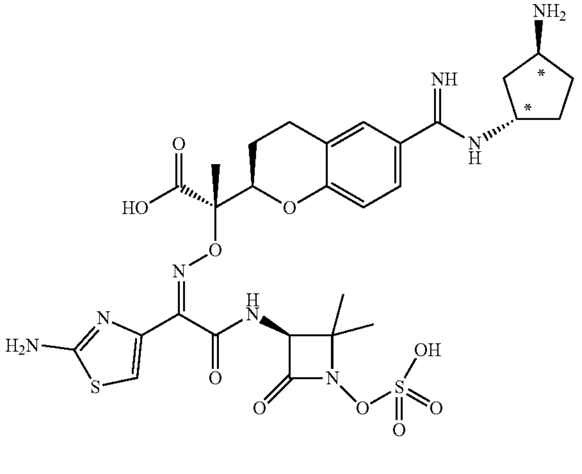

Compound 47
Compound 48

Step A—Synthesis of Intermediates 21a-1 and 21a-2 To a solution of intermediate 3c (800 mg, 1.715 mmol) in MeOH (17 mL) was added trans-3-((tert-butoxycarbonyl)amino) cyclo-pentanaminium carboxyformate (572 mg, 1.972 mmol), and acetic acid (0.393 mL, 6.86 mmol) at 25° C. Then potassium acetate (505 mg, 5.14 mmol) was added. The reaction mixture was stirred at 80° C. for 20 minutes (under a $N_2$ atmosphere). The reaction mixture was then concentrated under reduced pressure, and the resulting residue was purified by a flash silica gel chromatography (ISCO; 12 g Agela Silica Flash Column, Eluent of 0~5% $CH_2Cl_2$/MeOH gradient @ 30 mL/min) to give a mixture of intermediate 21a-1 and intermediate 21a-2. LC-MS (ESI): m/z 619.4 $[M+H]^+$. The mixture of intermediates was further separated by SFC (DAICEL CHIRALCEL OD-H (250 mm*30 mm, 5 um); 0.1% $NH_3 \cdot H_2O$/EtOH; Begin B: 30%; End B: 30%; FlowRate (mL/min): 60; Injections: 120) to give intermediate 21a-1 (the first eluting compound) and intermediate 21a-2 (the second eluting compound). LC-MS (ESI): m/z 619.3 $[M+H]^+$.

Step B—Synthesis of Intermediate 21b-1 A solution of intermediate 21a-1 (170 mg, 0.275 mmol) in DCM (0.9 mL) and TFA (1.8 mL) was stirred at 25° C. for 0.5 h. Then the reaction mixture was concentrated under vacuum to give intermediate 21b-1, which was used in the next step without further purification. LC-MS (ESI): m/z 418.9 $[M+H]^+$.

Step C—Synthesis of Intermediate 21c-1 A mixture of intermediate 21b-1 (115 mg, 0.275 mmol) and intermediate 4 (115 mg, 0.248 mmol) in MeOH (2.8 mL) was stirred at 25° C. for 3 h. Then the reaction mixture was concentrated under vacuum to afford intermediate 21c-1, which was used in the next step without further purification. LC-MS (ESI): m/z 865.7 $[M+H]^+$.

Step D—Synthesis of Compounds 47 and 48 To a solution of intermediate 21c-1 (238 mg, 0.275 mmol) in DCM (0.900 mL) was added TFA (1.8 mL). The reaction was stirred at 25° C. for 30 minutes, then the solvent was removed with $N_2$ to give the crude product, which was purified by HPLC (Column: Boston Uni C18 40*150*5 um; Condition: water (0.1% TFA)-ACN Begin B 1, End B 31; Gradient Time (min) 10; 100% B Hold Time (min) 2; FlowRate (mL/min) 60; Injections: 1) to give compound 47 as its TFA salt. The TFA salt was converted to the formic acid salt by passing it through a reverse phase HPLC (Column: Welch Xtimate C18 150*25 mm 5 um; Condition: water (0.225% FA)-ACN; Begin B 0, End B 19; Gradient Time (min) 15; 100% B Hold Time (min) 2; FlowRate (mL/min) 25; injections: 2) to give compound 47 as the formic acid salt. MS (ESI) m/z:

709.4 [M+H]$^+$. $^1$H NMR (400 MHz, $D_2O$+$CD_3CN$) δ: 7.39-7.31 (m, 2H), 6.87 (br d, J=8.6 Hz, 1H), 6.79 (s, 1H), 4.61 (s, 1H), 4.48-4.40 (m, 1H), 4.25-4.14 (m, 1H), 3.80-3.71 (m, 1H), 2.84-2.69 (m, 2H), 2.31-2.17 (m, 3H), 2.14-2.02 (m, 2H), 1.83-1.61 (m, 3H), 1.49 (s, 3H), 1.42 (s, 3H), 1.24 (s, 3H).

Compound 48 was prepared starting from intermediate 21a-2 according to the procedure in Step B to Step D of this Example 25. LC-MS (ESI): m/z 709.3 [M+H]$^+$. $^1$H NMR (400 MHz, $D_2O$+$CD_3CN$) δ: 7.39-7.29 (m, 2H), 6.90-6.77 (m, 2H), 4.61 (s, 1H), 4.38 (br d, J=11.0 Hz, 1H), 4.23-4.13 (m, 1H), 3.83-3.72 (m, 1H), 2.83-2.69 (m, 2H), 2.31-2.17 (m, 3H), 2.16-2.00 (m, 2H), 1.83-1.63 (m, 3H), 1.49 (s, 3H), 1.41 (s, 3H), 1.23 (s, 3H). *Each compound is a single diastereomer; stereochemistry at * marked carbon centers is unassigned.

Example 26: Preparation of Compounds 49-50

Starting from intermediate 3c, Compounds 49-50 were prepared using the procedure described in Step A through Step D of Example 25 replacing trans-3-((tert-butoxycarbonyl)amino)cyclo-pentanaminium carboxyformate with the appropriate racemic amines in Step A:

Example 27: Preparation of Intermediates 22c-1 and 22c-2

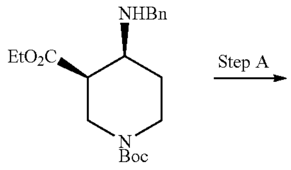

Cis, racemic

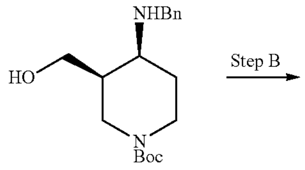

Int-22a

| Compound | Structure | LC-MS [M + H]$^+$ | $^1$H NMR |
|---|---|---|---|
| 49 (stereoisomer 1) | 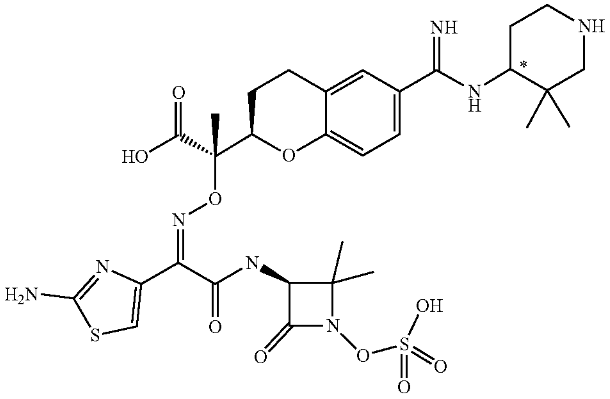 (S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((S or R)-3,3-dimethylpiperidin-4-yl)carbamimidoyl)chroman-2-yl)propanoic acid | 737.1 | $^1$H NMR (400 MHz, $CD_3CN$ + $D_2O$) δ: 7.43-7.35 (m, 2H), 6.88 (d, J = 8.2 Hz, 1H), 6.84 (s, 1H), 4.63 (s, 1H), 4.40 (br d, J = 10.6 Hz, 1H), 3.85-3.76 (m, 1H), 3.44-3.35 (m, 1H), 3.17 (d, J = 13.7 Hz, 1H), 3.09-2.95 (m, 1H), 2.90 (d, J = 12.9 Hz, 1H), 2.83-2.69 (m, 2H), 2.14-1.97 (m, 3H), 1.79-1.64 (m, 1H), 1.50 (s, 3H), 1.41 (s, 3H), 1.22 (s, 3H), 1.10 (s, 3H), 1.03 (s, 3H). |
| 50 (stereoisomer 2) | 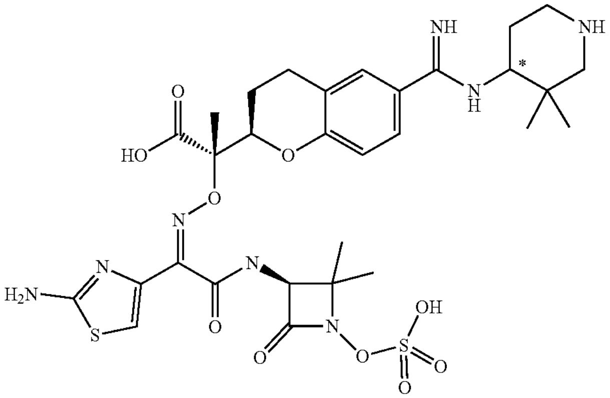 (S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-2-((R)-6-(N-((R or S)-3,3-dimethylpiperidin-4-yl)carbamimidoyl)chroman-2-yl)propanoic acid | 737.3 | $^1$H NMR (400 MHz, $CD_3CN$ + $D_2O$) δ: 7.43-7.34 (m, 2H), 6.89 (d, J = 9.0 Hz, 1H), 6.81 (s, 1H), 4.64 (s, 1H), 4.39 (br d, J = 11.0 Hz, 1H), 3.84-3.76 (m, 1H), 3.44-3.34 (m, 1H), 3.16 (d, J = 13.7 Hz, 1H), 3.09-2.95 (m, 1H), 2.89 (d, J = 12.9 Hz, 1H), 2.86-2.71 (m, 2H), 2.12-1.97 (m, 3H), 1.78-1.62 (m, 1H), 1.50 (s, 3H), 1.42 (s, 3H), 1.25 (s, 3H), 1.09 (s, 3H), 1.03 (s, 3H). |

-continued

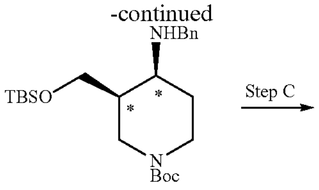

Int-22b-1 (enantiomer 1)
Int-22b-2 (enantiomer 2)

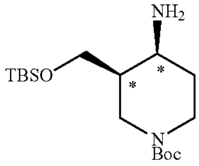

Int-22c-1 (enantiomer 1)
Int-22c-2 (enantiomer 2)

Step A—Synthesis of Intermediate 22a To a solution of racemic (3,4-cis)-1-tert-butyl 3-ethyl 4-(benzylamino)piperidine-1,3-dicarboxylate (2 g, 5.52 mmol) in THF (10 mL), stirred at 0° C., was added portion wise LAH (0.6 g, 15.81 mmol). The reaction mixture was stirred at 0° C. for 0.5 h, and then at 22° C. for 15 min. Then the reaction mixture was quenched by sequentially adding water (0.6 mL), 10% NaOH (1.2 mL) and water (1.8 mL). The resulting mixture was stirred at ambient temperature for 15 minutes, then filtered. The filtrate was concentrated under reduced pressure to give intermediate 22a, was used in the next step without further purification. LC-MS (ESI): m/z 321.5 $[M+H]^+$.

Step B—Synthesis of Intermediate 22b To a stirred solution of intermediate 22a (2 g, 6.24 mmol), imidazole (1.062 g, 15.60 mmol) and DMAP (0.153 g, 1.248 mmol) in DCM (50 mL) was added TBS-Cl (1.882 g, 12.48 mmol) in one portion. The reaction mixture was stirred at 25° C. for 12 h, then diluted with DCM (70 mL), and washed with saturated $NH_4Cl$ solution (100 mL) and brine (100 mL×2). The combined organic layers were dried over anhydrous $Na_2SO_4$, filtered and concentrated under reduced pressure. The resulting residue was purified by a flash silica gel chromatography (ISCO; 20 g Agela Silica Flash Column, Eluent of 0~28% EtOAc/Petroleum ether gradient @ 36 mL/min) to give intermediate 22b as a racemic mixture. This mixture was further separated by SFC (Method: Column: DAICEL CHIRALCEL OD (250 mm*30 mm, 10 um). Condition: 0.1% $NH_3H_2O$/EtOH; Begin B 15%, End B 15%; FlowRate (mL/min) 180; Injections 150) to give intermediate 22b-1 (the first eluting compound) and intermediate 22b-2 (the second eluting compound). Intermediate 22b-1: LC-MS (ESI): m/z 436.1 $[M+H]^+$. Intermediate 22b-2: LC-MS (ESI): m/z 435.6 $[M+H]^+$.

Step C—Synthesis of Intermediates 22c-1 and 22c-2 To a solution of intermediate 22b-1 (1 g, 2.301 mmol) in MeOH (30 mL), was added Pd/C (0.184 g, 0.345 mmol). The reaction mixture was stirred at 25° C. under $H_2$ atmosphere (50 psi) for 20 h. Then the mixture was filtered through Celite™, and the filtrate was concentrated in vacuo to give intermediate 22c-1, which was used in the next reaction without further purification. $^1H$ NMR (400 MHz, $CDCl_3$) δ: 3.67-3.58 (m, 2H), 3.58-3.48 (m, 2H), 3.41-3.23 (m, 2H), 1.82 (br s, 1H), 1.73-1.65 (m, 1H), 1.61 (br s, 1H), 1.58-1.51 (m, 1H), 1.46 (s, 9H), 0.90 (s, 9H), 0.06 (s, 6H).

Intermediate 22c-2 was prepared from intermediate 22b-2 using the procedure described in Example 27. $^1H$ NMR (400 MHz, $CDCl_3$-d) δ: 3.66-3.52 (m, 4H), 3.39-3.22 (m, 2H), 1.82 (br s, 1H), 1.73-1.61 (m, 2H), 1.53 (dt, J=4.7, 9.2 Hz, 1H), 1.46 (s, 9H), 0.90 (s, 9H), 0.06 (s, 6H).

Example 28: Preparation of Compounds 51 and 52

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((3R,4S)-3-(hydroxymethyl)piperidin-4-yl)carbamimidoyl)chroman-2-yl)propanoic acid, and (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((3S,4R)-3-(hydroxymethyl)piperidin-4-yl)carbamimidoyl)chroman-2-yl)propanoic acid*

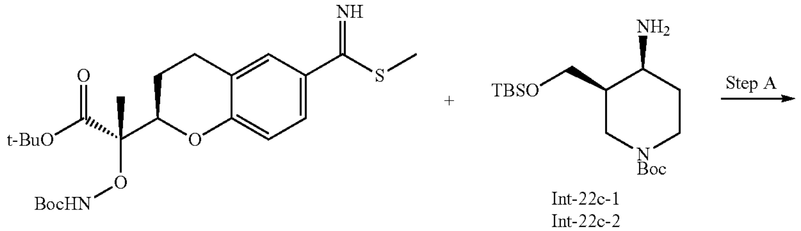

Int-3c

Int-22c-1
Int-22c-2

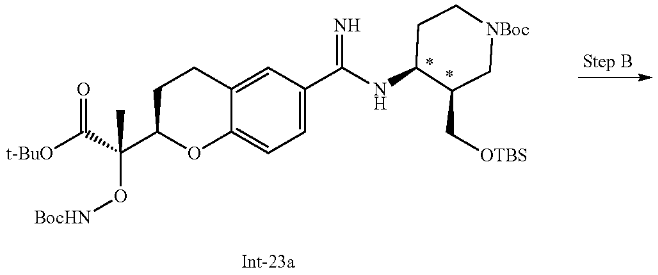

Int-23a

-continued

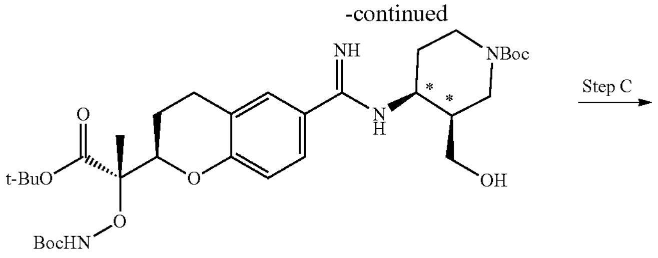

Int-23b

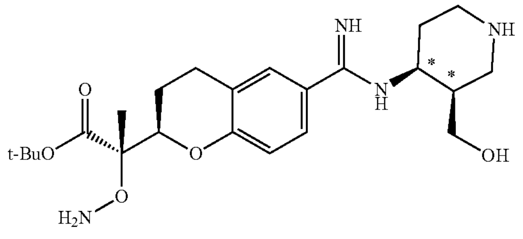

Int-23c

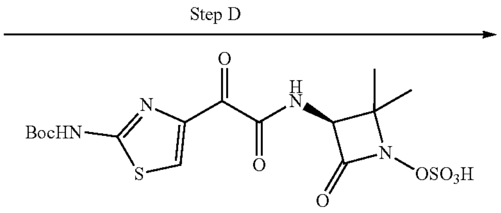

Int-4

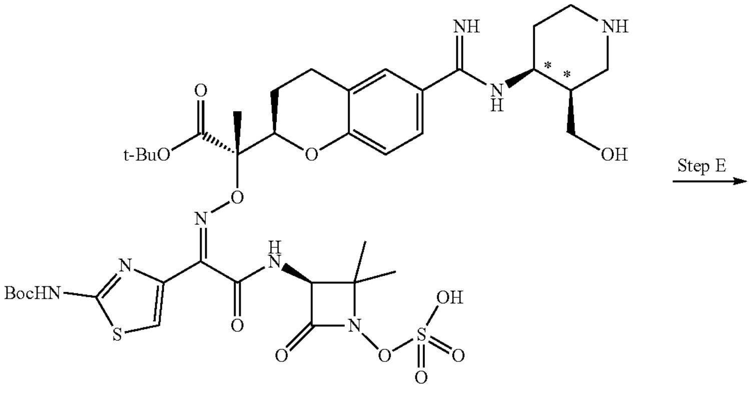

Int-23d

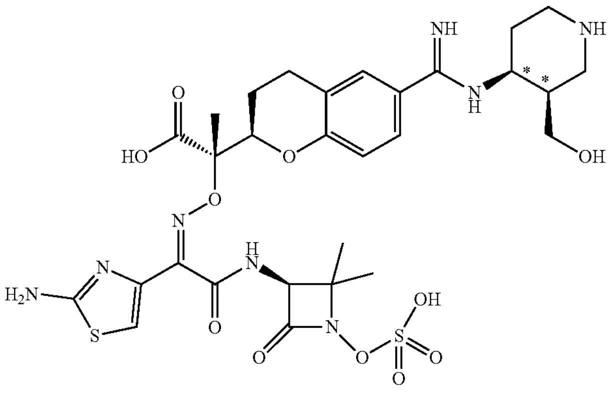

Compound 51
Compound 52

Step A—Synthesis of Intermediate 23a To a stirred mixture of intermediate 22c-1 (792 mg, 1.839 mmol), potassium acetate (246 mg, 2.508 mmol) and intermediate 3c (390 mg, 0.836 mmol) in MeOH (15 mL) was added acetic acid (0.191 mL, 3.34 mmol). The reaction was stirred at 80° C. for 20 minutes, then the solvent was removed under reduced pressure. The resulting residue was purified by a flash silica gel chromatography (ISCO; 20 g Agela Silica Flash Column, Eluent of 0-8% $MeOH/CH_2Cl_2$ gradient @ 20 mL/min) to give intermediate 23a. LC-MS (ESI): m/z 763.5 $[M+H]^+$.

Step B—Synthesis of Intermediate 23b To a solution of intermediate 23a (500 mg, 0.655 mmol) in THF (2 mL) was added TBAF solution in THF (1 M, 0.917 mL, 0.917 mmol). The reaction mixture was stirred at 27° C. for 2 h. Then the reaction mixture was filtered, and the filtrate was concentrated in vacuo to give intermediate 23b, which was used in the next reaction without further purification. LC-MS (ESI): m/z 649.4 $[M+H]^+$.

Step C—Synthesis of Intermediate 23c To a solution of intermediate 23b (500 mg, 0.771 mmol) in DCM (4 mL) was added dropwise TFA (2 mL, 26.0 mmol) at 0° C. The reaction mixture was stirred at 25° C. for 1 h. Then the solvent was removed under reduced pressure to give intermediate 23c, which was used in the next reaction without further purification. LC-MS (ESI): m/z 449.2 $[M+H]^+$.

Step D—Synthesis of Intermediate 23d To a solution of intermediate 23c (400 mg, 0.892 mmol) in MeOH (8 mL) was added intermediate 4 (331 mg, 0.713 mmol). The reaction was stirred at 25° C. for 2 h. Then the solvent was removed under reduced pressure to give intermediate 23d, which was used in the next reaction without further purification. LC-MS (ESI): m/z 448.0 $[M/2+H]^+$.

Step E—Synthesis of Compound 51 To a solution of intermediate 23d (570 mg, 0.637 mmol) in DCM (2 mL) was added dropwise TFA (4 mL) at 0° C. The resulting solution was stirred at 25° C. for 60 min. Then the solvent was removed under vacuum and the resulting residue was purified by a reverse phase HPLC (Column: Boston Uni C18 40*150*5 um; Condition: water (0.1% TFA)-ACN; Begin B 1, End B 31; Gradient Time (min) 10; 100% B Hold Time (min) 2; FlowRate (mL/min) 60). The product fractions were combined and lyophilized to give compound 51 as its TFA salt. The TFA salt which was converted to the formic acid salt by passing through a reverse phase HPLC (Column: Welch Xtimate C18 150*25 mm*5 um; Condition: water (0.225% FA)-ACN; Begin B 0. End B 15; Gradient Time (min) 15; 100% B Hold Time (min) 2; FlowRate (mL/min) 25). The resulting product was further purified by a reverse phase HPLC (Column: Welch Xtimate C18 150*25 mm*5 um; Condition water (10 mM $NH_4HCO_3$)-ACN; Begin B 0, End B 28; Gradient Time (min) 15; 100% B Hold Time (min) 2; FlowRate (mL/min) 25) to give compound 51 as the formic acid salt. LC-MS (ESI): m/z 739.1 $[M+H]^+$. $^1H$ NMR (400 MHz, DMSO-$d_6$) δ: 7.48-7.40 (m, 2H), 6.96 (d, J=8.6 Hz, 1H), 6.76 (s, 1H), 4.60 (s, 1H), 4.42 (br d, J=11.0 Hz, 1H), 4.21-4.13 (m, 1H), 3.54-3.42 (m, 2H), 3.34-3.23 (m, 1H), 3.23-3.03 (m, 3H), 2.91-2.71 (m, 2H), 2.28-2.21 (m, 1H), 2.08-1.97 (m, 2H), 1.94-1.83 (m, 1H), 1.65-1.52 (m, 1H), 1.51 (s, 3H), 1.40 (s, 3H), 1.24 (s, 3H).

Compound 52 was prepared starting from intermediate 22c-2, by following the procedure described in Step A to Step E of Example 28. LC-MS (ESI): m/z 739.5 $[M+H]^+$. $^1H$ NMR (400 MHz, DMSO-$d_6$) δ: 7.49-7.38 (m, 2H), 6.97 (d, J=8.6 Hz, 1H), 6.75 (s, 1H), 4.60 (s, 1H), 4.43 (br d, J=12.1 Hz, 1H), 4.20-4.13 (m, 1H), 3.52-3.44 (m, 2H), 3.35-3.25 (m, 1H), 3.15-2.99 (m, 3H), 2.87-2.71 (m, 2H), 2.27-2.20 (m, 1H), 2.08-1.93 (m, 2H), 1.92-1.81 (m, 1H), 1.61-1.47 (m, 1H), 1.49 (s, 3H), 1.39 (s, 3H), 1.24 (s, 3H). *Each compound is a single diastereomer; stereochemistry at * marked carbon centers is unassigned.

Example 29: Preparation of Intermediates 24e-1 and 24e-2

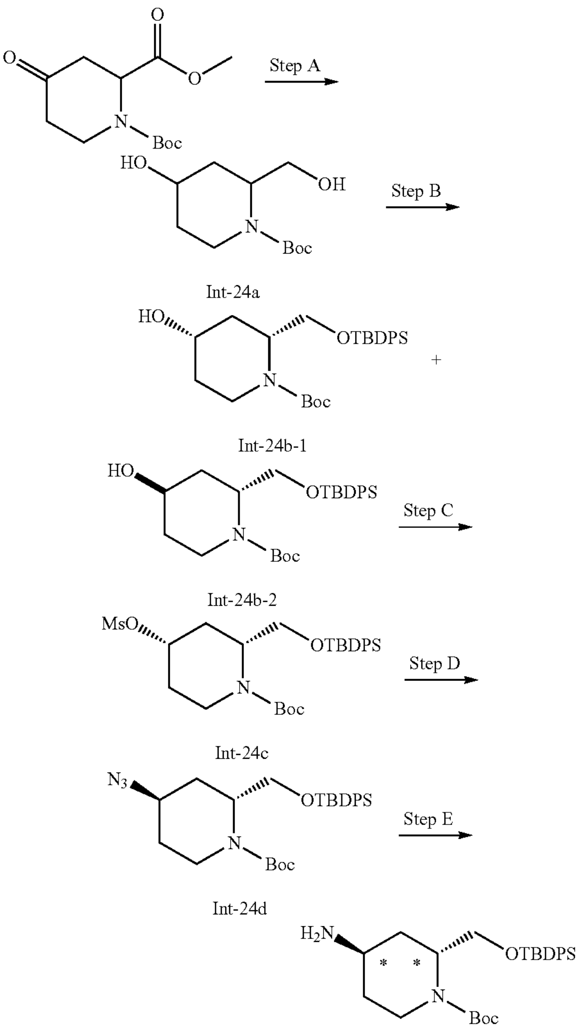

Int-24a

Int-24b-1

Int-24b-2

Int-24c

Int-24d

Int-24e-1
Int-24e-2

Step A—Synthesis of Intermediate 24a To a solution of 1-tert-butyl 2-methyl 4-oxopiperidine-1, 2-dicarboxylate (5 g, 19.43 mmol) in THF (10 mL) was added $LiBH_4$ (1.693 g, 78 mmol) at 0° C. The reaction mixture was stirred at 25° C. for 18 h, then diluted with water (50 mL) and extracted with ethyl acetate (130 mL×3). The combined organic layers were washed with brine (50 mL), dried over $Na_2SO_4$, filtered and the filtrate was concentrated in vacuo to give a cis/trans mixture of intermediate 24a, which was used in the next reaction without further purification.

Step B—Synthesis of Intermediates 24b-1 and 24b-2 To a solution of intermediate 24a (4 g, 10.38 mmol) in DMF (40 mL) was added TEA (2.169 mL, 15.56 mmol), imidazole (0.071 g, 1.038 mmol) and TBDPS-Cl (3.20 mL, 12.45 mmol) sequentially. The reaction was stirred at 20° C. for 16 h. The resulting mixture was poured into 100 mL of water, then extracted with EtOAc (100 mL×3). The organic layers were combined, washed with brine (100 mL), dried over anhydrous $Na_2SO_4$, filtered and concentrated. The resulting residue was purified by a flash silica gel chromatography (ISCO®; 20 g SepaFlash® Silica Flash Column, Eluent of 10% ethyl acetate/petroleum ether gradient @ 45 mL/min) to give separated intermediates 24b-1 and 24b-2.

Intermediate 24b-1: $^1$H NMR (400 MHz, $CDCl_3$) δ: 7.69-7.61 (m, 4H), 7.46-7.33 (m, 6H), 4.24 (br s, 1H), 4.08-4.03 (m, 1H), 3.96 (br d, J=12.2 Hz, 1H), 3.90 (dd, J=5.1, 10.5 Hz, 1H), 3.66 (dd, J=4.3, 10.4 Hz, 1H), 3.46 (br s, 1H), 3.35-3.25 (m, 1H), 1.75-1.57 (m, 2H), 1.44-1.35 (m, 11H), 1.05 (s, 9H).

Intermediate 24b-2: $^1$H NMR (400 MHz, $CDCl_3$) δ: 7.68-7.62 (m, 4H), 7.47-7.37 (m, 6H), 4.47 (br s, 1H), 4.16-4.13 (m, 1H), 3.79 (br s, 1H), 3.64 (br d, J=6.65 Hz, 2H), 2.75 (br t, J=12.52 Hz, 1H), 2.24-2.11 (m, 1H), 1.91-1.78 (m, 1H), 1.47-1.64 (m, 2H), 1.43 (s, 9H), 1.06 (s, 9H).

Step C—Synthesis of Intermediate 24c To a solution of intermediate 24b-1 (3 g, 6.39 mmol) in DCM (10 mL) stirred at 0° C. was added TEA (3.56 mL, 25.5 mmol), followed by the dropwise addition of methanesulfonyl chloride (2.237 mL, 28.7 mmol). The reaction mixture was stirred at 25° C. for 12 h, then poured into 50 mL of water, and extracted with DCM (100 mL×3). The organic layers were combined, washed with brine (70 mL), dried over anhydrous $Na_2SO_4$, filtered and concentrated to give intermediate 24c, which was used in the next reaction without further purification. LC-MS (ESI): m/z 548.1 $[M+H]^+$.

Step D—Synthesis of Intermediate 24d To a solution of intermediate 24c (3.5 g, 6.39 mmol) in DMF (30 mL) was added sodium azide (1.495 g, 23.00 mmol). The reaction mixture was stirred at 60° C. for 18 h, then diluted with water (50 mL) and extracted with ethyl acetate (80 mL×3). The combined organic layers were washed with brine (50 mL), dried over $Na_2SO_4$, and filtered. The filtrate was concentrated in vacuo to give intermediate 24d, which was used in the next reaction without further purification. LC-MS (ESI): m/z 495.2 $[M+H]^+$.

Step E—Synthesis of Intermediates 24e-1 and int-24e-2 To a solution of intermediate 24d (3 g, 6.06 mmol) in MeOH (30 mL) was added 10% Pd/C (0.645 g, 0.606 mmol). The reaction mixture was stirred under 15 psi of $H_2$ at 25° C. for 12 h. Then the mixture was filtered, and the filtrate was concentrated in vacuo. The resulting residue was purified by Flash Column Silica-CS (4 g) ($SiO_2$, 50% ethyl acetate in petroleum ether) to give a racemic mixture of enantiomers of intermediate 24e-1. LC-MS (ESI): m/z 369.2 $[M+H-100]^+$. The enantiomers of this racemic mixture were separated by SFC (Phenomenex-Cellulose-2 (250 mm*50 mm, 10 um) Condition: 0.1% $NH_3$—$H_2O$/MeOH; Begin B 45%, End B 45%; Flow Rate (mL/min) 200; Injections 90) to give intermediate 24e-1 (the first eluting component) and intermediate 24e-2 (the second eluting component). Intermediate 24e-1: LC-MS (ESI): m/z 469.2 $[M+H]^+$. Intermediate 24e-2: LC-MS (ESI): m/z 469.2 $[M+H]^+$.

Example 30: Preparation of Compounds 53 and 54

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((2S,4S)-2-(hydroxymethyl)piperidin-4-yl)carbamimidoyl)chroman-2-yl)propanoic acid, and (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((2R,4R)-2-(hydroxymethyl)piperidin-4-yl)carbamimidoyl)chroman-2-yl)propanoic acid*

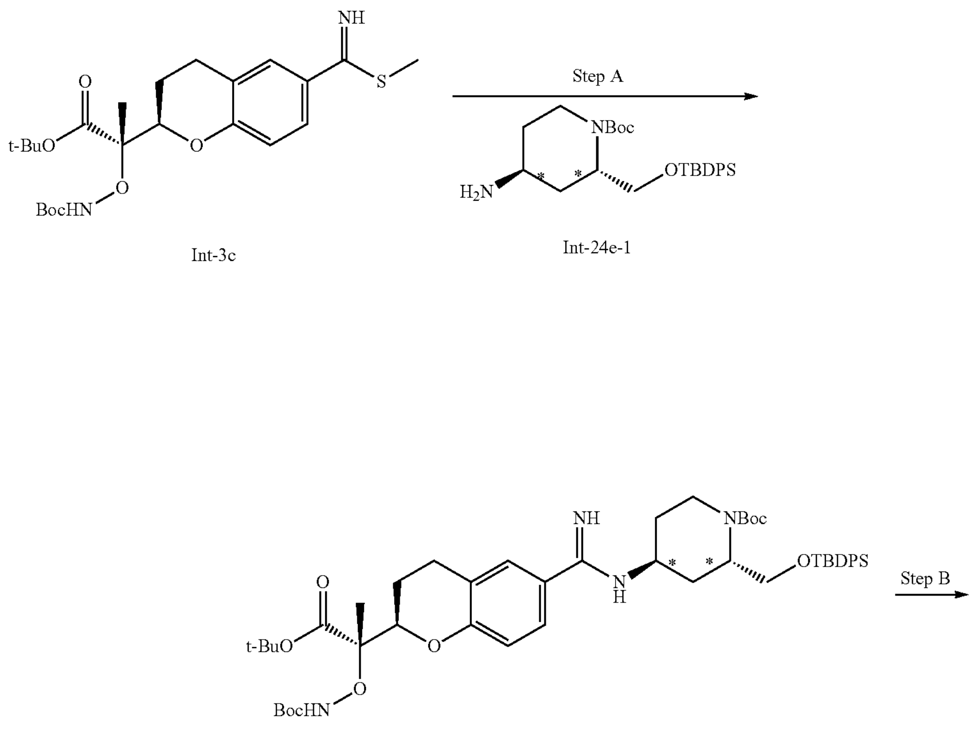

Int-3c Int-24e-1

Int-25a

-continued
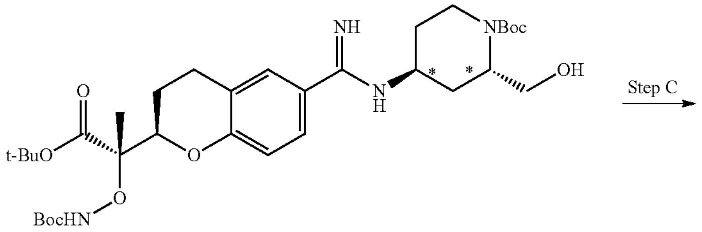
Int-25b
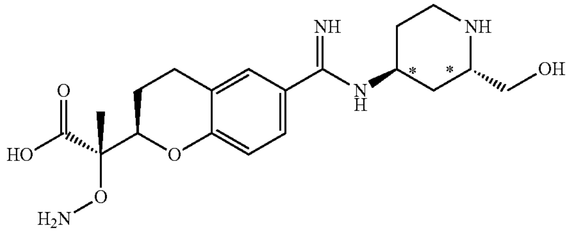
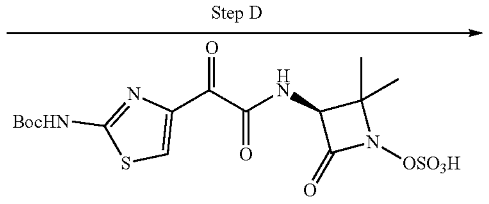
Int-25c
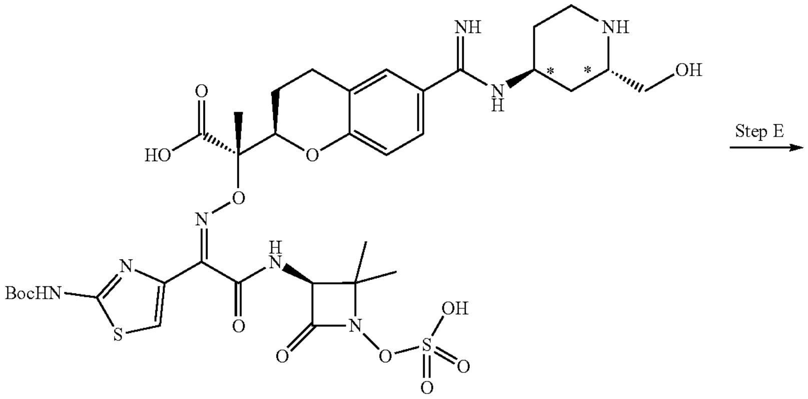
Int-25d
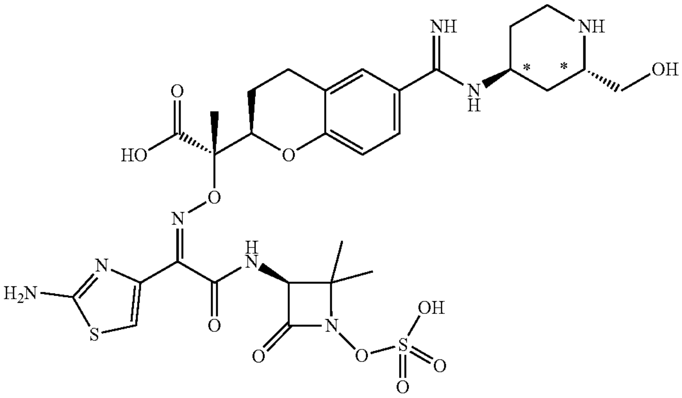
Compound 53

-continued

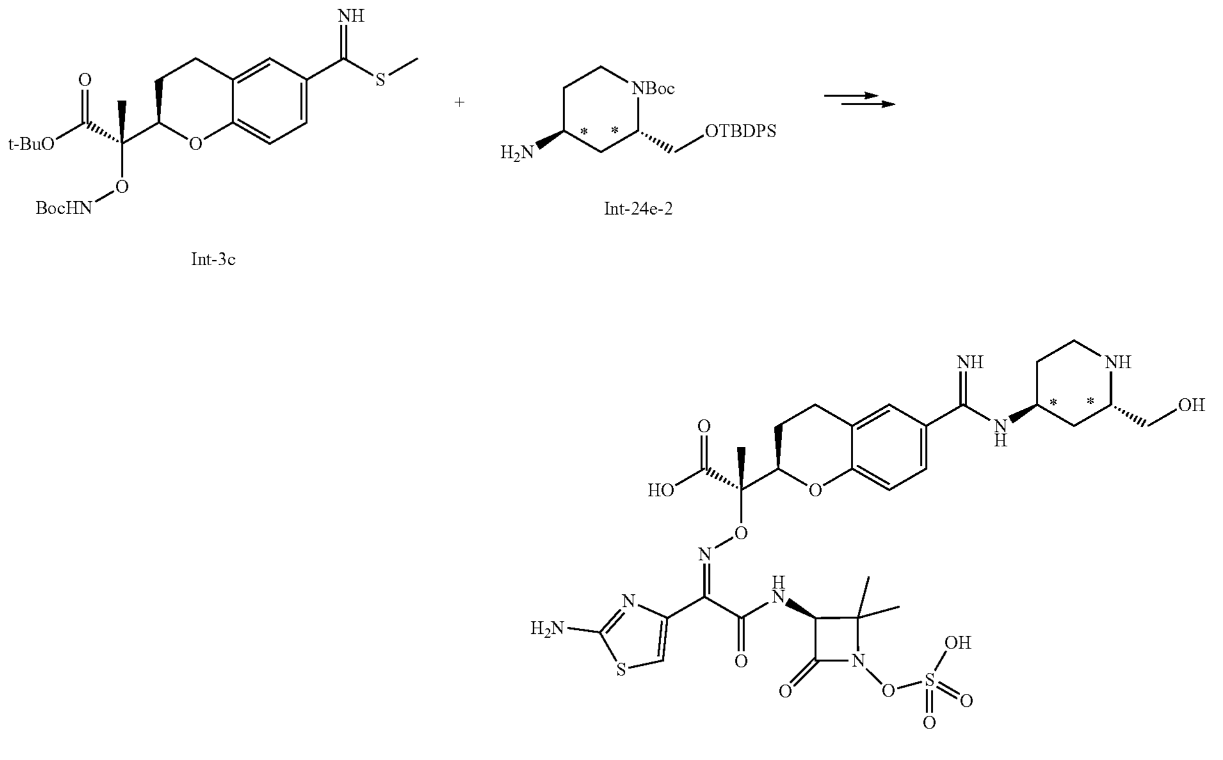

Int-3c

Int-24e-2

Compound 54

Step A—Synthesis of Intermediate 25a To a stirred solution of intermediate 3c (500 mg, 1.072 mmol) and intermediate 24e-1 (552 mg, 1.179 mmol) in MeOH (10 mL) were added acetic acid (0.245 mL, 4.29 mmol) and potassium acetate (316 mg, 3.21 mmol) sequentially at 25° C. The reaction mixture was stirred at 85° C. for 30 min, then concentrated under reduced pressure to give intermediate 25a, which was used in the next step without further purification. LC-MS (ESI): m/z 887.5 $[M+H]^+$.

Step B—Synthesis of Intermediate 25b To a solution of intermediate 25a (900 mg, 1.014 mmol) in THF (8 mL) was added tetrabutylammonium fluoride (1.420 mL, 1.420 mmol) at 0° C. The reaction was stirred at 25° C. for 2 h, then diluted with water (20 mL) and extracted with ethyl acetate (80 mL×3). The combined organic layers were washed with brine (20 mL), dried over $Na_2SO_4$, filtered and the filtrate was concentrated in vacuo to give intermediate 25b, which was used in the next step without further purification. LC-MS (ESI): m/z 649.4 $[M+H]^+$.

Step C—Synthesis of Intermediate 25c To a solution of intermediate 25b (600 mg, 0.925 mmol) in DCM (1 mL) was added TFA (2 mL) at 0° C. The reaction was stirred at 40° C. for 1 h, then concentrated in vacuo to give intermediate 25c, which was used in the next step without further purification. LC-MS (ESI): m/z 393.1 $[M+H]^+$.

Step D—Synthesis of Intermediate 25d To a solution of intermediate 25c (350 mg, 0.892 mmol) in MeOH (4 mL) was added intermediate 4 (373 mg, 0.803 mmol) at 25° C. The reaction was stirred at 25° C. for 2 h. Then the reaction was concentrated under reduced pressure to give intermediate 25d, which was used in the next step without further purification. LC-MS (ESI): m/z 759.1 $[M+H—SO_3]^+$.

Step E—Synthesis of Compound 53 To a solution of intermediate 25d (700 mg, 0.834 mmol) in DCM (1 mL) was added TFA (2 mL) at 25° C. The reaction was stirred at 25° C. for 45 min. Then MTBE (1.5 mL) was added dropwise at −10-0° C. and the resulting mixture was centrifuged. The collected solid was purified by a reverse phase HPLC (Column: Boston Uni C18 40*150*5 um; Condition: water (0.1% TFA)-ACN; Begin B 1, End B 31; Gradient Time (min) 10; 100% B Hold Time (min) 2; FlowRate 60 mL/min). The product fractions were combined and lyophilized to give compound 53 as the TFA salt form. The TFA salt was converted to the formic acid salt by passing through a reverse phase HPLC (Column: Agela DuraShell C18 150*25 mm*5 um; Mobile phase: water (0.225% FA)-acetonitrile; Detective wavelength: 220 nm), followed by lyophilization to give compound 53 as the formic acid salt. LC-MS (ESI): m/z 739.1 $[M+H]^+$. $^1H$ NMR (400 MHz, DMSO-$D_6$) δ: 7.53-7.41 (m, 2H), 6.97 (d, J=7.4 Hz, 1H), 6.74 (s, 1H), 4.62 (s, 1H), 4.47 (br d, J=11.7 Hz, 1H), 4.07 (br s, 1H), 3.50-3.45 (m, 1H), 3.23-3.03 (m, 3H), 2.98-2.65 (m, 3H), 2.07-1.98 (m, 1H), 1.92-1.84 (m, 3H), 1.78-1.72 (m, 1H), 1.62-1.52 (m, 1H), 1.48 (s, 3H), 1.39 (s, 3H), 1.22 (br s, 3H).

Compound 54 was prepared starting from intermediate 24e-2 according to the procedure of Step A to Step E of Example 30. LC-MS (ESI): m/z 738.9 $[M+H]^+$. $^1H$ NMR (400 MHz, DMSO-$D_6$) δ: 7.47 (br d, J=16.8 Hz, 2H), 6.95 (br d, J=8.2 Hz, 1H), 6.74 (br s, 1H), 4.59 (br s, 1H), 4.44 (br d, J=10.6 Hz, 1H), 4.09 (br s, 1H), 3.69-3.64 (m, 1H), 3.30-3.04 (m, 3H), 2.98-2.65 (m, 3H), 2.11-1.74 (m, 5H), 1.64-1.52 (m, 1H), 1.49 (br s, 3H), 1.38 (br s, 3H), 1.23 (br s, 3H). *Each compound is a single diastereomer; stereochemistry at * marked carbon centers is unassigned.

Example 31: Preparation of Compounds 55 and 56

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((2R,4R)-2-methylpiperidin-4-yl)carbamimidoyl)chroman-2-yl) propanoic acid, and (S)-2-((((Z)-1-(2-aminothiazol-4-yl)-2-(((S)-2,2-dimethyl-4-oxo-1-(sulfooxy) azetidin-3-yl)amino)-2-oxoethylidene)amino)oxy)-2-((R)-6-(N-((2S,4S)-2-methylpiperidin-4-yl) carbamimidoyl)chroman-2-yl)propanoic acid*

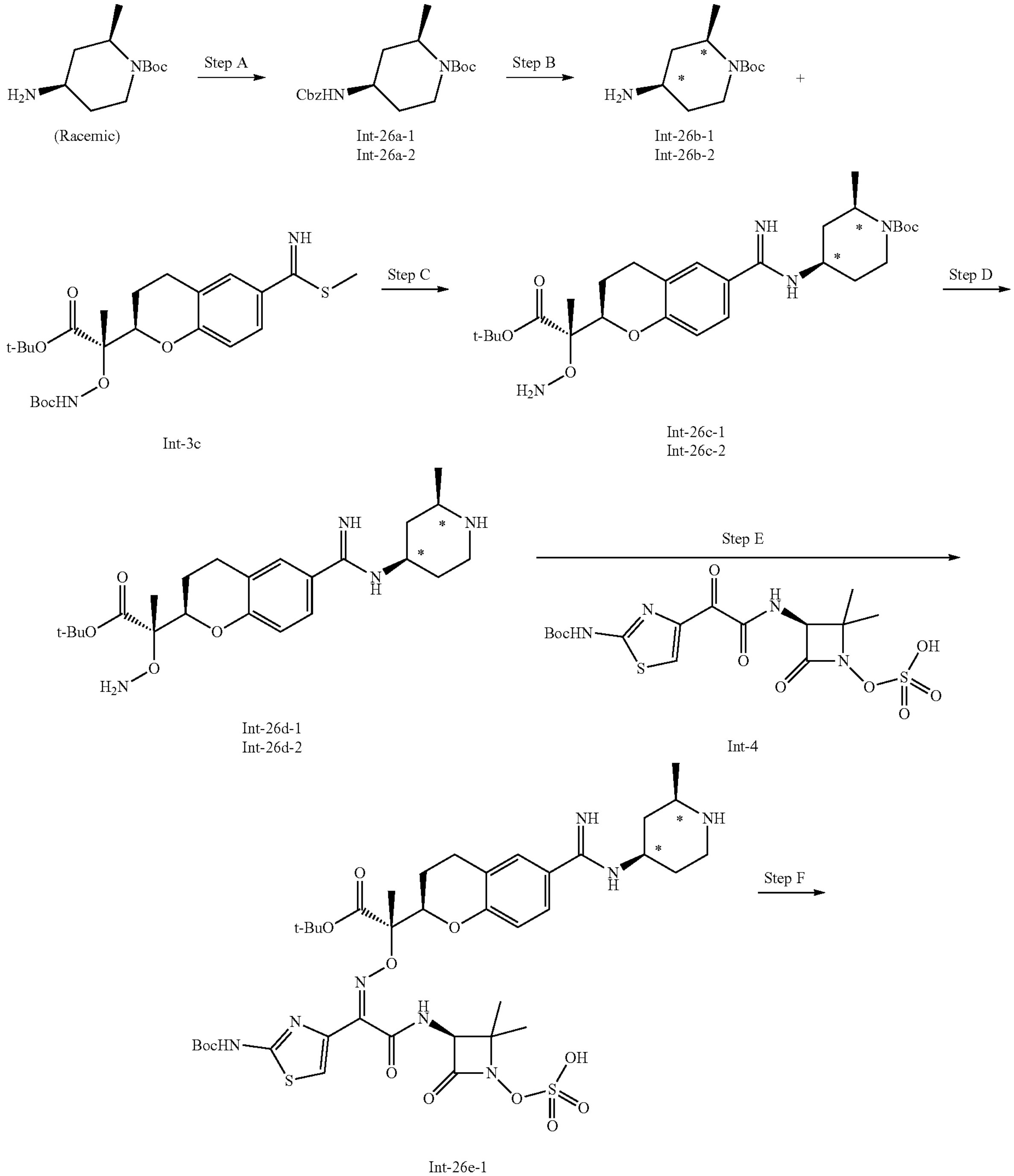

(Racemic)

Int-26a-1
Int-26a-2

Int-26b-1
Int-26b-2

Int-3c

Int-26c-1
Int-26c-2

Int-26d-1
Int-26d-2

Int-4

Int-26e-1
Int-26e-2

-continued

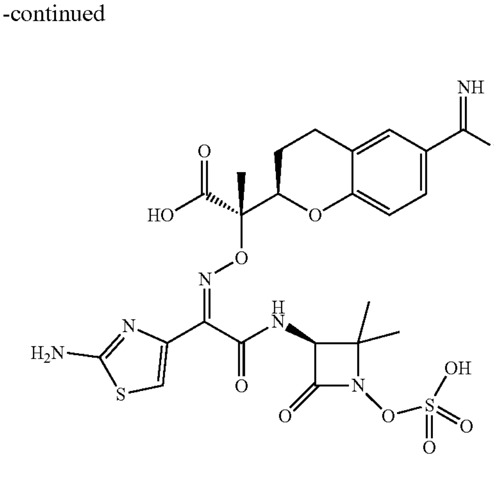

Compound 55
Compound 56

Step A— Synthesis of Intermediates 26a-1 and 26a-2 To a solution of cis-tert-butyl 4-amino-2-methylpiperidine-1-carboxylate (755 mg, 3.52 mmol) in THF (18 mL) and water (9 mL) were added sodium carbonate (747 mg, 7.05 mmol) and benzyl chloroformate (0.480 mL, 3.52 mmol) at 0° C. The reaction mixture was stirred at 25° C. for 16 h, then diluted with water (20 mL), extracted with EtOAc (10 mL×4), dried over $Na_2SO_4$, filtered and the filtrate was concentrated under vacuum. The resulting residue was purified by HPLC (Column: Boston Uni C18 40*150 5 um; Condition: water (0.1% TFA)-ACN Begin B 45, End B 75; Gradient Time (min) 10; 100% B Hold Time (min) 2; Flow Rate (mL/min) 60; Injections 3) to give the product as a racemic mixture (LC-MS (ESI): m/z 349.2 $[M+H]^+$), which was further purified by a chiral SFC (Column: DAICEL CHIRALCEL OJ, 250 mm*30 mm, 10 um. Conditions: 0.1% $NH_3$—$H_2O$/EtOH; Begin B: 10%, End B: 10%; Flow-Rate (mL/min): 60; Injections: 250) to individually afford intermediate 26a-1 (the first eluting enantiomer), and intermediate 26a-2 (the second eluting enantiomer).

Step B—Synthesis of Intermediates 26b-1 and 26b-2 A mixture of intermediate 26a-1 (166.8 mg, 0.479 mmol) and Pd/C (153 mg, 10 wt. %) in MeOH (10 mL) was stirred at 20° C. for 1 h under a hydrogen atmosphere (15 psi). The reaction mixture was filtered, and the filtrate was concentrated under vacuum to afford intermediate 26b-1, which was used in the next reaction without further purification. H NMR (400 MHz, $CD_3OD$) h: 3.97-3.87 (mi, 1H), 3.74-3.63 (mi, 1H), 3.35 (s, 2H), 3.27-3.18 (m, 1H), 2.07-1.92 (m, 1H), 1.89 (s, 1H), 1.46 (s, 9H), 1.44-1.37 (m, 1H), 1.31-1.20 (m, 3H).

Intermediate 26b-2 was prepared from intermediate 26a-2 according to the procedure used to make 26b-1. $^1H$ NMR (400 MHz, $CD_3OD$) δ: 3.98-3.86 (m, 1H), 3.67 (ddd, J=3.5, 6.6, 13.8 Hz, 1H), 3.29-3.18 (m, 1H), 3.17-3.04 (m, 1H), 2.09-1.91 (m, 1H), 1.89 (s, 1H), 1.91-1.88 (m, 1H), 1.46 (s, 9H), 1.42 (br d, J=3.5 Hz, 1H), 1.33-1.21 (m, 3H).

Step C—Synthesis of Intermediate 26c-1 To a solution of intermediate 3c (298 mg, 0.639 mmol) in MeCN (4 mL) were added potassium acetate (188 mg, 1.916 mmol), intermediate 26b-1 (137 mg, 0.639 mmol) and acetic acid (0.146 mL, 2.55 mmol). The reaction mixture was stirred at 80° C. for 10 min under $N_2$ atmosphere. Then the reaction mixture was filtered, and the filtrate was concentrated under reduced pressure. The resulting residue was purified by flash silica gel chromatography (ISCO®; 20 g SepaFlash® Silica Flash Column, Eluent of 5% $CH_2Cl_2$/MeOH gradient @ 30 mL/min) to give intermediate 26c-1. LC-MS (ESI): m/z 633.5 $[M+H]^+$.

Step D—Synthesis of Intermediate 26d-1 To a solution of intermediate 26c-1 (404 mg, 0.638 mmol) in DCM (2 mL) was added TFA (1 mL). The reaction was stirred at 28° C. for 40 min., then concentrated in vacuo (15° C.) to give intermediate 26d-1, which was used in the next reaction without further purification. LC-MS (ESI): m/z: 433.3 $[M+H]^+$.

Step E—Synthesis of Intermediate 26e-1 To a solution of intermediate 26d-1 (276 mg, 0.638 mmol) in MeOH (4 mL) was added intermediate 4 (207 mg, 0.447 mmol) at 20° C. The reaction was stirred at 28° C. for 2 h. Then the reaction mixture was concentrated in vacuo to give intermediate 26e-1, which was used for the next reaction without further purification. LC-MS (ESI): m/z 879.7 $[M+H]^+$.

Step F—Synthesis of Compounds 55 and 56 To a solution of intermediate 26e-1 (561 mg, 0.638 mmol) in DCM (1 mL) was slowly added TFA (2.000 mL) at 20° C. The reaction mixture was stirred at 28° C. for 50 minutes, then concentrated in vacuo. The resulting residue was purified by a reverse phase HPLC (Column: Boston Uni C18 40*150*5 um; Condition: water (0.1% TFA)-ACN; Begin B 1, End B 31; Gradient Time (min) 10; 100% B Hold Time (min) 2; Flow Rate (mL/min) 60; Injections 1) to give compound 55 as the TFA salt. The TFA salt was converted to the formic acid salt by passing through a reverse phase HPLC (Column: Welch Xtimate C18 150*25 mm*5 um; Condition water (0.225% FA)-ACN; Begin B 0, End B 18; Gradient Time (min) 15; 100% Hold Time (min) 2; Flow Rate (mL/min) 25; Injections 1) to give compound 55 as the formic acid salt. LC-MS (ESI): m/z 723.1 $[M+H]^+$. $^1H$ NMR (400 MHz, $D_2O+CD_3CN$) δ: 7.36 (s, 1H), 7.33 (br d, J=9.4 Hz, 1H), 6.91-6.78 (m, 2H), 4.59 (s, 1H), 4.40 (br d, J=11.7 Hz, 1H), 3.98-3.85 (m, 1H), 3.49-3.40 (m, 1H), 3.36-3.25 (m, 1H), 3.08-2.99 (m, 1H), 2.81-2.70 (m, 2H), 2.33-2.22 (m, 2H), 2.07-1.98 (m, 1H), 1.77-1.65 (m, 2H), 1.62-1.55 (m, 1H), 1.49 (s, 3H), 1.38 (s, 3H), 1.30-1.24 (m, 3H), 1.17 (s, 3H).

Compound 56 was prepared starting from intermediate 26b-2 according to the procedure of Step C to Step E of Example 31. LC-MS (ESI): m/z 723.3 $[M+H]^+$. $^1H$ NMR (400 MHz, $D_2O$+$CD_3CN$) δ: 7.43-7.34 (m, 2H), 6.87 (d, J=8.6 Hz, 1H), 6.84 (s, 1H), 4.60 (s, 1H), 4.40 (br d, J=9.4 Hz, 1H), 3.98-3.86 (m, 1H), 3.53-3.44 (m, 1H), 3.37-3.24 (m, 1H), 3.10-3.01 (m, 1H), 2.86-2.71 (m, 2H), 2.35-2.21 (m, 2H), 2.13-2.02 (m, 1H), 1.85-1.65 (m, 2H), 1.65-1.52 (m, 1H), 1.50 (s, 3H), 1.41 (s, 3H), 1.29 (d, J=6.7 Hz, 3H), 1.21 (s, 3H). *Each compound is a single diastereomer; stereochemistry at * marked carbon centers is unassigned.

Example 32: Preparation of Compound 57

(S)-2-((R)-6-(N-((1r,4R)-4-amino-4-methylcyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

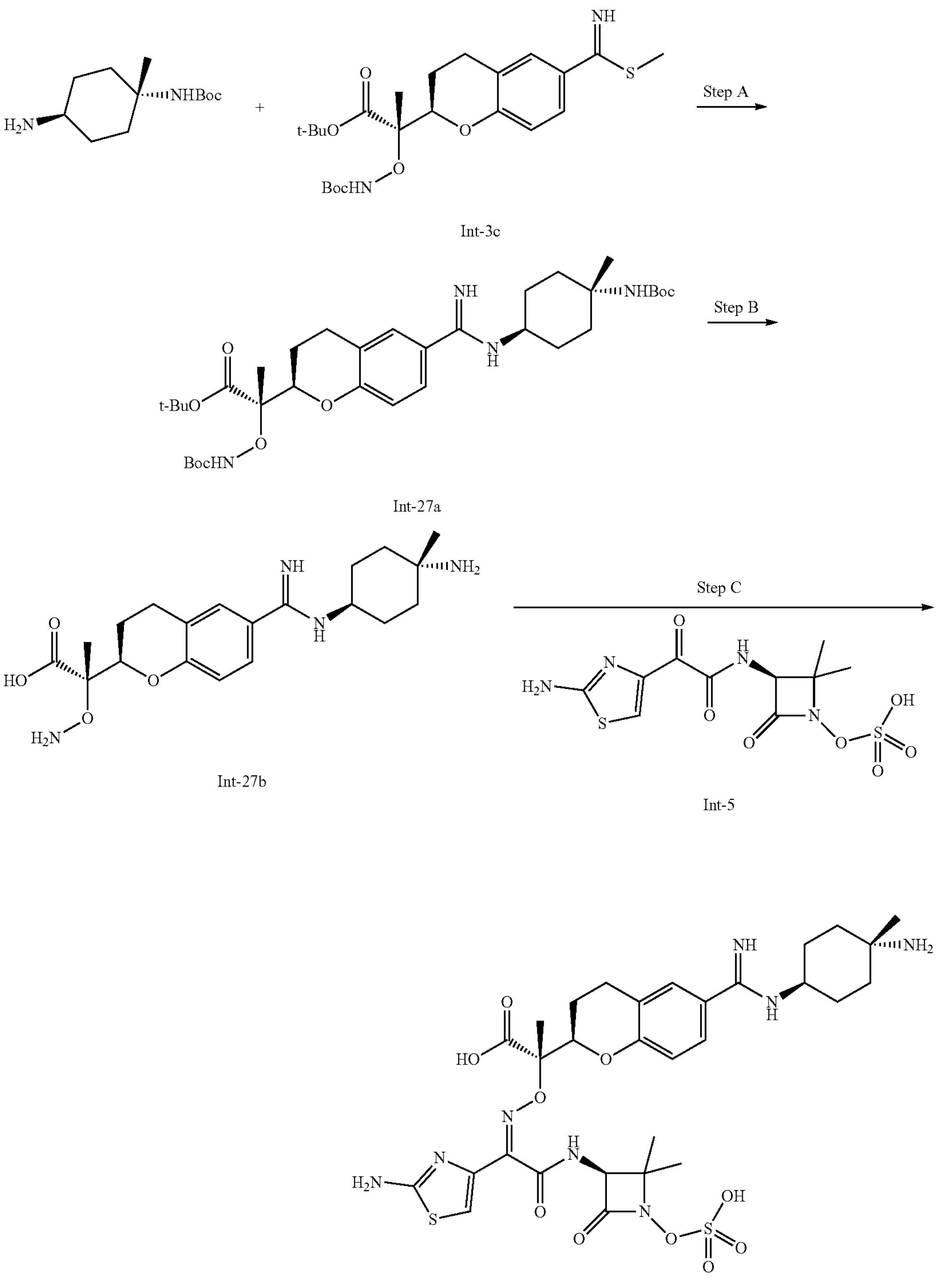

Int-3c

Int-27a

Int-27b

Int-5

Compound 57

Step A—Synthesis of Intermediate 27a To a solution of intermediate 3c (200 mg, 0.429 mmol) and tert-butyl ((trans)-4-amino-1-methylcyclohexyl)carbamate (117 mg, 0.514 mmol) in MeCN (2.5 mL) were added acetic acid (0.098 mL, 1.715 mmol) and potassium acetate (126 mg, 1.286 mmol) sequentially at 25° C. The reaction was stirred at 80° C. for 30 min., then diluted with water (10 mL) and extracted with ethyl acetate (10 mL×3). The combined organic layers were washed with brine (10 mL), dried over anhydrous $Na_2SO_4$, filtered and the filtrate was concentrated in vacuo. The resulting residue was purified by silica gel chromatography eluting with $CH_2Cl_2$/MeOH (10:1) to give intermediate 27a. LC-MS (ESI): m/z 647.5 $[M+H]^+$. Step B—Synthesis of Intermediate 27b To a solution of intermediate 27a (300 mg, 0.464 mmol) in DCM (1.5 mL) was added aqueous HCl (12 N, 1.5 mL) at 0° C. The reaction was stirred at 25° C. for 30 min., then the solvent was removed under a $N_2$ gas flow. The resulting residue was purified by a reverse phase HPLC (Boston Uni C18 40*150*5 um; Condition: water (0.1% TFA)-ACN; Begin B 1, End B 31; Gradient Time (min) 11; 100% B Hold Time (min) 2; FlowRate (mL/min) 60; Injections: 2), followed by lyophilization to give intermediate 27b. LC-MS (ESI): m/z 391.2 $[M+H]^+$.

Step C—Synthesis of Compound 57 A solution of intermediate 27b (60 mg, 0.154 mmol) and intermediate 5 (69.8 mg, 0.154 mmol) in DMA (0.6 mL) was stirred at 25° C. for 16 h. Then the reaction mixture was concentrated under a $N_2$ gas flow. The resulting residue was purified by prep-HPLC (Boston Uni C18 40*150*5 um; Condition: water (0.1% TFA)-ACN; Begin B 1, End B 31; Gradient Time (min) 11; 100% B Hold Time (min) 2; FlowRate (mL/min) 60; Injections 1), followed by lyophilization to give compound 57 as the TFA salt. The TFA salt was solubilized in $H_2O$ (2 mL) and a minimal amount of DMSO, and purified by a reverse phase HPLC (Welch Xtimate C18 150*25 mm*5 um; Condition: water (0.225% FA)-ACN; Begin B 0, End B 1; 8 Gradient Time (min) 10; 100% B Hold Time (min) 2; FlowRate (mL/min) 25; Injections 2), followed by lyophilization to give compound 57 as the formic acid salt. LC-MS (ESI): m/z 737.3 $[M+H]^+$. $^1$H NMR (400 MHz, $CD_3CN$) δ: 7.44-7.34 (m, 2H), 6.93-6.85 (m, 1H), 6.79 (s, 1H), 4.61 (s, 1H), 4.35-4.43 (m, 1H), 3.62-3.50 (m, 1H), 2.90-2.72 (m, 2H), 2.13-2.04 (m, 1H), 2.01-1.96 (m, 2H), 1.90-1.80 (m, 2H), 1.78-1.57 (m, 5H), 1.51 (s, 3H), 1.42 (s, 3H), 1.34 (s, 3H), 1.25 (s, 3H).

Example 33: Preparation of Compound 58

(S)-2-((R)-6-(N-((1s,4S)-4-amino-4-methylcyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

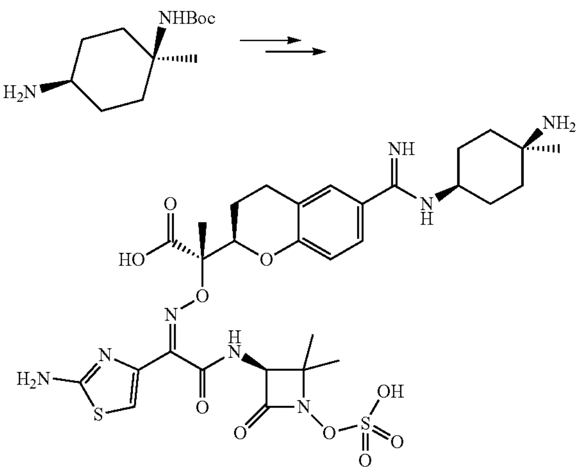

Compound 58

Compound 58 was prepared according to the procedure of Step A to Step C of Example 32 by replacing tert-butyl ((trans)-4-amino-1-methylcyclohexyl)-carbamate in Step A with tert-butyl ((cis)-4-amino-1-methylcyclohexyl)carbamate. LC-MS (ESI): m/z 759.4 $[M+Na]^+$. $^1$H NMR (400 MHz, $CD_3CN$) δ: 7.44-7.35 (m, 2H), 6.88 (d, J=8.61 Hz, 1H), 6.78 (s, 1H), 4.62 (s, 1H), 4.38 (br d, J=9.78 Hz, 1H), 3.69-3.55 (m, 1H), 2.89-2.71 (m, 2H), 2.13-2.03 (m, 1H), 2.01-1.95 (m, 2H), 1.91-1.81 (m, 2H), 1.76-1.59 (m, 5H), 1.50 (s, 3H), 1.43 (s, 3H), 1.30 (s, 3H), 1.25 (s, 3H).

Example 34: Preparation of Compound 59

(S)-2-((R)-6-(N-((1s,4S)-4-(aminomethyl)-4-hydroxycyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

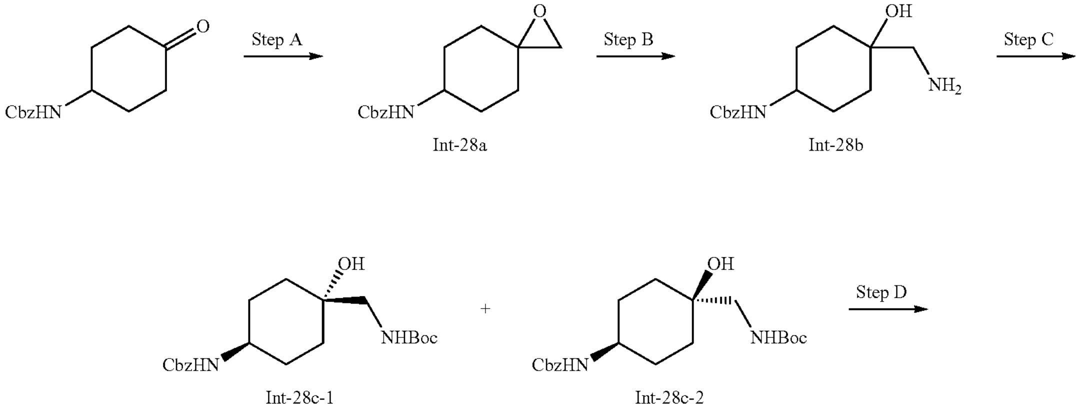

Int-28a

Int-28b

Int-28c-1

Int-28c-2

-continued

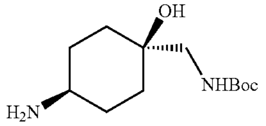

Int-28d-2

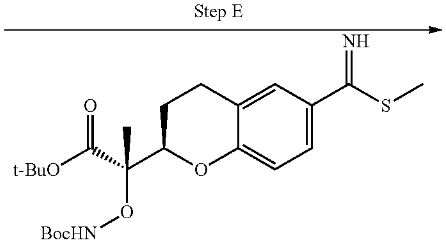

Int-3c

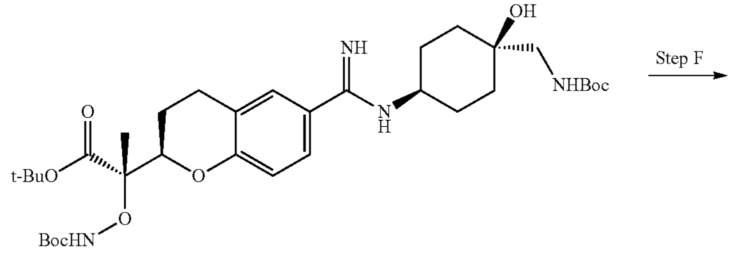

Int-28e-2

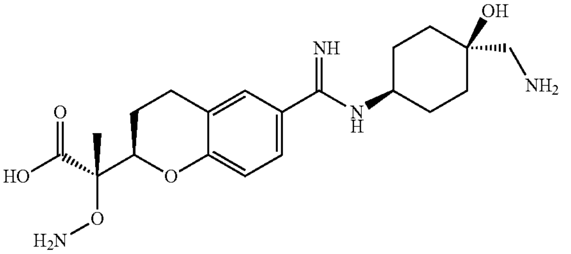

Int-28f-2

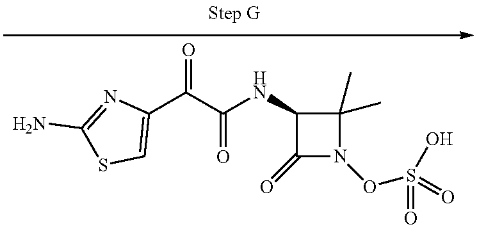

Int-5

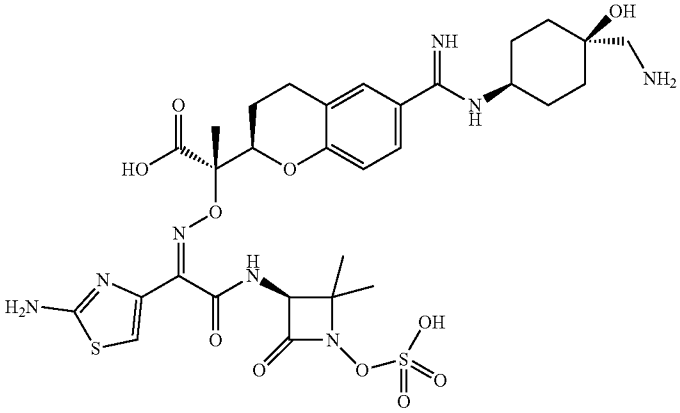

Compound 59

Step A—Synthesis of Intermediate 28a A solution of $Me_3SO^+I^-$ (6.41 g, 29.1 mmol) in DMSO (30 mL) was treated with sodium hydride (60 wt. % in oil) (1.067 g, 26.7 mmol). The mixture was stirred at 25° C. for 1 h, then benzyl (4-oxocyclohexyl)carbamate (3.0 g, 12.13 mmol) was added. The resulting mixture was stirred at 25° C. for 16 h, then diluted with water (80 mL) and extracted with EtOAc (40 mL×3). The organic layers were combined, washed with brine (60 mL), dried over anhydrous $Na_2SO_4$, filtered and concentrated under reduced pressure. The resulting residue was purified by flash silica gel chromatography (ISCO; 12 g Agela Silica Flash Column, Eluent of 0~40% Petroleum ether:EtOAc gradient @ 30 mL/min) to give intermediate 28a. $^1H$ NMR ($CDCl_3$, 400 MHz) δ: 7.43-7.30 (m, 5H), 5.11 (s, 2H), 4.70 (br s, 1H), 3.66 (br d, J=8.3 Hz, 1H), 2.67 (s, 2H), 2.19-1.72 (m, 4H), 1.67-1.28 (m, 4H).

Step B—Synthesis of Intermediate 28b To a stirred solution of intermediate 28a (1.0 g, 3.83 mmol) in MeOH (60 mL) at 25° C. was added a solution of aqueous $NH_3 \cdot H_2O$ (20 mL, 3.83 mmol, 30 wt. %). The reaction was stirred for 16 h at 80° C., then concentrated under reduced pressure to give intermediate 28b, which was used in the next step without further purification. $^1$H NMR ($CDCl_3$, 400 MHz) δ: 7.42-7.29 (m, 5H), 5.09 (s, 2H), 4.77 (br d, J=7.8 Hz, 1H), 3.55-3.40 (m, 1H), 2.64-2.55 (m, 2H), 1.71-1.20 (m, 8H).

Step C—Synthesis of Intermediates 28c-1 and 28c-2 To a stirred solution of intermediate 28b (1.05 g, 3.77 mmol) in EtOH (50 mL) was added di-tert-butyl dicarbonate (2.190 mL, 9.43 mmol) at 25° C. The reaction was stirred at 25° C. for 12 h. Then the solvent was removed under reduced pressure, and the resulting residue was purified by flash silica gel chromatography (ISCO; 12 g Agela Silica Flash Column, Eluent of 0-30% EtOAc/Petroleum ether gradient @ 30 mL/min) to give a mixture of intermediate 28c-1 and intermediate 28c-2. The mixture was further purified by SFC (Column: DAICEL CHIRALCEL OD (250 mm*30 mm, 10 um; Condition: 0.1% $NH_3 \cdot H_2O$/EtOH; Begin B 20%, End B 20%; FlowRate (mL/min) 200; Injections 80) to afford intermediate 28c-1 (the first eluting isomer; LC-MS (ESI): m/z 401.3 $[M+Na]^+$) and intermediate 28c-2 (the second eluting isomer; LC-MS (ESI): m/z 379.3 $[M+H]^+$).

Step D—Synthesis of Intermediate 28d-2 To a solution of intermediate 28c-2 (250 mg, 0.661 mmol) in MeOH (5 mL) was added Pd/C (70.3 mg, 0.066 mmol, 10 wt. %). The reaction mixture was stirred at 25° C. under a $H_2$ atmosphere (15 psi) for 2 h, and then filtered through Celite™. The filtrate was concentrated under reduced pressure to give intermediate 28d-2, which was used in the next reaction without further purification. $^1$H NMR ($CDCl_3$, 400 MHz) δ: 5.09 (td, J=1.6, 3.2 Hz, 2H), 4.78 (s, 2H), 4.43-4.22 (m, 1H), 3.48-3.25 (m, 5H), 3.22 (s, 9H), 3.19-3.11 (m, 2H).

Step E—Synthesis of Intermediate 28e-2 To a stirred mixture of intermediate 28d-2 (157 mg, 0.643 mmol) and intermediate 3c (300 mg, 0.643 mmol) in acetonitrile (6 mL) were added acetic acid (0.110 mL, 1.929 mmol) and potassium acetate (189 mg, 1.929 mmol). The reaction mixture was stirred at 80° C. for 20 min. Then the solvent was removed in vacuo, and the resulting residue was purified by a preparative TLC ($SiO_2$, DCM:MeOH=10:1) to give intermediate 28e-2. LC-MS (ESI): m/z 663.4 $[M+H]^+$.

Step F—Synthesis of Intermediate 28f-2 A mixture of intermediate 28e-2 (160 mg, 0.241 mmol) in aqueous HCl (12 N, 0.4 mL) was stirred at 25° C. for 1 h. Then the solvent was removed by nitrogen gas flow, and the resulting residue was purified by a reverse-phase HPLC (Column: Boston Uni C18 40*150*5 um; Condition: water (0.1% TFA)-ACN; Begin B 1, End B 31; Gradient Time (min) 10; 100% B Hold Time (min) 2; FlowRate (mL/min) 60; Injections 1) to give intermediate 28f-2. LC-MS (ESI): m/z 407.3 $[M+H]^+$.

Step G—Synthesis of Compound 59 To a mixture of intermediate 5 (53.6 mg, 0.148 mmol) and 4 Å molecular sieves (60 mg) in DMA (0.8 mL) was added intermediate 28f-2 (60 mg, 0.148 mmol) at 0° C. The reaction was stirred at 25° C. for 16 h. Then the solvent was removed by nitrogen gas flow, and the resulting residue was purified by reverse-phase HPLC (Column: Boston Uni C18 40*150*5 um; Condition: Begin B 1, End B 31; Gradient Time (min) 11; 100% B Hold Time (min) 2; FlowRate (mL/min) 60; Injections 1) to give compound 59 as the TFA salt. The TFA salt was converted to the formic acid salt by passing through a second reverse-phase HPLC (Column: YMC-Actus Triart C18 150*30 mm*5 um; Condition: water (0.225% FA)-ACN; Begin B 0, End B 18; Gradient Time (min) 11; 100% Hold Time (min) 2; Flow Rate (mL/min) 25; Injections 2), and lyophilizing the product fractions. LC-MS (ESI): m/z 753.2 $[M+H]^+$. $^1$H NMR ($CD_3CN+D_2O$, 400 MHz) δ: 7.44-7.28 (m, 2H), 6.94-6.80 (m, 2H), 4.62 (s, 1H), 4.39 (br d, J=10.2 Hz, 1H), 3.61-3.46 (m, 1H), 2.89 (s, 2H), 2.8-2.72 (m, 2H), 2.12-1.99 (m, 1H), 1.92-1.82 (m, 2H), 1.80-1.62 (m, 5H), 1.57-1.42 (m, 5H), 1.41 (s, 3H), 1.24 (s, 3H).

Example 35: Preparation of Compound 60

(S)-2-((R)-6-(N-((1r,4R)-4-(aminomethyl)-4-hydroxycyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

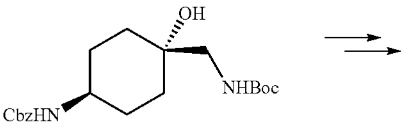

Int-28c-1

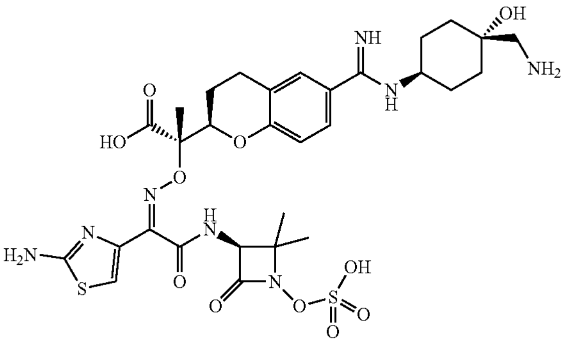

Compound 60

Compound 60 was prepared starting from intermediate 28c-1 according to the procedure of Step D to Step G of Example 34. Compound 60: LC-MS (ESI): m/z 753.2 $[M+H]^+$. $^1$H NMR ($CD_3CN+D_2O$, 400 MHz) δ: 7.41-7.30 (m, 2H), 6.87 (br d, J=9.0 Hz, 1H), 6.81 (s, 1H), 4.60 (s, 1H), 4.38 (br d, J=12.5 Hz, 1H), 3.75-3.65 (m, 1H), 3.03 (s, 2H), 2.85-2.71 (m, 2H), 2.12-1.95 (m, 2H), 1.84-1.52 (m, 8H), 1.49 (s, 3H), 1.41 (s, 3H), 1.22 (s, 3H).

Example 36: Preparation of Intermediates 29a-1 and 29a-2

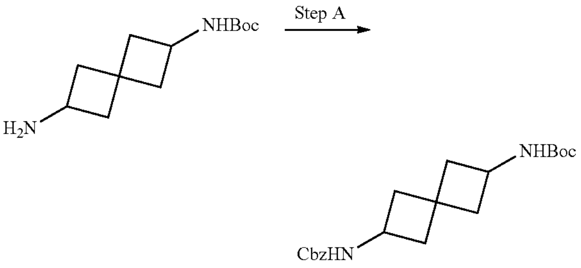

Int-29a-1 (isomer 1)
Int-20a-2 (isomer 2)

Step A—Synthesis of Intermediates 29a-1 and 29a-2 To a solution of tert-butyl (6-aminospiro-[3.3]heptan-2-yl)carbamate (1.055 g, 4.66 mmol) in THF (30 mL) and water (15 mL) stirred at 0° C., were added sodium carbonate (0.988 g, 9.32 mmol) and benzyl chloroformate (0.636 mL, 4.66 mmol). The reaction was stirred at 25° C. for 16 h, then filtered and the filtrate was concentrated in vacuo. The resulting residue was purified by flash silica gel chromatography (ISCO®; 12 g SepaFlash® Silica Flash Column, Eluent of 0-15% Petroleum ether/EtOAc gradient @ 30 mL/min) to give a racemic mixture of intermediate 29a-1 and intermediate 29a-2. The racemic mixture was separated via SFC (Column: DAICEL CHIRALCEL OJ 250 mm*30 mm, 10 um; Condition: 0.1% $NH_3$—$H_2O$/EtOH; Begin B: 20%, End B: 20%; FlowRate (mL/min): 70; Injections: 100) to individually afford intermediate 29a-1 (the first eluting isomer, LC-MS (ESI): m/z 383.2 $[M+Na]^+$) and intermediate 29a-2 (the second eluting isomer, LC-MS (ESI): m/z 383.2 $[M+Na]^+$.

Example 37: Preparation of Compounds 61 and 62

(S)-2-((R)-6-(N-((2R,4r,6R)-6-aminospiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene) amino)oxy)propanoic acid, and (S)-2-((R)-6-(N-((2S,4s,6S)-6-aminospiro[3.3]heptan-2-yl) carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene) amino)oxy)propanoic acid

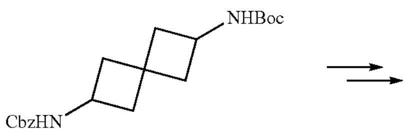

Int-29a-1 (isomer 1)
Int-20a-2 (isomer 2)

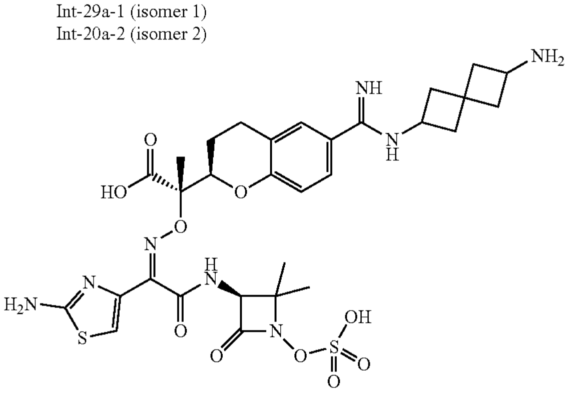

Compound 61 (diastereomer 1)
Compound 62 (diastereomer 2)

Compounds 61 and 62 were prepared according to the procedure of Step D to Step G of Example 34 by replacing intermediate 28c-2 in Step D with intermediate 29a-1 or intermediate 29a-2 respectively. Compound 61: LC-MS (ESI): m/z 735.5 $[M+H]^+$. $^1H$ NMR ($D_2O$+$CD_3CN$, 400 MHz) δ: 7.43-7.29 (m, 2H), 6.92-6.79 (m, 2H), 4.58 (s, 1H), 4.39 (br d, J=9.8 Hz, 1H), 4.09-3.97 (m, 1H), 3.72-3.61 (m, 1H), 2.86-2.70 (m, 2H), 2.62-2.55 (m, 1H), 2.52-2.40 (m, 2H), 2.38-2.28 (m, 1H), 2.23-2.10 (m, 4H), 2.09-2.03 (m, 1H), 1.79-1.64 (m, 1H), 1.49 (s, 3H), 1.41 (s, 3H), 1.22 (s, 3H). Compound 62: LC-MS (ESI): m/z 735.3 $[M+H]^+$. $^1H$ NMR ($D_2O$+$CD_3CN$, 400 MHz) δ: 7.39-7.31 (m, 2H), 6.89-6.82 (m, 2H), 4.59 (s, 1H), 4.41 (br d, J=9.0 Hz, 1H), 4.08-4.01 (m, 1H), 3.72-3.62 (m, 1H), 2.86-2.68 (m, 2H), 2.64-2.55 (m, 1H), 2.50-2.38 (m, 2H), 2.37-2.26 (m, 1H), 2.22-2.11 (m, 4H), 2.08-2.02 (m, 1H), 1.79-1.62 (m, 1H), 1.50 (s, 3H), 1.40 (s, 3H), 1.21 (s, 3H).

Example 38: Preparation of Intermediates 30e-1 and 30e-2

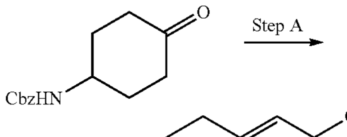

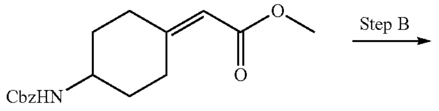

Int-30a

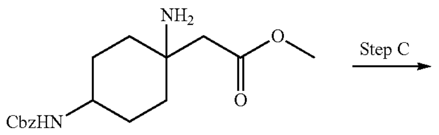

Int-30b

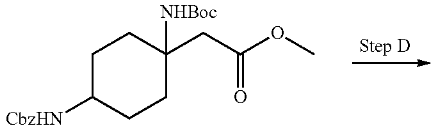

Int-30c

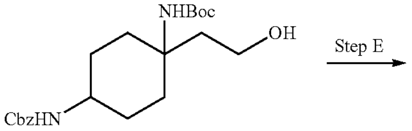

Int-30d

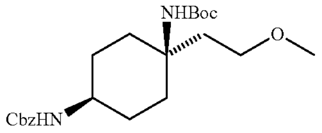

and

Int-30e-1

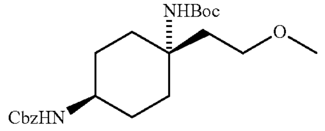

Int-30e-2

Step A—Synthesis of Intermediate 30a To a suspension of NaH (1.051 g, 26.3 mmol, 60% in oil) in THF (120 mL) was added methyl 2-(dimethoxyphosphoryl)acetate (4.42 g, 24.26 mmol) at 0° C. The reaction mixture was stirred at 0° C. for 20 min, and benzyl (4-oxocyclohexyl)-carbamate (5 g, 20.22 mmol) was added. The reaction mixture was warmed to ambient temperature and stirred for 1 h, then concentrated in vacuo. To the resulting residue was added saturated aqueous $NH_4Cl$ (80 mL), and the mixture was extracted with MTBE (150 mL). The combined organic layers were concentrated to give intermediate 30a, which was used in the next reaction without further purification. LC-MS (ESI): m/z 304.1 $[M+H]^+$.

Step B—Synthesis of Intermediate 30b A solution of intermediate 30a (2 g, 6.59 mmol) in $NH_3$/MeOH (7 M, 47.1 mL, 330 mmol) was stirred at 100° C. for 16 h in a sealed tube. Then the solvent was removed under reduced pressure. The resulting residue was purified by flash silica gel chromatography (ISCO; 12 g Agela Silica Flash Column, Eluent of 0-8% $CH_2Cl_2$/MeOH (gradient) @ 20 mL/min) to afford intermediate 30b. LC-MS (ESI): m/z 321.2 $[M+H]^+$.

Step C—Synthesis of Intermediate 30c To a mixture of intermediate 30b (4.9 g, 15.29 mmol) and $(Boc)_2O$ (3.55 mL, 15.29 mmol) in THF (50 mL) and water (50.0 mL) was added DIEA (2.67 mL, 15.29 mmol). The reaction was heated at 85° C. for 4 h, then cooled to ambient temperature, and extracted with EtOAc (3×50 mL). The combined organic layers were washed with brine (100 mL), dried over anhydrous $Na_2SO_4$, filtered and the filtrate was concentrated under reduced pressure. The resulting residue was purified by flash silica gel chromatography (ISCO; 40 g Agela Silica Flash Column, Eluent of 25% Petroleum ether/EtOAc gradient @ 40 mL/min) to afford intermediate 30c. LC-MS (ESI): m/z 421.4 $[M+H]^+$.

Step D—Synthesis of Intermediate 30d To a solution of intermediate 30c (2.6 g, 6.18 mmol) in THF (35 mL) at 0° C. was added $LiBH_4$ (0.606 g, 27.8 mmol). The reaction mixture was stirred at 20° C. for 16 h, then quenched with saturated aqueous $NH_4Cl$ (20 mL), extracted with EtOAc (50 mL), dried over anhydrous $Na_2SO_4$, and filtered. The filtrate was concentrated under reduced pressure. The resulting residue was purified by flash silica gel chromatography (ISCO; 20 g Agela Silica Flash Column, Eluent of 0-35% Petroleum ether/EtOAc (gradient) @ 30 mL/min) to afford intermediate 30d. LC-MS (ESI): m/z 293.2 $[M\text{-}Boc+H]^+$.

Step E—Synthesis of Intermediates 30e-1 and 30e-2 A mixture of intermediate 30d (1 g, 2.55 mmol), $Ag_2O$ (11.81 g, 51.0 mmol) and MeI (6.37 mL, 102 mmol) in MeCN (100 mL) was stirred in the dark at 25° C. under nitrogen for 36 h. Then the reaction mixture was filtered, and the filtrate was concentrated under vacuum. The resulting residue was purified by flash silica gel chromatography (ISCO; 12 g Agela Silica Flash Column, Eluent of 0-30% EtOAc/Petroleum Ether gradient @ 30 mL/min) to give a mixture of intermediates 30e-1 and 30e-2. The intermediate mixture was further separated by a reverse phase HPLC (Column: Phenomenex Synergi C18 150*30 mm*4 um; Condition: water (0.1% TFA)-ACN; Begin B 51, End B 81; Gradient Time (min) 11; 100% B Hold Time (min) 2; FlowRate (mL/min) 25; Injections 9) to individually give intermediate 30e-1 and intermediate 30e-2.

Intermediate 30e-1: $^1H$ NMR (400 MHz, $CD_3OD$) δ: 7.36-7.26 (m, 5H), 5.05 (s, 2H), 3.44 (t, J=6.8 Hz, 2H), 3.37 (br t, J=11.5 Hz, 1H), 3.29 (s, 3H), 2.24 (br d, J=12.5 Hz, 2H), 1.89 (br t, J=6.7 Hz, 2H), 1.70 (br d, J=10.0 Hz, 2H), 1.43 (s, 10H), 1.40-1.37 (m, 1H), 1.33-1.25 (m, 2H).

Intermediate 30e-2: $^1H$ NMR (400 MHz, $CD_3OD$) δ: 7.37-7.26 (m, 5H), 5.06 (s, 2H), 3.54 (br s, 1H), 3.44 (t, J=6.7 Hz, 2H), 3.30 (s, 3H), 2.01 (br t, J=6.7 Hz, 2H), 1.81-1.71 (m, 5H), 1.51-1.45 (m, 2H), 1.42 (s, 10H).

Example 39: Preparation of Compounds 63 and 64

(S)-2-((R)-6-(N-((1s,4S)-4-amino-4-(2-methoxyethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,4R)-4-amino-4-(2-methoxyethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

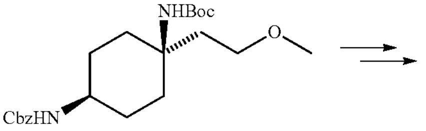

Int-30e-1

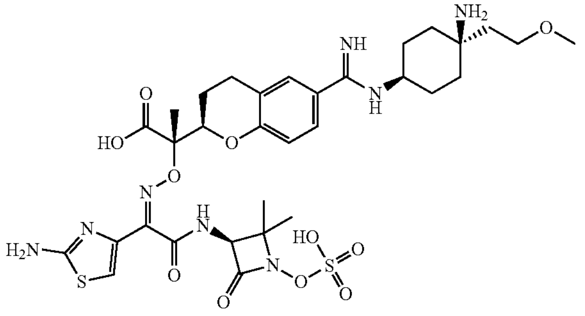

Compound 63

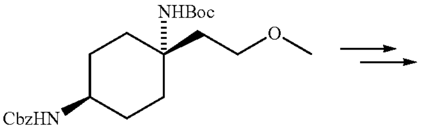

Int-30e-2

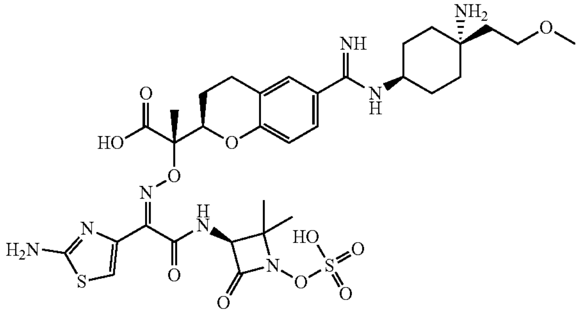

Compound 64

Compounds 63 and 64 were prepared, starting from intermediates 30e-1 and 30e-2 respectively, according to the procedure of Step D to Step G of Example 34.

Compound 63: LC-MS (ESI): m/z 781.1 $[M+H]^+$. $^1H$ NMR (400 MHz, DMSO-$d_6$) δ: 7.47-7.37 (m, 2H), 6.88 (d, J=8.2 Hz, 1H), 6.75 (s, 1H), 4.58 (s, 1H), 4.34 (br d, J=11.7 Hz, 1H), 3.69-3.56 (m, 1H), 3.50-3.41 (m, 2H), 3.22 (s, 3H), 2.84-2.68 (m, 2H), 2.03-1.74 (m, 8H), 1.73-1.53 (m, 4H), 1.44 (s, 3H), 1.38 (s, 3H), 1.22 (s, 3H).

Compound 64: LC-MS (ESI): m/z 781.1 $[M+H]^+$. $^1H$ NMR (400 MHz, DMSO-$d_6$) δ: 7.48-7.35 (m, 2H), 6.98 (d, J=8.6 Hz, 1H), 6.75 (s, 1H), 4.59 (s, 1H), 4.48 (br d, J=12.1

Hz, 1H), 3.54-3.40 (m, 3H), 3.25 (s, 3H), 2.90-2.68 (m, 2H), 2.11-2.01 (m, 1H), 1.95-1.75 (m, 6H), 1.71-1.50 (m, 5H), 1.50 (s, 3H), 1.39 (s, 3H), 1.23 (s, 3H).

Example 40: Preparation of Intermediates 31-1 and 31-2

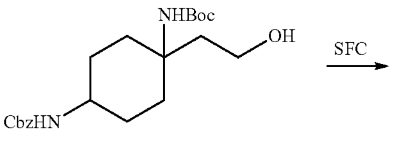

Int-30d

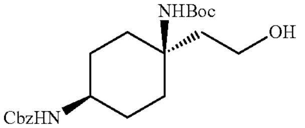

+

Int-31-1

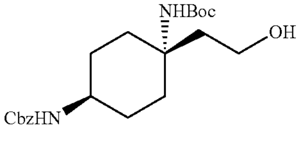

Int-31-2

The stereoisomers of intermediate 30d (0.9 g, 2.293 mmol) were separated by SFC (DAICEL CHIRALPAK AD (250 mm*50 mm, 10 um); Condition: 0.1% $NH_3 \cdot H_2O$/IPA; Begin B 35, End B 35; FlowRate (mL/min) 60; Injections 80) to individually give intermediate 31-1 (LC-MS (ESI): m/z 415.4 $[M+Na]^+$) and intermediate 31-2 (LC-MS (ESI): m/z 415.4 $[M+Na]^+$).

Example 41: Preparation of Compounds 65 and 66

(S)-2-((R)-6-(N-((1s,4S)-4-amino-4-(2-hydroxyethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,4R)-4-amino-4-(2-hydroxyethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

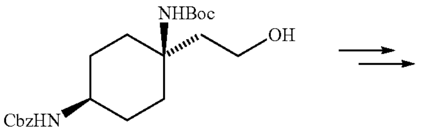

Int-31-1

-continued

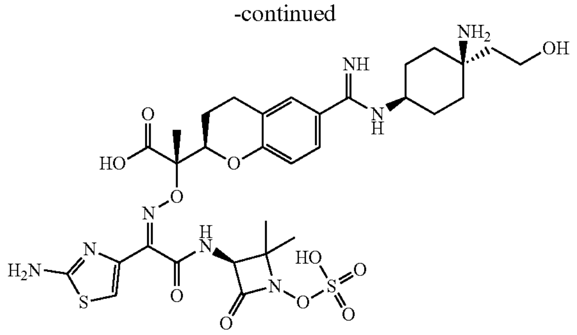

Compound 65

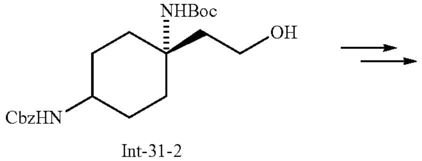

Int-31-2

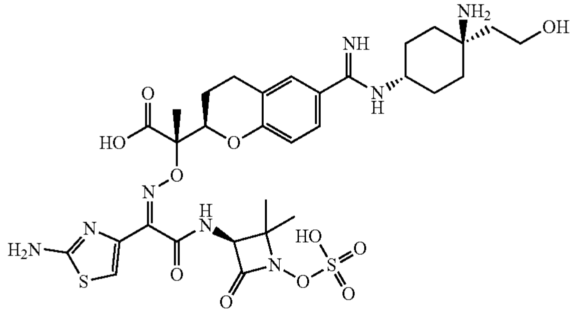

Compound 66

Compounds 65 and 66 were prepared, starting from intermediate 31-1 and intermediate 31-2 respectively, according to the procedure of Step D to Step G of Example 34.

Compound 65: LC-MS (ESI): m/z 767.3 $[M+H]^+$. $^1H$ NMR (400 MHz, DMSO-$d_6$) δ: 7.48-7.39 (m, 2H), 6.88 (br d, J=8.2 Hz, 1H), 6.77 (s, 1H), 4.62 (s, 1H), 4.38 (br d, J=10.6 Hz, 1H), 3.68 (br s, 1H), 3.51-3.49 (m, 2H), 2.74-2.58 (m, 2H), 2.22-2.04 (m, 1H), 1.95-1.53 (in, 10H), 1.39 (s, 3H), 1.34 (br s, 3H), 1.23 (s, 3H), 1.07-0.83 (in, 1H).

Compound 66: LC-MS (ESI): m/z 767.3 $[M+H]^+$. $^1H$ NMR (400 MHz, DMSO-$d_6$) δ: 7.49-7.36 (m, 2H), 6.92 (d, J=8.2 Hz, 1H), 6.76 (s, 1H), 4.57 (s, 1H), 4.45-4.35 (m, 1H), 3.80-3.75 (m, 1H), 3.65-3.53 (m, 2H), 2.96-2.74 (m, 2H), 2.09-2.01 (m, 1H), 1.93-1.78 (m, 6H), 1.68-1.46 (m, 7H), 1.38 (s, 3H), 1.22 (s, 3H), 1.13 (t, J=7.2 Hz, 1H).

Example 42: Preparation of Intermediates 32b-1 and 32b-2

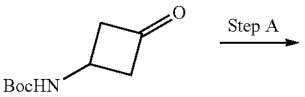

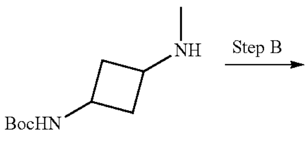

Int-32a

-continued

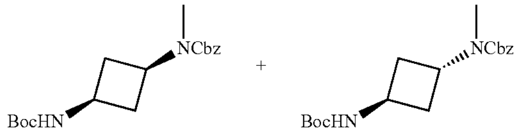

Int-32b-1 Int-32b-2

Step A—Synthesis of Intermediate 32a To a mixture tert-butyl (3-oxocyclobutyl) carbamate (1.5 g, 8.10 mmol) and acetic acid (0.844 mL) in ethanol (9.71 mL) stirred at 0° C., was added methylamine (33% in ethanol) (9.71 mL, 81 mmol). The reaction was stirred at 0° C. for 1.5 h, then warmed to 20° C. and stirred for an additional 2 h. The mixture was cooled to −70° C., then $LiBH_4$ (0.390 g, 17.90 mmol) was added portion wise. The reaction was stirred at −70° C. for 1 hour, then warmed to 20° C. and stirred for 16 h. The reaction mixture was then quenched with water (40 mL), and concentrated under vacuum. The resulting aqueous mixture was acidified with concentrated hydrochloric acid to pH 2, and washed with ethyl acetate (2×40 mL). The aqueous layer was then basified with 10% sodium hydroxide to pH 9-10 and extracted with dichloromethane (3×50 mL). The combined organic layers were washed with brine (60 mL), dried over anhydrous sodium sulfate, and concentrated under vacuum to obtain intermediate 32a, which was used in the next reaction without further purification. $^1H$ NMR (400 MHz, $CDCl_3$) δ: 4.63 (br s, 1H), 3.82 (br d, J=7.3 Hz, 1H), 2.96-2.80 (m, 1H), 2.74-2.61 (m, 2H), 2.33 (s, 3H), 2.20-2.00 (m, 1H), 1.50 (br d, J=10.8 Hz, 2H), 1.43 (s, 9H).

Step B—Synthesis of Intermediates 32b-1 and 32b-2 To a solution of intermediate 32a (1.3 g, 6.49 mmol) in THF (40 mL) and water (20.00 mL) stirred at 0° C., were added $Na_2CO_3$ (1.376 g, 12.98 mmol) and benzyl chloroformate (1.205 mL, 8.44 mmol). The reaction was stirred at 20° C. for 16 h. Then the reaction was diluted with water (50 mL), extracted with EtOAc (50 mL×3), dried over anhydrous $Na_2SO_4$, filtered and concentrated under vacuum. The resulting residue was purified by flash silica gel chromatography (ISCO; 12 g Agela Silica Flash Column, Eluent of 0-30% EtOAc/Petroleum Ether (gradient) @ 30 mL/min) to give the desired product as a mixture of cis- and trans-stereoisomers. The mixture was separated by SFC (Column: DAICEL CHIRALPAK AD-H 250 mm*30 mm, 5 um; Condition: 0.1% $NH_3{\cdot}H_2O$/EtOH; Begin B 25, End B 25; FlowRate (mL/min) 60; Injections 180) to give intermediate 32b-1 (the first eluting component, LC-MS (ESI): m/z 335.4 $[M+H]^+$) and intermediate 32b-2 (the second eluting component, LC-MS (ESI): m/z 235.3 [M-Boc]+).

Example 43: Preparation of Intermediates 33c-1 and 33c-2

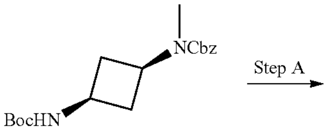

Int-32b-1

-continued

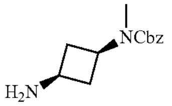

Int-33a-1

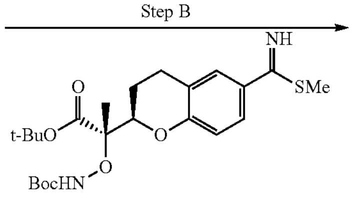

Int-3c

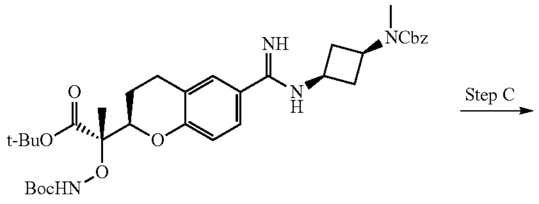

Int-33b-1

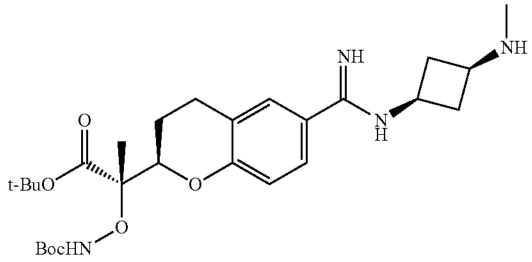

Int-33c-1

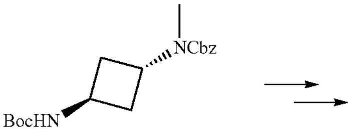

Int-32b-2

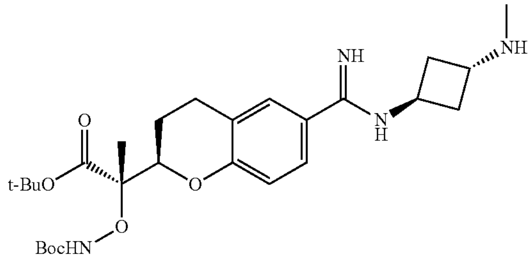

Int-33c-2

Step A—Synthesis of Intermediate 33a-1 A solution of intermediate 32b-1 (400 mg, 1.196 mmol) in HCl/EtOAc (4 M, 8 mL) was stirred at 20° C. for 0.5 h. The reaction mixture was then concentrated under reduced pressure to give intermediate 33a-1, which was used in the next reaction without further purification. LC-MS (ESI): m/z 235.1 $[M+H]^+$.

Step B—Synthesis of Intermediate 33b-1 To a solution of intermediate 33a-1 (261 mg, 1.114 mmol) in MeCN (8 mL) at 25° C. were added intermediate 3c (400 mg, 0.857 mmol), acetic acid (0.196 mL, 3.43 mmol), and potassium acetate (252 mg, 2.57 mmol) sequentially. The reaction mixture was stirred at 80° C. for 30 min under a $N_2$ atmosphere, then filtered. The filtrate was concentrated under vacuum. The resulting residue was purified by a reverse phase HPLC (Biotage; 20 g Agela C18 column, Eluent of 0-40% MeCN/$H_2O$ (0.5% TFA) gradient @ 50 mL/min) to give intermediate 33b-1. LC-MS (ESI): m/z 653.7 $[M+H]^+$.

Step C—Synthesis of Intermediates 33c-1 and 33c-2 A mixture of intermediate 33b-1 (365 mg, 0.559 mmol) and Pd/C (179 mg, 0.168 mmol, 10 wt. %) in EtOAc (8 mL) was stirred at 25° C. under $H_2$ (15 psi) for 5 h. Then the reaction mixture was filtered, and the filtrate was concentrated under vacuum to give intermediate 33c-1, which was used in the next reaction without further purification. LC-MS (ESI): m/z 519.5 $[M+H]^+$.

Intermediate 33c-2 was prepared from intermediate 32b-2 using the procedure of step A to Step C of Example 43. LC-MS (ESI): m/z 519.5 $[M+H]^+$.

Example 44: Preparation of Compounds 67 and 68

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-(trans-3-(methylamino)cyclobutyl)carbamimidoyl)chroman-2-yl)propanoic acid, and (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-(cis-3-(methylamino)cyclobutyl)carbamimidoyl)chroman-2-yl)propanoic acid

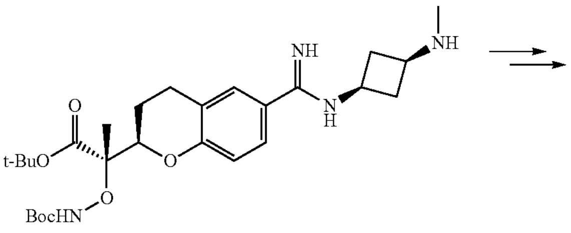

Int-33c-1

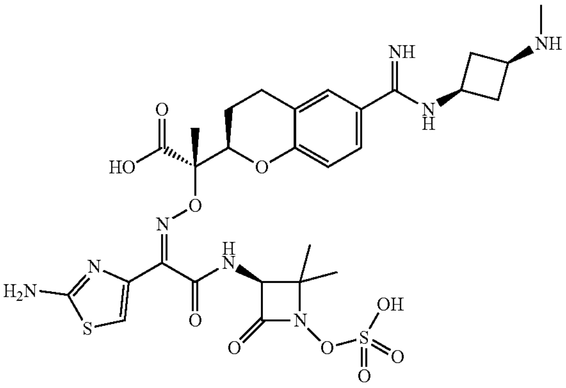

Compound 67

-continued

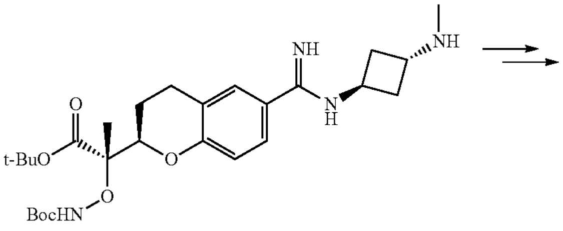

Int-33c-2

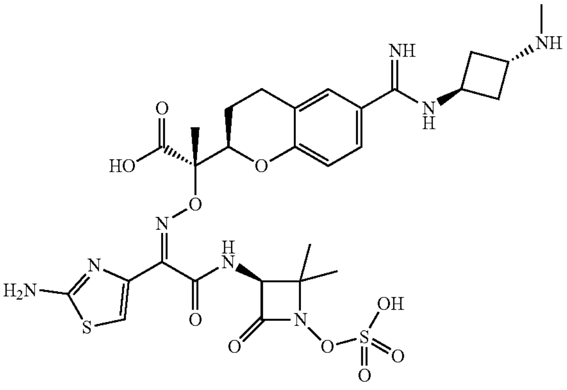

Compound 68

Compounds 67 and 68 were prepared starting from intermediate 33c-1 and intermediate 33c-2 respectively according to the procedure in Step B to Step C of Example 32.

Compound 67: LC-MS (ESI): m/z 709.1 $[M+H]^+$. $^1H$ NMR (400 MHz, $D_2O+CD_3CN$) δ: 7.45-7.31 (m, 2H), 6.96-6.69 (m, 2H), 4.60 (s, 1H), 4.36 (br d, J=11.3 Hz, 1H), 4.07-3.88 (m, 1H), 3.59-3.44 (m, 1H), 2.98-2.67 (m, 4H), 2.54 (s, 3H), 2.37-2.23 (m, 2H), 2.09-2.00 (m, 1H), 1.74-1.59 (m, 1H), 1.48 (s, 3H), 1.41 (s, 3H), 1.23 (s, 3H).

Compound 68: LC-MS (ESI): m/z 709.1 $[M+H]^+$. $^1H$ NMR (400 MHz, $D_2O+CD_3CN$) δ: 7.45-7.29 (m, 2H), 6.90-6.78 (m, 2H), 4.60 (s, 1H), 4.44-4.34 (m, 1H), 4.30-4.16 (m, 1H), 3.90-3.77 (m, 1H), 2.90-2.48 (m, 9H), 2.09-2.00 (m, 1H), 1.77-1.60 (m, 1H), 1.50 (s, 3H), 1.41 (s, 3H), 1.23 (s, 3H).

Example 45: Preparation of Intermediates 34g-1 and 34g-2

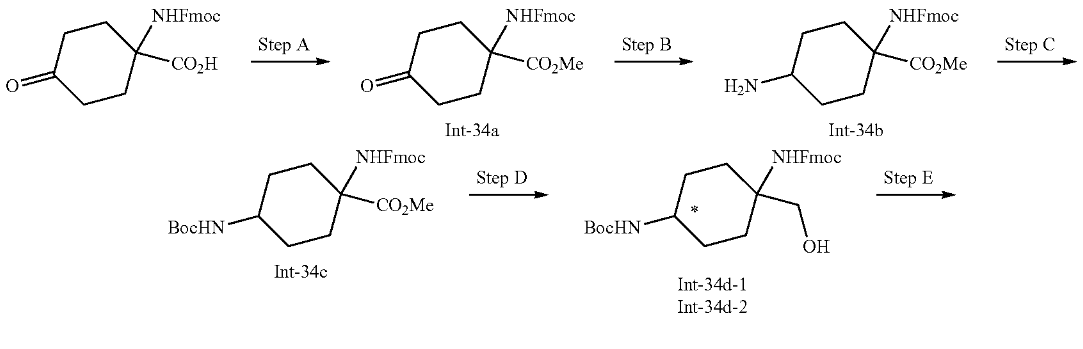

-continued

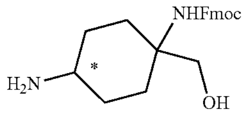

Int-34e-1

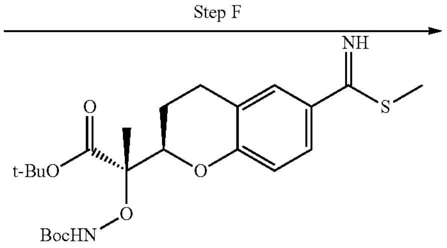

Int-3c

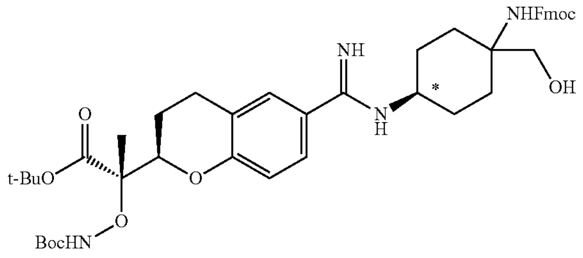

Int-34f-1

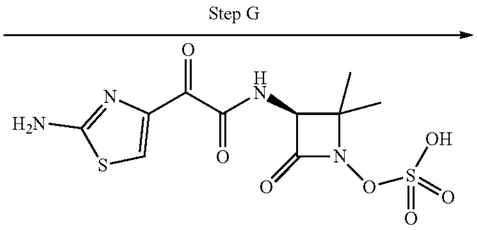

Int-5

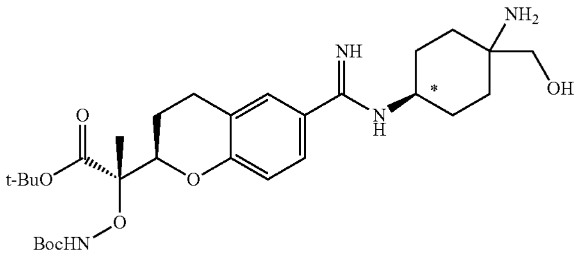

Int-34g-1
Int-34g-2

Step A—Synthesis of Intermediate 34a To a stirred solution of 1-((((9H-fluoren-9-yl)methoxy)-carbonyl)amino)-4-oxocyclohexane-1-carboxylic acid (5 g, 13.18 mmol) in DCM (40 mL) and MeOH (10 mL) was added (trimethylsilyl)diazomethane (2 M in hexanes) (13.18 mL, 26.4 mmol) dropwise at 0° C. The reaction was stirred at 25° C. for 12 h, then cooled to 0° C., and AcOH (1 mL) was added dropwise. The reaction mixture was diluted with DCM (80 mL), washed sequentially with saturated aqueous $NaHCO_3$ (50 mL), and brine (30 mL), dried over anhydrous $Na_2SO_4$, and filtered. The filtrate was concentrated under vacuum to give intermediate 34a, which was used in the next reaction without further purification. LC-MS (ESI): m/z 394.1 $[M+H]^+$.

Step B—Synthesis of Intermediate 34b To a stirred solution of intermediate 34a (3 g, 7.63 mmol) and ammonium acetate (5.88 g, 76 mmol) in MeOH (200 mL) was added sodium triacetoxyborohydride (8.08 g, 38.1 mmol) in one portion at 15° C. The reaction mixture was stirred at 25° C. for 12 h, then quenched by adding saturated aqueous $NH_4Cl$ (100 mL). The mixture was extracted with DCM (200 mL). The organic phase was separated, dried over anhydrous $Na_2SO_4$, filtered and the filtrate was concentrated under reduced pressure. The resulting residue was purified by flash silica gel chromatography (ISCO; 40 g Agela Silica Flash Column, Eluent of 0-10% $MeOH/CH_2Cl_2$ gradient @ 30 mL/min) to afford intermediate 34b. LC-MS (ESI): m/z 395.2 $[M+H]^+$.

Step C—Synthesis of Intermediate 34c A solution of intermediate 34b (1.7 g, 4.31 mmol) and $(Boc)_2O$ (5.00 mL, 21.55 mmol) in $CHCl_3$ (40 mL) was stirred at 80° C. for 16 h. The reaction was cooled to room temperature and then purified via flash silica gel chromatography (ISCO; 20 g Agela Silica Flash Column, Eluent of 35% Petroleum ether/EtOAc gradient @ 30 mL/min) to afford intermediate 34c. LC-MS (ESI): m/z 507.3 $[M+Na]^+$.

Step D—Synthesis of Intermediates 34d-1 and 34d-2 To a solution of intermediate 34c (1.3 g, 2.63 mmol) in THF (20 mL) stirred at 0° C., was added $LiBH_4$ (0.258 g, 11.83 mmol). The reaction mixture was stirred at 20° C. for 16 h, then quenched with saturated aqueous $NH_4Cl$ (20 mL). The resulting mixture was extracted with EtOAc (50 mL). The organic phase was separated, dried over anhydrous $Na_2SO_4$, filtered and the filtrate was concentrated under reduced pressure. The resulting residue was purified by flash silica gel chromatography (ISCO; 12 g Agela Silica Flash Column, Eluent of 0-35% Petroleum ether/EtOAc gradient @ 30 mL/min) to afford intermediate 34d-1 (the first eluting stereoisomer) and intermediate 34d-2 (the second eluting stereoisomer). LC-MS (ESI): m/z 467.2 $[M+H]^+$.

Intermediate 34d-1: $^1H$ NMR (400 MHz, $CDCl_3$) δ: 7.77 (d, J=7.4 Hz, 2H), 7.57 (d, J=7.4 Hz, 2H), 7.44-7.38 (m, 2H), 7.35-7.30 (m, 2H), 4.45 (br s, 3H), 3.71 (br s, 2H), 3.54 (br s, 1H), 1.93 (br s, 2H), 1.81 (br s, 1H), 1.49 (br s, 1H), 1.44 (s, 11H), 1.37 (br s, 2H).

Intermediate 34d-2: $^1H$ NMR (400 MHz, $CDCl_3$) δ: 7.79 (d, J=7.4 Hz, 2H), 7.60 (d, J=7.4 Hz, 2H), 7.43 (t, J=7.6 Hz, 2H), 7.38-7.32 (m, 2H), 4.52 (br s, 2H), 4.39 (br s, 1H), 3.58 (br s, 3H), 2.02 (br s, 1H), 1.86 (br s, 3H), 1.47-1.45 (m, 11H), 1.40-1.12 (m, 2H).

Step E—Synthesis of Intermediate 34e-1 A solution of intermediate 34d-1 (200 mg, 0.429 mmol) in HCl/MeOH (4 M, 2 mL) was stirred at 25° C. for 0.5 h. The reaction mixture was then concentrated under vacuum to give intermediate 34e-1, which was used in the next reaction without further purification. LC-MS (ESI): m/z 367.1 $[M+H]^+$.

Step F—Synthesis of Intermediate 34f-1 Potassium acetate (88 mg, 0.900 mmol) was added to a stirred mixture of intermediate 34e-1 (132 mg, 0.360 mmol), intermediate 3c (140 mg, 0.300 mmol), and acetic acid (0.069 mL, 1.200 mmol) in MeCN (4 mL). The reaction was stirred at 80° C. for 30 min, then filtered and the filtrate was concentrated under reduced pressure. The resulting residue was purified by a preparative TLC plate ($CH_2Cl_2$/MeOH=10:1) to afford intermediate 34f-1. LC-MS (ESI): m/z 785.8 $[M+H]^+$.

Step G—Synthesis of Intermediates 34g-1 and 34g-2 To a solution of intermediate 34f-1 (120 mg, 0.153 mmol) in DMF (2 mL) was added piperidine (15.62 mg, 0.183 mmol). The reaction was stirred at 25° C. for 0.5 h, and then concentrated under vacuum to give intermediate 34g-1, which was used in the next reaction without further purification. LC-MS (ESI): m/z 563.5 $[M+H]^+$.

Intermediate 34g-2 was prepared from intermediate 34d-2 according to the procedure of Step E to Step G of Example 45s. LC-MS (ESI): m/z 563.3 $[M+H]^+$.

Example 46: Preparation of Compounds 69 and 70

(S)-2-((R)-6-(N-((1r,4R)-4-amino-4-(hydroxymethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1s,4S)-4-amino-4-(hydroxymethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

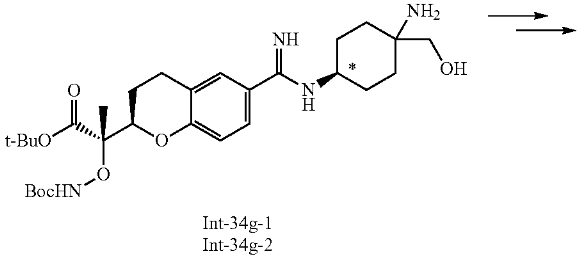

Int-34g-1
Int-34g-2

-continued

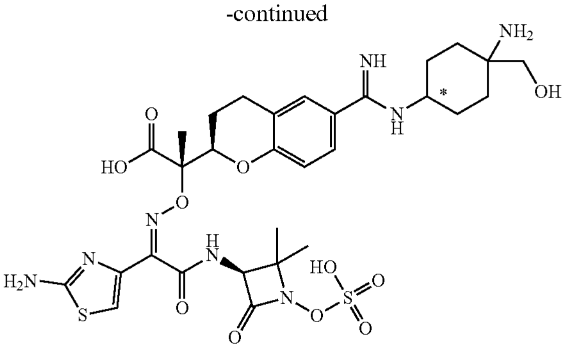

Compound 69
Compound 70

Compounds 69 and 70 were prepared starting from intermediate 34g-1 and intermediate 34g-2 respectively according to the procedure in Step F to Step G of Example 34.

Compound 69: LC-MS (ESI): m/z 753.2 $[M+H]^+$. $^1H$ NMR (400 MHz, DMSO-$d_6$) δ: 7.45-7.32 (m, 2H), 6.91 (d, J=8.6 Hz, 1H), 6.74 (s, 1H), 4.58 (s, 1H), 4.39 (br d, J=11.7 Hz, 1H), 3.60-3.45 (m, 3H), 2.85-2.66 (m, 2H), 2.09-1.99 (m, 1H), 1.92-1.71 (m, 4H), 1.63-1.40 (m, 8H), 1.38 (s, 3H), 1.23 (s, 3H).

Compound 70: LC-MS (ESI): m/z 753.4 $[M+H]^+$. $^1H$ NMR (400 MHz, DMSO-$d_6$) δ: 7.49-7.38 (m, 2H), 6.91 (br d, J=9.4 Hz, 1H), 6.75 (s, 1H), 4.61 (s, 1H), 4.39 (br d, J=11.7 Hz, 1H), 3.48-3.34 (m, 3H), 2.84-2.65 (m, 2H), 2.05-1.44 (m, 10H), 1.38 (apparent s, 6H), 1.23 (s, 3H).

Example 47: Preparation of Intermediates 35b-1 and 35b-2

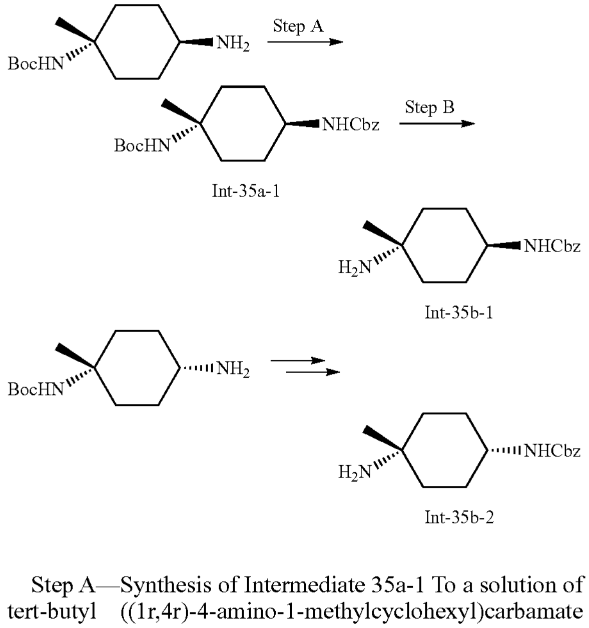

Int-35a-1

Int-35b-1

Int-35b-2

Step A—Synthesis of Intermediate 35a-1 To a solution of tert-butyl ((1r,4r)-4-amino-1-methylcyclohexyl)carbamate (100 mg, 0.438 mmol) in THF (1.8 mL) and water (0.6 mL) was added sodium carbonate (139 mg, 1.314 mmol) and benzyl chloroformate (0.072 mL, 0.526 mmol) at 0° C. The reaction was stirred at 20° C. for 16 h, then diluted with water (10 mL). The resulting mixture was extracted with EtOAc (3×20 mL). The combined organic fractions were washed with brine (10 mL), dried over anhydrous $Na_2SO_4$, filtered and the filtrate was concentrated under reduced pressure. The resulting residue was purified by preparative TLC plate (eluting with 3:1 petroleum ether/EtOAc, $SiO_2$) to give intermediate 35a-1. LC-MS (ESI): m/z 385.3 $[M+Na]^+$. $^1H$ NMR (400 MHz, $CDCl_3$) δ: 7.35-7.39 (m, 5H), 5.07 (s, 2H), 4.74 (br s, 1H), 4.41 (br s, 1H), 3.68-3.54 (m, 1H), 1.93-1.77 (m, 2H), 1.77-1.58 (m, 4H), 1.43 (s, 9H), 1.46-1.34 (m, 2H), 1.32 (s, 3H).

Step B—Synthesis of Intermediates 35b-1 and 35b-2 A solution of intermediate 35a-1 (500 mg, 1.379 mmol) in HCl/EtOAc (4 M, 10 mL) was stirred at 20° C. for 2 h. Then the reaction mixture was concentrated under vacuum to give intermediate 35b-1, which was used in the subsequent reaction without further purification. $^1H$ NMR (400 MHz, $CD_3OD$) δ: 7.44-7.19 (m, 5H), 5.07 (s, 2H), 3.51-3.34 (m, 1H), 1.94-1.80 (m, 4H), 1.75-1.65 (m, 2H), 1.56-1.44 (m, 2H), 1.37 (s, 3H).

Intermediate 35b-2 was prepared from tert-butyl ((1s,4s)-4-amino-1-methylcyclohexyl)-carbamate according to the procedure in Step A and Step B of Example 47. LC-MS (ESI): m/z 263.2 $[M+H]^+$.

Example 48: Preparation of Compound 71

(S)-2-((R)-6-(N-((1r,4R)-4-amino-1-methylcyclohexyl) carbamimidoyl)chroman-2-yl)-2-((((Z)-1-(2-aminothiazol-4-yl)-2-(((S)-2,2-dimethyl-4-oxo-1-(sulfooxy)azetidin-3-yl) amino)-2-oxoethylidene)amino)oxy)propanoic acid

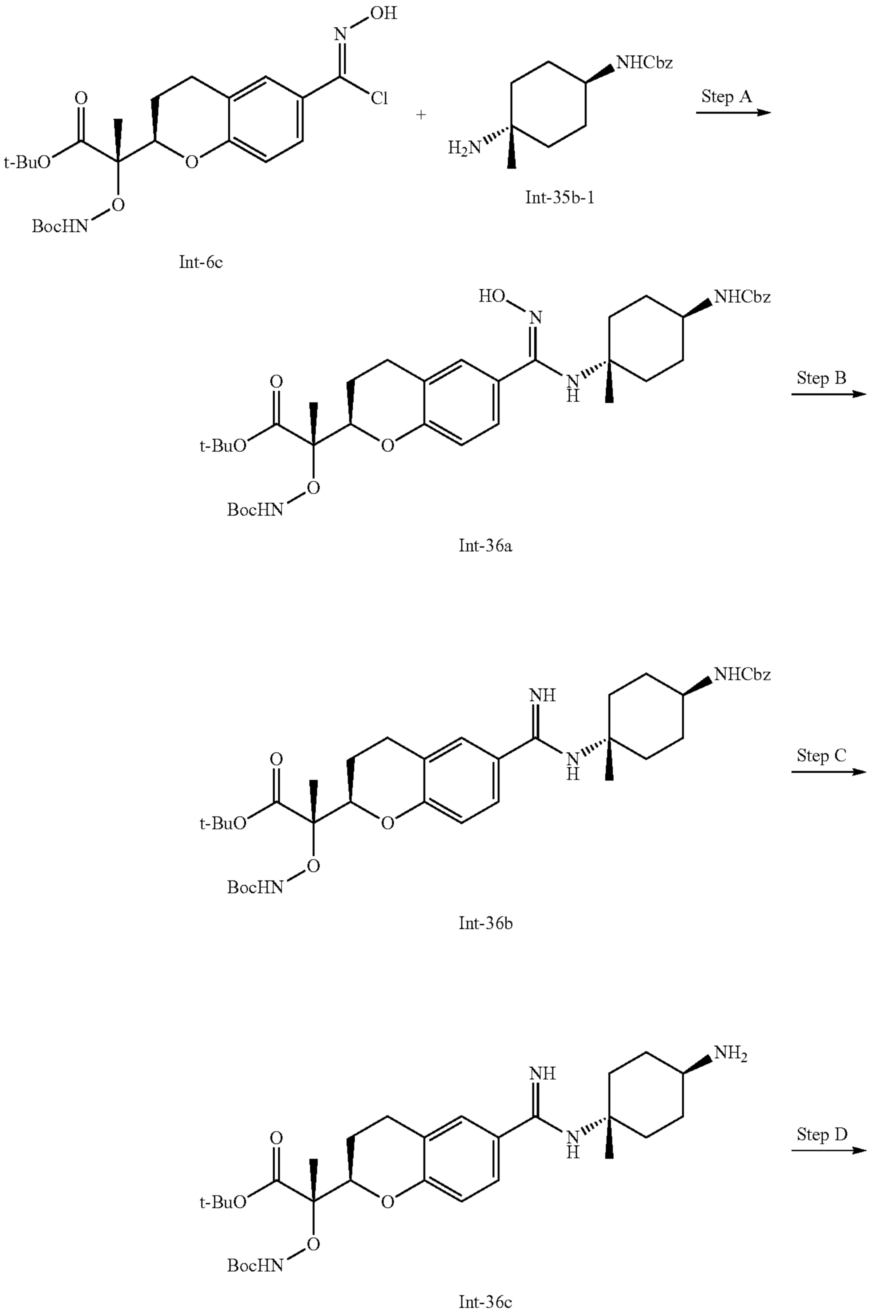

Int-6c

Int-35b-1

Int-36a

Int-36b

Int-36c

-continued

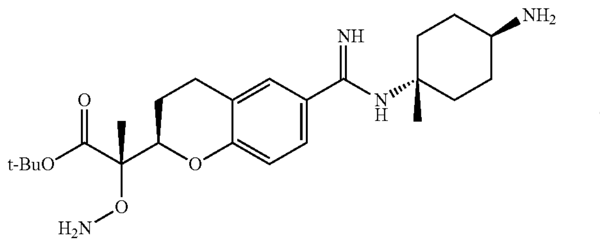

Int-36d

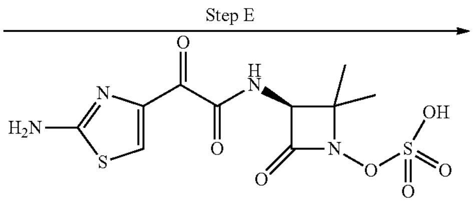

Int-5

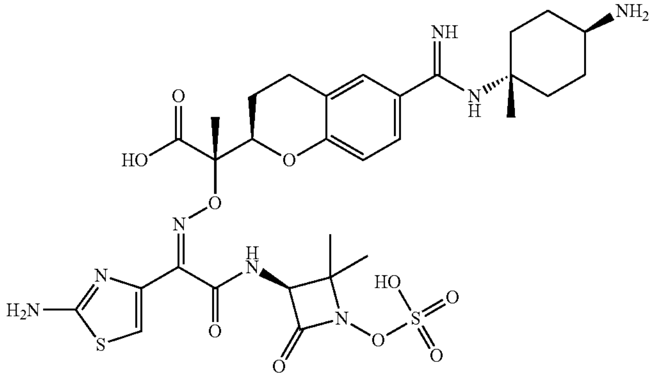

Compound 71

Step A— Synthesis of Intermediate 36a To a solution of intermediate 35b-1 (156 mg, 0.595 mmol) in DMF (6 mL) was added TEA (0.237 mL, 1.699 mmol) and intermediate 6c (400 mg, 0.849 mmol). The reaction was stirred at 25° C. for 2 h. Then the reaction mixture was diluted with ice water (20 mL) and extracted with ethyl acetate (40 mL×2). The combined organic layers were washed with brine (20 mL), dried over anhydrous $Na_2SO_4$, and filtered. The filtrate was concentrated in vacuo to give intermediate 36a, which was used in the next reaction without further purification. LC-MS (ESI): m/z 697.2 $[M+H]^+$.

Step B— Synthesis of Intermediate 36b To a solution of $K_2CO_3$ (297 mg, 2.153 mmol) in MeOH (2.8 mL) was added formic acid (198 mg, 4.31 mmol) at 20° C. under $N_2$. The reaction mixture was stirred at 20° C. for 10 minutes, and then added to a solution of intermediate 36a (300 mg, 0.431 mmol) in AcOH (1.8 mL) and acetic anhydride (48.3 mg, 0.474 mmol). Then Pd/C (183 mg, 0.172 mmol, 10% wt.) was added, and the reaction was stirred at 25° C. for 12 h. The reaction mixture was then filtered and the filtrate was concentrated under reduce pressure to give intermediate 36b. which was used in the next reaction without further purification. LC-MS (ESI): m/z 681.6 $[M+H]^+$.

Step C— Synthesis of Intermediate 36c To a solution of intermediate 36b (400 mg, 0.588 mmol) in ethyl acetate (20 mL) was added Pd/C (31.3 mg, 0.294 mmol, 10 wt. %) at 20° C. The reaction mixture was stirred at 25° C. under an atmosphere of $H_2$ for 1 h. Then the reaction mixture was filtered, and the filtrate was concentrated in vacuo to give intermediate 36c, which was used in the next reaction without further purification. LC-MS (ESI): m/z 547.4 $[M+H]^+$.

Step D—Synthesis of Intermediate 36d To a solution of intermediate 36c (420 mg, 0.768 mmol) in DCM (1.5 mL) was added aqueous HCl (1.5 mL, 12 N) at 0° C. The reaction mixture was stirred at 25° C. for 1.5 h, then the solvent was removed with a nitrogen gas flow. The resulting residue was purified by a reverse phase HPLC (Boston Uni C18 40*150*5 um; Condition: water (0.1% TFA)-ACN; Begin B 0, End B 30; Gradient Time (min) 10; 100% B Hold Time (min) 2; FlowRate (mL/min) 60; Injections 1). The product fractions were combined and lyophilized to give intermediate 36d. LC-MS (ESI) m/z: 391.2 $[M+H]^+$.

Step E—Synthesis of Compound 71 To a solution of intermediate 36d (220 mg, 0.563 mmol) in DMA (4 mL) were added 4 Å molecular sieve (100 mg) and intermediate 5 (301 mg, 0.620 mmol) at 0° C. The reaction mixture was stirred at 25° C. for 12 h, and then filtered. The filtrate was diluted with MeOH (1 mL) and purified by a reverse phase HPLC (Boston Uni C18 40*150 5 um; Condition: water (0.1% TFA)-ACN; Begin B 0, End B 30; Gradient Time (min) 10; 100% B Hold Time (min) 2; FlowRate (mL/min) 60; Injections 1), followed by lyophilization to give compound 71 as the TFA salt. The TFA salt was further purified by a reverse phase HPLC (Welch Xtimate C18 150*25 mm*5 um; Condition: water (0.225% FA)-ACN; Begin B 0, End B 20; Gradient Time (min) 15; 100% B Hold Time (min) 2; FlowRate (mL/min) 25; Injections 2), followed by lyophilization to give compound 71 as the formic acid salt. LC-MS (ESI): m/z 737.2 $[M+H]^+$. $^1H$ NMR (400 MHz, $D_2O+CD_3CN$) δ: 7.39-7.31 (m, 2H), 6.88 (d, J=8.6 Hz, 1H), 6.79 (s, 1H), 4.63 (s, 1H), 4.38 (br d, J=10.6 Hz, 1H), 3.28-3.15 (m, 1H), 2.92-2.70 (m, 2H), 2.15-2.01 (m, 3H), 2.01-1.92 (m, 2H), 1.94-1.66 (m, 3H), 1.65-1.51 (m, 2H), 1.50 (s, 3H), 1.47 (s, 3H), 1.43 (s, 3H), 1.26 (s, 3H).

Example 49: Preparation of Compound 72

(S)-2-((R)-6-(N-((1s,4S)-4-amino-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

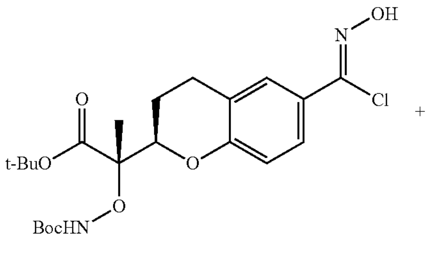

Int-6c

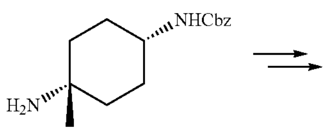

Int-35b-2

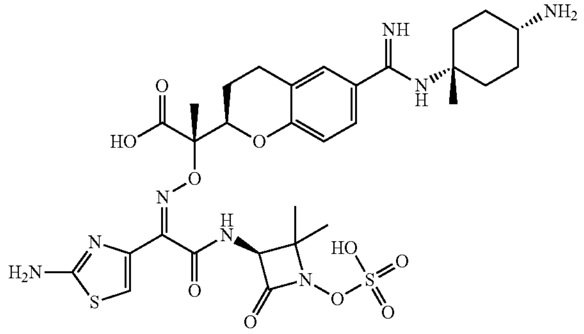

Compound 72

Compound 72 was prepared starting from intermediate 35b-2 and intermediate 6c according to the procedure in Step A to Step E of Example 48. Compound 72: LC-MS (ESI): m/z 737.3 $[M+H]^+$. $^1H$ NMR (400 MHz, $D_2O$+$CD_3CN$) δ: 7.44-7.38 (m, 2H), 6.89 (d, J=8.2 Hz, 1H), 6.79 (s, 1H), 4.64 (s, 1H), 4.37 (br d, J=9.8 Hz, 1H), 3.25-3.10 (m, 1H), 2.90-2.70 (m, 2H), 2.40-2.25 (m, 2H), 2.17-2.02 (m, 1H), 2.01-1.88 (m, 2H), 1.82-1.63 (m, 1H), 1.64-1.47 (m, 4H), 1.50 (s, 3H), 1.43 (s, 3H), 1.39 (s, 3H), 1.26 (s, 3H).

Example 50: Preparation of Intermediates 37d-1 and 37d-2

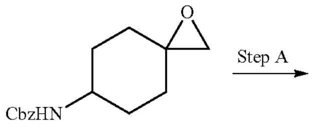

Int-28a

-continued

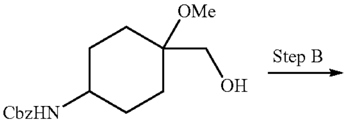

Int-37a

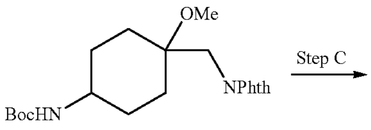

Int-37b

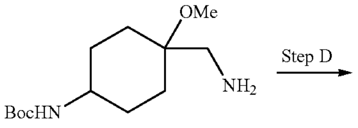

Int-37c

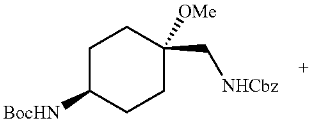

Int-37d-1

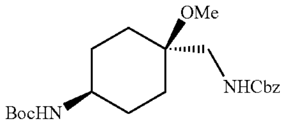

Int-37d-2

Step A—Synthesis of Intermediate 37a To a stirred solution of intermediate 28a (5.0 g, 22.00 mmol) in MeOH (100 mL) was added p-toluenesulfonic acid monohydrate (0.837 g, 4.40 mmol) at 0° C. The reaction was stirred at 25° C. for 2 h, then diluted with saturated aqueous $NaHCO_3$ (60 mL), extracted with EtOAc (40 mL×3). The organic layers were combined, dried over anhydrous $Na_2SO_4$, filtered and the filtrate was concentrated under reduced pressure. The resulting residue was purified by flash silica gel chromatography (ISCO; 40 g Agela Silica Flash Column, Eluent of 0~50% EtOAc/Petroleum ether gradient @ 40 mL/min) to give intermediate 37a. LC-MS (ESI): m/z 294.4 $[M+H]^+$.

Step B—Synthesis of Intermediate 37b To a solution of intermediate 37a (1.8 g, 6.94 mmol) in anhydrous THF (30 mL) was added $Ph_3P$ (2.185 g, 8.33 mmol) and phthalimide (1.328 g, 9.02 mmol) at 0° C. under nitrogen. To the reaction mixture was treated added DIAD (1.754 mL, 9.02 mmol) at 0° C. The reaction was allowed to warm up to 25° C. and stirred at 25° C. for 16 h, concentrated in vacuo. The resulting residue was purified by flash silica gel chromatography (Biotage; 20 g Agela Silica Flash Column, Eluent of 0-30% EtOAc/Petroleum ether gradient @30 mL/min) to give intermediate 37b. LC-MS (ESI): m/z 777.4 $[2M+H]^+$.

Step C—Synthesis of Intermediate 37c A mixture of intermediate 37b (2.0 g, 5.15 mmol) and hydrazine hydrate (1.516 g, 25.7 mmol) in MeCN (20 mL) was stirred at 25° C. for 2 h under a nitrogen atmosphere, and then concentrated under vacuum. The resulting residue was diluted with water (25 mL), and extracted with a mixed solvent of 10:1 DCM/MeOH (20 mL×3). The combined organic layers were washed with brine (30 mL), dried over anhydrous $Na_2SO_4$, and filtered. The filtrate was concentrated in vacuo to afford intermediate 37c, which was used in the next reaction without further purification. LC-MS (ESI): m/z 259.3 $[M+H]^+$.

Step D—Synthesis of Intermediates 37d-1 and 37d-2 To a solution of intermediate 37c (1.3 g, 5.03 mmol) in THF (10 mL) and water (5 mL) were added dropwise benzyl chloroformate (1.288 g, 7.55 mmol) and sodium carbonate (1.067 g, 10.06 mmol) at 0° C. The reaction was stirred at 25° C. for 16 h, and then concentrated under reduced pressure. The resulting residue was purified by a reverse phase HPLC (Column: Boston Uni C18 40*150*5 um; Condition: water (0.1% TFA)-ACN; Begin B 45, End B 75; Gradient Time (min) 10; 100% B Hold Time (min) 2; Flow Rate (mL/min) 60; Injections 2) to give the product as a mixture of stereoisomers. The mixture of stereoisomers (1.0 g, 2.55 mmol) was further separated by SFC (Column: DAICEL CHIRALCEL OJ-H 250 mm*30 mm, 5 um; Condition: 0.1% $NH_3 \cdot H_2O$-EtOH; Begin B 25%; Flow Rate (mL/min) 60; Injections 75) to individually afford intermediate 37d-1 (the first eluting stereoisomer) and intermediate 37d-2 (the second eluting stereoisomer).

Intermediate 37d-1: $^1H$ NMR ($CDCl_3$, 400 MHz) δ: 7.42-7.29 (m, 5H), 5.11 (s, 2H), 4.99 (br s, 1H), 4.50 (br s, 1H), 3.58-3.45 (m, 1H), 3.34 (d, J=5.9 Hz, 2H), 3.16 (s, 3H), 1.95-1.75 (m, 2H), 1.69-1.52 (m, 4H), 1.49-1.33 (m, 2H), 1.44 (s, 9H).

Intermediate 37d-2: $^1H$ NMR ($CDCl_3$, 400 MHz) δ: 7.57-7.30 (m, 5H), 5.07 (s, 2H), 4.90 (s, 1H), 4.48 (s, 1H), 3.49-3.32 (m, 1H), 3.20 (d, J=5.2 Hz, 2H), 3.14 (s, 3H), 1.87-1.71 (m, 4H), 1.44 (s, 9H), 1.37-1.15 (m, 4H).

Example 51: Preparation of Compound 73

(S)-2-((R)-6-(N-((1s,4S)-4-(aminomethyl)-4-methoxycyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

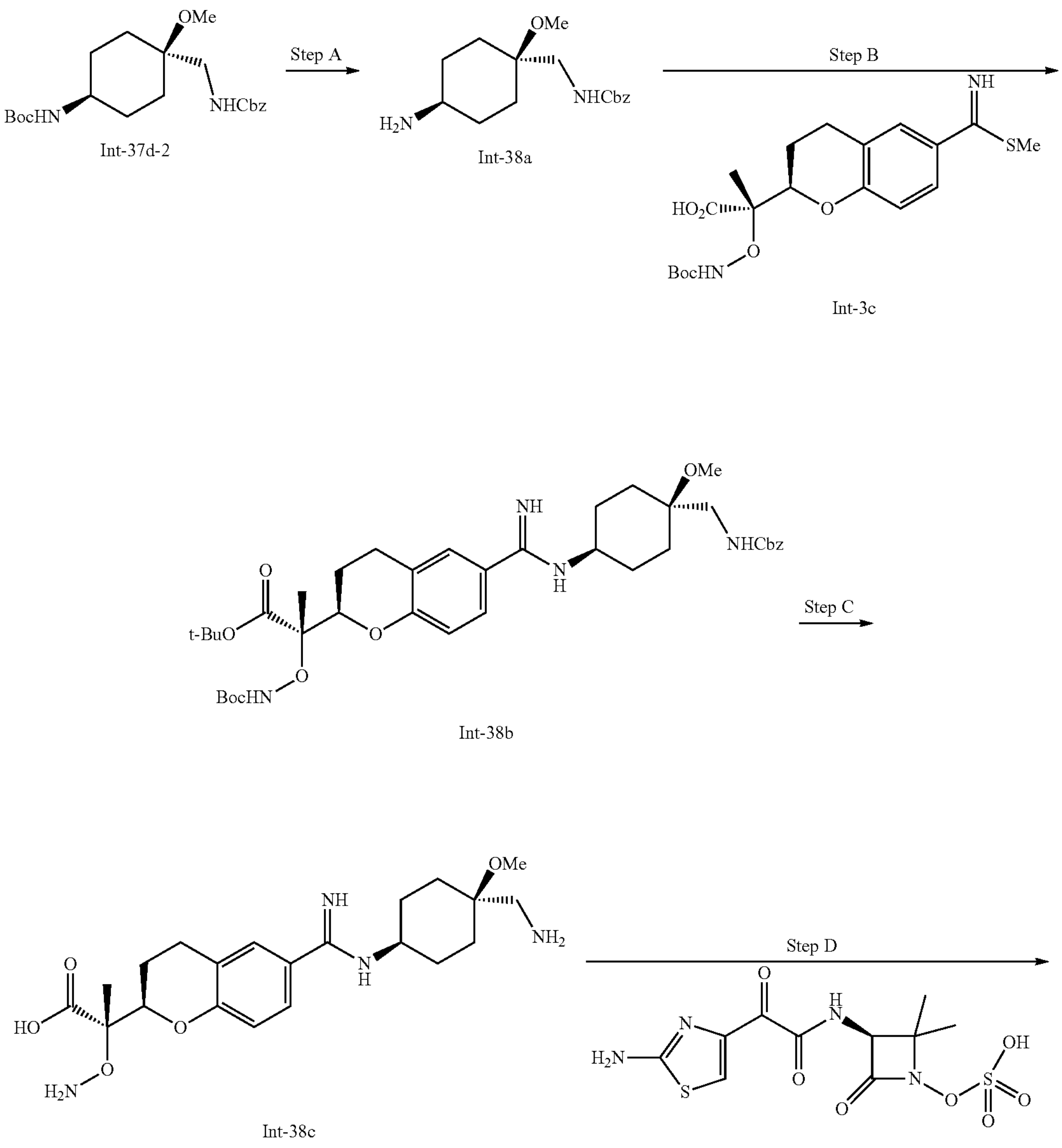

Int-37d-2 Int-38a Int-3c

Int-38b

Int-38c Int-5

-continued

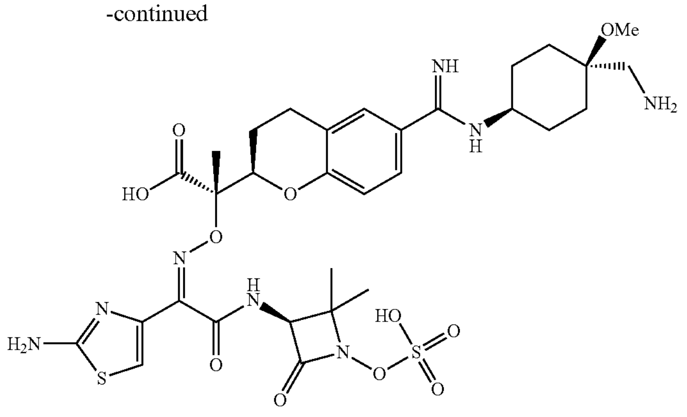

Compound 73

Step A—Synthesis of Intermediate 38a A solution of intermediate 37d-2 (450 mg, 1.147 mmol) in HCl/EtOAc (4 M, 6 mL) was stirred at 25° C. for 0.5 h. Then the reaction mixture was concentrated to give intermediate 38a, which was used in the next reaction without further purification. LC-MS (ESI): m/z 293.2 $[M+H]^+$.

Step B—Synthesis of Intermediate 38b To a stirred solution of intermediate 3c (535 mg, 1.147 mmol) and intermediate 38a (335 mg, 1.147 mmol) in MeCN (10 mL) were added acetic acid (0.197 mL, 3.44 mmol)) and potassium acetate (338 mg, 3.44 mmol) sequentially at 25° C. The reaction was stirred at 80° C. for 30 m 5, then diluted with water (30 mL) and extracted with EtOAc (50 mLx3). The organic layers were combined, dried over anhydrous $Na_2SO_4$, filtered and concentrated under reduced pressure. The resulting residue was purified by flash silica gel chromatography (ISCO; 20 g Agela Silica Flash Column, Eluent of 0-5% DCM/MeOH gradient @30 mL/min) to afford intermediate 38b. LC-MS (ESI): m/z 711.4 $[M+H]^+$.

Step C—Synthesis of Intermediate 38c A solution of intermediate 38b (400 mg, 0.563 mmol) in HBr/AcOH (8 mL, 40%) was stirred at 25° C. for 2 h. Then the reaction mixture was filtered, and the filtrate was concentrated under reduced pressure. The resulting residue was purified by a reverse phase HPLC (Column: Boston Uni C18 40*150*5 un; Condition: water (0.1% TFA)-ACN; Begin B 0, End B 30; Gradient Time (min) 10; 100% B Hold Time (mi) 2; Flow Rate (mL/min) 60; Injections 1) to give intermediate 38c. LC-MS (ESI): m/z 421.0 $[M+H]^+$.

Step D—Synthesis of Compound 73 To a mixture of intermediate 38c (150 mg, 0.357 mmol) in DMA (5 mL) was added intermediate 5 (130 mg, 0.357 mmol) at 0° C. The reaction was stirred at 25° C. for 16 h. Then the reaction solvent was evaporated with nitrogen gas flow, and the resulting residue was purified by a reverse phase HPLC (Column: Boston Uni C18 40*150*5 um; Condition: water (0.1% TFA)-ACN; Begin B 0, End B 30; Gradient Time (min) 10; 100% B Hold Time (min) 2; FlowRate (mL/min) 60; Injections 2) to give crude product. The crude product was purified by a second reverse phase HPLC (Column: Phenomenex Luna C18 75*30 mm*3 um; Condition: water (0.1% TFA)-ACN; Begin B 0, End B 30; Gradient Time (min) 11; 100% B Hold Time (min) 2; FlowRate (mL/min) 30; Injections 9) to give compound 73 as the TFA salt. The TFA salt was converted to the formic acid salt by passing through a reverse phase HPLC (Column: Welch Xtimate C18 150*25 mm*5 um; Condition: water (10 mM $NH_4HCO_3$)— ACN; Begin B 0, End B 18; Gradient Time (min) 15; 100% B Hold Time (min) 2; FlowRate (mL/min) 25; Injections 2) to afford compound 73 as the formic acid salt. LC-MS (ESI): m/z 767.4 $[M+H]^+$. $^1H$ NMR ($CD_3CN$+$D_2O$, 400 MHz) δ: 7.42-7.33 (m, 2H), 6.89 (d, J=8.6 Hz, 1H), 6.78 (s, 1H), 4.61 (s, 1H), 4.38 (br d, J=10.2 Hz, 1H), 3.62-3.46 (m, 1H), 3.12 (s, 3H), 2.96 (s, 2H), 2.89-2.70 (m, 2H), 2.15-2.00 (m, 1H), 1.92-1.78 (m, 4H), 1.80-1.65 (m, 1H), 1.60-1.47 (m, 2H), 1.52 (s, 3H), 1.43 (s, 3H), 1.40-1.32 (m, 2H), 1.26 (s, 3H).

Example 52: Preparation of Intermediates 39d-1 and 39d-2

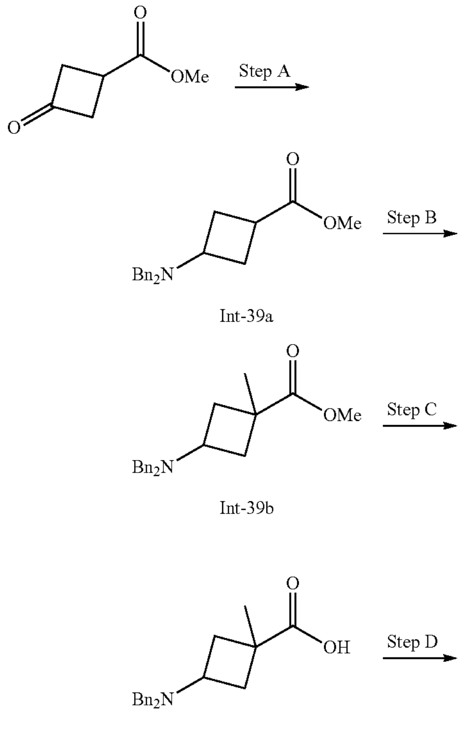

Int-39a

Int-39b

Int-39c

-continued

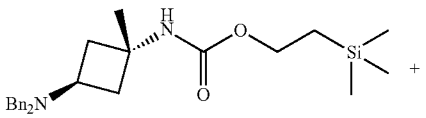

Int-39d-1

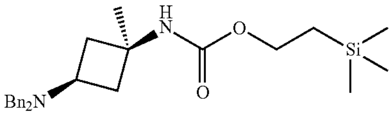

Int-39d-2

Step A—Synthesis of Intermediate 39a To a solution of methyl 3-oxocyclobutane-1-carboxylate (13.48 g, 105 mmol) in THF (300 mL) and AcOH (6 mL, 105 mmol) was added dibenzylamine (20.76 g, 105 mmol). After stirring at room temperature (22° C.) for 10 min, sodium cyanoborohydride (19.83 g, 316 mmol) was added portion wise over 30 min. The reaction mixture was stirred at room temperature (22° C.) for 16 h, then added to a stirred saturated aqueous $NaHCO_3$ solution (200 mL). After stirring at 22° C. for 10 min, the resulting mixture was extracted with EtOAc (100 mL×3). The combined organic layers were washed with brine (150 mL×2), dried over anhydrous $Na_2SO_4$, filtered and the filtrate was concentrated under vacuum. The resulting residue was purified by flash silica gel chromatography (Biotage; 80 g Agela Silica Flash Column; Eluent of 7.5-100% EtOAc/Petroleum ether gradient @ 45 mL/min) to give intermediate 39a. TLC:Petroleum ether/EtOAc (20:1), $R_f$=0.6 (Ninhydrin stain).

Step B—Synthesis of Intermediate 39b To a solution of diisopropylamine (9.58 mL, 67.9 mmol) in THF (50 mL) was added n-butyllithium (27.1 mL, 67.9 mmol, 2.5 M in hexanes) at −70° C. The reaction was stirred at −70° C. for 30 min. Then a solution of intermediate 39a (7.0 g, 22.62 mmol) in THF (25 mL) was added while maintaining the temperature at −70° C. After stirring the reaction mixture at −70° C. for 20 min., a solution of iodomethane (8.35 mL, 134 mmol) in THF (25 mL) was added. The reaction was stirred at −70° C. for 1 h, then quenched with saturated aqueous $NH_4Cl$ (40 mL). The resulting mixture was stirred at 0° C. for 15 min. and then extracted with EtOAc (3×40 mL). The combined organic layers were washed with brine (50 mL), dried over anhydrous $Na_2SO_4$, filtered and concentrated under vacuum. The resulting residue was purified by flash silica gel chromatography (Biotage; 40 g Agela Silica Flash Column, Eluent of 0-9% EtOAc/petroleum ether gradient @ 40 mL/min) to give intermediate 39b. LC-MS (ESI): m/z 324.6 $[M+H]^+$.

Step C—Synthesis of Intermediate 39c To a solution of intermediate 39b (6.55 g, 20.25 mmol) in MeOH (150 mL) was added a solution of NaOH (2.430 g, 60.8 mmol) in $H_2O$ (30 mL). The reaction was stirred at 70° C. for 1.5 h, then the solvent was removed in vacuo. The resulting residue was diluted with $H_2O$ (10 mL), then pH-adjusted to pH 4-5 with aqueous HCl (2 M). The resulting mixture was filtered, and the filter cake was dried to give intermediate 39c. Additional product was obtained by extracting the filtrate with EtOAc (40 mL×4), and concentrating the combined organic layers. LC-MS (ESI): m/z 310.2 $[M+H]^+$.

Step D—Synthesis of Intermediates 39d-1 and 39d-2 To a mixture of intermediate 39c (2000 mg, 4.85 mmol) in toluene (45 mL), were added 4 Å molecular sieve (50 mg) and triethylamine (2.70 mL, 19.39 mmol), followed by the slow addition of diphenylphosphinyl azide (1769 mg, 7.27 mmol) at 0° C. The reaction was heated to 45° C. and stirred at 45° C. for 2 h. Then the temperature was then raised to 85° C., and 2-(trimethylsilyl)ethanol (2293 mg, 19.39 mmol) was added. The reaction mixture was stirred at 85° C. for 16 h. Then the reaction mixture was filtered, and the filtrate was concentrated in vacuo. The resulting residue was purified by flash silica gel chromatography (Biotage; 40 g Agela Silica Flash Column, Eluent of EtOAc/Petroleum ether 0-8% gradient @ 30 mL/min) to give the product as a mixture of stereoisomers. LC-MS (ESI): m/z 425.3 $[M+H]^+$. The mixture of stereoisomers was further purified by SFC (Column: Daicel chiralpak IG (250 mm*30 mm, 10 um); Condition: 0.1% $NH_3H_2O$ EtOH; Begin B 30%; Flow Rate (mL/min) 200; Injections 120) to give intermediate 39d-1 (the first eluting stereoisomer) and intermediate 39d-2 (the second eluting stereoisomer).

Intermediate 39d-1: LC-MS (ESI): m/z 425.3 $[M+H]^+$. $^1H$ NMR (400 MHz, $CDCl_3$) δ: 7.32-7.21 (m, 10H), 4.66 (br s, 1H), 4.13 (br t, J=8.4 Hz, 2H), 3.47 (s, 4H), 3.32-3.18 (m, 1H), 2.32-2.18 (m, 2H), 1.97-1.81 (m, 2H), 1.42 (s, 3H), 0.97 (t, J=8.4 Hz, 2H), 0.04 (s, 9H).

Intermediate 39d-2: LC-MS (ESI): m/z 425.3 $[M+H]^+$. $^1H$ NMR (400 MHz, $CDCl_3$) δ: 7.34-7.16 (m, 10H), 4.71 (br s, 1H), 4.10 (t, J=8.4 Hz, 2H), 3.48 (s, 4H), 3.06-2.93 (m, 1H), 2.23-2.01 (m, 4H), 1.37 (s, 3H), 0.96 (t, J=8.4 Hz, 2H), 0.03 (s, 9H).

Example 53: Preparation of Compound 74

(S)-2-((R)-6-(N-((1r,3R)-3-amino-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

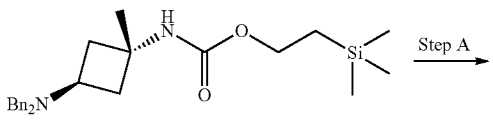

Int-39d-1

-continued

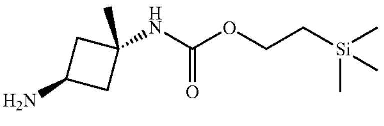

Int-40a

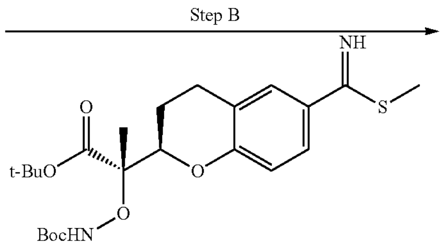

Int-3c

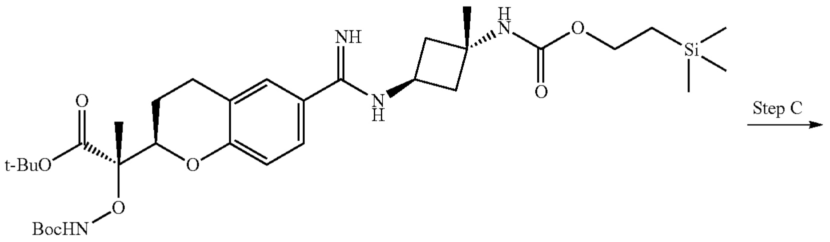

Int-40b

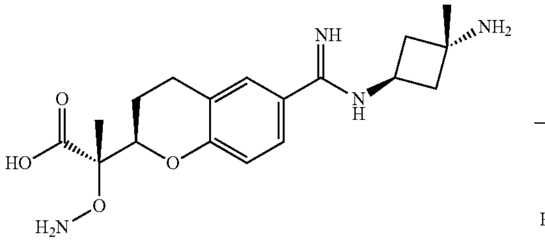

Int-40c

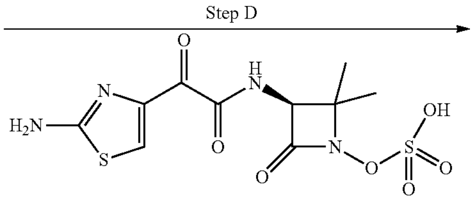

Int-5

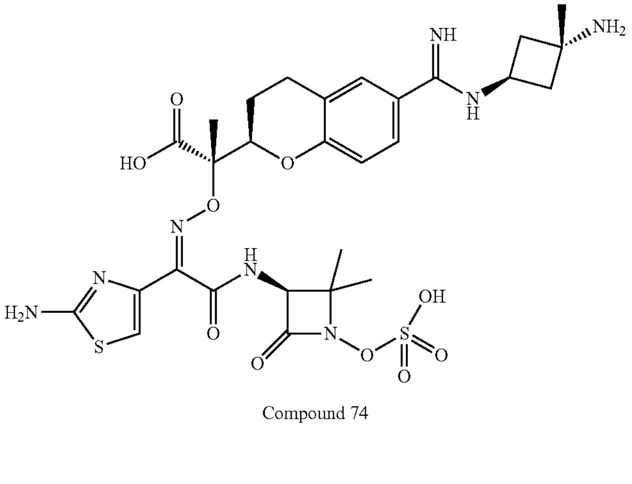

Compound 74

Step A—Synthesis of Intermediate 40a To a solution of intermediate 39d-1 (700 mg, 1.648 mmol) in MeOH (20 mL) as added palladium hydroxide (579 mg, 0.824 mmol, 20 wt. %). The mixture was stirred at 20° C. under $H_2$ atmosphere (45 psi) for 20 h. Then the reaction mixture was filtered, and the filtrate was concentrated in vacuo to give intermediate 40a, which was used in the next reaction without further purification. $^1$H NMR (400 MHz, $CDCl_3$) δ: 4.69 (br s, 1H), 4.12 (t, J=8.0 Hz, 2H), 3.62-3.48 (m, 1H), 2.62-2.39 (m, 2H), 1.75-1.61 (m, 2H), 1.43 (s, 3H), 0.97 (t, J=8.0 Hz, 2H), 0.04 (s, 9H).

Step B—Synthesis of Intermediate 40b To a stirred mixture of intermediate 40a (150 mg, 0.614 mmol) and intermediate 3c (360 mg, 0.606 mmol) in MeCN (6 mL) was added acetic acid (0.141 mL, 2.455 mmol). The reaction was stirred at 80° C. for 20 min. Then the reaction mixture was concentrated in vacuo to give crude intermediate 40b, which was used in the next reaction without further purification. LC-MS (ESI): m/z 663.8 $[M+H]^+$.

Step C—Synthesis of Intermediate 40c A mixture of intermediate 40b (407 mg, 0.614 mmol) in DCM (2.5 mL) and aqueous HCl (2.5 mL, 12 N) was stirred at 20° C. for 30 min. Then the reaction solvent was removed in vacuo, and the resulting residue was purified by a reverse phase HPLC (Boston Uni C18 40*150*5 um; Condition: water (0.1% TFA)-ACN; Begin B 0, End B 30; Gradient Time (min) 10;

100% B Hold Time (min) 2; FlowRate (mL/min) 20; Injections 1) to give intermediate 40c. LC-MS (ESI): m/z 363 $[M+H]^+$.

Step D—Synthesis of Compound 74 To a solution of intermediate 40c (200 mg, 0.386 mmol) in DMA (2.5 mL) was added intermediate 5 (194 mg, 0.425 mmol). The reaction mixture was stirred at 24° C. for 16 h. Then the reaction mixture was diluted with MeOH (2.0 mL) and purified by a reverse phase HPLC (Boston Uni C18 40*150*5 um; Condition: water (0.1% TFA)-ACN; Begin B 0, End B 30; Gradient Time (min) 10; 100% B Hold Time (min) 2; FlowRate (mL/min) 60; Injections 1) to give compound 74 as the TFA salt. The TFA salt was converted to the formic acid salt by passing through a reverse phase HPLC (Welch Xtimate C18 150*25 mm*5 um; Condition: water (0.225% FA)-ACN; Begin B 0, End B 1; 8 Gradient Time (min) 15; 100% B Hold Time (min) 2; Flow Rate (mL/min) 25; Injections 2) to give compound 74 as the formic acid salt. LC-MS (ESI): m/z 709.0 $[M+H]^+$. $^1H$ NMR (400 MHz, $D_2O+CD_3CN$) δ: 7.37-7.27 (m, 2H), 6.86 (d, J=8.6 Hz, 1H), 6.79 (s, 1H), 4.61 (s, 1H), 4.39 (br d, J=11.7 Hz, 1H), 4.31-4.19 (m, 1H), 2.94-2.71 (m, 4H), 2.50-2.26 (m, 2H), 2.20-2.05 (m, 1H), 1.82-1.65 (m, 1H), 1.54 (s, 3H), 1.48 (s, 3H), 1.43 (s, 3H), 1.26 (s, 3H).

Example 54: Preparation of Compound 75

(S)-2-((R)-6-(N-((1s,3S)-3-amino-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

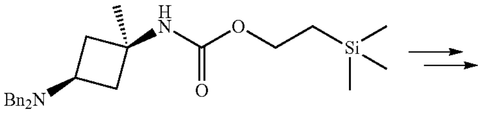

Int-39d-2

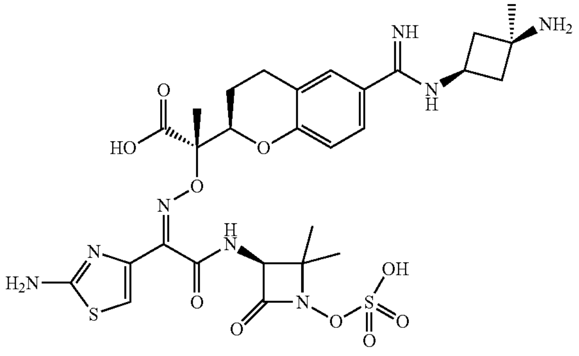

Compound 75

Compound 75 was prepared from intermediate 39d-2 according to the procedure in Step A to Step D of Example 53. Compound 75: LC-MS (ESI): m/z 709.3 $[M+H]^+$. $^1H$ NMR (400 MHz, $D_2O+CD_3CN$) δ: 7.42-7.34 (m, 2H), 6.86 (d, J=8.6 Hz, 1H), 6.78 (s, 1H), 4.60 (s, 1H), 4.35 (br d, J=10.4 Hz, 1H), 4.19-4.06 (m, 1H), 2.86-2.68 (m, 2H), 2.70-2.55 (m, 2H), 2.54-2.44 (m, 2H), 2.16-1.95 (m, 1H), 1.76-1.58 (m, 1H), 1.48 (s, 3H), 1.45 (s, 3H), 1.42 (s, 3H), 1.24 (s, 3H).

Example 55: Preparation of Intermediates 41b-1 and 41b-2

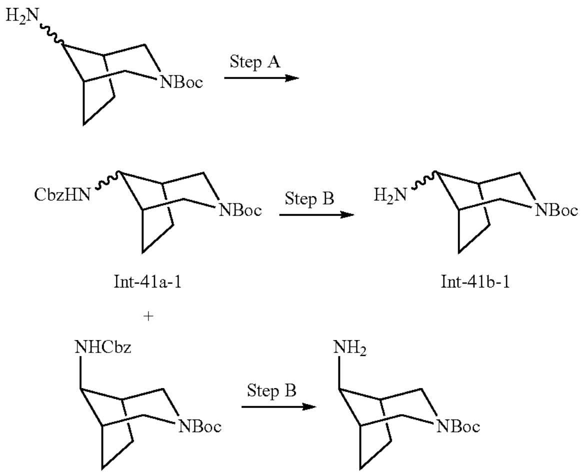

Int-41a-1 + Int-41a-2 Int-41b-1 Int-41b-2

Step A—Synthesis of Intermediates 41a-1 and 41a-2 To a solution of tert-butyl (1R,5S)-8-amino-3-azabicyclo[3.2.1]octane-3-carboxylate (1.28 g, 5.66 mmol) in DCM (45 mL) were added TEA (1.971 mL, 14.14 mmol) and n-(benzyloxycarbonyloxy)succinimide (1.550 g, 6.22 mmol). The reaction was stirred at 25° C. for 16 h, then diluted with water (50 mL) and extracted with DCM (50 mL×3). The organic layers were combined, washed with brine (50 mL), dried over anhydrous $Na_2SO_4$, filtered and the filtrate was concentrated under vacuum. The resulting residue was purified by flash silica gel chromatography (ISCO; 12 g Agela Silica Flash Column, Eluent of 0-30% EtOAc/Petroleum Ether gradient @ 30 m/min) to give the product as a mixture of stereoisomers. LC-MS (ESI): m/z 383.3 $[M+Na]^+$. The mixture of stereoisomers was further purified by SFC (Column: DAICEL CHIRALCEL OJ-H 250 mm*30 mm, 5 um; Condition 0.1% $NH_3H_2O$/IPA; Begin B 15%, End B 15%; FlowRate (mL/min) 60; Injections 220) to individually give intermediate 41a-1 (the first eluting stereoisomer; LC-MS (ESI): m/z 383.3 $[M+Na]^+$) and intermediate 41a-2 (the second eluting stereoisomer; LC-MS (ESI): m/z 383.3 $[M+Na]^+$).

Step B—Synthesis of Intermediates 41b-J and 41b-2 A mixture of intermediate 41a-1 (340 mg, 0.943 mmol) and Pd/C (10 wt. %, 200 mg, 0.188 mmol) in MeOH (10 mL) was stirred at 25° C. under $H_2$ (15 psi) for 2 h. Then the reaction was filtered, and the filtrate was concentrated under vacuum to give intermediate 41b-1, which was used in the next reaction without further purification. $^1H$ NMR (400 MHz, $CD_3OD$) δ: 3.89-3.75 (m, 2H), 2.98-2.86 (m, 1H), 2.94 (s, 1H), 2.86-2.76 (m, 1H), 2.01-1.89 (m, 2H), 1.94-1.74 (m, 2H), 1.47-1.43 (br s, 2H) 1.47 (s, 9H).

Intermediate 41b-2 was prepared from intermediate 41a-2 according to the procedure in Step B of Example 55.

Example 56: Preparation of Compounds 76 and 77

(S)-2-((R)-6-(N-((1R,5S,8s)-3-azabicyclo[3.2.1]octan-8-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1R,5S,8r)-3-azabicyclo[3.2.1]octan-8-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

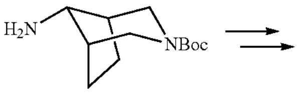

Int-41b-1

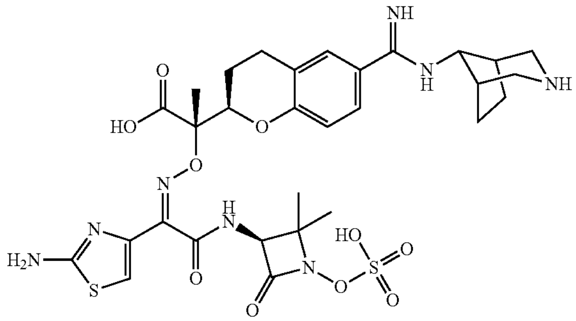

Compound 76

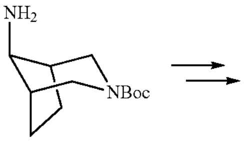

Int-41b-2

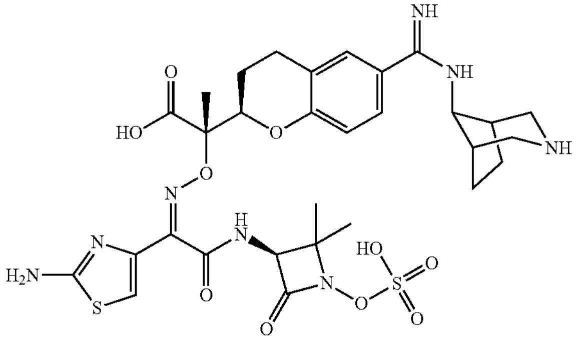

Compound 77

Compounds 76 and 77 were prepared starting from intermediate 41b-1 and intermediate 41b-2 respectively according to the procedure in Step E to Step G of Example 34.

Compound 76: LC-MS (ESI): m/z 735.3 $[M+H]^+$. $^1H$ NMR (400 MHz, $D_2O+CD_3CN$) S: 7.39-7.27 (m, 2H), 6.87 (d, J=8.2 Hz, 1H), 6.79 (s, 1H), 4.62 (s, 1H), 4.45-4.38 (m, 1H), 3.89 (s, 1H), 3.24 (s, 4H), 2.89-2.71 (m, 2H), 2.71-2.56 (m, 2H), 2.23-2.01 (m, 3H), 1.84-1.61 (m, 3H), 1.49 (s, 3H), 1.42 (s, 3H), 1.25 (s, 3H).

Compound 77: LC-MS (ESI): m/z 735.6 $[M+H]^+$. $^1H$ NMR ($DMSO-d_6+D_2O$, 400 MHz) δ: 7.56-7.46 (m, 2H), 6.93 (d, J=8.6 Hz, 1H), 6.75 (s, 1H), 4.60 (s, 1H), 4.38 (br d, J=11.3 Hz, 1H), 3.76-3.65 (m, 1H), 3.55-3.41 (m, 1H), 3.38-3.23 (m, 1H), 3.01-2.89 (m, 2H), 2.88-2.68 (m, 2H), 2.56-2.48 (m, 2H), 2.01-1.85 (m, 3H), 1.76-1.65 (m, 2H), 1.45 (s, 3H), 1.45-1.35 (m, 1H), 1.39 (s, 3H), 1.24 (s, 3H).

Example 57: Preparation of Intermediates 42g-1 and 42g-2

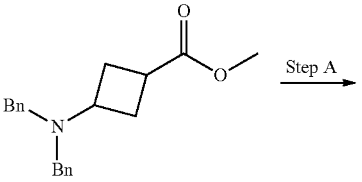

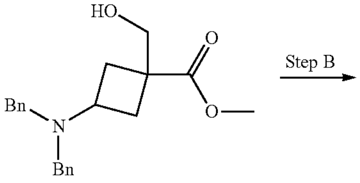

Int-42a

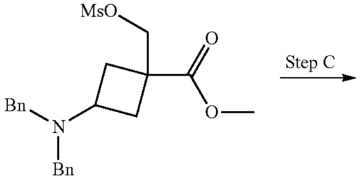

Int-42b

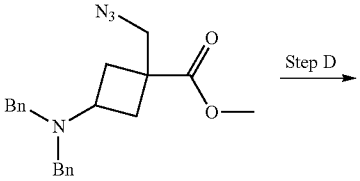

Int-42c

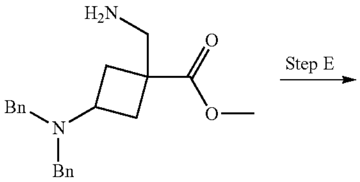

Int-42d

-continued

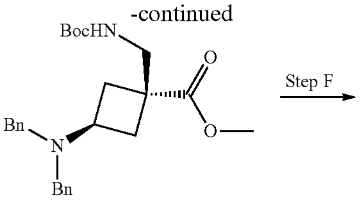

Int-42a-1

+

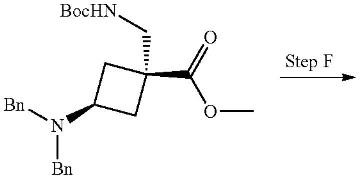

Int-42e-2

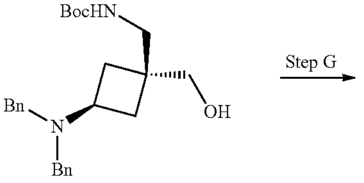

Int-42f-1

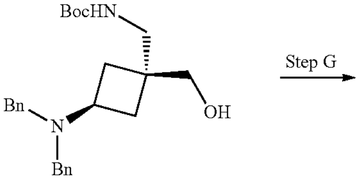

Int-42f-2

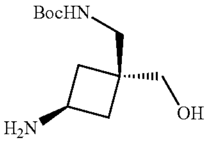

Int-42g-1

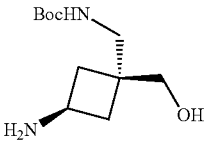

Int-42g-2

Step A—Synthesis of Intermediate 42a To a stirred solution of diisopropylamine (7.94 mL, 56.2 mmol) in THF (65 mL) at −70° C. was added n-butyllithium (24.05 ML, 60.1 mmol, 2.5 M in hexanes). The reaction was stirred at −70° C. for 30 minutes, then a solution of methyl 3-(dibenzylamino)cyclobutane-1-carboxylate (6.0 g, 19.39 mmol) in THF (10 mL) was added. The reaction mixture was stirred at −70° C. for 30 min. Then (1H-benzo[d][1,2,3]triazol-1-yl)methanol (8.26 g, 38.8 mmol) was added in portions and the reaction was stirred at −70° C. for 1 h. The reaction was then quenched with saturated aqueous $NH_4Cl$ (20 mL). The resulting mixture was stirred at 0° C. for 15 minutes, and then extracted with EtOAc (3×20 mL). The combined organic layers were washed with brine (30 mL), dried over anhydrous $Na_2SO_4$, filtered, and the filtrate was concentrated under vacuum. The resulting residue was purified by flash silica gel chromatography (Biotage; 80 g Agela Silica Flash Column, Eluent of Petroleum ether/EtOAc=23% gradient @ 45 mL/min) to give intermediate 42a. LC-MS (ESI): m/z 340.5 $[M+H]^+$.

Step B—Synthesis of Intermediate 42b To a stirred solution of intermediate 42a (5.0 g, 14.73 mmol) and TEA (4.11 mL, 29.5 mmol) in THF (130 mL) at 0° C. was added dropwise a solution of methanesulfonyl chloride (2.109 mL, 27.3 mmol) in THF (5 mL). The reaction mixture was warmed to 25° C. and stirred at 25° C. for 1.5 h, then cooled to 0° C. and quenched by the dropwise addition of saturated aqueous $NaHCO_3$ (60 mL). The resulting mixture was extracted with MTBE (60 mL×3). The organic layers were combined, dried over anhydrous $Na_2SO_4$, and filtered. The filtrate was concentrated under reduced pressure to give intermediate 42b as a mixture of cis/trans stereoisomers, which was used in the next step without further purification. $^1H$ NMR (400 MHz, $CDCl_3$) δ:=7.34-7.24 (m, 10H), 4.42-4.37 (two s, 2H), 3.76-3.72 (two s, 3H), 3.57-3.45 (two s, 4H), 3.44-3.20 (m, 1H), 3.02-2.99 (two s, 3H), 2.49-2.37 (m, 2H), 2.15-1.94 (m, 2H).

Step C—Synthesis of Intermediate 42c To a solution of intermediate 42b (6.0 g, 12.93 mmol) in DMF (60 mL) stirred at 20° C. was added sodium azide (1.360 g, 20.92 mmol) in one portion. The reaction mixture was warmed to 70° C. and stirred for 16 h. The reaction mixture was then diluted with water (400 mL) and extracted by EtOAc (150 mL×3). The combined organic layers were washed with brine (100 mL×2), dried over anhydrous $Na_2SO_4$, and filtered. The filtrate was concentrated in vacuo to provide intermediate 42c, which was used in the next step without further purification. LC-MS (ESI): m/z 365.2 $[M+H]^+$.

Step D—Synthesis of Intermediate 42d To a stirred solution of intermediate 42c (4.7 g, 12.90 mmol) in water (18 mL) and THF (90 mL) was added $Ph_3P$ (5.75 g, 21.92 mmol). The reaction was stirred at 25° C. for 16 h, then most of the solvent was removed under vacuum. The resulting residue was dried by lyophilization to give intermediate 42d, which was used in the next step without further purification. LC-MS (ESI): m/z 339.1 $[M+H]^+$.

Step E—Synthesis of Intermediates 42e-1 and 42e-2 To a solution of intermediate 42d (4.36 g, 12.88 mmol) and TEA (2.155 mL, 15.46 mmol) in DCM (75 mL) was added di-tert-butyl dicarbonate (3.09 g, 14.17 mmol). The reaction was stirred at 25° C. for 16 h. Then the solvent was removed under reduced pressure, and the resulting residue was purified by flash silica gel chromatography (Biotage; 80 g Agela Silica Flash Column, Eluent of 6% EtOAc/Petroleum ether gradient @ 60 mL/min) to afford the product as a mixture of stereoisomers. LC-MS (ESI): m/z 439.5 $[M+H]^+$. The mixture of diastereomers was further purified by SFC (Column: DAICEL CHIRALPAK AD 250 mm*50 mm, 10 um; Condition: 0.1% $NH_3H_2O$ EtOH; Begin B 30%, End B 30%; FlowRate (mL/min) 200; Injections 120) to give intermediate 42e-1 (the first eluting stereoisomer, LC-MS (ESI): m/z 439.3 $[M+H]^+$) and intermediate 42e-2 (the second eluting stereoisomer, LC-MS (ESI): m/z 439.6 $[M+H]^+$).

Step F—Synthesis of Intermediate 42f-1 To a stirred solution of intermediate 42e-1 (650 mg, 1.482 mmol) in THF (14 mL) at 0° C. was slowly added lithium aluminum hydride (170 mg, 4.48 mmol). The reaction was stirred at 25° C. for 2.0 h, then cooled to 0° C., followed by the slow sequential addition of water (0.18 mL), 15% sodium hydroxide solution (0.36 mL), and water (0.540 mL). The resulting mixture was filtered through Celite™, and the filtrate was dried over anhydrous $Na_2SO_4$, and concentrated in vacuo to give intermediate 42f-1, which was used in the next step without further purification. $^1H$ NMR (400 MHz, $CDCl_3$) δ: 7.34-7.28 (m, 8H), 7.28-7.21 (m, 2H), 4.87 (br s, 1H), 3.64-3.54 (m, 1H), 3.47 (s, 4H), 3.45 (br s, 2H), 3.19 (d, J=6.6 Hz, 2H), 3.16-3.02 (m, 1H), 1.99-1.90 (m, 2H), 1.67-1.55 (m, 2H), 1.45 (s, 9H).

Step G—Synthesis of Intermediate 42g-1 To a solution of intermediate 42f-1 (600 mg, 1.461 mmol) and acetic acid (0.251 mL, 4.38 mmol) in MeOH (10 mL) was added Pd/C (10 wt. %, 311 mg, 0.292 mmol). The reaction was stirred at 25° C. under $H_2$ atmosphere (15 psi) for 16 h, then filtered. The filtrate was concentrated in vacuo, and freeze-dried to give intermediate 42g-1, which was used without further purification. $^1H$ NMR (400 MHz, $CD_3OD$) δ: 3.76-3.61 (m, 1H), 3.49 (s, 2H), 3.13 (s, 2H), 2.26-2.17 (m, 2H), 1.96-1.86 (m, 2H), 1.42 (s, 9H).

Intermediate 42g-2 was prepared from intermediate 42e-2 according to the procedure described in Step F and Step G of Example 57. $^1H$ NMR (400 MHz, $CD_3OD$) δ: 3.78-3.61 (m, 1H), 3.42 (s, 2H), 3.18 (s, 2H), 2.31-2.19 (m, 2H), 2.03-1.84 (m, 2H), 1.44 (s, 9H).

Example 58: Preparation of Compound 78

(S)-2-((R)-6-(N-((1r,3R)-3-(aminomethyl)-3-(hydroxymethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

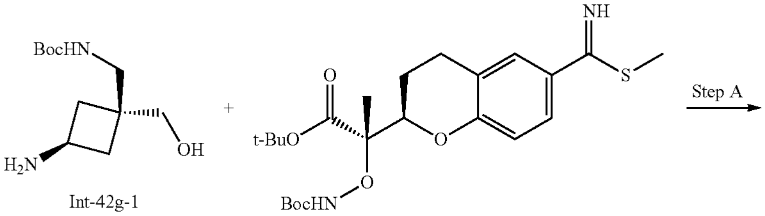

Int-42g-1

Int-3c

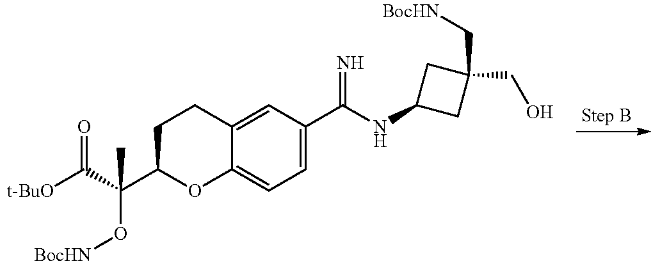

Int-43a

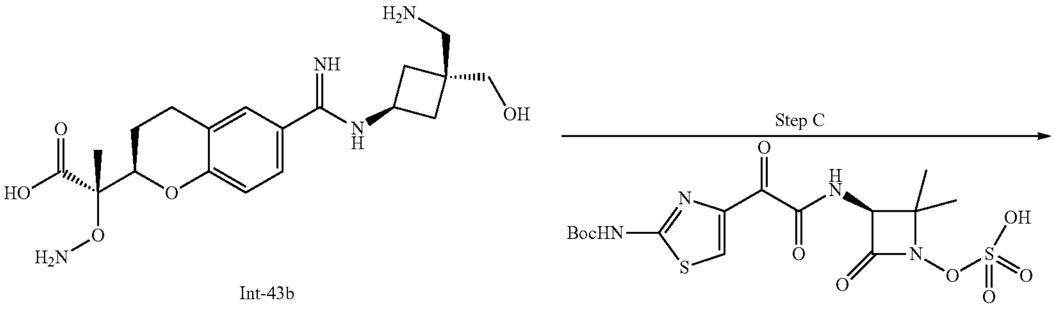

Int-43b

Int-4

-continued

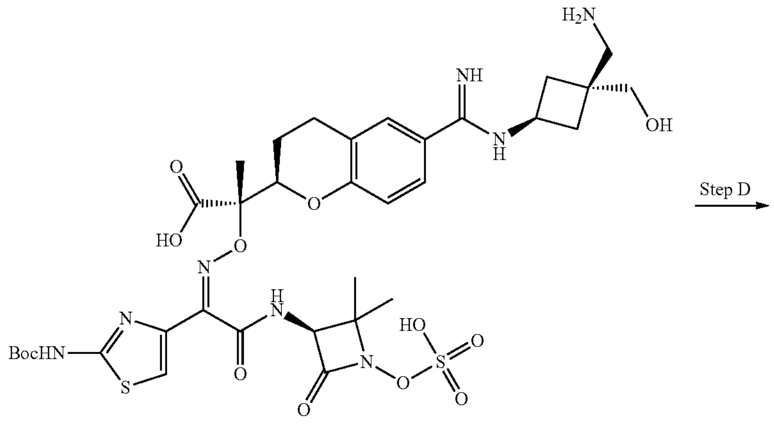

Int-43c

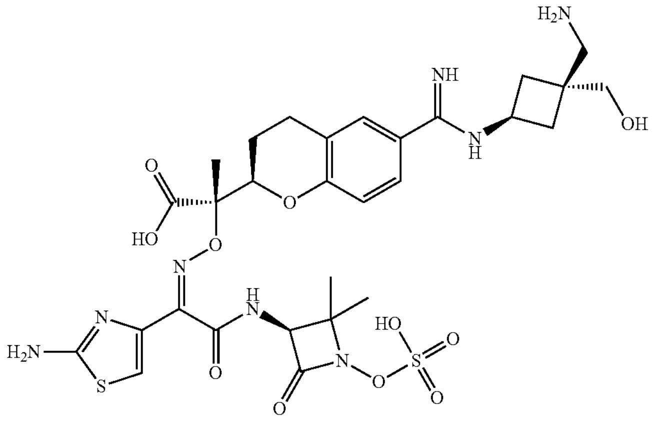

Compound 78

Step A—Synthesis of Intermediate 43a To a mixture of intermediate 42g-1 (180 mg, 0.664 mmol) and intermediate 3c (355 mg, 0.598 mmol) in MeCN (8 mL) stirred at room temperature, was added acetic acid (0.152 mL, 2.66 mmol). The reaction was stirred at 80° C. for 20 minutes, and then concentrated in vacuo. The resulting residue was purified by a reverse phase HPLC (Biotage; 20 g Agela, C18, 20~35 μm, Eluent of 50% MeCN/$H_2O$ (0.5% TFA) gradient @ 50 mL/min) to give intermediate 43a. LC-MS (ESI): m/z 649.4 $[M+H]^+$.

Step B—Synthesis of Intermediate 43b A solution of tert-butyl intermediate 43a (300 mg, 0.462 mmol) in TFA (7 mL) was stirred at 40° C. for 1.5 h. Then the reaction mixture was concentrated in vacuo to give intermediate 43b, which was used in the next reaction without further purification. LC-MS (ESI): m/z 393.1 $[M+H]^+$.

Step C—Synthesis of Intermediate 43c A solution of intermediate 43b (180 mg, 0.459 mmol) and intermediate 4 (213 mg, 0.459 mmol) in MeOH (10 mL) was stirred at 25° C. for 16 h. Then the reaction mixture was concentrated in vacuo to give intermediate 43c, which was used in the next reaction without further purification. LC-MS (ESI): m/z 839.4 $[M+H]^+$.

Step D—Synthesis of Compound 78 A solution of intermediate 43c (180 mg, 0.215 mmol) in 1:1 DCM/TFA (2 mL) was stirred at 25° C. for 50 min. Then the reaction mixture was concentrated in vacuo, and the resulting residue was purified by prep. HPLC (Boston Uni C18, 40*150*5 um; Condition: water (0.1% TFA)-ACN; Begin B 0, End B 30; Gradient Time (min) 10; 100% B Hold Time (min) 2; FlowRate (m/min) 60; Injections 3) to give the product as the TFA salt. The TFA salt was further purified by preparative HPLC (Welch Xtimate C18, 150*25 mm*5 um; Condition: water (0.225% FA)-ACN; Begin B 0, End B 19; Gradient Time (min) 15; 100% B Hold Time (min) 2; Flow Rate (mL/min) 25; Injections 2) to give compound 78 as the formic acid salt. LC-MS (ESI): m/z 739.2 $[M+H]^+$. $^1H$ NMR (400 MHz, $D_2O+CD_3CN$) δ: 7.44-7.37 (m, 2H), 6.90 (d, J=8.6 Hz, 1H), 6.78 (s, 1H), 4.60 (s, 1H), 4.38 (br d, J=10.6 Hz, 1H), 4.21-4.12 (m, 1H), 3.67 (s, 2H), 3.10 (s, 2H), 2.89-2.68 (m, 2H), 2.49-2.39 (m, 2H), 2.12-2.01 (m, 3H), 1.85-1.62 (m, 1H), 1.49 (s, 3H), 1.43 (s, 3H), 1.25 (s, 3H).

Example 59: Preparation of Compound 79

(S)-2-((R)-6-(N-((1s,3S)-3-(aminomethyl)-3-(hydroxymethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

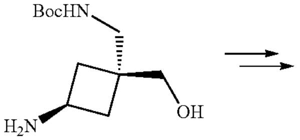

Int-42g-2

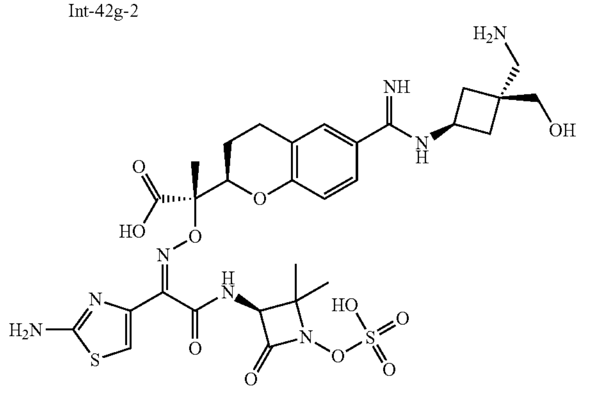

Compound 79

Compound 79 was prepared starting from the corresponding intermediate 42g-2 according to the procedure illustrated in Step A to Step C of Example 32. LC-MS (ESI): m/z 739.3 $[M+H]^+$. $^1H$ NMR (400 MHz, $D_2O+CD_3CN$) δ: 7.46-7.32 (m, 2H), 6.90 (d, J=8.6 Hz, 1H), 6.79 (s, 1H), 4.60 (s, 1H), 4.40 (br d, J=10.6 Hz, 1H), 4.35-4.22 (m, 1H), 3.62 (s, 2H), 3.18 (s, 2H), 2.89-2.68 (m, 2H), 2.47-2.39 (m, 2H), 2.12-2.01 (m, 3H), 1.85-1.62 (m, 1H), 1.51 (s, 3H), 1.43 (s, 3H), 1.25 (s, 3H).

Example 60: Preparation of Compounds 80 and 81

(S)-2-((R)-6-(N-((1 s,3S)-3-(aminomethyl)-3-hydroxycyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,3R)-3-(aminomethyl)-3-hydroxycyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

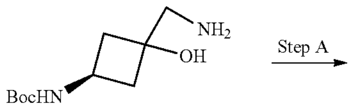

Step A

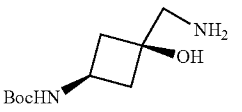

Int-44a-1

+

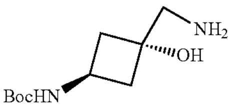

Int-44a-2

Step B

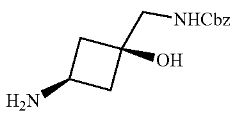

Int-44b-1

Step C

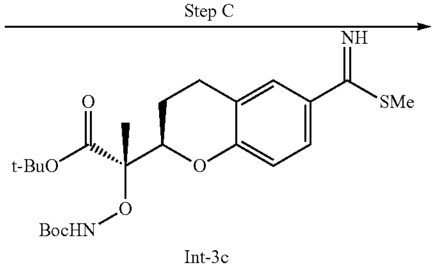

Int-3c

-continued
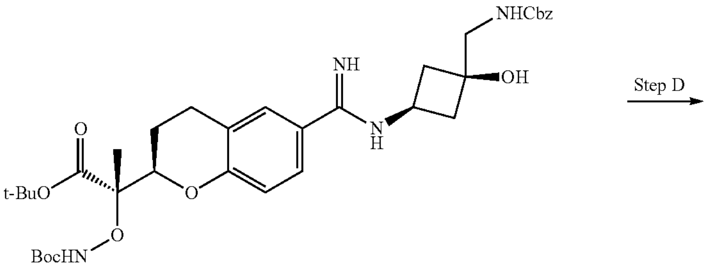
Int-44c-1
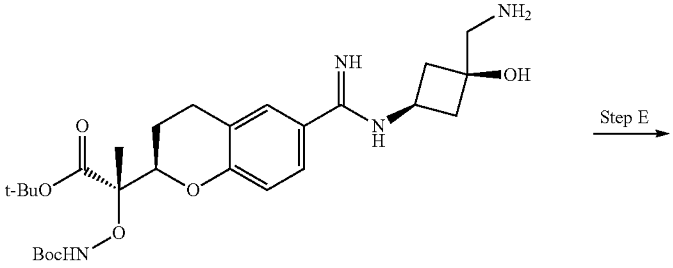
Int-44d-1
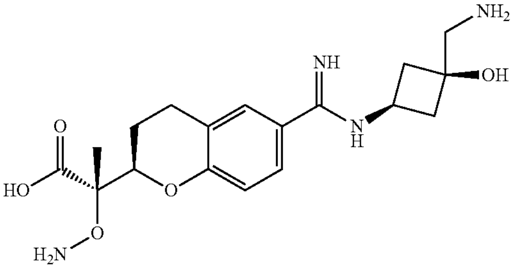
Int-44e-1
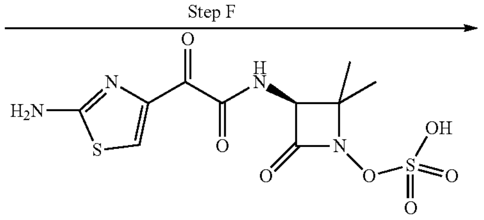
Int-5
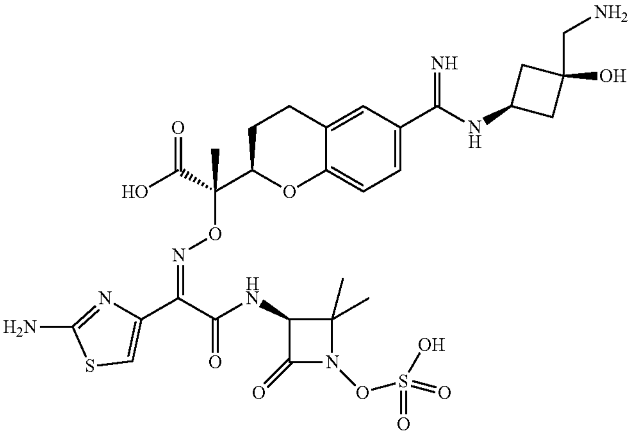
Compound 80

-continued

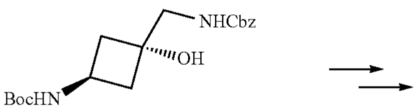

Int-44a-2

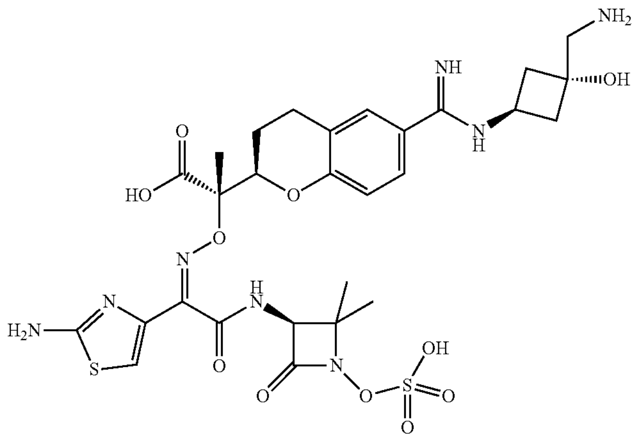

Compound 81

Step A—Synthesis of Intermediates 44a-1 and 44a-2 To a mixture of tert-butyl (3-(amino-methyl)-3-hydroxycyclobutyl)carbamate (3.36 g, 15.54 mmol) and sodium carbonate (4.12 g, 38.8 mmol) in THF (40 mL) and water (20 mL) stirred at 0° C. was added dropwise benzyl chloroformate (3.71 g, 21.75 mmol). The reaction mixture was stirred at 25° C. for 16 h, then the solvent was removed under reduced pressure. The resulting residue was purified by flash silica gel chromatography (Biotage; 120 g Agela Silica Flash Column, Eluent of 8% EtOAc/Petroleum ether gradient @ 60 mL/min) to give crude product as a cis/trans mixture. The cis/trans mixture was further purified by SFC (Column: DAICEL CHIRALCEL OJ, 250 mm*50 mm*10 um; Condition: 0.1% $NH_3$—$H_2O$/EtOH; Begin B 25%, End B 25%; FlowRate (mL/min) 200; Injections 120) to afford intermediate 44a-1 (the later eluting compound) and intermediate 44a-2 (the earlier eluting compound).

Intermediate 44a-1: $^1$H NMR ($CD_3OD$, 400 MHz) δ: 7.48-7.27 (m, 5H), 5.11 (s, 2H), 3.70-3.52 (m, 1H), 3.23 (s, 2H), 2.61-2.40 (m, 2H), 1.90-1.81 (m, 2H), 1.43 (s, 9H).

Intermediate 44a-2: $^1$HNMR ($CD_3OD$, 400 MHz) δ: 7.56-7.27 (m, 5H), 5.08 (s, 2H), 4.28-4.06 (m, 1H) 3.23 (s, 2H), 2.48-2.26 (m, 2H), 2.12-2.04 (m, 2H), 1.40 (s, 9H).

Step B—Synthesis of Intermediate 44b-1 A solution of intermediate 44a-1 (400 mg, 1.142 mmol) in HCl/EtOAc (8 mL, 4 M) was stirred at 25° C. for 0.5 h. Then the reaction mixture was concentrated under vacuum to give intermediate 44b-1, which was used in the next reaction without further purification. LC-MS (ESI): m/z 251.1 $[M+H]^+$.

Step C—Synthesis of Intermediate 44c-1 To a stirred solution of intermediate 3c (380 mg, 0.814 mmol) and intermediate 44b-1 (285 mg, 0.814 mmol) in MeCN (8 mL) was added sequentially acetic acid (0.140 mL, 2.443 mmol) and potassium acetate (240 mg, 2.443 mmol) at 25° C. The reaction mixture was stirred at 80° C. for 30 minutes, then diluted with water (30 mL), and extracted with EtOAc (50 mL×3). The organic layers were combined, dried over anhydrous $Na_2SO_4$, filtered and concentrated under reduced pressure. The resulting residue was purified by flash silica gel chromatography (ISCO; 20 g Agela Silica Flash Column, Eluent of 5% DCM/MeOH gradient @ 30 mL/min) to afford intermediate 44c-1. LC-MS (ESI): m/z 669.3 $[M+H]^+$.

Step D—Synthesis of Intermediate 44d-1 A mixture of intermediate 44c-1 (366 mg, 0.547 mmol) and Pd/C (349 mg, 0.328 mmol, 10 wt. %) in EtOAc (8 mL) was stirred under $H_2$ (15 psi) at 25° C. for 3 h. Then the reaction mixture was filtered, and the filtrate was concentrated to give intermediate 44d-1, which was used in the next reaction without further purification. LC-MS (ESI): m/z 535.8 $[M+H]^+$.

Step E—Synthesis of Intermediate 44e-1 A solution of intermediate 44d-1 (250 mg, 0.468 mmol) in TFA (5 mL) was stirred at 40° C. for 1 h. The reaction mixture was filtered, and concentrated to give intermediate 44e-1, which was used in the next reaction without further purification. LC-MS (ESI): m/z 379.1 $[M+H]^+$.

Step F—Synthesis of Compounds 80 and 81 To a stirred solution of intermediate 44e-1 (177 mg, 0.468 mmol) in MeOH (5 mL) was added intermediate 5 (189 mg, 0.468 mmol) at 0° C. The reaction mixture was stirred at 25° C. for 12 h. Then the solvent was removed by purging with nitrogen gas flow, and the resulting residue was purified by preparative HPLC (Column: Boston Uni C18 40*150*5 um; Condition: water (0.1% TFA)-ACN; Begin B 0, End B 30; Gradient Time (min) 10; 100% B Hold Time (min) 2; Flow Rate (mL/min) 60; Injections 3) to afford compound 80 as the TFA salt. The TFA salt was further purified by preparative HPLC (Column: Welch Xtimate C18 150*25 mm*5 um; Condition: water (0.225% FA)-ACN; Begin B 0, End B 18; Gradient Time (min) 15; 100% B Hold Time (min) 2; FlowRate (mL/min) 25; Injections 3) to give compound 80 as the formic acid salt. LC-MS (ESI): m/z 725.3 $[M+H]^+$. $^1$H NMR (400 MHz, $D_2O+CD_3CN$): δ: 7.42-7.35 (m, 2H), 6.88 (d, J=8.6 Hz, 1H), 6.79 (s, 1H), 4.61 (s, 1H), 4.38 (br d, J=11.3 Hz, 1H), 3.83-3.73 (m, 1H), 3.07 (s, 2H), 2.84-2.69 (m, 4H), 2.35-2.24 (m, 2H), 2.09-2.01 (m, 1H), 1.84-1.64 (m, 1H), 1.49 (s, 3H), 1.42 (s, 3H), 1.25 (s, 3H).

Compound 81 was prepared from intermediate 44a-2 according to the procedure in Step B to Step F of Example 60. LC-MS (ESI): m/z 725.3 $[M+H]^+$. $^1$H NMR (400 MHz, $D_2O+CD_3CN$) δ: 7.43-7.35 (m, 2H), 6.88 (d, J=8.6 Hz, 1H), 6.80 (s, 1H), 4.60 (s, 1H), 4.45-4.32 (m, 1H), 4.32-4.26 (m, 1H), 3.08 (s, 2H), 2.92-2.76 (m, 2H), 2.59 (br dd, J=8.0, 13.9 Hz, 2H), 2.35 (br dd, J=6.7, 14.1 Hz, 2H), 2.09-2.01 (m, 1H), 1.75-1.64 (m, 1H), 1.49 (s, 3H), 1.42 (s, 3H), 1.24 (s, 3H).

Example 61: Preparation of Compounds 82 and 83

(S)-2-((R)-6-(N-((1r,3R)-3-(aminomethyl)-3-methoxycyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1s,3S)-3-(aminomethyl)-3-methoxycyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

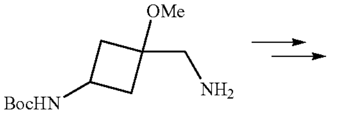

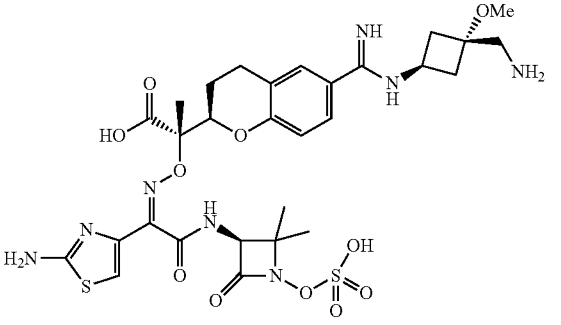

Compound 82

+

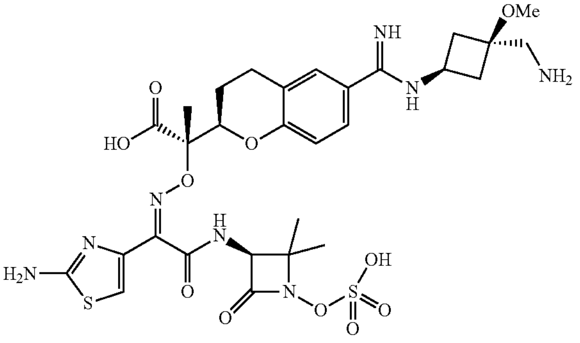

Compound 83

Compounds 82 and 83 were prepared starting from commercially available tert-butyl (3-(aminomethyl)-3-methoxycyclobutyl)carbamate according to the procedure in Step A to Step F of Example 60.

Compound 82: LC-MS (ESI): m/z 739.2 $[M+H]^+$. $^1H$ NMR (400 MHz, $D_2O+CD_3CN$) δ: 7.46-7.32 (m, 2H), 6.88 (d, J=9.2 Hz, 1H), 6.79 (s, 1H), 4.60 (s, 1H), 4.43-4.29 (m, 1H), 4.25-4.19 (m, 1H), 3.20 (s, 5H), 2.89-2.63 (m, 4H), 2.23 (br dd, J=6.7, 13.4 Hz, 2H), 2.09-2.01 (m, 1H), 1.74-1.61 (m, 1H), 1.48 (s, 3H), 1.42 (s, 3H), 1.24 (s, 3H).

Compound 83: LC-MS (ESI): m/z 739.3 $[M+H]^+$. $^1H$ NMR (400 MHz, $D_2O+CD_3CN$) δ: 7.43-7.33 (m, 2H), 6.89 (d, J=8.6 Hz, 1H), 6.79 (s, 1H), 4.61 (s, 1H), 4.45-4.33 (m, 1H), 3.93-3.80 (m, 1H), 3.18 (s, 2H), 3.16 (s, 3H), 2.91-2.72 (m, 2H), 2.60 (br dd, J=7.6, 13.1 Hz, 2H), 2.48-2.34 (m, 2H), 2.09-2.01 (m, 1H), 1.74-1.58 (m, 1H), 1.49 (s, 3H), 1.42 (s, 3H), 1.25 (s, 3H).

Example 62: Preparation of Intermediates 45b-1 and 45b-2

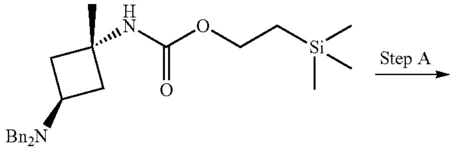

Int-39d-1

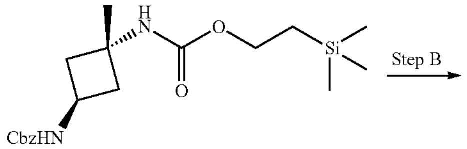

Int-45a-1

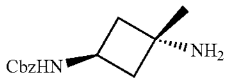

Int-45b-1

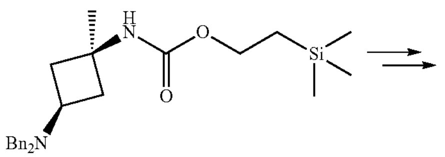

Int-39d-2

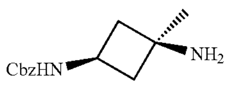

Int-45b-2

Step A—Synthesis of Intermediate 45a-1 To a solution of intermediate 39d-1 (900 mg, 2.119 mmol) in MeOH (10 mL) was added palladium hydroxide (744 mg, 1.060 mmol, 20 wt. %). The reaction was stirred at 20° C. under $H_2$ atmosphere (45 psi) for 20 h. Then the reaction mixture was filtered, and the filtrate was concentrated undervacuum. The resulting residue was dissolved in 2:1 THF/water (10 mL), and $Na_2CO_3$ (0.650 g, 6.14 mmol) was added, followed by Cbz-Cl (0.6 mL, 4.20 mmol). The reaction was stirred at room temperature 16-22° C. for 16 h, then diluted with water (20 mL), extracted with EtOAc (10 mL×3), washed with brine, and dried over anhydrous $Na_2SO_4$, and filtered. The filtrate was concentrated and the resulting residue was purified by silica gel chromatography (Biotage; 4 g Agela Silica Flash Column, Eluent of 50% EtOAc/Petroleum ether gradient @ 40 mL/min) to afford crude intermediate 45a-1. LC-MS (ESI): m/z 757.6 $[2M+H]^+$.

Step B—Synthesis of Intermediates 45b-1 and 45b-2 A solution of intermediate 45a-1 (0.5 g, 1.321 mmol) in 5:1 TFA/DCM (3 mL) was stirred at 25° C. for 0.5 h. Then the reaction solvent was removed with nitrogen gas flow to afford intermediate 45b-1, which was used in the next reaction without further purification. LC-MS (ESI): m/z 235.1 $[M+H]^+$.

Intermediate 45b-2 was prepared from intermediate 39d-2 according to the procedure used in Example 62. LC-MS (ESI): m/z 235.1 $[M+H]^+$.

Example 63: Preparation of Compounds 84 and 85

(S)-2-((R)-6-(N-((1r,3R)-3-amino-1-methylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1s,3S)-3-amino-1-methylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

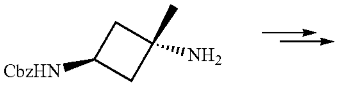

Int-45b-1

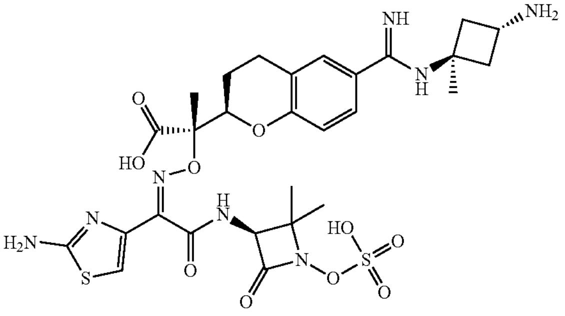

Compound 84

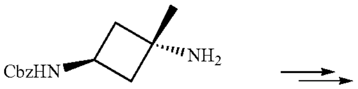

Int-45b-2

-continued

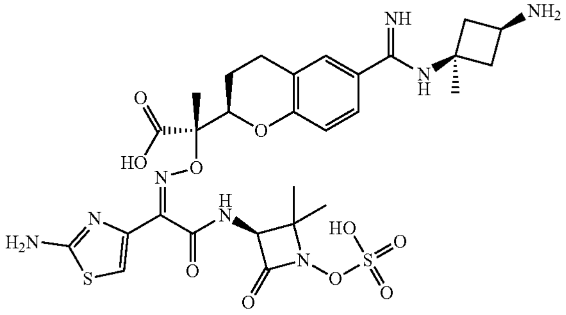

Compound 85

Compounds 84 and 85 were prepared starting from the corresponding intermediate 45b-1 and intermediate 45b-2 according to the procedure in Step A to Step E of Example 48.

Compound 84: LC-MS (ESI): m/z 709.5 $[M+H]^+$. $^1H$ NMR (400 MHz, $D_2O$) δ: 7.47-7.33 (m, 2H), 6.95-6.86 (m, 2H), 4.66 (s, 1H), 4.46 (br d, J=9.4 Hz, 1H), 4.01-3.91 (m, 1H), 3.01-2.88 (m, 2H), 2.88-2.72 (m, 2H), 2.41 (br t, J=11.2 Hz, 2H), 2.16-2.04 (m, 1H), 1.89-1.75 (m, 1H), 1.56 (s, 3H), 1.55 (s, 3H), 1.44 (s, 3H), 1.23 (s, 3H).

Compound 85: LC-MS (ESI): m/z 709.3 $[M+H]^+$. $^1H$ NMR (400 MHz, $D_2O+CD_3CN$) S: 7.43-7.35 (m, 2H), 6.88 (d, J=8.6 Hz, 1H), 6.79 (s, 1H), 4.59 (s, 1H), 4.38 (br d, J=11.0 Hz, 1H), 3.82-3.68 (m, 1H), 2.88-2.67 (m, 4H), 2.57-2.47 (m, 2H), 2.12-2.01 (m, 1H), 1.77-1.61 (m, 1H), 1.49 (s, 6H), 1.42 (s, 3H), 1.25 (s, 3H).

Example 64: Preparation of Intermediates 46c-1 and 46c-2

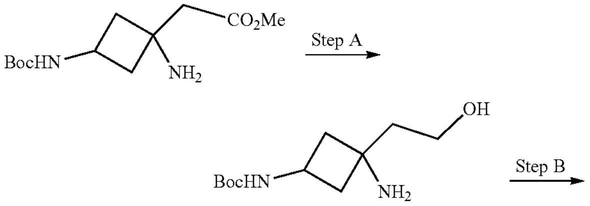

Int-46a

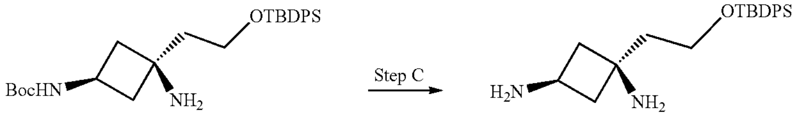

Int-46b-1 Int-46c-1

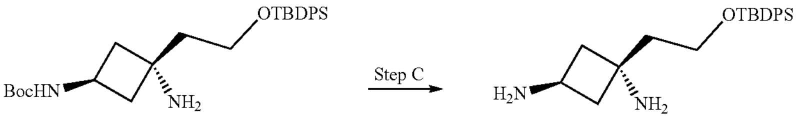

Int-46b-2 Int-46c-2

Step A— Synthesis of Intermediate 46a To a stirred solution of methyl 2-(1-amino-3-((tert-butoxycarbonyl) amino)cyclobutyl)acetate (1.2 g, 4.65 mmol) in THF (30 mL) at 0° C. was added $LiAlH_4$ (0.4 g, 10.54 mmol). The reaction was stirred at 0° C. for 1.5 h, followed by the sequential addition of water (0.4 mL), 10% NaOH (0.8 mL) and water (1.2 mL). The resulting mixture was filtered, and the filter cake was rinsed with 10:1 DCM/MeOH. The combined filtrate was concentrated under vacuum to afford intermediate 46a, which was used in the next reaction without further purification. $^1$H NMR (400 MHz, $CD_3OD$) δ: 3.76-3.65 (m, 3H), 2.52-2.40 (m, 1H), 2.28-2.14 (m, 1H), 2.01-1.93 (m, 1H), 1.84-1.71 (m, 3H), 1.42 (s, 9H).

Step B—Synthesis of Intermediates 46b-1 and 46b-2 To a solution of intermediate 46a (1.0 g, 4.34 mmol) in MeCN (40 mL) stirred at 0° C. was added 1H-imidazole (0.887 g, 13.03 mmol), followed by tert-butyl (3-amino-3-(2-hydroxyethyl)cyclobutyl)carbamate (1 g, 4.34 mmol). The reaction mixture was stirred at 25° C. for 16 h, then the solvent was removed under vacuum. The resulting residue was purified by silica gel chromatography (Biotage; 25 g Agela Silica Flash Column; Eluent of 100% EtOAc gradient; @ 40 mL/min) to afford the d product as a cis/trans mixture. LC-MS (ESI): m/z 469.1 $[M+H]^+$. The cis/trans mixture was separated by SFC (Phenomenex-Cellulose-2 (250 mm*50 mm, 10 um); Condition: 0.1% $NH_3 \cdot H_2O$/EtOH; Begin B 25%, End B 25%; Flow Rate (mL/min) 200; Injections 120) to afford intermediate 46b-1 (the first eluting isomer) and intermediate 46b-2 (the second eluting isomer).

Intermediate 46b-1: $^1$H NMR (400 MHz, $CD_3OD$) δ: 7.75-7.65 (m, 4H), 7.49-7.35 (m, 6H), 3.85 (br. t, J=6.2 Hz, 2H), 3.74-3.60 (m, 1H), 2.49-2.37 (m, 2H), 1.89-1.74 (m, 4H), 1.43 (s, 9H), 1.04 (s, 9H).

Intermediate 46b-2: $^1$H NMR (400 MHz, $CD_3OD$) δ: 7.74-7.61 (m, 4H), 7.51-7.34 (m, 6H), 4.26-4.09 (m, 1H), 3.82 (t, J=7.60 Hz, 2H), 2.30-2.19 (m, 2H), 2.05-1.92 (m, 2H), 1.84 (t, J=7.60 Hz, 2H), 1.42 (s, 9H), 1.04 (s, 9H).

Step C—Synthesis of Intermediates 46c-1 and 46c-2 A solution of intermediate 46b-1 (450 mg, 0.960 mmol) in a mixed solvent of 5:1 DCM:TFA (8 mL) was stirred at 0° C. for 30 min. Then TFA (1 mL) was added, and the reaction was stirred at 0° C. for another 0.5 h. The reaction mixture was dried with a nitrogen gas flow to afford intermediate 46c-1, which was used in the next reaction without further purification. LC-MS (ESI): m/z 369.1 $[M+H]^+$.

Intermediate 46c-2 was prepared starting from intermediate 46b-2 according to the procedure in Step C of Example 64. LC-MS (ESI): m/z 369.1 $[M+H]^+$.

Example 65: Preparation of Compounds 86 and 87

(S)-2-((R)-6-(N-((1s,3S)-3-amino-3-(2-hydroxyethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,3R)-3-amino-3-(2-hydroxyethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

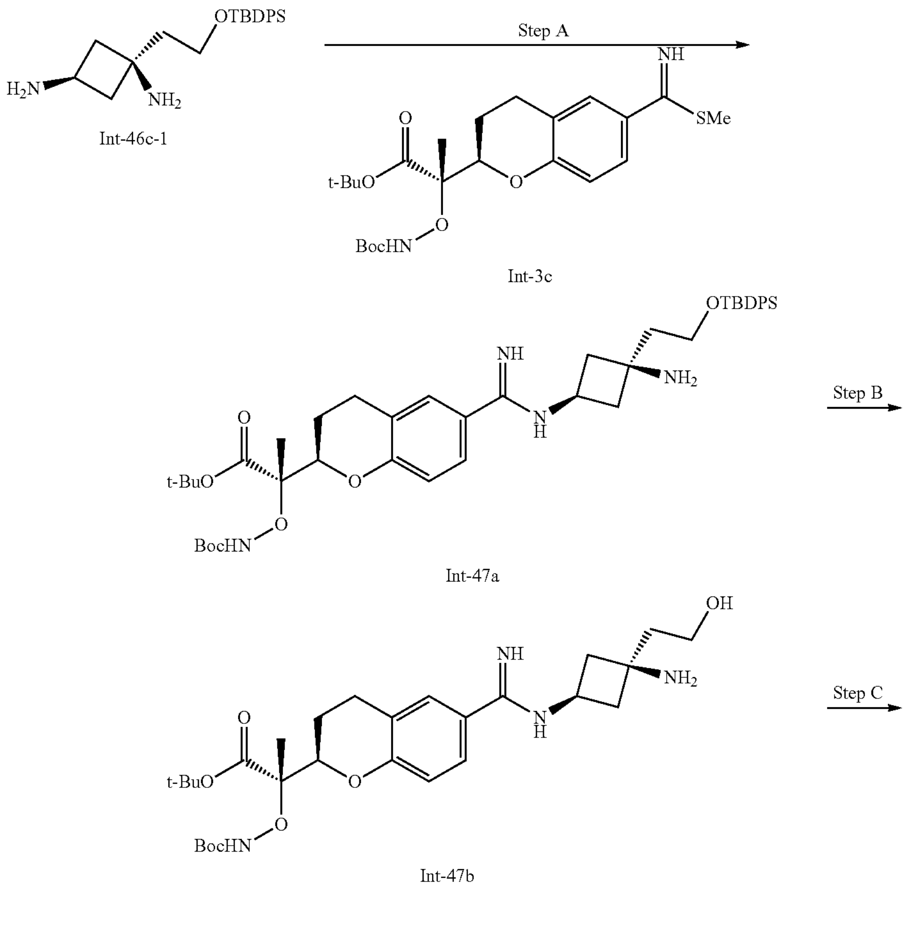

Int-46c-1

Int-3c

Int-47a

Int-47b

-continued

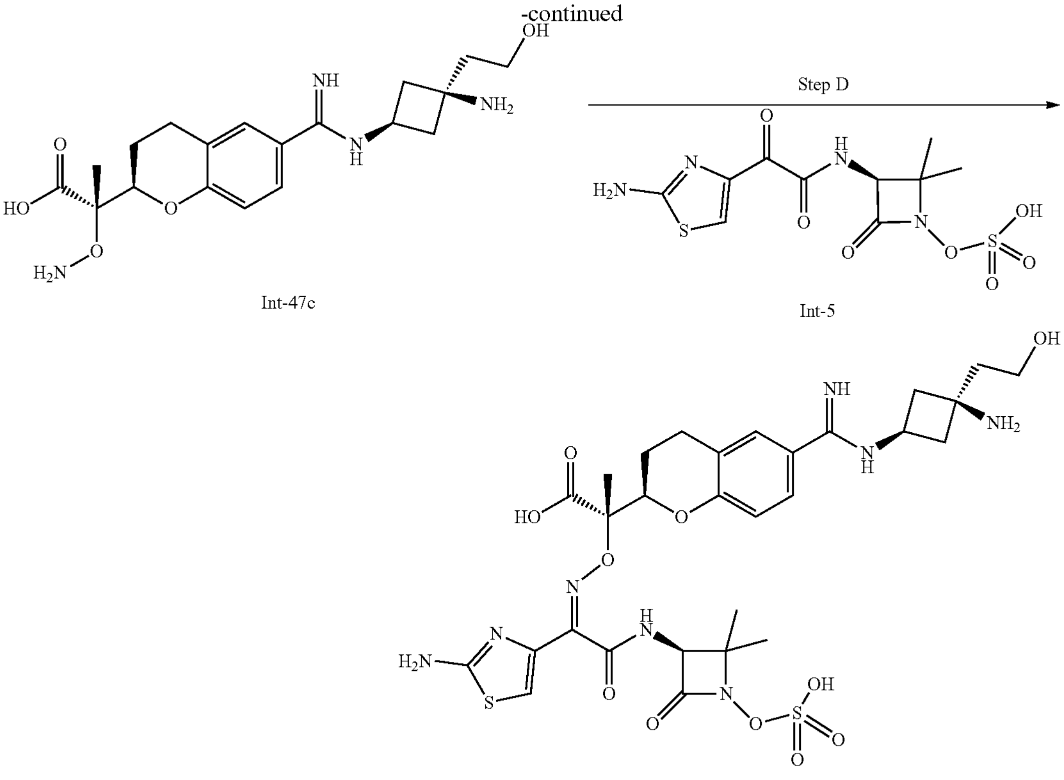

Int-47c

Int-5

Compound 86

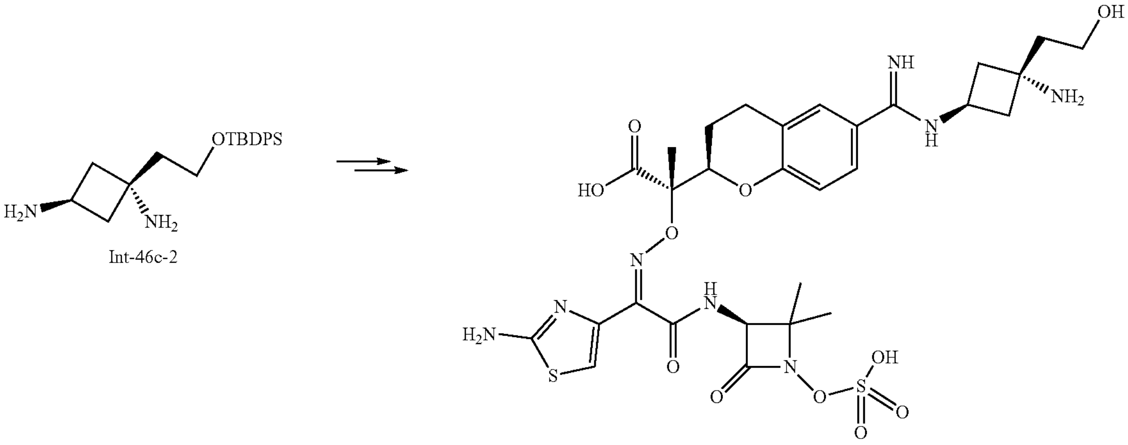

Int-46c-2

Compound 87

Step A—Synthesis of intermediate 47a To a solution of intermediate 46c-1 (354 mg, 0.960 mmol) in MeCN (5 mL) was added potassium acetate (200 mg, 2.038 mmol). After stirring at 25° C. for 5 min, acetic acid (206 mg, 3.43 mmol) was added and the reaction was stirred at 25° C. for 5 min, followed by the addition of intermediate 3c (400 mg, 0.857 mmol). The reaction was stirred at 80° C. for 1.5 h. Then the solvent was removed under vacuum to afford intermediate 47a, which was used in the next reaction without further purification. LC-MS (ESI): m/z 787.1 $[M+H]^+$.

Step B—Synthesis of intermediate 47b To a stirred solution of intermediate 47a (650 mg, 0.826 mmol) in THF (10 mL) at 0 CC was added TBAF (2 mL, 2.000 mmol, 1 N in THF). The reaction was stirred at 0° C. for 0.5 h. Then the reaction solvent was removed under vacuum while keeping the bath temperature below 30° C. to afford intermediate 47b, which was used in the next reaction without further purification. LC-MS (ESI): m/z 549.1 $[M+H]^+$.

Step C—Synthesis of intermediate 47c A solution of intermediate 47b (400 mg, 0.729 mmol) in TFA (5 mL) was stirred at 50° C. for 0.5 h. Then the reaction solution was dried with a nitrogen gas flow, and the resulting residue was purified by a reverse phase HPLC (Column: Boston Uni C18 40*150*5 um; Condition: water (0.1% TFA)-ACN; Begin B 1, End B 30; Gradient Time (min) 10; 100% B Hold Time (min) 2; Flow Rate (mL/min) 60; Injections 1) to afford intermediate 47c. LC-MS (ESI): m/z 393.1 $[M+H]^+$.

Step D—Synthesis of Compound 86 A solution of intermediate 47c (100 mg, 0.255 mmol) and intermediate 5 (93 mg, 0.255 mmol) in DMA (2 mL) was stirred at 30° C. for 16 h. Then the reaction mixture was purified by a reverse phase HPLC (Column: Boston Uni C18 40*150*5 um; Condition: water (0.1% TFA)-ACN; Begin B 0, End B 30; Gradient Time (min) 10; 100% B Hold Time (min) 2; FlowRate (mL/min) 60; Injections 1) to afford compound 86 as the TFA salt. The TFA salt was further purified by a reverse phase HPLC (Column: Welch Xtimate C18 150*25 mm*5 um; Condition: water (0.225% FA)-ACN; Begin B 0, End B 18; Gradient Time (min) 15; 100% B Hold Time (min) 2; Flow Rate (mL/min) 25; Injections 2) to afford compound 86 as the formic acid salt. LC-MS (ESI): m/z 739.3 $[M+H]^+$. $^1H$ NMR (400 MHz, $DMSO-d_6+D_2O$) δ: 7.48-7.31 (m, 2H), 6.85 (d, J=8.6 Hz, 1H), 6.74 (s, 1H), 4.56 (s, 1H), 4.35 (br d, J=12.1 Hz, 1H), 4.10-3.95 (m, 1H), 3.64 (br t, J=5.7 Hz, 2H), 2.78-2.63 (m, 4H), 2.47-2.31 (m, 2H), 2.02-1.92 (m, 1H), 1.88 (br t, J=5.7 Hz, 2H), 1.54-1.40 (m, 1H), 1.42 (s, 3H), 1.36 (s, 3H), 1.21 (s, 3H).

Compound 87 was prepared from intermediate 46c-2 according to the procedure in Step A to Step D of Example 66. LC-MS (ESI): m/z 739.2 $[M+H]^+$. H NMR (400 MHz, $DMSO-d_6+D_2O$) δ: 7.41-7.25 (m, 2H), 6.86 (d, J=8.6 Hz, 1H), 6.73 (s, 1H), 4.54 (s, 1H), 4.35 (br d, J=12.1 Hz, 1H), 4.31-4.16 (m, 1H), 3.59 (t, J=6.0 Hz, 2H), 2.86-2.64 (m, 4H), 2.45-2.30 (m, 2H), 2.16-2.03 (m, 1H), 1.89 (t, J=6.0 Hz, 2H), 1.66-1.51 (m, 1H), 1.49 (s, 3H), 1.36 (s, 3H), 1.21 (s, 3H).

Example 66: Preparation of Compounds 88 and 89

(S)-2-((R)-6-(N-((1r,3R)-3-amino-3-(hydroxymethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1s,3S)-3-amino-3-(hydroxymethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

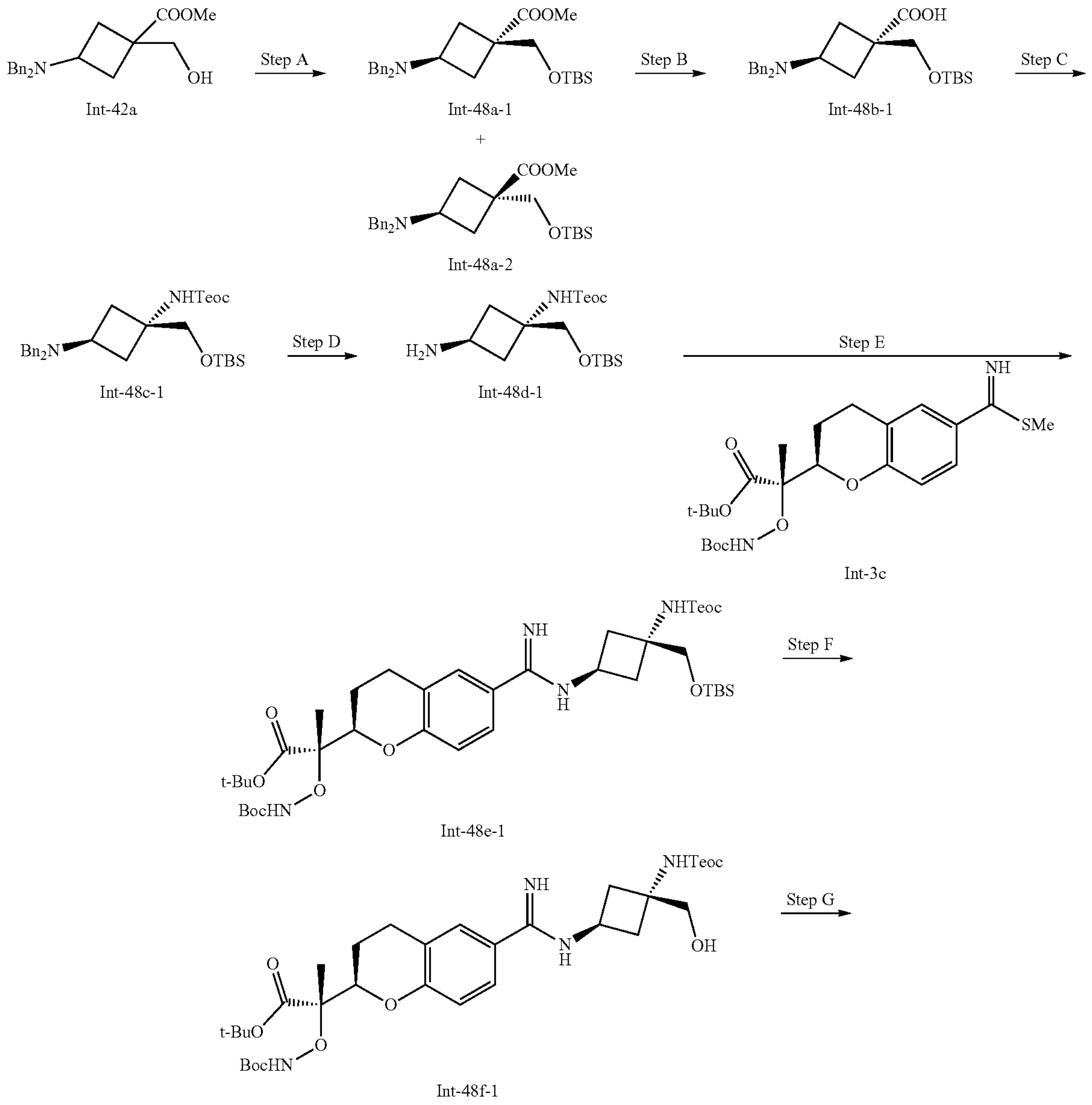

Int-42a

Int-48a-1

+

Int-48a-2

Int-48b-1

Int-48c-1

Int-48d-1

Int-3c

Int-48e-1

Int-48f-1

-continued

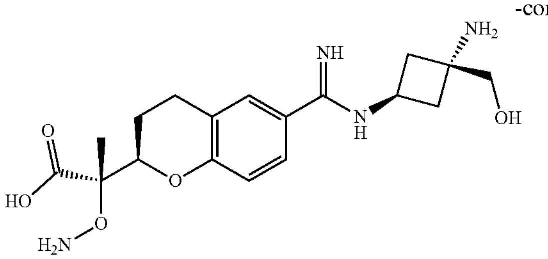

Int-48g-1

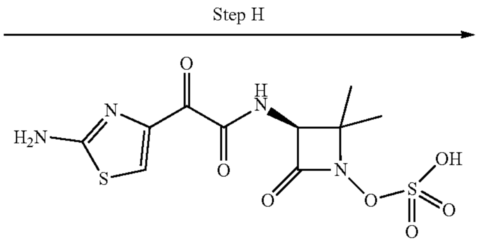

Int-5

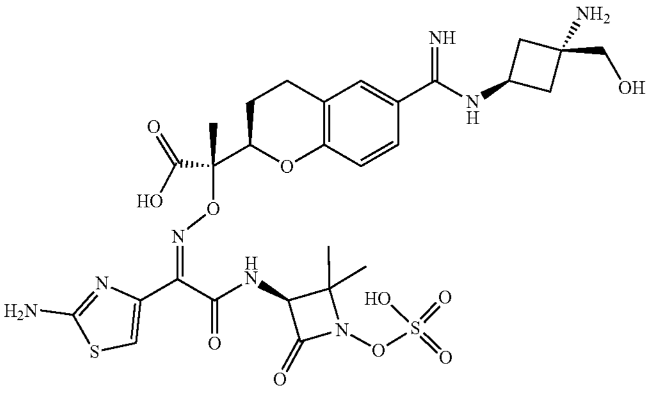

Compound 88

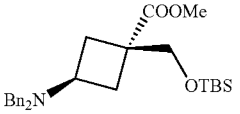

Int-48a-2

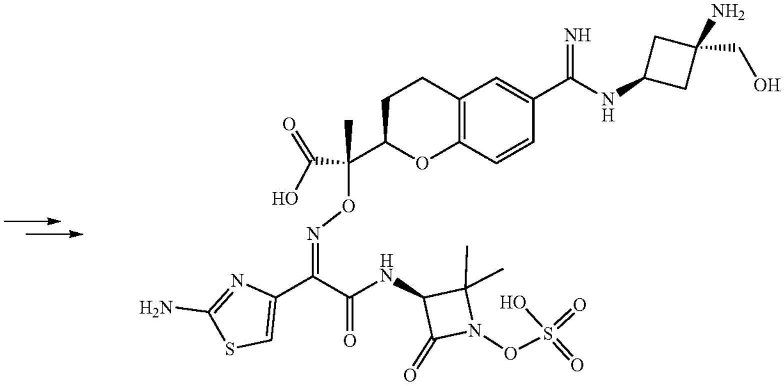

Compound 89

Step A—Synthesis of Intermediates 48a-1 and 48a-2 To a solution of intermediate 42a (1.62 g, 4.77 mmol) and 1H-imidazole (0.877 g, 12.89 mmol) in DCM (45 mL) stirred at 0° C. was added a solution of TBSCl (1.439 g, 9.55 mmol) in DCM (3 mL). The reaction was stirred at 28° C. for 48 h. Then the reaction mixture was diluted with DCM (100 mL), washed with brine (50 mL), dried over anhydrous $Na_2SO_4$, and filtered. The filtrate was concentrated under reduced pressure, and the resulting residue was purified by flash silica gel chromatography (ISCO; 24 g Agela Silica Flash Column, Eluent of 0-5% EtOAc/Petroleum Ether gradient @ 40 mL/min) to individually give intermediate 48a-1, and intermediate 48a-2.

Intermediate 48a-1: $^1H$ NMR (400 MHz, $CDCl_3$) δ: 7.34-7.28 (m, 8H), 7.26-7.19 (m, 2H), 3.69 (s, 3H), 3.68 (s, 2H), 3.48 (s, 4H), 3.27-3.19 (m, 1H), 2.36-2.27 (dm, 2H), 2.11-1.96 (m, 2H), 0.91 (s, 9H), 0.03 (s, 6H).

Intermediate 48a-2: $^1H$ NMR (400 MHz, $CDCl_3$) δ: 7.33-7.28 (m, 8H), 7.26-7.21 (m, 2H), 3.76 (s, 2H), 3.69 (s, 3H), 3.50 (s, 4H), 3.24-3.11 (m, 1H), 2.38-2.24 (m, 2H), 2.17-2.09 (m, 2H), 0.86 (s, 9H), 0.03 (s, 6H).

Step B—Synthesis of Intermediate 48b-1 To a solution of intermediate 48a-1 (939 mg, 2.070 mmol) in MeOH (14.1 mL) and water (4.7 mL) stirred at 28° C. was added NaOH (497 mg, 12.42 mmol) in one portion. The reaction was stirred at 28° C. for 16 h, then concentrated under reduced pressure to remove most of the MeOH. The resulting residue was diluted with water (30 mL) and extracted with 2-isopropoxypropane (15 mL×4). The organic layers were combined, dried over anhydrous $Na_2SO_4$, filtered and the filtrate was concentrated under reduced pressure to give intermediate 48b-1, which was used in the next reaction without further purification. LC-MS (ESI): m/z 440.2 $[M+H]^+$.

Step C—Synthesis of Intermediate 48c-1 To a solution of intermediate 48b-1 (650 mg, 1.478 mmol) and TEA (0.309 mL, 2.218 mmol) in toluene (6.5 mL) and THF (6.5 mL) was added DPPA (488 mg, 1.774 mmol) at 28° C., under a $N_2$ atmosphere. The reaction was stirred for 2 h at 65° C. and then 2-(trimethylsilyl)ethanol (1748 mg, 14.78 mmol) was added at same temperature. The reaction mixture was stirred for another 60 h at 90° C., then diluted with saturated aqueous $NaHCO_3$ (35 mL), and extracted with EtOAc (15 mL×3). The organic layers were combined, washed with brine, dried over anhydrous $Na_2SO_4$, filtered and the filtrate was concentrated under reduced pressure. The resulting residue was purified by flash silica gel chromatography (ISCO; 12 g Agela Silica Flash Column, Eluent of 0~3% EtOAc/Petroleum Ether gradient @ 30 mL/min) to give intermediate 48c-1. LC-MS (ESI): m/z 555.3 $[M+H]^+$.

Step D—Synthesis of Intermediate 48d-1 A mixture of intermediate 48c-1 (400 mg, 0.721 mmol), AcOH (0.165 mL, 2.88 mmol) and Pd/C (120 mg, 1.128 mmol, 10 wt. %) in MeOH (10 mL) was stirred at 28° C. for 12 h under a hydrogen atmosphere (15 psi). Then the reaction mixture was filtered, and the filtrate was concentrated under vacuum to give intermediate 48d-1, which was used in the next reaction without further purification.

Step E—Synthesis of Intermediate 48e-1 To a stirred solution of intermediate 3c (335 mg, 0.718 mmol) and intermediate 48d-1 (269 mg, 0.718 mmol) in MeOH (6 mL) were added sequentially acetic acid (0.164 mL, 2.87 mmol) and potassium acetate (211 mg, 2.154 mmol) at 28° C. The reaction was stirred at 85° C. for 40 min, then diluted with water (20 mL), and extracted with EtOAc (15 mL×3). The organic layers were combined, washed with brine, dried over anhydrous $Na_2SO_4$, and filtered. The filtrate was concentrated under vacuum to give intermediate 48e-1, which used in the next reaction without further purification. LC-MS (ESI): m/z 793.4 $[M+H]^+$.

Step F—Synthesis of Intermediate 48f-1 To a stirred solution of intermediate 48e-1 (569 mg, 0.717 mmol) in THF (7 mL) was added dropwise TBAF (1.793 mL, 1.793 mmol) at 28° C. The reaction was stirred at 28° C. for 12 h, then diluted with water (20 mL) and extracted with EtOAc (15 mL×3). The organic layers were combined, washed with brine, dried over anhydrous $Na_2SO_4$, and filtered. The filtrate was concentrated under reduced pressure, and the resulting residue was purified by a reverse phase HPLC (Biotage; 20 g Agela, C18, 20~35 μm column; Eluent of 50% $MeCN/H_2O$ (0.5% TFA) gradient @ 50 mL/min) to give intermediate 48f-1. LC-MS (ESI): m/z 679.3 $[M+H]^+$.

Step G—Synthesis of Intermediate 48g-1 A solution of intermediate 48f-1 (220 mg, 0.324 mmol) in TFA (2.2 mL, 28.6 mmol) was stirred at 40° C. for 70 min. Then the reaction solution was concentrated under reduced pressure to give intermediate 48g-1, which was used in the next reaction without further purification. LC-MS (ESI): m/z 379.1 $[M+H]^+$.

Step H—Synthesis of Compound 88 To a mixture of intermediate 48g-1 (123 mg, 0.325 mmol) and 4 Å molecular sieves (120 mg) in MeOH (4 mL) was added intermediate 5 (118 mg, 0.325 mmol). The reaction was stirred at 28° C. for 12 h, then filtered and the filtrate was concentrated under reduced pressure. The resulting residue was purified by reverse phase HPLC (Boston Uni C18 40*150*5 um; Condition: water (0.1% TFA)-ACN; Begin B 0, End B 30; Gradient Time (min) 10; 100% B Hold Time (min) 2; Flow Rate (mL/min) 60; Injections 2), followed by lyophilization to give compound 88 as the TFA salt. The TFA salt was further purified by reverse phase HPLC (Welch Xtimate C18 150*25 mm*5 um; Condition water (0.225% FA)-ACN; Begin B 0, End B 17; Gradient Time (min) 15; 100% B Hold Time (min) 2; Flow Rate (mL/min) 25; Injections 3), followed by lyophilization to give compound 88 as the formic acid salt. LC-MS (ESI): m/z 725.5 $[M+H]^+$. $^1H$ NMR (400 MHz, $D_2O+CD_3CN$) δ: 7.43-7.33 (m, 2H), 6.88 (d, J=8.2 Hz, 1H), 6.81 (s, 1H), 4.61 (s, 1H), 49-4.26-4 (m, 2H), 3.69 (s, 2H), 2.87-2.69 (m, 4H), 2.51-2.40 (m, 2H), 14-2.022 (m, 1H), 1.79-1.66 (m, 1H), 1.50 (s, 3H), 1.42 (s, 3H), 1.23 (s, 3H).

Compound 89 was prepared from intermediate 48a-2 according to the procedure in Step B to Step H of Example 66. LC-MS (ESI): m/z 725.2 $[M+H]^+$. H NMR (400 MHz, $D_2O+CD_3CN$) δ: 7.43-7.33 (m, 2H), 6.85 (d, J=8.6 Hz, 1H), 6.82 (s, 1H), 4.61 (s, 1H), 4.35 (br d, J=9.0 Hz, 1H), 4.16-4.02 (m, 1H), 3.70 (s, 2H), 2.84-2.67 (m, 4H), 2.55-2.41 (m, 2H), 2.12-2.01 (m, 1H), 1.77-1.63 (m, 1H), 1.48 (s, 3H), 1.41 (s, 3H), 1.23 (s, 3H).

Example 67: Preparation of Intermediates 49a-1 and 49a-2

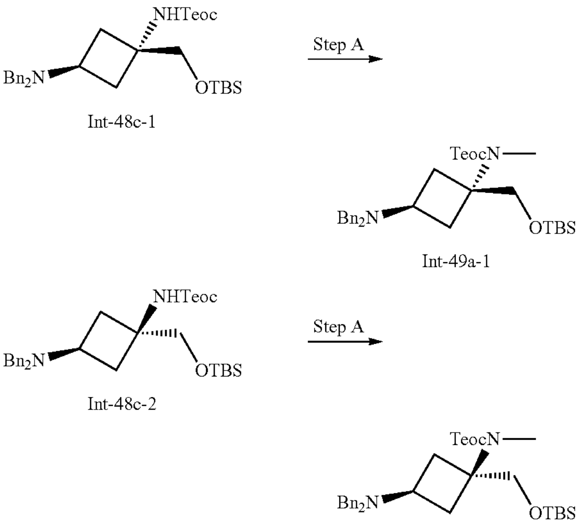

Int-48c-1

Int-49a-1

Int-48c-2

Int-49a-2

Step A—Synthesis of Intermediate 49a-1 and Intermediate 49a-2 To a stirred solution of intermediate 48c-1 (700 mg, 1.261 mmol) in DMF (9.5 mL) at 0° C. was added NaH (111 mg, 2.78 mmol, 60 wt. % in mineral oil). The mixture was stirred at 0° C. under $N_2$ for 20 min., then a solution of iodomethane (269 mg, 1.892 mmol) in DMF (1.0 mL) was added dropwise. The reaction mixture was stirred for 15 min at 0° C., then at 28° C. for 2 h. The reaction was quenched with saturated aqueous $NH_4Cl$ (50 mL) at 0° C., and extracted with EtOAc (15 mL×3). The organic layers were combined, washed with brine (10 mL), dried over anhydrous $Na_2SO_4$, and filtered. The filtrate was concentrated under reduced pressure, and the resulting residue was purified by flash silica gel chromatography (ISCO; 12 g Agela Silica Flash Column, Eluent of 0-5% EtOAc/Petroleum ether gradient @ 30 mL/min) to give intermediate 49a-1. LC-MS (ESI): m/z 569.3 $[M+H]^+$.

Intermediate 49a-2 was prepared from intermediate 48c-2 according to the procedure of Step A of Example 67. LC-MS (ESI): m/z 569.3 $[M+H]^+$.

Example 68: Preparation of Compounds 90 and 91

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((1r,3R)-3-(hydroxymethyl)-3-(methylamino)cyclobutyl)carbamimidoyl)chroman-2-yl)propanoic acid, and (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((1s,3S)-3-(hydroxymethyl)-3-(methylamino)cyclobutyl)carbamimidoyl)chroman-2-yl)propanoic acid

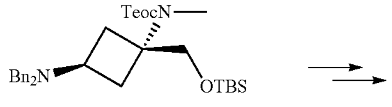

Int-49a-1

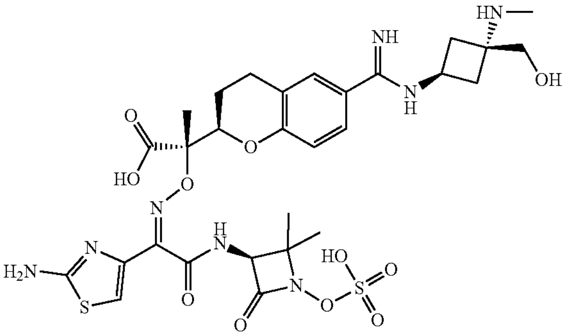

Compound 90

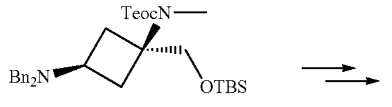

Int-49a-2

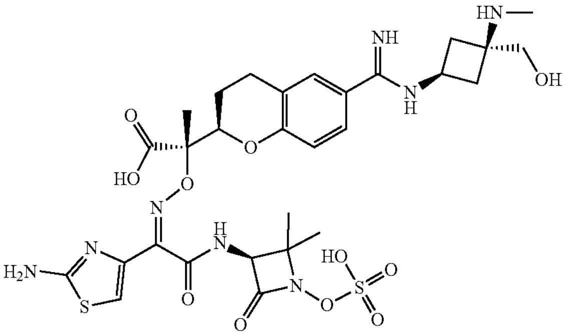

Compound 91

Compounds 90 and 91 were prepared from the corresponding intermediate 49a-1 and intermediate 49a-2 according to the procedure in Step E to Step H of Example 66.

Compound 90: LC-MS (ESI): m/z 739.3 $[M+H]^+$. $^1H$ NMR (400 MHz, $D_2O+CD_3CN$) δ: 7.41-7.32 (m, 2H), 6.87 (d, J=8.6 Hz, 1H), 6.81 (s, 1H), 4.61 (s, 1H), 4.39 (br d, J=11.3 Hz, 1H), 4.34-4.23 (m, 1H), 3.77 (s, 2H), 2.90-2.74 (m, 4H), 2.58 (s, 3H), 2.49-2.35 (m, 2H), 2.12-2.01 (m, 1H), 1.78-1.62 (m, 1H), 1.49 (s, 3H), 1.42 (s, 3H), 1.23 (s, 3H).

Compound 91: LC-MS (ESI): m/z 739.2 $[M+H]^+$. $^1H$ NMR (400 MHz, $D_2O+CD_3CN$) δ: 7.44-7.33 (m, 2H), 6.88-6.76 (m, 2H), 4.60 (s, 1H), 4.35 (br d, J=9.4 Hz, 1H), 4.15-4.04 (m, 1H), 3.77 (s, 2H), 2.84-2.65 (m, 4H), 2.55 (s, 3H), 2.52-2.39 (m, 2H), 2.12-2.01 (m, 1H), 1.77-1.62 (m, 1H), 1.48 (s, 3H), 1.41 (s, 3H), 1.22 (s, 3H).

Example 69: Preparation of Intermediates 50d-1 and 50d-2

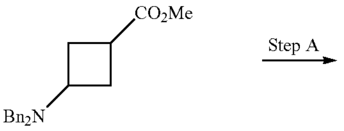

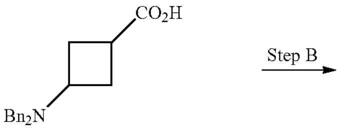

Int-50a

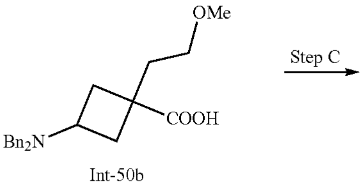

Int-50b

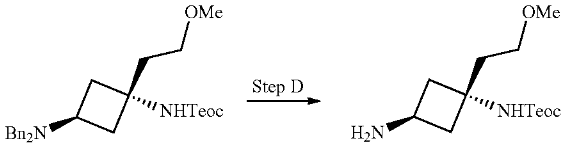

Int-50c-1 Int-50d-1

+

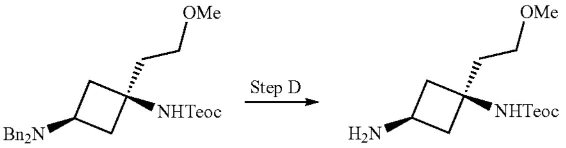

Int-50c-2 Int-50d-2

Step A—Synthesis of Intermediate 50a To a solution of methyl 3-(dibenzylamino)-cyclobutane-1-carboxylate (7.4 g, 23.92 mmol) in $H_2O$ (21 mL) and $CH_3OH$ (63 mL) was added sodium hydroxide (2.87 g, 71.7 mmol) at room temperature. The reaction was stirred at room temperature for 16 h, then concentrated in vacuo. To the resulting residue was slowly added aqueous HCl solution (1M) to adjust the pH to pH 4. The resulting mixture was extracted with 1:10 IPA/DCM (4×220 mL). The combined organic layers were concentrated in vacuo to afford intermediate 50a, which was used in the next reaction without further purification. LC-MS (ESI): m/z 295.9 $[M+H]^+$.

Step B—Synthesis of Intermediate 50b To a solution of intermediate 50a (5.8 g, 19.64 mmol) in THF (120 mL) stirred at −65° C., was added lithium diisopropylamide (34.4 mL, 68.7 mmol, 2 M in THF/heptanes). The reaction was stirred at −65° C. for 50 minutes, then 1-iodo-2-methoxy-ethane (5.48 g, 29.5 mmol) was added. The reaction was stirred at 0° C. for 5 min. and then at 25° C. for 1 h. Then the reaction mixture was diluted with water (50 mL), and the pH was adjusted to pH 3-4 by adding aqueous HCl solution (1 M). The resulting mixture was extracted with 1:10 isopropyl alcohol/dichloromethane (200 mL×4), and the combined organic layers were concentrated in vacuo. The resulting residue was purified by a flash silica gel chromatography (ISCO®; 40 g SepaFlash® Silica Flash Column, Eluent of 0-40% ethyl acetate/petroleum ether gradient @ 60 m/min) to give intermediate 50b. LC-MS (ESI): m/z 354.1 $[M+H]^+$.

Step C—Synthesis of Intermediates 50c-1 and 50c-2 To a stirred solution of intermediate 50b (2.0 g, 5.66 mmol) in THF (20 mL) and toluene (20 mL) at 25° C., were added TEA (1.183 mL, 8.49 mmol) and diphenyl phosphorazidate (1.869 g, 6.79 mmol). The resulting mixture was stirred for 2 h at 65° C. under a $N_2$ atmosphere, then 2-(trimethylsilyl) ethanol (6.69 g, 56.6 mmol) was added. The reaction was stirred at 90° C. for 12 h, then quenched with water (15 mL), and extracted with EtOAc (100 mL xr 3). The combined organic layers were concentrated under reduced pressure, and the resulting residue was purified by a flash silica gel chromatography (ISCO@; 25 g SepaFlash® Silica Flash Column, Eluent of 0-20% ethyl acetate/petroleum ether gradient @ 40 m/min) to give the desired product as a mixture of cis- and trans-stereoisomers. LC-MS (ESI): m/z 469.1 $[M+H]^+$. The cis/trans mixture was further separated by SFC (Column: DAICEL CHIRALCEL OD (250 mm×50 mm, 10 um); Condition: 0.1% $NH_3H_2O$—IPA; Begin B 20%, End B 20%; FlowRate (m/min) 180; Injections 180) to individually give intermediate 50c-1 and intermediate 50c-2.

Intermediate 50c-1: LC-MS (ESI): m/z 469.2 $[M+H]^+$. $^1H$ NMR (400 MHz, $CDCl_3$) δ: 7.32-7.19 (m, 10H), 5.01 (br s, 1H), 4.11 (br t, J=8.4 Hz, 2H), 3.46 (s, 4H), 3.39 (t, J=6.1 Hz, 2H), 3.33-3.26 (m, 1H), 3.27 (s, 3H), 2.43-2.31 (m, 2H), 2.04 (br t, J=5.9 Hz, 2H), 1.98-1.90 (m, 2H), 0.98-0.94 (m, 2H), 0.06 (s, 9H).

Intermediate 50c-2: LC-MS (ESI): m/z 469.0 $[M+H]^+$. $^1H$ NMR (400 MHz, $CDCl_3$) δ: 7.34-7.17 (m, 10H), 4.23-4.00 (m, 2H), 3.51 (s, 4H), 3.43 (t, J=6.1 Hz, 2H), 3.29 (s, 3H), 3.04-2.90 (m, 1H), 2.49-2.26 (m, 2H), 2.26-2.14 (m, 2H), 1.94 (t, J=6.1 Hz, 2H), 1.01-0.90 (m, 2H), 0.00 (s, 9H).

Step D—Synthesis of Intermediates 50d-1 and 50d-2 To a solution of intermediate 50c-1 (700 mg, 1.493 mmol) in MeOH (20 mL) were added Pd/C (12 mg, 0.011 mmol, 10 wt. %) and AcOH (0.342 mL, 5.97 mmol). The reaction was stirred at 25° C. under $H_2$ (15 psi) for 3 h. Then the reaction mixture was filtered, and the filtrate was concentrated in vacuo to give intermediate 50d-1, which was used in the next reaction without further purification. LC-MS (ESI): m/z 289.0 $[M+H]^+$.

Intermediate 50d-2 was prepared from intermediate 50c-2 according to the procedure in Step D of Example 69. LC-MS (ESI): m/z 289.0 $[M+H]^+$.

Example 70: Preparation of Compounds 92 and 93

(S)-2-((R)-6-(N-((1r,3R)-3-amino-3-(2-methoxyethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1s,3S)-3-amino-3-(2-methoxyethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

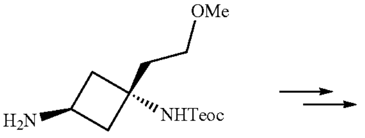

Int-50d-1

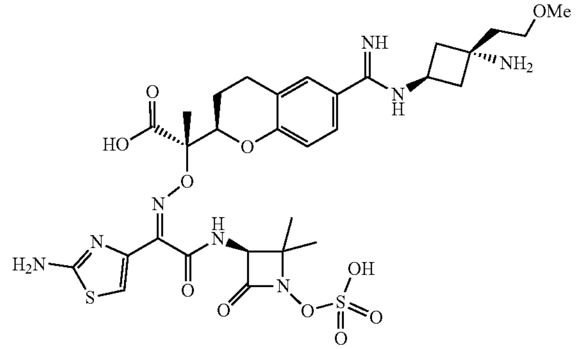

Compound 92

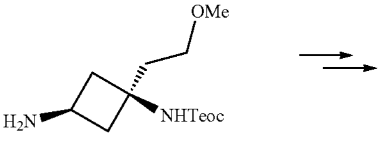

Int-50d-2

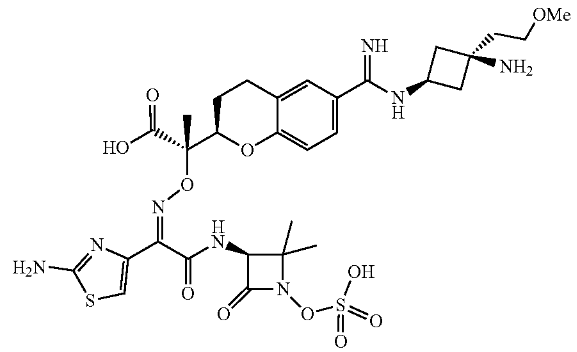

Compound 93

Compounds 92 and 93 were prepared from the corresponding intermediate 50d-1 and intermediate 50d-2 according to the procedure of Step E, Step G and Step H of Example 66.

Compound 92: LC-MS (ESI): m/z 753.3 $[M+H]^+$. $^1H$ NMR (400 MHz, $D_2O+CD_3CN$) S: 7.37-7.29 (m, 2H), 6.86 (d, J=8.6 Hz, 1H), 6.79 (s, 1H), 4.61 (s, 1H), 4.39 (br d, J=8.4 Hz, 1H), 4.35-4.27 (m, 1H), 3.54 (t, J=5.5 Hz, 2H), 3.25 (s, 3H), 2.87-2.73 (m, 4H), 2.55-2.41 (m, 2H), 2.17-2.08 (m, 1H), 2.03 (br t, J=5.5 Hz, 2H), 1.79-1.67 (m, 1H), 1.53 (s, 3H), 1.43 (s, 3H), 1.25 (s, 3H).

Compound 93: LC-MS (ESI): m/z 753.3 $[M+H]^+$. $^1H$ NMR (400 MHz, $D_2O+CD_3CN$) S: 7.46-7.35 (m, 2H), 6.87 (br d, J=8.6 Hz, 1H), 6.78 (s, 1H), 4.61 (s, 1H), 4.34 (br d, J=11.0 Hz, 1H), 4.12-3.99 (m, 1H), 3.59 (t, J=5.5 Hz, 2H), 3.27 (s, 3H), 2.85-2.66 (m, 4H), 2.60-2.40 (m, 2H), 2.12-2.02 (m, 1H), 2.01 (t, J=5.5 Hz, 2H), 1.75-1.57 (m, 1H), 1.48 (s, 3H), 1.43 (s, 3H), 1.25 (s, 3H).

Example 71: Preparation of Compounds 94 and 95

(S)-2-((R)-6-(N-((1S,3R)-3-amino-3-((S)-2,3-dihydroxypropyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1R,3R)-3-amino-3-((R)-2,3-dihydroxypropyl)cyclobutyl)carbamimidoyl) chroman-2-yl)-2-((((Z)-1-(2-aminothiazol-4-yl)-2-(((S)-2,2-dimethyl-4-oxo-1-(sulfooxy)azetidin-3-yl) amino)-2-oxoethylidene)amino)oxy)propanoic acid*

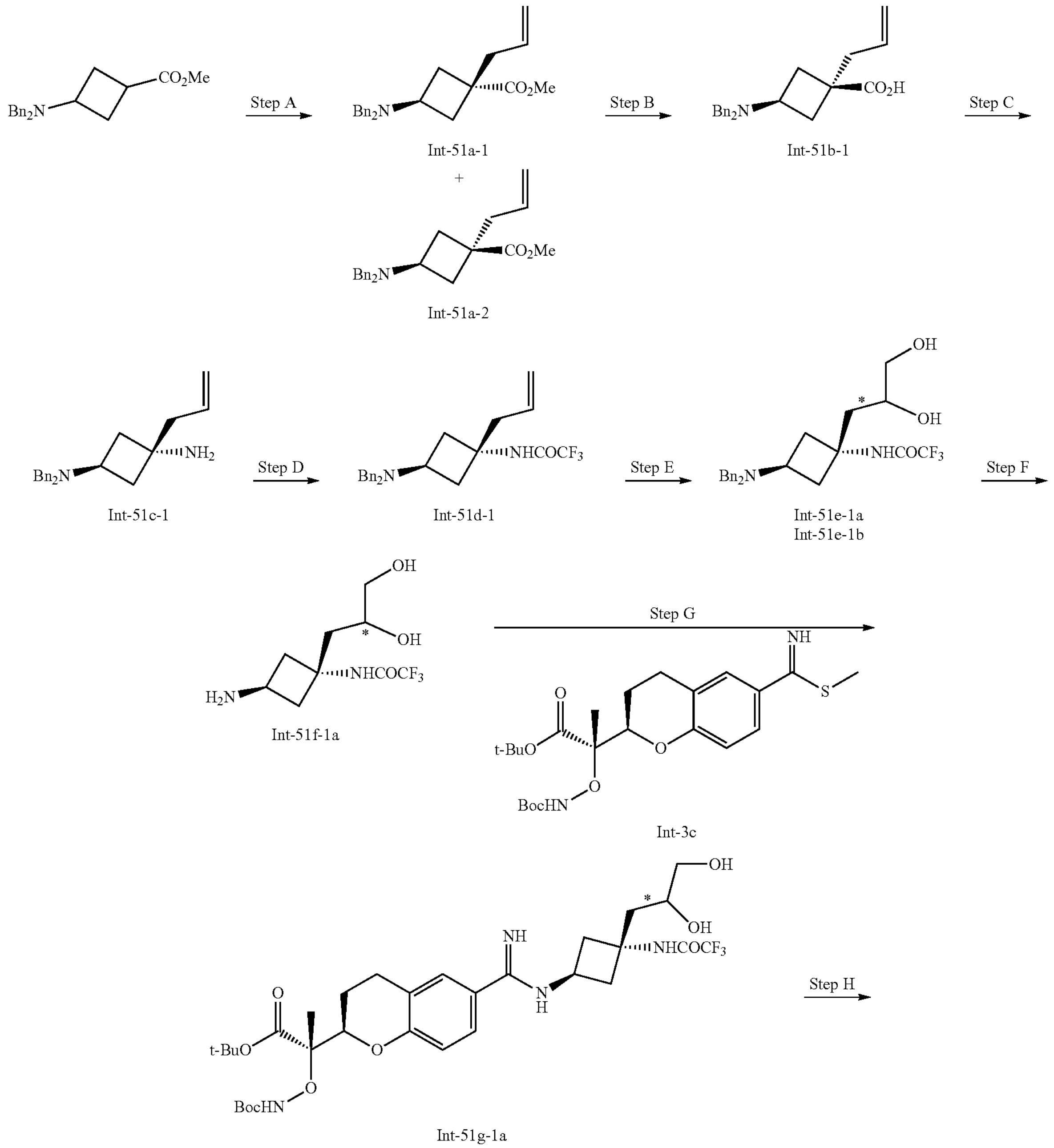

Int-51a-1
+
Int-51a-2
Int-51b-1
Int-51c-1
Int-51d-1
Int-51e-1a
Int-51e-1b
Int-51f-1a
Int-3c
Int-51g-1a

-continued

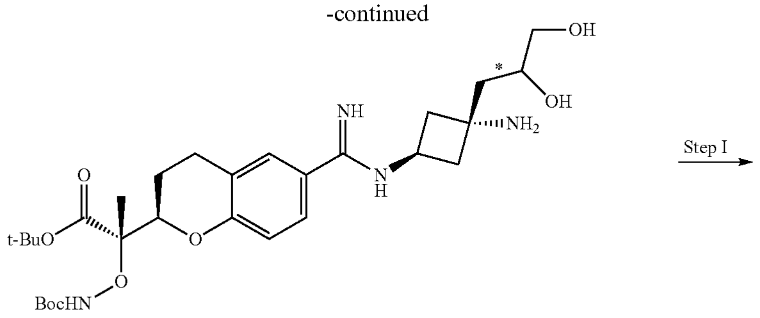

Int-51h-1a

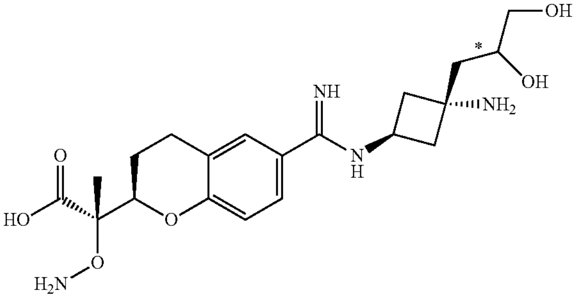

Int-51i-1a

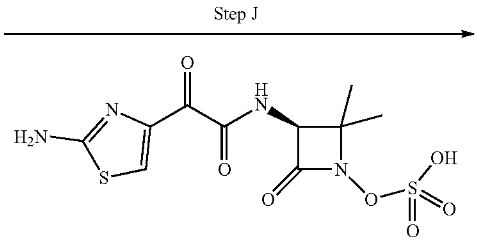

Int-5

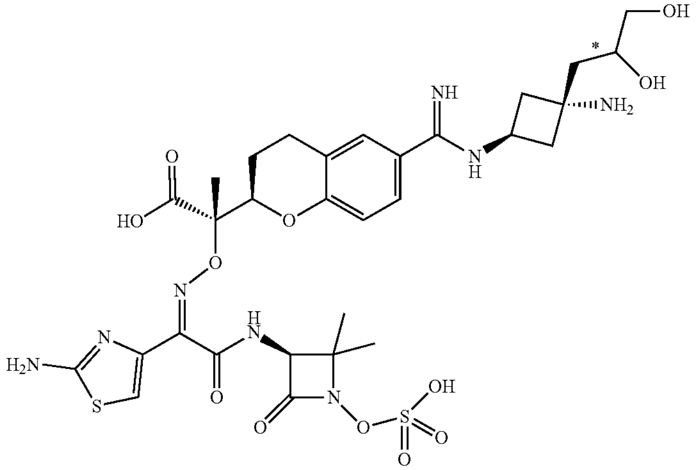

Compound 94

Int-51e-1b → Compound 95

Step A—Synthesis of Intermediates 51a-1 and 51a-2 To a stirred solution of methyl 3-(dibenzylamino)cyclobutane-1-carboxylate (10g, 32.3 mmol) in THF at −70° C. (160 mL) was added a solution of LiHMDS in THF (1 M, 97 mL, 97 mmol). The reaction mixture was stirred at −70° C. for 15 min. before adding allyl bromide (7.82 g, 64.6 mmol). The reaction mixture was stirred at −70° C. for 1.5 h at 0° C., then quenched with saturated aqueous $NH_4Cl$ (200 mL) at 0° C. and stirred for 10 min. The reaction mixture was then extracted with EtOAc (3×100 mL), and the combined organics were washed with brine (200 mL), dried over anhydrous $Na_2SO_4$, and filtered. The filtrate was concentrated under reduced pressure, and the resulting residue was purified by flash silica gel chromatography (Biotage; 120 g Agela Silica Flash Column, Eluent of 3% EtOAc/Petroleum ether gradient @ 60 mL/min) to afford the product as a mixture of stereoisomers. The mixture of stereoisomers was separated by SFC (Column: DAICEL CHIRALPAK AD (250 mm×50 mm, 10 um); Condition: 0.1% $NH_3H_2O$ IPA; Begin B 10%, End B 10%; FlowRate (m/min) 220; Injections 120) to individually give intermediate 51a-1 (the first eluting isomer) and intermediate 51a-2 (the second eluting isomer).

Intermediate 51a-1: LC-MS (ESI): m/z 350.5 $[M+H]^+$. $^1H$ NMR (400 MHz, $CDCl_3$) δ: 7.34-7.28 (m, 8H), 7.26-7.20 (m, 2H), 5.74-5.57 (m, 1H), 5.08-4.97 (m, 2H), 3.69 (s, 3H), 3.47 (s, 4H), 3.26-3.14 (m, 1H), 2.52-2.43 (m, 4H), 1.92-1.82 (m, 2H).

Intermediate 51a-2: LC-MS (ESI): m/z 350.6 $[M+H]^+$. $^1H$ NMR (400 MHz, $CDCl_3$) δ: 7.32-7.28 (m, 8H), 7.27-7.21 (m, 2H), 5.76-5.63 (m, 1H), 5.12-4.99 (m, 2H), 3.68 (s, 3H), 3.49 (s, 4H), 3.24-3.11 (m, 1H), 2.46 (d, J=6.8 Hz, 2H), 2.37-2.28 (m, 2H), 2.13-2.01 (m, 2H).

Step B—Synthesis of Intermediate 51b-1 To a solution of intermediate 51a-1 (3.6 g, 10.30 mmol) in MeOH (65 mL)

and $H_2O$ (16 mL) was added sodium hydroxide (1.21 g, 30.3 mmol). The reaction was stirred at 75° C. for 5 h and then concentrated in vacuo. The resulting residue was diluted with $H_2O$ (25 mL), and the pH was adjusted to pH 5-6 with aqueous HCl (2 M, 8 mL). The resulting mixture was extracted with EtOAc (30 mL×3). The combined organic layers were dried over anhydrous $Na_2SO_4$, filtered, and the filtrate was concentrated under vacuum to give intermediate 51b-1. $^1$H NMR (400 MHz, $CD_3OD$) δ: 7.62-7.40 (m, 10H), 5.71-5.56 (m, 1H), 5.10-5.01 (m, 2H), 4.27 (s, 4H), 4.07-3.94 (m, 1H), 2.57-2.50 (m, 2H), 2.47 (d, J=7.1 Hz, 2H), 2.26-2.18 (m, 2H).

Step C—Synthesis of Intermediate 51c-1 To a stirred solution of intermediate 51b-1 (3.96 g, 11.81 mmol) in toluene (40 mL) and THF (40 mL) at 0° C., were added TEA (4.94 mL, 35.4 mmol) and diphenyl phosphorazidate (3.31 mL, 15.35 mmol). The reaction mixture was slowly warmed to 22° C. over 1 h, then stirred at 50° C. for 3.5 h. Then the solvent was removed under reduced pressure with the bath temperature maintained at 22° C. The resulting residue was washed with water (30 mL). The organic layer was separated, and cooled to 0° C. before adding aqueous potassium hydroxide (50% w/v, 25 mL, 11.81 mmol) and tetrabutylammonium iodide (220 mg, 0.596 mmol). The reaction mixture was stirred at 22° C. for 1.5 h, then cooled to 0° C., and acidified to pH 2 with aqueous HCl (20 mL, 4 M). The resulting aqueous mixture was washed with EtOAc (30 mL), and then basified with aqueous KOH solution (15 mL, 50 wt. %), and extracted with EtOAc (25 mL×3). The combined organic layers were dried over anhydrous $Na_2SO_4$, and the solvent was evaporated under reduced pressure to give intermediate 51c-1, which was used in the next reaction without further purification. LC-MS (ESI): m/z 307.2 $[M+H]^+$.

Step D—Synthesis of Intermediate 51d-1 To a solution of intermediate 51c-1 (900 mg, 2.94 mmol) and TEA (0.819 mL, 5.87 mmol) in DCM (22 mL) stirred at 0° C. was added 2,2,2-trifluoroacetic anhydride (925 mg, 4.41 mmol). The reaction was stirred at 24° C. for 3 h, then diluted with water (30 mL) and extracted with DCM (15 mL×3). The combined organic layers were washed with brine (30 mL), dried over anhydrous $Na_2SO_4$, filtered and the filtrate was concentrated under vacuum. The resulting residue was purified by flash silica gel chromatography (Biotage; 12 g Agela Silica Flash Column, Eluent of 3% EtOAc/Petroleum ether gradient @ 30 mL/min) to give intermediate 53d-1. LC-MS (ESI): m/z 403.5 $[M+H]^+$.

Step E—Synthesis of Intermediates 51e-1a and 51e-1b To a solution of intermediate 51d-1 (930 mg, 2.311 mmol) in THF (20 mL) and $H_2O$ (4 mL) stirred at 0° C. was added osmium (VIII) oxide (58.7 mg, 0.231 mmol). The reaction was stirred at 0° C. for 15 min., then 4-methyl-morpholine 4-oxide (541 mg, 4.62 mmol) was added. The reaction was stirred at 24° C. for 18 h, then added to a saturated solution of $Na_2SO_3$ (30 mL) at 0° C. with stirring. The resulting mixture was extracted with 9:1 DCM/MeOH (20 mL×3). The combined organic layers were dried over anhydrous $Na_2SO_4$, filtered and the filtrate was concentrated under vacuum. The resulting residue was purified by flash silica gel chromatography (Biotage; 12 g Agela Silica Flash Column, Eluent of 60% EtOAc/Petroleum ether gradient @ 30 mL/min) to give the product as a mixture of stereoisomers. LC-MS (ESI): m/z LC-MS (ESI): m/z 437.4 $[M+H]^+$. The mixture of stereoisomers was further separated by SFC (Column: DAICEL CHIRALPAK AS (250 mm×30 mm, 10 um); Condition: 0.1% $NH_3H_2O$ EtOH; Begin B 20, End B 20; FlowRate (mL/min) 60; Injections 130) to give intermediate 51e-1a (the first eluting stereoisomer, LC-MS (ESI): m/z 437.2 $[M+H]^+$) and intermediate 51e-1b (the second eluting stereoisomer, LC-MS (ESI): m/z 437.3 $[M+H]^+$).

Step F—Synthesis of Intermediate 51f-1a To a solution of intermediate 51e-1a (261 mg, 0.598 mmol) in MeOH (6 mL) was added palladium on carbon (127 mg, 0.120 mmol, 10 wt. %). The reaction was stirred at 30° C. under $H_2$ atmosphere (15 psi) for 16 h, and then filtered. The filtrate was concentrated to give intermediate 51f-1a, which was used in the next reaction without further purification. LC-MS (ESI): m/z 257 $[M+H]^+$.

Step G—Synthesis of Intermediate 51g-1a To a stirred mixture of intermediate 51f-1a (165 mg, 0.644 mmol) and intermediate 3c (294 mg, 0.631 mmol) in MeCN (4.0 mL) were added potassium acetate (190 mg, 1.932 mmol) and acetic acid (155 mg, 2.58 mmol). The reaction was stirred at 80° C. for 20 minutes, then diluted with $H_2O$ (20 mL) and extracted with EtOAc (10 mL×3). The combined organic layers were washed with brine (30 mL), dried over anhydrous $Na_2SO_4$, and filtered. The filtrate was concentrated under vacuum to give intermediate 51g-1a, which was used in the next reaction without further purification. LC-MS (ESI): m/z 675.6 $[M+H]^+$.

Step H—Synthesis of Intermediate 51h-1a To a solution of intermediate 51g-1a (430 mg, 0.637 mmol) in 5:1 MeOH/$H_2O$ (4 mL) was added $K_2CO_3$ (370 mg, 2.68 mmol). The reaction was stirred at 22° C. for 3 h, and then filtered. The filtrate was concentrated in vacuo to give intermediate 51h-1a, which was used in the next reaction without further purification. LC-MS (ESI): m/z 579.5 $[M+H]^+$.

Step I—Synthesis of Intermediate 51i-1a To a solution of intermediate 51h-1a (350 mg, 0.605 mmol) in 1 mL of DCM was added aqueous HCl solution (12 N, 2 mL). The reaction was stirred at 22° C. for 30 min, then the solvent was removed in vacuo. The resulting residue was purified by a reverse phase HPLC (Biotage; 20 g Agela C18, 20~35 μm, Eluent of 0-20% gradient MeCN/$H_2O$ (0.5% TFA) @ 50 mL/min) to give intermediate 51i-1a. LC-MS (ESI): m/z 422.8 $[M+H]^+$.

Step J—Synthesis of Compounds 94 and 95 To a solution of intermediate 51i-1a (200 mg, 0.473 mmol) in 4:1 MeOH/DMA (3 mL) was added intermediate 5 (172 mg, 0.473 mmol). The reaction was stirred at 28° C. for 16 h, and then filtered. The filtrate was purified by a reverse phase HPLC (Column: Boston Uni C18 40×150×5 um; Condition: water (0.1% TFA)-ACN; Begin B 0, End B 30; Gradient Time (min) 11; 100% B Hold Time (min) 2; FlowRate (mL/min) 60; Injections 1) to give crude product. The crude product was further purified by a reverse phase HPLC (Waters Xselect C18 150×19 mm×5 um; Condition: water (0.1% TFA)-ACN; Begin B 0, End B 13; Gradient Time (min) 25; 100% B Hold Time (min) 2; FlowRate (mL/min) 20; Injections 4) to give the product as the TFA salt. The TFA salt was dissolved in $H_2O$ (3.0 mL) and purified by preparative HPLC (Column: Welch Xtimate C18 150×25 mm×5 um; Condition: water (0.225% FA)-ACN; Begin B 0, End B 18; Gradient Time (min) 15; 100% B Hold Time (min) 2; FlowRate (mL/min) 25; Injections 3) to give compound 94 as the formic acid salt. LC-MS (ESI): m/z 769.3 $[M+H]^+$. H NMR (400 MHz, $D_2O$+$CD_3CN$) δ: 7.39-7.31 (m, 2H), 6.87 (d, J=8.6 Hz, 1H), 6.78 (s, 1H), 4.61 (s, 1H), 4.60-4.29 (m, 2H), 3.95-3.80 (m, 1H), 3.47-3.34 (m, 2H), 2.96-2.70 (m, 4H), 2.56-2.40 (m, 2H), 2.12-2.01 (m, 1H) 1.92-1.83 (m, 2H), 1.81-1.60 (m, 1H) 1.50 (s, 3H), 1.42 (s, 3H), 1.25 (s, 3H).

Compound 95 was prepared from intermediate 51e-Ib according to the procedure in Step F to Step J of Example 71. LC-MS (ESI): m/z 769.2 $[M+H]^+$. $^1H$ NMR (400 MHz, $D_2O+CD_3CN$) δ: 7.38-7.29 (m, 2H), 6.87 (d, J=8.2 Hz, 1H), 6.78 (s, 1H), 4.60 (s, 1H), 4.45-4.30 (m, 2H), 3.95-3.81 (m, 1H) 3.47-3.37 (m, 2H), 2.95-2.70 (m, 4H), 2.56 (br dd, J=6.1, 13.9 Hz, 1H), 2.44 (br dd, J=6.7, 13.7 Hz, 1H), 2.12-2.02 (m, 1H), 1.92-1.82 (m, 2H), 1.80-1.61 (m, 1H), 1.50 (s, 3H), 1.42 (s, 3H), 1.25 (s, 3H). *Each compound is a single diastereomer; absolute stereochemistry at * marked carbon center is unassigned.

Example 72: Preparation of Intermediates 52e-1 and 52e-2

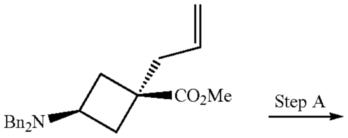

Int-51a-2

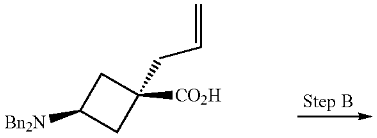

Int-52a

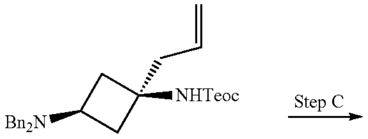

Int-52b

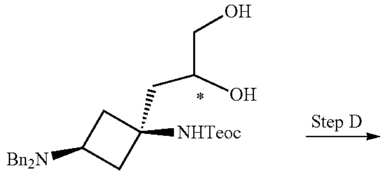

Int-52c-1
Int-52c-2

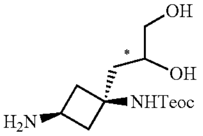

Int-52d-1

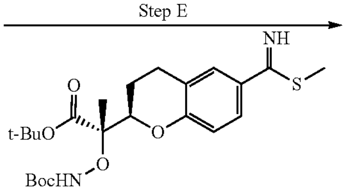

Int-3c

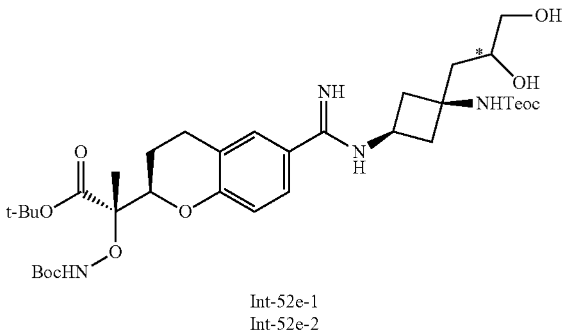

Int-52e-1
Int-52e-2

Step A—Synthesis of Intermediate 52a To a solution of intermediate 51a-2 (3.27 g, 9.36 mmol) in MeOH (42 mL) and $H_2O$ (10.50 mL) was added sodium hydroxide (1.684 g, 42.1 mmol). The reaction mixture was stirred at 75° C. for 4.5 h, then concentrated in vacuo. The resulting residue was diluted with $H_2O$ (20 mL), and the pH was adjusted to pH 2-3 with aqueous HCl solution (2 N). The resulting mixture was extracted with EtOAc (30 mL×3), and the combined organic layers were dried over anhydrous $Na_2SO_4$, and filtered. The filtrate was concentrated under vacuum to give intermediate 52a, which was used in the next reaction without further purification. LC-MS (ESI): m/z 336.4 $[M+H]^+$. $^1H$ NMR (400 MHz, $CD_3OD$) δ: 7.62-7.42 (m, 10H), 5.84-5.59 (m, 1H), 5.29-5.03 (m, 2H), 4.25 (s, 4H), 4.02-3.89 (m, 1H), 2.57-2.49 (m, 2H), 2.46 (d, J=7.4 Hz, 2H), 2.26-2.16 (m, 2H).

Step B—Synthesis of Intermediate 52b To a solution of intermediate 52a (3.18 g, 9.48 mmol) in toluene (25 mL)) and THF (25 mL) stirred at 0° C. were added TEA (3.96 mL, 28.4 mmol) and diphenyl phosphorazidate (3.06 mL, 14.22 mmol). The mixture was stirred at 20° C. for 1 h under a $N_2$ atmosphere, and then at 45° C. for 2 h. Then the reaction temperature was raised to 80° C. and 2-(trimethylsilyl) ethanol (3.66 mL, 37.9 mmol) was added. The reaction was stirred at 80° C. for 16 h, then the solvent was removed in vacuo. The resulting residue was purified by a reverse phase HPLC (Biotage; 20 g Agela, C18, 20-35 μm, Eluent of 65% $MeCN/H_2O$ (0.5% TFA) gradient @ 50 mL/min) to give intermediate 52b. LC-MS (ESI): m/z 451.9 $[M+H]^+$. $^1H$ NMR (400 MHz, $CDCl_3$) δ: 7.48-7.38 (m, 10H), 5.82-5.56 (m, 1H), 5.19-5.03 (m, 2H), 4.08-3.98 (m, 4H), 4.01-3.82 (m, 2H), 3.27-3.16 (m, 1H), 3.04-2.91 (m, 2H), 2.51 (br d, J=7.1 Hz, 2H), 2.37-2.27 (m, 2H), 0.94-0.87 (m, 2H), 0.00 (s, 9H).

Step C—Synthesis of Intermediates 52c-1 and 52c-2 To a stirred solution of intermediate 52b (2.8 g, 6.21 mmol) in THF (35 mL) and $H_2O$ (7.00 mL) at 0° C. was added osmium (VIII) oxide (0.160 g, 0.629 mmol). The reaction was stirred at 0° C. for 15 minutes, then 4-methylmorpholine 4-oxide (1.46 g, 12.46 mmol) was added. The reaction was then stirred at 20° C. for 16 h, then added to saturated aqueous $Na_2SO_3$ (30 mL) at 0° C. with stirring, and extracted with 9:1 DCM/MeOH (30 mL×3). The combined organic layers were dried over anhydrous $Na_2SO_4$, filtered and the filtrate was concentrated under vacuum. The resulting residue was purified by flash silica gel chromatography (Biotage; 12 g Agela Silica Flash Column, Eluent of 60% EtOAc/petroleum ether gradient @ 30 mL/min) to give the product as a mixture of stereoisomers. The mixture of stereoisomers was further separated by SFC (Column: DAICEL CHIRALCEL OD (250 mm×50 mm, 10 um); Condition: 0.1% $NH_3H_2O$/IPA; Begin B 30%, End B 30%; Flow Rate (m/min) 200; Injections 120) to give pure intermediate 52c-1 (the first eluting stereoisomer, LC-MS (ESI): m/z 485.8 $[M+H]^+$) and impure intermediate 52c-2 (the second eluting stereoisomer). Impure intermediate 52c-2 was further purified by a second SFC (Column: DAICEL CHIRALCEL OD-H (250 mm×30 mm, 5 um); Condition: 0.1% $NH_3H_2O$/IPA; Begin B 30, End B 30; Flow Rate (m/min) 60; Injections 150) to afford pure intermediate 52c-2. LC-MS (ESI): m/z 485.8 $[M+H]^+$.

Step D—Synthesis of Intermediate 52d-1 To a solution of intermediate 52c-1 (585 mg, 1.207 mmol) in MeOH (10 mL) was added Pd/C (257 mg, 0.241 mmol, 10 wt. %) and the mixture was stirred at 30° C. under a $H_2$ atmosphere (15 psi) for 16 h. Then the reaction mixture was filtered, and the filtrate was concentrated under vacuum to give intermediate 52d-1, which was used in the next reaction without further purification. LC-MS (ESI): m/z 305.2 $[M+H]^+$.

Step E—Synthesis of Intermediates 52e-1 and 52e-2 To a stirred mixture of intermediate 52d-1 (380 mg, 0.749 mmol) and intermediate 3c (332 mg, 0.711 mmol) in MeCN (6.0 mL) was added acetic acid (0.171 mL, 3.00 mmol). The reaction was stirred at 80° C. for 20 minutes, then diluted with $H_2O$ (30 mL) and extracted with EtOAc (15 mL×3). The combined organic layers were dried over anhydrous $Na_2SO_4$, and filtered. The filtrate was concentrated under vacuum to give intermediate 52e-1, which was used in the next reaction without further purification. LC-MS (ESI): m/z 723.9 $[M+H]^+$.

Intermediate 52e-2 was prepared from intermediate 52c-2 according to the procedure in Step D and Step E of Example 72. LC-MS (ESI): m/z 723.3 $[M+H]^+$.

Example 73: Preparation of Compounds 96 and 97

(S)-2-((R)-6-(N-((1R,3S)-3-amino-3-((S)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1S,3S)-3-amino-3-((R)-2,3-dihydroxypropyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

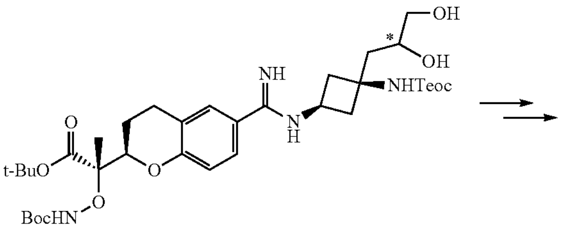

Int-52e-1
Int-52e-2

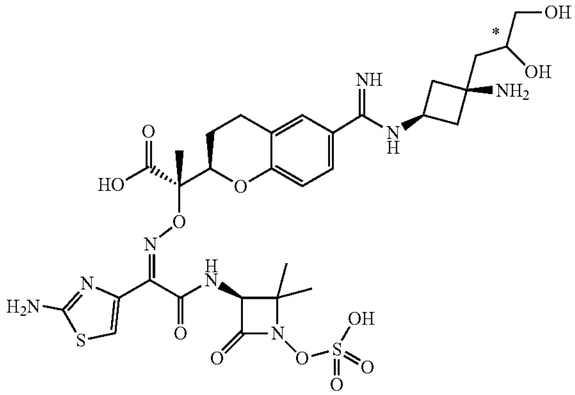

Compound 96
Compound 97

Compounds 96 and 97 were prepared from the corresponding intermediate 52e-1 and intermediate 52e-2 according to the procedure of Step C to Step D of Example 53.

Compound 96: LC-MS (ESI): m/z 769.2 $[M+H]^+$. $^1H$ NMR (400 MHz, $D_2O$ and $CD_3CN$) S: 7.44-7.34 (m, 2H), 6.84 (d, J=8.2 Hz, 1H), 6.79 (s, 1H), 4.59 (s, 1H), 4.35-4.33 (m, 1H), 4.15-4.01 (m, 1H), 3.97-3.82 (m, 1H), 3.50-3.38 (m, 2H), 2.90-2.79 (m, 1H), 2.55-2.67 (m, 3H), 2.56-2.47 (m, 2H), 2.08-2.00 (m, 1H), 1.90-1.83 (m, 2H), 1.74-1.56 (m, 1H), 1.48 (s, 3H), 1.42 (s, 3H), 1.24 (s, 3H)

Compound 97: LC-MS (ESI): m/z 769.3 $[M+H]^+$. $^1H$ NMR (400 MHz, DMSO-$d_6$+$D_2O$) δ: 7.45 (s, 1H), 7.40 (br d, J=9.0 Hz, 1H), 6.81 (d, J=8.6 Hz, 1H), 6.73 (s, 1H), 4.56 (s, 1H), 4.26 (br d, J=11.7 Hz, 1H), 4.12-4.05 (m, 1H), 3.85-3.74 (m, 1H), 3.39-3.25 (m, 2H), 2.86-2.73 (m, 1H), 2.71-2.54 (m, 4H), 2.47-2.38 (m, 1H), 1.96-1.78 (m, 2H), 1.78-1.67 (m, 1H), 1.41 (s, 3H), 1.55-1.35 (m, 1H), 1.36 (s, 3H), 1.21 (s, 3H). *Each compound is a single diastereomer; absolute stereochemistry at * marked carbon center is unassigned.

Example 74: Preparation of Intermediates 53e-cis-1, 53e-cis-2, 53e-trans-1 and 53e-trans-2

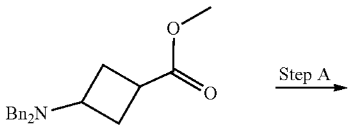

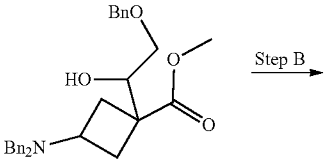

Int-53a

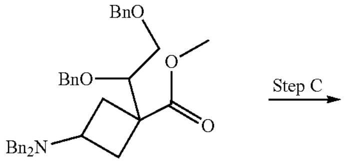

Int-53b

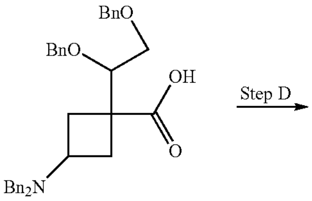

Int-53c

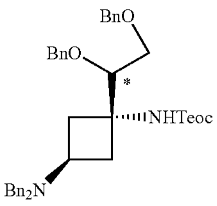

and

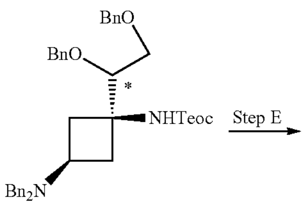

Int-53d-trans-1
Int-53d-trans-2

Int-53d-cis-1
Int-53d-cis-2

-continued

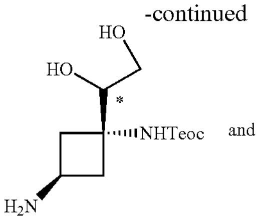

and

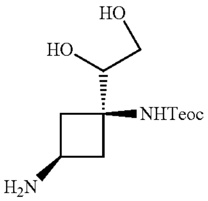

Int-53e-trans-1
Int-53e-trans-2

Int-53e-cis-1
Int-53e-cis-2

Step A—Synthesis of Intermediate 53a To a solution of methyl 3-(dibenzylamino)-cyclobutane-1-carboxylate (8 g, 25.9 mmol) in THF (130 mL) was added LDA (38.8 mL, 78 mmol, 2M in THF/heptanes) at −60° C. The reaction was stirred at −60° C. for 30 minutes, then a solution of 2-(benzyloxy)acetaldehyde (5.82 g, 38.8 mmol) was added dropwise at −60° C. The reaction was stirred at 0° C. for 1.5 h, then diluted with water (90 mL) and extracted with ethyl acetate (70 mLx$_3$). The combined organic layers were washed with brine (80 mL), dried over anhydrous $Na_2SO_4$, filtered and the filtrate was concentrated in vacuo. The crude product was purified by a flash silica gel chromatography (ISCO@; 40 g SepaFlash® Silica Flash Column, Eluent of 0-30% ethyl acetate/petroleum ether gradient @ 45 mL/min) to give intermediate 53a. LC-MS (ESI): m/z 460.5 $[M+H]^+$.

Step B—Synthesis of Intermediate 53b To a stirred solution of intermediate 53a (7 g, 15.23 mmol) in DMF (30 mL) at 0° C., was added NaH (0.731 g, 18.28 mmol, 60°/in mineral oil). The reaction mixture was stirred at 0° C. for 30 minutes, then a solution of (bromomethyl)benzene (3.13 g, 18.28 mmol) was added dropwise at 0° C. The reaction was warmed to 25° C. and stirred at 25° C. for 1 h. Then the reaction mixture was diluted with water (100 mL) and extracted with ethyl acetate (80 mLx3). The combined organic layers were washed with brine (70 mL), dried over anhydrous $Na_2SO_4$, filtered and the filtrate was concentrated in vacuo. The resulting crude product was purified by a flash silica gel chromatography (ISCO@; 40 g SepaFlash® Silica Flash Column, Eluent of 0-30% ethyl acetate/petroleum ether gradient @ 45 m/min) to give intermediate 53b, which was used in the next reaction without further purification. LC-MS (ESI): m/z 550.2 $[M+H]^+$.

Step C—Synthesis of Intermediate 53c To a solution of intermediate 53b (3.7 g, 6.73 mmol) in MeOH (30 mL) and water (10 mL) was added NaOH (1.615 g, 40.4 mmol). The reaction was stirred at 80° C. for 12 h, then concentrated in vacuo. The resulting residue was diluted with water (40 mL), and the pH was adjusted to pH 3 with HCl (1 M). The mixture was extracted with ethyl acetate (80 mLx3) and the combined organic layers were washed with brine (90 mL), dried over anhydrous $Na_2SO_4$, and filtered. The filtrate was concentrated in vacuo to give intermediate 53c, which was used in the next reaction without further purification. LC-MS (ESI): m/z 536.4 $[M+H]^+$.

Step D—Synthesis of intermediates 53d-cis-1, 53d-cis-2, 53d-trans-1 and 53d-trans-2 To a solution of intermediate 53c (3 g, 5.60 mmol) in THF (30 mL) and toluene (30 mL) were added TEA (2.342 mL, 16.80 mmol) and diphenyl phosphorazidate (1.448 mL, 6.72 mmol) at 25° C. under a $N_2$ atmosphere. The reaction mixture was stirred at 65° C. for 2 h, then 2-(trimethylsilyl)-ethanol (8.03 mL, 56.0 mmol) was added at 65° C. The reaction was stirred for 12 h at 90° C., then diluted with water (50 mL) and extracted with ethyl acetate (30 mLx3). The combined organic layers were washed with brine (50 mL), dried over anhydrous $Na_2SO_4$, filtered and the filtrate was concentrated in vacuo. The resulting crude product was purified by a flash silica gel chromatography (ISCO@; 40 g SepaFlash® Silica Flash Column, Eluent of 30% ethyl acetate/petroleum ether gradient @ 45 mL/min) to give the product as a mixture of stereoisomers. LC-MS (ESI): m/z 651.3 $[M+H]^+$. The mixture of stereoisomers was purified by SFC (DAICEL CHIRALCEL OD (250 mm×50 mm, 10 um); Condition: 0.1% $NH_3H_2O$/MeOH; Begin B 35%, End B 35%; FlowRate (m/min) 200; Injections 180) to individually give the trans-stereoisomer and the cis-stereoisomer.

The enantiomers of the trans-stereoisomer were further separated by SFC (DAICEL CHIRALPAK IG (250 mm×30 mm, 10 um); Condition: 0.1% $NH_3 \cdot H_2O$/MeOH; Begin B 35%, End B 35%; FlowRate (mL/min) 200; Injections 180) to individually give intermediate 53d-trans-1 (the first eluting isomer) and intermediate 53d-trans-2 (the second eluting isomer). The enantiomers of the cis stereoisomer were further separated by SFC (DAICEL CHIRALPAK AD (250 mm×50 mm, 10 um); Condition: 0.1% $NH_3 \cdot H_2O$/EtOH; Begin B 30%, End B 30%; FlowRate (mL/min) 200; Injections 120) to individually give intermediate 53d-cis-1 (the first eluting isomer) and intermediate 53d-cis-2 (the second eluting isomer).

Intermediate 53d-trans-1: LC-MS (ESI): m/z 651.3$[M+H]^+$. $^1$H NMR (400 MHz, $CDCl_3$) δ: 7.45-7.11 (m, 20H), 4.83 (br s, 1H), 4.76-4.53 (m, 2H), 4.51-4.40 (m, 2H), 4.11-3.99 (m, 2H), 3.94-3.81 (m, 1H), 3.72-3.61 (m, 1H), 3.61-3.51 (m, 1H), 3.43 (br s, 4H), 3.42-3.24 (m, 1H), 2.59-2.44 (m, 1H), 2.37-2.23 (m, 1H), 2.21-2.09 (m, 1H), 2.03-1.84 (m, 1H), 0.98-0.84 (m, 2H), 0.00 (s, 9H)

Intermediate 53d-trans-2: $^1$H NMR (400 MHz, $CDCl_3$) δ: 7.44-7.13 (m, 20H), 4.83 (br s, 1H), 4.52-4.77 (m, 2H), 4.54-4.39 (m, 2H), 4.10-4.00 (m, 2H), 3.92-3.78 (m, 1H), 3.73-3.61 (m, 1H), 3.57-3.48 (m, 1H), 3.48-3.37 (m, 4H), 3.37-3.20 (m, 1H), 2.61-2.38 (m, 1H), 2.37-2.24 (m, 1H), 2.22-2.13 (m, 1H), 2.04-1.85 (m, 1H), 0.99-0.82 (m, 2H), 0.00 (s, 9H).

Intermediate 53d-cis-1: LC-MS (ESI): m/z 651.2 $[M+H]^+$. $^1$H NMR (400 MHz, $CDCl_3$) δ: 7.47-7.13 (m, 20H), 5.00 (br s, 1H), 4.79 (d, J=11.7 Hz, 1H), 4.64-4.42 (m, 3H), 4.12-3.99 (m, 2H), 3.79-3.67 (m, 2H), 3.64-3.56 (m, 1H), 3.52-3.36 (m, 4H), 3.08-2.87 (m, 1H), 2.56-2.35 (m, 3H), 2.06-1.91 (m, 1H), 0.99-0.85 (m, 2H), 0.00 (s, 9H).

Intermediate 53d-cis-2: $^1$H NMR (400 MHz, $CDCl_3$) δ: 7.47-7.13 (m, 20H), 5.00 (br s, 1H), 4.79 (d, J=11.7 Hz, 1H), 4.64-4.42 (m, 3H), 4.12-3.99 (m, 2H), 3.78-3.65 (m, 2H), 3.64-3.56 (m, 1H), 3.52-3.36 (m, 4H), 3.07-2.92 (m, 1H), 2.56-2.35 (m, 3H), 2.11-1.90 (m, 1H), 0.99-0.85 (m, 2H), 0.00 (s, 9H).

Step E—Synthesis of intermediates 53e-cis-1, 53e-cis-2, 53e-trans-1 and 53e-trans-2 To a solution of intermediate 53d-trans-1 (300 mg, 0.461 mmol) in MeOH (10 mL) and acetic acid (2.5 mL) was added 10 wt. % Pd/C (98 mg, 0.092 mmol). The reaction mixture was stirred at 20° C. under 15 psi of $H_2$ for 12 h. It was filtered, and the filtrate was concentrated in vacuo to give crude intermediate 53e-trans-1. This material was used in the subsequent reaction without further purification. LC-MS (ESI): m/z 291.3 $[M+H]^+$.

Intermediates 53e-cis-2, 53e-trans-1 and 53e-trans-2 were prepared from the corresponding intermediates 53d-cis-2, 53d-trans-1 and 53d-trans-2 according to the procedure of Example 74. LC-MS (ESI): m/z 291.3 $[M+H]^+$.

Example 75

Preparation of Compounds 98-101(S)-2-((R)-6-(N-((1S,3R)-3-amino-3-((S)-1,2-dihydroxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, (S)-2-((R)-6-(N-((1R,3R)-3-amino-3-((R)-1,2-dihydroxyethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, (S)-2-((R)-6-(N-((1S,3S)-3-amino-3-((R)-1,2-dihydroxyethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)-oxy)propanoic acid, and (S)-2-((R)-6-(N-((1R,3S)-3-amino-3-((S)-1,2-dihydroxyethyl)-cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)-oxy)propanoic acid*

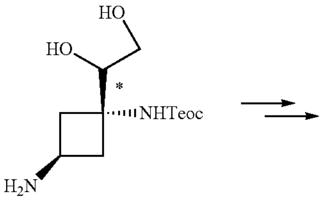

Int-53e-trans-1
Int-53e-trans-2

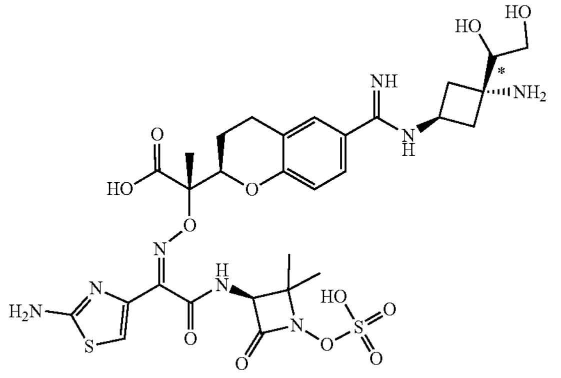

Compound 98
Compound 99

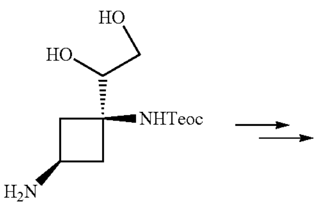

Int-53e-cis-1
Int-53e-cis-2

-continued

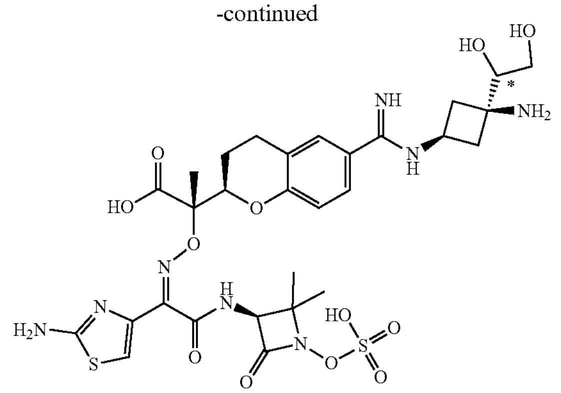

Compound 100
Compound 101

Compounds 98, 99, 100, and 101 were prepared starting from the corresponding intermediates 53e-trans-1, 53e-trans-2, 53e-cis-1, and 53e-cis-2 according to the procedure of Step B to Step D of Example 53.

Compound 98: LC-MS (ESI): m/z 755.3 $[M+H]^+$. $^1H$ NMR (400 MHz, $D_2O+CD_3CN$) δ: 7.35-7.26 (m, 2H), 6.84 (d, J=8.6 Hz, 1H), 6.78 (s, 1H), 4.61 (s, 1H), 4.42-4.29 (m, 2H), 3.82 (t, J=4.1 Hz, 1H), 3.74-3.61 (m, 2H), 2.89-2.69 (m, 4H), 2.65-2.49 (m, 2H), 2.17-2.05 (m, 1H), 1.82-1.63 (m, 1H), 1.53 (s, 3H), 1.43 (s, 3H), 1.25 (s, 3H).

Compound 99: LC-MS (ESI): m/z 755.3 $[M+H]^+$. $^1H$ NMR (400 MHz, $D_2O+CD_3CN$) δ: 7.38-7.28 (m, 2H), 6.86 (d, J=8.6 Hz, 1H), 6.78 (s, 1H), 4.59 (s, 1H), 4.42-4.30 (m, 2H), 3.82 (t, J=4.1 Hz, 1H), 3.74-3.62 (m, 2H), 2.87-2.69 (m, 4H), 2.64-2.50 (m, 2H), 2.14-2.03 (m, 1H), 1.79-1.63 (m, 1H), 1.50 (s, 3H), 1.42 (s, 3H), 1.24 (s, 3H).

Compound 100: LC-MS (ESI): m/z 755.4 $[M+H]^+$. $^1H$ NMR (400 MHz, $D_2O+CD_3CN$) δ: 7.43-7.35 (m, 2H), 6.85 (d, J=8.6 Hz, 1H), 6.78 (s, 1H), 4.60 (s, 1H), 4.33 (br d, J=10.6 Hz, 1H), 4.13-3.97 (m, 1H), 3.81 (t, J=4.4 Hz, 1H), 3.74 (d, J=3.9 Hz, 2H), 2.99-2.81 (m, 2H), 2.81-2.66 (m, 2H), 2.60-2.39 (m, 2H), 2.10-1.99 (m, 1H), 1.74-1.60 (m, 1H), 1.48 (s, 3H), 1.42 (s, 3H), 1.24 (s, 3H).

Compound 101: LC-MS (ESI): m/z 755.4 $[M+H]^+$. $^1H$ NMR (400 MHz, $D_2O+CD_3CN$) δ: 7.43-7.35 (m, 2H), 6.85 (d, J=8.6 Hz, 1H), 6.78 (s, 1H), 4.60 (s, 1H), 4.33 (br d, J=10.6 Hz, 1H), 4.12-4.00 (m, 1H), 3.81 (t, J=4.4 Hz, 1H), 3.74 (d, J=3.9 Hz, 2H), 2.97-2.85 (m, 2H), 2.85-2.67 (m, 2H), 2.63-2.39 (m, 2H), 2.10-1.98 (m, 1H), 1.74-1.55 (m, 1H), 1.48 (s, 3H), 1.42 (s, 3H), 1.24 (s, 3H). *Each compound is a single diastereomer; absolute stereochemistry at * marked carbon center is unassigned.

Example 76: Preparation of Intermediates 54d-1 and 54d-2

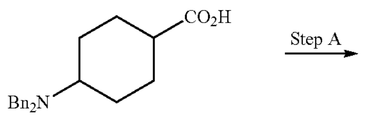

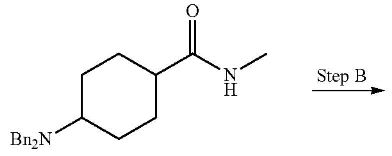

Int-54a

-continued

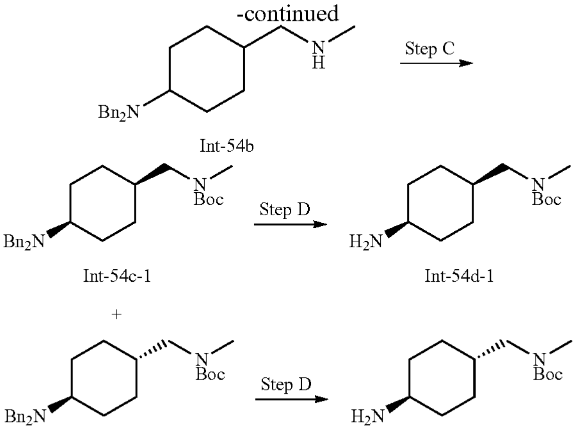

Int-54b

Int-54c-1

Int-54d-1

+

Int-54c-2

Int-54d-2

Step A—Synthesis of Intermediate 54a A solution of 4-(dibenzylamino)cyclohexane-1-carboxylic acid (10 g, 30.9 mmol), DIEA (16.20 mL, 93 mmol) and HATU (17.63 g, 46.4 mmol) in DMF (155 mL) was stirred at 25° C. for 0.5 h, then the reaction mixture was cooled to 0° C. and methylamine hydrochloride (2.505 g, 37.1 mmol) was added. The reaction was stirred at 25° C. for 2 h, then diluted with water (500 mL) and extracted with EtOAc (150 mL×3). The combined organic layers were washed with brine (600 mL×2), dried over anhydrous $Na_2SO_4$, and filtered. The filtrate was concentrated in vacuo to afford intermediate 54a, which was used in the next reaction without further purification. LC-MS (ESI): m/z 336.9 $[M+H]^+$.

Step B—Synthesis of Intermediate 54b To a solution of intermediate 54a (5 g, 14.86 mmol) in THF (150 mL) was added LAH (2.3 g, 60.6 mmol) at 0° C. The reaction was stirred at 85° C. for 16 h. Then the reaction was cooled to room temperature and quenched sequentially by the addition of water (2.3 mL), aqueous NaOH (4.6 mL, 1 N), and water (6.9 mL). The resulting mixture was filtered, and the filtrate was concentrated under vacuum to afford intermediate 54b. LC-MS (ESI): m/z 323.1 $[M+H]^+$.

Step C—Synthesis of Intermediates 54c-1 and 54c-2 A solution of $(Boc)_2O$ (6.90 mL, 29.7 mmol), $Et_3N$ (6.21 mL, 44.6 mmol) and intermediate 54b (4.79 g, 14.85 mmol) in DCM (100 mL) was stirred at 23° C. for 16 h. The reaction solution was purified directly via silica gel chromatography eluting with petroleum ether/EtOAc (5:1) to afford the product as a mixture of stereoisomers. LC-MS (ESI): m/z 423.5 $[M+H]^+$. The mixture of stereoisomers was further separated by SFC (Column: DAICEL CHIRALPAK AD (250 mm×50 mm, 10 um); Condition: 0.1% $NH_3 \cdot H_2O$/EtOH; Begin B 20%, End B 20%; FlowRate (mL/min) 200; Injections 120) to individually afford intermediate 54c-1 (the first eluting isomer), and intermediate 54c-2 (the second eluting isomer).

Intermediate 54c-1: $^1H$ NMR (400 MHz, $CD_3OD$) δ: 7.37-7.29 (m, 4H), 7.26 (t, J=7.5 Hz, 4H), 7.21-7.12 (m, 2H), 3.63 (s, 4H), 3.38-3.26 (m, 2H), 2.79 (br s, 3H), 2.57-2.44 (m, 1H), 1.97-1.84 (m, 1H), 1.73-1.55 (m, 6H), 1.45 (s, 9H), 1.41-1.25 (m, 2H).

Intermediate 54c-2: $^1H$ NMR (400 MHz, $CD_3OD$) δ: 7.36-7.29 (m, 4H), 7.24 (t, J=7.5 Hz, 4H), 7.19-7.12 (m, 2H), 3.58 (s, 4H), 3.01-1.91 (m, 2H), 2.79 (br s, 3H), 2.50-2.38 (m, 1H), 1.90 (br d, J=12.0 Hz, 2H), 1.70 (br d, J=12.7 Hz, 2H), 1.58-1.48 (m, 1H), 1.41 (br s, 9H), 1.39-1.32 (m, 2H), 0.89-0.74 (m, 2H).

Step D—Synthesis of Intermediates 54d-1 and 54d-2 A mixture of intermediate 54c-1 (700 mg, 1.656 mmol) and Pd/C (176 mg, 0.166 mmol, 10 wt. %) in EtOH (20 mL) was stirred at 25° C. under a hydrogen atmosphere (15 psi) for 16 h. Then the reaction mixture was filtered, and the filtrate was concentrated under vacuum to afford intermediate 54d-1, which was used in the next reaction without further purification. LC-MS (ESI): m/z 243.1 $[M+H]^+$.

Intermediate 54d-2 was prepared from intermediate 54c-2 according to the procedure in Step D of Example 76. LC-MS (ESI): m/z 243.1 $[M+H]^+$.

Example 77: Preparation of Compounds 102 and 103

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((1s,4S)-4-((methylamino)-methyl)cyclohexyl)carbamimidoyl)chroman-2-yl)propanoic acid, and (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((1r,4R)-4-((methylamino)-methyl)cyclohexyl)carbamimidoyl)chroman-2-yl)propanoic acid

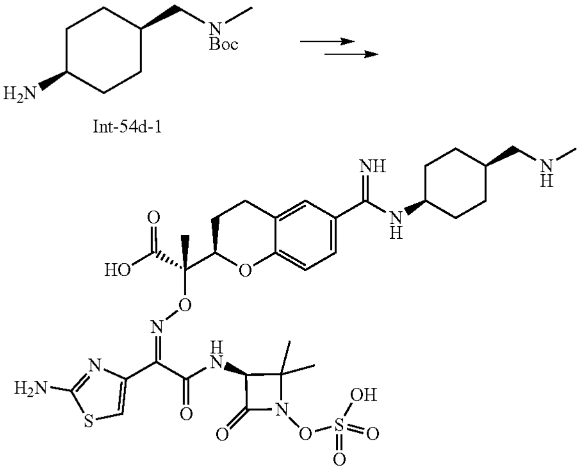

Int-54d-1

Compound 102

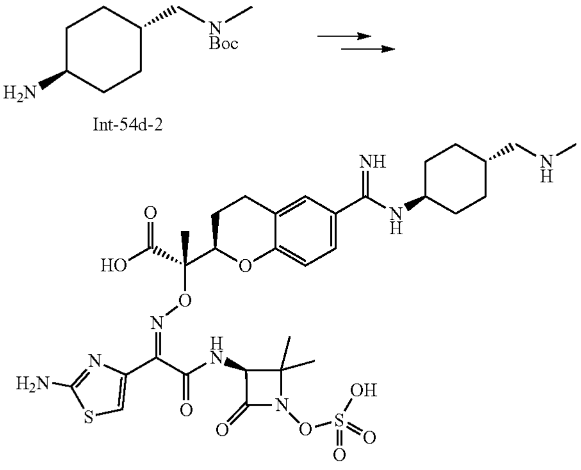

Int-54d-2

Compound 103

Compounds 102 and 103 were prepared starting from the corresponding intermediate 54d-1 and intermediate 54d-2 according to the procedure of Step A to Step C of Example 32.

Compound 102: LC-MS (ESI): m/z 751.3 $[M+H]^+$. $^1H$ NMR (400 MHz, DMSO-$d_6$+$D_2O$) δ: 7.47-7.33 (m, 2H), 6.91 (d, J=8.6 Hz, 1H), 6.73 (s, 1H), 4.58 (s, 1H), 4.39 (br d, J=12.1 Hz, 1H), 3.74-3.66 (m, 1H), 2.89-2.68 (m, 4H), 2.50 (s, 3H), 2.09-1.95 (m, 1H), 1.93-1.76 (m, 1H), 1.75-1.49 (m, 9H), 1.46 (s, 3H), 1.38 (s, 3H), 1.22 (s, 3H).

Compound 103: LC-MS (ESI): m/z 751.3 $[M+H]^+$. $^1H$ NMR (400 MHz, DMSO-$d_6$+$D_2O$) δ: 7.45-7.31 (m, 2H), 6.93 (d, J=8.6 Hz, 1H), 6.75 (s, 1H), 4.60 (s, 1H), 4.36 (br d, J=11.7 Hz, 1H), 3.54-3.43 (m, 1H), 2.90-2.61 (m, 4H), 2.50 (br s, 3H), 2.12-1.98 (m, J=9.8 Hz, 1H), 1.91-1.68 (m, 4H), 1.69-1.48 (m, 2H), 1.51 (s, 3H), 1.39 (s, 3H), 1.35-1.1.18 (m, 2H), 1.24 (s, 3H), 1.13-0.95 (m, 2H).

Example 78: Preparation of Intermediates 55b-1 to 55b-4

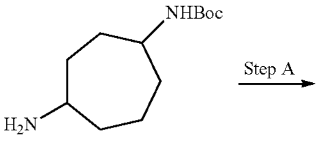

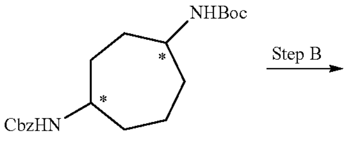

Int-55a-1
Int-55a-2
Int-55a-3
Int-55a-4

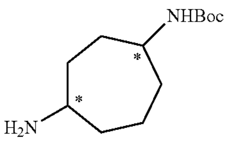

Int-55b-1
Int-55b-2
Int-55b-3
Int-55b-4

Step A—Synthesis of Intermediates 55a-1 to 55a-4 To a flask charged with tert-butyl (4-aminocycloheptyl)carbamate (1.1 g, 4.8 mmol) was added DCM (48 mL). The mixture was cooled to 0° C. under $N_2$, and Hunig's Base (1.7 mL, 9.6 mmol) was added, followed by the dropwise addition of a solution of CBZ—Cl (0.74 ml, 5.1 mmol) in DCM (6 mL). The reaction was stirred at 0° C. for 15 minutes, then quenched with ice-cold saturated $NH_4C_1$ solution (30 mL). The aqueous layer was extracted with DCM (20 mL). The combined organic layers were dried over anhydrous $MgSO_4$, filtered, and the filtrate was concentrated under vacuum. The resulting residue was purified by Isco silica gel column (120 g) eluting with 0-70% EtOAc/hexanes (gradient) over 12 CV to provide the product as a mixture of stereoisomers. LC-MS: m/z 385.4 $[M+Na]^+$. The mixture of stereoisomers was further separated by SFC (OJ-H (2×25 cm), 15% MeOH/$CO_2$ (100 bar), 70 mL/min, 220 nm) to provide each enantiomerically pure intermediates as follows: Intermediate 55a-1, $1^{st}$ peak off chiral column, LC-MS: m/z 363.3 $[M+H]^+$; Intermediate 55a-2, $2^{nd}$ peak off chiral column, LC-MS: m/z 363.3 $[M+H]^+$; Intermediate 55a-3, $3^{rd}$ peak off chiral column, LC-MS: m/z 363.2 $[M+H]^+$; and Intermediate 55a-4, $4^{th}$ peak off chiral column, LC-MS: m/z 363.4 $[M+H]^+$.

Step B—Synthesis of Intermediates 55b-1 to 55b-4 Å flask charged with intermediate 55a-2 (310 mg, 0.86 mmol) and Pd/C (45 mg, 0.043 mmol, 10 wt. %.) was evacuated and refilled with $N_2$ (3×). Then MeOH (8.6 mL) was added, and the reaction container was evacuated and refilled with $H_2$ (3×). The reaction was run under a hydrogen balloon (1 atm), then filtered. The resulting filter cake was rinsed with MeOH. The filtrate was concentrated under vacuum to provide intermediate 57b-2.

Intermediates 55b-1, 55b-3 and 55b-4 were prepared starting with the corresponding intermediates 55a-1, 55a-3, and 55a-4 according to the procedure of Step B of Example 78.

Intermediate 55b-1, LC-MS: m/z 229.3 $[M+H]^+$.

Intermediate 55b-2, LC-MS: m/z 229.3 $[M+H]^+$.

Intermediate 55b-3, LC-MS: m/z 229.4 $[M+H]^+$.

Intermediate 55b-4, LC-MS: m/z 229.3 $[M+H]^+$.

Example 79: Preparation of Compound 104

(S)-2-((R)-6-(N-((1R or S,4S or R)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

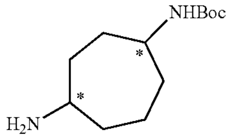

Int-55b-3

+

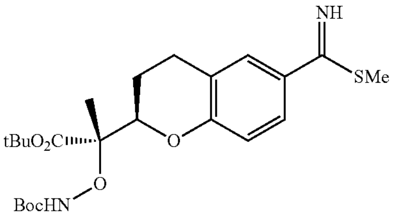

Int-3c

-continued

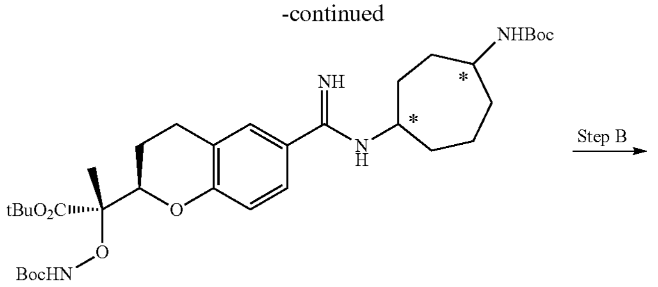

Int-56a

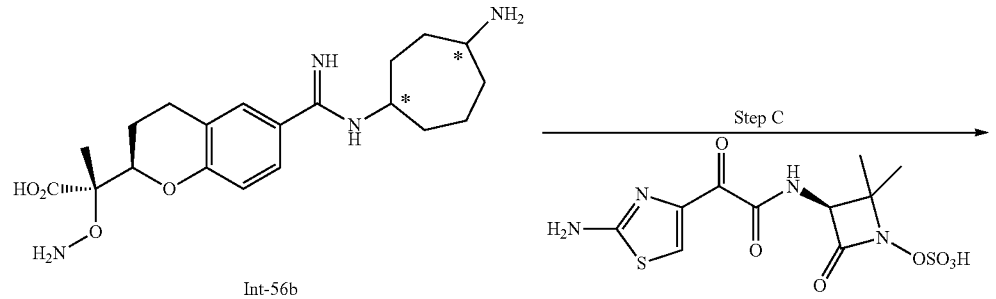

Int-56b

Int-5

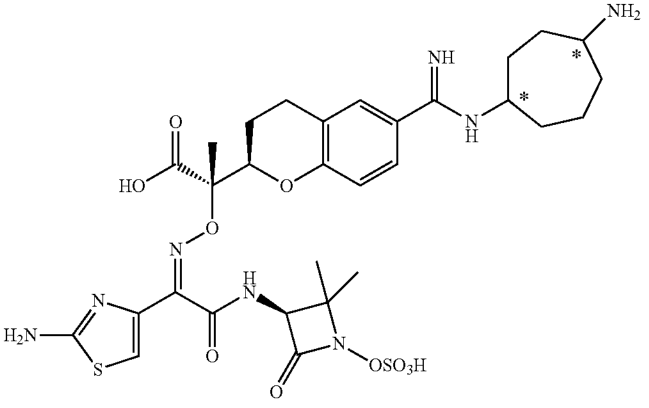

Compound 104

Step A—Synthesis of Intermediate 56a To a mixture of intermediate 3c (937 mg, 1.6 mmol) and intermediate 55b-3 (360 mg, 1.6 mmol) in MeCN (15.8 mL) was added acetic acid (0.54 mL, 9.5 mmol). The reaction was stirred at 70° C. for 4 h, then cooled down to room temperature, and purified directly by reverse phase HPLC (Isco; column: C18 (150 g); begin with 2 CV of 10%/MeCN—$H_2O$ (0.05% TFA), then 11 CV of 10-100% (gradient) MeCN—$H_2O$ (0.05% TFA)) to give intermediate 56a after lyophilization. LC-MS: m/z 647.3 $[M+H]^+$.

Step B—Synthesis of Intermediate 56b A solution of intermediate 56a (570 mg, 0.75 mmol) in DCM (5 mL) and TFA (10 mL) was heated to 40° C. and stirred for 90 min. Then the reaction mixture was cooled to ambient temperature and concentrated under vacuum. The resulting residue was dried under high vacuum for 2 h to provide intermediate 56b. LC-MS: m/z 391.2 $[M+H]^+$.

Step C—Synthesis of Compound 104 A mixture of intermediate 56b (464 mg, 0.75 mmol), intermediate 5 (301 mg, 0.83 mmol), and molecular sieves 4 Å (~500 mg) in MeOH (7.5 mL) was stirred at room temperature for 18 h. Then the mixture was filtered through a Celite™ pad, and the filtrate was concentrated in vacuo. The resulting residue was dissolved in water and purified by reverse phase HPLC (Isco; $C_{18}$-Aq 150 g column) with gradient elution of 0-30% MeCN (0.05% TFA)/water (0.05% TFA). The product fractions were collected and lyophilized to give the title compound as the TFA salt. The TFA salt was further purified by reverse phase HPLC (Isco; C18-Aq 50 g column) with gradient elution of 0-25% MeCN (0.1% FA)/water (0.1% FA). The product fractions were collected and lyophilized to give the title compound as the formic acid salt. LC-MS: m/z 737.3 $[M+H]^+$. $^1$HNMR (500 MHz, $D_2O$) δ: 7.54 (s, 1H), 7.51 (d, J=8.5 Hz, 1H), 7.04 (d, J=8.7 Hz, 1H), 7.01 (s, 1H), 4.60 (d, J=10.7 Hz, 1H), 3.96 (s, 1H), 3.56 (s, 1H), 3.04-2.91 (m, 2H), 2.34-2.28 (m, 1H), 2.28-2.14 (m, 4H), 2.00-1.91 (m, 1H), 1.91-1.75 (m, 6H), 1.69 (s, 3H), 1.59 (s, 3H), 1.38 (s, 3H). *One single diastereomer; absolute stereochemistry at * marked carbon centers is not assigned.

Example 80: Preparation of Compounds 105, 106 and 107

(S)-2-((R)-6-(N-((1R or S,4S or R)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (the Remaining Three Diastereomers of the Structure)

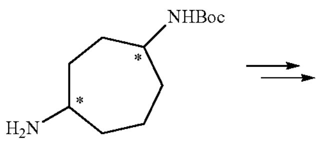

Int-55b-1
Int-55b-2
Int-55b-4

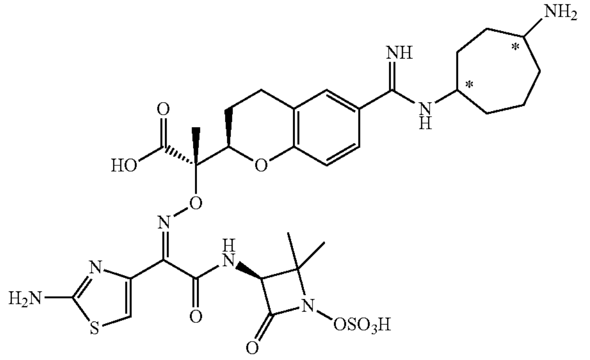

Compound 105
Compound 106
Compound 107

Compounds 105, 106, and 107 were prepared from the corresponding intermediates 55b-1, 55b-2, and 55b-4 according to the procedure of Step A to Step C of Example 79.

Compound 105: LC-MS: m/z 737.1 $[M+H]^+$. $^1$HNMR (500 MHz, $D_2O/CD_3CN$=4:1) δ: 7.71 (s, 1H), 7.71 (d, J=15.1 Hz, 1H), 7.21 (s, 1H), 7.21 (d, J=15.1 Hz, 1H), 4.95 (s, 1H), 4.12 (s, 1H), 3.67 (s, 1H), 3.23-3.08 (m, 2H), 2.52-2.39 (m, 3H), 2.25 (s, 3H), 2.14 (d, J=11.8 Hz, 3H), 1.99-1.89 (m, 1H), 1.86 (s, 3H), 1.82 (d, J=11.5 Hz, 1H), 1.76 (s, 3H), 1.70 (d, J=12.4 Hz, 1H), 1.56 (s, 3H).

Compound 106: LC-MS: m/z 737.1 $[M+H]^+$. $^1$HNMR (500 MHz, $D_2O/CD_3CN$=4:1): δ: 7.72 (s, 1H), 7.72 (d, J=7.1 Hz, 1H), 7.22 (d, J=7.1 Hz, 1H), 7.18 (s, 1H), 4.94 (s, 1H), 4.11 (s, 1H), 3.67 (s, 1H), 3.22-3.05 (m, 2H), 2.42 (s, 3H), 2.25 (s, 3H), 2.14 (s, 3H), 1.89 (d, J=12.5 Hz, 1H), 1.84 (s, 3H), 1.81-1.79 (m, 1H), 1.76 (s, 3H), 1.69 (d, J=12.1 Hz, 1H), 1.57 (s, 3H).

Compound 107: LC-MS: m/z 737.3 $[M+H]^+$. HNMR (500 MHz, $D_2O/CD_3CN$=4:1) δ: δ: 7.71 (s, 1H), 7.71 (d, J=8.0 Hz, 1H), 7.21 (d, J=8.0 Hz, 1H), 7.17 (s, 1H), 4.94 (s, 1H), 4.09 (s, 1H), 3.68 (s, H), 3.12-3.04 (i, 2H), 2.48-2.40 (m, 2H), 2.40-2.30 (m, 4H), 2.13-2.04 (m, 1H), 2.04-1.88 (i, 6H), 1.84 (s, 3H), 1.76 (s, 3H), 1.57 (s, 3H).

Example 81: Preparation of Compounds 108-111

Starting from the appropriate commercially available enantiomerically pure mono-Boc protected diamines, the following compounds were prepared according to the procedure in Step A to Step C of Example 79.

| Compound | Structure | $^1$H NMR | LCMS $[M + H]^+$ |
|---|---|---|---|
| 108 | 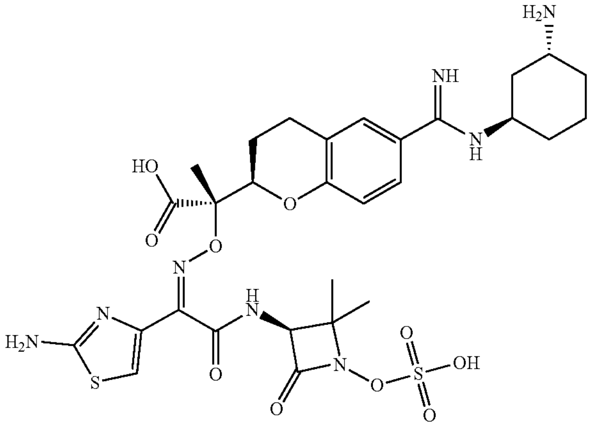 [SMILES: CC1(C)[C@H](NC(=O)/C(=N\O[C@](C)(C(=O)O)[C@H]2CCc3cc(C(=N)N[C@@H]4CCC[C@@H](N)C4)ccc3O2)c2csc(N)n2)C(=O)N1OS(=O)(=O)O] (S)-2-((R)-6-(N-((1R,3R)-3-aminocyclohexyl)-carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxo-ethylidene)-amino)oxy) propanoic acid | $^1$HNMR (500 MHz, $D_2O/CD_3CN$ = 4:1) δ: 7.83 (s, 1H), 7.84 (d, J = 13.1 Hz, 1H), 7.35 (d, J = 8.3 Hz, 1H), 7.26 (s, 1H), 5.09 (s, 1H), 4.48 (s, 1H), 3.99-3.91 (m, 1H), 3.35-3.19 (m, 2H), 2.62-2.50 (m, 3H), 2.24 (d, J = 24.7 Hz, 2H), 2.15 (d, J = 14.5 Hz, 4H), 1.94-1.92 (m, 1H), 1.96 (s, 3H), 1.89 (s, 3H), 1.71 (s, 3H). | 723.6 |

-continued

| Compound | Structure | $^1$H NMR | LCMS $[M + H]^+$ |
|---|---|---|---|
| 109 | 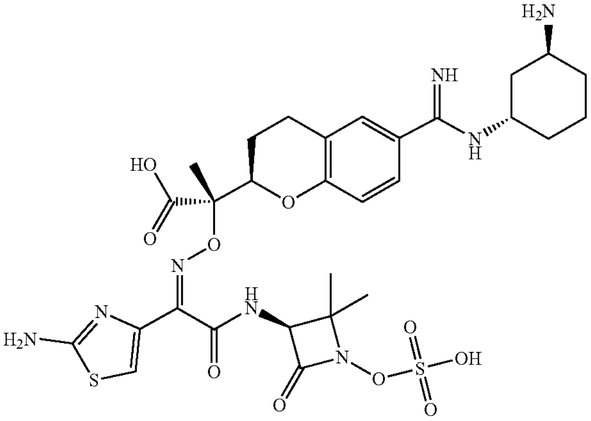 [SMILES: CC1(C)[C@H](NC(=O)/C(=N\O[C@](C)(C(=O)O)[C@H]2CCc3cc(C(=N)N[C@H]4CCC[C@H](N)C4)ccc3O2)c2csc(N)n2)C(=O)N1OS(=O)(=O)O] (S)-2-((R)-6-(N-((1S,3S)-3-aminocyclohexyl)-carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxo-ethylidene)-amino)-oxy)propanoic acid | $^1$HNMR (500 MHz, $D_2O/CD_3CN$ = 4:1) δ: 7.83 (s, 1H), 7.82 (d, J = 12.4 Hz, 1H), 7.33 (d, J = 7.0 Hz, 1H), 7.24 (s, 1H), 5.08 (s, 1H), 4.47 (s, 1H), 3.97-3.88 (m, 1H), 3.34-3.18 (m, 2H), 2.61-2.43 (m, 3H), 2.29-2.18 (m, 2H), 2.13 (d, J = 14.1 Hz, 4H), 1.92-1.90 (m, 1H), 1.92-1.90 (s, 3H), 1.87 (s, 3H), 1.69 (s, 3H). | 723.5 |
| 110 | 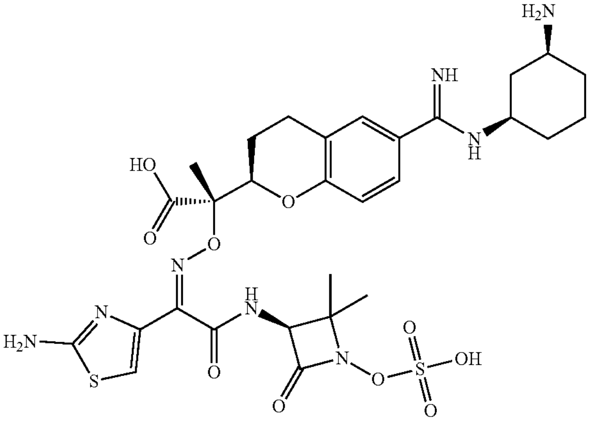 [SMILES: CC1(C)[C@H](NC(=O)/C(=N\O[C@](C)(C(=O)O)[C@H]2CCc3cc(C(=N)N[C@@H]4CCC[C@H](N)C4)ccc3O2)c2csc(N)n2)C(=O)N1OS(=O)(=O)O] (S)-2-((R)-6-(N-((1R,3S)-3-aminocyclohexyl)-carbamimidoyl)chroman-2-yl)-2-((((Z)-1-(2-amino-thiazol-4-yl)-2-(((S)-2,2-dimethyl-4-oxo-1-(sulfooxy)azetidin-3-yl)amino)-2-oxo-ethylidene)-amino)oxy)propanoic acid | $^1$HNMR (500 MHz, $D_2O/CD_3CN$ = 4:1) δ: 7.83 (s, 1H), 7.82 (d, J = 14.7 Hz, 1H), 7.33 (d, J = 7.9 Hz, 1H), 7.23 (s, 1H), 5.04 (s, 1H), 4.12-4.02 (m, 1H), 3.69-3.59 (m, 1H), 3.32-3.15 (m, 2H), 2.77-2.70 (m, 1H), 2.57-2.47 (m, 1H), 2.46-2.42 (m, 1H), 2.34-2.28 (m, 1H), 2.15-2.09 (m, 1H), 1.90-1.88 (m, 1H), 1.93 (s, 3H), 1.86 (s, 3H), 1.83-1.71 (m, 4H), 1.69 (s, 3H). | 723.5 |

-continued

| Compound | Structure | $^1$H NMR | LCMS $[M + H]^+$ |
|---|---|---|---|
| 111 | 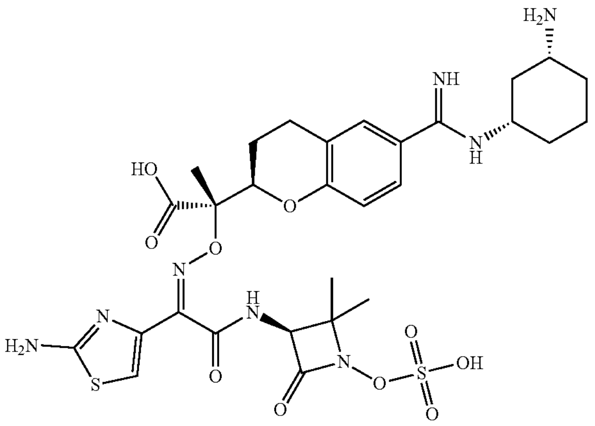 [SMILES: CC1(C)[C@H](NC(=O)/C(=N\O[C@](C)(C(=O)O)[C@H]2CCc3cc(C(=N)N[C@H]4CCC[C@@H](N)C4)ccc3O2)c2csc(N)n2)C(=O)N1OS(=O)(=O)O] (S)-2-((R)-6-(N-((1S,3R)-3-aminocyclohexyl)-carbamimidoyl)chroman-2-yl)-2-(((Z)-1-(2-aminothiazol-4-yl)-2-(((S)-2,2-dimethyl-4-oxo-1-(sulfooxy)azetidin-3-yl)amino)-2-oxo-ethylidene)amino)oxy) propanoic acid | $^1$HNMR (500 MHz, $D_2O/CD_3CN$ = 4:1) δ: 7.83 (s, 1H), 7.82 (d, J = 14.7 Hz, 1H), 7.33 (d, J = 7.9 Hz, 1H), 7.23 (s, 1H), 5.04 (s, 1H), 4.14-4.04 (m, 1H), 3.72-3.64 (m, 1H), 3.35-3.18 (m, 2H), 2.81-2.72 (m, 1H), 2.58-2.50 (m, 1H), 2.37-2.32 (m, 1H), 2.34-2.29 (m, 1H), 2.24-2.12 (m, 1H), 1.94-1.92 (m, 1H), 1.93 (s, 3H), 1.86 (s, 3H), 1.83-1.71 (m, 4H), 1.69 (s, 3H). | 723.7 |

Example 82: Preparation of Compound 112

(S)-2-((R)-6-(N-((1s,3S)-3-(aminomethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

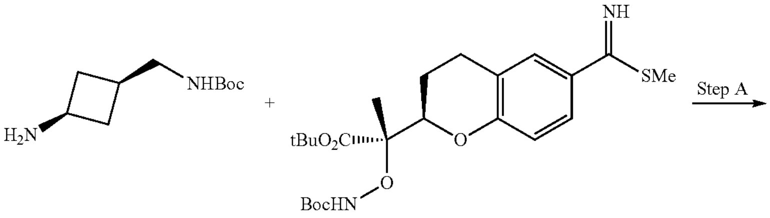

Int-3c

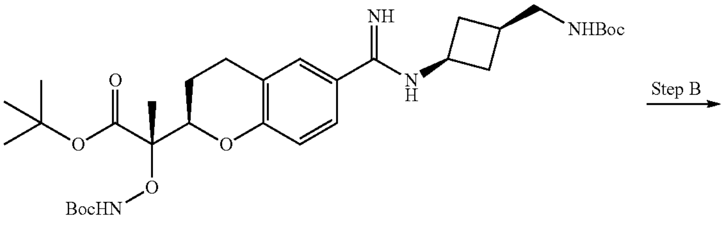

Int-57a

-continued

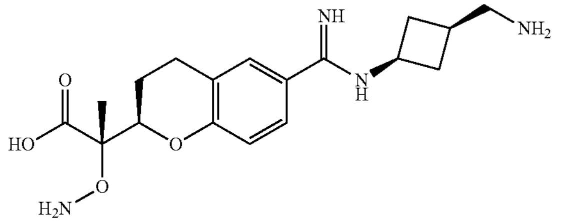

Int-57b

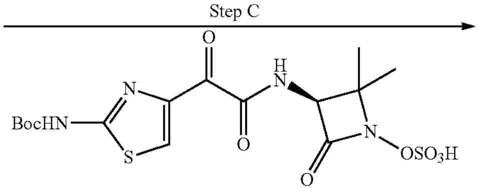

Int-4

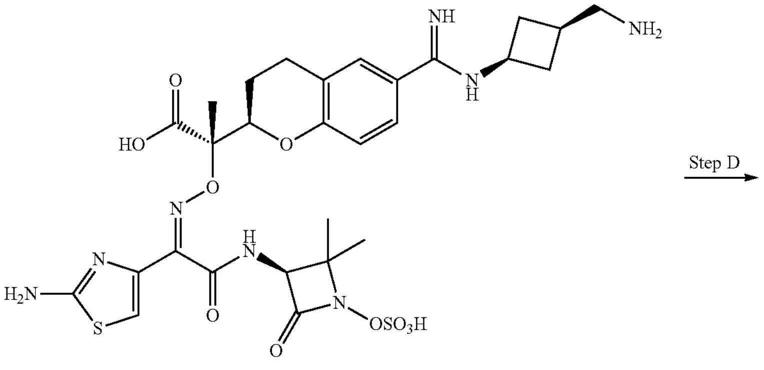

Int-57c

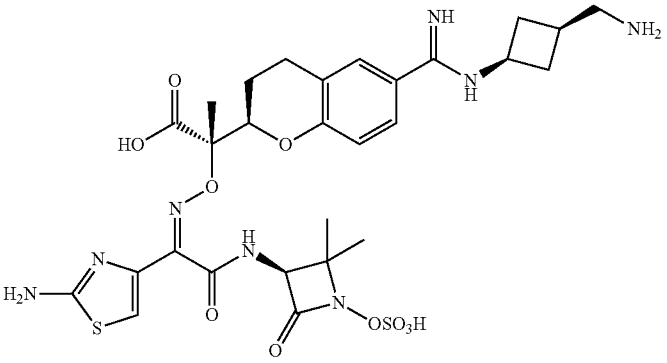

Compound 112

Step A—Synthesis of Intermediate 57a To a vial containing a mixture of cis-3-(Boc-aminomethyl)cyclobutylamine (86 mg, 0.429 mmol) in anhydrous acetonitrile (4 mL) were added intermediate 3c (0.2 g, 0.429 mmol) and acetic acid (0.086 mL, 1.50 mmol). The reaction mixture was heated at 65° C. for 3 h. Then the reaction mixture was cooled to ambient temperature and purified on reverse phase Isco Combiflash (C 18, 50 g column; 0-100% (gradient) water+0.05% TFA/ACN+0.05% TFA) to give the desired compound. LC-MS: m/z 619.8 $[M+H]^+$.

Step B—Synthesis of Intermediate 57b To a vial containing intermediate 57a (0.235 g, 0.38 mmol) was added 2:1 trifluoroacetic acid/anhydrous dichloromethane (6 mL) at ambient temperature. The reaction was stirred for 16 h, then a solution of 4:1 toluene/MeOH (10 mL) was added, and the reaction mixture was concentrated in vacuo. The resulting residue was azeotroped with 4:1 toluene/MeOH (10 mL) and dried under high vacuum to give intermediate 57b. LC-MS: m/z 363.2 $[M+H]^+$.

Step C—Synthesis of Intermediate 57c To a vial charged with intermediate 57b (0.138 g, 0.381 mmol) and intermediate 4 (0.177 g, 0.381 mmol) was added MeOH (5.0 mL) at ambient temperature. The reaction mixture was stirred for 6 h and then concentrated in vacuo to afford intermediate 57c, which was used in the next reaction without further purification. LC-MS: m/z 809.0 $[M+H]^+$.

Step D—Synthesis of Compound 112 To a vial charged with intermediate 57c (0.308 g, 0.381 mmol) was added a mixture of 1:2 trifluoroacetic acid/anhydrous dichloromethane (6 mL) at ambient temperature. The reaction mixture was stirred for 1 h, then cooled to 0° C., followed by the slow addition of ethyl ether (6 mL). The resulting solid was collected by centrifugation (1400 rpm) and purified via reverse phase HPLC (Gilson, C18, 5 um, OBD 30λ150 mm, ACN+0.05% TFA/water+0.05% TFA, 0-40% gradient over 18 min., 30 mL/min.). The product fractions were collected, concentrated in vacuo, and the resulting aqueous layer was directly purified on an Amberchrom CG161M column (26 g), washed with 9 CV of (water+0.1% FA), and eluted off with 3 CV of 100% (MeCN+0.1% FA) followed by 3 CV of 50% (MeCN+0.1% FA)/(water+0.1% FA). The product fractions were collected, concentrated in vacuo, and the resulting aqueous residue was lyophilized to give compound 112 as the formic acid salt. LC-MS: m/z 709.4 $[M+H]^+$. $^1$HNMR (500 MHz, 400 uL $D_2O$/100 uL $CD_3CN$) δ: 7.59-7.55 (m, 2H), 7.08-7.07 (d, J=5 Hz, 1H), 7.00 (s, 1H), 4.79 (s, 1H), 4.59-4.56 (m, 1H), 4.27-4.19 (m, 1H), 3.18-3.16 (d, J=10 Hz, 2H), 3.02-2.94 (m, 2H), 2.86-2.78 (m, 1H), 2.58-2.50 (m, 1H), 2.26 (br, 1H), 2.15-2.04 (m, 3H), 1.90 (m, 1H), 1.69 (s, 3H), 1.61 (s, 3H), 1.42 (s, 3H).

Example 83: Preparation of Compounds 113 and 114

The following compounds were prepared from commercially available mono-Boc protected diamines using the procedure of Step A to Step D of Example 82.

| Compound | Structure | $^1$H NMR | LC-MS $[M + H]^+$ |
|---|---|---|---|
| 113 | 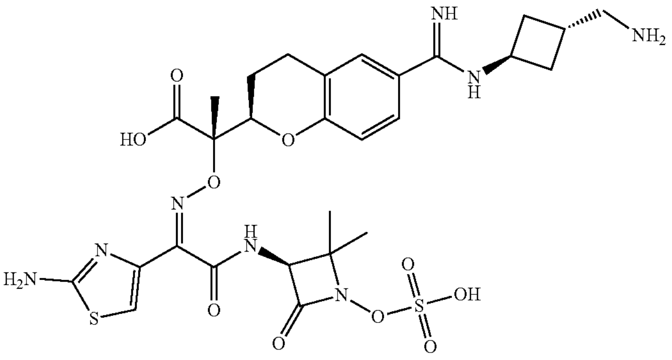 [SMILES: CC1(C)[C@H](NC(=O)/C(=N\O[C@](C)(C(=O)O)[C@H]2CCc3cc(C(=N)N[C@H]4C[C@H](CN)C4)ccc3O2)c2csc(N)n2)C(=O)N1OS(=O)(=O)O] (S)-2-((R)-6-(N-((1r,3R)-3-(aminomethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxo-ethylidene)amino)oxy) propanoic acid | $^1$HNMR (500 MHz, 400 uL $D_2O$/100 uL $CD_3CN$) δ: 7.50-7.46 (m, 2H), 6.98-6.94 (m, 2H), 4.51 (d, J = 15 Hz, 1H), 4.32-4.25 (m, 1H), 3.16-3.14 (d, J = 10 Hz, 2H), 2.96-2.83 (m, 2H), 2.75 (br s, 1H), 2.48-2.36 (m, 4H), 2.14 (br s, 1H), 2.06-2.01 (m, 1H), 1.82 (br s, 1H), 1.55 (s, 3H), 1.49 (s, 3H), 1.31 (s, 3H). | 708.0 |
| 114 | 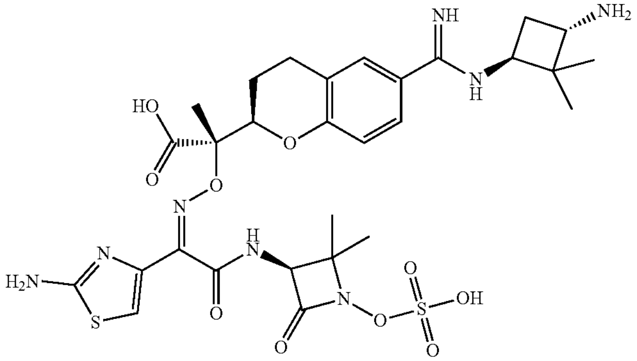 [SMILES: CC1(C)[C@@H](NC(=N)c2ccc3c(c2)CC[C@H]([C@](C)(O/N=C(\C(=O)N[C@@H]2C(=O)N(OS(=O)(=O)O)C2(C)C)c2csc(N)n2)C(=O)O)O3)C[C@@H]1N] (S)-2-((R)-6-(N-((1S,3S)-3-amino-2,2-dimethylcyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxo-ethylidene)amino)oxy) propanoic acid | $^1$HNMR (500 MHz, 400 uL $D_2O$/100 uL $CD_3CN$) δ: 7.43-7.39 (m, 2H), 6.92-6.83 (m, 2H), 4.43-4.40 (m, 1H), 4.08 (br s, 1H), 3.61 (br s, 1H), 3.34 (s, 1H), 2.98 (s, 1H), 2.81 (br s, 2H), 2.64 (br s, 1H), 2.60 (br s, 1H), 2.10 (br s, 1H), 1.97-1.95 (m, 4H), 1.77 (br s, 1H), 1.52 (s, 3H), 1.43 (s, 3H), 1.30 (s, 3H), 1.24-1.09 (m, 6H). | 723.5 |

Example 84: Preparation of Intermediates 58c-1 and 58c-2

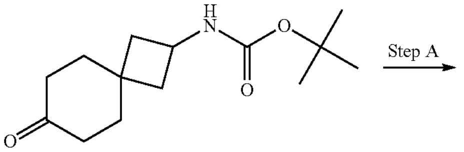

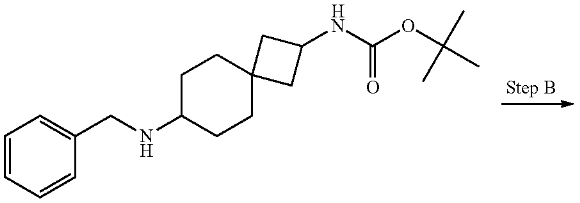

Int-58a

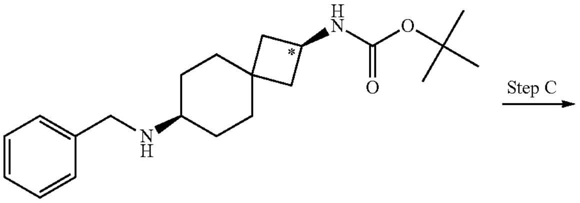

Int-58b-1

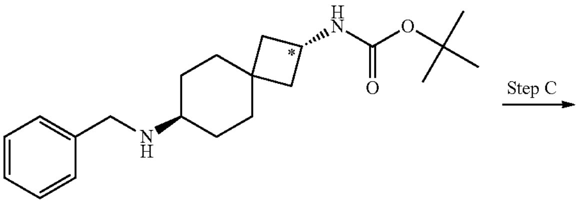

Int-58b-2

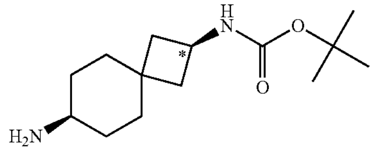

Int-58c-1

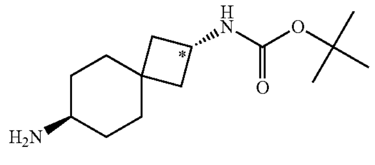

Int-58c-2

Step A—Synthesis of Intermediate 58a To a stirred solution of tert-butyl (7-oxospiro[3.5]nonan-2-yl)carbamate (500 mg, 1.974 mmol) in MeOH (8 mL) under $N_2$ was added benzylamine (0.432 mL, 3.95 mmol). The reaction was stirred at ambient temperature for 2 h. Then sodium cyanoborohydride (496 mg, 7.89 mmol) was added portion wise, and the reaction mixture was stirred at ambient temperature for 18 h. Then the reaction mixture was partitioned between ethyl acetate (100 mL) and water (100 mL). The organic layers were separated, washed with brine, dried over anhydrous $MgSO_4$, and filtered. The filtrate was concentrated under vacuum, and the resulting residue was purified by silica gel chromatography (ISCO 80 g, eluting with 0-100% EtOAc/hexanes (gradient)) to afford intermediate 58a as a mixture of enantiomers. LC-MS: m/z 345.3 $[M+H]^+$.

Step B—Synthesis of Intermediate 58b-1 and Intermediate 58b-2 Enantiomers of intermediate 58a (546 mg, 1.585 mmol) were further separated by chiral SFC (AD-H 250 mm column, 25% MeOH+0.2% DIPA, 210 nm wavelength, injection volume 1.8 mL, flow rate 50 ml/min) to individually afford intermediate 58b-1 (the first eluting isomer, LC-MS: m/z 345.3 $[M+H]^+$) and intermediate 58b-2 (the second eluting isomer, LC-MS: m/z 345.3 $[M+H]^+$).

Step C—Synthesis of Intermediates 58c-1 and 58c-2 To a solution of intermediate 58b-1 (190 mg, 0.552 mmol) in MeOH (3 mL) was added Pd/C (58.7 mg, 0.055 mmol, 10 wt. %) and the reaction was stirred at ambient temperature under $H_2$ (1 atm) for 1 h. Then the reaction mixture was filtered, and the filtrate was concentrated under vacuum to afford intermediate 58c-1 which was used in the next step without further purification. TLC: EtOAc/hexanes 1/1, Rf=0.1.

Intermediate 58c-2 was prepared from intermediate 58b-2 according to the procedure of Step C of Example 84. TLC: EtOAc/hexanes 1/1, $R_f$=0.1.

Example 85: Preparation of Compounds 115 and 116

(S)-2-((R)-6-(N-((2S,4s,7S)-2-aminospiro[3.5]nonan-7-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid and (S)-2-((R)-6-(N-((2R,4r,7R)-2-aminospiro[3.5]nonan-7-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (Stereochemistry at * Marked Center was Unassigned)

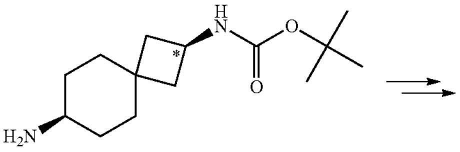

Int-58c-1

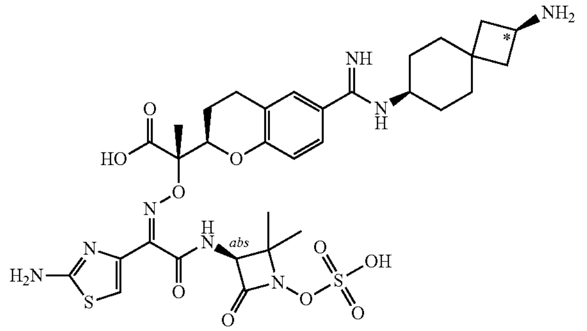

Compound 115

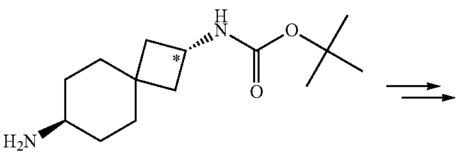

Int-58c-2

-continued

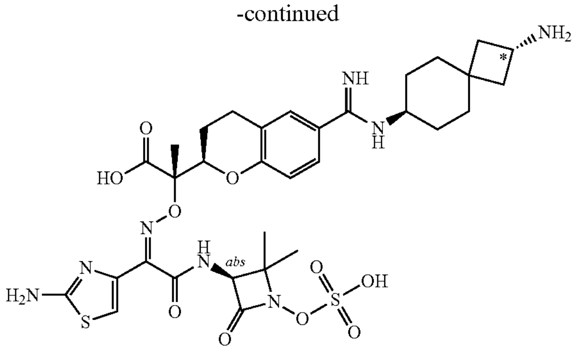

Compound 116

Compounds 115 and 116 were prepared from intermediate 58c-1 and intermediate 58c-2 according to the procedure in Step A to Step D of Example 82.

Compound 115: LC-MS: m/z 763.6 $[M+H]^+$. $^1$HNMR (500 MHz, 400 uL $D_2O$/100 uL $CD_3CN$) δ: 7.62-7.58 (m, 2H), 7.13 (d, J=10 Hz, 1H), 7.03 (s, 1H), 4.85 (s, 1H), 4.60-4.56 (m, 1H), 3.97-3.88 (m, 1H), 3.71 (br s, 1H), 3.03 (br s, 2H), 2.52 (br s, 1H), 2.32 (br s, 2H), 2.20-2.17 (m, 3H), 2.13-1.89 (m, 8H), 1.73 (s, 3H), 1.65 (s, 3H), 1.49 (s, 3H).

Compound 116: LC-MS: m/z 763.5 $[M+H]^+$. $^1$HNMR (500 MHz, 400 uL $D_2O$/100 uL $CD_3CN$) δ: 7.57-7.53 (m, 2H), 7.09 (d, J=15 Hz, 1H), 7.01 (s, 1H), 4.80 (s, 1H), 4.60-4.56 (m, 1H), 3.90-3.84 (m, 1H), 3.67 (br s, 1H), 2.99 (br s, 2H), 2.47 (br s, 1H), 2.29 (br s, 2H), 2.17-2.14 (m, 3H), 2.08-1.83 (m, 8H), 1.69 (s, 3H), 1.62 (s, 3H), 1.44 (s, 3H).

Example 86: Preparation of Intermediates 59e-1 and 59e-2

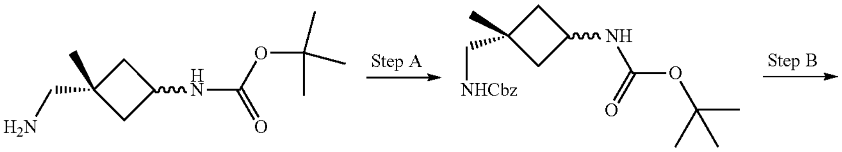

Int-59a

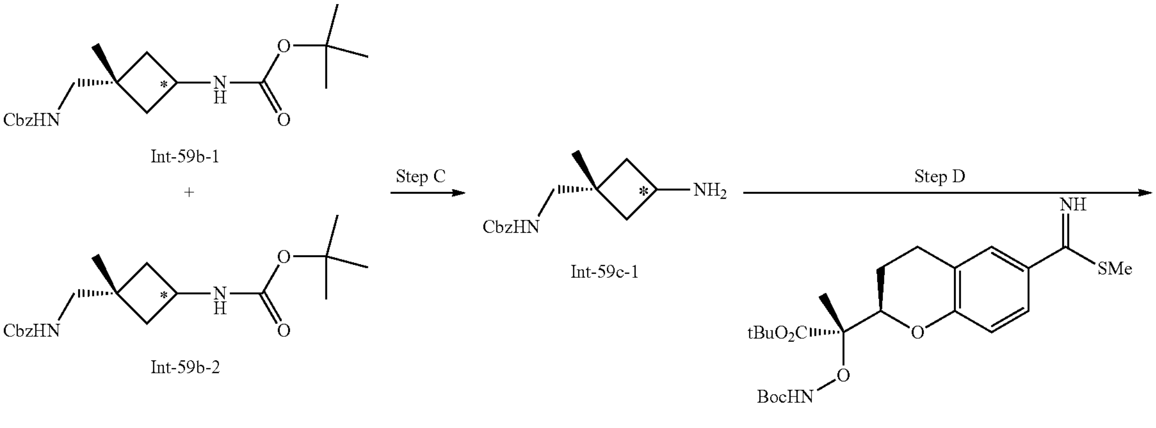

Int-59b-1

+

Int-59b-2

Int-59c-1

Int-3c

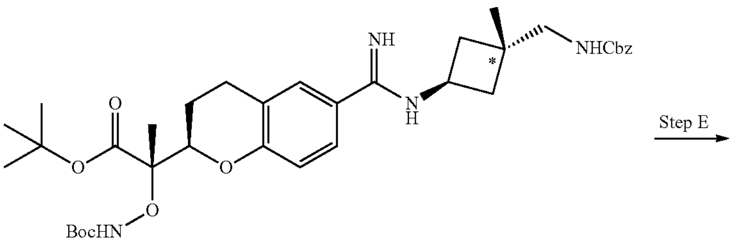

Int-59d-1

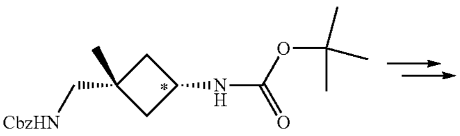

Int-59b-2

-continued

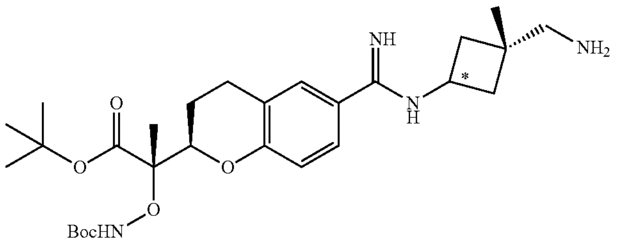

Int-59e-1

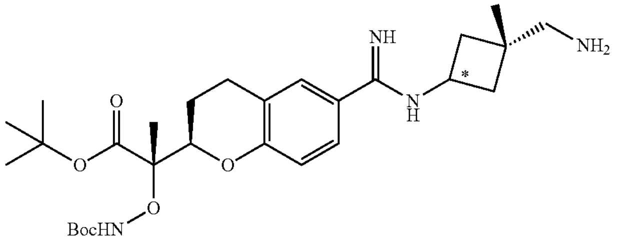

Int-59e-2

Step A—Synthesis of Intermediate 59a To a mixture of tert-butyl (3-(aminomethyl)-3-methylcyclobutyl)carbamate (350 mg, 1.633 mmol) in DCM (5 mL) was added TEA (0.341 mL, 2.450 mmol), followed by benzyl chloroformate (0.281 mL, 1.960 mmol). The reaction mixture was stirred at ambient temperature for 18 h, then diluted with DCM and washed with saturated aqueous $NaHCO_3$ solution. The organic layer was separated, dried over anhydrous $MgSO_4$, and filtered. The filtrate was concentrated under vacuum. The resulting residue was purified by silica gel chromatography (Isco, 40 g column, 0-50% EtOAc in hexane, gradient) to give intermediate 59a as a mixture of stereoisomers. LC-MS: m/z 349.3 $[M+H]^+$.

Step B—Synthesis of Intermediates 59b-1 and 59b-2 Intermediate 59a (420 mg, 1.205 mmol) was further separated by SFC (AD-H, 21×250 mm column, eluting with 15% $IPA/CO_2$, 100 bar, 220 nm wavelength, injection volume 0.3 mL, flow rate 60 mL/min) to individually afford intermediate 59b-1 (the first eluting stereoisomer) and intermediate 59b-2 (the second eluting stereoisomer). LC-MS: m/z 349.3 $[M+H]^+$.

Step C—Synthesis of Intermediate 59c-1 To a solution of intermediate 59b-1 (140 mg, 0.402 mmol) in DCM (5 mL) stirred at 0° C., was added TFA (0.615 mL, 8.04 mmol). The reaction was stirred at 0° C. for 1 h. The reaction mixture was diluted with 30% toluene/MeOH (6 mL) and concentrated under vacuum to afford intermediate 59c-1, which was used in the next reaction without further purification. LC-MS: m/z 249.3 $[M+H]^+$.

Step D—Synthesis of Intermediate 59d-1 To a mixture of intermediate 59c-1 (102 mg, 0.411 mmol) in anhydrous acetonitrile (4 mL) were added intermediate 3c (0.16 g, 0.343 mmol) and acetic acid (0.069 mL, 1.20 mmol). The reaction mixture was heated at 65° C. for 1 h. Then the reaction was cooled to ambient temperature and purified via reverse phase HPLC (C18, 100 g column, 0-100% 0.05% TFA water/ACN, (gradient)) to give intermediate 59d-1. LC-MS: m/z 667.6 $[M+H]^+$.

Step E—Synthesis of Intermediates 59e-1 and 59e-2 To a solution of intermediate 59d-1 (215 mg, 0.322 mmol) in EtOH (5 mL) was added Pd/C (30 mg, 10 wt. %, 50% moisture). The reaction mixture was stirred at ambient temperature under $H_2$ (1 atm) for 1 h. Then the reaction mixture was filtered, and the filtrate was concentrated under vacuum to afford intermediate 59e-1, which was used in the next reaction without further purification. LC-MS: m/z 533.5 $[M+H]^+$.

Intermediate 59e-2 was prepared from intermediate 59b-2 using the procedure of Step C to Step D of Example 86. LC-MS: m/z 533.4 $[M+H]^+$.

Example 87: Preparation of Compounds 117 and 118

(S)-2-((R)-6-(N-((1s,3S)-3-(aminomethyl)-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid. and (S)-2-((R)-6-(N-((1r,3R)-3-(aminomethyl)-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

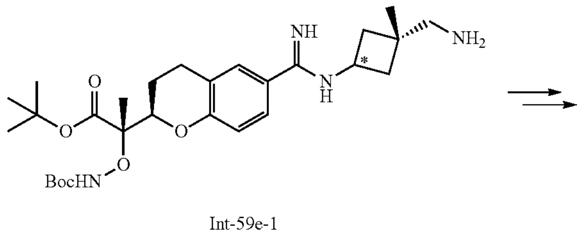

Int-59e-1
Int-59e-2

-continued

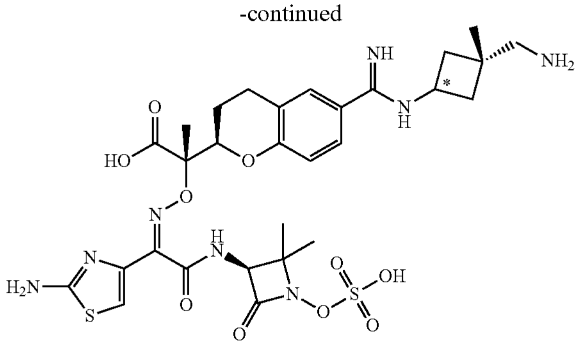

Compound 117
Compound 118

Compounds 117 and 118 were prepared from intermediate 59e-1 and intermediate 59e-2 according to the procedure of Step B to Step D of Example 82.

Compound 117: LC-MS: m/z 723.6 $[M+H]^+$. $^1$HNMR (500 MHz, 400 uL $D_2O$/100 uL $CD_3CN$) δ: 7.51-7.47 (m, 2H), 7.00-6.96 (m, 2H), 4.52-4.50 (m, 1H), 4.39-4.31 (m, 1H), 3.08 (s, 2H), 2.89 (br s, 2H), 2.47-2.42 (m, 2H), 2.21-2.16 (m, 2H), 2.07-2.04 (m, 2H), 1.85 (br s, 1H), 1.61 (s, 3H), 1.52 (s, 3H), 1.33 (s, 6H).

Compound 118: LC-MS: m/z 723.6 $[M+H]^+$. $^1$HNMR (500 MHz, 400 uL $D_2O$/100 uL $CD_3CN$) δ: 7.56-7.53 (m, 2H), 7.06 (d, J=10 Hz, 1H), 6.99 (s, 1H), 4.77 (s, 1H), 4.58-4.55 (m, 1H), 4.30-4.26 (m, 1H), 3.20 (s, 2H), 2.95 (br s, 2H), 2.65 (br s, 2H), 2.21 (br s, 2H), 2.12-2.10 (m, 2H), 1.88 (br s, 1H), 1.67 (s, 3H), 1.58 (s, 3H), 1.40 (s, 3H), 1.35 (s, 3H). *Each compound is a single diastereomer; stereochemistry at * marked carbon center is unassigned.

Example 88: Preparation of Intermediate 60i-1

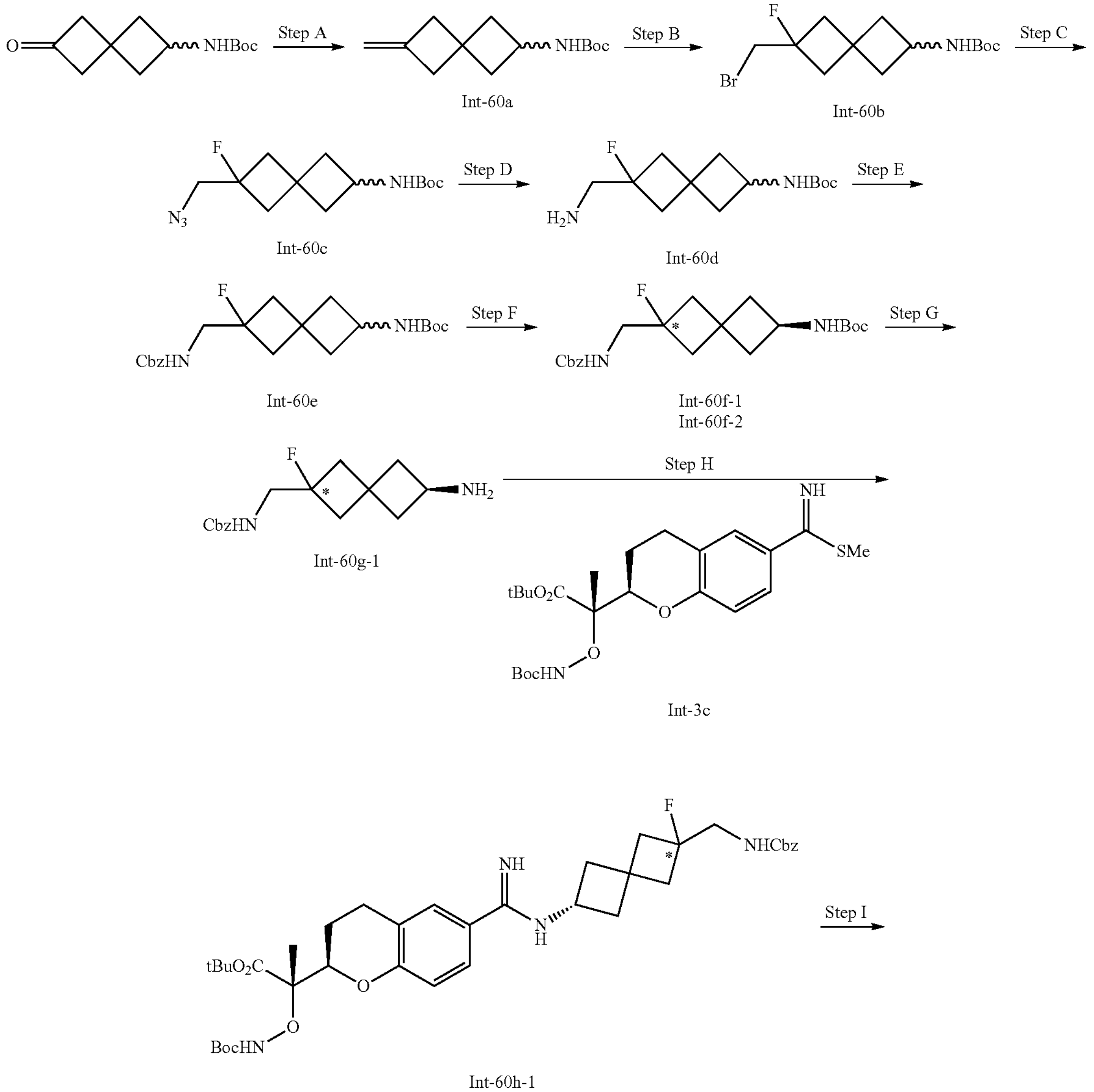

Int-60a
Int-60b
Int-60c
Int-60d
Int-60e
Int-60f-1
Int-60f-2
Int-60g-1
Int-3c
Int-60h-1

-continued

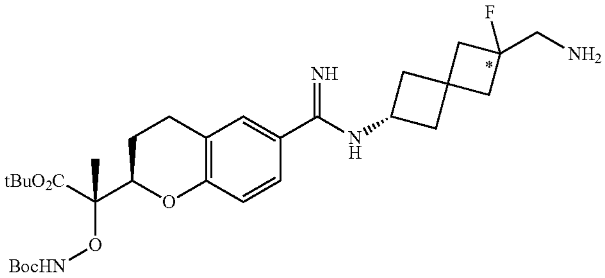

Int-60i-1

Step A—Synthesis of Intermediate 60a NaH (0.568 g, 14.20 mmol) was added in one portion to a stirred mixture of methyltriphenylphosphonium bromide (5.07 g, 14.20 mmol) in DMSO (18 mL) at ambient temperature. The reaction mixture was stirred for 30 minutes, then tert-Butyl (6-oxospiro[3.3]heptan-2-yl)carbamate (2 g, 8.88 mmol) was added in one portion. The reaction mixture was stirred for 1.5 h, then poured into a flask containing ~ 200 g of ice. $Et_2O$ (150 mL) was added to the mixture, followed by another addition of EtOAc (50 mL), and the mixture was stirred for one hour. Then the layers were separated and the aqueous layer was extracted with 1:1 $Et_2O$/EtOAc (100 mL). The organic layers were combined, washed with brine and dried over anhydrous magnesium sulfate, and filtered. The filtrate was concentrated under vacuum. The resulting residue was dissolved in $CH_2Cl_2$ and loaded onto a dry Biotage 120 g silica gel column. The solvent was removed from the column via a nitrogen stream. Gradient elution (0% to 50% EtOAc in hexanes) afforded intermediate 60a. TLC: 50% EtOAc/hexanes, $R_f$=0.8.

Step B—Synthesis of Intermediate 60b Triethylamine trihydrofluoride (2.92 mL, 17.91 mmol) was added to a stirred mixture of intermediate 60a (1.6 g, 7.16 mmol) in DCM (20 mL). The reaction was stirred at ambient temperature for 10 minutes, then a solution of N-bromosuccinimide (1.913 g, 10.75 mmol) in DCM (30 mL) was added dropwise. The reaction mixture was stirred at ambient temperature for 3 h, then partitioned between DCM and saturated sodium thiosulfate solution for 1 h with stirring. The layers were then separated and the aqueous layer was extracted with 1:1 $Et_2O$/EtOAc (100 mL). The organic layers were combined, washed with brine, dried over anhydrous magnesium sulfate, and filtered. The filtrate concentrated under vacuum. The resulting residue was dissolved in $CH_2Cl_2$ and loaded onto a dry Biotage 120 g silica gel column. The solvent was removed from the column via nitrogen stream. Gradient elution (0% to 50% EtOAc in hexanes) provided intermediate 60b. TLC: 50% EtOAc/hexanes, $R_f$=0.6.

Step C—Synthesis of Intermediate 60c A mixture of intermediate 60b (1.93 g, 5.99 mmol) and $NaN_3$ (0.506 g, 7.79 mmol) in DMSO (10 mL) was stirred at 120° C. for 18 h. Then the reaction mixture was partitioned between EtOAc (150 mL) and brine (150 mL). The layers were separated and the organic layer was washed with brine, dried over anhydrous $MgSO_4$, and filtered. The filtrate was concentrated under vacuum to give intermediate 60c. TLC: 50% EtOAc/hexanes, $R_f$=0.5.

Step D—Synthesis of Intermediate 60d To a stirred mixture of intermediate 60c (0.7 g, 2.462 mmol) in THF (12 mL) and water (10 mL) at room temperature, was added polymer-bound $PPh_3$ (3 mmol/g, 1.23 g, 3.69 mmol). The reaction mixture was stirred at room temperature overnight, then filtered. The filtrate was concentrated to afford intermediate 60d, which was used in the next reaction without further purification. TLC: 50% EtOAc/hexanes, $R_f$=0.1.

Step E—Synthesis of Intermediate 60e To a mixture of intermediate 60d (295 mg, 1.142 mmol) in DCM (5 mL) was added TEA (0.318 mL, 2.284 mmol), followed by the addition of benzyl chloroformate (0.246 mL, 1.713 mmol). The reaction mixture was stirred at ambient temperature overnight, then diluted with DCM, and washed with saturated aqueous $NaHCO_3$ solution. The organic phase was dried over anhydrous $MgSO_4$ and filtered. The filtrate was concentrated under vacuum, and the resulting residue was purified by silica gel chromatography (ISCO, 40 g column, gradient elution of 0-50% EtOAc in hexanes) provided intermediate 60e as a mixture of enantiomers. LC-MS: m/z 393.3[M+H]$^+$.

Step F—Synthesis of Intermediate 60f-1 and Intermediate 60f-2 The enantiomers of intermediate 60e (247 mg, 0.629 mmol) were further separated by AD-H column (21×250 mm, co-solvent: 15% EtOH/$CO_2$, 210 nm wavelength, injection volume 1.5 mL, flow rate 50 mL/min) to afford intermediate 60f-1 (the first eluting enantiomer) and intermediate 60f-2 (the second eluting enantiomer). LC-MS: m/z 393.3 [M+H]$^+$.

Step G—Synthesis of Intermediate 60g-1 To a solution of intermediate 60f-1 (100 mg, 0.255 mmol) in DCM (4 mL) stirred at 0° C., was added TFA (0.39 mL, 5.1 mmol). The reaction was stirred at ambient temperature for 1 h, then diluted with 30% toluene/MeOH (6 mL) and concentrated under vacuum to afford intermediate 60g-1, which was used in the next reaction without further purification. LC-MS: m/z 293.3 [M+H]$^+$.

Step H—Synthesis of Intermediate 60h-1 To a vial containing a mixture of intermediate 60g-1 (75 mg, 0.257 mmol) in anhydrous acetonitrile (4 mL) were added intermediate 3c (0.10 g, 0.214 mmol) and acetic acid (0.043 mL, 0.75 mmol). The reaction mixture was heated at 65° C. for 1 h. Then the reaction was cooled to ambient temperature and purified on reverse phase HPLC (ISCO, C18, 100 g column, gradient elution with 0-100% ACN+0.05% TFA/water+0.05% TFA) to give intermediate 60h-1. LC-MS: m/z 711.6[M+H]+.

Step I—Synthesis of Intermediate 60i-1 To a solution of intermediate 60h-1 (80 mg, 0.113 mmol) in ethanol (5 mL) was added Pd/C (30 mg, 10 wt. %, 50% moisture). The reaction mixture was stirred at ambient temperature under $H_2$ (1 atm) for 1 h, and then filtered. The filtrate was concentrated under vacuum to afford a intermediate 60i-1. LC-MS: m/z 577.5 [M+H]+.

Example 89: Preparation of Compound 119

(S)-2-((R)-6-(N-(6-(aminomethyl)-6-fluorospiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (Single Diastereomer, Stereochemistry at * Marked Carbon Center was Unassigned)

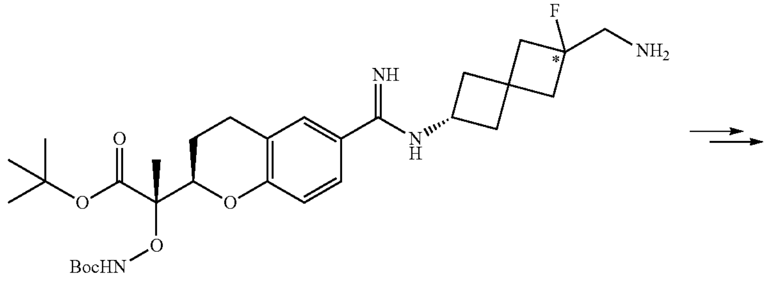

Int-60i-1

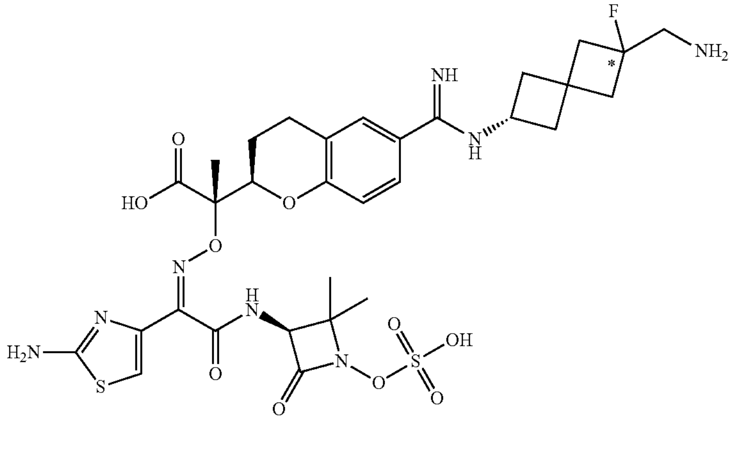

Compound 119

Compound 119 was prepared from intermediate 60i-1 according to the procedure in Step B to Step D of Example 82. Compound 119: LC-MS: m/z 767.6 [M+H]+. $^1$HNMR (500 MHz, 400 uL $D_2O$/100 uL $CD_3CN$) δ: 7.42-7.39 (m, 2H), 6.93-6.88 (m, 2H), 4.45-4.42 (m, 1H), 4.12-4.08 (m, 1H), 3.27-3.21 (m, 2H), 2.81 (br s, 2H), 2.65-2.22 (m, 7H), 2.10 (br s, 1H), 1.99-1.97 (m, 2H), 1.78 (br s, 1H), 1.54 (s, 3H), 1.45 (s, 3H), 1.26 (s, 3H).

Example 90: Preparation of Intermediate 61f

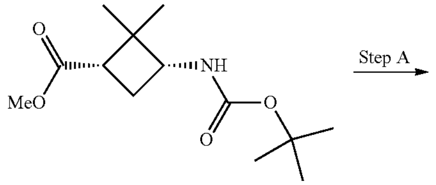

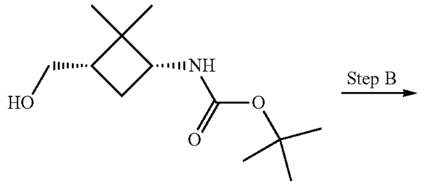

Int-61a

-continued

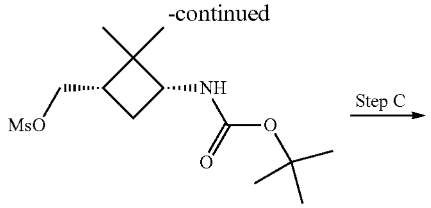

Int-61b

-continued

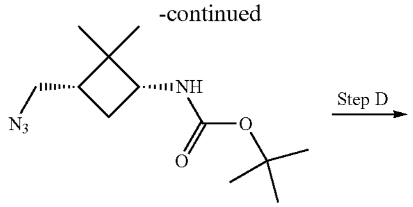

Int-61c

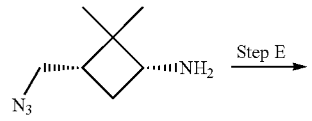

Int-61d

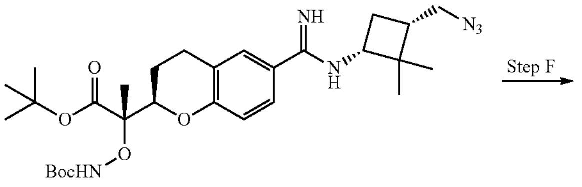

Int-61e

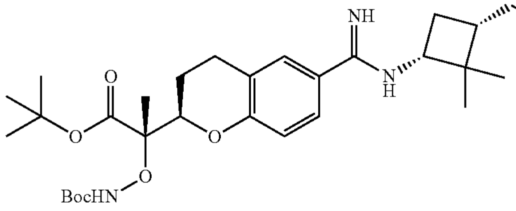

Int-61f

Step A—Synthesis of Intermediate 61a To a stirred solution of methyl (1S,3R)-3-((tert-butoxycarbonyl)amino)-2,2-dimethylcyclobutane-1-carboxylate (510 mg, 1.982 mmol) in THF (15 mL) at −12° C. (ice/acetone bath) was added a solution of LAH in THF (2 M, 1.486 mL, 2.97 mmol). The reaction was stirred at −10° C. for 45 minutes, then quenched with NaOH (1 N, 20 mL), and extracted with EtOAc (2×50 mL). The combined organic layers were washed with brine, dried over anhydrous $MgSO_4$, and filtered. The filtrate was concentrated under vacuum to give intermediate 61a, which was used in the next reaction without further purification. TLC: 50% EtOAc/hexanes, $R_f$=0.3.

Step B—Synthesis of Intermediate 61b To a stirred solution of intermediate 61a (456 mg, 1.988 mmol) and TEA (0.416 ml, 2.98 mmol) in THF (15 mL) at 0° C., was added methanesulfonyl chloride (0.185 mL, 2.386 mmol). The reaction was allowed to warm to ambient temperature and stirred for 1 h. Then the reaction was quenched with saturated $NaHCO_3$ solution, and extracted with EtOAc. The organic layer was separated, washed with brine, dried over anhydrous $MgSO_4$, and filtered. The filtrate was concentrated under vacuum to give intermediate 61b, which was used in the next reaction without further purification. TLC: 50% EtOAc/hexanes, $R_f$=0.5.

Step C—Synthesis of Intermediate 61c $NaN_3$ (258 mg, 3.97 mmol) was added to a stirred solution of intermediate 61b (610 mg, 1.984 mmol) in DMF (10 mL) at ambient temperature. The reaction was stirred at 70° C. for 3 h, then quenched with saturated $NaHCO_3$ solution, extracted with EtOAc. The combined organic layers were washed with brine, dried over anhydrous $MgSO_4$, and filtered. The filtrate was concentrated under vacuum, and the resulting residue was purified by silica gel chromatography (ISCO, 40 g column, gradient elution with 0-70% EtOAc in hexanes) to give intermediate 61c. TLC: 50% EtOAc/hexanes, $R_f$=0.8.

Step D—Synthesis of Intermediate 61d To a solution of intermediate 61c (250 mg, 0.983 mmol) in DCM (5 mL) was added TFA (1 mL). The reaction was stirred at ambient temperature for 1 h. Then the reaction mixture was concentrated under vacuum to afford the intermediate 61d, which was used in the next reaction without further purification. TLC: 50% EtOAc/hexanes, $R_f$=0.

Step E—Synthesis of Intermediate 61e To a vial containing a mixture of intermediate 61d (124 mg, 0.804 mmol) in anhydrous acetonitrile (5 mL) were added intermediate 3c (0.25 g, 0.536 mmol) and acetic acid (0.107 mL, 1.875 mmol). The reaction mixture was heated at 65° C. for 1 h. Then the reaction mixture was cooled to ambient temperature and purified on reverse phase HPLC (ISCO, $C_{18}$, 50 g column, gradient elution with 0-100% ACN+0.05% TFA/water+0.05% TFA) to give intermediate 61e. LC-MS: m/z 573.5 $[M+H]^+$.

Step F—Synthesis of Intermediate 61f To a solution of intermediate 61e (170 mg, 0.297 mmol) in ethanol (5 mL) was added Pd/C (50 mg, 10 wt. %, 50% moisture). The reaction mixture was stirred at ambient temperature under $H_2$ (1 atm) for 1 h, and then filtered. The filtrate was concentrated under vacuum to afford intermediate 61f, which was used in the next reaction without further purification. LC-MS: m/z 547.6 $[M+H]^+$.

Example 91: Preparation of Compound 120

(S)-2-((R)-6-(N-((1R,3S)-3-(aminomethyl)-2,2-dimethylcyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

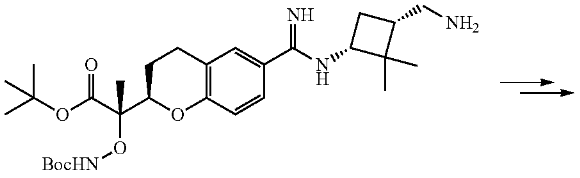

Int-61f

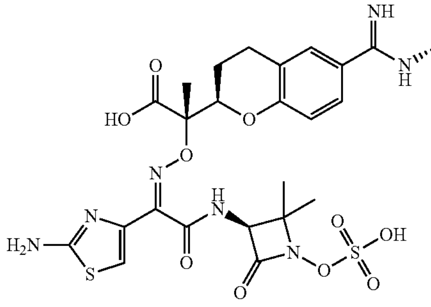

Compound 120

Compound 120 was prepared from intermediate 61f according to the procedure in Step B to Step D of Example 82. LC-MS: m/z 737.5 $[M+H]^+$. $^1$HNMR (500 MHz, 400 uL $D_2O$/100 uL $CD_3CN$) δ: 7.30-7.27 (m, 2H), 6.80-6.77 (m, 2H), 4.56 (s, 1H), 4.38-4.35 (m, 1H), 3.89-3.85 (m, 1H), 3.03-2.98 (m, 1H), 2.87-2.82 (m, 1H), 2.71 (br s, 2H), 2.47-2.41 (m, 1H), 2.02 (br s, 2H), 1.87-1.79 (m, 1H), 1.71 (br s, 1H), 1.45 (s, 3H), 1.33 (s, 3H), 1.16 (s, 3H), 1.12 (s, 3H), 0.97 (s, 3H).

Example 92: Preparation of Intermediate 62c-1

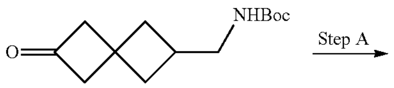

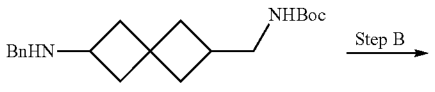

Int-62a

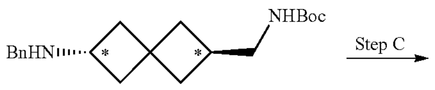

Int-62b-1
Int-62b-2

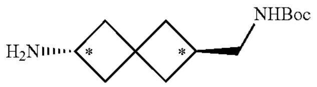

Int-62c-1

Step A—Synthesis of Intermediate 62a To a solution of tert-butyl ((6-oxospiro[3.3]heptan-2-yl)methyl)carbamate (500 mg, 2.089 mmol) in DCM (8 mL) was added benzylamine (0.297 mL, 2.72 mmol). The mixture was stirred at ambient temperature for 10 min, then $NaBH(OAc)_3$ (886 mg, 4.18 mmol) and acetic acid (1.196 μL, 0.021 mmol) were added sequentially. The reaction was stirred at ambient temperature for 3 h, then cooled to 0° C. and quenched with NaOH (1 N). The resulting mixture was extracted with EtOAc. The combined organic layers were washed with brine, dried over anhydrous $MgSO_4$, and filtered. The filtrate was concentrated under vacuum. The resulting residue was purified by silica gel chromatography (ISCO, 40 g column, gradient elution with 0-100% EtOAc in hexanes) to give intermediate 62a. LC-MS: m/z $[M+H]^+$.

Step B—Synthesis of Intermediate 62b-1 Enantiomers of intermediate 62a (440 mg, 1.331 mmol) were further separated by AS-H column (21×250 mm, co-solvent, 10% EtOH+0.2% DIPA, 210 nm wavelength, injection volume 1.0 mL, flow rate 50 ml/min) to afford intermediate 62b-1 (the first eluting stereoisomer) and intermediate 62b-2 (the second eluting stereoisomer). LC-MS: m/z 331.4 $[M+H]^+$.

Step C—Synthesis of Intermediate 62c-1 To a solution of intermediate 62b-1 (110 mg, 0.333 mmol) in EtOH (5 mL) was added Pd/C (30 mg, 10 wt. %, 50% moisture). The mixture was stirred at ambient temperature under $H_2$ (1 atm) for 40 minutes and then filtered. The filtrate was concentrated under vacuum to afford the intermediate 62c-1, which was used in the next reaction without further purification. TLC: EtOAc/Hexane 1/1, $R_f$=0.1.

Example 93: Preparation of Compound 121

(2S)-2-((2R)-6-(N-(6-(aminomethyl)spiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

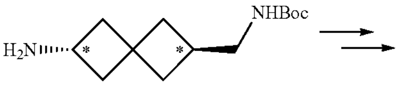

Int-62c-1

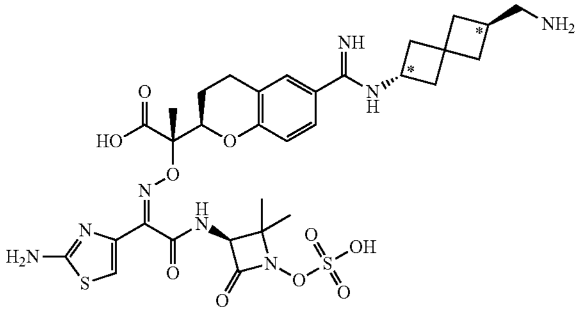

Compound 121

Compound 121 was prepared from intermediate 62c-1 according to the procedure in Step A to Step D of Example 82. Compound 121: LC-MS: m/z 749.4 $[M+H]^+$. $^1$HNMR (500 MHz, 400 uL $D_2O$/100 uL $CD_3CN$) δ: 7.35-7.32 (m, 2H), 6.86-6.83 (m, 2H), 4.58 (s, 1H), 4.41-4.39 (m, 1H), 4.02-3.94 (m, 1H), 2.91-2.89 (m, 2H), 2.76 (br s, 2H), 2.56 (br s, 1H), 2.43-2.38 (m, 2H), 2.24-2.04 (m, 5H), 1.95-1.92 (m, 1H), 1.82-1.71 (m, 2H), 1.49 (s, 3H), 1.39 (s, 3H), 1.20 (s, 3H).

*A single diastereomer; stereochemistry at* marked carbon center is unassigned.

Example 94: Preparation of Compounds 122 and 123

(2S)-2-((2R)-6-(N-((1S)-1-aminospiro[2.3]hexan-5-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (2S)-2-((2R)-6-(N-((1R)-1-aminospiro[2.3]hexan-5-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid*

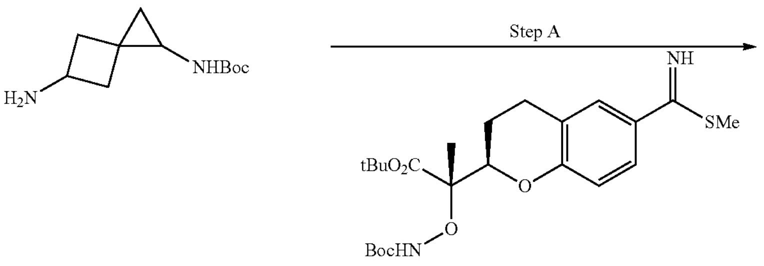

Int-3c

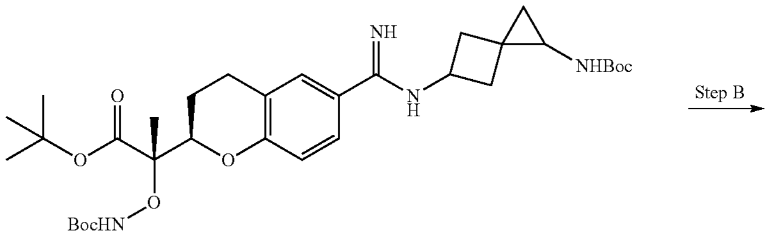

Int-63a

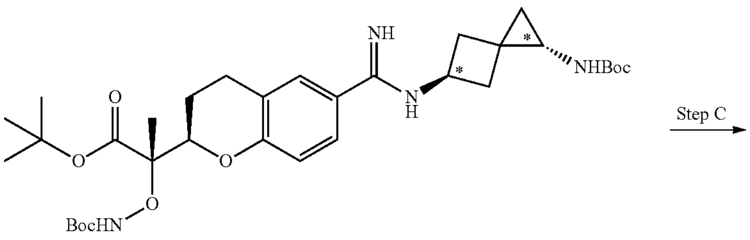

Int-63b-1
Int-63b-2

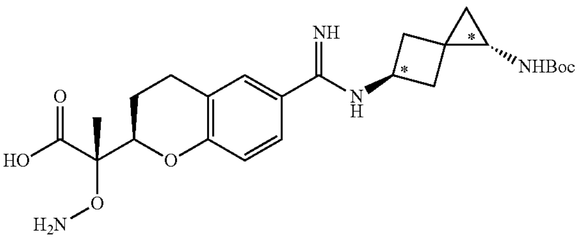

Int-63c-2

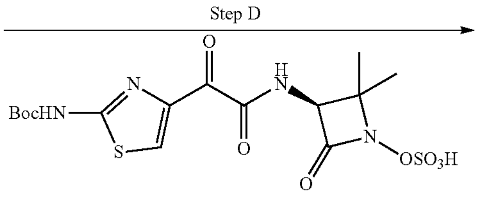

Int-4

-continued

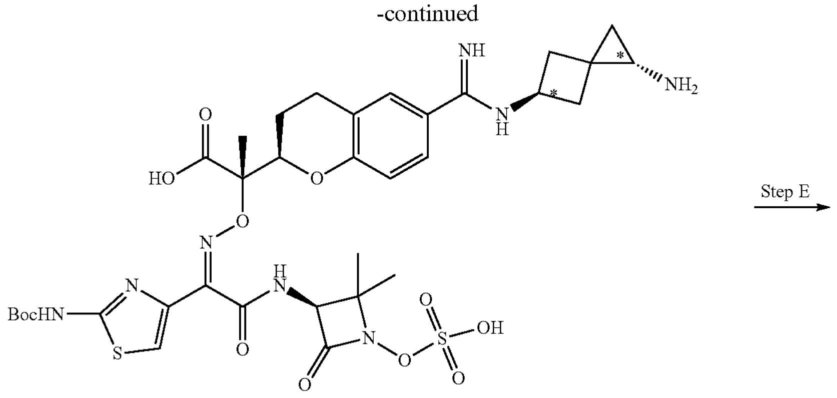

Int-63d-2

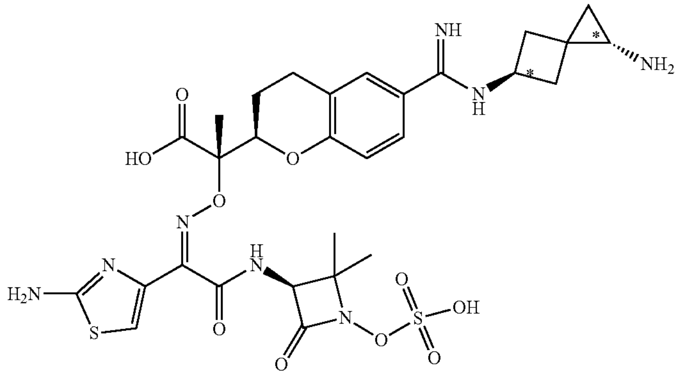

Compound 122

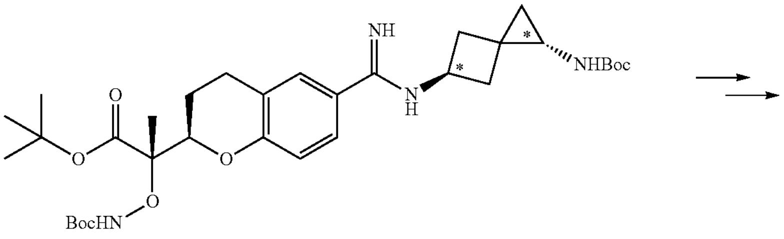

Int-63b-1

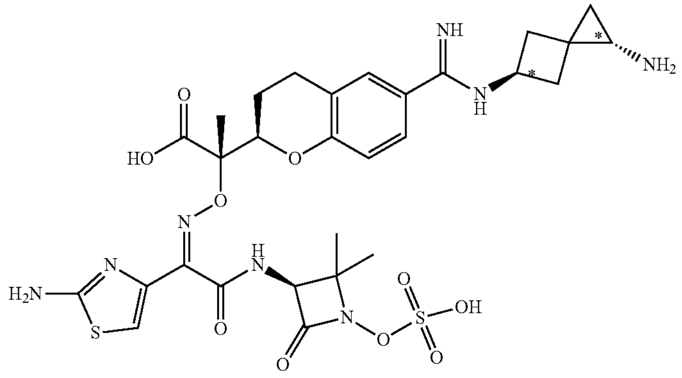

Compound 123

Step A—Synthesis of Intermediate 63a To a vial containing a mixture of tert-butyl (5-aminospiro[2.3]hexan-1-yl) carbamate (291 mg, 1.372 mmol) in anhydrous ACN (8 mL) was added acetic acid (0.172 mL, 3.00 mmol), followed by the addition of intermediate 3c (400 mg, 0.857 mmol). The reaction mixture was stirred at 65° C. for 4 h, then cooled to ambient temperature and purified on a reverse phase HPLC (ISCO, C18, 150 g column; gradient elution with 0-100% ACN+0.05% TFA/water+0.05% TFA) to give intermediate 63a, as a mixture of diastereomers. LC-MS: m/z 631.4 $[M+H]^+$.

Step B—Synthesis of Intermediates 63b-1 and 63b-2 Two diastereomers of intermediate 63a (370 mg, 0.587 mmol) were further separated by SFC (AS-H, 250 mm column, co-solvent, 25% MeOH/ACN 1:1+0.2% DIPA, 210 nm wavelength, injection volume 1.5 mL, flow rate 50 mL/min)

to afford intermediate 63b-1 (the first eluting stereoisomer) and intermediate 63b-2 (the second eluting stereoisomer). LC-MS: m/z 631.4 $[M+H]^+$.

Step C—Synthesis of Intermediate 63c-2 To a vial containing intermediate 63b-2 (0.21 g, 0.333 mmol) was added 2:1 trifluoroacetic acid/anhydrous DCM (6 mL) at ambient temperature. The reaction was stirred for 16 h, then a solution of 4:1 toluene/MeOH (10 mL) was added, and the reaction mixture was concentrated in vacuo. The resulting residue was azeotroped with 4:1 toluene/MeOH (10 mL) and dried under high vacuum to afford crude intermediate 63c-2, which was used in the next reaction without further purification. LC-MS: m/z 375.2 $[M+H]^+$.

Step D—Synthesis of Intermediate 63d-2 To a vial charged with intermediate 63c-2 (0.125 g, 0.334 mmol) and intermediate 4 (0.155 g, 0.334 mmol) was added MeOH (5.0 mL) at ambient temperature. The reaction mixture was stirred for 6 h, then concentrated in vacuo to afford crude intermediate 63d-2, which used without further purification in the next reaction. LC-MS: m/z 822.0 $[M+H]^+$.

Step E—Synthesis of Compounds 122 and 123 To a vial charged with intermediate 63d-2 (0.274 g, 0.334 mmol) was added 1:2 trifluoroacetic acid/anhydrous dichloromethane (6 mL) at ambient temperature. The reaction mixture was stirred for 1 h, then cooled to 0° C., followed by the slow addition of ethyl ether (6 mL) at 0° C. The resulting precipitate was collected by centrifugation (1400 rpm) and further purified by reverse phase HPLC (Gilson; C18, 5 um, OBD 30×150 mm column; gradient elution with 0-40% ACN+0.05% TFA/water+0.05% TFA over 18 min; 30 mL/min). The product fractions were collected and concentrated in vacuo. The resulting aqueous layer was directly loaded onto an Amberchrom CG161M column (26 g), washed with 9 CV of (water+0.1% FA), and eluted off with 3 CV of 100% (MeCN+0.1% FA) followed by 3 CV of 50% (MeCN+0.1% FA)/(water+0.1% FA). The product fractions were collected, concentrated in vacuo, and the resulting aqueous residue was lyophilized to give compound 122 as the formic acid salt. LC-MS: m/z 721.4 $[M+H]^+$. $^1$HNMR (500 MHz, 400 uL $D_2O$/100 uL $CD_3CN$) δ: 7.38-7.27 (m, 2H), 6.91 (s, 1H), 6.78 (d, J=15 Hz, 1H), 4.57 (s, 1H), 4.44-4.29 (m, 2H), 2.72 (br s, 2H), 2.60-2.37 (m, 5H), 2.03 (br s, 1H), 1.72 (br s, 1H), 1.49 (s, 3H), 1.32 (s, 3H), 1.05 (s, 3H), 1.04-1.01 (m, 1H), 0.85-0.79 (m, 1H).

Compound 123 was prepared from intermediate 63b-1 according to the procedure of Step C to Step E of Example 94. LC-MS (ESI): m/z 721.4 $[M+H]^+$. $^1$HNMR (500 MHz, 400 uL $D_2O$/100 uL $CD_3CN$) δ: 7.49-7.44 (m, 2H), 6.99-6.91 (m, 2H), 4.51-4.48 (m, 1H), 4.40 (br s, 1H), 2.88 (br s, 2H), 2.65 (br s, 4H), 2.16 (br s, 1H), 2.04-2.00 (m, 2H), 1.82 (br s, 1H), 1.52 (s, 3H), 1.49 (s, 3H), 1.31 (s, 3H), 1.12-1.05 (m, 1H), 0.93-0.85 (m, 1H). *Each compound is a single diastereomer; stereochemistry at * marked carbon center is unassigned.

Example 95: Preparation of Intermediates 64c-1 and 64c-2

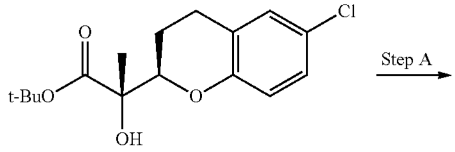

Int-1c

-continued

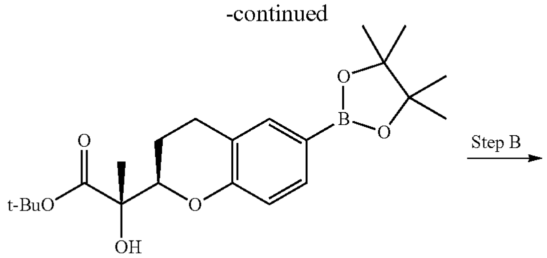

Int-64a

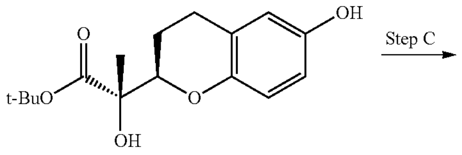

Int-64b

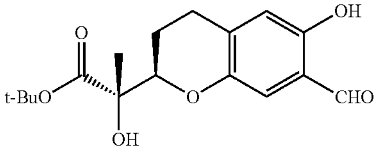

+

Int-64c-1

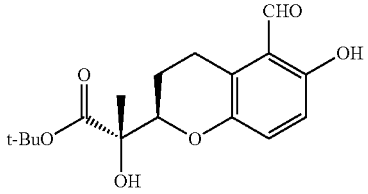

Int-64c-2

Step A—Synthesis of Intermediate 64as To a mixture of intermediate 1c (500 mg, 1.599 mmol), bis(pinacolato) diboron (507 mg, 1.998 mmol), 2-dicyclohexylphosphino-2',6'-dimethoxy-biphenyl (131 mg, 0.320 mmol), diacetoxypalladium (35.9 mg, 0.160 mmol), and potassium acetate (471 mg, 4.80 mmol) was added THF (14 mL). The reaction flask was filled with $N_2$, and sealed. The reaction mixture was heated at 70° C. for 18 h, then filtered, and the filtrate was concentrated under vacuum. The resulting residue was purified by silica gel column (Redish, 40 g, gradient: 0-100% TBME/hexanes) to give the desired compound. LC-MS: m/z 831.6 $[2M+Na]^+$.

Step B—Synthesis of Intermediate 64b To a stirred solution of intermediate 64a (606 mg, 1.499 mmol) in 15 mL of THF at 0° C., was added 2 M aqueous sodium hydroxide (3.75 ml, 7.49 mmol), followed by 30% aqueous hydrogen peroxide (0.759 ml, 7.49 mmol). The reaction was stirred at 0° C. for 20 minutes, then quenched by adding aqueous HCl solution (2 N, 2.5 mL). The resulting mixture was diluted with water (100 mL) and extracted with EtOAc (100 mL). The organic layer was separated, and concentrated in vacuo. The resulting residue was purified by a reverse phase HPLC (150 g C18 column, gradient: 0-100% ACN+0.05% TFA/water+0.05% TFA) to give intermediate 64b. LC-MS (ESI): m/z LC-MS (ESI): m/z 317.2 $[M+Na]^+$.

Step C—Synthesis of Intermediates 64c-1 and 64c-2 To a solution of intermediate 64b (400 mg, 1.359 mmol) in acetonitrile (11 mL) were added paraformaldehyde (612 mg, 6.79 mmol), $NEt_3$ (2.462 mL, 17.67 mmol) and magnesium chloride (647 mg, 6.79 mmol) sequentially. The reaction was stirred at 85° C. for 5 h, then HCl (2 N, 10 mL) and 30 mL of water were added. The mixture was extracted with EtOAc (30 mL×3). The organic layers were combined, washed with brine (30 mL), dried over anhydrous $Na_2SO_4$, filtered and the filtrate was concentrated under reduced pressure. The resulting residue was purified by flash silica gel chromatography (ISCO; 4 g Agela Silica Flash Column, Eluent of 0-15% EtOAc/Petroleum Ether gradient @ 30 mL/min) to give intermediate 64c-1 (the first eluting isomer), and intermediate 64c-2 (the second eluting isomer).

Intermediate 64c-1: $^1H$ NMR (400 MHz, $CDCl_3$) δ: 10.49 (s, 1H), 9.75 (s, 1H), 6.88 (s, 1H), 6.70 (s, 1H), 4.14 (dd, J=2.3, 11.0 Hz, 1H), 3.42 (s, 1H), 2.95-2.84 (m, 2H), 2.12-1.93 (m, 2H), 1.54-1.52 (m, 1H), 1.54 (s, 9H), 1.40 (s, 3H).

Intermediate 64c-2: $^1H$ NMR (400 MHz, $CDCl_3$) δ: 11.62 (s, 1H), 10.26 (s, 1H), 6.95 (d, J=9.0 Hz, 1H), 6.75 (d, J=9.0 Hz, 1H), 4.12-4.03 (m, 1H), 3.42 (s, 1H), 3.31 (br dd, J=4.3, 16.8 Hz, 1H), 3.14-2.99 (m, 1H), 2.22-2.11 (m, 1H), 2.09-1.95 (m, 1H), 1.52 (s, 9H), 1.41 (s, 3H).

Example 96: Preparation of Compound 124

(S)-2-((R)-6-(N-((1s,3S)-3-aminocyclobutyl)carbamimidoyl)-5-(methoxymethyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

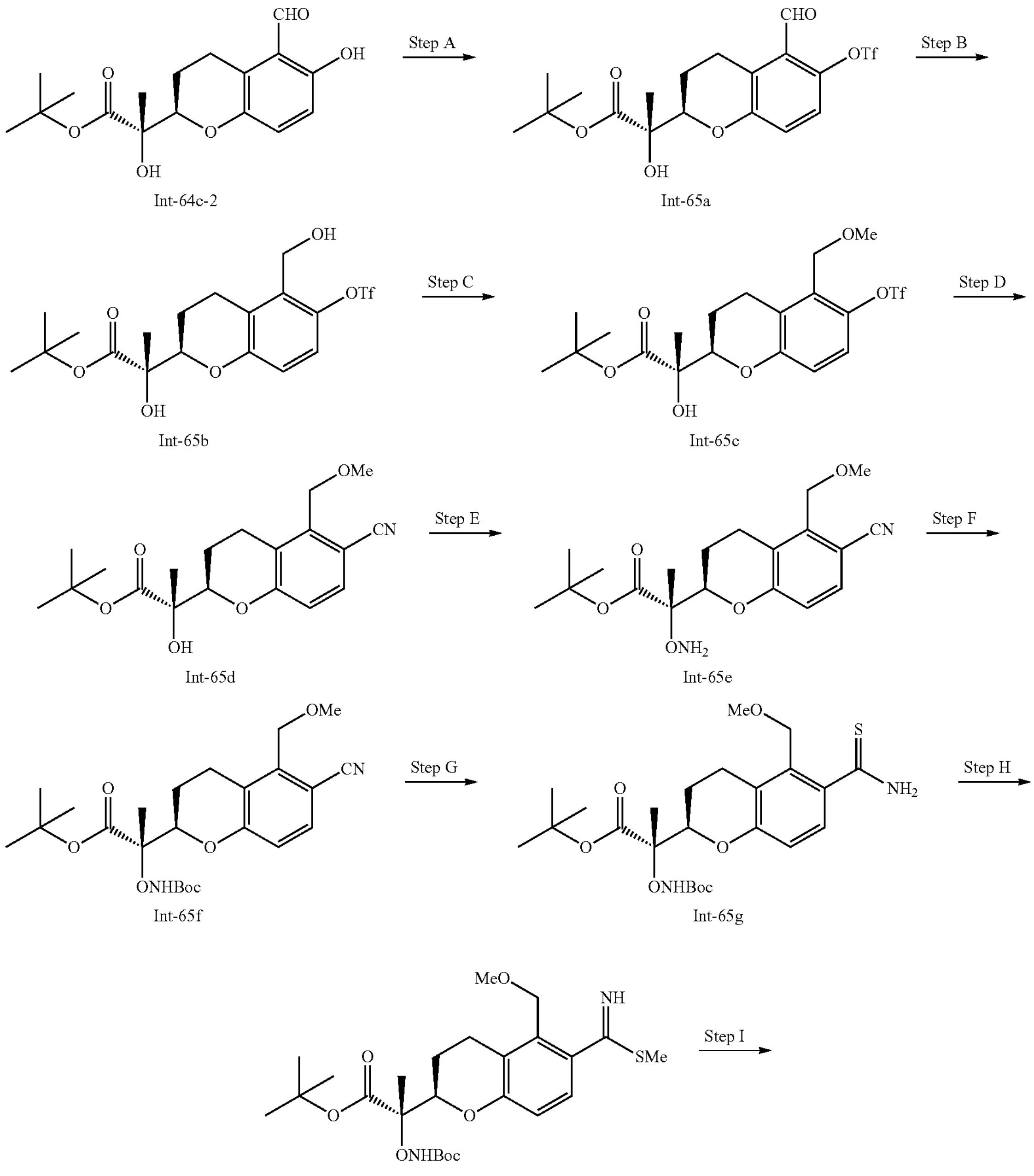

Int-64c-2

Int-65a

Int-65b

Int-65c

Int-65d

Int-65e

Int-65f

Int-65g

Int-65h

-continued

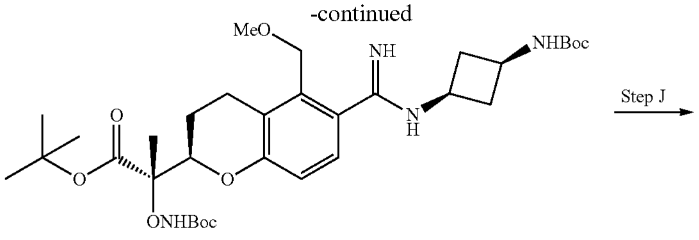

Int-65i

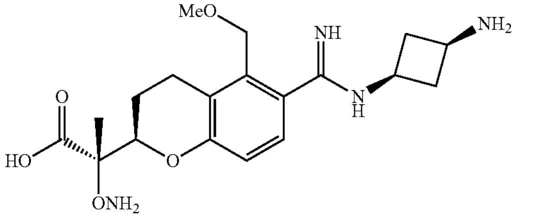

Int-65j

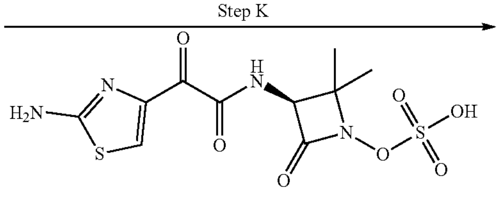

Int-5

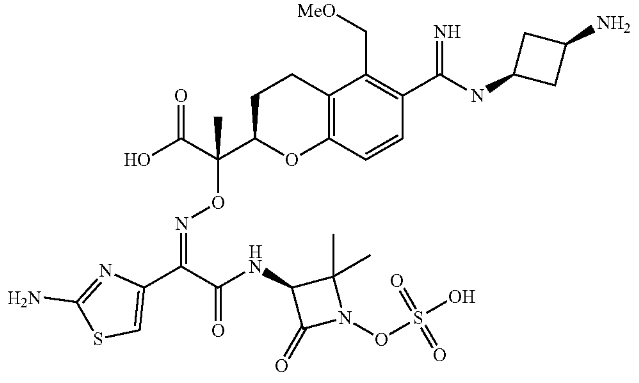

Compound 124

Step A—Synthesis of Intermediate 65a To a stirred solution of intermediate 64c-2 (7 g, 21.72 mmol) in DCM (217 mL) at 25° C. were added triethylamine (15.13 mL, 109 mmol) and 1,1,1-trifluoro-N-phenyl-N-((trifluoromethyl)sulfonyl)methanesulfonamide (23.27 g, 65.1 mmol). The reaction was stirred at 25° C. for 14 h, then concentrated under reduced pressure to give crude product which was purified by a flash silica gel chromatography (ISCO; 80 g Agela Silica Flash Column, Eluent of 0-8% EtOAc/Petroleum Ether gradient @ 30 mL/min) to give intermediate 65a. $^1$H NMR (400 MHz, $CDCl_3$) δ:10.40 (s, 1H), 7.12 (d, J=9.0 Hz, 1H), 6.99 (d, J=9.0 Hz, 1H), 4.16 (dd, J=11.3, 2.0 Hz, 1H), 3.43 (s, 1H), 3.41-3.29 (m, 1H), 3.04 (ddd, J=18.6, 12.5, 6.5 Hz, 1H), 2.18-2.08 (m, 1H), 1.97-1.81 (m, 1H), 1.50 (s, 9H), 1.39 (s, 3H).

Step B—Synthesis of Intermediate 65b To a stirred solution of intermediate 65a (3 g, 6.60 mmol) in MeOH (66.0 mL) was added $NaBH_4$ (0.749 g, 19.81 mmol) portion wise at 0° C. The reaction was stirred at 0° C. for 0.5 h, then diluted with of water (100 mL) and concentrated to remove most of the MeOH. The resulting mixture was extracted with EtOAc (80 mL×3). The organic layers were combined, washed with brine (100 mL), dried over anhydrous $Na_2SO_4$, and filtered. The filtrate was concentrated under reduced pressure to afford crude intermediate 65b, which was used in the next reaction without further purification. $^1$H NMR (400 MHz, $CDCl_3$) δ: 6.99 (br d, J=9.0 Hz, 1H), 6.74 (d, J=9.0 Hz, 1H), 4.76-4.61 (m, 2H), 4.15 (br s, 1H), 3.15 (br dd, J=17.1, 4.9 Hz, 1H), 3.00-2.85 (m, 1H), 2.14 (br dd, J=13.6, 4.8 Hz, 1H), 2.01-1.91 (m, 1H), 1.51 (s, 9H), 1.40 (s, 3H).

Step C—Synthesis of Intermediate 65c To a stirred solution of intermediate 65b (2.8 g, 6.13 mmol) in DCM (61.3 mL) at 0° C. was added 2,6-di-tert-butylpyridine (12.32 g, 64.4 mmol), silver trifluoromethanesulfonate (14.19 g, 55.2 mmol), and iodomethane (4.01 mL, 64.4 mmol) sequentially. The reaction was stirred at 20° C. for 72 h, then filtered. The filtrate was diluted with $H_2O$ (80 mL) and extracted with DCM (60 mL×3). The organic layers were combined, washed with brine, dried over anhydrous $Na_2SO_4$, filtered, and the filtrate was concentrated under reduced pressure. The resulting residue was purified by a flash silica gel chromatography (ISCO; 40 g Agela Silica Flash Column, Eluent of 0-20% EtOAc/Petroleum Ether gradient @ 30 mL/min) to give intermediate 65c. $^1$H NMR (400 MHz, $CDCl_3$) δ: 7.00 (d, J=9.4 Hz, 1H), 6.74 (d, J=9.4 Hz, 1H), 4.57-4.39 (m, 2H), 4.12 (br d, J=11.0 Hz, 1H), 3.39 (s, 3H), 3.10-2.99 (m, 1H), 2.97-2.79 (m, 1H), 2.12 (br dd, J=13.5, 6.1 Hz, 1H), 1.96 (dq, J=12.5, 5.5 Hz, 1H), 1.50 (s, 9H), 1.39 (s, 3H).

Step D—Synthesis of Intermediate 65d To a mixture of intermediate 65c (800 mg, 1.700 mmol) and sodium carbonate (21.63 mg, 0.204 mmol) in MeCN (8 mL) and $H_2O$ (6 mL), were added potassium ferrocyanide trihydrate (359 mg, 0.850 mmol) and chloro(2-dicyclohexylphosphino-2', 4',6'-triisopropyl-1,1'-biphenyl)[2-(2'-amino-1,1'-biphenyl)] palladium(II) (268 mg, 0.340 mmol) under $N_2$. The reaction was stirred at 100° C. for 40 minutes under microwave irradiation, then filtered, and the filtrate was diluted with $H_2O$ (40 mL) and extracted with EtOAc (30 mL×3). The organic layers were combined, washed with brine, dried over anhydrous $Na_2SO_4$, filtered and the filtrate was concentrated under reduced pressure. The resulting residue was purified by flash silica gel chromatography (ISCO; 4 g Agela Silica Flash Column, Eluent of 0-15% EtOAc/Petroleum Ether gradient @ 30 mL/min) to give intermediate 65d. $^1H$ NMR (400 MHz, $CDCl_3$) δ: 7.38 (d, J=8.6 Hz, 1H), 6.76 (d, J=8.6 Hz, 1H), 4.62 (q, J=11.2 Hz, 2H), 4.18 (dd, J=11.0, 2.0 Hz, 1H), 3.42 (s, 3H), 3.10-2.99 (m, 1H), 2.92-2.77 (m, 1H), 2.14 (br dd, J=13.7, 6.3 Hz, 1H), 2.03-1.92 (m, 1H), 1.50 (s, 9H), 1.40 (s, 3H).

Step E—Synthesis of Intermediate 65e To a stirred solution of intermediate 65d (710 mg, 2.044 mmol) in THF (21 mL) at 0° C., was added sodium hydride (245 mg, 6.13 mmol, 60% in mineral oil) under $N_2$. The mixture was stirred at 0° C. for 20 min. before O-diphenylphosphinylhydroxylamine (858 mg, 3.68 mmol) was added. Then the reaction was stirred at 0° C. for 1.5 h, and at 20° C. for 3 h. The reaction mixture was quenched with saturated aqueous $NH_4Cl$ solution (20 mL) and extracted with EtOAc (50 mL×3). The organic layers were combined, dried over anhydrous $Na_2SO_4$, filtered and the filtrate was concentrated under reduced pressure. The resulting residue was purified by a flash silica gel chromatography (ISCO; 12 g Agela Silica Flash Column, Eluent of 0-15% Petroleum ether/EtOAc gradient @ 30 mL/min) to give intermediate 65e. $^1H$ NMR (400 MHz, $CDCl_3$) δ: 7.38 (d, J=8.6 Hz, 1H), 6.85 (d, J=8.6 Hz, 1H), 5.47 (br s, 2H), 4.66-4.55 (m, 2H), 4.24 (br d, J=11.3 Hz, 1H), 3.41 (s, 3H), 3.04-2.96 (m, 1H), 2.90-2.77 (m, 1H), 2.21-2.09 (m, 1H), 1.85 (dq, J=12.8, 5.1 Hz, 1H), 1.51 (s, 12H).

Step F—Synthesis of Intermediate 65f To a stirred solution of intermediate 65e (520 mg, 1.435 mmol) in DCE (14 mL) was added $Boc_2O$ (1.155 mL, 5.02 mmol) at 20° C. The reaction was stirred at 55° C. for 16 h. Then the reaction mixture was concentrated under reduced pressure, and the resulting residue was purified by a flash silica gel chromatography (ISCO; 4 g Agela Silica Flash Column, Eluent of 0-18% Petroleum ether/EtOAc gradient @ 30 mL/min) to give intermediate 65f. $^1H$ NMR (400 MHz, $CDCl_3$) δ: 7.53 (s, 1H), 7.37 (d, J=8.6 Hz, 1H), 6.80 (d, J=8.6 Hz, 1H), 4.71-4.54 (m, 2H), 4.29 (dd, J=11.0, 2.3 Hz, 1H), 3.41 (s, 3H), 3.05 (br dd, J=17.2, 3.1 Hz, 1H), 2.88-2.76 (m, 1H), 2.27-2.07 (m, 2H), 1.55 (s, 3H), 1.50 (s, 9H), 1.45 (s, 9H).

Step G—Synthesis of Intermediate 65g To a mixture of intermediate 65f (520 mg, 1.124 mmol) and TEA (0.548 mL, 3.93 mmol) in pyridine (6 mL) was added $(NH_4)_2S$ (5.75 mL, 16.86 mmol, 20% in water). The mixture was stirred for 18 h at 60° C., then cooled and concentrated in vacuo to remove residual solvent. The resulting residue was washed with brine (20 mL) and extracted with ethyl acetate (30 mL×3). The organic layer was dried over anhydrous $Na_2SO_4$, filtered and the filtrate was concentrated under vacuum. The resulting residue was purified by a flash silica gel chromatography (ISCO; 4 g Agela Silica Flash Column, Eluent of 0-35% EtOAc/Petroleum Ether gradient @ 30 mL/min) to give intermediate 65g. LC-MS (ESI): m/z 496.9 $[M+H]^+$.

Step H—Synthesis of Intermediate 65h To a solution of intermediate 65g (350 mg, 0.705 mmol) in MeCN (7 mL) was added dropwise iodomethane (0.219 mL, 3.52 mmol) at 25° C. The reaction was stirred at 25° C. for 16 h. Then the reaction mixture was concentrated under vacuum to give crude intermediate 65h, which was used in the next reaction without purification. LC-MS (ESI): m/z 511.4 $[M+H]^+$.

Step I—Synthesis of Intermediate 65i To a solution of intermediate 65h (300 mg, 0.587 mmol) in MeCN (3 mL) stirred at 20° C. were added (tert-butyl ((1s,3s)-3-aminocyclobutyl)carbamate (207 mg, 1.111 mmol) and AcOH (0.3 mL, 5.24 mmol) in MeCN (3 mL). The reaction was stirred at 85° C. for 5 h, then filtered and the filtrate was concentrated under reduced pressure. The resulting residue was purified by a reverse phase MPLC (Biotage; 20 g Agela, C18, 20~35 μm, Eluent of 20% MeCN/$H_2O$ (0.5% TFA) gradient @ 50 mL/min) to give intermediate 65i. LC-MS (ESI): m/z 649.4 $[M+H]^+$.

Step J—Synthesis of Intermediate 65j A solution of intermediate 65i (400 mg, 0.462 mmol) in TFA (6 mL) was stirred at 40° C. for 2 h. The solvent was removed under vacuum, and the resulting residue was purified by reverse phase HPLC (Column: Boston Uni C18 40×150×5 um; Condition: water (0.1% TFA)-ACN; Begin B 0, End B 30; Gradient Time (min) 10; 100% B Hold Time (min) 2; FlowRate (mL/min) 60; Injections 1) to give intermediate 65j. LC-MS (ESI): m/z 392.8 $[M+H]^+$.

Step K—Synthesis of Compound 124 A mixture of 4 Å molecular sieves (50 mg), intermediate 65j (130 mg, 0.331 mmol) and intermediate 5 (121 mg, 0.331 mmol) in DMA (2.5 mL) was stirred at 28° C. for 16 h. Then the reaction mixture was filtered. The filtrate was diluted with MeOH (2 mL) and purified by a reverse phase HPLC (Column: Boston Uni C18 40×150×5 um; Condition: water (0.1% TFA)-ACN; Begin B 0, End B 30; Gradient Time (min) 10; 100% B Hold Time (min) 2; FlowRate (mL/min) 60; Injections 1) to give the product as the TFA salt. The TFA salt was dissolved in 2:1 $H_2O$/MeCN (2 mL) and purified by reverse phase HPLC (Column: Welch Xtimate C18 150×25 mm×5 um; Condition: water (0.225% FA)-ACN; Begin B 0, End B 19; Gradient Time (min) 15; 100% B Hold Time (min) 2; FlowRate (mL/min) 25; Injections 2). The product fractions were collected, concentrated in vacuo, and the resulting aqueous residue was lyophilized to give compound 124 as the formic acid salt. LC-MS (ESI): m/z 739.4 $[M+H]^+$. $^1H$ NMR (400 MHz, $D_2O+CD_3CN$) δ: 7.17 (d, J=8.6 Hz, 1H), 6.90-6.79 (m, 2H), 4.66 (s, 1H), 4.42 (br s, 2H), 4.29 (br d, J=10.2 Hz, 1H), 4.10-3.95 (m, 1H), 3.67-3.52 (m, 1H), 3.25 (s, 3H), 2.96-2.79 (m, 3H), 2.77-2.63 (m, 1H), 2.33-2.19 (m, 2H), 2.13-2.01 (m, 1H), 1.81-1.60 (m, 1H), 1.49 (s, 3H), 1.43 (s, 3H), 1.24 (s, 3H).

Example 97: Preparation of Compound 125

(S)-2-((R)-6-(N-((1s,3S)-3-aminocyclobutyl)carbamimidoyl)-7-(methoxymethyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

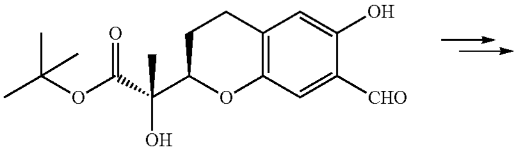

Int-64c-1

-continued

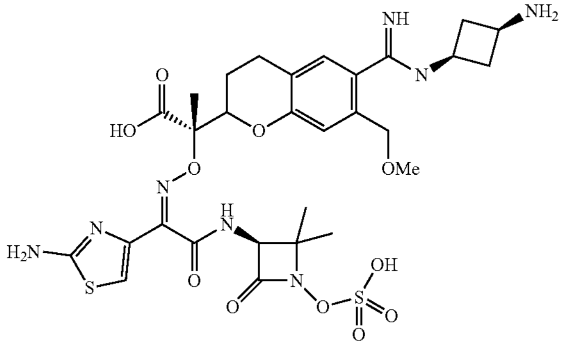

Compound 125

Compound 125 was prepared from intermediate 64c-1 according to the procedures in Step A to Step K of Example 96. LC-MS (ESI): m/z 739.3 $[M+H]^+$. $^1H$ NMR (400 MHz, $D_2O+CD_3CN$) δ: 7.23 (s, 1H), 6.83 (s, 1H), 6.79 (s, 1H), 4.65 (s, 1H), 4.41 (s, 2H), 4.34 (br d, J=10.2 Hz, 1H), 3.99 (quin, J=7.9 Hz, 1H), 3.60 (quin, J=8.3 Hz, 1H), 3.22 (s, 3H), 2.93-2.82 (m, 2H), 2.81-2.68 (m, 2H), 2.33-2.21 (m, 2H), 2.08-1.98 (m, 1H), 1.78-1.62 (m, 1H), 1.48 (s, 3H), 1.43 (s, 3H), 1.25 (s, 3H).

Example 98: Preparation of Compounds 126 and 127

(S)-2-((R)-6-(N-((1s,4S)-4-amino-1-(methoxymethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,4R)-4-amino-1-(methoxymethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

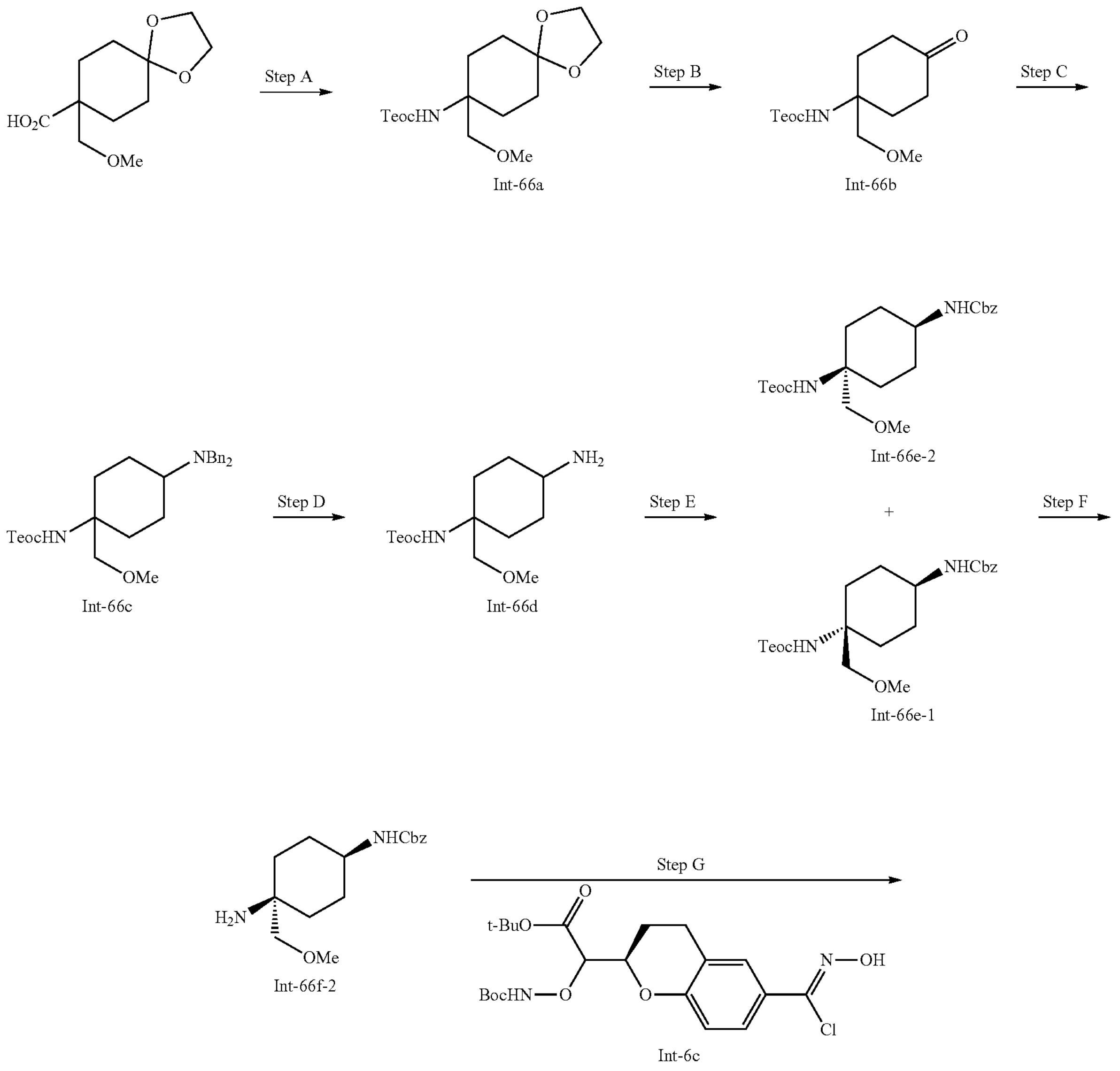

-continued
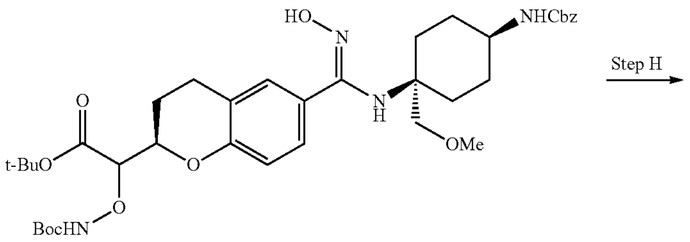
Int-66g-2
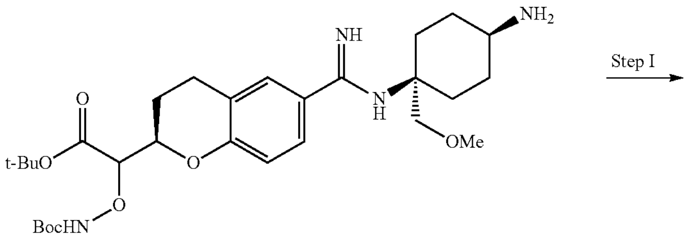
Int-66h-2
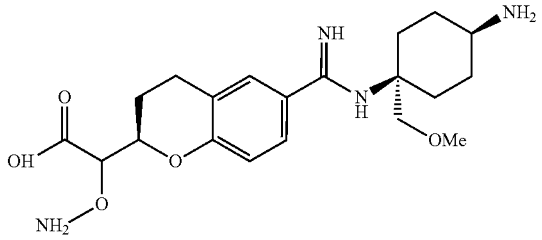
Int-66i-2
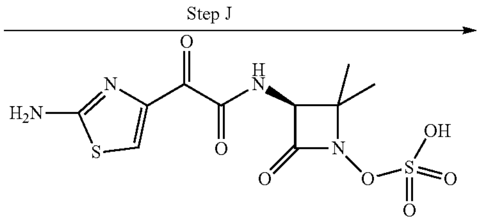
Int-5
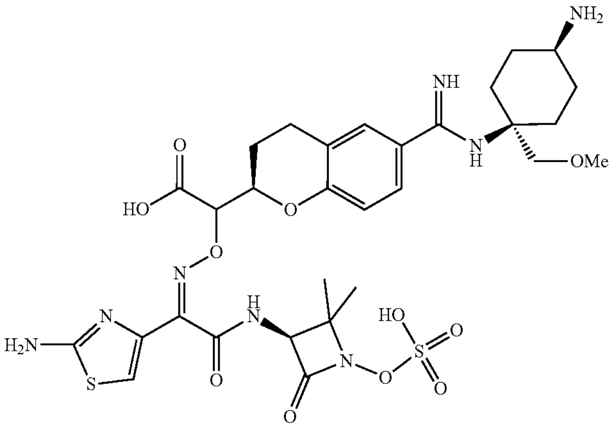
Compound 126

-continued

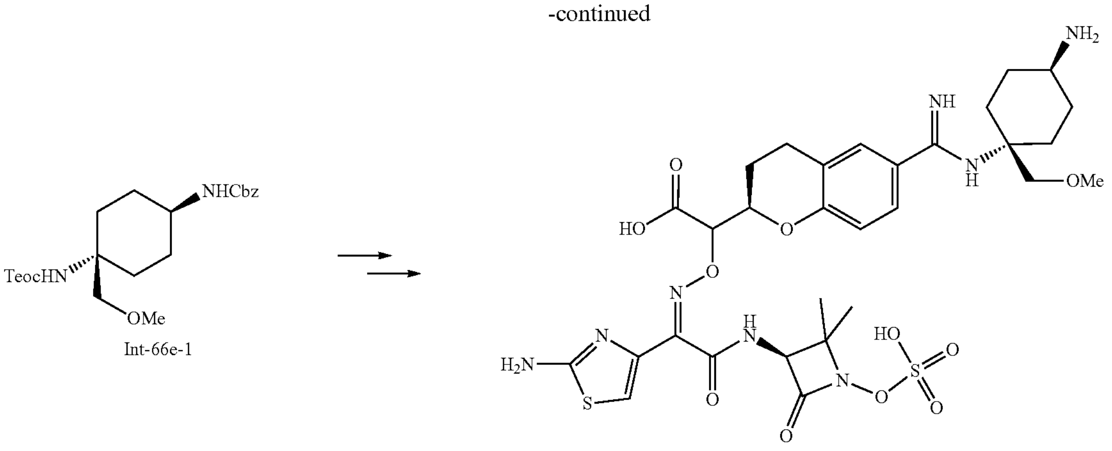

Int-66e-1

Compound 127

Step A—Synthesis of Intermediate 66a A solution of TEA (8.84 mL, 63.4 mmol), diphenyl phosphorazidate (7.31 mL, 33.9 mmol) and 8-(methoxymethyl)-1,4-dioxaspiro[4.5]decane-8-carboxylic acid (7.3 g, 31.7 mmol) in toluene (30 mL) and THF (30 mL) was stirred at 65° C. for 3 h. Then the reaction mixture was cooled to ambient temperature, diluted with EtOAc (50 mL), washed with brine (200 mL), dried over anhydrous $Na_2SO_4$, and filtered. The filtrate was concentrated under vacuum. The resulting residue was dissolved in THF (50 mL) and toluene (50 mL), and then 2-(trimethylsilyl)ethanol (7.28 g, 61.6 mmol) was added. The reaction was stirred at 95° C. for 16 h, then cooled to ambient temperature, and concentrated under vacuum. The resulting residue was purified by a flash silica gel chromatography (Biotage; 40 g Agela Silica Flash Column, Eluent of 0-13% EtOAc/Petroleum ether gradient @ 45 mL/min) to give intermediate 66a. $^1$H NMR (400 MHz, $CDCl_3$) δ: 4.49 (s, 1H), 4.12-3.98 (m, 2H), 3.95-3.83 (m, 4H), 3.52-3.39 (m, 2H), 3.36-3.17 (m, 3H), 2.15-2.01 (m, 2H), 1.81-1.48 (m, 6H), 1.04-0.85 (m, 2H), −0.01 (s, 9H).

Step B—Synthesis of Intermediate 66b A solution of intermediate 66a (6.9 g, 19.97 mmol) and p-toluenesulfonic acid (27.5 g, 160 mmol) in 1:1 THF/water (100 mL) was stirred at 19° C. for 16 h. Then the reaction mixture was diluted with EtOAc (80 mL), washed with brine (80 mL), dried over anhydrous $Na_2SO_4$, filtered and the filtrate was concentrated under vacuum. The resulting residue was purified by silica gel column chromatography eluting with 3:1 petroleum ether/EtOAc to afford intermediate 66b. $^1$H NMR (400 MHz, $CDCl_3$) δ: 4.71 (s, 1H), 4.18-4.06 (m, 2H), 3.49 (s, 2H), 3.36 (s, 3H), 2.56-2.37 (m, 4H), 2.33-2.24 (m, 2H), 1.87-1.74 (m, 2H), 1.02-0.92 (m, 2H), 0.03 (s, 9H).

Step C—Synthesis of Intermediate 66c To a stirred solution of intermediate 66b (4.0 g, 13.27 mmol) in THF (40 mL) at 0° C. was added dibenzylamine (3.06 mL, 15.92 mmol). After stirring at 25° C. for 2 h, the reaction was cooled to 0° C. and AcOH (0.836 mL, 14.60 mmol) was added, followed by sodium triacetoxyborohydride (7.03 g, 33.2 mmol). The reaction was stirred at 25° C. for 12 h. Then the pH of the reaction mixture was adjusted to pH 6-7 with saturated aqueous $NaHCO_3$ (50 mL), and the mixture was extracted with EtOAc (50 mL×3). The combined organic layers were washed with brine (50 mL) and concentrated in vacuo. The residue was purified by a flash silica gel chromatography MPLC (ISCO®; 40 g SepaFlash® Silica Flash Column, Eluent of 0~10% ethyl acetate/petroleum ether gradient @ 40 mL/min) to give intermediate 66c. LC-MS (ESI): m/z 483.8 $[M+H]^+$.

Step D—Synthesis of Intermediate 66d To a solution of intermediate 66c (3.5 g, 7.25 mmol) in a mixed solvent of MeOH (10 mL) and EtOAc (50 mL) was added palladium hydroxide (20%, 5.09 g, 7.25 mmol), Pd/C (7.72 g, 7.25 mmol, 10 wt. %) and ammonium hydroxide solution (25 wt. %, 1.016 g, 7.25 mmol) under $N_2$ atmosphere. The suspension was degassed under vacuum and purged with $H_2$ three times. The the reaction mixture was stirred at 30° C. for 12 h under $H_2$ (30 psi), then filtered. The filtrate was concentrated in vacuo to give crude intermediate 66d, which was used in the next reaction without further purification. LC-MS (ESI): m/z 303.0 $[M+H]^+$.

Step E—Synthesis of Intermediates 66e-1 and 66e-2 To a stirred mixture of intermediate 66d (1.5 g, 4.96 mmol) and $K_2CO_3$ (1.713 g, 12.40 mmol) in MeOH (30 mL) at 0° C., was added CbzCl (0.991 mL, 6.94 mmol). The reactions mixture was stirred at 20° C. for 12 h, then diluted with water (40 mL), and extracted with EtOAc (30 mL×3). The combined organic layers were washed with brine (80 mL), dried over anhydrous $Na_2SO_4$, filtered and the filtrate was concentrated under vacuum. The resulting residue was purified by a flash silica gel chromatography (Biotage; 12 g Agela Silica Flash Column, Eluent of 0-25% EtOAc/petroleum ether gradient @ 40 mL/min) to give the product as a mixture of cis- and trans-stereoisomers. The mixture of stereoisomers was further separated by SFC (DAICEL CHIRALPAK AD (250 mm×50 mm, 10 um); Condition 0.1% $NH_3H_2O$/EtOH; Begin B 25%, End B 25%; Flow Rate (mL/min) 200; Injections 120) to individually afford intermediate 66e-1 (the first eluting stereoisomer, LC-MS (ESI): m/z 437.4 $[M+H]^+$) and intermediate 66e-2 (the second eluting stereoisomer, LC-MS (ESI): m/z 437.4 $[M+H]^+$).

Step F—Synthesis of Intermediate 66f-2 To a solution of intermediate 66e-2 (900 mg, 2.061 mmol) in DCM (10 mL) was added TFA (1 mL). The reaction was stirred at 20° C. for 2 h, then concentrated in vacuo to give crude intermediate 66f-2, which was used in the next reaction without further purification. LC-MS (ESI): m/z 293.1 $[M+H]^+$.

Step G—Synthesis of Intermediate 66g-2 To a solution of the crude intermediate 66f-2 (233 mg, 0.573 mmol) in DMF (3 mL) was added a solution of TEA (0.240 mL, 1.720 mmol) at 0° C., followed by the dropwise addition of a solution of intermediate 6c (270 mg, 0.573 mmol) in DMF (3 mL). The reaction was stirred at 20° C. for 12 h, then diluted with water (40 mL) and extracted with ethyl acetate (30 mL×2). The combined organic layers were washed with brine (40 mL), dried over anhydrous $Na_2SO_4$, filtered and the filtrate was concentrated in vacuo to give crude intermediate 66g-2, which was used in the next reaction without further purification. LC-MS (ESI): m/z 727.4 $[M+H]^+$.

Step H—Synthesis of Intermediate 66h-2 To a stirred mixture of $K_2CO_3$ (665 mg, 4.82 mmol) in MeOH (5 mL) was added formic acid (443 mg, 9.63 mmol) at 20° C. under $N_2$. The mixture was stirred for 10 minutes, and then diluted with MeOH (10 mL). The resulting solution was added to a solution of intermediate 66g-2 (700 mg, 0.963 mmol) and acetic anhydride (108 mg, 1.059 mmol) in acetic acid (12.79 mL) which has been pre-stirred at ambient temperature for 5 minutes. Then Pd/C (10 wt. %, 41.0 mg, 0.385 mmol) was added, and the reaction mixture was stirred at 20° C. for 12 h. The reaction mixture was filtered, and the solvent was removed under vacuum. The resulting residue was purified by a reverse phase MPLC (Biotage; 20 g Agela, eluent of 0-38% MeCN/$H_2O$ (0.5% TFA) gradient @ 50 mL/min) to give intermediate 66h-2. LC-MS (ESI): m/z 577.4 $[M+H]^+$.

Step I—Synthesis of Intermediate 66i-2 A solution of intermediate 66h-2 (240 mg, 0.416 mmol) in TFA (5 mL) was stirred at 40° C. for 1 h. Then the reaction mixture was concentrated in vacuo. The resulting residue was purified by reverse phase HPLC (Boston Uni C18 40×150×5 um; Condition: water (0.1% TFA)-ACN; Begin B 0, End B 30; Gradient Time (min) 10; 100% B Hold Time (min) 2; Flow Rate (mL/min) 60; Injections 2) to give intermediate 66i-2. LC-MS (ESI): m/z 421.2 $[M+H]^+$.

Step J—Synthesis of Compound 126 and Compound 127 To a stirred solution of intermediate 66i-2 (115 mg, 0.273 mmol) in DMA (3 mL) at 20° C., was added intermediate 5 (100 mg, 0.273 mmol). The reaction mixture was stirred at 20° C. for 12 h, then dried with a nitrogen gas flow. The resulting residue was purified by reverse phase HPLC (Boston Uni C18 40×150×5 um; Condition: water (0.1% TFA)-ACN; Begin B 0, End B 30; Gradient Time (min) 10; 100% B Hold Time (min) 2; Flow Rate (mL/min) 60; Injections 2) to give the product as the TFA salt. The TFA salt was dissolved in $H_2O$ (3 mL) and purified by HPLC (Welch Xtimate C18 150×25 mm×5 um; Condition water (0.225% FA)-ACN; Begin B 0, End B 19; Gradient Time (min) 15; 100% B Hold Time (min) 2; Flow Rate (mL/min) 25; Injections 2), followed by lyophilization to give compound 126 as the formic acid salt. LC-MS (ESI): m/z 767.2 $[M+H]^+$. $^1H$ NMR (400 MHz, $D_2O+CD_3CN$) δ: 7.52-7.39 (m, 2H), 6.90 (br d, J=9.3 Hz, 1H), 6.79 (s, 1H), 4.62 (s, 1H), 4.39 (br d, J=11.1 Hz, 1H), 3.51 (s, 2H), 3.37 (s, 3H), 3.26-3.14 (m, 1H), 2.89-2.76 (m, 2H), 2.43-2.29 (m, 2H), 2.15-2.05 (m, 2H), 1.81-1.66 (m, 1H), 1.64-1.46 (m, 5H), 1.51 (s, 3H), 1.43 (s, 3H), 1.25 (s, 3H).

Compound 127 was prepared from intermediate 66e-1 according to the procedure in step F to step J of Example. LC-MS (ESI): m/z 767.4 $[M+H]^+$. $^1H$ NMR (400 MHz, $D_2O+CD_3CN$) δ: 7.40-7.33 (m, 2H), 6.88 (d, J=8.6 Hz, 1H), 6.78 (s, 1H), 4.61 (s, 1H), 4.39 (br d, J=10.2 Hz, 1H), 3.67 (s, 2H), 3.41 (s, 3H), 3.32-3.21 (m, 1H), 2.86-2.73 (m, 2H), 2.24-2.15 (m, 2H), 2.13-2.02 (m, 1H), 2.01-1.95 (m, 2H), 1.78-1.65 (m, 3H), 1.61-1.45 (m, 5H), 1.43 (s, 3H), 1.25 (s, 3H).

Example 99: Preparation of Compounds 128 and 129

(S)-2-((R)-6-(N-((1s,4S)-4-amino-4-(methoxymethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,4R)-4-amino-4-(methoxymethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

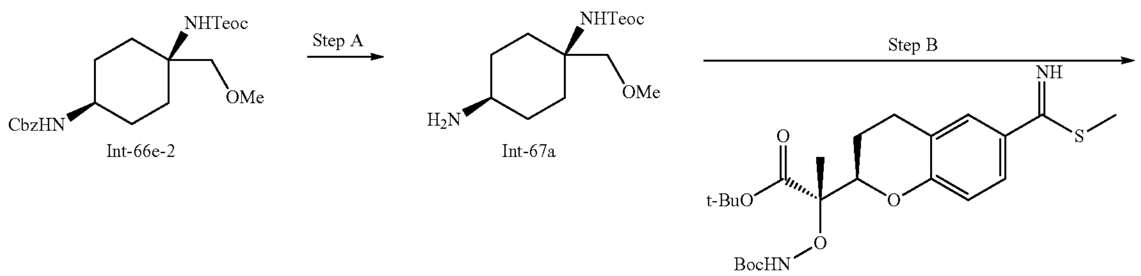

Int-66e-2 Int-67a Int-3c

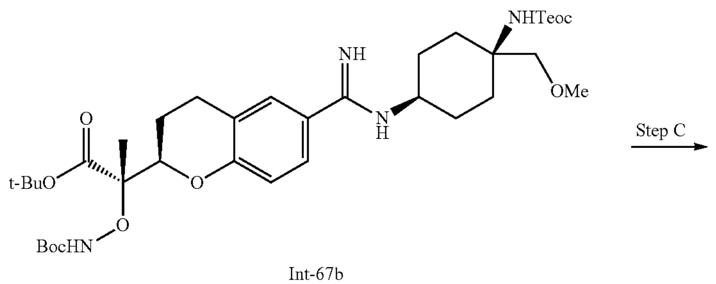

Int-67b

-continued

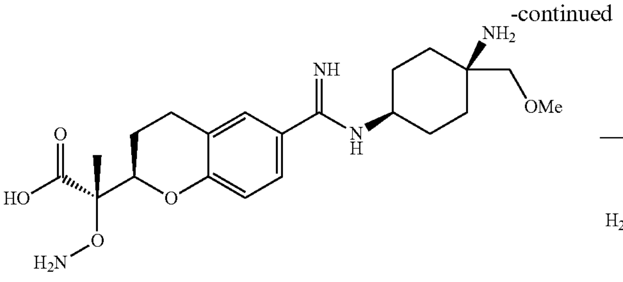

Int-67c

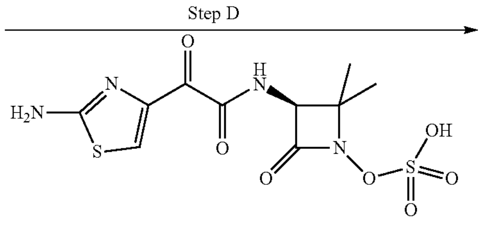

Int-5

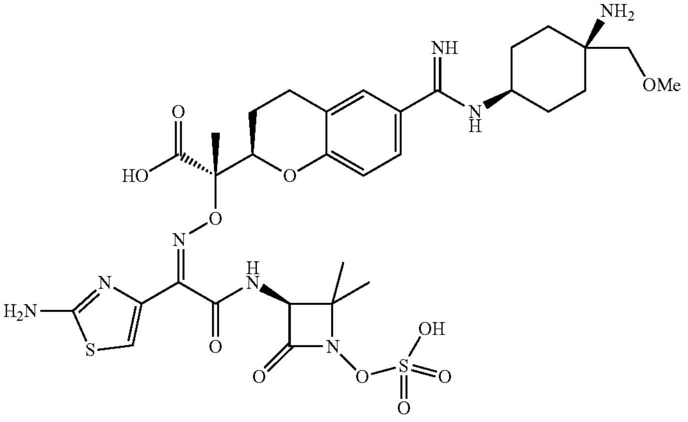

Compound 128

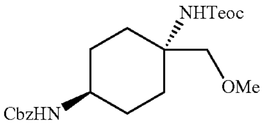

Int-66e-1

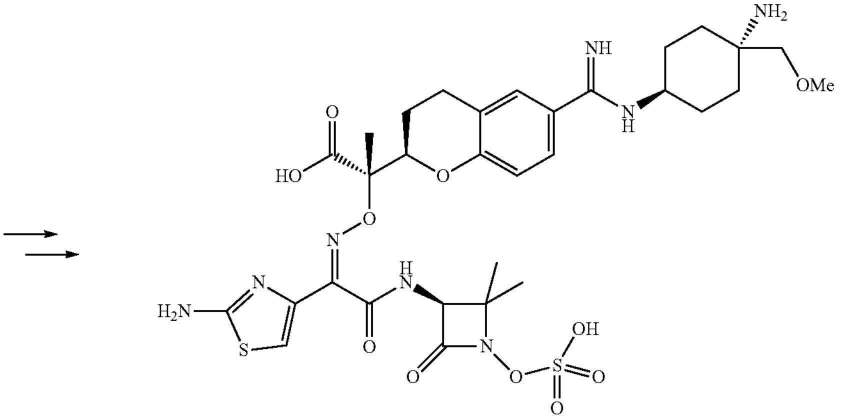

Compound 129

Step A—Synthesis of Intermediate 67a To a solution of intermediate 66e-2 in MeOH (10 mL) was added Pd/C (11.21 mg, 10 wt. %, 0.105 mmol). The mixture was stirred at 25° C. under a $H_2$ atmosphere (15 psi) for 1.5 h. Then the reaction mixture was filtered through Celite™, and the filtrate was concentrated under reduced pressure to give intermediate 67a, which was used in the next reaction without further purification. LC-MS (ESI): m/z 303.2 $[M+H]^+$.

Step B—Synthesis of Intermediate 67b To a stirred solution of intermediate 3c (470 mg, 1.007 mmol) and intermediate 67a (305 mg, 1.007 mmol) in MeCN (9 mL) were added sequentially AcOH (0.231 mL, 4.03 mmol) and potassium acetate (297 mg, 3.02 mmol) at 22° C. The reaction was stirred at 80° C. for 30 minutes, then diluted with water (30 mL), and extracted with EtOAc (50 mL×3). The organic layers were combined, dried over anhydrous $Na_2SO_4$, filtered and the filtrate was concentrated under reduced pressure. The resulting residue was purified by reverse phase MPLC (Biotage; 40 g Agela, C18, 20~35 μm, Eluent of 0-40% $MeCN/H_2O$ (0.5% TFA) gradient @ 50 mL/min) to give intermediate 67b. LC-MS (ESI): m/z 721.4 $[M+H]^+$.

Step C—Synthesis of Intermediate 67c A solution of intermediate 67b (460 mg, 0.638 mmol) in TFA (6 mL) was stirred at 40° C. for 1 h. Then the reaction mixture was concentrated in vacuo to give intermediate 67c, which was used in the next reaction without further purification. LC-MS (ESI): m/z 421.1 $[M+H]^+$.

Step D—Synthesis of Compound 128 To a solution of intermediate 67c (268 mg, 0.637 mmol) in MeOH (5 mL) was added intermediate 5 (232 mg, 0.637 mmol). The reaction was stirred at 26° C. for 16 h, then diluted with MeOH (3 mL) and purified by reverse phase HPLC (Column: Boston Uni C18 40×150×5 um; Condition: water (0.1% TFA)-ACN; Begin B 0, End B 30; Gradient Time (min) 11; 100% B Hold Time (min) 2; Flow Rate (mL/min) 60; Injections 2) to give the product as the TFA salt. The TFA salt was further purified by reverse phase HPLC (Column: Welch Xtimate C18 150×25 mm×5 um; Condition: water (0.225% FA)-ACN; Begin B 0, End B 19; Gradient Time (min) 15; 100% B Hold Time (min) 2; FlowRate (mL/min) 25; Injections 2), followed by lyophilization to give compound 128 as the formic acid salt. LC-MS (ESI): m/z 767.3 $[M+H]^+$. $^1H$ NMR (400 MHz, DMSO-$d_6$) δ 7.42 (br s, 2H), 6.91 (br d, J=9.0 Hz, 1H), 6.75 (s, 1H), 4.62 (s, 1H), 4.41 (br d, J=11.3 Hz, 1H), 3.74-3.63 (m, 1H), 3.38-3.29 (m, 2H), 3.30 (s, 3H), 2.80-2.65 (m, 2H), 1.99-1.55 (m, 9H), 1.40 (s, 3H), 1.39 (s, 3H), 1.27-1.18 (m, 4H).

Compound 129 was prepared according to the procedure in Step A to Step D of Example 99 by replacing intermediate 66e-2 with intermediate 66e-1. LC-MS (ESI): m/z 767.2 $[M+H]^+$. $^1H$ NMR (400 MHz, $D_2O$) δ: 7.45-7.28 (m, 2H), 6.87 (d, J=8.6 Hz, 1H), 6.82 (s, 1H), 4.59 (s, 1H), 4.40 (br d, J=11.3 Hz, 1H), 3.58 (s, 3H), 3.34 (s, 3H), 2.87-2.68 (m, 2H), 2.10-1.96 (m, 5H), 1.78-1.52 (m, 5H), 1.50 (s, 3H), 1.41 (s, 3H), 1.23 (s, 3H).

Example 100: Preparation of Intermediates 68d-1 and 68d-2

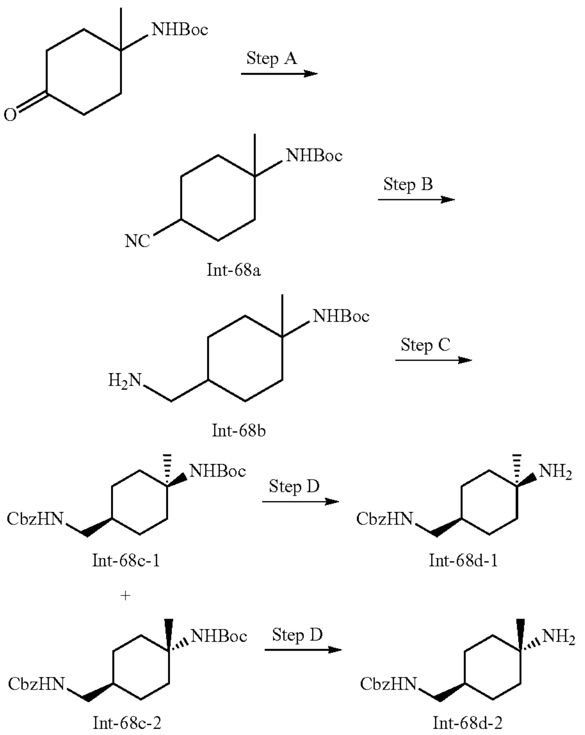

Step A—Synthesis of Intermediate 68a To a stirred solution of tert-butyl (1-methyl-4-oxocyclo-hexyl)carbamate (2 g, 8.80 mmol) and 1-((isocyanomethyl)sulfonyl)-4-methylbenzene (1.890 g, 9.68 mmol) in DME (20 mL) at −20° C., was added dropwise potassium 2-methylpropan-2-olate (1 M in t-BuOH) (15.84 mL, 15.84 mmol) under $N_2$. The reaction was warmed to 20° C. and stirred for 12 h, then diluted with saturated aqueous $NH_4Cl$ (60 mL), and extracted with EtOAc (90 mL×3). The organic layers were combined, washed with brine (60 mL), dried over anhydrous $Na_2SO_4$, filtered and the filtrate was concentrated under reduced pressure. The resulting residue was purified by a silica gel column eluting with petroleum ether/EtOAc: 20:1 to 10:1 gradient to give intermediate 68a. $^1H$ NMR (400 MHz, $CDCl_3$) δ: 4.27 (br s, 1H), 2.77 (br t, J=4.7 Hz, 0.5H), 2.50-2.39 (m, 0.5H), 2.17-2.08 (m, 1H), 2.05-1.96 (m, 1H), 1.93-1.73 (m, 4H), 1.71-1.55 (m, 2H), 1.63-1.43 (m, 9H), 1.33-1.31 (m, 3H).

Step B—Synthesis of Intermediate 68b To a solution of intermediate 68a (2.9 g, 12.17 mmol) in THF (25 mL) was added $LiAlH_4$ (0.748 g, 19.71 mmol) at 0° C. The reaction was stirred at 25° C. for 2.5 h. then quenched with 1 M NaOH (20 mL) and $H_2O$ (10 mL) at 0° C. The resulting mixture was extracted with ethyl acetate (3×150 mL). The combined organic layers were dried over anhydrous $MgSO_4$, filtered and the filtrate was concentrated in vacuo to give intermediate 68b, which was used in the next reaction without further purification. LC-MS (ESI): m/z 243.2 $[M+H]^+$.

Step C—Synthesis of Intermediates 68c-1 and 68c-2 To a solution of intermediate 68b (1.4 g, 5.78 mmol) in THF (16 mL) and water (8 mL) was added $Na_2CO_3$ (1.837 g, 17.33 mmol) and benzyl chloroformate (1.024 mL, 7.51 mmol) at 0° C. The reaction mixture was stirred at 20° C. for 12 h, then diluted with water (50 mL) and extracted with ethyl acetate (130 mL×3). The combined organic layers were washed with brine (60 mL), dried over anhydrous $Na_2SO_4$, and filtered. The filtrate was concentrated in vacuo, and the resulting residue was purified by a silica gel column eluting with petroleum ether: EtOAc 8:1 to 5:1 gradient to give the product as a mixture of cis and trans isomers. The cis/trans mixture was further purified by SFC (Column: DAICEL CHIRALCEL OJ (250 mm*50 mm, 10 um); Conditions: 0.1% $NH_3 \cdot H_2O$/EtOH; Begin: B 30%, End: B 30%; FlowRate (mL/min): 200; Injections: 300) to individually give intermediate 68c-1 (the first eluting isomer) and intermediate 68c-2 (the second eluting isomer). Intermediate 68c-1: $^1H$ NMR (400 MHz, $CDCl_3$) δ: 7.42-7.28 (m, 5H), 5.13-5.06 (m, 2H), 4.82 (br s, 1H), 4.26 (br s, 1H), 3.07 (br t, J=6.5 Hz, 2H), 2.09 (br d, J=12.1 Hz, 2H), 1.65 (br d, J=11.0 Hz, 1H), 1.56 (br d, J=13.7 Hz, 2H), 1.43 (s, 9H), 1.29 (s, 3H), 1.21-1.06 (m, 4H).

Intermediate 68c-2: $^1H$ NMR (400 MHz, $CDCl_3$) δ: 7.40-7.29 (m, 5H), 5.09 (s, 2H), 4.77 (br s, 1H), 4.44 (br s, 1H), 3.09 (br t, J=6.5 Hz, 2H), 1.83 (br d, J=12.5 Hz, 2H), 1.63 (br t, J=11.9 Hz, 5H), 1.43 (s, 9H), 1.29 (s, 3H), 1.19-1.07 (m, 2H).

Step D—Synthesis of Intermediates 68d-1 and 68d-2 A solution of intermediate 68c-1 (300 mg, 0.797 mmol) in HCl in 1,4-dioxane (5 mL, 4 M) was stirred at 20° C. for 2 h. The reaction mixture was then concentrated in vacuo to give intermediate 68d-1, which was used in the next reaction without further purification. LC-MS (ESI): m/z 277.1 $[M+H]^+$.

Intermediate 68d-2 was prepared from intermediate 68c-2 according to the procedure in Step D of Example 100. $^1H$ NMR (400 MHz, $CD_3OD$) δ: 7.40-7.26 (m, 5H), 5.07 (s, 2H), 3.02 (d, J=6.6 Hz, 2H), 1.86-1.70 (m, 4H), 1.69-1.42 (m, 3H), 1.34 (s, 3H), 1.20 (q, J=12.0 Hz, 2H).

Example 101: Preparation of Compounds 130 and 131

(S)-2-((R)-6-(N-((1s,4S)-4-(aminomethyl)-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,4R)-4-(aminomethyl)-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

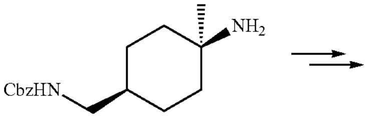

Int-68d-1

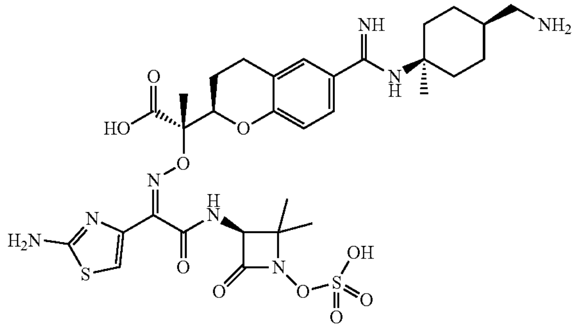

Compound 130

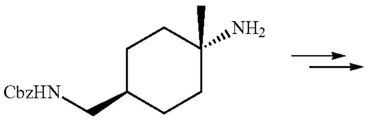

Int-68d-2

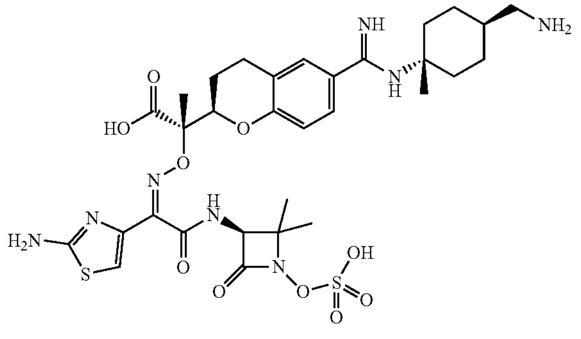

Compound 131

Compounds 130 and 131 were prepared from intermediate 68d-1 and intermediate 68d-2 according to the procedure in Step A to Step E of Example 48.

Compound 130: LC-MS (ESI): m/z 751.2 $[M+H]^+$. $^1H$ NMR (400 MHz, $D_2O+CD_3CN$) δ: 7.39-7.30 (m, 2H), 6.88 (d, J=9.6 Hz, 1H), 6.80 (s, 1H), 4.62 (s, 1H), 4.38 (br d, J=11.4 Hz, 1H), 2.89-2.73 (m, 4H), 2.25 (br d, J=14.2 Hz, 2H), 2.08 (br d, J=14.7 Hz, 1H), 1.80-1.63 (m, 4H), 1.50 (s, 3H), 1.55-1.45 (m, 2H), 1.50 (s, 3H), 1.38 (s, 3H), 1.25 (s, 3H), 1.20-1.07 (m, 2H). Compound 131: LC-MS (ESI): m/z 751.2 $[M+H]^+$. $^1H$ NMR (400 MHz, $D_2O+CD_3CN$) δ: 7.40-7.30 (m, 2H), 6.87 (d, J=8.5 Hz, 1H), 6.79 (s, 1H), 4.62 (s, 1H), 4.37 (br d, J=10.3 Hz, 1H), 2.90-2.70 (m, 4H), 2.12-1.98 (m, 3H), 1.80-1.60 (m, 6H), 1.49 (s, 3H), 1.42 (s, 6H), 1.30-1.14 (m, 2H), 1.24 (s, 3H).

Example 102: Preparation of Intermediates 69e-1 and 69e-2

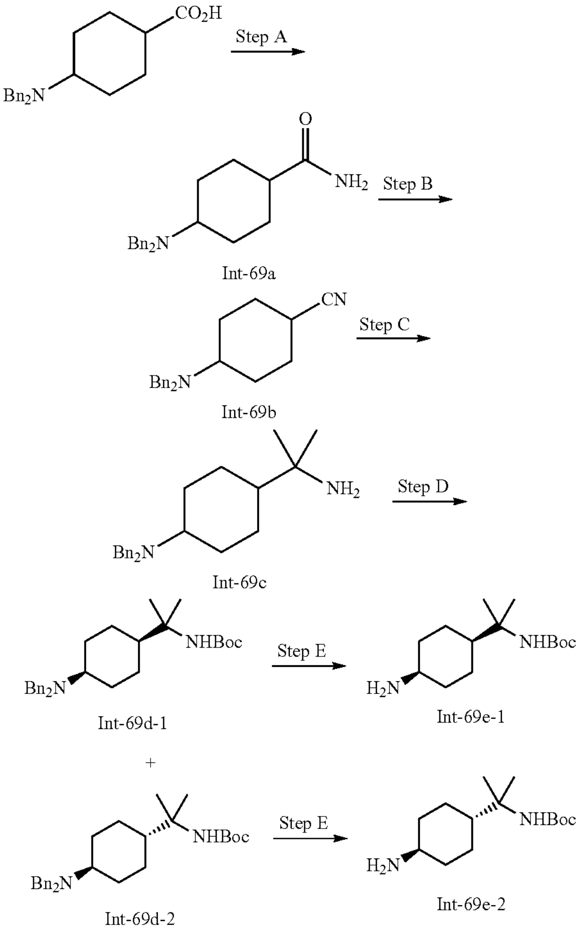

Int-69a

Int-69b

Int-69c

Int-69d-1 + Int-69e-1

Int-69d-2 Int-69e-2

Step A—Synthesis of Intermediate 69a To a stirred solution of 4-(dibenzylamino)cyclohexane-1-carboxylic acid (8.4 g, 26.0 mmol) in THF (88 mL) at 0° C., were added di-tert-butyl dicarbonate (7.76 mL, 33.8 mmol) and ammonium bicarbonate (5.34 g, 67.5 mmol). Then pyridine (2.06 mL, 26.0 mmol) was added, and the reaction was stirred at room temperature for 12 h. The reaction mixture was then poured into saturated aqueous sodium bicarbonate solution (50 mL), and extracted with ethyl acetate (50 mLx3). The combined organic layers were washed with brine (30 mL), dried over anhydrous $Na_2SO_4$, and filtered. The filtrate was concentrated in vacuo to afford intermediate 69a. which was used in the next reaction without further purification. LC-MS (ESI): m/z 323.3 $[M+H]^+$.

Step B—Synthesis of Intermediate 69b To a stirred solution of intermediate 69a (8.37 g, 26.0 mmol) and triethylamine (14.43 mL, 104 mmol) in dry THF (179 mL) at 0° C. was added trifluoroacetic anhydride (5.77 mL, 41.5 mmol). The reaction was stirred at 0-10° C. for 2 h under a nitrogen atmosphere, then quenched with ice-cold water and extracted with ethyl acetate (3×60 mL). The combined organic layers were washed with brine (50 mL), dried over anhydrous $Na_2SO_4$, filtered, and the filtrate was concentrated in vacuo. The resulting residue was purified by a flash silica gel chromatography MPLC (ISCO®; 120 g SepaFlash® Silica Flash Column, Eluent of 0-12.4% ethyl acetate/petroleum ether gradient @ 60 mL/min) to give intermediate 69b as a mixture of cis/trans stereoisomers. LC-MS (ESI): m/z 305.2 $[M+H]^+$.

Step C—Synthesis of Intermediate 69c Cerium (III) chloride (18.31 g, 74.3 mmol) was dried with stirring at 140° C. under vacuum for 2 h, then THF (130 mL) was added. The resulting suspension was cooled to −65° C., followed by the dropwise addition of a solution of 1.6 N methyllithium in $Et_2O$ (47.6 mL, 76 mmol). The reaction mixture was stirred at −65° C. for 1 hour. Then a solution of intermediate 69b (5.8 g, 19.05 mmol) in THF (10 mL) was added dropwise at −65° C. The reaction mixture was allowed to warm to room temperature and stirred for 16 h. The reaction mixture was then filtered, and the filtrate was concentrated under vacuum. The resulting residue was partitioned between saturated aqueous $NH_4Cl$ (100 mL) and $CH_2Cl_2$ (20 mL). The aqueous layer was separated, and extracted with $CH_2Cl_2$ (50 mL×3). The combined organic layers were washed with brine (50 mL), dried over anhydrous $Na_2SO_4$, and concentrated under vacuum to give intermediate 69c, which was used in the next reaction without further purification. LC-MS (ESI): m/z 337.0 $[M+H]^+$.

Step D—Synthesis of Intermediates 69d-1 and 69d-2 To a stirred solution of intermediate 69c (6.41 g, 19.05 mmol) and TEA (9.29 mL, 66.7 mmol) in DCM (121 mL) at 15° C., was added $(Boc)_2O$ (7.96 mL, 34.3 mmol). The reaction was stirred at 15° C. for 16 h, and then concentrated in vacuo. The resulting residue was purified directly by flash silica gel chromatography MPLC (ISCO®; 80 g SepaFlash® Silica Flash Column, Eluent of 0-15% ethyl acetate/petroleum ether gradient @ 45 mL/min). The product fractions were combined and concentrated under vacuum. To the resulting residue was added petroleum ether, and the mixture was filtered. The insoluble solids were collected to give intermediate 69d-2 (LC-MS (ESI): m/z 437.5 $[M+H]^+$). The filtrate was concentrated in vacuo to give intermediate 69d-1 (LC-MS (ESI): m/z 437.5 $[M+H]^+$).

Step E—Synthesis of Intermediates 69e-1 and 69e-2 To a solution of intermediate 69d-1 (850 mg, 1.947 mmol)) in a mixture of MeOH (3 mL) and EtOAc (15 mL) was added 20% palladium hydroxide (200 mg, 0.285 mmol), Pd/C (200 mg, 10 wt. %, 0.188 mmol) and aqueous ammonium hydroxide (85 mg, 0.603 mmol) under a $N_2$ atmosphere. The suspension was degassed under vacuum and purged with $H_2$ three times. The reaction mixture was stirred at 20° C. for 2 h under $H_2$ (15 psi), and then filtered. The filtrate was concentrated in vacuo to give intermediate 69e-1, which was used in the next reaction without further purification. $^1H$ NMR (500 MHz, $CD_3OD$) δ: 3.10 (br s, 1H), 1.83 (br t, J=11.9 Hz, 1H), 1.74 (br d, J=13.4 Hz, 2H), 1.63-1.50 (m, 4H), 1.46-1.32 (m, 11H), 1.22 (s, 6H).

Intermediate 69e-2 was prepared according to the procedure used for the synthesis of intermediate 69d-2. $^1H$ NMR (400 MHz, $CD_3OD$) δ: 2.95 (br t, J=11.7 Hz, 1H), 2.07 (br d, J=10.8 Hz, 2H), 1.96 (br s, 1H), 1.84 (br d, J=12.2 Hz, 2H), 1.42 (s, 11H), 1.34 (br d, J=13.9 Hz, 2H), 1.20 (s, 6H).

Example 103: Preparation of Compounds 132 and 133

(S)-2-((R)-6-(N-((1s,4S)-4-(2-aminopropan-2-yl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid, and (S)-2-((R)-6-(N-((1r,4R)-4-(2-aminopropan-2-yl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

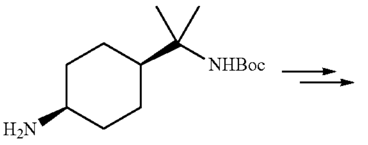

Int-68e-1

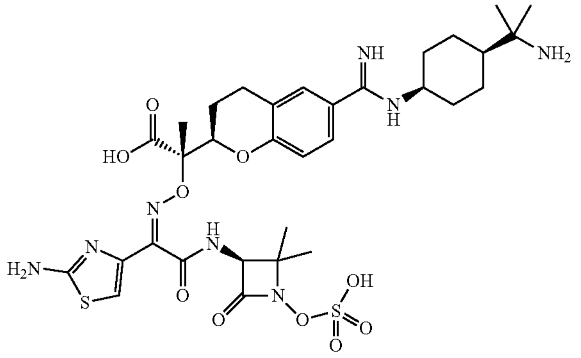

Compound 132

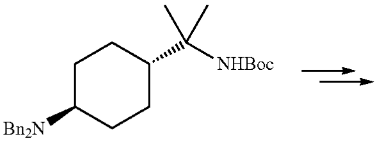

Int-68d-2

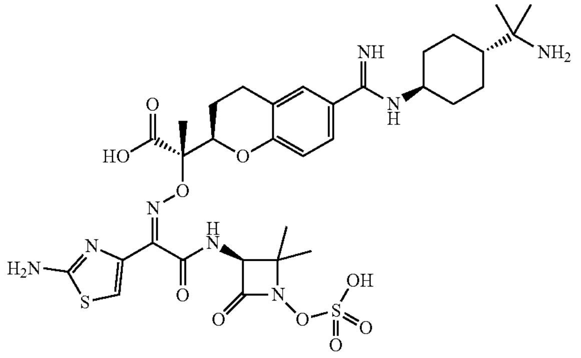

Compound 133

Compounds 132 and 133 were prepared from the corresponding intermediate 69e-1 and intermediate 69e-2 according to the procedure in Step I to Step K of Example 96.

Compound 132: LC-MS (ESI): m/z 765.4 $[M+H]^+$. $^1H$ NMR (400 MHz, $CD_3CN+D_2O$) δ: 7.40-7.31 (m, 2H), 6.89 (d, J=8.6 Hz, 1H), 6.79 (s, 1H), 4.63 (s, 1H), 4.38 (br d, J=11.3 Hz, 1H), 3.91 (br s, 1H), 2.84-2.77 (m, 2H), 2.15-

2.03 (m, 3H), 1.76-1.54 (m, 6H), 1.50 (s, 3H), 1.43 (s, 3H), 1.38-1.30 (m, 2H), 1.29 (s, 3H), 1.26 (s, 6H).

Compound 133: LC-MS (ESI): m/z 765.2 $[M+H]^+$. $^1H$ NMR (400 MHz, $D_2O+CD_3CN$+formic acid) δ: 7.76-7.62 (m, 2H), 7.34 (s, 1H), 7.19 (d, J=8.6 Hz, 1H), 5.19-5.04 (m, 1H), 4.75-4.57 (m, 1H), 3.90-3.78 (m, 1H), 3.19-3.10 (m, 2H), 2.53-2.40 (m, 3H), 2.32-2.25 (m, 3H), 2.15-2.03 (m, 3H), 1.89-1.77 (m, 1H), 1.75-1.65 (m, 5H), 1.62-1.48 (m, 8H), 1.47 (s, 3H).

Example 104: Preparation of Intermediate 70c

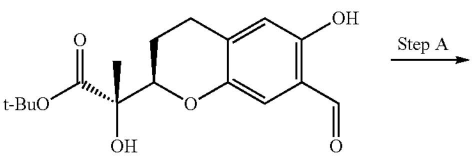

Int-64c-1

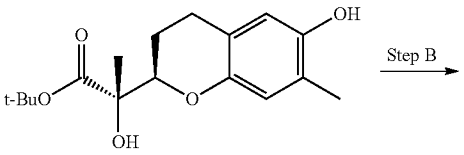

Int-70a

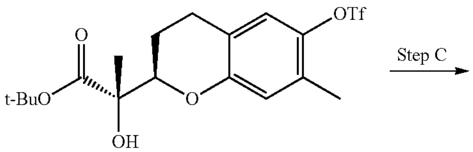

Int-70b

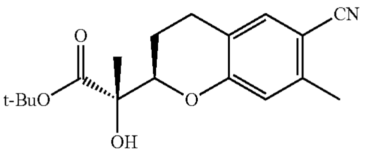

Int-70c

Step A—Synthesis of Intermediate 70a To a stirred solution of intermediate 64c-1 (480 mg, 1.489 mmol) in EtOH (20 mL) was added palladium on carbon (317 mg, 10 wt. %, 0.298 mmol) in one portion at 28° C. The reaction was stirred under $H_2$ (50 psi) at 28° C. for 18 h, then filtered. The filtrate was concentrated under reduced pressure to give intermediate 70a, which was used in the next reaction without further purification. $^1H$ NMR (400 MHz, $CD_3OD$) δ: 6.41 (d, J=10.3 Hz, 2H), 4.03 (dd, J=1.7, 11.2 Hz, 1H), 2.85-2.73 (m, 1H), 2.71-2.63 (m, 1H), 2.08 (s, 3H), 2.01 (br dd, J=6.2, 13.3 Hz, 1H), 1.84 (dt, J=5.6, 12.2 Hz, 1H), 1.51 (s, 9H), 1.35 (s, 3H).

Step B—Synthesis of Intermediate 70b To a stirred solution of intermediate 70a (0.550 g, 1.784 mmol) in DCM (15 mL) were added sequentially TEA (0.870 mL, 6.24 mmol) and 1,1,1-trifluoro-N-phenyl-N-((trifluoromethyl)sulfonyl) methanesulfonamide (1.27 g, 3.56 mmol) at 15° C. The reaction was stirred at 15° C. for 16 h, then concentrated under reduced pressure. The resulting residue was purified by flash silica gel chromatography (ISCO; 20 g Agela Silica Flash Column, Eluent of 0-15% EtOAc/Petroleum Ether gradient @ 30 mL/min) to give intermediate 70b. $^1H$ NMR (400 MHz, $CDCl_3$) δ: 6.92 (s, 1H), 6.62 (s, 1H), 4.18-4.12 (m, 1H), 3.40 (s, 1H), 2.92-2.77 (m, 2H), 2.27 (s, 3H), 2.12-2.06 (m, 1H), 2.02-1.89 (m, 1H), 1.53 (s, 9H), 1.39 (s, 3H).

Step C—Synthesis of Intermediate 70c To a mixture of intermediate 70b (730 mg, 1.657 mmol), sodium carbonate (26.4 mg, 0.249 mmol) in MeCN (6 mL) and $H_2O$ (5 mL) were added potassium ferrocyanide trihydrate (350 mg, 0.829 mmol) and chloro(2-dicyclohexylphosphino-2',4',6'-triisopropyl-1,1'-biphenyl)[2-(2'-amino-1,1'-biphenyl)]palladium(II) (261 mg, 0.331 mmol) under $N_2$. The reaction was stirred at 100° C. for 50 minutes under microwave irradiation. Then the reaction mixture was filtered, and the filtrate was diluted with $H_2O$ (40 mL), and extracted with EtOAc (20 mL×3). The organic layers were combined, washed with brine, dried over anhydrous $Na_2SO_4$, and filtered. The filtrate was concentrated under reduced pressure, and the resulting residue was purified by flash silica gel chromatography (ISCO; 12 g Agela Silica Flash Column, Eluent of 0-15% EtOAc/Petroleum Ether gradient @ 30 mL/min) to give intermediate 70c. $^1H$ NMR (400 MHz, $CDCl_3$) δ: 7.29 (s, 1H), 6.61 (s, 1H), 4.19 (dd, J=2.3, 11.0 Hz, 1H), 3.40 (s, 1H), 2.87-2.76 (m, 2H), 2.42 (s, 3H), 2.14-2.05 (m, 1H), 2.01-1.89 (m, 1H), 1.52 (s, 9H), 1.39 (s, 3H).

Example 105: Preparation of Compound 134

(S)-2-((R)-6-(N-((1s,3S)-3-aminocyclobutyl)carbamimidoyl)-7-methylchroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

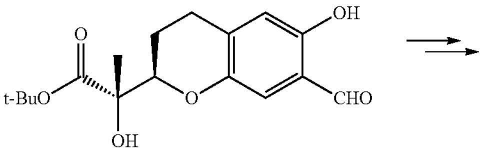

Int-70c

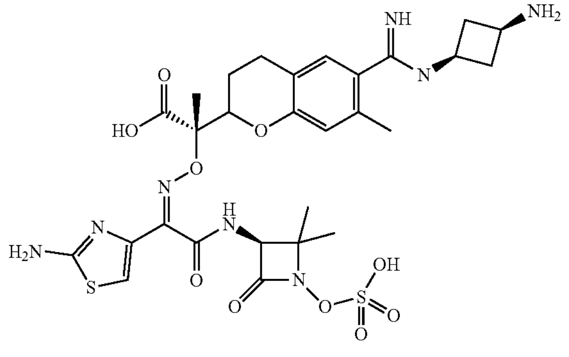

Compound 134

Compound 134 was prepared from intermediate 70c according to the procedure in Step E to Step K of Example 96. LC-MS (ESI): m/z 709.2 $[M+H]^+$. $^1H$ NMR (400 MHz, $D_2O+CD_3CN$) δ: 7.08 (s, 1H), 6.80 (s, 1H), 6.68 (s, 1H), 4.66 (s, 1H), 4.30 (br d, J=11.3 Hz, 1H), 4.05-3.95 (m, 1H), 3.64-3.54 (m, 1H), 2.93-2.82 (m, 2H), 2.81-2.63 (m, 2H), 2.34-2.24 (m, 2H), 2.22 (s, 3H), 2.09-2.00 (m, 1H), 1.75-1.60 (m, 1H), 1.48 (s, 3H), 1.44 (s, 3H), 1.26 (s, 3H).

Example 106: Preparation of Compound 135
(S)-2-((R)-6-(N-((1r,4R)-4-amino-4-(hydroxymethyl)-1-methylcyclohexyl)-carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid
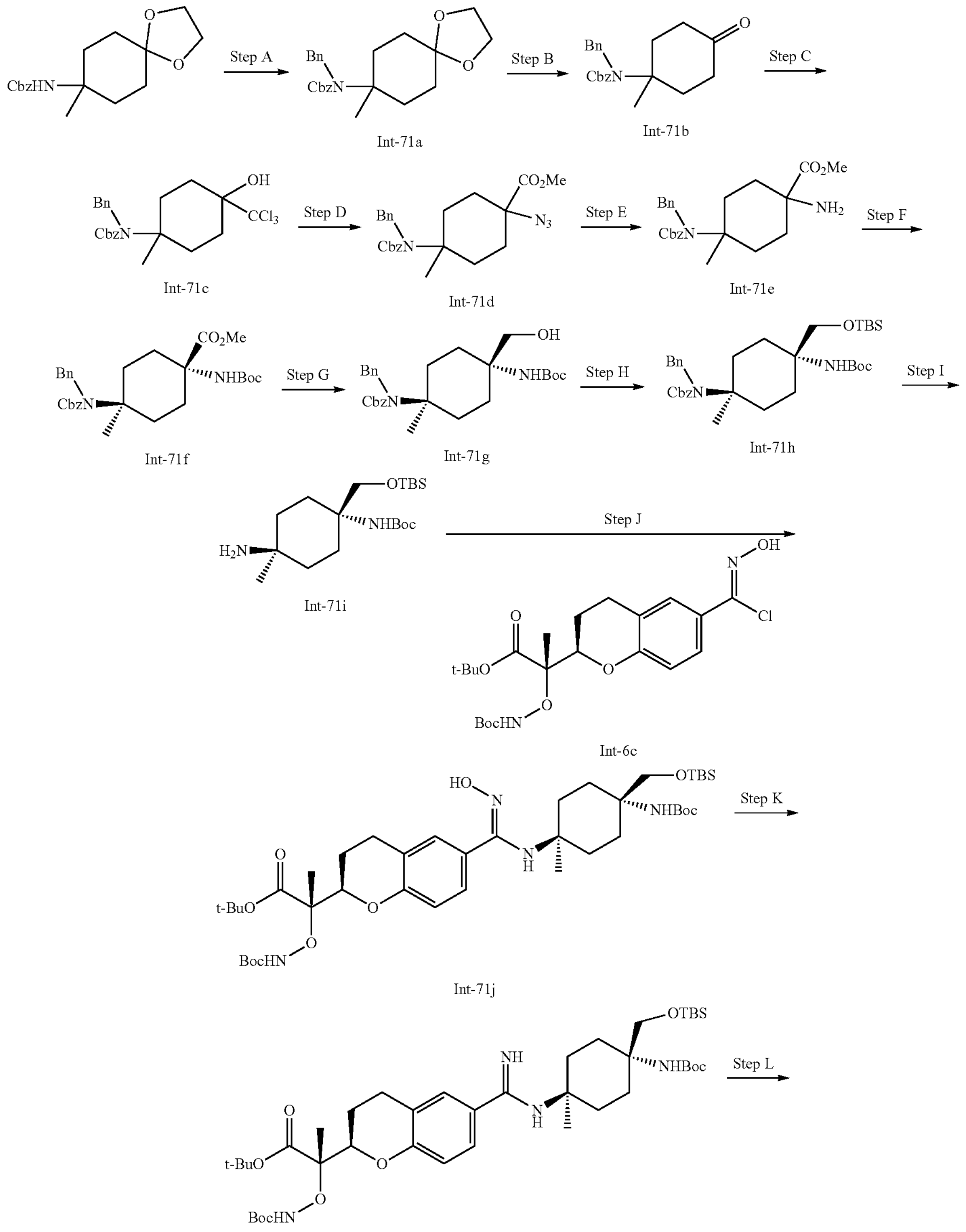
Int-71a
Int-71b
Int-71c
Int-71d
Int-71e
Int-71f
Int-71g
Int-71h
Int-71i
Int-6c
Int-71j
Int-71k -continued

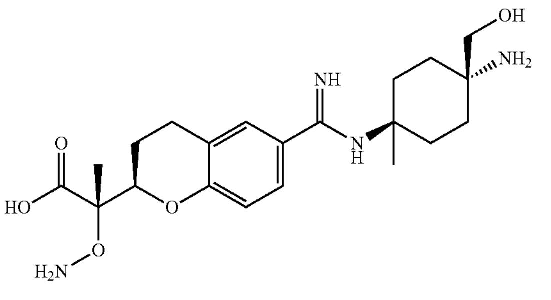

Int-711

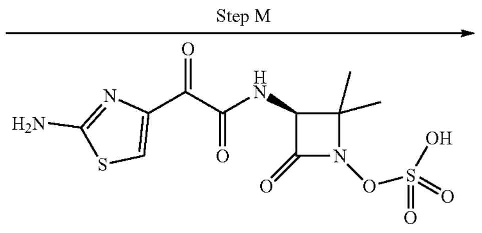

Int-5

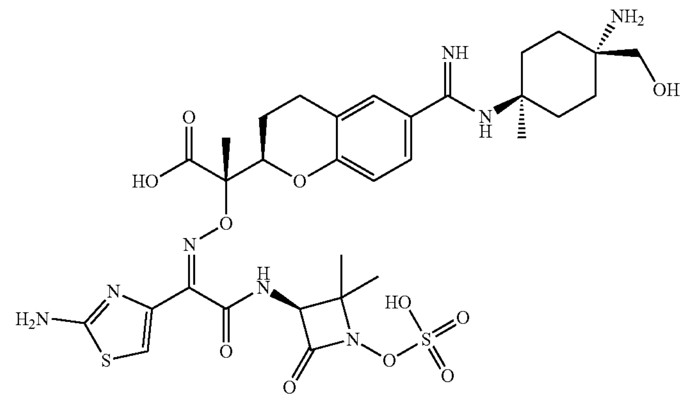

Compound 135

Step A—Synthesis of Intermediate 71a To a solution of benzyl (8-methyl-1,4-dioxaspiro[4.5]-decan-8-yl)carbamate (5.6 g, 18.34 mmol) in DMF (180 mL) stirred at 0° C. was added NaH (1.467 g, 60 wt. %, 36.7 mmol) portion wise. The reaction was stirred 20 minutes, then BnBr (3.92 mL, 33.0 mmol) was added dropwise at 0° C. The reaction mixture was stirred at 30° C. for 2.5 h, then diluted with saturated aqueous $NH_4Cl$ solution (200 mL), and extracted with EtOAc (50 mL×5). The combined organic layers were washed with brine (50 mL), dried over anhydrous $Na_2SO_4$, and filtered. The filtrate was concentrated under vacuum, and the resulting residue was purified by flash silica gel chromatography (ISCO; 40 g Agela Silica Flash Column, Eluent of 0-25% EtOAc/Petroleum Ether gradient @ 40 mL/min) to give intermediate 71a. LC-MS (ESI): m/z 396.2 $[M+H]^+$.

Step B—Synthesis of Intermediate 71b To a stirred solution of intermediate 71a (11.238 g, 28.4 mmol) in THF (140 mL) and water (140 mL) at 15° C. was added 4-methylbenzenesulfonic acid hydrate (10.81 g, 56.8 mmol). The reaction mixture was stirred at 30° C. for 72 h, then diluted with saturated aqueous $NaHCO_3$ solution (280 mL), and extracted with EtOAc (80 mL×3). The organic layers were combined, washed with brine (100 mL), dried over anhydrous $Na_2SO_4$, filtered and the filtrate was concentrated under reduced pressure. The resulting residue was purified by flash silica gel chromatography (ISCO; 80 g Agela Silica Flash Column, Eluent of 0-28% EtOAc/Petroleum Ether gradient @ 60 mL/min) to give intermediate 71b. LC-MS (ESI): m/z 352.1 $[M+H]^+$.

Step C—Synthesis of Intermediate 71c To a stirred solution of intermediate 71b (7.738 g, 22.02 mmol) and chloroform (7.5 mL, 93 mmol) in THF (114 mL) at −78° C. was added dropwise LiHMDS (1 M in THF, 48.4 mL, 48.4 mmol). The reaction was stirred at −78° C. for 1 h, then poured into a saturated aqueous solution of $NH_4Cl$ (300 mL) and extracted with EtOAc (100 mL×3). The organic layers were combined, washed with brine (50 mL), dried over anhydrous $Na_2SO_4$, filtered and the filtrate was concentrated under vacuum. The resulting residue was purified by flash silica gel chromatography (ISCO; 120 g Agela Silica Flash Column, Eluent of 0-25% EtOAc/Petroleum Ether gradient @ 70 mL/min) to give intermediate 71c. LC-MS (ESI): m/z 470.0 and 472.0 $[M+H]^+$.

Step D—Synthesis of Intermediate 71d To a solution of intermediate 71c (5.06 g, 10.75 mmol) in MeOH (237 mL) were added $NaN_3$ (2.13 g, 32.8 mmol) and 18-crown-6 (0.568 g, 2.149 mmol). Then DBU (8.10 mL, 53.7 mmol) was slowly added, and the reaction was stirred at 28° C. for 12 h. Then the reaction mixture was diluted with MTBE (500 mL) and washed with saturated aqueous $NH_4Cl$ solution (450 mL). The organic layer was separated, dried over anhydrous $Na_2SO_4$, filtered and the filtrate was concentrated in vacuo. The resulting residue was purified by flash silica gel chromatography (ISCO; 40 g Agela Silica Flash Column, Eluent of 0-12% EtOAc/Petroleum Ether gradient @ 40 mL/min) to give intermediate 71d. LC-MS (ESI): m/z 459.1 $[M+Na]^+$.

Step E—Synthesis of Intermediate 71e To a solution of intermediate 71d (4.4 g, 10.08 mmol) in THF (44 mL) and AcOH (44 mL) was added zinc powder (3.30 g, 50.4 mmol) in one portion. The reaction mixture was stirred at 28° C. for 1.5 h, then filtered. The filter cake was rinsed with EtOAc (200 mL). The filtrate was concentrated under vacuum to remove most of the solvent. The resulting residue was dissolved in EtOAc (300 mL) and washed with saturated aqueous $NaHCO_3$ (50 mL) and brine (50 mL). The organic layer was dried over anhydrous $Na_2SO_4$, and filtered. The filtrate was concentrated under vacuum to give intermediate 71e, which was used in the next reaction without further purification. LC-MS (ESI): m/z 411.2 $[M+H]^+$.

Step F—Synthesis of Intermediate 71f To a stirred solution of di-tert-butyl dicarbonate (5.75 g, 26.4 mmol) and triethylamine (3.20 g, 31.6 mmol) in EtOH (43 mL) at 65° C., was added dropwise a solution of intermediate 71e (4.328 g, 10.54 mmol) in DMF (13 mL). The reaction was stirred at 65° C. for 1 h, then cooled to room temperature, diluted with water (150 mL), and extracted with EtOAc (40 mL×4). The organic layers were combined, washed with brine (30 mL), dried over anhydrous $Na_2SO_4$, and filtered. The filtrate was concentrated under vacuum, and the resulting residue was purified by flash silica gel chromatography (ISCO; 80 g Agela Silica Flash Column, Eluent of 0-40% EtOAc/Petroleum Ether gradient @ 60 mL/min) to give intermediate 71f. LC-MS (ESI): m/z 511.2 $[M+Na]^+$. $^1H$ NMR (400 MHz, $CDCl_3$) δ: 7.35-7.14 (m, 10H), 5.12 (s, 2H), 4.77 (s, 1H), 4.65 (s, 2H), 3.66 (s, 3H), 2.47 (br d, J=14.1 Hz, 2H), 2.08-1.96 (m, 2H), 1.82 (br d, J=13.7 Hz, 2H), 1.69-1.57 (m, 2H), 1.42 (s, 9H), 1.25 (s, 3H).

Step G—Synthesis of Intermediate 71g A solution of intermediate 71f (3.556 g, 6.96 mmol) in THF (36 mL) was slowly added dropwise to a stirred mixture of $LiBH_4$ (1.517 g, 69.6 mmol) in THF (36 mL) at 0° C. Then the cooling bath was removed and the reaction was stirred at 28° C. for 12 h. The reaction was then cooled in an ice bath, and quenched by the dropwise addition of aqueous hydrochloric acid (1 M, 30 mL). The resulting mixture was extracted with EtOAc (25 mL×3). The organic layers were combined, dried over anhydrous $Na_2SO_4$, and filtered. The filtrate was concentrated under vacuum, and the resulting residue was purified by flash silica gel chromatography (ISCO; 20 g Agela Silica Flash Column, Eluent of 0-100% EtOAc/Petroleum Ether gradient @ 35 mL/min) to give intermediate 71g. LC-MS (ESI): m/z 505.2 $[M+Na]^+$.

Step H—Synthesis of Intermediate 71h To a stirred solution of intermediate 71g (1.74 g, 3.61 mmol) and TBS-Cl (0.652 g, 4.33 mmol) in DCM (26 mL) was added imidazole (0.368 g, 5.41 mmol). The reaction was stirred at 28° C. for 12 h, then diluted with DCM (100 mL), washed with brine (30 mL), dried over $Na_2SO_4$, and filtered. The filtrate was concentrated under vacuum, and the resulting residue was purified by flash silica gel chromatography (ISCO; 20 g Agela Silica Flash Column, Eluent of 0-30% EtOAc/Petroleum Ether gradient @ 35 mL/min) to give intermediate 71h. LC-MS (ESI): m/z 597.3 $[M+H]^+$.

Step I—Synthesis of Intermediate 71i A mixture of intermediate 71h (1500 mg, 2.51 mmol), acetic acid (0.719 mL, 12.57 mmol) and Pd/C (600 mg, 10 wt. %, 0.564 mmol) in MeOH (40 mL) was stirred at 20° C. under a hydrogen atmosphere (15 psi) for 12 h. Then the reaction mixture was filtered, and the filtrate was concentrated under vacuum to give intermediate 71i, which was used in the next reaction without further purification. $^1H$ NMR (400 MHz, $CD_3OD$) δ: 3.70 (s, 2H), 2.15-2.05 (m, 2H), 1.83-1.47 (m, 6H), 1.43 (s, 9H), 1.36 (s, 3H), 0.92 (s, 9H), 0.07 (s, 6H).

Step J—Synthesis of Intermediate 71j To a stirred solution of intermediate 71i (689 mg, 1.849 mmol) in DMF (5.2 mL) at 0° C. was added TEA (0.991 mL, 7.11 mmol). Then a solution of intermediate 6c (670 mg, 1.423 mmol) in DMF (2.1 mL) was added dropwise. The reaction was stirred at 28° C. for 1 h, then diluted with water (30 mL) and extracted with ethyl acetate (10 mL×4). The combined organic layers were washed with brine (5 mL), dried over anhydrous $Na_2SO_4$, and filtered. The filtrate was concentrated in vacuo to give intermediate 71j, which was used in the next reaction without further purification. LC-MS (ESI): m/z 807.5 $[M+H]^+$.

Step K—Synthesis of Intermediate 71k To a mixture of $K_2CO_3$ (0.983 g, 7.11 mmol) in MeOH (15 mL) was added formic acid (0.655 g, 14.22 mmol). The reaction was stirred under $N_2$ for 10 minutes, then added to a solution of intermediate 71j (1.148 g, 1.422 mmol) in acetic acid (9 mL) and acetic anhydride (0.160 g, 1.565 mmol) that had been pre-stirred at ambient temperature for 5 minutes. Then Pd/C (0.605 g, 10 wt. %, 0.569 mmol) was added, and the reaction was stirred at 28° C. for 12 h. The reaction mixture was then filtered and the filtrate was concentrated in vacuo. The resulting residue was dissolved in EtOAc (100 mL), washed sequentially with saturated aqueous $NaHCO_3$ solution (25 mL) and brine (15 mL), dried over anhydrous $Na_2SO_4$, and filtered. The filtrate was concentrated under vacuum, and the resulting residue was purified by MPLC (Biotage; 20 g Agela, C18, 20~35 μm, Eluent of 0-45% $MeCN/H_2O$ (0.5% TFA) gradient @ 50 mL/min) to give intermediate 71k. LC-MS (ESI): m/z 791.5 $[M+H]^+$.

Step L—Synthesis of Intermediate 71l A mixture of intermediate 71k (325 mg, 0.411 mmol) and TFA (3.2 mL, 41.5 mmol) was stirred at 40° C. for 70 minutes. Then the reaction mixture was concentrated under vacuum to give intermediate 71l, which was used in the next reaction without further purification. LC-MS (ESI): m/z 420.8 $[M+H]^+$.

Step M—Synthesis of Compound 135 To a solution of intermediate 71l (173 mg, 0.411 mmol) in MeOH (4.4 mL) was added intermediate 5 (150 mg, 0.411 mmol). The reaction was stirred at ambient temperature for 12 h, filtered, and the filtrate was concentrated under reduced pressure. The resulting residue was dissolved in MeOH (4 mL) and purified by reverse phase HPLC (Column: Boston Uni C18 40×150×5 um; Condition: water (0.1% TFA)-ACN; Begin B 0, End B 30; Gradient Time (min) 10; 100% B Hold Time (min) 2; Flow Rate (mL/min) 60; Injections 2) to give the product as the TFA salt. The TFA salt was purified by another reverse phase HPLC (Column: Welch Xtimate C18 150×25 mm×5 um; Condition: water (0.225% FA)-ACN; Begin B 0, End B 18; Gradient Time (min) 15; 100% B Hold Time (min) 2; Flow Rate (mL/min) 25; Injections 3). The product fractions were combined and lyophilized to give compound 135 as the formic acid salt. LC-MS (ESI): m/z 767.2 $[M+H]^+$. $^1H$ NMR (400 MHz, $D_2O+CD_3CN$) δ: 7.38-7.29 (m, 2H), 6.89-6.79 (m, 2H), 4.63 (s, 1H), 4.38 (br d, J=10.2 Hz, 1H), 3.59 (s, 2H), 2.88-2.71 (br s, 2H), 2.13-2.01 (m, 3H), 1.88-1.63 (m, 7H), 1.50 (s, 3H), 1.45 (s, 3H), 1.42 (s, 3H), 1.23 (s, 3H).

Example 107: Preparation of Compound 136

(S)-2-((R)-6-(N-((1R,3r,5S)-8-azabicyclo[3.2.1]octan-3-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

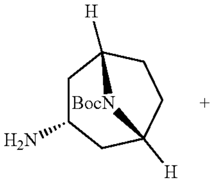

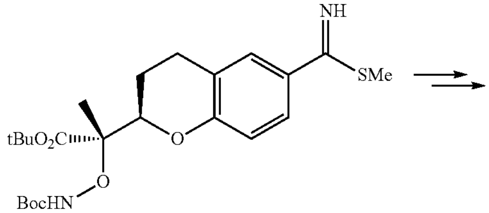

Int-3c

-continued

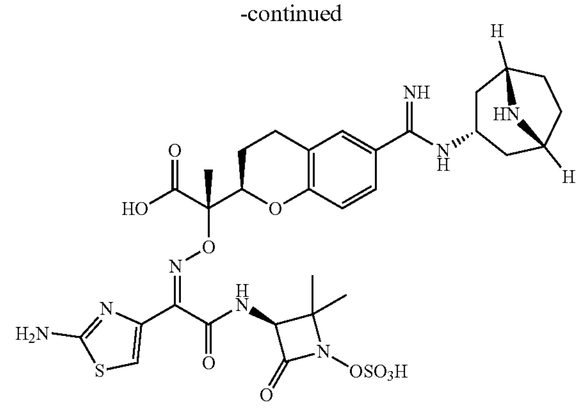

Compound 136

Compound 136 was prepared according to the procedure of Example 11 starting from intermediate 3c and commercially available N-Boc-endo-3-aminotropane to give the title compound as the formic acid salt. LC-MS: m/z 735.5 $[M+H]^+$. $^1$HNMR (400 MHz, 4:1 $D_2O$/DMSO-$d_6$) δ: 7.36 (s, 1H), 7.33 (d, J=10.4 Hz, 1H), 6.85 (d, J=8.7 Hz, 1H), 6.81 (s, 1H), 4.59 (s, 1H), 4.34 (d, J=10.7 Hz, 1H), 4.03-4.15 (m, 3H), 2.68-2.85 (m, 2H), 2.18 (d, J=16.4 Hz, 2H), 1.98-2.11 (m, 5H), 1.88 (t, J=12.3 Hz, 2H), 1.60-1.75 (m, 1H), 1.46 (s, 3H), 1.38 (s, 3H), 1.20 (s, 3H).

Example 108: Preparation of Compound 137

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((3S,5S)-5-(hydroxymethyl)pyrrolidin-3-yl)carbamimidoyl)chroman-2-yl)propanoic acid

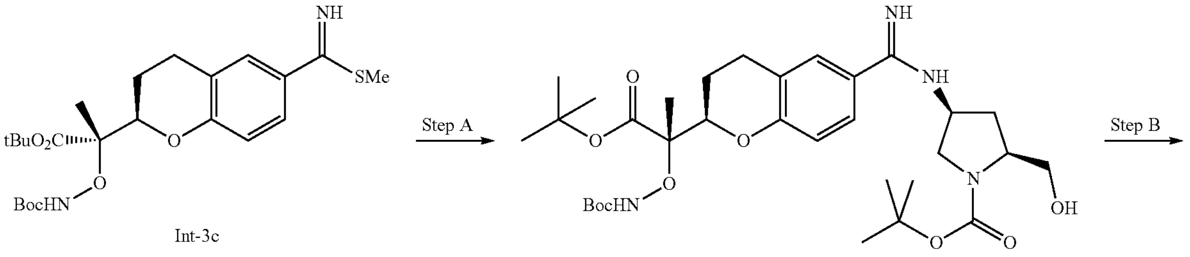

Int-3c

Int-72a

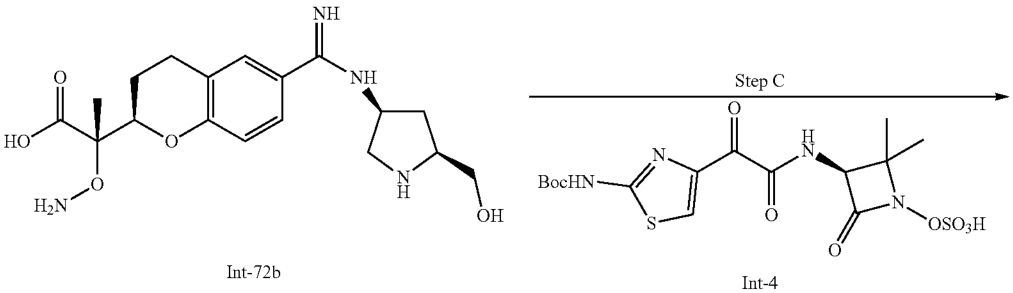

Int-72b

Int-4

-continued

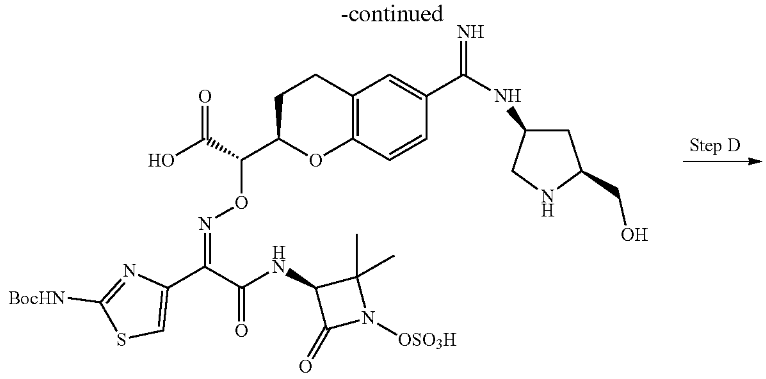

Int-72c

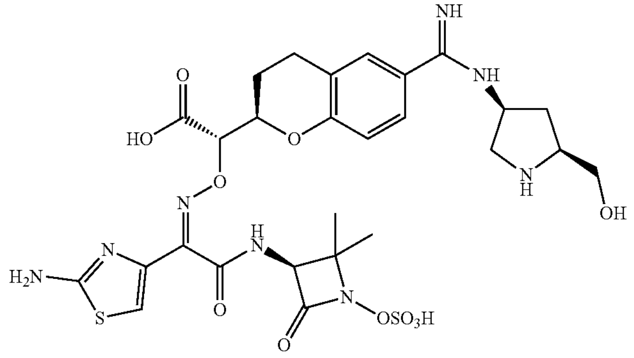

Compound 137

Step A—Synthesis of Intermediate 72a To a vial containing a mixture of (2S,4S)-1-boc-2-hydroxymethyl-4-amino pyrrolidine-HCl (130 mg, 0.514 mmol) in anhydrous acetonitrile (6 mL) was added acetic acid (0.086 mL, 1.500 mmol), followed by the addition of intermediate 3c (200 mg, 0.429 mmol) and N,N-diisopropylethylamine (0.224 ml, 1.286 mmol). The reaction mixture was heated at 65° C. for 1 h, then cooled to ambient temperature and purified on reverse phase Isco Combiflash (150 g, 0-100% 0.05% TFA in ACN/0.05% in water) to give intermediate 72a. LC-MS: m/z 635.4 $[M+H]^+$.

Step B—Synthesis of Intermediate 72b To a vial containing intermediate 72a (0.068 g, 0.107 mmol) was added 2:1 trifluoroacetic acid/anhydrous dichloromethane (6 mL) at ambient temperature. The reaction was stirred for 16 h. Then a solution of 4:1 toluene/MeOH (5 mL) was added, and the reaction mixture was concentrated in vacuo. The resulting residue was azeotroped with 4:1 toluene/MeOH (5 mL) and then dried under high vacuum to give crude intermediate 72b, which was used in the next reaction without further purification. LC-MS: m/z 379.3 $[M+H]^+$.

Step C—Synthesis of Intermediate 72c To a vial charged with intermediate 72b (0.04 g, 0.108 mmol) and intermediate 4 (0.05 g, 0.108 mmol) was added MeOH (4.0 mL) at ambient temperature. The reaction mixture was stirred for 6 h, then concentrated in vacuo to afford intermediate 72c, which was used in the next reaction without further purification. LC-MS: m/z 825.6 $[M+H]^+$.

Step D—Synthesis of Compound 137 To a vial charged with intermediate 72c (0.089 g, 0.108 mmol) was added 1:2 trifluoroacetic acid/anhydrous dichloromethane (6 mL) at ambient temperature. The reaction mixture was stirred for 1 h, then cooled to 0° C., and ethyl ether (6 mL) was slowly added with stirring. The resulting solids were collected by centrifugation (1400 rpm) and purified via reverse phase HPLC (Gilson, C18, 5 um, OBD 30×150 mm, 0.05% TFA in ACN/0.05% TFA in water 0-40% gradient over 18 min; 30 ml/min; injection 3). The product fractions were collected, and concentrated in vacuo. The aqueous layer was directly loaded onto an Amberchrom CG161M column (26 g), washed with 9 CV of (water+0.1% FA), and eluted off with 3 CV of 100% (AcCN+0.1% FA) followed by 3 CV of 50% (AcCN+0.1% FA)/(water+0.1% FA). The product fractions were collected, concentrated in vacuo, and the resulting aqueous residue was lyophilized to give compound 137 as the formic acid salt. LC-MS: m/z 725.5 $[M+H]^+$. $^1$HNMR (500 MHz, 400 uL $D_2O$/100 uL $CD_3CN$) δ: 7.34-7.28 (m, 2H), 6.89 (s, 1H), 6.80-6.79 (d, J=5 Hz, 1H), 4.57-4.49 (m, 1H), 4.42-4.39 (m, 1H), 3.91-3.79 (m, 2H), 3.70-3.62 (m, 2H), 3.45-3.40 (m, 1H), 2.77-2.71 (br s, 2H), 2.66-2.60 (m, 1H), 2.06-1.93 (m, 3H), 1.78-1.66 (m, 1H), 1.47 (s, 3H), 1.34 (s, 3H), 1.10 (s, 3H).

Example 109: Preparation of Intermediate 73b

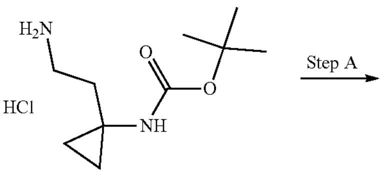

-continued

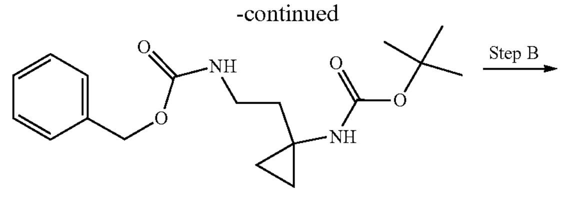

Int-73a

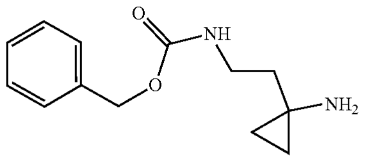

Int-73b

Step A—Synthesis of Intermediate 73a To a vial containing a mixture of tert-butyl (1-(2-aminoethyl)cyclopropyl) carbamate hydrochloride (150 mg, 0.634 mmol) in DCM (5 mL) was added triethylamine (0.442 ml, 3.17 mmol), followed by the dropwise addition of benzyl chloroformate (0.625 mL, 0.950 mmol). The reaction mixture was stirred at ambient temperature for 2 h, then diluted with DCM, and washed with saturated aqueous $NaHCO_3$ solution. The organic layer was dried over anhydrous $MgSO_4$, filtered, and the filtrate was concentrated under vacuum to afford intermediate 73a, which was used in the next reaction without further purification. TLC:Rf=0.5 EtOAc/hexanes (1/1), $KMnO_4$ stain).

Step B—Synthesis of Intermediate 73b To a stirred solution of intermediate 73a (230 mg, 0.688 mmol) in DCM (5 mL) at 0° C. was added TFA (0.527 mL, 6.88 mmol). The reaction was stirred at ambient temperature for 1 h, then diluted with 30% toluene/MeOH. The resulting mixture was concentrated under vacuum to give the intermediate 73b, which was used in the next reaction without further purification. TLC:Rf=0.0, EtOAc/hexanes (1/1), $KMnO_4$ stain).

Example 110: Preparation of Intermediate 74b

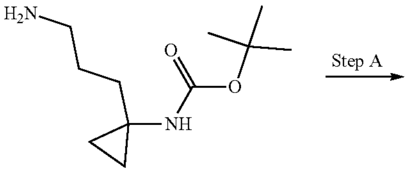

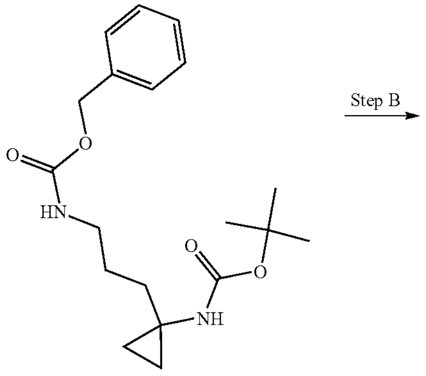

Int-74a

-continued

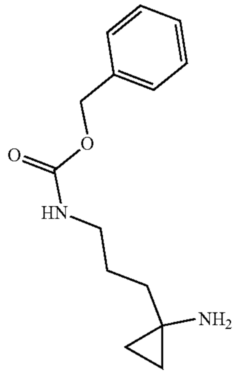

Int-74b

Step A—Synthesis of Intermediate 74a To a vial containing a mixture of tert-butyl (1-(3-aminopropyl)cyclopropyl) carbamate (200 mg, 0.933 mmol) in DCM (5 mL) was added triethylamine (0.65 mL, 4.67 mmol), followed by the dropwise addition of benzyl chloroformate (0.92 mL, 1.40 mmol). The reaction mixture was stirred at ambient temperature for 4 h, then diluted with DCM, and washed with saturated aqueous $NaHCO_3$ solution. The organic layer was dried over anhydrous $MgSO_4$, filtered, and the filtrate was concentrated under vacuum to afford intermediate 74a, which was used in the next reaction without further purification. TLC:Rf=0.5, EtOAc/hexanes (1/1), $KMnO_4$ stain).

Step B—Synthesis of Intermediate 74b To a stirred solution of intermediate 74a (300 mg, 0.861 mmol) in DCM (5 mL) at 0° C. was added TFA (0.66 mL, 8.61 mmol). The reaction was stirred at ambient temperature for 1 h, then diluted with 30% toluene/MeOH. The resulting mixture was concentrated under vacuum to give the intermediate 74b, which was used in the next reaction without further purification. TLC:Rf=0.0, EtOAc/hexanes (1/1), $KMnO_4$ stain).

Example 111: Preparation of Intermediate 75c

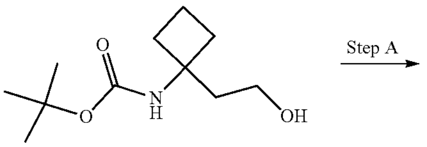

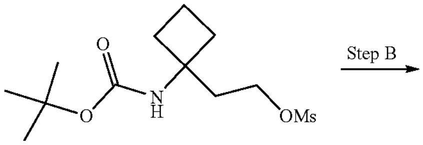

Int-75a

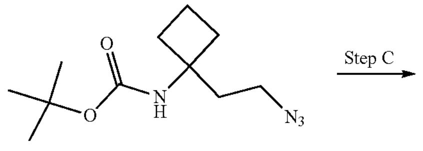

Int-75b

-continued

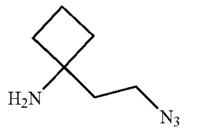

Int-75c

Step A—Synthesis of Intermediate 75a To a stirred solution of tert-butyl (1-(2-hydroxy-ethyl)cyclobutyl)carbamate (500 mg, 2.322 mmol) and triethylamine (0.483 mL, 3.48 mmol) in THF (10 mL) at 0° C. was added methanesulfonyl chloride (0.216 mL, 2.79 mmol). The reaction was warmed to ambient temperature and stirred for 1 h, then quenched with saturated aqueous $NaHCO_3$ solution, and extracted with EtOAc. The combined organic layers were washed with brine, dried over anhydrous $MgSO_4$, and filtered. The filtrate was concentrated under vacuum to give intermediate 75a, which was used in the next reaction without further purification. TLC:Rf=0.6 EtOAc/Hexane (1/1), $KMnO_4$ stain).

Step B—Synthesis of Intermediate 75b Sodium azide (241 mg, 3.71 mmol) was added to a stirred solution of intermediate 75a (680 mg, 2.318 mmol) in DMF (10 mL). The resulting mixture was heated to 70° C. and stirred at this temperature for 18 h. The reaction was then quenched with saturated aqueous $NaHCO_3$ solution, and extracted with EtOAc. The combined organic layers were washed with brine (2×), dried over anhydrous $MgSO_4$, and filtered. The filtrate was concentrated under vacuum to give intermediate 75b, which was used in the next reaction without further purification. TLC:Rf=0.7 EtOAc/Hexane (1/1), $KMnO_4$ stain).

Step C—Synthesis of Intermediate 75c A mixture of intermediate 75b (200 mg, 0.832 mmol) in DCM (5 mL)/TFA (1.00 mL) was stirred at ambient temperature for 1 h. Then the solvent was removed under vacuum to give intermediate 75b, which was used in the next reaction without further purification. TLC:Rf=0.0 EtOAc/Hexane (1/1), $KMnO_4$ stain).

Example 112: Preparation of Compound 138

(S)-2-((R)-6-(N-(1-(2-aminoethyl)cyclopropyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

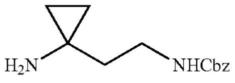

Int-73b

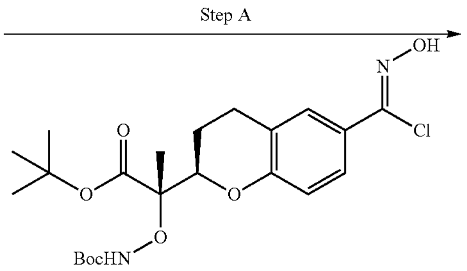

Int-6c

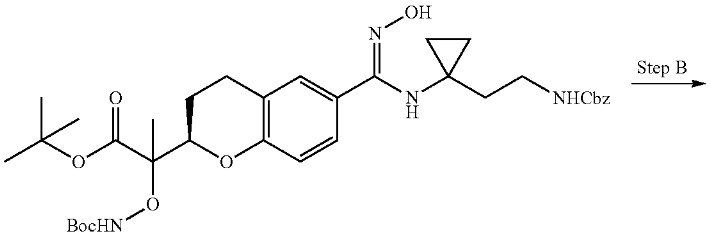

Int-76a

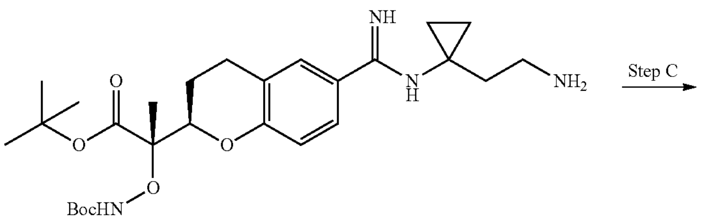

Int-76b

-continued

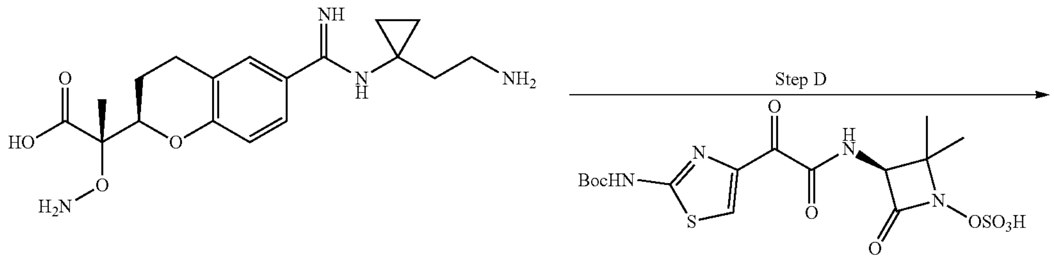

Int-76c

Int-4

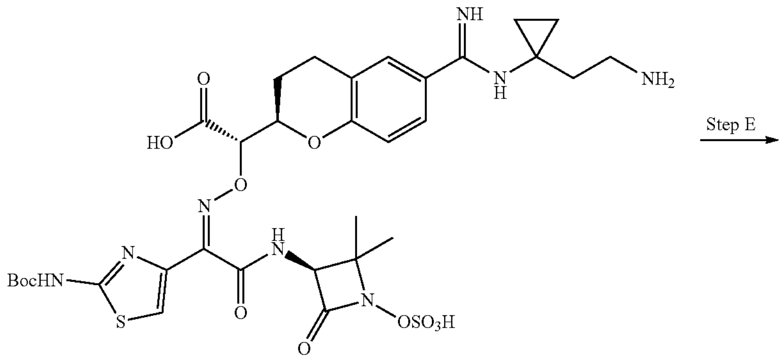

Int-72c

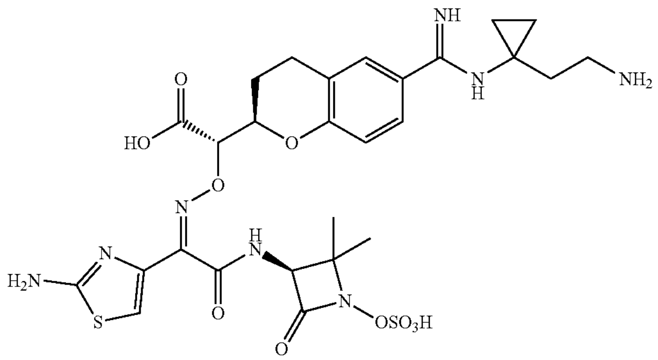

Compound 138

Step A—Synthesis of Intermediate 76a To a stirred solution of intermediate 73b (149 mg, 0.637 mmol) and intermediate 6c (200 mg, 0.425 mmol) in anhydrous DMF (3 mL) at ambient temperature, was added triethylamine (0.592 ml, 4.25 mmol). The reaction mixture was stirred for 1 h, then directly purified via reverse-phase MPLC (ISCO; C18, 50 g column; 0-100% 0.05% TFA+water/0.05% TFA+ACN gradient). The product fractions were combined and concentrated in vacuo. The resulting aqueous mixture was extracted with EtOAc (2×). The combined organic layer was washed with brine, dried over anhydrous $Na_2SO_4$, filtered and the filtrate was concentrated in vacuo to give intermediate 76a. LC-MS [M+1]: m/z 669.0.

Step B—Synthesis of Intermediate 76b To a mixture of potassium carbonate (238 mg, 1.720 mmol) in MeOH (2 mL) was added formic acid (0.132 ml, 3.44 mmol). The mixture was stirred for 10 minutes, then added to a solution of intermediate 76a (230 mg, 0.344 mmol) in AcOH (1.5 mL)/acetic anhydride (0.049 mL, 0.516 mmol). Palladium on Carbon (146 mg, 10 wt. % 50% moisture, 0.138 mmol) was subsequently added. The reaction mixture was stirred at ambient temperature for 18 h, and then filtered. The filtrate was directly purified by reverse-phase (ISCO; C18, 50 g column; 0-100% 0.05% TFA+ACN/0.05% TFA+water; gradient). The product fractions were combined and concentrated in vacuo. The resulting aqueous mixture was extracted with EtOAc (2×). The organic layer was washed with brine, dried over anhydrous $Na_2SO_4$, filtered and the filtrate was concentrated in vacuo to give intermediate 76b. LC-MS [M+1]: m/z 519.5.

Step C—Synthesis of Intermediate 76c To a vial containing a mixture of intermediate 76b (140 mg, 0.270 mmol) in $CH_2Cl_2$ (2 mL) was added TFA (4 mL). The reaction was stirred at ambient temperature for 18 h, then concentrated under vacuum. To the resulting residue was added 30% toluene/MeOH (2×6 mL), and the mixture was concentrated under vacuum to afford intermediate 76c, which was used in the next reaction without further purification. LC-MS [M+1]: m/z 363.3.

Step D—Synthesis of Intermediate 76d To a vial charged with intermediate 76c (86 mg, 0.237 mmol) and intermediate 4 (110 mg, 0.237 mmol) was added MeOH (4.0 mL) at ambient temperature. The reaction mixture was stirred for 6 h. Then the solvent was removed in vacuo to afford intermediate 76d, which was used in the next reaction without further purification. LC-MS [M+1]: m/z 809.6.

Step E—Synthesis of Compound 138 To a vial charged with intermediate 76d (191 mg, 0.236 mmol) was added 1:2 trifluoroacetic acid/anhydrous dichloromethane (6 mL) at ambient temperature. The reaction was stirred at ambient temperature for 1 h, then cooled to 0° C., followed by the slow addition of ethyl ether (6 mL). The resulting solid was collected by centrifugation (1400 rpm), and purified via reverse phase HPLC (Gilson, preparative C18, 5 um, OBD 30×150 mm column; 0.05% TFA+ACN/0.05%/TFA+water 0-40% gradient over 18 min, 30 mL/min., injection 3). The product fractions were combined and concentrated in vacuo, and the resulting aqueous solution was directly loaded onto an Amberchrom CG161M column (26 g), washed with 9 CV of (water+0.1% FA), and eluted off with 3 CV of 100% (AcCN+0.1% FA) followed by 3 CV of 50% (AcCN+0.1% FA)/(water+0.1% FA). The product fractions were combined and concentrated in vacuo, the resulting aqueous residue was lyophilized to give compound 138 as the formic acid salt. LC-MS [M+1]: m/z 709.6. $^1$HNMR (500 MHz, 400 uL $D_2O$/100 uL $CD_3CN$) δ: 7.46-7.43 (m, 2H), 6.96-6.95 (m, 2H), 4.57-4.49 (m, 1H), 4.53-4.51 (m, 1H), 3.24-3.21 (m, 2H), 2.92-2.85 (m, 2H), 2.19-2.06 (m, 3H), 1.90-1.82 (m, 1H), 1.61 (s, 3H), 1.50 (s, 3H), 1.27 (s, 3H), 1.15 (s, 2H), 1.05 (s, 2H).

Example 113: Preparation of Compounds 139 and 140

Compounds 139 and 140 were prepared from the corresponding intermediates 74b and 75c according to the procedure in Step A to Step E of Example 112.

| Compound | Structure | $^1$H NMR | LC-MS [M + H]$^+$ |
|---|---|---|---|
| 139 | 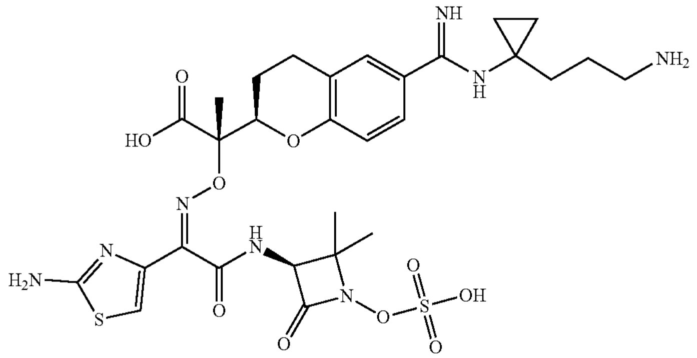 [SMILES: CC1(C)[C@H](NC(=O)/C(=N\O[C@](C)(C(=O)O)[C@H]2CCc3cc(C(=N)NC4(CCCN)CC4)ccc3O2)c2csc(N)n2)C(=O)N1OS(=O)(=O)O] (S)-2-((R)-6-(N-(1-(3-amino-propyl)cyclopropyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxo-ethylidene)amino)oxy) propanoic acid | $^1$HNMR (500 MHz, 400 uL $D_2O$/100 uL $CD_3CN$) δ: 7.38-7.34 (m, 2H), 6.89-6.87 (m, 2H), 4.64 (m, 1H), 4.46-4.43 (m, 1H), 2.99-2.96 (m, 2H), 2.85-2.77 (m, 2H), 2.11-2.07 (m, 3H), 1.82-1.79 (m, 3H), 1.54 (s, 3H), 1.42 (s, 3H), 1.20 (s, 3H), 1.01 (s, 2H), 0.90 (s, 2H). | 723.6 |
| 140 | 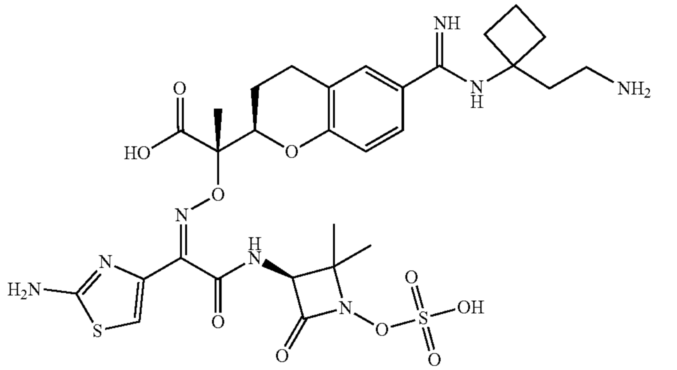 [SMILES: CC1(C)[C@H](NC(=O)/C(=N\O[C@](C)(C(=O)O)[C@H]2CCc3cc(C(=N)NC4(CCN)CCC4)ccc3O2)c2csc(N)n2)C(=O)N1OS(=O)(=O)O] (S)-2-((R)-6-(N-(1-(2-aminoethyl)cyclo-butyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxo-ethylidene)amino)oxy)propanoic acid | $^1$HNMR (500 MHz, 400 uL $D_2O$/100 uL $CD_3CN$) δ: 7.49-7.45 (m, 2H), 6.97-6.96 (m, 2H), 4.52-4.50 (m, 1H), 3.10-3.05 (m, 2H), 2.89-2.85 (m, 2H), 2.54-2.49 (m, 2H), 2.39-2.36 (m, 5H), 2.19-2.16 (m, 1H), 2.07-1.98 (m, 2H), 1.88 (br s, 1H), 1.62 (s, 3H), 1.55 (s, 3H), 1.29 (s, 3H). | 723.5 |

Biological Assays

Antibiotic Activity: Determination of Growth Inhibitory Concentration

The concentrations of compounds required to inhibit the growth of various strains of bacteria were determined in an assay that assessed bacterial growth by measuring optical density at 600 nm (OD600). The bacterial strains tested included the clinical strains *Escherichia coli* expressing NDM-1 (CLB30016), *Klebsiella pneumoniae* expressing KPC-1 (CL6569), *Acinetobacter baumannii* expressing TEM-1, AmpC, and Oxa-24/40 (CL6188) and *Pseudomonas aeruginosa* expressing AmpC (CL5701). All compounds were tested in the presence of a β lactamase inhibitor (BLi, Relebactam) in 384-well microplates.

The clinical strains were stored as frozen single use stocks, thawed and diluted into 1.1× cation-adjusted Mueller-Hinton II broth to achieve approximately $2\times10^5$ CFU/mL. Test compounds were dissolved in DMSO and diluted 1:50 in the assay, resulting in a final concentration range of 100 μM to 0.098 μM. On the day of the assay, 1 μL of test compound was added to the plate followed by 4 μL of 50 μg/mL BLi in MOPS buffer and 45 μL of diluted bacteria. Plates were centrifuged at 1000 rpm for 30 seconds, shaken at approximately 800 rpm for 1 minute, and incubated at 35 t 2° C. for 22 hours. The concentration of BLi used in the assay was 4 μg/mL. At the end of the incubation, absorbance at 600 nm was determined using a spectrophotometer. Inhibition was quantitated by identifying the lowest concentration of test compound that was required to inhibit 95% of the growth of the bacteria. The results for Examples 1-39 are reported in Table I, expressed as the concentration of compound that inhibited 95% of bacterial growth (Minimum Inhibitory Threshold Concentration; MITC95).

Representative compounds of the present invention display a growth inhibitory effect. For example, representative Compounds 1-140 were determined to inhibit growth at concentrations of 100 μM or less.

TABLE I

Antibacterial activity of Compounds 1-140

| Compound | AB_CL6188 MITC95 (μM) | EC_CLB30016 MITC95 (μM) | KP_CL6569 MITC95 (μM) | PA_CL5701 MITC95 (μM) |
|---|---|---|---|---|
| 1 | 4.688 | 14.06 | 0.3906 | 2.344 |
| 2 | 3.125 | 3.125 | 0.3906 | 1.563 |
| 3 | 6.25 | 6.25 | 0.7813 | 1.563 |
| 4 | 12.5 | 12.5 | 0.7813 | 6.25 |
| 5 | 3.125 | 9.375 | 0.3906 | 1.563 |
| 6 | 3.125 | 6.25 | 0.7813 | 2.344 |
| 7 | 5.729 | 4.688 | 0.3906 | 1.563 |
| 8 | 3.125 | 3.125 | 0.293 | 1.172 |
| 9 | 6.25 | 3.125 | 0.1953 | 1.563 |
| 10 | 6.25 | 6.25 | 0.3906 | 1.563 |
| 11 | 6.25 | 3.125 | 0.3906 | 1.563 |
| 12 | 3.125 | 6.25 | 0.3906 | 1.563 |
| 13 | 3.125 | 3.125 | 0.1953 | 1.563 |
| 14 | 3.125 | 6.25 | 0.3906 | 1.563 |
| 15 | 6.25 | 6.25 | 0.7813 | 1.563 |
| 16 | 6.25 | 3.125 | 0.7813 | 3.125 |
| 17 | 3.125 | 3.125 | 0.3906 | 1.563 |
| 18 | 3.125 | 6.25 | 0.3906 | 1.563 |
| 19 | 3.125 | 3.125 | 0.3906 | 3.125 |
| 20 | 6.25 | 6.25 | 0.3906 | 3.125 |
| 21 | 3.125 | 3.125 | 0.3906 | 1.563 |
| 22 | 3.125 | 3.125 | 0.3906 | 1.563 |
| 23 | 6.25 | 6.25 | 0.7813 | 3.125 |
| 24 | 2.083 | 5.208 | 0.3255 | 1.302 |
| 25 | 6.25 | 3.125 | 0.3906 | 0.7813 |
| 26 | 6.25 | 6.25 | 0.3906 | 1.563 |
| 27 | 2.083 | 5.208 | 0.3906 | 1.563 |
| 28 | 3.646 | 5.208 | 0.4557 | 1.563 |
| 29 | 3.125 | 2.344 | 0.1953 | 0.7813 |
| 30 | 3.125 | 2.344 | 0.1953 | 0.7813 |
| 31 | 3.125 | 4.688 | 0.3906 | 1.563 |
| 32 | 3.125 | 3.125 | 0.3906 | 1.563 |
| 33 | 6.25 | 6.25 | 0.3906 | 1.563 |
| 34 | 3.125 | 6.25 | 0.3906 | 1.563 |
| 35 | 3.125 | 3.125 | 0.3906 | 1.563 |
| 36 | 6.25 | 3.125 | 0.3906 | 1.563 |
| 37 | 6.25 | 3.125 | 0.3906 | 1.563 |
| 38 | 6.25 | 12.5 | 0.3906 | 1.563 |
| 39 | 6.25 | 6.25 | 0.3906 | 1.563 |
| 40 | 6.25 | 3.125 | 0.3906 | 1.563 |
| 41 | 6.25 | 6.25 | 0.3906 | 1.563 |
| 42 | 3.125 | 14.06 | 0.3906 | 1.563 |
| 43 | 3.125 | 6.25 | 0.3906 | 1.563 |
| 44 | 3.125 | 6.25 | 0.3906 | 1.563 |
| 45 | 6.25 | 6.25 | 0.3906 | 1.563 |
| 46 | 6.25 | 6.25 | 0.3906 | 1.563 |
| 47 | 3.125 | 6.25 | 0.3906 | 1.563 |
| 48 | 6.25 | 6.25 | 0.3906 | 1.563 |
| 49 | 6.25 | 6.25 | 0.7813 | 1.563 |
| 50 | 6.25 | 6.25 | 0.7813 | 1.563 |
| 51 | 6.25 | 12.5 | 0.7813 | 1.563 |
| 52 | 6.25 | 6.25 | 0.3906 | 3.125 |
| 53 | 6.25 | 12.5 | 0.7813 | 3.125 |
| 54 | 6.25 | 12.5 | 0.7813 | 3.125 |

TABLE I-continued

| Antibacterial activity of Compounds 1-140 | | | | |
|---|---|---|---|---|
| Compound | AB_CL6188 MITC95 (μM) | EC_CLB30016 MITC95 (μM) | KP_CL6569 MITC95 (μM) | PA_CL5701 MITC95 (μM) |
| 55 | 3.125 | 6.25 | 0.7813 | 1.563 |
| 56 | 6.25 | 6.25 | 0.7813 | 1.563 |
| 57 | 3.125 | 3.125 | 0.3906 | 1.563 |
| 58 | 6.25 | 6.25 | 0.7813 | 3.125 |
| 59 | 3.125 | 12.5 | 0.3906 | 1.563 |
| 60 | 3.125 | 6.25 | 0.7813 | 1.563 |
| 61 | 6.25 | 3.125 | 0.3906 | 1.563 |
| 62 | 6.25 | 3.125 | 0.3906 | 1.563 |
| 63 | 6.25 | 12.5 | 0.7813 | 3.125 |
| 64 | 6.25 | 6.25 | 0.7813 | 3.125 |
| 65 | 6.25 | 6.25 | 0.3906 | 1.563 |
| 66 | 3.125 | 3.125 | 0.7813 | 1.563 |
| 67 | 6.25 | 6.25 | 0.3906 | 1.563 |
| 68 | 3.125 | 3.125 | 0.3906 | 1.563 |
| 69 | 4.688 | 6.25 | 0.3906 | 1.563 |
| 70 | 4.688 | 6.25 | 0.293 | 1.563 |
| 71 | 4.688 | 9.375 | 0.7813 | 1.563 |
| 72 | 6.25 | 12.5 | 0.7813 | 3.125 |
| 73 | 6.25 | 6.25 | 0.7813 | 3.125 |
| 74 | 7.813 | 7.813 | 0.5859 | 1.563 |
| 75 | 6.25 | 6.25 | 0.3906 | 1.563 |
| 76 | 3.125 | 3.125 | 0.3906 | 1.563 |
| 77 | 6.25 | 6.25 | 0.7813 | 1.563 |
| 78 | 4.688 | 6.25 | 0.3906 | 1.563 |
| 79 | 4.688 | 6.25 | 0.3906 | 1.563 |
| 80 | 3.125 | 6.25 | 0.3906 | 1.563 |
| 81 | 6.25 | 6.25 | 0.3906 | 1.563 |
| 82 | 6.25 | 6.25 | 0.7813 | 3.125 |
| 83 | 6.25 | 3.125 | 0.3906 | 1.563 |
| 84 | 6.25 | 6.25 | 0.7813 | 1.563 |
| 85 | 6.25 | 12.5 | 0.3906 | 1.563 |
| 86 | 6.25 | 6.25 | 0.3906 | 1.563 |
| 87 | 4.688 | 6.25 | 0.3906 | 1.563 |
| 88 | 6.25 | 6.25 | 0.3906 | 1.563 |
| 89 | 9.375 | 6.25 | 0.3906 | 1.563 |
| 90 | 6.25 | 6.25 | 0.3906 | 1.563 |
| 91 | 3.125 | 6.25 | 0.3906 | 1.563 |
| 92 | 6.25 | 6.25 | 0.3906 | 1.563 |
| 93 | 6.25 | 6.25 | 0.7813 | 3.125 |
| 94 | 6.25 | 3.125 | 0.3906 | 1.563 |
| 95 | 6.25 | 6.25 | 0.3906 | 1.563 |
| 96 | 6.25 | 6.25 | 0.3906 | 1.563 |
| 97 | 6.25 | 6.25 | 0.7813 | 1.563 |
| 98 | 6.25 | 12.5 | 0.7813 | 1.563 |
| 99 | 12.5 | 6.25 | 0.7813 | 3.125 |
| 100 | 6.25 | 6.25 | 0.7813 | 1.563 |
| 101 | 12.5 | 6.25 | 0.3906 | 1.563 |
| 102 | 6.25 | 6.25 | 0.7813 | 3.125 |
| 103 | 3.125 | 6.25 | 0.3906 | 1.563 |
| 104 | 3.125 | 4.688 | 0.5859 | 1.563 |
| 105 | 3.125 | 6.25 | 0.3906 | 1.563 |
| 106 | 3.125 | 6.25 | 0.3906 | 1.563 |
| 107 | 1.563 | 3.125 | 0.3906 | 1.563 |
| 108 | 6.25 | 3.125 | 0.3906 | 1.563 |
| 109 | 6.25 | 6.25 | 0.7813 | 1.563 |
| 110 | 3.125 | 3.125 | 0.3906 | 1.563 |
| 111 | 3.125 | 3.125 | 0.3906 | 0.7813 |
| 112 | 4.688 | 4.688 | 0.3906 | 1.563 |
| 113 | 3.125 | 3.125 | 0.3906 | 1.563 |
| 114 | 6.25 | 6.25 | 0.7813 | 1.563 |
| 115 | 6.25 | 6.25 | 0.7813 | 3.125 |
| 116 | 6.25 | 6.25 | 0.7813 | 3.125 |
| 117 | 6.25 | 6.25 | 0.3906 | 3.125 |
| 118 | 3.125 | 12.5 | 0.3906 | 1.563 |
| 119 | 6.25 | 6.25 | 0.3906 | 1.563 |
| 120 | 6.25 | 12.5 | 0.7813 | 3.125 |
| 121 | 6.25 | 3.125 | 0.3906 | 1.563 |
| 122 | 6.25 | 12.5 | 0.3906 | 1.563 |
| 123 | 6.25 | 3.125 | 0.3906 | 1.563 |
| 124 | 12.5 | 50 | 1.563 | 3.125 |
| 125 | 12.5 | 25 | 1.563 | 1.563 |
| 126 | 12.5 | 25 | 1.563 | 6.25 |
| 127 | 12.5 | 6.25 | 0.7813 | 3.125 |
| 128 | 6.25 | 12.5 | 0.3906 | 1.563 |
| 129 | 6.25 | 6.25 | 0.7813 | 3.125 |

TABLE I-continued

Antibacterial activity of Compounds 1-140

| Compound | AB_CL6188 MITC95 (μM) | EC_CLB30016 MITC95 (μM) | KP_CL6569 MITC95 (μM) | PA_CL5701 MITC95 (μM) |
|---|---|---|---|---|
| 130 | 12.5 | 25 | 0.7813 | 3.125 |
| 131 | 6.25 | 6.25 | 0.3906 | 1.563 |
| 132 | 6.25 | 6.25 | 0.7813 | 3.125 |
| 133 | 3.125 | 6.25 | 0.3906 | 1.563 |
| 134 | 6.25 | 25 | 0.7813 | 1.563 |
| 135 | 12.5 | 12.5 | 0.7813 | 3.125 |
| 136 | 6.25 | 6.25 | 0.7813 | 1.563 |
| 137 | 12.5 | 3.125 | 0.7813 | 1.563 |
| 138 | 6.25 | 25 | 0.7813 | 1.563 |
| 139 | 12.5 | 6.25 | 0.7813 | 1.563 |
| 140 | 12.5 | 12.5 | 1.563 | 3.125 |

What is claimed is:

1. A compound of Formula I (I)

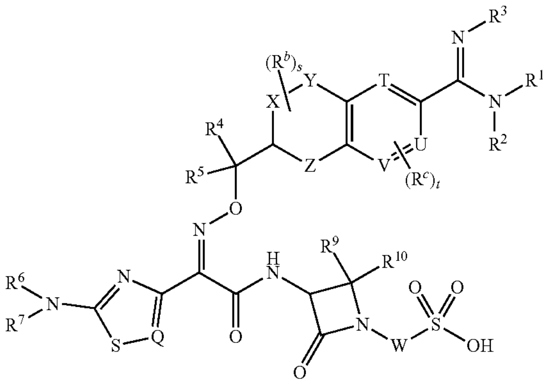

or a pharmaceutically acceptable salt thereof, wherein:

T is CH, or N, provided that no more than two of T, U and V are N;

U is CH, or N;

V is CH or N;

X is selected from:
1) O, and
2) $CH_2$;

Y is selected from:
1) O,
2) $NR^8$,
3) S, and
4) $CH_2$, provided that when Y is O, $NR^8$ or S then X is not O;

Z is
1) O,
2) S,
3) $CH_2$, or
4) NH, provided that when Z is O, S or NH, then X is not O;

W is selected from:
1) bond, and
2) O;

Q is selected from:
1) N, and
2) $CR^8$;

$R^1$ is selected from:
1) —$C_{3-12}$cycloalkyl,
2) —$C_{3-12}$cycloalkenyl,
3) —$C_{2-11}$cycloheteroalkyl,
4) —$C_{2-11}$cycloheteroalkenyl,
5) aryl, and
6) heteroaryl, wherein alkyl, cycloalkyl, cycloalkenyl, cycloheteroalkyl, cycloheteroalkenyl, aryl and heteroaryl are unsubstituted or substituted with one to five substituents selected from $R^a$;

$R^2$ is selected from:
1) hydrogen,
2) —$C_{1-6}$alkyl,
3) —$C_{1-6}$alkyl-$OR^4$, and
4) —$C_{1-6}$alkyl-$NHR^4$, wherein alkyl is unsubstituted or substituted with one to three halogens;

$R^3$ is selected from:
1) hydrogen, and
2) OH;

$R^4$ is selected from:
1) hydrogen,
2) $C_{1-3}$alkyl, and
3) $C_3$cycloalkyl, wherein alkyl and cycloalkyl are unsubstituted or substituted with one to three halogens or $OC_{1-3}$alkyl;

$R^5$ is selected from:
1) —$CO_2H$, and
2) tetrazole;

$R^6$ and $R^7$ are selected from:
1) hydrogen, and
2) $C_{1-6}$alkyl, wherein alkyl is unsubstituted or substituted with one to three halogens, provided that at least one of $R^6$ and $R^7$ is hydrogen;

each $R^8$ is independently selected from:
1) hydrogen,
2) $C_{1-4}$alkyl,
3) halogen, and
4) $C_{3-7}$cycloalkyl, wherein alkyl and cycloalkyl are unsubstituted or substituted with one to three substituents selected from: —OH, halogen, $NH_2$, and —$OC_{1-3}$alkyl;

$R^9$ and $R^{10}$ are selected from:
1) hydrogen, and
2) $C_{1-6}$alkyl, wherein alkyl is unsubstituted or substituted with one to three substituents selected from:

halogen, OH, —$OC_{1-3}$alkyl, —NHC(O)$C_{1-3}$alkyl, —C(O)NH$C_{1-3}$alkyl, NH$C_{1-3}$alkyl, and S$C_{1-3}$alkyl, provided that one or both of $R^9$ and $R^{10}$ are $C_{1-6}$alkyl, or alternatively $R^9$ and $R^{10}$ together with the carbon to which they are attached form a monocyclic $C_{3-5}$cycloalkyl or a monocyclic $C_{2-5}$cycloheteroalkyl, wherein cycloalkyl and cycloheteroalkyl are unsubstituted or substituted with one to three substituents independently selected from halogen, —OH and —$OC_{1-3}$alkyl;

each $R^a$ is independently selected from:

1)halogen,
2) —$C_{1-6}$alkyl,
3) —$C_{0-6}$alkyl-O—$C_{1-6}$alkyl,
4) —$C_{0-6}$alkyl-OH,
5) —$C_{0-6}$alkyl $S(O)_rR^i$,
6) —$C_{0-6}$alkyl $S(O)_rNR^kR^l$,
7) —$C_{0-6}$alkyl $C(O)R^i$,
8) —$C_{0-6}$alkyl $OC(O)R^i$,
9) —$C_{0-6}$alkyl $C(O)OR^i$,
10) —$C_{0-6}$alkyl CN,
11) —$C_{0-6}$alkyl $C(O)NR^kR^l$,
12) —$C_{0-6}$alkyl $C(NH)NR^kR^l$,
13) —$C_{0-6}$alkyl$NR^kR^l$,
14) —$C_{0-6}$alkyl $N(R^k)(C(O)R^i)$,
15) —$C_{0-6}$alkyl $N(R^k)(C(O)OR^h)$,
16) —$C_{0-6}$alkyl $N(R^k)(C(O)NR^fR^g)$, and
17) —$C_{0-6}$alkyl $N(R^k)(S(O)_vR^j)$, wherein alkyl is unsubstituted or substituted with one to three substituents selected from: halogen, OH, —$OC_{1-3}$alkyl, —$C_{1-3}$alkyl, —$CO_2C_{1-3}$alkyl, —C(O)$NH_2$, —$C_{0-6}$alkyl$NH_2$, and —$C_{0-6}$alkylNH($C_{1-3}$alkyl);

each $R^b$ is independently selected from:

1) hydrogen,
2) —$C_{1-6}$alkyl,
3) —$C_{0-6}$alkyl-O—$C_{1-6}$alkyl,
4) —$C_{0-6}$alkyl-OH,
5) —$C_{0-6}$alkyl-$S(O)_uR^d$,
6) —$C_{1-6}$alkyl-C(O—$N(R^e)_2$,
7) —$C_{1-6}$alkylN(Re)C(O)$R^e$,
8) —$C_{0-6}$alkyl-$N(R^e)_2$, and
9) halogen, wherein alkyl is unsubstituted or substituted with one to three halogens, or optionally, two $R^b$ substituents, together with the atoms to which they are attached, can cyclize to form a monocyclic $C_{3-6}$cycloalkyl or a monocyclic $C_{2-6}$cycloheteroalkyl ring;

each $R^c$ is independently selected from:

1) hydrogen,
2) —$C_{1-6}$alkyl,
3) —$C_{0-6}$alkyl-O—$C_{1-6}$alkyl,
4) —$C_{0-6}$alkyl-OH,
5) —$C_{0-6}$alkyl-$S(O)_vR^f$,
6) —$C_{0-6}$alkyl-$S(O)_vN(R^g)_2$,
7) —$C_{1-6}$alkyl C(O)—$N(R^g)_2$,
8) —$C_{1-6}$alkyl$N(R^g)C(O)R^g$,
9) —$C_{0-6}$alkyl-$N(R^g)_2$, and
10) halogen, wherein alkyl is unsubstituted or substituted with one to three halogens;

each $R^d$ is independently selected from:

1) hydrogen, and
2) —$C_{1-6}$ alkyl, wherein each alkyl is unsubstituted or substituted with one to three halogens;

each $R^e$ is independently selected from:

1) hydrogen, and
2) —$C_{1-6}$ alkyl, wherein each alkyl is unsubstituted or substituted with one to three halogens;

each $R^f$ is independently selected from:

1) hydrogen, and
2) —$C_{1-6}$alkyl, wherein each alkyl is unsubstituted or substituted with one to three halogens;

each $R^g$ is independently selected from:

1) hydrogen, and
2) —$C_{1-6}$ alkyl, wherein each alkyl is unsubstituted or substituted with one to three halogens;

each $R^h$ is independently selected from:

1) hydrogen, and
2) —$C_{1-6}$ alkyl, wherein each alkyl is unsubstituted or substituted with one to three halogens;

each $R^i$ is —$C_{1-6}$ alkyl, wherein each alkyl is unsubstituted or substituted with one to three halogens;

each $R^j$ is independently selected from:

1) hydrogen,
2) OH, and
3) —$C_{1-6}$ alkyl, wherein each alkyl is unsubstituted or substituted with one to three halogens;

each $R^k$ is independently selected from:

1) hydrogen, and
2) —$C_{1-6}$ alkyl, wherein each alkyl is unsubstituted or substituted with one to three halogens;

each $R^l$ is independently selected from:

1) hydrogen, and
2) —$C_{1-6}$ alkyl, wherein each alkyl is unsubstituted or substituted with one to three halogens;

each r is independently 0, 1 or 2;

each s is independently 0, 1, 2, 3, 4 or 5;

each t is independently 0, 1, 2 or 3;

each u is independently selected from 0, 1 or 2; and each v is independently selected from 0, 1 or 2.

2. The compound of claim 1 wherein

T is CH;

U is CH; and

V is CH;

or a pharmaceutically acceptable salt thereof.

3. The compound of claim 1 wherein

X is $CH_2$;

or a pharmaceutically acceptable salt thereof.

4. The compound of claim 1 wherein

Y is O or $CH_2$; and

Z is O or $CH_2$;

or a pharmaceutically acceptable salt thereof.

5. The compound of claim 4 wherein

Y is $CH_2$; and

Z is O;

or a pharmaceutically acceptable salt thereof.

6. A compound of claim 1 wherein

W is O;

or a pharmaceutically acceptable salt thereof.

7. The compound of claim 1 wherein

Q is $CR^8$; and $R^8$ is hydrogen;

or a pharmaceutically acceptable salt thereof.

8. The compound of claim 1 wherein
$R^2$ is hydrogen; and
$R^3$ is hydrogen;
or a pharmaceutically acceptable salt thereof.

9. The compound of claim 5 wherein
$R^5$ is —$CO_2H$; or a pharmaceutically acceptable salt thereof.

10. The compound of claim 1 wherein $R^4$ is selected from:
1) $C_{1-3}$alkyl, and
2) $C_3$cycloalkyl,
wherein alkyl and cycloalkyl are unsubstituted or substituted with one to three substituents selected from: halogen and $OC_{1-3}$alkyl; or a pharmaceutically acceptable salt thereof.

11. The compound of claim 1 wherein $R^4$ is $C_{1-3}$alkyl, wherein alkyl is unsubstituted or substituted with one to three substituents selected from: halogen or $OC_{1-3}$alkyl; or a pharmaceutically acceptable salt thereof.

12. The compound of claim 1 wherein
$R^6$ is hydrogen; and
$R^7$ is hydrogen;
or a pharmaceutically acceptable salt thereof.

13. The compound of claim 1 wherein
$R^9$ is $C_{1-6}$alkyl, and
$R^{10}$ is $C_{1-6}$alkyl;
or a pharmaceutically acceptable salt thereof.

14. The compound of claim 1 wherein $R^1$ is selected from:
1) —$C_{3-9}$cycloalkyl,
2) —$C_{2-8}$cycloheteroalkyl,
3) aryl, and
4) heteroaryl,
wherein cycloalkyl, cycloheteroalkyl, aryl and heteroaryl are unsubstituted or substituted with one to five substituents selected from $R^a$; or a pharmaceutically acceptable salt thereof.

15. The compound of claim 1 wherein $R^1$ is selected from:
1) —$C_{3-9}$cycloalkyl, and
2) —$C_{2-8}$cycloheteroalkyl,
wherein cycloalkyl, and cycloheteroalkyl are unsubstituted or substituted with one to five substituents selected from $R^a$; or a pharmaceutically acceptable salt thereof.

16. The compound of claim 1 wherein
T is CH;
U is CH;
V is CH;
X is $CH_2$;
Y is O or $CH_2$;
Z is O or $CH_2$;
W is bond or O;
Q is $CR^8$;
$R^1$ is selected from:
1) —$C_{3-9}$cycloalkyl,
2) —$C_{2-8}$cycloheteroalkyl,
3) aryl, and
4) heteroaryl,
wherein cycloalkyl, cycloheteroalkyl, aryl and heteroaryl are unsubstituted or substituted with one to five substituents selected from $R^a$;
$R^2$ is hydrogen;
$R^3$ is hydrogen;
$R^4$ is selected from:
1) $C_{1-3}$alkyl, and
2) $C_3$cycloalkyl,
wherein alkyl and cycloalkyl are unsubstituted or substituted with one to three substituents selected from: halogen and $OC_{1-3}$alkyl;
$R^5$ is —$CO_2H$ or tetrazole;
$R^6$ is hydrogen;
$R^7$ is hydrogen;
$R^8$ is hydrogen;
$R^9$ is $C_{1-6}$alkyl, and
$R^{10}$ is $C_{1-6}$alkyl;
or a pharmaceutically acceptable salt thereof.

17. The compound of claim 1 wherein
T is CH;
U is CH;
V is CH;
X is $CH_2$;
Y is $CH_2$;
Z is O;
W is O;
Q is $CR^8$;
$R^1$ is selected from:
1) —$C_{3-9}$cycloalkyl,
2) —$C_{2-8}$cycloheteroalkyl, and
3) aryl,
wherein cycloalkyl, cycloheteroalkyl, and aryl are unsubstituted or substituted with one to five substituents selected from $R^a$;
$R^2$ is hydrogen;
$R^3$ is hydrogen;
$R^4$ is $C_{1-3}$alkyl;
$R^5$ is —$CO_2H$;
$R^6$ is hydrogen;
$R^7$ is hydrogen;
$R^8$ is hydrogen;
$R^9$ is $C_{1-6}$alkyl, and
$R^{10}$ is $C_{1-6}$alkyl;
or a pharmaceutically acceptable salt thereof.

18. The compound of claim 1 wherein
T is CH;
U is CH;
V is CH;
X is $CH_2$;
Y is $CH_2$;
Z is O;
W is O;
Q is $CR^8$;
$R^1$ is selected from:
1) —$C_{3-9}$cycloalkyl, and
2) —$C_{2-8}$cycloheteroalkyl,
wherein cycloalkyl, and cycloheteroalkyl are unsubstituted or substituted with one to five substituents selected from $R^a$;
$R^2$ is hydrogen;
$R^3$ is hydrogen;
$R^4$ is $C_{1-3}$alkyl;
$R^5$ is —$CO_2H$;
$R^6$ is hydrogen;
$R^7$ is hydrogen;
$R^8$ is hydrogen;
$R^9$ is $C_{1-6}$alkyl, and
$R^{10}$ is $C_{1-6}$alkyl;
or a pharmaceutically acceptable salt thereof.

19. The compound of claim 1 which is selected from:
1) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-pyrrolidin-3-yl)carbamimidoyl)-chroman-2-yl)propanoic acid;

2) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-pyrrolidin-3-yl)-carbamimidoyl)-chroman-2-yl)propanoic acid;

3) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3S,5R)-5-(hydroxymethyl)-pyrrolidin-3-yl)carbamimidoyl)chroman-2-yl)propanoic acid;

4) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3R,5R)-5-(hydroxymethyl)pyrrolidin-3-yl)carbamimidoyl)chroman-2-yl)propanoic acid;

5) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-azepan-4-yl)carbamimidoyl)chroman-2-yl)propanoic acid;

6) (S)-2-((R)-6-(N-((1s,4S)-4-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxo-ethylidene)amino)oxy)propanoic acid;

7) (S)-2-((R)-6-(N-((1s,3S)-3-aminocyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

8) (S)-2-((R)-6-(N-((1r,3R)-3-aminocyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

9) (S)-2-((R)-6-(N-(3-(aminomethyl)bicyclo[1.1.1]pentan-1-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

10) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-azepan-3-yl)carbamimidoyl)-chroman-2-yl)propanoic acid;

11) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-azepan-3-yl)carbamimidoyl)-chroman-2-yl)propanoic acid;

12) (S)-2-((R)-6-(N-(1-(aminomethyl)-2-oxabicyclo[2.1.1]hexan-4-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

13) (S)-2-((R)-6-(N-(2-azaspiro[3.5]nonan-7-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

14) (S)-2-((R)-6-(N-(2-azaspiro[3.3]heptan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

15) (S)-2-((R)-6-(N-(5-aminobicyclo[3.1.1]heptan-1-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

16) (2S)-2-((2R)-6-(N-((1S,5R)-3-azabicyclo[3.2.0]heptan-6-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

17) (S)-2-((R)-6-(N-((4R,6s)-1-azaspiro[3.3]heptan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

18) (S)-2-((R)-6-(N-((4S,6r)-1-azaspiro[3.3]heptan-6-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

19) (S)-2-((R)-6-(N-((2s,4R)-6-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

20) (S)-2-((R)-6-(N-((2r,4S)-6-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

21) (S)-2-((R)-6-(N-(7-azaspiro[3.5]nonan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

22) (S)-2-((R)-6-(N-((2r,4S)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

23) (S)-2-((R)-6-(N-((2s,4R)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

24) (S)-2-((R)-6-(N-((1S,2R,5R,6R)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

25) (S)-2-((R)-6-(N-((1R,2R,5S,6S)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

26) (S)-2-((R)-6-(N-((1S,2S,5R,6R)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

27) (S)-2-((R)-6-(N-((1R,2S,5S,6S)-5-aminobicyclo[4.1.0]heptan-2-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

28) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(piperidin-4-yl)carbamimidoyl)chroman-2-yl)propanoic acid;

29) (S)-2-((R)-6-(N-(1-((R)-3-amino-2-hydroxypropyl)piperidin-4-yl)carbamimidoyl)-chroman-2-yl)-2-((((Z)-1-(2-aminothiazol-4-yl)-2-(((S)-2,2-dimethyl-4- oxo-1-(sulfooxy)azetidin-3-yl)amino)-2-oxoethylidene)amino)oxy)propanoic acid;

30) (S)-2-((R)-6-(N-(1-((S)-3-amino-2-hydroxypropyl)piperidin-4-yl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

31) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-azepan-4-yl)carbamimidoyl)chroman-2-yl)propanoic acid;

32) (S)-2-((R)-6-(N-((1r,4R)-4-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)propanoic acid;

33) (S)-2-((((Z)-1-(2-aminothiazol-4-yl)-2-(((S)-2,2-dimethyl-4-oxo-1-(sulfooxy)azetidin-3-yl)-amino)-2-oxoethylidene)amino)oxy)-2-((R)-6-(N-((3R,5S)-5-(hydroxymethyl)pyrrolidin-3-yl)carbamimidoyl)chroman-2-yl)propanoic acid;

34) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1r,4R)-4-(methylamino)cyclohexyl)-carbamimidoyl)chroman-2-yl)propanoic acid;

35) (S)-2-((R)-6-(N-(4-aminobicyclo[2.2.2]octan-1-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

36) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(azetidin-3-yl)carbamimidoyl)chroman-2-yl)propanoic acid;

37) (S)-2-((R)-6-(N-((1R,5S,6s)-3-azabicyclo[3.1.0]hexan-6-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

38) (S)-2-((R)-6-(N-(4-(aminomethyl)phenyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

39) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-piperidin-3-yl)carbamimidoyl)-chroman-2-yl)propanoic acid;

40) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-piperidin-3-yl)carbamimidoyl)-chroman-2-yl)propanoic acid;

41) (S)-2-((R)-6-(N-((1s,4S)-4-(aminomethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

42) (S)-2-((R)-6-(N-((1r,4R)-4-(aminomethyl)cyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

43) (S)-2-((R)-6-(N-((2s,4R)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

44) (S)-2-((R)-6-(N-((2r,4S)-6-azaspiro[3.4]octan-2-yl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

45) (S)-2-((R)-6-(N-((1R,3S)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

46) (S)-2-((R)-6-(N-((1S,3R)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

47) (S)-2-((R)-6-(N-((1S,3S)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

48) (S)-2-((R)-6-(N-((1R,3R)-3-aminocyclopentyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid);

49) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((S)-3,3-dimethylpiperidin-4-yl)carbamimidoyl)chroman-2-yl)propanoic acid;

50) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N—((R)-3,3-dimethylpiperidin-4-yl)carbamimidoyl)chroman-2-yl)propanoic acid;

51) (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-((R)-6-(N-((3R,4S)-3-(hydroxymethyl)-piperidin-4-yl)carbamimidoyl)chroman-2-yl)propanoic acid;

52) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3S,4R)-3-(hydroxymethyl)-piperidin-4-yl)carbamimidoyl)chroman-2-yl)propanoic acid;

53) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2S,4S)-2-(hydroxymethyl)-piperidin-4-yl)carbamimidoyl)chroman-2-yl)propanoic acid;

54) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2R,4R)-2-(hydroxymethyl)-piperidin-4-yl)carbamimidoyl)chroman-2-yl)propanoic acid;

55) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2R,4R)-2-methylpiperidin-4-yl)carbamimidoyl)chroman-2-yl)propanoic acid;

56) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((2S,4S)-2-methylpiperidin-4-yl)carbamimidoyl)chroman-2-yl)propanoic acid;

57) (S)-2-((R)-6-(N-((1r,4R)-4-amino-4-methylcyclohexyl)carbamimidoyl)chroman-2-yl)-2-((((Z)-1-(2- aminothiazol-4-yl)-2-(((S)-2,2-dimethyl-4-oxo-1-(sulfooxy)-azetidin-3-yl)amino)-2-oxoethylidene)amino)oxy)propanoic acid;

58) (S)-2-((R)-6-(N-((1s,4S)-4-amino-4-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

59) (S)-2-((R)-6-(N-((1s,4S)-4-(aminomethyl)-4-hydroxycyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

60) (S)-2-((R)-6-(N-((1r,4R)-4-(aminomethyl)-4-hydroxycyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

61) (S)-2-((R)-6-(N-((2R,4r,6R)-6-aminospiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

62) (S)-2-((R)-6-(N-((2S,4s,6S)-6-aminospiro[3.3]heptan-2-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

63) (S)-2-((R)-6-(N-((1s,4S)-4-amino-4-(2-methoxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

64) (S)-2-((R)-6-(N-((1r,4R)-4-amino-4-(2-methoxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

65) (S)-2-((R)-6-(N-((1s,4S)-4-amino-4-(2-hydroxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

66) (S)-2-((R)-6-(N-((1r,4R)-4-amino-4-(2-hydroxyethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

67) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(trans-3-(methylamino)cyclobutyl)-carbamimidoyl)chroman-2-yl)propanoic acid;

68) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-(cis-3-(methylamino)cyclobutyl)-carbamimidoyl)chroman-2-yl)propanoic acid;

69) (S)-2-((R)-6-(N-((1r,4R)-4-amino-4-(hydroxymethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

70) (S)-2-((R)-6-(N-((1s,4S)-4-amino-4-(hydroxymethyl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

71) (S)-2-((R)-6-(N-((1r,4R)-4-amino-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

72) (S)-2-((R)-6-(N-((1s,4S)-4-amino-1-methylcyclohexyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

73) (S)-2-((R)-6-(N-((1s,4S)-4-(aminomethyl)-4-methoxycyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

74) (S)-2-((R)-6-(N-((1r,3R)-3-amino-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

75) (S)-2-((R)-6-(N-((1s,3S)-3-amino-3-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

76) (S)-2-((R)-6-(N-((1R,5S,8s)-3-azabicyclo[3.2.1]octan-8-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

77) (S)-2-((R)-6-(N-((1R,5S,8r)-3-azabicyclo[3.2.1]octan-8-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

78) (S)-2-((R)-6-(N-((1r,3R)-3-(aminomethyl)-3-(hydroxymethyl)cyclobutyl)-carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)-oxy)propanoic acid;

79) (S)-2-((R)-6-(N-((1s,3S)-3-(aminomethyl)-3-(hydroxymethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

80) (S)-2-((R)-6-(N-((1s,3S)-3-(aminomethyl)-3-hydroxycyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

81) (S)-2-((R)-6-(N-((1r,3R)-3-(aminomethyl)-3-hydroxycyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

82) (S)-2-((R)-6-(N-((1r,3R)-3-(aminomethyl)-3-methoxycyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

83) (S)-2-((R)-6-(N-((1s,3S)-3-(aminomethyl)-3-methoxycyclobutyl)carbamimidoyl)-chroman-2-yl)-2-((((Z)-1-(2-aminothiazol-4-yl)-2-(((S)-2,2-dimethyl-4- oxo-1-(sulfooxy)azetidin-3-yl)amino)-2-oxoethylidene)amino)oxy)propanoic acid;

84) (S)-2-((R)-6-(N-((1r,3R)-3-amino-1-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

85) (S)-2-((R)-6-(N-((1s,3S)-3-amino-1-methylcyclobutyl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

86) (S)-2-((R)-6-(N-((1s,3S)-3-amino-3-(2-hydroxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

87) (S)-2-((R)-6-(N-((1r,3R)-3-amino-3-(2-hydroxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

88) (S)-2-((R)-6-(N-((1r,3R)-3-amino-3-(hydroxymethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

89) (S)-2-((R)-6-(N-((1s,3S)-3-amino-3-(hydroxymethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

90) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1r,3R)-3-(hydroxymethyl)-3-(methylamino)cyclobutyl)carbamimidoyl)chroman-2-yl)propanoic acid;

91) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1s,3S)-3-(hydroxymethyl)-3-(methylamino)cyclobutyl)carbamimidoyl)chroman-2-yl)propanoic acid;

92) (S)-2-((R)-6-(N-((1r,3R)-3-amino-3-(2-methoxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

93) (S)-2-((R)-6-(N-((1s,3S)-3-amino-3-(2-methoxyethyl)cyclobutyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

94) (S)-2-((R)-6-(N-((1S,3R)-3-amino-3-((S)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

95) (S)-2-((R)-6-(N-((1R,3R)-3-amino-3-((R)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

96) (S)-2-((R)-6-(N-((1R,3S)-3-amino-3-((S)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

97) (S)-2-((R)-6-(N-((1S,3S)-3-amino-3-((R)-2,3-dihydroxypropyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

98) (S)-2-((R)-6-(N-((1S,3R)-3-amino-3-((S)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

99) (S)-2-((R)-6-(N-((1R,3R)-3-amino-3-((R)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

100) (S)-2-((R)-6-(N-((1S,3S)-3-amino-3-((R)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

101) (S)-2-((R)-6-(N-((1R,3S)-3-amino-3-((S)-1,2-dihydroxyethyl)cyclobutyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

102) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1s,4S)-4-((methylamino)methyl)-cyclohexyl)carbamimidoyl)chroman-2-yl)propanoic acid;

103) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((1r,4R)-4-((methylamino)methyl)cyclohexyl)carbamimidoyl)chroman-2-yl)propanoic acid;

104) (S)-2-((R)-6-(N-((1R,4S)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

105) (S)-2-((R)-6-(N-((1R,4R)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

106) (S)-2-((R)-6-(N-((1S,4S)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)propanoic acid;

107) (S)-2-((R)-6-(N-((1S,4R)-4-aminocycloheptyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

108) (S)-2-((R)-6-(N-((1R,3R)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

109) (S)-2-((R)-6-(N-((1S,3S)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

110) (S)-2-((R)-6-(N-((1R,3S)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

111) (S)-2-((R)-6-(N-((1S,3R)-3-aminocyclohexyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

112) (S)-2-((R)-6-(N-((1s,3S)-3-(aminomethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

113) (S)-2-((R)-6-(N-((1r,3R)-3-(aminomethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

114) (S)-2-((R)-6-(N-((1S,3S)-3-amino-2,2-dimethylcyclobutyl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

115) (S)-2-((R)-6-(N-((2S,4s,7S)-2-aminospiro[3.5]nonan-7-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

116) (S)-2-((R)-6-(N-((2R,4r,7R)-2-aminospiro[3.5]nonan-7-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

117) (S)-2-((R)-6-(N-((1s,3S)-3-(aminomethyl)-3-methylcyclobutyl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

118) (S)-2-((R)-6-(N-((1r,3R)-3-(aminomethyl)-3-methylcyclobutyl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

119) (S)-2-((R)-6-(N-(6-(aminomethyl)-6-fluorospiro[3.3]heptan-2-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

120) (S)-2-((R)-6-(N-((1R,3S)-3-(aminomethyl)-2,2-dimethylcyclobutyl)-carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

121) (2S)-2-((2R)-6-(N-(6-(aminomethyl)spiro[3.3]heptan-2-yl)carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

122) (2S)-2-((2R)-6-(N-((1S)-1-aminospiro[2.3]hexan-5-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

123) (2S)-2-((2R)-6-(N-((1R)-1-aminospiro[2.3]hexan-5-yl)carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

124) (S)-2-((R)-6-(N-((1s,3S)-3-aminocyclobutyl)carbamimidoyl)-5-(methoxymethyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

125) (S)-2-((R)-6-(N-((1s,3S)-3-aminocyclobutyl)carbamimidoyl)-7-(methoxymethyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

126) (S)-2-((R)-6-(N-((1s,4S)-4-amino-1-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

127) (S)-2-((R)-6-(N-((1r,4R)-4-amino-1-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

128) (S)-2-((R)-6-(N-((1s,4S)-4-amino-4-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

129) (S)-2-((R)-6-(N-((1r,4R)-4-amino-4-(methoxymethyl)cyclohexyl)-carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

130) (S)-2-((R)-6-(N-((1s,4S)-4-(aminomethyl)-1-methylcyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

131) (S)-2-((R)-6-(N-((1r,4R)-4-(aminomethyl)-1-methylcyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

132) (S)-2-((R)-6-(N-((1s,4S)-4-(2-aminopropan-2-yl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

133) (S)-2-((R)-6-(N-((1r,4R)-4-(2-aminopropan-2-yl)cyclohexyl)carbamimidoyl)-chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

134) (S)-2-((R)-6-(N-((1s,3S)-3-aminocyclobutyl)carbamimidoyl)-7-methylchroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

135) (S)-2-((R)-6-(N-((1r,4R)-4-amino-4-(hydroxymethyl)-1-methylcyclohexyl)-carbamimidoyl)chroman-2-yl)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid;

136) (S)-2-((R)-6-(N-((1R,3r,5S)-8-azabicyclo[3.2.1]octan-3-yl)carbamimidoyl)-chroman-2-yl)-2-((((Z)-1-(2- aminothiazol-4-yl)-2-(((S)-2,2-dimethyl-4-oxo-1-(sulfooxy)-azetidin-3-yl)amino)-2-oxoethylidene)amino)oxy)propanoic acid;

137) (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-((R)-6-(N-((3S,5S)-5-(hydroxymethyl)pyrrolidin-3-yl)carbamimidoyl)chroman-2-yl)propanoic acid;

138) (S)-2-((R)-6-(N-(1-(2-aminoethyl)cyclopropyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

139) (S)-2-((R)-6-(N-(1-(3-aminopropyl)cyclopropyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid; and 140) (S)-2-((R)-6-(N-(1-(2-aminoethyl)cyclobutyl)carbamimidoyl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid;

or a pharmaceutically acceptable salt thereof.

20. The compound of claim 1 which is selected from:

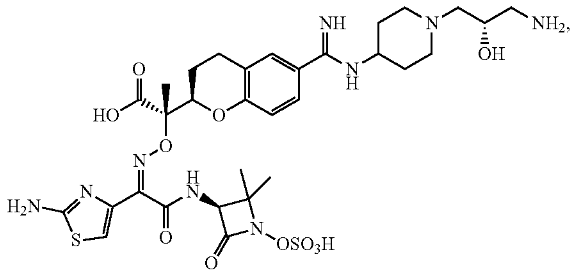
,

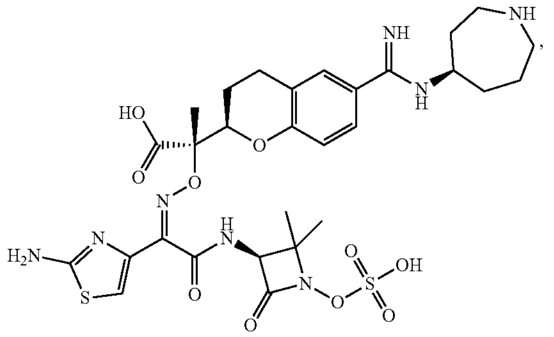
,

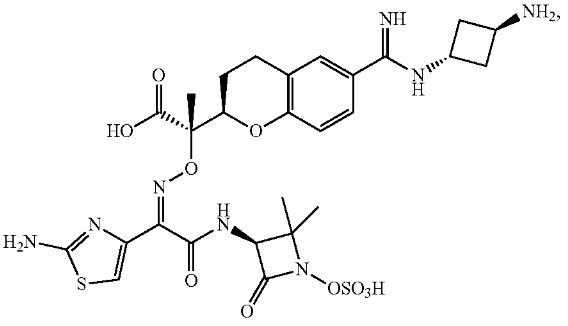
,

-continued

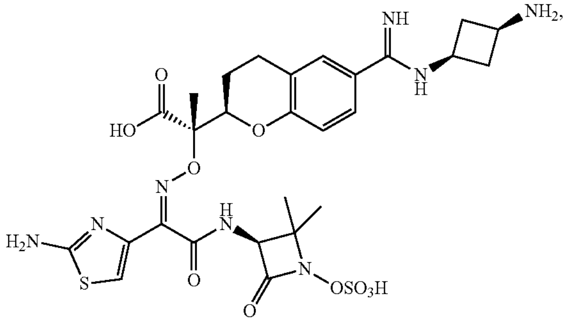
,

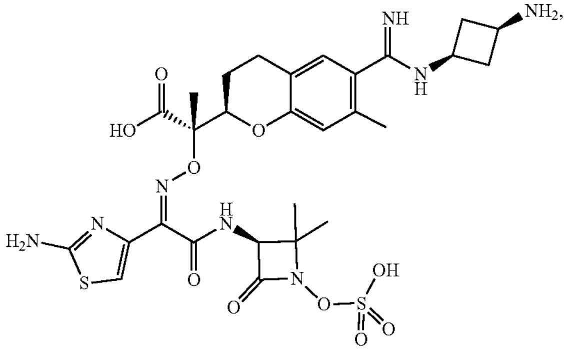
,

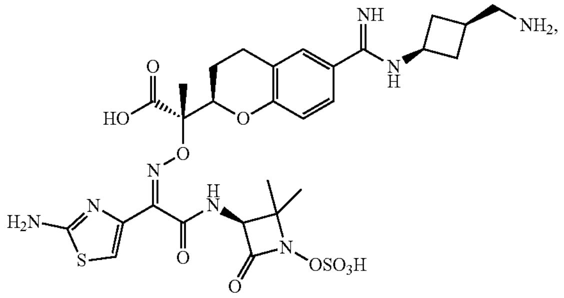
,

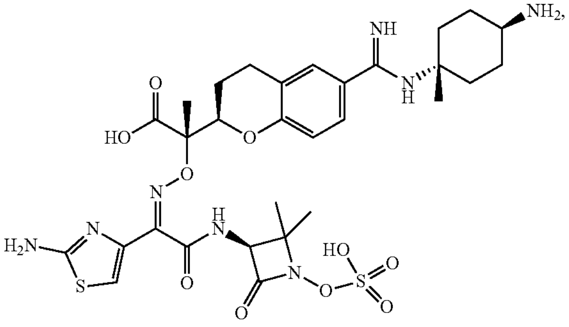
,

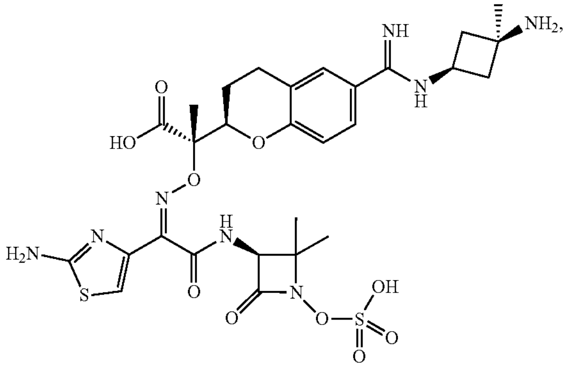
,

-continued

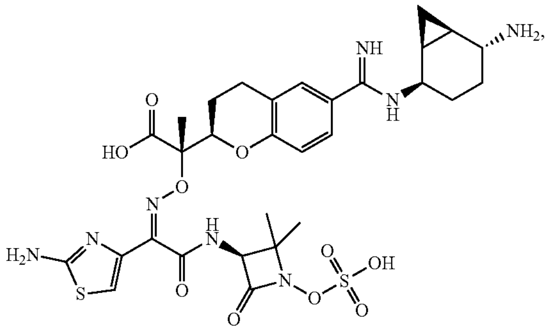

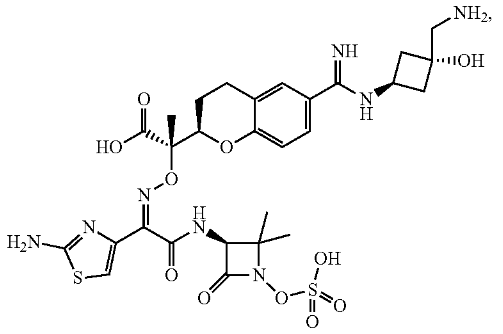

and

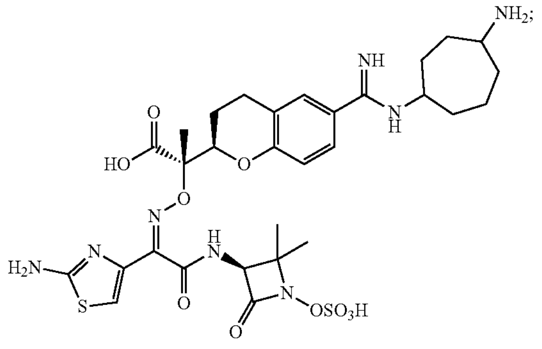

or a pharmaceutically acceptable salt thereof.

21. A pharmaceutical composition comprising a therapeutically effective amount of a compound of claim 1, or a pharmaceutically acceptable salt thereof, and a pharmaceutically acceptable carrier.

22. A pharmaceutical composition according to claim 21, which further comprises a therapeutically effective amount of a beta-lactamase inhibitor compound.

23. A pharmaceutical composition according to claim 22 wherein the beta-lactamase inhibitor compound is selected from relebactam, tazobactam, clavulanic acid, sulbactam, avibactam, taniborbactam, nacubactam, vaborbactam, zidebactam, and durlobactam.

24. A method for treating a bacterial infection which comprises administering to a subject in need of such treatment a therapeutically effective amount of a compound of claim 1, or a pharmaceutically acceptable salt thereof.

25. The method of claim 24 further comprising administering to a subject in need of such treatment a therapeutically effective amount of a beta-lactamase inhibitor compound.

26. The method of claim 25 wherein the beta-lactamase inhibitor compound is selected from relebactam, tazobactam, clavulanic acid, sulbactam, avibactam, taniborbactam, nacubactam, vaborbactam, zidebactam, and durlobactam.

27. The method of claim 24 wherein the bacterial infection is due to *Pseudomonas* spp., *Klebsiella* spp., *Enterobacter* spp., *Escherichia* spp., *Morganella* spp., *Citrobacter* spp., *Serratia* spp. or *Acintetobacter* spp.

28. A compound which is

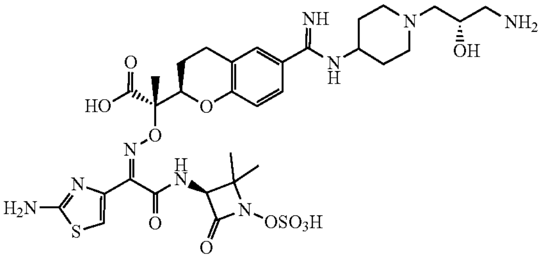

;

or a pharmaceutically acceptable salt thereof.

29. A compound which is

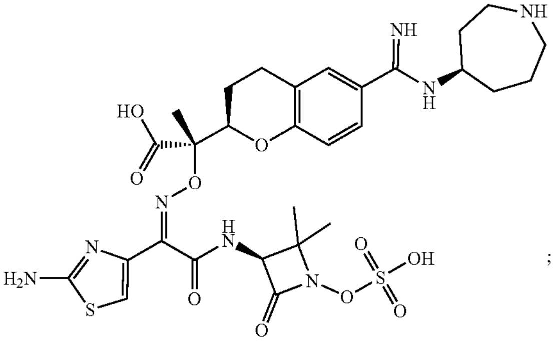 [SMILES: CC1(C)[C@H](NC(=O)/C(=N\O[C@](C)(C(=O)O)[C@H]2CCc3cc(C(=N)N[C@@H]4CCCNCC4)ccc3O2)c2csc(N)n2)C(=O)N1OS(=O)(=O)O ; ";"]

;

or a pharmaceutically acceptable salt thereof.

30. A compound which is

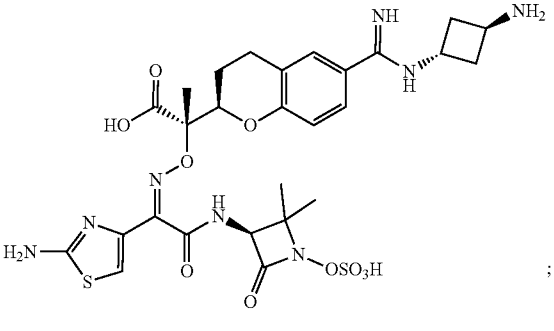

;

or a pharmaceutically acceptable salt thereof.

31. A compound which is

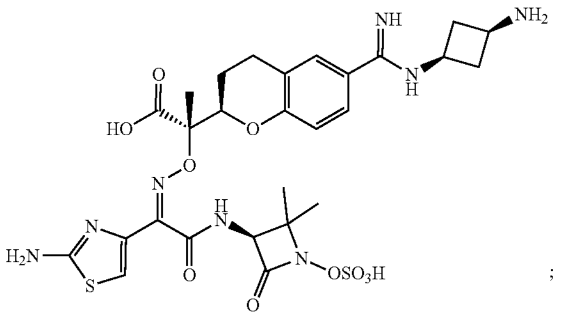

or a pharmaceutically acceptable salt thereof.

32. A compound which is

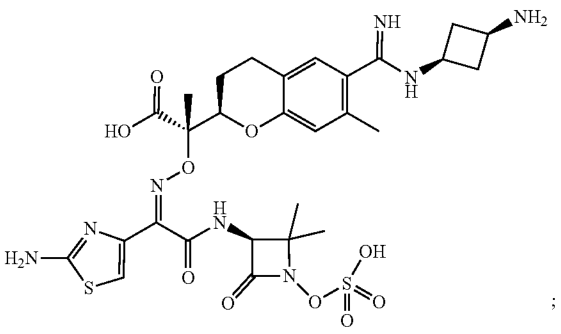 [SMILES: Cc1cc2c(cc1C(=N)N[C@H]1C[C@@H](N)C1)CC[C@H]([C@](C)(O/N=C(\C(=O)N[C@@H]1C(=O)N(OS(=O)(=O)O)C1(C)C)c1csc(N)n1)C(=O)O)O2 ; ";"]

or a pharmaceutically acceptable salt thereof.

33. A compound which is

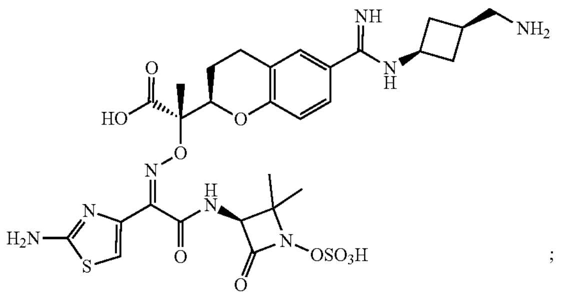

or a pharmaceutically acceptable salt thereof.

34. A compound which is

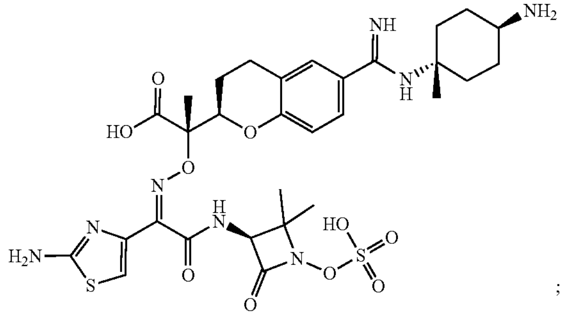 [SMILES: CC1(C)[C@H](NC(=O)/C(=N\O[C@](C)(C(=O)O)[C@H]2CCc3cc(C(=N)N[C@]4(C)CC[C@@H](N)CC4)ccc3O2)c2csc(N)n2)C(=O)N1OS(=O)(=O)O ; ";"]

or a pharmaceutically acceptable salt thereof.

35. A compound which is

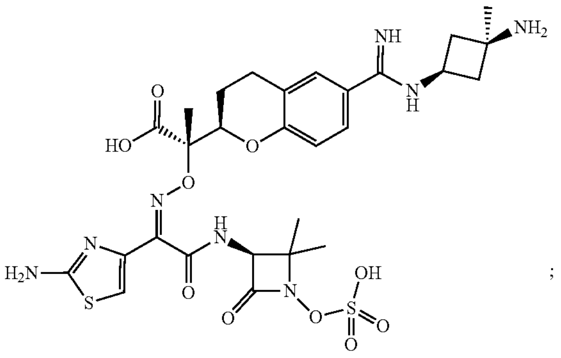 [SMILES: CC1(C)[C@H](NC(=O)/C(=N\O[C@](C)(C(=O)O)[C@H]2CCc3cc(C(=N)N[C@H]4C[C@@](C)(N)C4)ccc3O2)c2csc(N)n2)C(=O)N1OS(=O)(=O)O ; ";"]

or a pharmaceutically acceptable salt thereof.

36. A compound which is

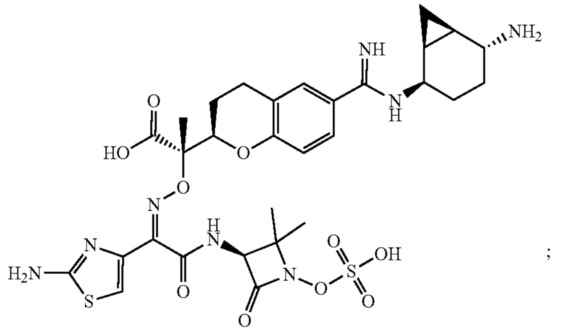 [SMILES: CC1(C)[C@H](NC(=O)/C(=N\O[C@](C)(C(=O)O)[C@H]2CCc3cc(C(=N)N[C@@H]4CC[C@@H](N)[C@@H]5C[C@@H]54)ccc3O2)c2csc(N)n2)C(=O)N1OS(=O)(=O)O ; ";"]

or a pharmaceutically acceptable salt thereof.

37. A compound which is
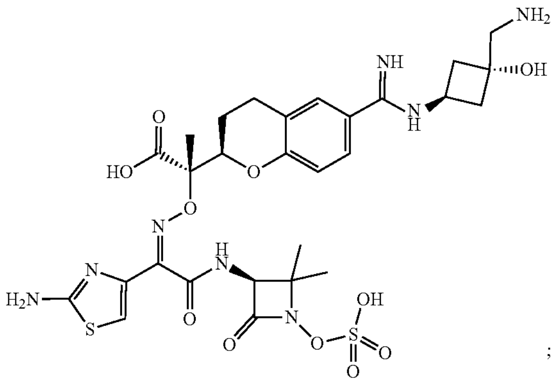 [SMILES: CC1(C)[C@H](NC(=O)/C(=N\O[C@](C)(C(=O)O)[C@H]2CCc3cc(C(=N)N[C@H]4C[C@@](O)(CN)C4)ccc3O2)c2csc(N)n2)C(=O)N1OS(=O)(=O)O ; ";"]
;
or a pharmaceutically acceptable salt thereof.
38. A compound which is
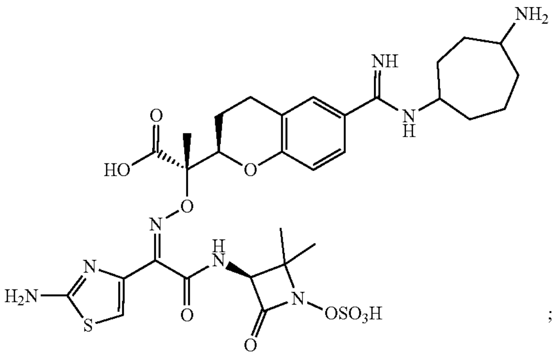
;
or a pharmaceutically acceptable salt thereof.
39. A compound which is
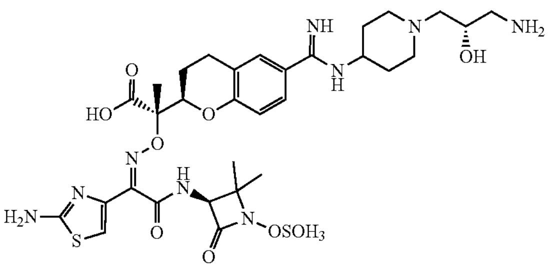
.
40. A compound which is
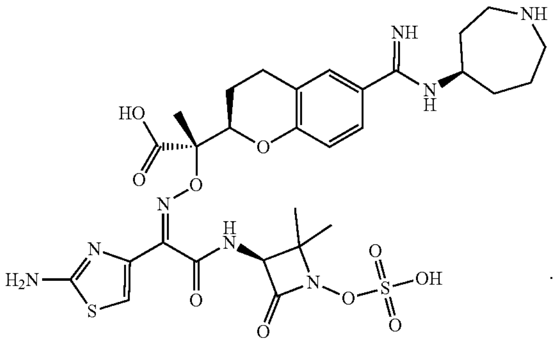 [SMILES: CC1(C)[C@H](NC(=O)/C(=N\O[C@](C)(C(=O)O)[C@H]2CCc3cc(C(=N)N[C@@H]4CCCNCC4)ccc3O2)c2csc(N)n2)C(=O)N1OS(=O)(=O)O ; "."]
.
41. A compound which is
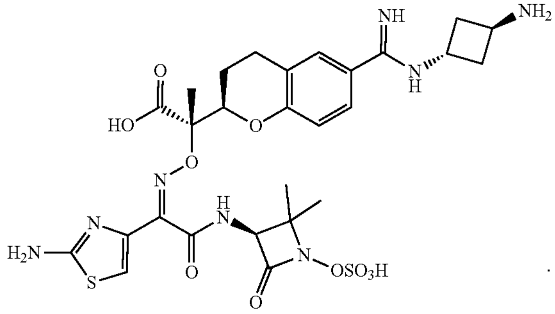
.
42. A compound which is
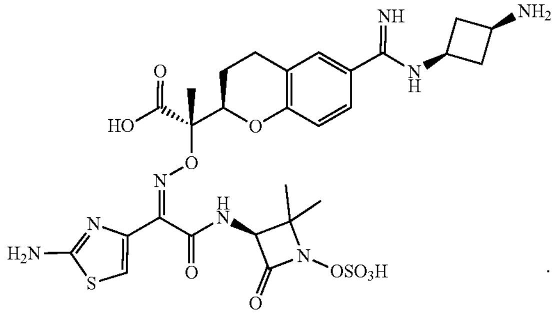
.
43. A compound which is
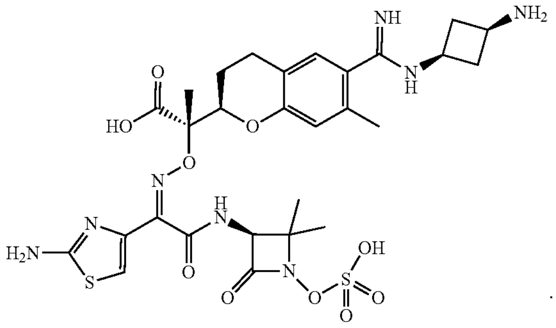
.

44. A compound which is
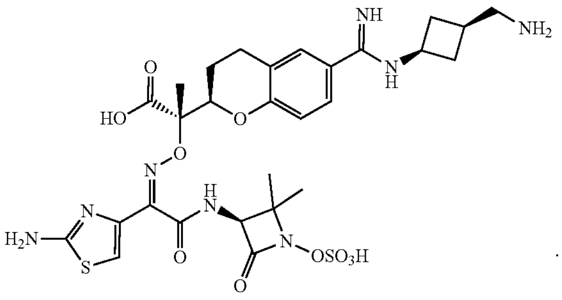
.
45. A compound which is
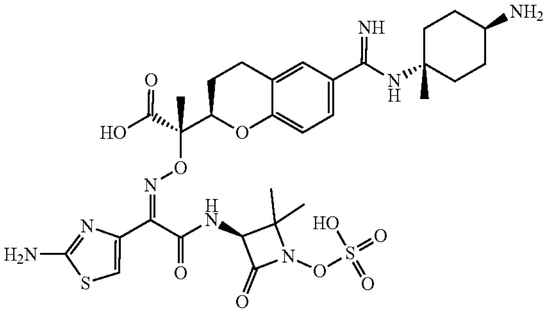
.
46. A compound which is
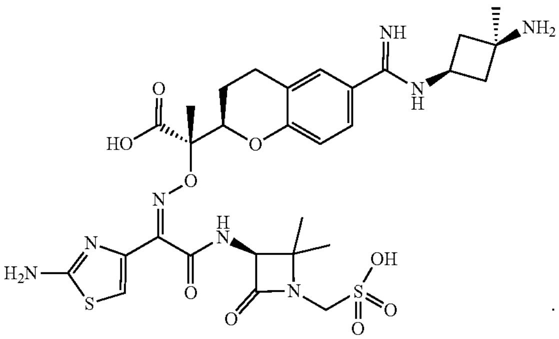 [SMILES: CC1(C)[C@H](NC(=O)/C(=N\O[C@](C)(C(=O)O)[C@H]2CCc3cc(C(=N)N[C@H]4C[C@@](C)(N)C4)ccc3O2)c2csc(N)n2)C(=O)N1CS(=O)(=O)O ; "."]
.
47. A compound which is
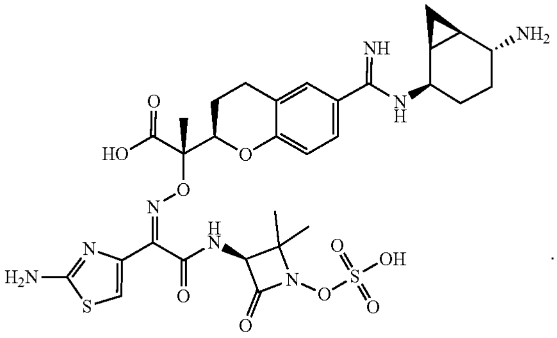 [SMILES: CC1(C)[C@H](NC(=O)/C(=N\O[C@](C)(C(=O)O)[C@H]2CCc3cc(C(=N)N[C@@H]4CC[C@@H](N)[C@@H]5C[C@@H]54)ccc3O2)c2csc(N)n2)C(=O)N1OS(=O)(=O)O ; "."]
.
48. A compound which is
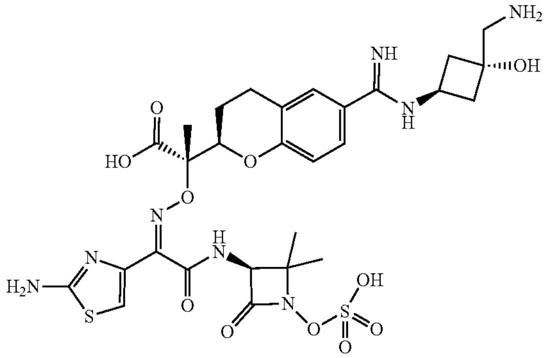
.
49. A compound which is
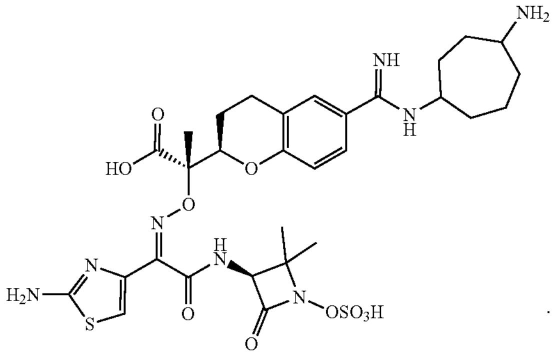
.
* * * * *

UNITED STATES PATENT AND TRADEMARK OFFICE

CERTIFICATE OF CORRECTION

PATENT NO. : 11,932,637 B2
APPLICATION NO. : 18/055874
DATED : March 19, 2024
INVENTOR(S) : Helen Y. Chen et al.

It is certified that error appears in the above-identified patent and that said Letters Patent is hereby corrected as shown below:

In the Claims

In Column 321, Line 13, Claim 1, should read:
1) halogen,
2) -C1-6alkyl,
3) –C0-6alkyl-O-C1-6alkyl,
4) –C0-6alkyl-OH,
5) -C0-6alkylS(O)rRj,
6) -C0-6alkylS(O) rNRkRl,
7) -C0-6alkylC(O)Ri,
8) -C0-6alkylOC(O)Ri,
9) -C0-6alkylC(O)ORi,
10) -C0-6alkylCN,
11) -C0-6alkylC(O)NRkRl,
12) -C0-6alkylC(NH)NRkRl,
13) -C0-6alkylNRkRl,
14) -C0-6alkylN(Rk)(C(O)Ri),
15) -C0-6alkylN(Rk)(C(O)ORh),
16) -C0-6alkylN(Rk)(C(O)NRfRg), and
17) -C0-6alkylN(Rk)(S(O)vRj), Signed and Sealed this
Ninth Day of July, 2024

Katherine Kelly Vidal

Katherine Kelly Vidal
*Director of the United States Patent and Trademark Office*